(12) United States Patent
Fayram et al.

(10) Patent No.: US 11,129,985 B2
(45) Date of Patent: Sep. 28, 2021

(54) DEVICES, SYSTEMS, AND METHODS FOR STIMULATION THERAPY

(71) Applicant: NeuSpera Medical Inc., San Jose, CA (US)

(72) Inventors: Timothy A. Fayram, Gilroy, CA (US); Alexander Yeh, Los Altos Hills, CA (US); Gary Shaw, Santa Clara, CA (US); Randolph Kerry Armstrong, Katy, TX (US); Milton M. Morris, Houston, TX (US); Elia Junco, Menlo Park, CA (US)

(73) Assignee: NEUSPERA MEDICAL, INC., San Jose, CA (US)

( * ) Notice: Subject to any disclaimer, the term of this patent is extended or adjusted under 35 U.S.C. 154(b) by 637 days.

(21) Appl. No.: 15/770,032

(22) PCT Filed: Oct. 20, 2016

(86) PCT No.: PCT/US2016/057952
§ 371 (c)(1),
(2) Date: Apr. 20, 2018

(87) PCT Pub. No.: WO2017/070372
PCT Pub. Date: Apr. 27, 2017

(65) Prior Publication Data
US 2019/0022394 A1 Jan. 24, 2019

Related U.S. Application Data

(60) Provisional application No. 62/397,620, filed on Sep. 21, 2016, provisional application No. 62/396,478, (Continued)

(51) Int. Cl.
*A61N 1/36* (2006.01)
*H02J 50/20* (2016.01)
(Continued)

(52) U.S. Cl.
CPC ....... *A61N 1/36062* (2017.08); *A61N 1/0551* (2013.01); *A61N 1/36185* (2013.01);
(Continued)

(58) Field of Classification Search
CPC ............. A61N 1/36062; A61N 1/0551; A61N 1/37518; A61N 1/36185; A61N 1/0558;
(Continued)

(56) References Cited

U.S. PATENT DOCUMENTS 6,434,429 B1    8/2002   Kraus et al.
7,228,183 B2    6/2007   Sun et al.
(Continued)

FOREIGN PATENT DOCUMENTS

CN      101395080      3/2009
CN      102711649      10/2012
(Continued)

OTHER PUBLICATIONS

"Canadian Application Serial No. 3,002,841, Voluntary Amendment Filed Aug. 20, 18", 17 pages.
(Continued)

*Primary Examiner* — Tammie K Marlen
(74) *Attorney, Agent, or Firm* — Schwegman Lundberg & Woessner, P.A.

(57) ABSTRACT

Generally discussed herein are systems, devices, and methods for providing a therapy (e.g., stimulation) and/or data signal using an implantable device. Systems, devices and methods for interacting with (e.g., communicating with, receiving power from) an external device are also provided.

23 Claims, 117 Drawing Sheets

Related U.S. Application Data filed on Sep. 16, 2016, provisional application No. 62/373,569, filed on Aug. 11, 2016, provisional application No. 62/367,995, filed on Jul. 28, 2016, provisional application No. 62/368,005, filed on Jul. 28, 2016, provisional application No. 62/350,674, filed on Jun. 15, 2016, provisional application No. 62/350,676, filed on Jun. 15, 2016, provisional application No. 62/350,681, filed on Jun. 15, 2016, provisional application No. 62/350,684, filed on Jun. 15, 2016, provisional application No. 62/291,379, filed on Feb. 4, 2016, provisional application No. 62/264,239, filed on Dec. 7, 2015, provisional application No. 62/244,495, filed on Oct. 21, 2015.

(51) Int. Cl.

| *H02J 50/80* | (2016.01) |
|---|---|
| *A61N 1/375* | (2006.01) |
| *A61N 1/378* | (2006.01) |
| *A61N 1/05* | (2006.01) |
| *H02J 7/02* | (2016.01) |
| *H02J 50/10* | (2016.01) |
| *H02J 50/40* | (2016.01) |
| *H02J 50/90* | (2016.01) |
| *A61N 1/372* | (2006.01) |
| *A61B 5/00* | (2006.01) |

(52) U.S. Cl.
CPC ......... *A61N 1/3756* (2013.01); *A61N 1/3787* (2013.01); *A61N 1/37223* (2013.01); *A61N 1/37247* (2013.01); *A61N 1/37252* (2013.01); *A61N 1/37518* (2017.08); *H02J 7/025* (2013.01); *H02J 50/10* (2016.02); *H02J 50/20* (2016.02); *H02J 50/40* (2016.02); *H02J 50/80* (2016.02); *H02J 50/90* (2016.02); *A61B 5/00* (2013.01); *A61N 1/0558* (2013.01); *A61N 1/37229* (2013.01)

(58) Field of Classification Search
CPC ............ A61N 1/37223; A61N 1/37247; A61N 1/37229; A61N 1/37252; A61N 1/3756; A61N 1/3787; H02J 50/80; H02J 50/10; H02J 50/20; H02J 50/90; H02J 50/40; H02J 7/025; A61B 5/00
See application file for complete search history.

(56) References Cited

U.S. PATENT DOCUMENTS

| 8,170,487 | B2 | 5/2012 | Sahota et al. | |
|---|---|---|---|---|
| 8,634,928 | B1 | 1/2014 | O'Driscoll et al. | |
| 2005/0159661 | A1 | 7/2005 | Connelly et al. | |
| 2006/0020306 | A1 | 1/2006 | Davis et al. | |
| 2007/0179552 | A1 | 8/2007 | Dennis et al. | |
| 2008/0106419 | A1 | 5/2008 | Sakama | |
| 2008/0114405 | A1 | 5/2008 | Palmer et al. | |
| 2008/0132981 | A1 | 6/2008 | Gerber et al. | |
| 2009/0171420 | A1 | 7/2009 | Brown et al. | |
| 2009/0270948 | A1 | 10/2009 | Nghiem et al. | |
| 2010/0181845 | A1 | 7/2010 | Fiorello et al. | |
| 2011/0115430 | A1 | 5/2011 | Saunamaeki | |
| 2011/0218605 | A1 | 9/2011 | Cryer | |
| 2012/0172690 | A1 | 7/2012 | Anderson et al. | |
| 2013/0079849 | A1 | 3/2013 | Perryman et al. | |
| 2014/0036409 | A1 | 2/2014 | Stevenson et al. | |
| 2014/0055088 | A1* | 2/2014 | Joshi ...................... | H02J 50/90 320/108 |
| 2014/0084855 | A1 | 3/2014 | Joshi | |
| 2014/0213202 | A1 | 7/2014 | Wang et al. | |
| 2015/0265842 | A1 | 9/2015 | Ridler et al. | |
| 2016/0336813 | A1 | 11/2016 | Yeh et al. | |
| 2016/0344240 | A1 | 11/2016 | Yeh et al. | |
| 2018/0085593 | A1 | 3/2018 | Fayram et al. | |
| 2019/0240490 | A1 | 8/2019 | Yeh et al. | |
| 2019/0255329 | A1 | 8/2019 | Yeh et al. | |

FOREIGN PATENT DOCUMENTS

| CN | 102716546 | | 10/2012 |
|---|---|---|---|
| CN | 102738906 | | 10/2012 |
| CN | 104145333 | A | 11/2014 |
| CN | 104467129 | A | 3/2015 |
| CN | 104704708 | | 6/2015 |
| CN | 104826231 | A | 8/2015 |
| CN | 107847267 | | 3/2018 |
| CN | 108463163 | | 8/2018 |
| CN | 110461218 | | 11/2019 |
| JP | 2014500097 | A | 1/2014 |
| JP | 2015008578 | | 1/2015 |
| WO | WO-2014205129 | A1 | 12/2014 |
| WO | WO-2015039108 | A2 | 3/2015 |
| WO | WO-2015039108 | A3 | 3/2015 |
| WO | WO-2015179225 | A1 | 11/2015 |
| WO | WO-2017070372 | A1 | 4/2017 |

OTHER PUBLICATIONS

"U.S. Appl. No. 16/398,057, Non Final Office Action dated Mar. 5, 20", 10 pages.
"U.S. Appl. No. 15/830,862, Final Office Action dated Mar. 26, 2020", 10 pages.
"U.S. Appl. No. 16/398,057, Examiner Interview Summary dated Apr. 6, 2020", 3 pages.
"U.S. Appl. No. 16/398,057, Response filed Jun. 4, 20 to Non Final Office Action dated Mar. 5, 2020", 10 pages.
"U.S. Appl. No. 16/398,057, Final Office Action dated Jun. 19, 2020", 10 pages.
"U.S. Appl. No. 15/830,862, Response filed Jun. 25, 20 to Final Office Action dated Mar. 26, 2020", 8 pages.
"U.S. Appl. No. 15/830,862, Advisory Action dated Jul. 2, 2020", 3 pages.
"Australian Application Serial No. 2016342197, First Examination Report dated Aug. 4, 2020", 5 pages.
"International Application Serial No. PCT/US2016/057952, International Search Report dated Mar. 27, 2017", 6 pgs.
"International Application Serial No. PCT/US2016/057952, Invitation to Pay Additional Fees and Partial Search Report dated Jan. 10, 2017", 3 pgs.
"International Application Serial No. PCT/US2016/057952, Written Opinion dated Mar. 27, 2017", 17 pgs.
"International Application Serial No. PCT US2016 057952, International Preliminary Report on Patentability dated May 3, 2018", 19 pgs.
"U.S. Appl. No. 16/398,057, Examiner Interview Summary dated Jul. 1, 2019", 4 pages.
"U.S. Appl. No. 15/830,862, Non Final Office Action dated Oct. 29, 2019", 13 pages.
"U.S. Appl. No. 16/398,057, Final Office Action dated Nov. 8, 2019", 9 pages.
"U.S. Appl. No. 16/398,057, Examiner Interview Summary dated Jan. 2, 2020", 3 pages.
"U.S. Appl. No. 15/830,862, Examiner Interview Summary dated Jan. 2, 2020", 3 pages.
"U.S. Appl. No. 16/398,057, Response filed Jan. 6, 2020 to Final Office Action dated Nov. 8, 2019", 8 pages.
"U.S. Appl. No. 15/830,862, Response filed Jan. 6, 20 to Non Final Office Action dated Oct. 29, 2019", 10 pages.
"U.S. Appl. No. 16/398,057, Advisory Action dated Jan. 16, 2020", 3 pages.
"U.S. Appl. No. 16/398,057, Non Final Office Action dated Jun. 10, 2019", 11 pgs.
"European Application Serial No. 16858234.4, Extended European Search Report dated Mar. 20, 2019", 9 pgs.

(56) References Cited

OTHER PUBLICATIONS

"European Application Serial No. 16858234.4, Response filed Dec. 17, 2018 to Communication Pursuant to Rules 161(2) and 162 EPC dated Jun. 6, 2018", w English Claims, 120 pgs.
"U.S. Appl. No. 15/830,862, Corrected Notice of Allowability dated Jan. 22, 2021", 2 pgs.
"U.S. Appl. No. 15/830,862, Notice of Allowance dated Dec. 23, 2020", 10 pgs.
"U.S. Appl. No. 16/398,057, Advisory Action dated Oct. 13, 2020", 4 pgs.
"U.S. Appl. No. 16/398,057, Response filed Sep. 21, 20 to Final Office Action dated Jun. 19, 2020", 12 pgs.
"U.S. Appl. No. 16/398,057, Response filed Oct. 19, 2020 to Advisory Action dated Oct. 13, 2020", 13 pgs.
"Australian Application Serial No. 2016342197, Response filed Sep. 21, 2020 to First Examination Report dated Aug. 4, 2020", 440 pgs.
"Chinese Application Serial No. 201680074833.X, Office Action dated Jul. 21, 2020", with English translation, 22 pages.
"European Application Serial No. 16858234.4, Communication Pursuant to Article 94(3) EPC dated Dec. 3, 2020", 4 pgs.
"Japanese Application Serial No. 2018-520448, Notification of Reasons for Refusal dated Sep. 1, 2020", with English translation, 17 pages.
"Chinese Application Serial No. 201680074833.X, Office Action dated Jul. 23, 2021", with English translation, 9 pages.

\* cited by examiner

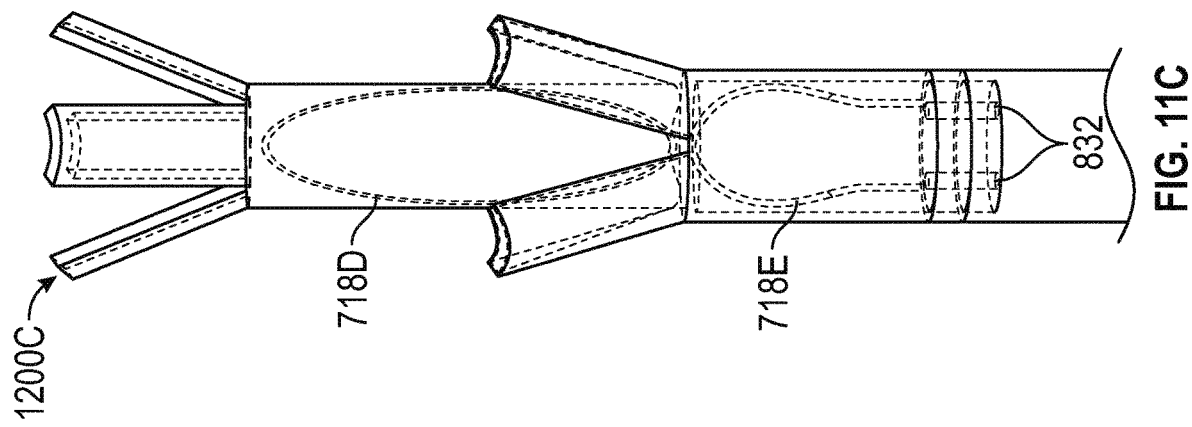
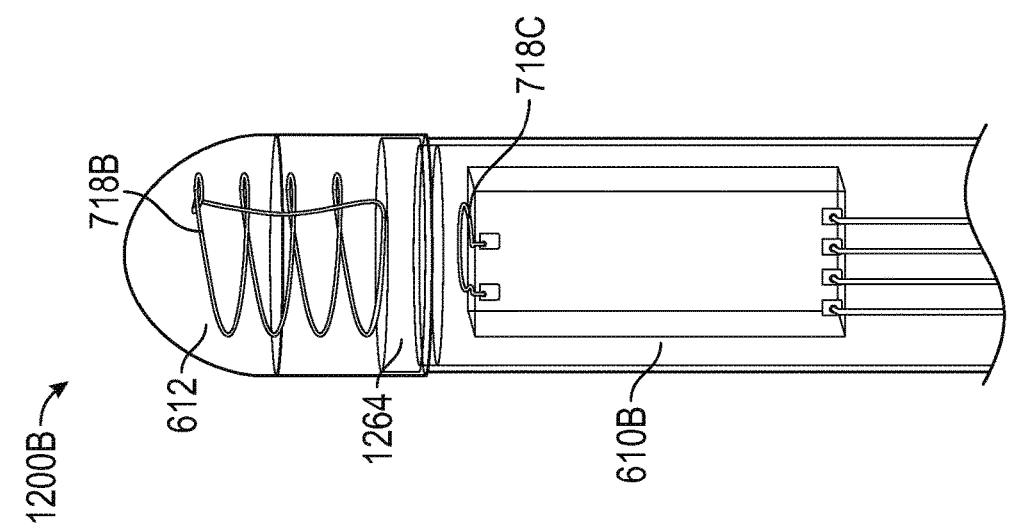
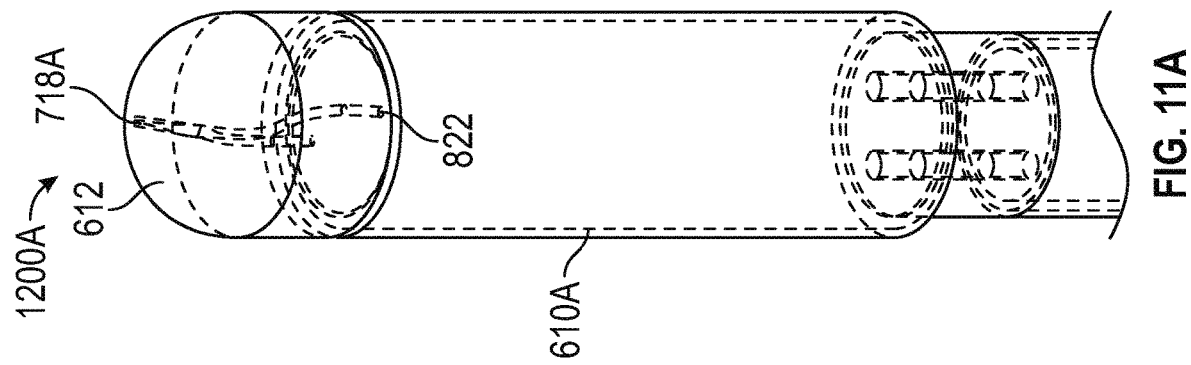

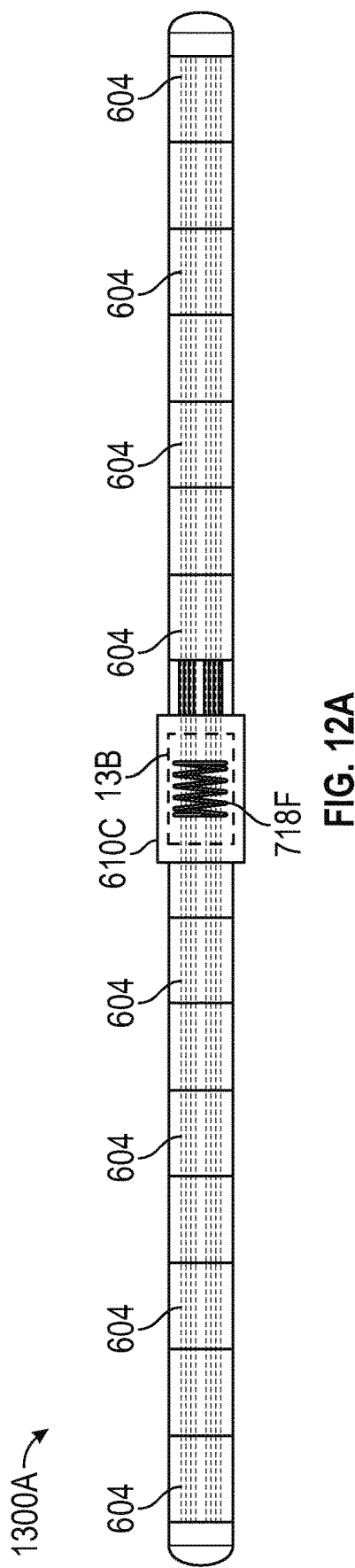
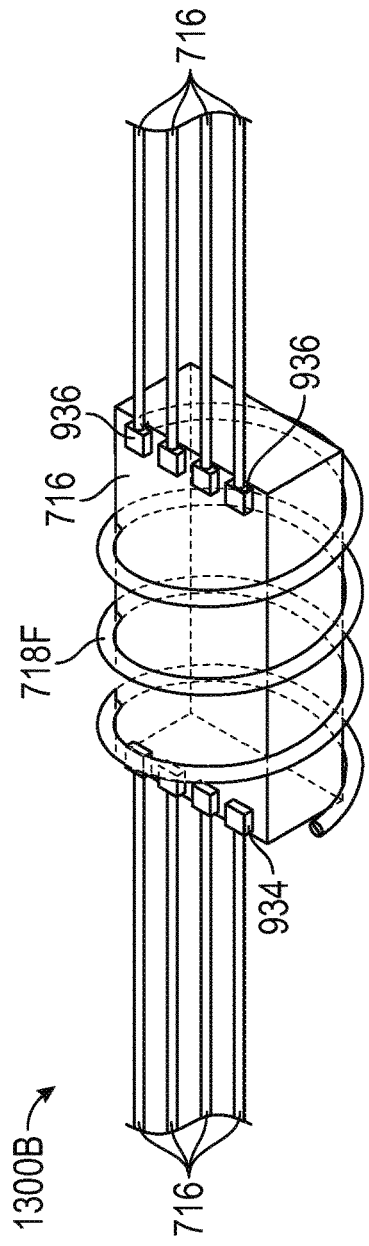
FIG. 12A
FIG. 12B

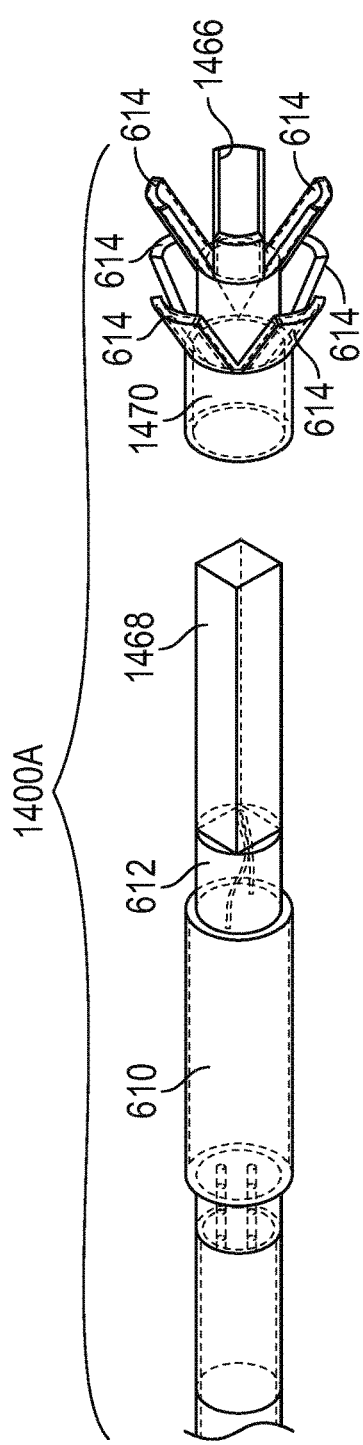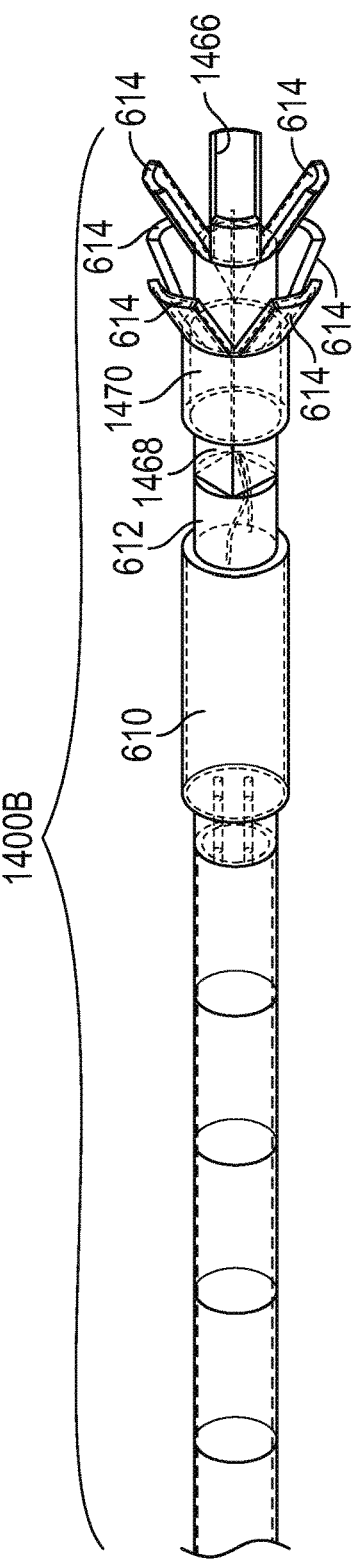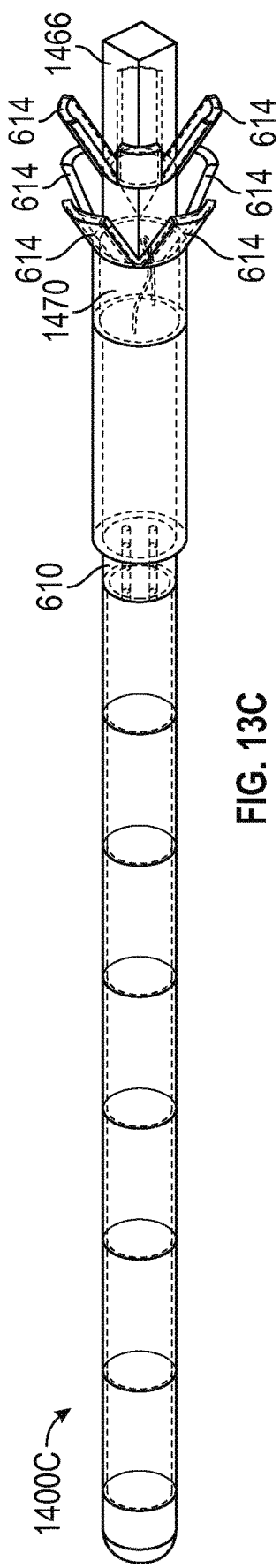
FIG. 13A
FIG. 13B
FIG. 13C

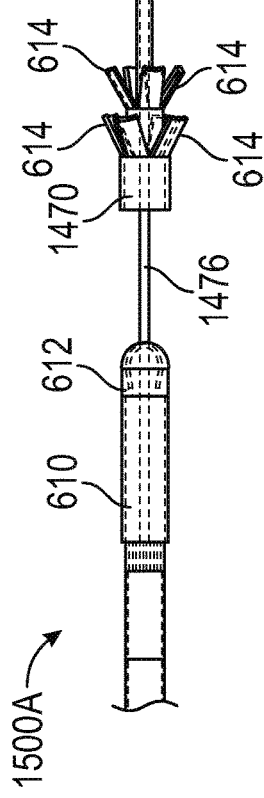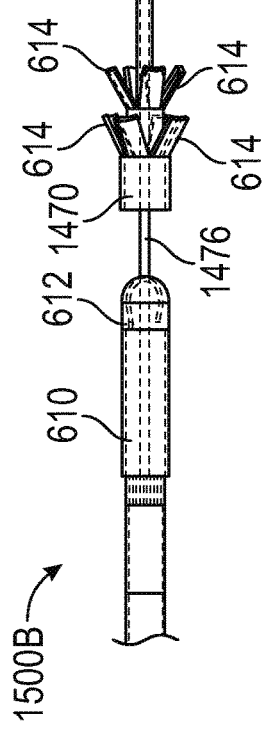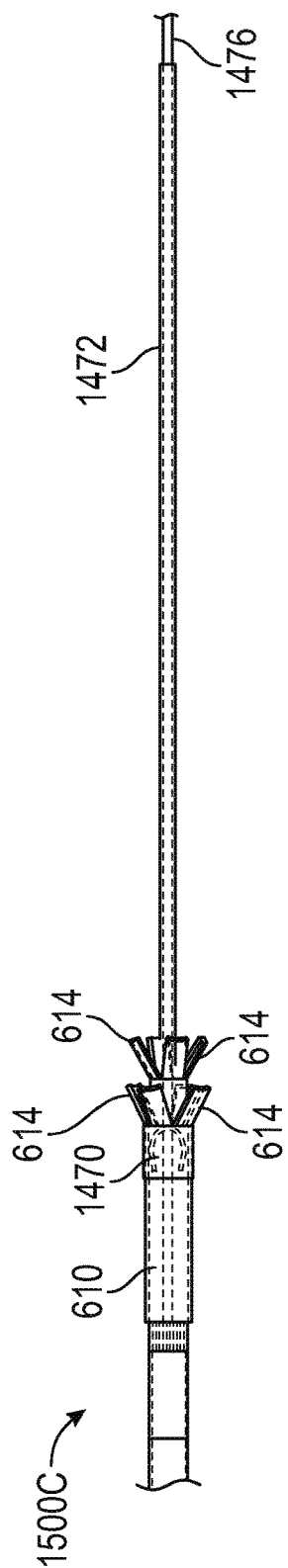
FIG. 14A
FIG. 14B
FIG. 14C

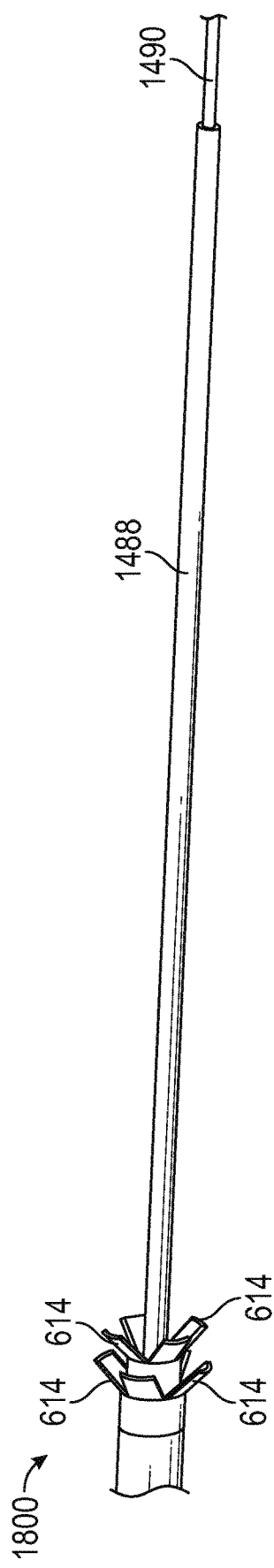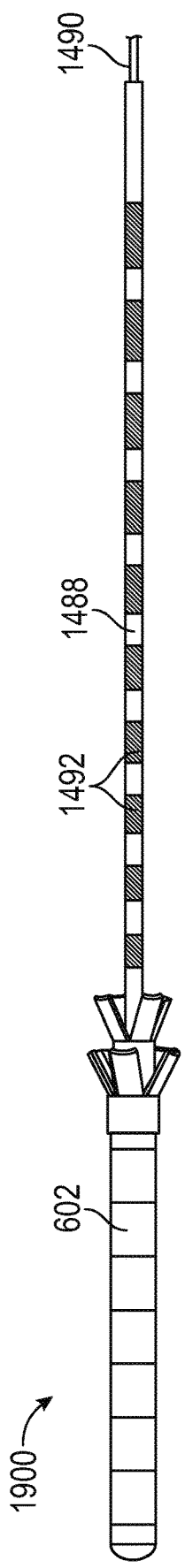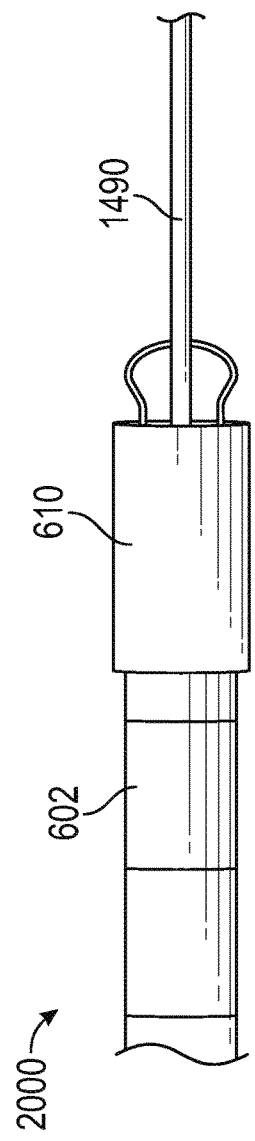

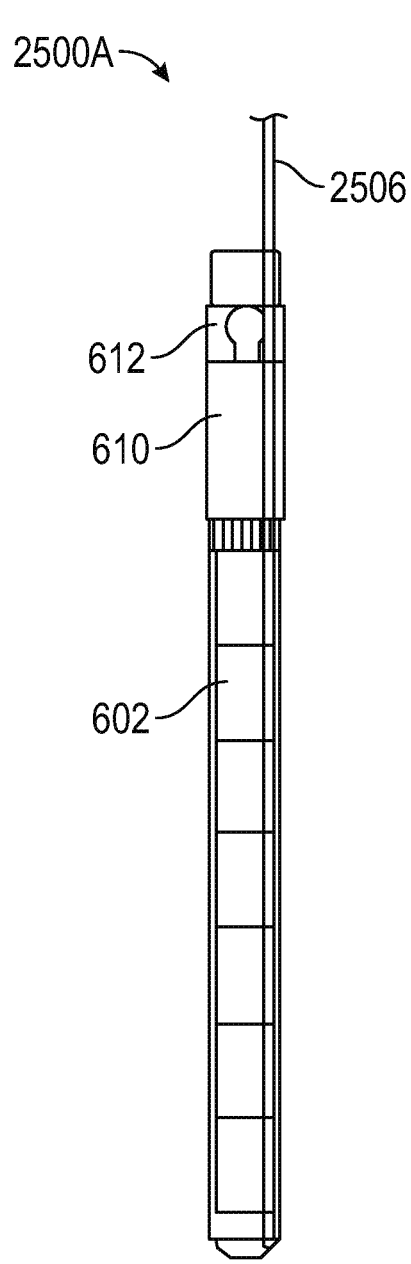
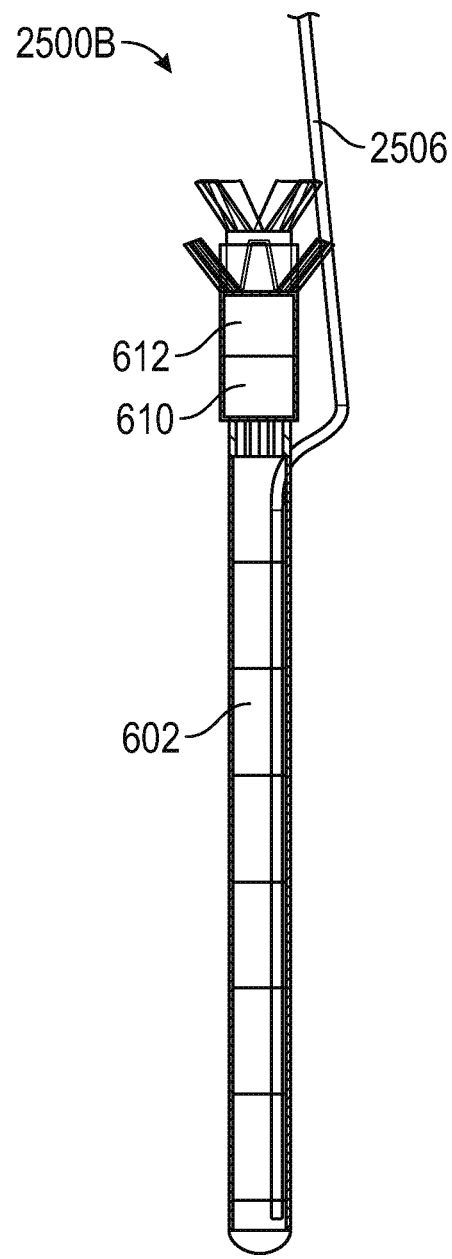
FIG. 25A
FIG. 25B

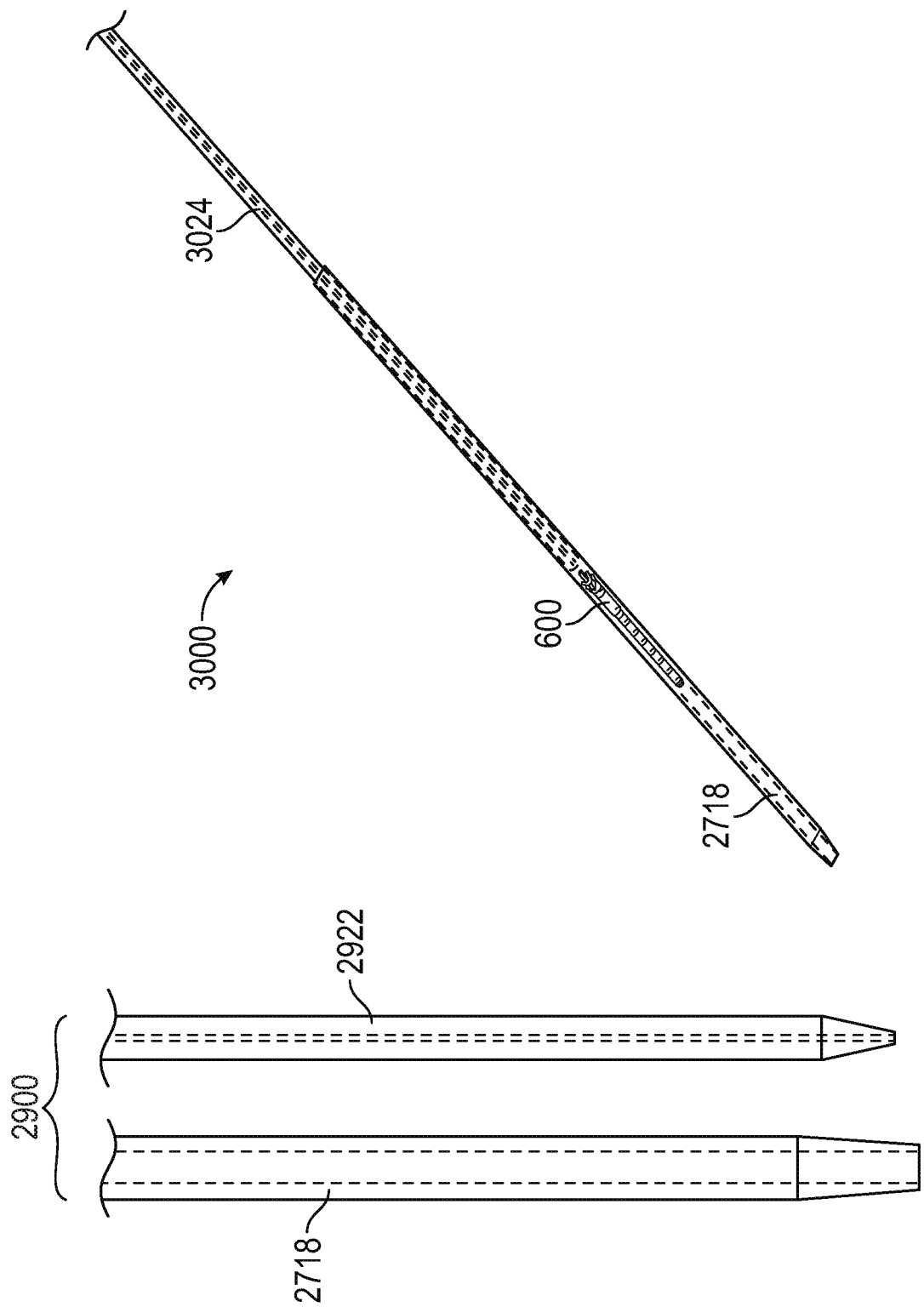

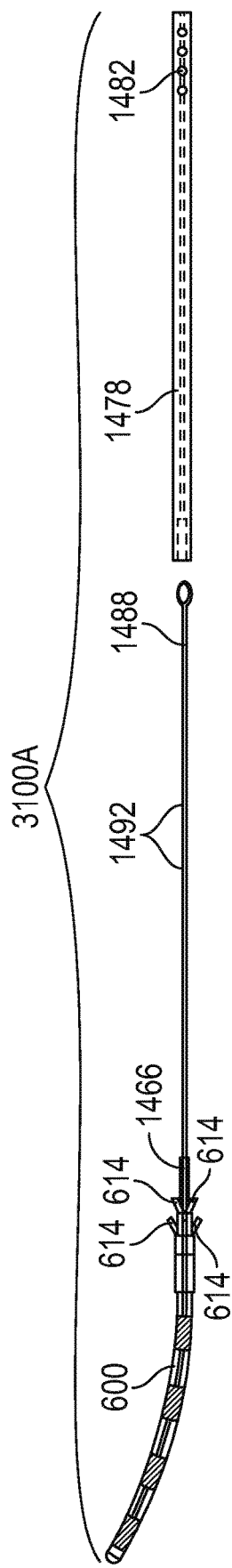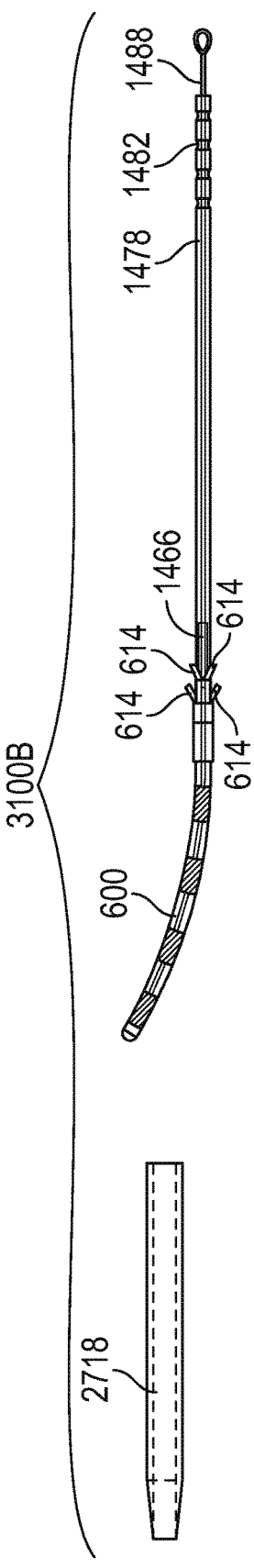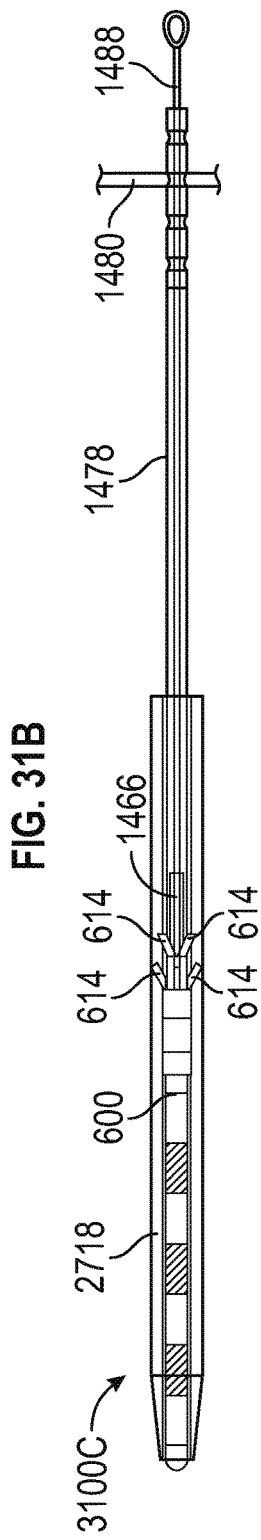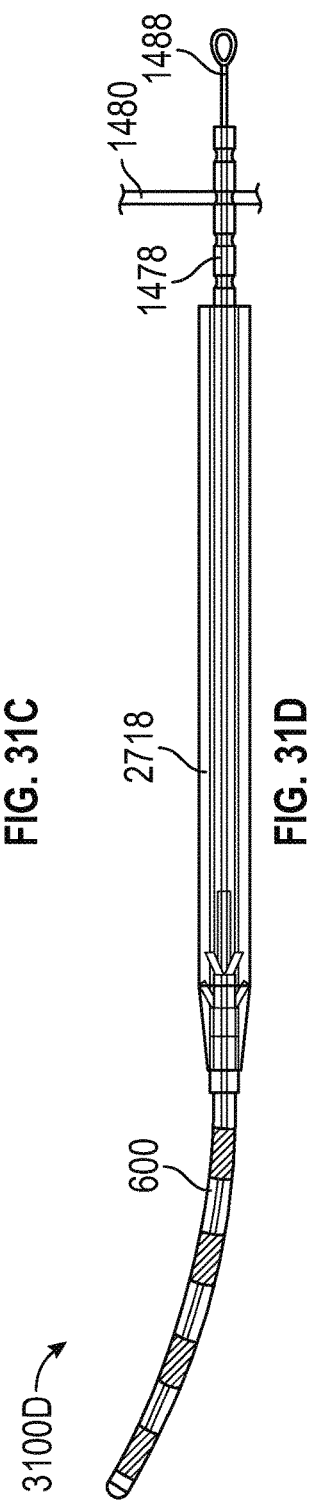
FIG. 31A
FIG. 31B
FIG. 31C
FIG. 31D

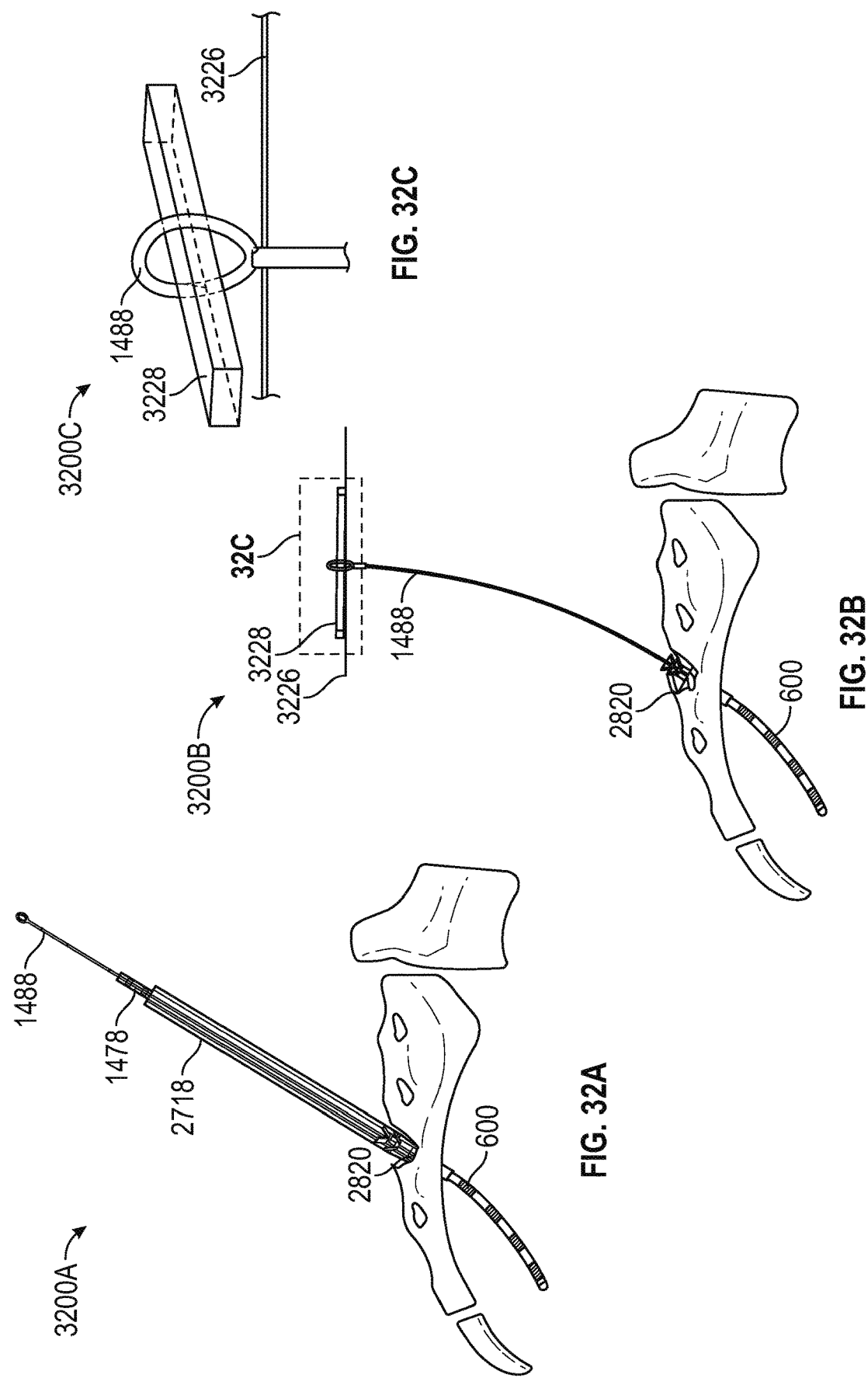

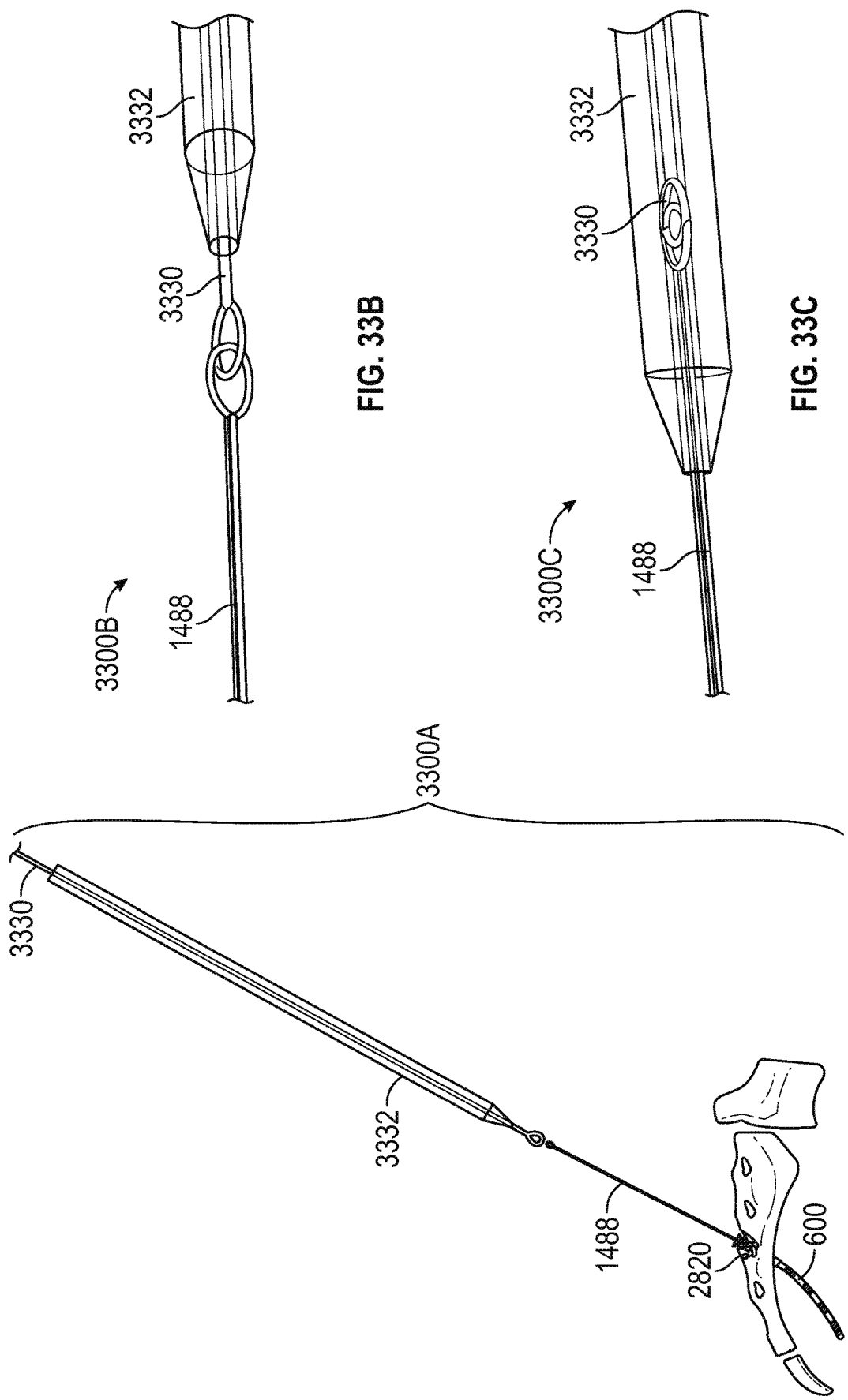

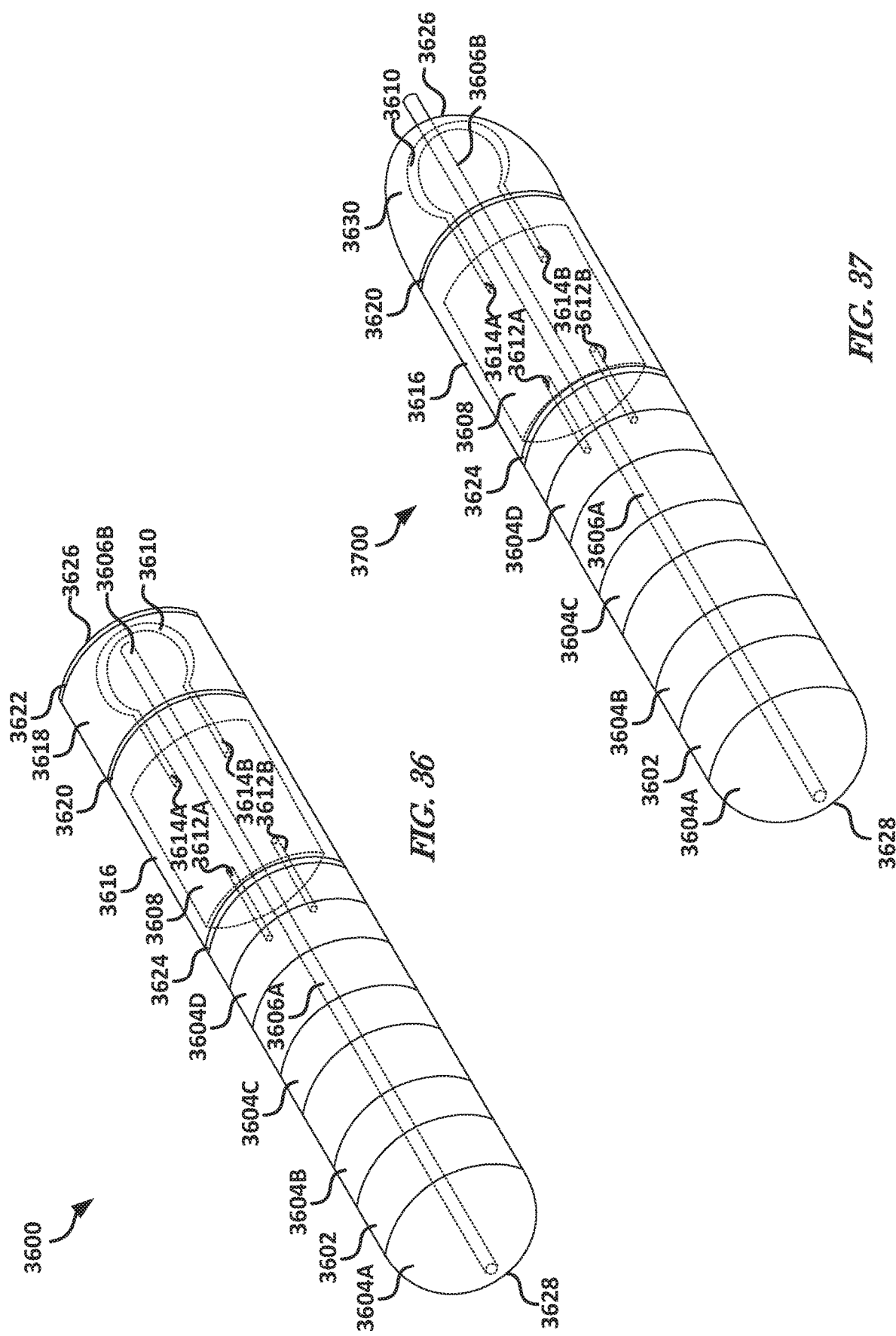

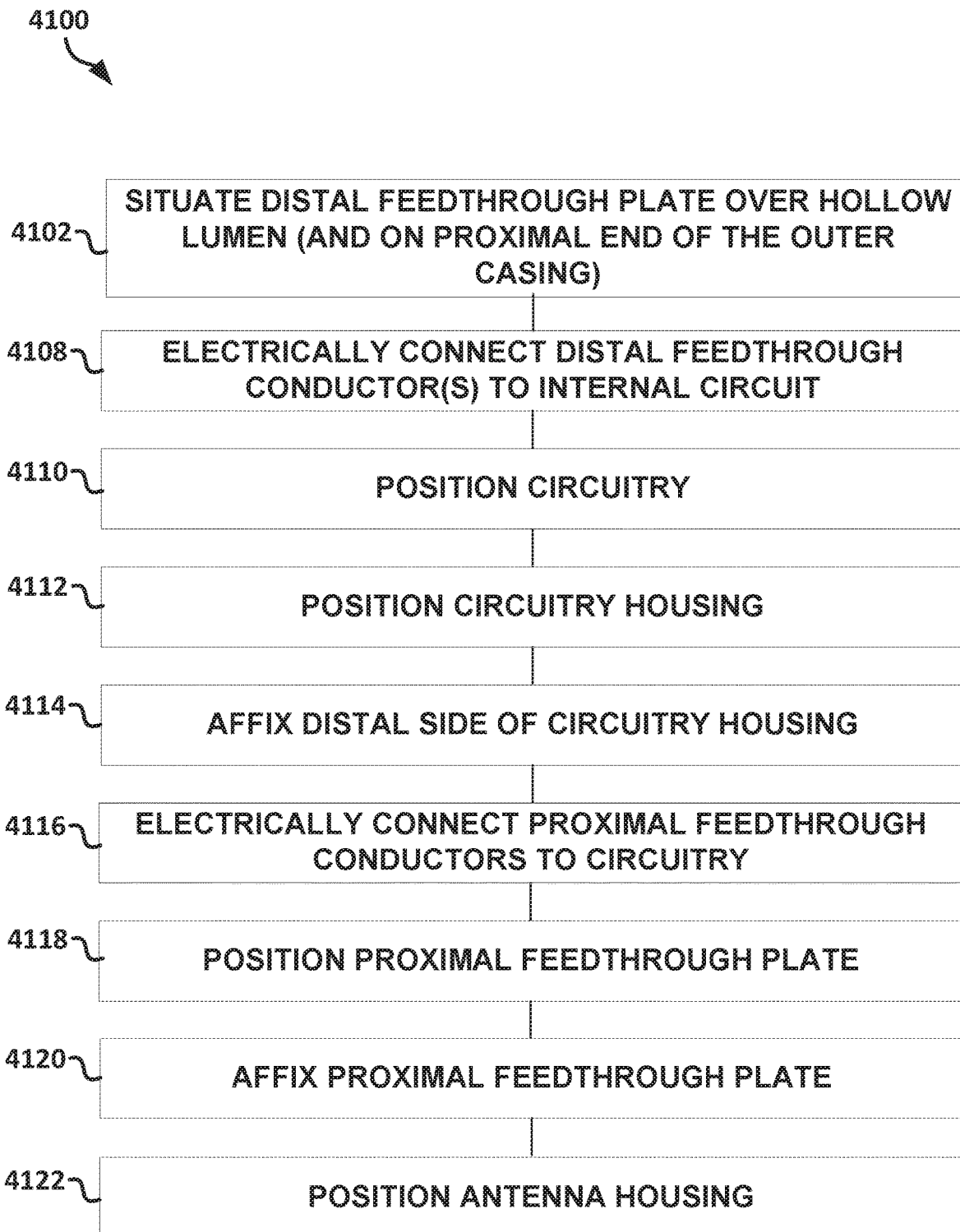
FIG. 41A(CONTINUED ON NEXT PAGE)

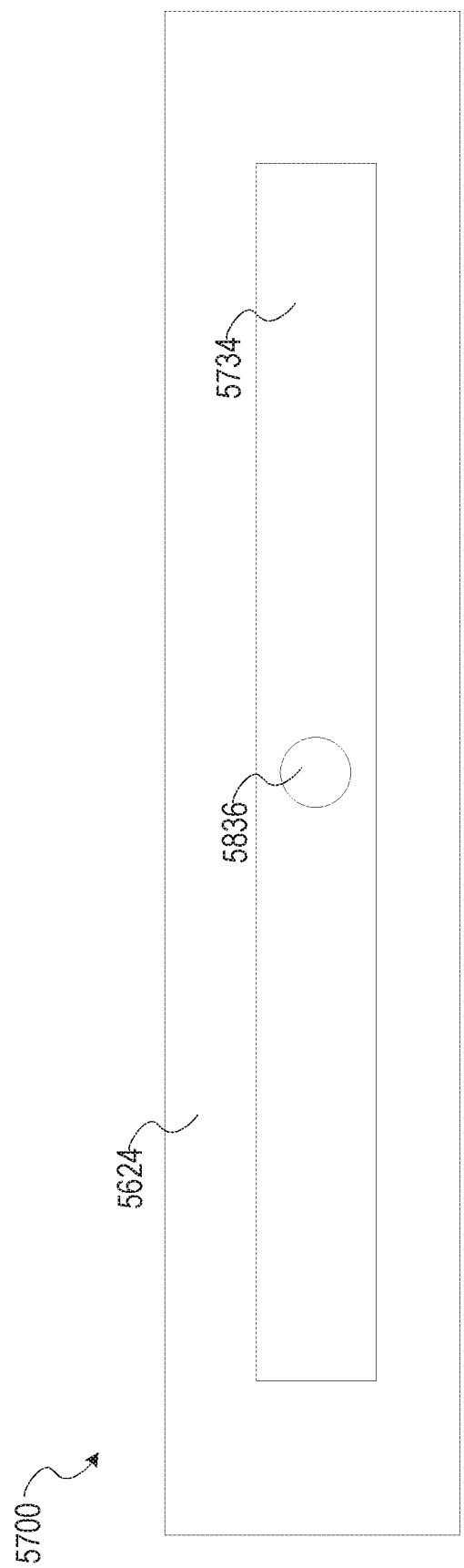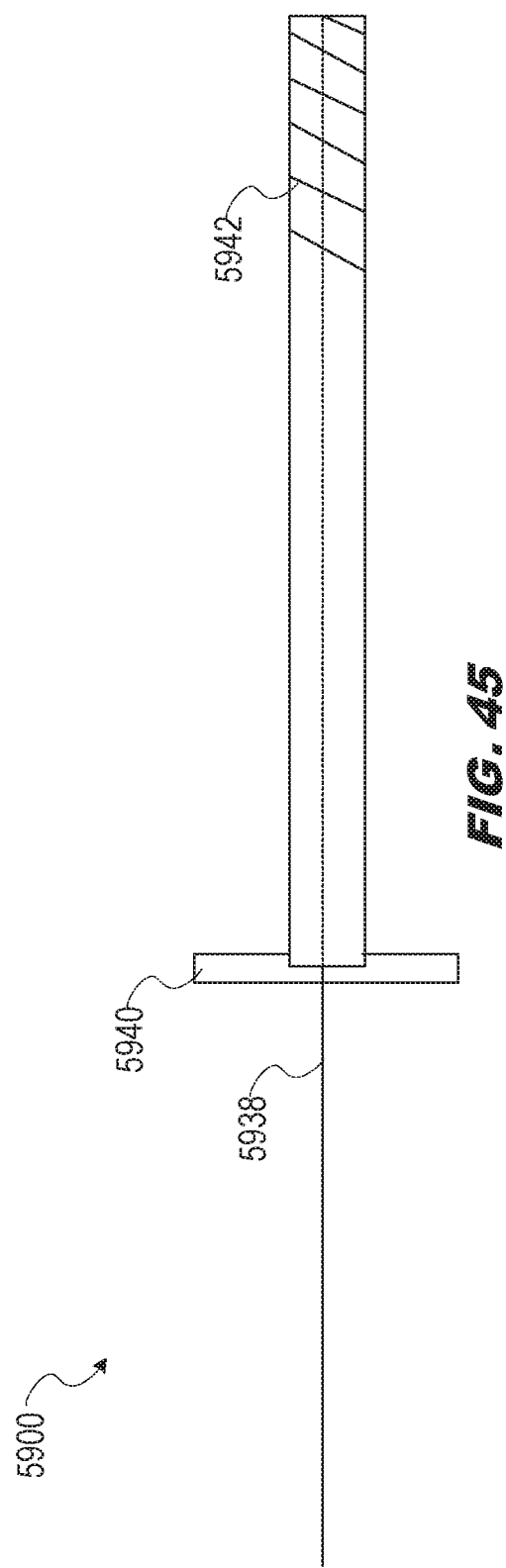

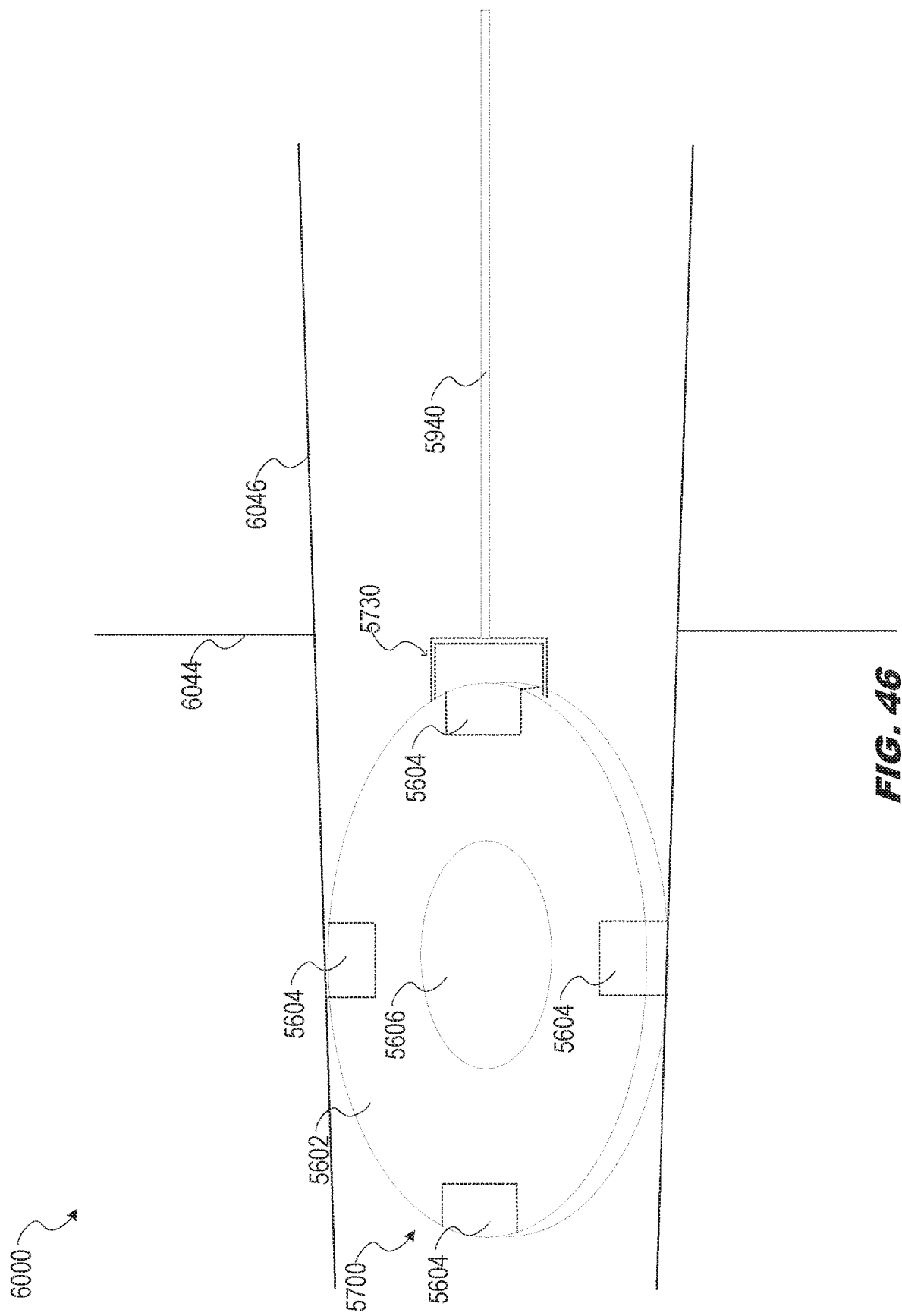

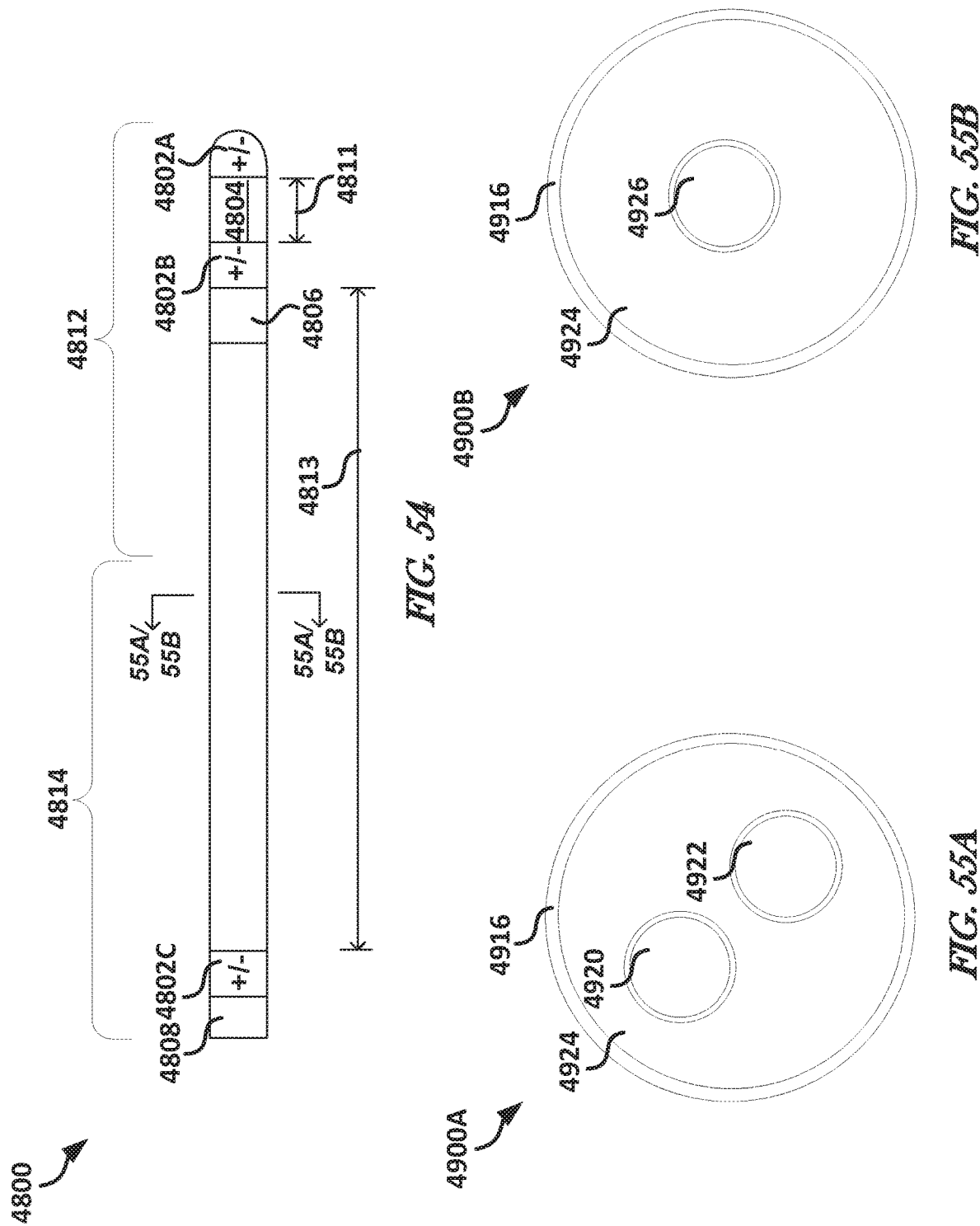

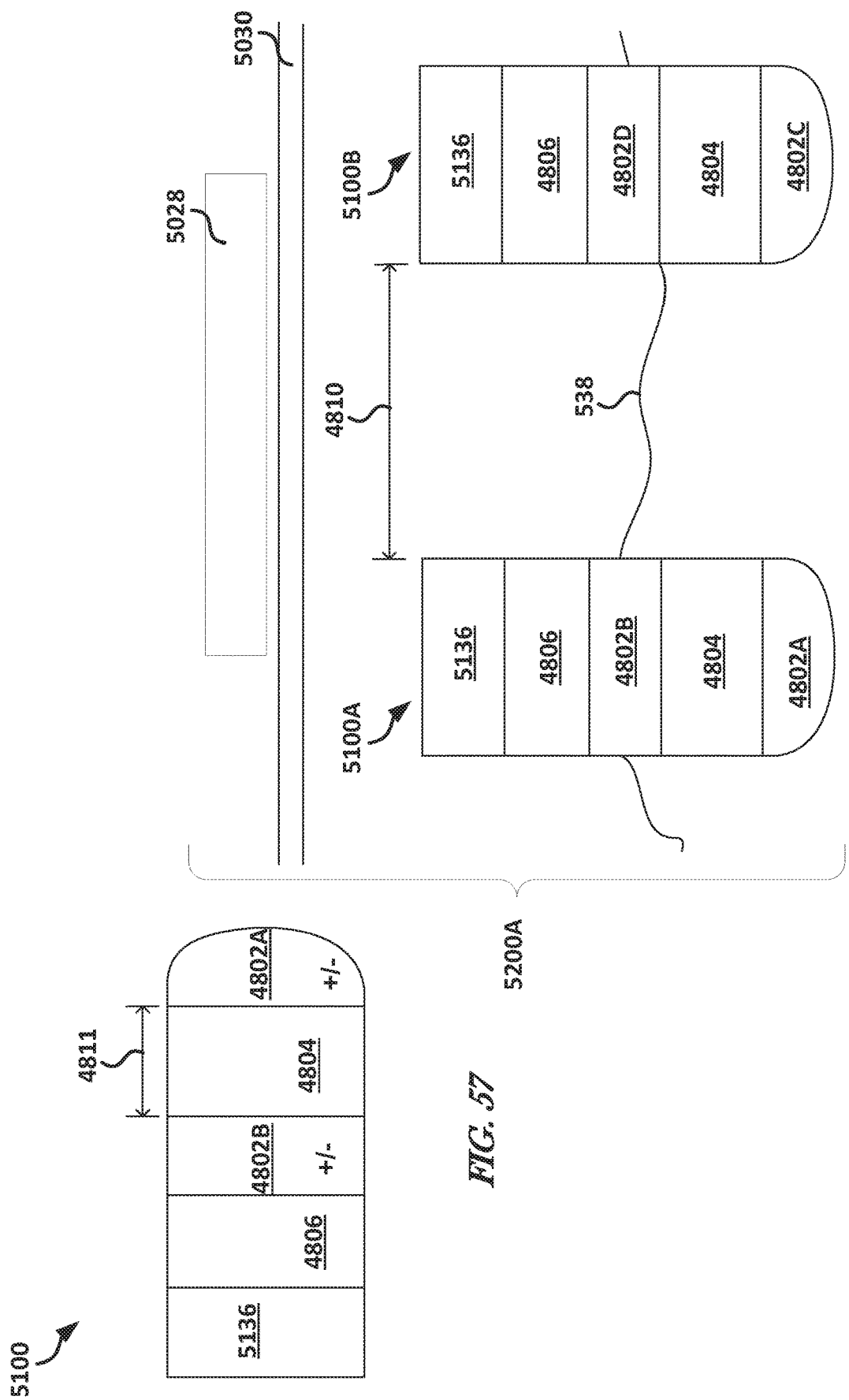

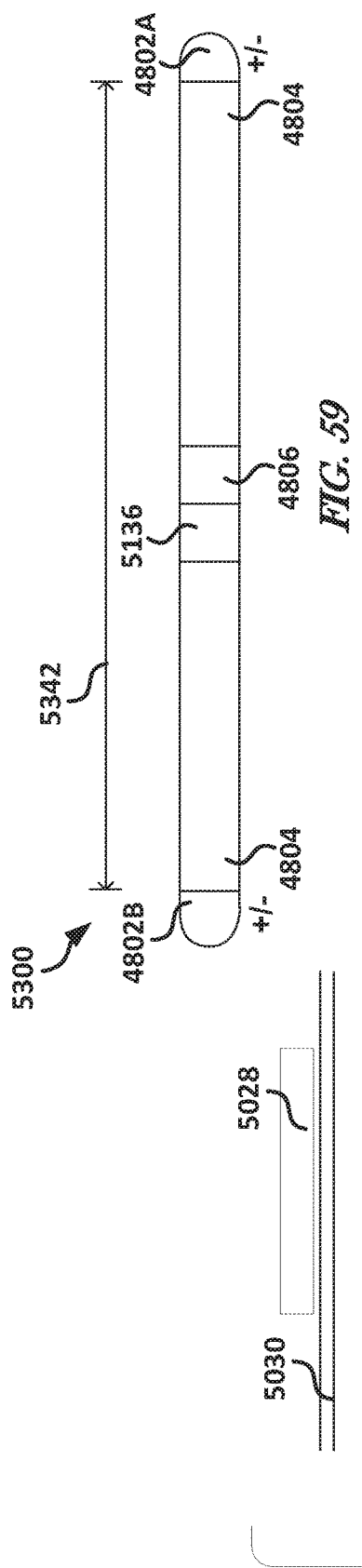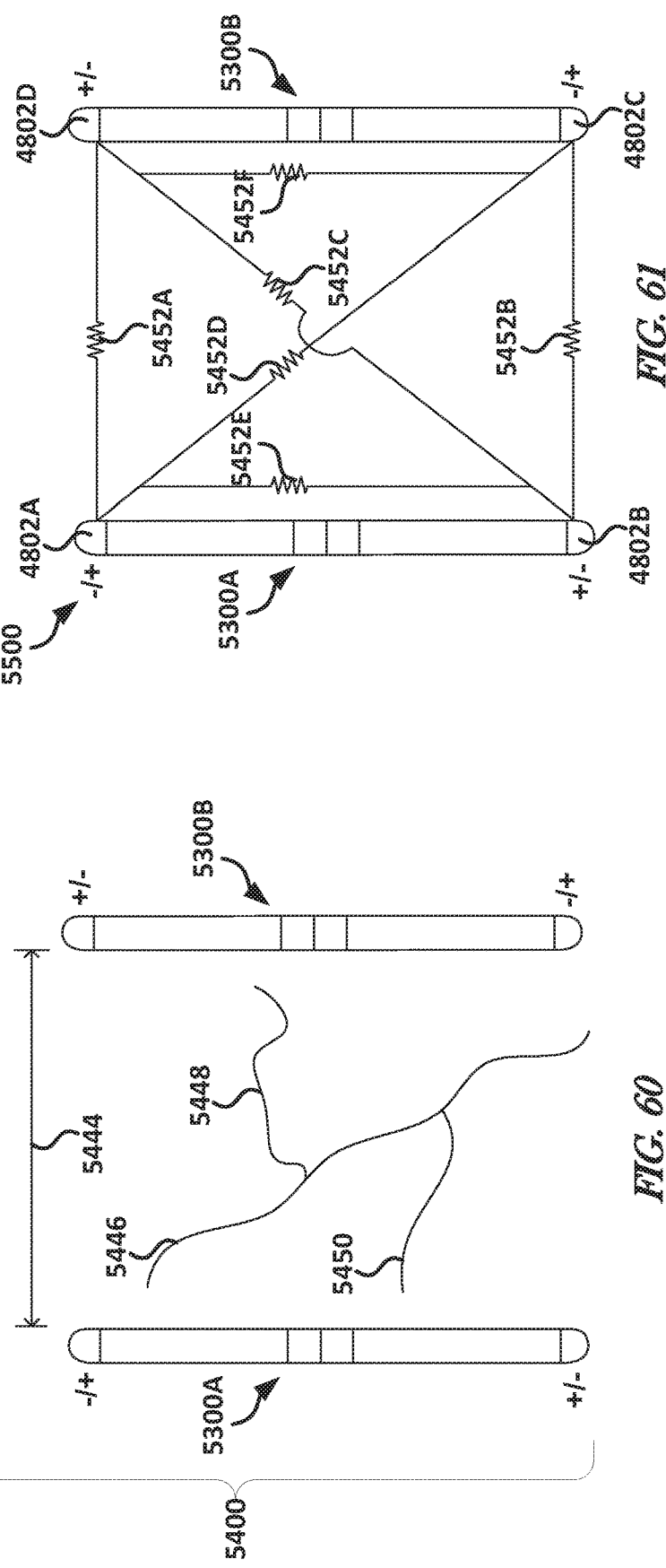

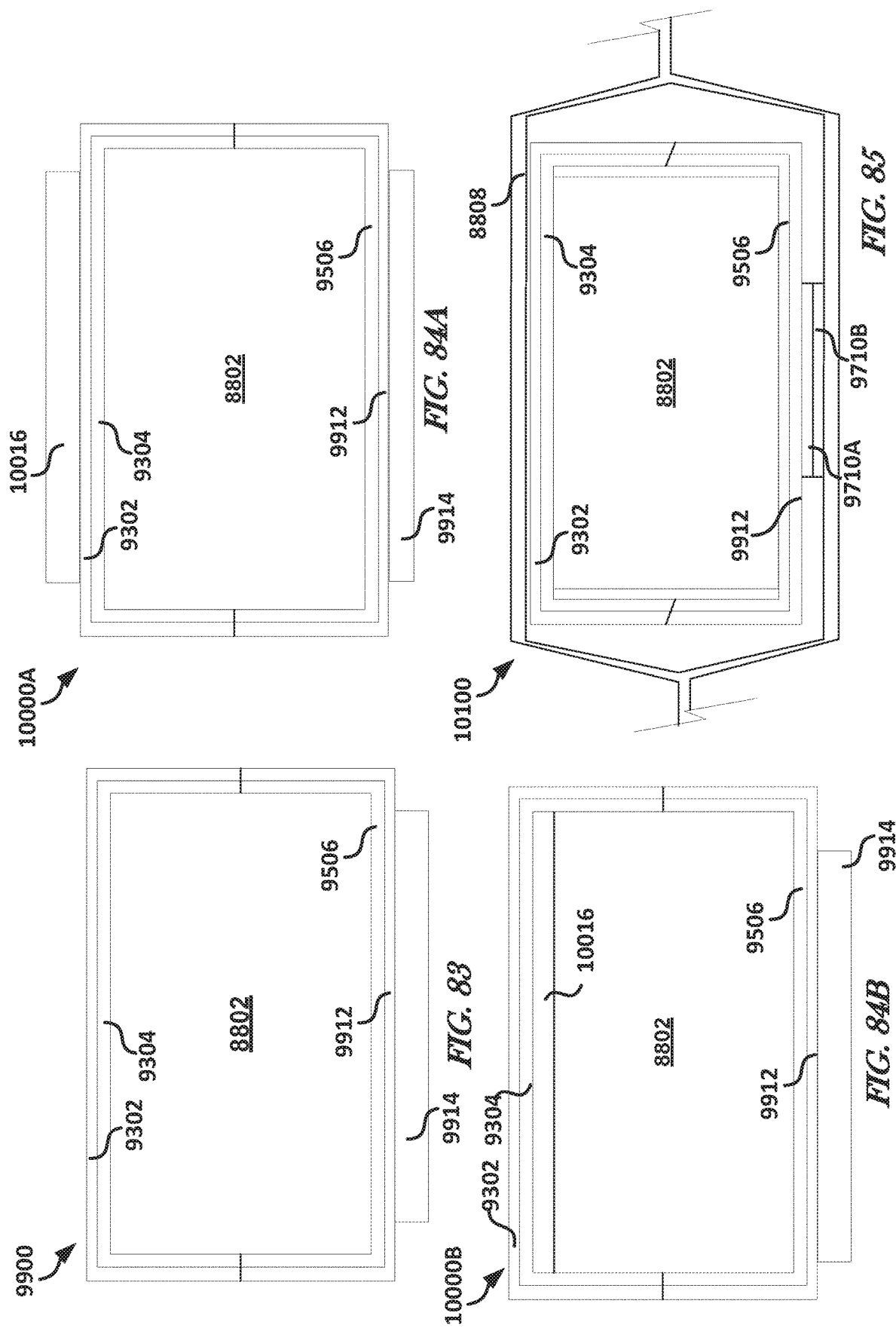

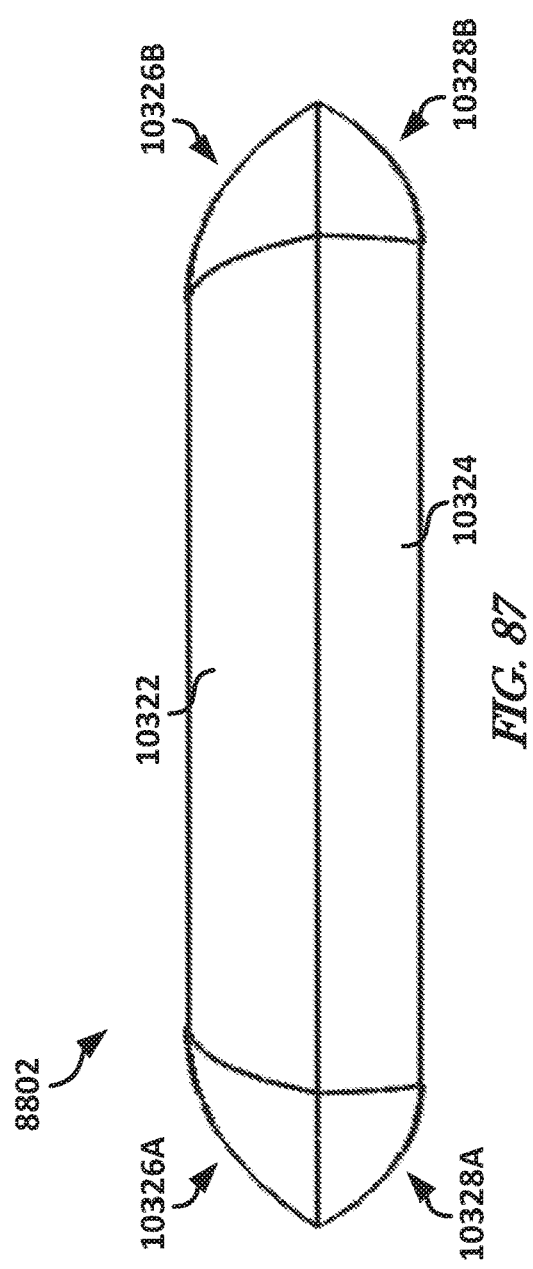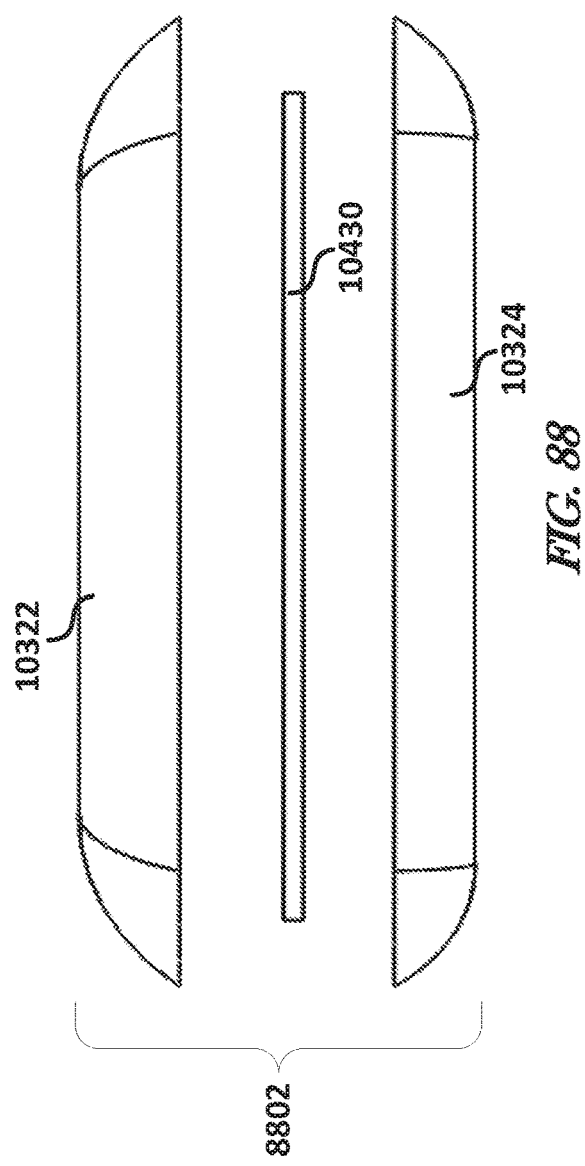

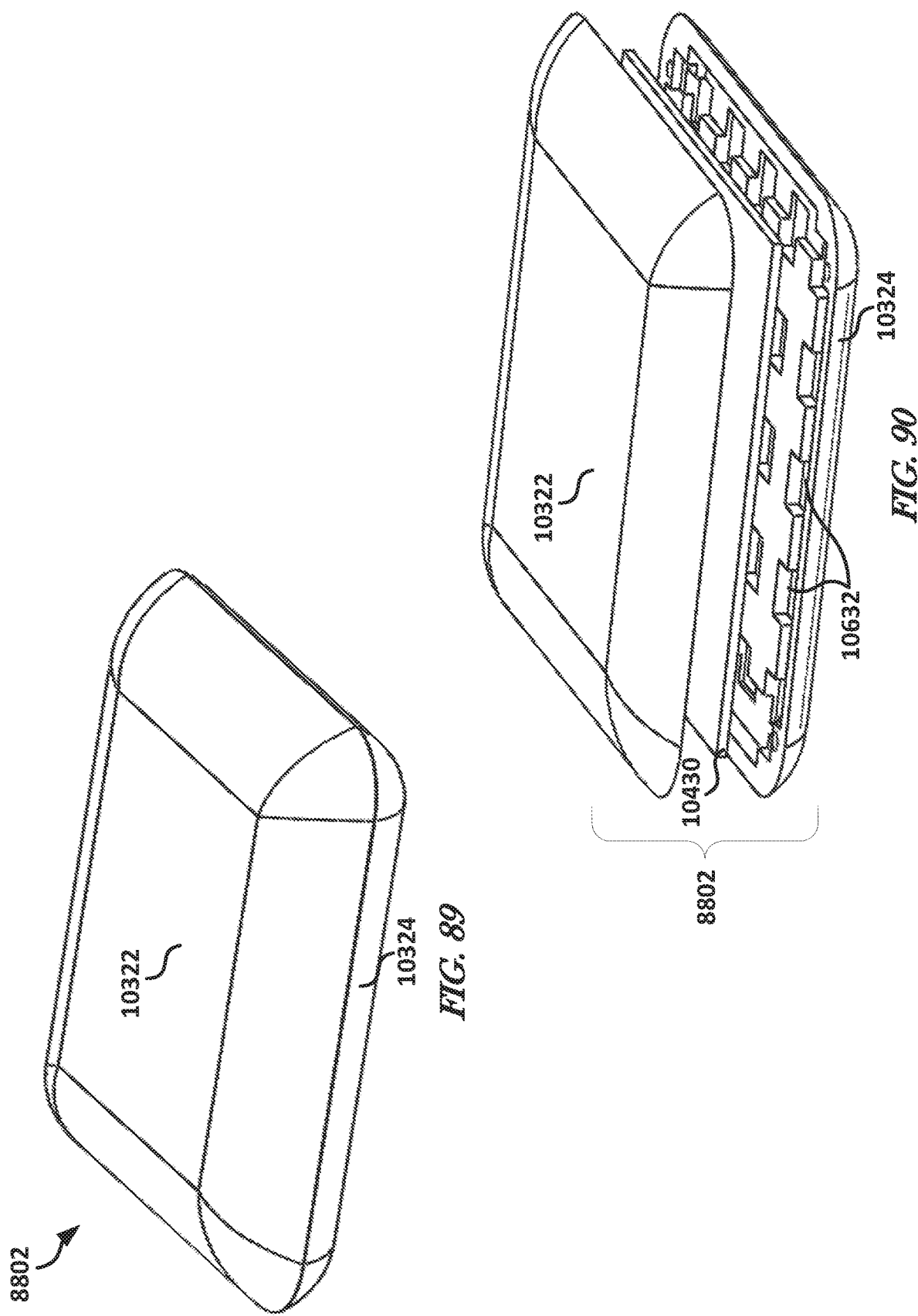

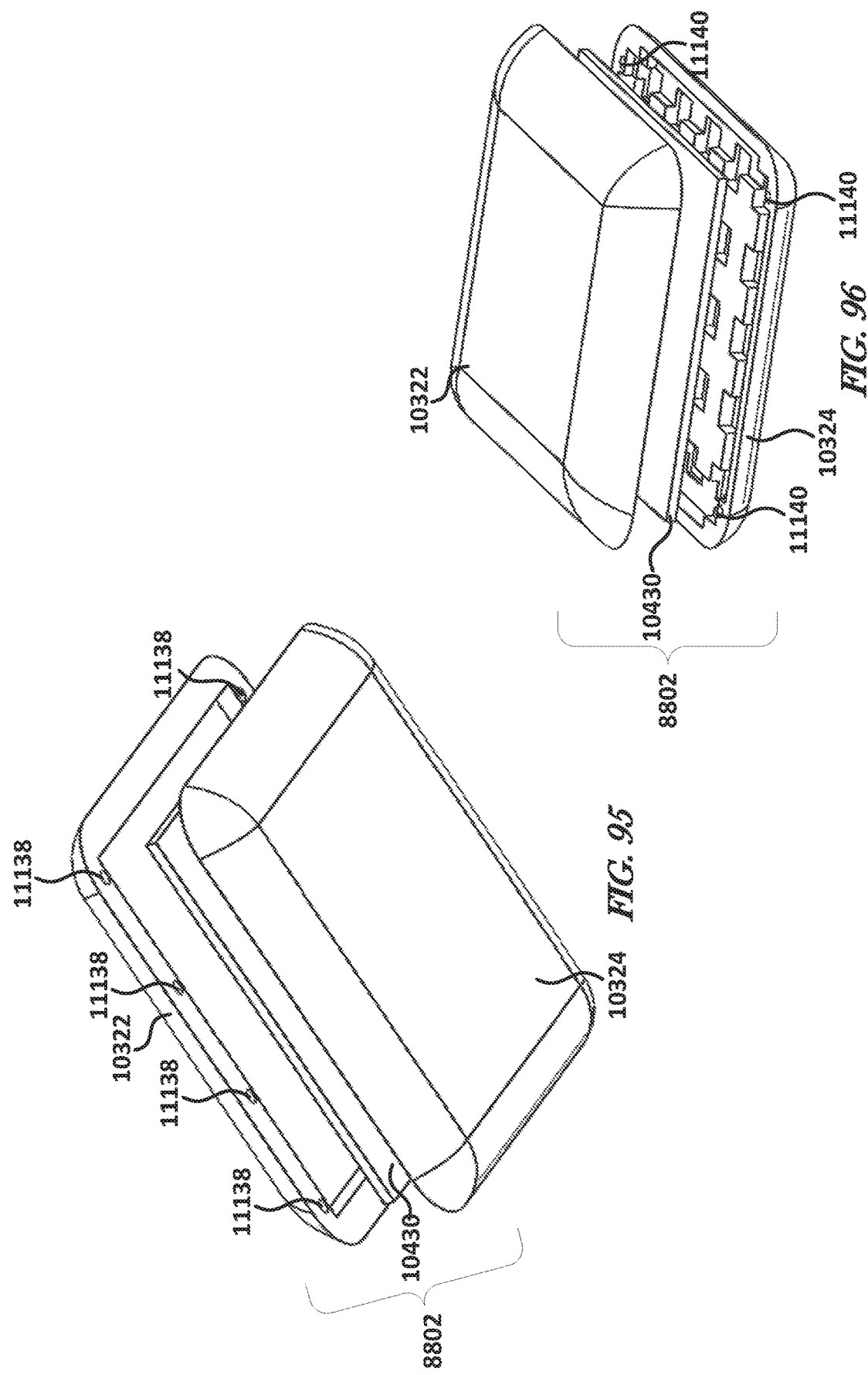

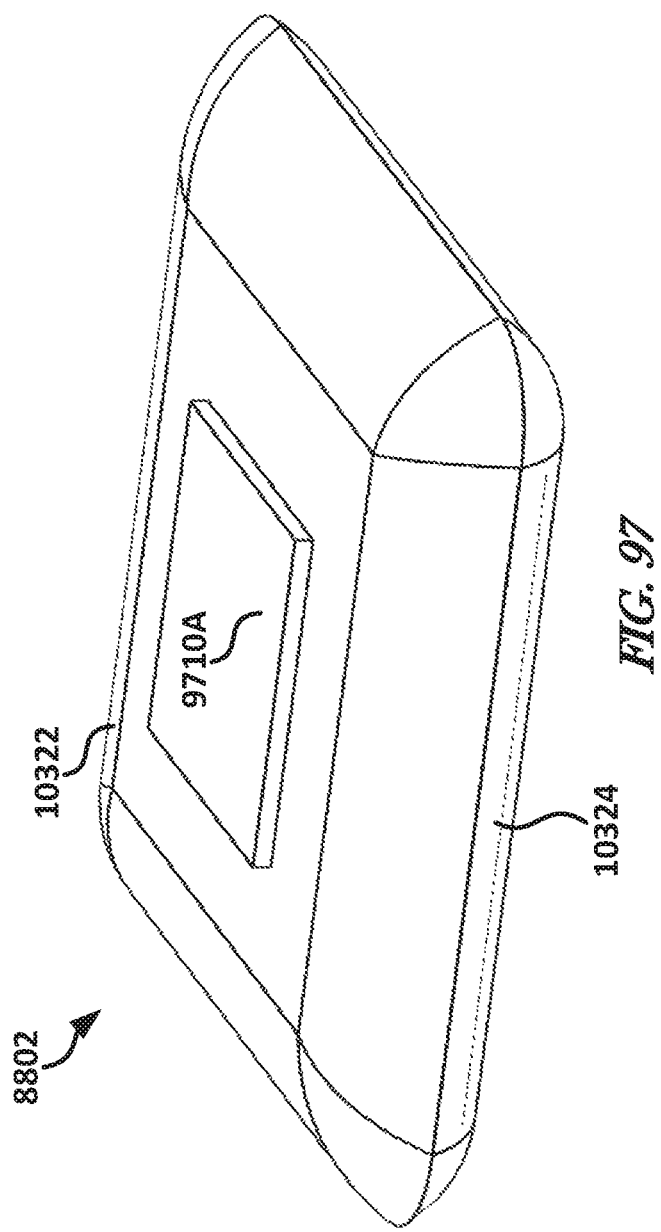

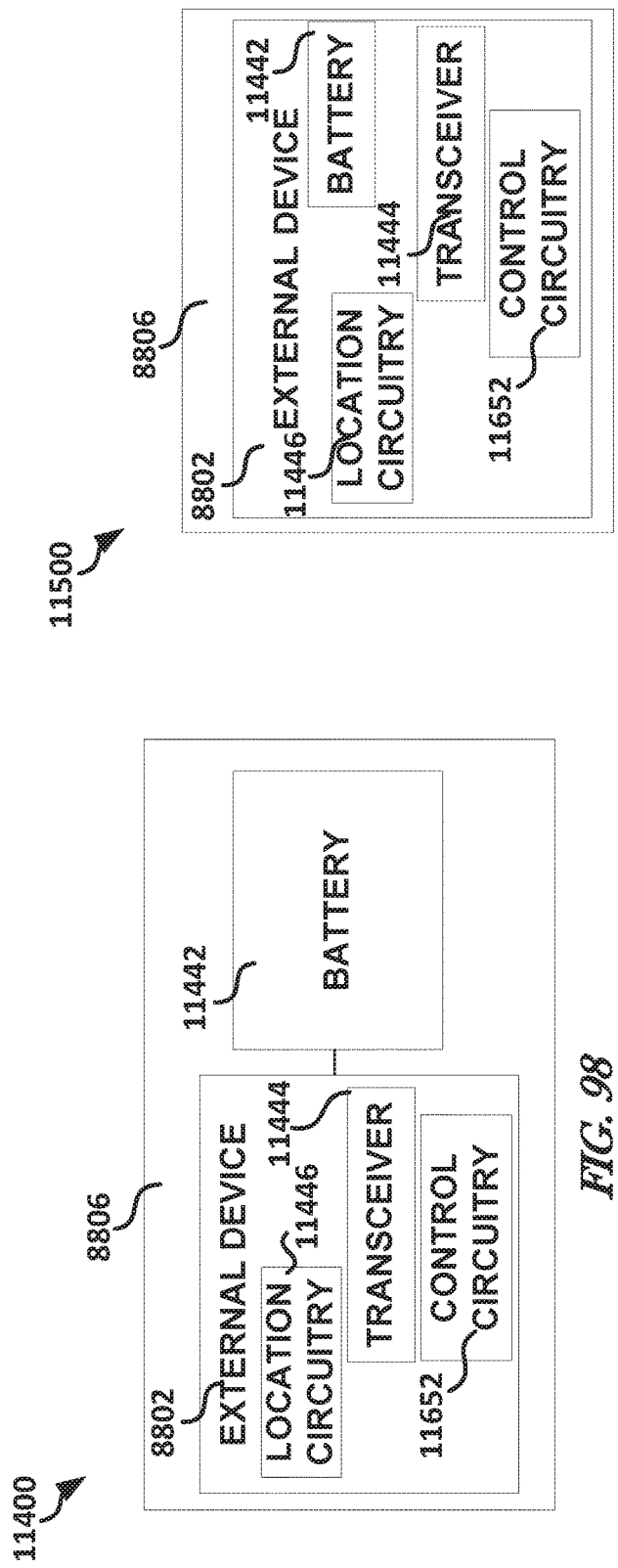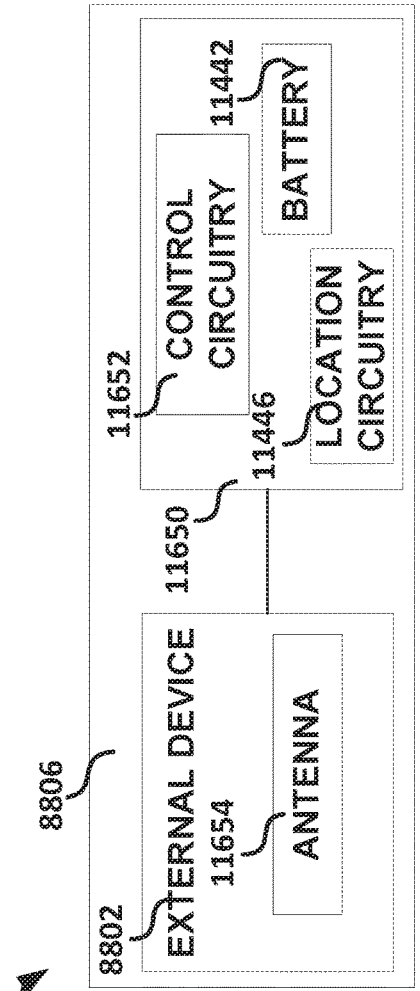

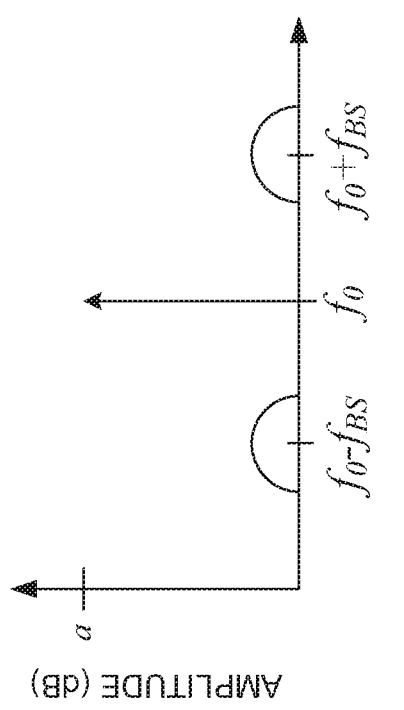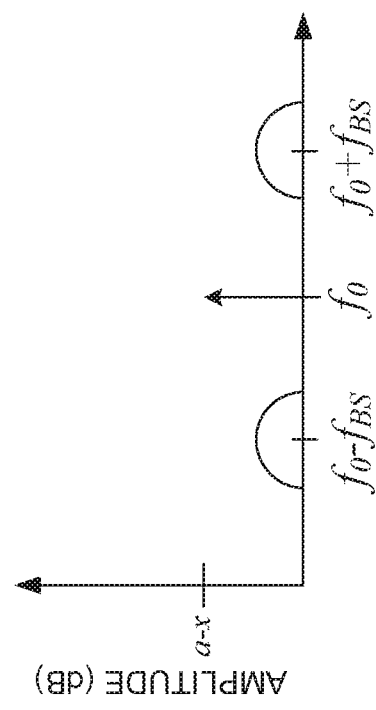

13100 ⇘

| Vector | Electrode | | | |
|---|---|---|---|---|
| | E0 | E1 | E2 | E3 |
| V0 | A | C | C | C |
| V1 | C | A | C | C |
| V2 | C | C | A | C |
| V3 | C | C | C | A |
| V4 | A | C | ///// | ///// |
| V5 | A | C | C | ///// |
| V6 | A | ///// | C | ///// |
| V7 | A | ///// | C | C |
| V8 | A | ///// | ///// | C |
| V9 | A | C | ///// | C |
| V10 | ///// | A | C | ///// |
| V11 | A | ///// | ///// | C |

FIG. 123

DEVICES, SYSTEMS, AND METHODS FOR STIMULATION THERAPY

RELATED APPLICATIONS

This application is a U.S. National Stage Application filed under 35 U.S.C. § 371 from International Application Serial No. PCT/US2016/057952, filed on Oct. 20, 2016, and published as WO 2017/070372 on Apr. 27, 2017, which claims priority benefit to the following U.S. provisional applications: U.S. Provisional Application No. 62/244,495 filed Oct. 21, 2015 and titled "COMPACT INTEGRATION OF ELECTRONIC CONTROL HARDWARE WITH ELECTROMAGNETIC TRANSMITTING ELEMENT"; U.S. Provisional Application No. 62/264,239 filed Dec. 7, 2015 and titled "DISCREET EXTERNAL DEVICE COUPLING TO IMPLANTED DEVICE"; U.S. Provisional Application No. 62/291,379 filed Feb. 4, 2016 and titled "IMPLANTABLE STIMULATION DEVICES AND STEERING AND AFFIXING MECHANISMS THEREFORE"; U.S. Provisional Application No. 62/350,674 filed Jun. 15, 2016 and titled "WIRELESS NEURAL THERAPY DELIVERY SYSTEMS AND METHODS USING A SERIES OF ELECTROSTIMULATION SIGNALS"; U.S. Provisional Application No. 62/350,676 filed Jun. 15, 2016 and titled "IMPLANTABLE STIMULATION DEVICES ANI) STEERING MECHANISMS THEREFORE"; U.S. Provisional Application No. 62/350,681 filed Jun. 15, 2016 and titled "IMPLANTABLE STIMULATION DEVICES, SYSTEMS, AND METHODS"; U.S. Provisional Application No. 62/350,684 filed Jun. 15, 2016 and titled "DUAL-FREQUENCY ELECTROSTIMULATION FOR NEURAL THERAPY"; U.S. Provisional Application No. 62/367,995 filed Jul. 28, 2016 and titled "IMPLANTABLE STIMULATION DEVICES INCLUDING HOLLOW LUMEN"; U.S. Provisional Application No. 62/368,005 filed Jul. 28, 2016 and titled "SURFACE ACOUSTIC' WAVE BASED COMMUNICATION DEVICE"; U.S. Provisional Application No. 62/373,569 filed Aug. 11, 2016 and titled "ACTIVE POWER MANAGEMENT TECHNIQUES FOR \\TIRELESS IMPLANTABLE DEVICES", U.S. Provisional Application No. 62/396,478 filed Sep. 19, 2016 and titled "SYSTEMS AND METHODS FOR EMBEDDING COMMUNICATION SIGNALS WITH ELECTROSTIMULATION THERAPY"; and U.S. Provisional Application No. 62/397,620 filed Sep. 21, 2016 and titled "BACKSCATTER COMMUNICATION TECHNIQUES." The entire content of each of the above identified applications is hereby incorporated by reference herein.

TECHNICAL FIELD

One or more embodiments discussed herein regard devices, systems, and methods for providing signals (e.g., wireless midfield powering signals) to an implantable device (e.g., stimulation device) using an external device (e.g., external midfield coupler or midfield power source). One or more embodiments discussed herein regard devices, systems, and methods for providing therapy (e.g., stimulation or other modulation) or diagnostics from an implantable device. One or more embodiments discussed herein regard configurations for the implantable device and the external device. One or more embodiments discussed herein regard communicating data from the implantable device to the external device. One or more embodiments discussed herein regard devices, systems, and methods for positioning the implantable device at or near a specific location and/or shaping the implantable device.

TECHNICAL BACKGROUND

Most of the known wireless powering methods for implantable electronics are based on the nearfield coupling method, and these and other suggested methods suffer from a number of disadvantages. The power harvesting structure in the implanted device is typically large (typically on the order of a centimeter or larger). The coils external to the body in near-field coupling methods are also typically bulky and inflexible. This presents difficulties with regard to the incorporation of the external device into daily life. The intrinsic exponential decay of the near field limits miniaturization of the implanted device beyond superficial depths (greater than 1 cm). On the other hand, the radiative nature of the far field severely limits the energy transfer efficiency.

SUMMARY

Although considerable progress has been made in the realm of medical device therapy, a need exists for therapy devices that provide stimulation or other therapy to targeted locations within a body. A need further exists for efficient, wireless power and data communication with an implanted therapy delivery device and/or an implanted diagnostic (e.g., sensor) device.

In accordance with several embodiments, a system for providing therapy to a subject comprises or consists essentially of an external midfield powering source positioned outside a body of the subject (e.g., outside the skin) and an internal therapy delivery device positioned within the body of the subject (e.g., beneath the skin). The external source comprises at least one sub-wavelength structure (e.g., one, two, three, four or more than four) configured to provide radiofrequency (RF) signals to a particular location in tissue of the subject (e.g., at a location beneath the skin of the subject where the internal therapy device is permanently or temporarily implanted). The RF signals are selected to manipulate an evanescent field (e.g., an oscillating electric and/or magnetic field that does not propagate as an electromagnetic wave) outside of the tissue (e.g., outside a surface of the skin) to thereby generate a propagating field inside the tissue beneath the surface of the skin.

The internal therapy delivery device comprises an at least partially implantable device configured to receive the RF signals from the external source. Partially implantable may mean that the device is not entirely implanted under the skin of the patient or that the device is temporarily implanted (e.g., for a trialing period or inserted and removed during a single procedure), as opposed to being permanently implanted for a long duration of time (e.g., several months or years). The implantable device comprises a distal portion and a proximal portion. The implantable device may comprise circuitry (e.g., receiver circuitry) in a first housing and may comprise an antenna in a separate second housing in the proximal portion. The first and/or second housing may also be positioned in the distal portion or any other portion of the implantable device. The antenna may be electrically coupled to the circuitry in the first housing. In some embodiments, the implantable device comprises a flexible, biocompatible, elongated member including the distal portion and the proximal portion and a plurality of energy delivery members (e.g., electrodes, emission elements, transducers) situated along the distal portion of the elongated member. The circuitry may be hermetically sealed or encased within the first housing and configured to receive electrical energy from the external source and to provide electrical energy to the plurality of energy delivery members (e.g., electrodes). The circuitry may comprise any receiver capable of receiving electrical energy from the external source (e.g., an ultra-high frequency receiver, very-high frequency receiver, a microwave receiver, or other receiver depending on the frequencies desired and/or required).

In some embodiments, the second housing is attached to the first housing at a proximal end of the first housing that is opposite to an end of the first housing along a length of the elongated member. In some embodiments, a hollow tubular member extends through the elongated member at least from a proximal end of the elongated member to a distal portion of the elongated member. The second housing may comprise a dielectric material having a dielectric constant between that of human tissue and air.

In some embodiments, the antenna is a primary antenna and the system further comprises a secondary antenna in the second housing, the secondary antenna shaped and positioned to provide a near field coupling with the primary antenna. In some embodiments, the implantable device further comprises a feedthrough plate between and connected to the separate first and second housings and an electrical conductor in a feedthrough of the feedthrough plate, the electrical conductor being electrically connected to the circuitry and the antenna.

In some embodiments, the circuitry in the first housing includes a surface acoustic wave (SAW) device. The SAW device may be configured to receive a portion of an RF signal received at the antenna on a first signal path, to convert the received portion to a mechanical wave to buffer the RF signal, and to provide the buffered RF signal on a second signal path to the antenna. The circuitry in the first housing may further comprise a modulator coupled between the antenna and the SAW device on the second signal path. The modulator may be adapted to adjust a baseband signal to embed a data signal with the baseband signal.

In various embodiments, the external source comprises a top cover, a bottom cover, and an antenna circuit situated between the top cover and the bottom cover. The top cover and the bottom cover may include a footprint that is rectangular with rounded corners, with the edges of the top cover and the bottom cover being rounded. The edges of the bottom cover may be rounded to include a smaller radius of curvature than edges of the top cover. In some embodiments, the footprint of the top cover and bottom cover is square, circular, triangular or any other shape.

The external source may comprise a Faraday cage on a top surface of a first layer of a circuit board (e.g., printed circuit board), circuitry housed in the Faraday cage and located on the top surface, a ground plane situated in a second layer of the circuit board, and resonating slots in a third layer of the circuit board. The resonating slots may be electrically connected to the circuitry in the Faraday cage. In some embodiments, the Faraday cage, ground plane, and resonating slots form an antenna. The ground plane may include ground slots formed therein and a footprint of the Faraday cage may be arranged so as not to overlap with the ground slots in the ground plane.

In some embodiments, the internal therapy device (e.g., at least partially implantable device) comprises one or more first electrodes (e.g., a first group or array of electrodes) coupled to the circuitry and situated along the distal portion of the implantable device and one or more second electrodes (e.g., a second group or array of electrodes) coupled to the circuitry and situated along the proximal portion of the implantable device. A distance between a most proximal one of the first electrodes and a most distal one of the second electrodes may be sufficiently distant so as to generate a far field stimulation signal therebetween. The one or more first electrodes may comprise at least two electrodes and the circuitry may comprise stimulation circuitry to configure an electrode of the first electrodes as an anode, another of the first electrodes as a cathode, and an electrode of the second electrodes as one of a cathode and an anode.

In some embodiments, the internal therapy device comprises at least three electrodes configured to deliver therapy (e.g., stimulation, denervation or other type of modulation) to tissue (e.g., one or more sacral nerves, tibial nerves or other neural, muscle or other normal or abnormal body tissue) or to support diagnostic evaluation (e.g., sensing) of the tissue and/or of parameters of the therapy being provided or delivered. The circuitry of the internal therapy device may comprise a therapy delivery circuit configured to provide a therapy signal via one or more of the electrodes. The therapy signal may comprise a series of at least two electrostimulation pulses provided using respective vectors corresponding to different combinations of the electrodes. In some embodiments, the therapy delivery circuit is configured to provide the therapy signal with a specified delay interval between each pulse. The series of pulses may be repeated at least twice (e.g., twice, three times, four times, five times, or more).

The circuitry of the internal therapy device may comprise a therapy delivery circuit configured to provide a phase-amplitude coupled therapy signal that includes a first signal component provided using a first neural electrostimulation vector and a second signal component provided using a different second neural electrostimulation vector, with the second signal component being provided substantially concurrently with the first signal component. In one embodiment, the at least partially implantable device comprises at least four electrodes that are axially spaced apart along a lead portion of the device, with two of the four electrodes being configured for use as the first neural electrostimulation vector and the other two of the four electrodes being configured for use as the second neural electrostimulation vector. In some embodiments, the therapy delivery circuit is configured to adjust an amplitude or frequency characteristic of at least one of the first and second signal components of the phase-amplitude coupled therapy signal to overcome a patient's neural pathophysiology or to otherwise improve neurologic function (e.g., to overcome symptoms, such as related to one or more of a body movement disorder, Parkinson's disease, dementia, Alzheimer's disease, Creutzfeldt-Jakob disease, Huntington's disease, depression (e.g., by stimulating a left cervical vagus nerve or trigeminal nerve), dystonia, or epilepsy, among others). Improved neurologic function can include improved cognitive and/or motor function.

In some embodiments, the external source further comprises an RF signal generator system configured to provide multiple different sets of RF signals to the sub-wavelength structures, with each set of RF signals comprising two or more separate signals, and a transmitter circuit comprising excitation ports coupled to respective ones of the sub-wavelength structures. The transmitter circuit may be coupled to the RF signal generator system and the transmitter circuit may be configured to transmit the multiple different sets of RF signals at respective different times to the excitation ports. The excitation ports receive respective ones of the separate signals from each set of RF signals. Each of the transmitted sets of RF signals by the transmitter circuit includes a non-negligible magnetic field (H-field) component that is substantially parallel to an external surface of the tissue and each set of transmitted RF signals is selected to differently manipulate an evanescent field at or near the external surface of the tissue to transmit a power or data signal to respective different target devices implanted in the tissue.

The circuitry in the implantable device may comprise a therapy delivery circuit configured to provide signal pulses to electrostimulation electrodes or other energy delivery members using a portion of a received midfield power signal from the external source. The signal pulses may comprise therapy pulses (e.g., electrostimulation therapy pulses) and/or data pulses. In some embodiments, the therapy delivery circuit is configured to interleave data pulses between successive therapy pulses or to embed multiple data pulses in a therapy pulse.

The external source and the implantable device may be configured to communicate at least in part using backscatter signals, wherein at least one of the sub-wavelength structures of the external source is configured to receive a first backscatter signal from the implantable device, and wherein the circuitry in the implantable device is configured to receive a midfield signal from the external source and provide the first backscatter signal based on the received midfield signal. In some embodiments, the system further comprises a second implantable device similar to a first implantable device, such that each of the implantable devices includes respective receiver circuits configured to receive at least one of the multiple different sets of RF signals transmitted by the transmitter circuit.

In some embodiments, the system can include one or more mechanisms for implanting/explanting the implantable device from a body. In such embodiments, the implantable device can include a connection structure in a proximal portion thereof that is configured to mate with a mating connection structure of a pushrod. The pushrod can be a hollow element, in some embodiments, such as to include a hole longitudinally therethrough. The pushrod can be used to position the implantable device inside the body. The implantable device can include a suture attached thereto, such as at a location more proximal than the antenna housing and/or deployment tines. The hole in the pushrod can be configured such that the pushrod can slide down the suture with the suture situated in the hole. In one or more embodiments, a second pushrod can be configured to be inserted (e.g., next to the suture) in the hole and contact the connection of the implantable device, such as to allow the pushrod to be separated from the implantable device. In some embodiments, the pushrod can be configured to help secure the suture in place, such as to help prevent the suture from slipping in and/or out of a body it is placed in. In such embodiments, the pushrod can include a female luer thread and the system can further comprise a male luer cap configured to be mated with female luer thread. The male luer cap can include a hole therethrough that is configured to be situated over the suture, such that when the male luer cap is mated with the female luer thread, the male luer cap presses on the suture, such as to help retain the position of the suture.

In accordance with several embodiments, an at least partially implantable electrical therapy delivery device comprises a flexible, biocompatible, elongated member including a distal portion and a proximal portion. The elongated member may have a generally uniform diameter along its length or may have varying diameters at different portions along its length. The electrical therapy delivery device may comprise a plurality of electrodes (e.g., cylindrical, ring, planar electrodes) situated along the distal portion of the elongated member and a circuitry housing (e.g., a cylindrical, hermetic housing) attached to the proximal portion of the elongated member. The circuitry housing may have a diameter substantially the same as the diameter of the elongated member. In this embodiment, circuitry is hermetically sealed within the circuitry housing. The circuitry is configured to provide electrical energy to the plurality of electrodes. An antenna housing is attached to the circuitry housing at a proximal end of the circuitry housing opposite to an end of the circuitry housing attached to the elongated member. An antenna (e.g., dipole antenna, coil antenna, helical antenna, patch antenna or other type of antenna) is located in the antenna housing.

In some embodiments, the antenna housing comprises a dielectric material with a dielectric constant between that of human tissue and air. For example, the dielectric material may be a ceramic material, such as aluminum or zirconium. The dielectric (e.g., ceramic) may at least partially cover the antenna. The elongated member may comprise a hollow channel extending through the elongated member from a proximal end of the elongated member to the distal portion of the elongated member. A memory metal wire may be situated in the channel. The memory metal wire may be pre-shaped in an orientation to provide curvature to the elongated member. In one embodiment, the memory metal is shaped to conform to a shape of a body structure or tissue (e.g., an S3 foramen) and to generally match a curve of a nerve (e.g., a sacral nerve). The antenna may be a primary antenna and the therapy delivery device may further comprise a secondary antenna in the antenna housing or in a separate housing, which may be attached to the antenna housing. The secondary antenna may be shaped and positioned to provide a near field coupling with the primary antenna. One or more sutures may be connected to the therapy delivery device. The one or more sutures may be attached at one or more of: (1) a proximal portion of the antenna housing; (2) a proximal portion of the circuitry housing, and (3) an attachment structure attached to a proximal end of the antenna housing. Other attachment locations are also possible. In some embodiments, the primary antenna is coupled to a conductive loop of the circuitry situated in a proximal portion of the circuitry housing. A ceramic material may be positioned between the antenna and the conductive loop.

In accordance with several embodiments, an implantable stimulation device comprises or consists essentially of an outer casing, a plurality of electrodes exposed on a surface of the outer casing, a circuitry housing affixed to the outer casing, circuitry encased by the circuitry housing and electrically connected to the plurality of electrodes, and a hollow lumen extending from a proximal end of the circuitry housing to a distal portion (e.g., distal end) of the outer casing. In some embodiments, the implantable stimulation device further comprises an antenna housing affixed to the circuitry housing, with an antenna encased or disposed in the antenna housing. The hollow lumen may extend through the antenna housing. In some embodiments, the implantable stimulation device comprises an antenna electrically connected to the circuitry at a proximal side of the circuitry housing, with an encapsulant hermetically sealing the antenna, and the hollow lumen extends through the encapsulant.

In some embodiments, the implantable stimulation device further comprises a distal feedthrough plate including a plurality of feedthroughs therethrough and a first lumen hole therethrough, wherein the hollow lumen is situated in the first lumen hole, and wherein the circuitry housing is affixed to the distal feedthrough plate at a distal end of the circuitry housing and the outer casing is affixed to the distal feedthrough plate at a proximal end of the outer casing. The implantable stimulation device can further comprise a proximal feedthrough plate including a plurality of feedthroughs therethrough and a second lumen hole therethrough, wherein the hollow lumen is situated in the second lumen hole, and wherein the circuitry housing is affixed to the proximal feedthrough plate at a proximal end of the circuitry housing. An antenna housing may be affixed to the proximal feedthrough plate at a distal end of the antenna housing. In some embodiments, an antenna is encased in the antenna housing and the hollow lumen extends through the antenna housing.

In some embodiments, the implantable stimulation device further comprises an end plate affixed to the antenna housing at a proximal end of the antenna housing, the end plate including a third lumen hole therethrough, and wherein the hollow lumen is situated in the third lumen hole. In some embodiments, an antenna is electrically connected to the circuitry, with the antenna situated at a proximal end of the circuitry housing. An encapsulant may hermetically seal the antenna and the hollow lumen may extend through the encapsulant. The encapsulant may seal proximal feedthroughs of the proximal feedthrough plate introduced above.

In some embodiments, the hollow lumen of the implantable stimulation device comprises a discrete first lumen portion and a discrete second lumen portion. The first lumen portion may extend from a distal end of the outer casing to a proximal side of a side of a distal feedthrough plate and the second lumen portion may extend from a proximal side of the distal feedthrough plate to a proximal end of the stimulation device. The first lumen portion may comprise a flexible material and the second lumen portion may comprise a rigid material. The flexible material of the first lumen portion may comprise a memory metal (e.g., a nickel-titanium alloy).

In accordance with several embodiments, a method of assembling an implantable stimulation device comprises situating a circuitry housing over a hollow lumen that extends to a distal end of an outer casing, positioning circuitry within the circuitry housing, electrically connecting electrodes exposed on an outer surface of the outer casing to the circuitry, and affixing the circuitry housing at a distal end of the circuitry housing. The hollow lumen may extend all the way through the circuitry housing to a proximal end of the circuitry housing. In one embodiment, the method further comprises situating a distal feedthrough plate over the hollow lumen such that the hollow lumen extends through a first lumen hole of the distal feedthrough plate, electrically connecting electrodes to respective distal feedthroughs in the distal feedthrough plate, and affixing the hollow lumen and the outer casing to the distal feedthrough plate before situating the circuitry housing over the hollow lumen. Affixing the outer casing to the distal feedthrough plate may comprise at least one of welding and brazing.

In some embodiments, the method further comprises positioning a proximal feedthrough plate over the hollow lumen such that the hollow lumen extends through a lumen hole of the proximal feedthrough plate, electrically connecting conductors in proximal feedthroughs of the proximal feedthrough plate to the circuitry, and affixing the proximal feedthrough plate to the proximal end of the circuitry housing. Affixing the proximal feedthrough plate to the circuitry housing may comprise at least one of welding and brazing. In some embodiments, the method further comprises electrically connecting an antenna to conductors in the proximal feedthroughs of the proximal feedthrough plate. The method may further comprise positioning an antenna housing around the antenna and the hollow lumen such that the hollow lumen extends all the way through the antenna housing, and affixing the antenna housing to the circuitry housing at the proximal end of the circuitry housing. Affixing the antenna housing to the circuitry housing may comprise at least one of welding and brazing. The method may also comprise situating an end plate on the antenna housing and over the hollow lumen such that the hollow lumen extends through a third lumen hole of the end plate, and affixing the end plate to the antenna housing at a proximal end of the antenna housing. Affixing the end plate to the antenna housing may comprise at least one of welding and brazing. In some embodiments, the method comprises hermetically sealing an area around the hollow lumen.

In some embodiments, the method of assembling comprises situating dielectric material around the hollow lumen and the antenna such that the antenna is encased in the dielectric material and the hollow lumen extends all the way through the dielectric material. Situating the dielectric material around the hollow lumen and the antenna may further comprise situating the dielectric material around the proximal feedthrough of the proximal feedthrough plate such that the proximal feedthroughs are hermetically sealed.

In accordance with several embodiments a method performed by an implantable device comprises wirelessly receiving an electromagnetic wave at an antenna of the implantable device, the electromagnetic wave including alternating active periods and non-active periods. The method further comprises providing at least a portion of the received electromagnetic wave to a surface acoustic wave (SAW) device electrically coupled to the antenna and buffering, using the SAW device, the provided electromagnetic wave. The method also comprises harvesting, during an active period of the active periods, energy from the provided electromagnetic wave using circuitry electrically coupled to the SAW device, and transmitting, using the antenna and during a non-active period of the non-active periods, the buffered electromagnetic wave. In some embodiments, after harvesting energy and before transmitting the signal, the method comprises altering, using a switch (e.g., a transmit/receive switch) electrically coupled to the SAW device, an electrical path of the buffered electromagnetic wave from a receive path to a transmit path. The method can further include dividing, using a power divider electrically coupled between a rectifier and the SAW device, the received electromagnetic wave into a first wave portion and a second wave portion, wherein the buffered electromagnetic wave is the first portion of the received electromagnetic wave, and wherein the harvested energy is from the second portion.

In accordance with several embodiments, an at least partially implantable device comprises or consists essentially of an antenna adapted to wirelessly receive an electromagnetic wave and convert the electromagnetic wave to an electrical signal including alternating active periods and non-active periods, and a SAW device adapted to receive at least a portion of the electrical signal and buffer the received portion, energy harvesting circuitry adapted to receive at least a portion of the electrical signal during an active period of the active periods and to convert the received signal to electrical power. The antenna may be configured to transmit the buffered signal during a non-active period of the non-active periods. The implantable device may further comprise a modulator adapted to receive the buffered signal and use the buffered signal as a radiofrequency source in modulating a baseband signal. Again, the antenna may be adapted to transmit the modulated baseband signal during the non-active period.

In some embodiments, the implantable device further comprises a switch (e.g., a transmit/receive switch) electrically coupled between the SAW device and the antenna, and a digital controller electrically coupled to the switch. The digital controller is adapted to select an electrical path of the switch. A first electrical path of the switch may be shunted to a reference voltage and a second electrical path of the switch may be electrically coupled to the buffered signal.

In accordance with several embodiments, a method of providing a wide area stimulation therapy is provided. The method may comprise wirelessly receiving a power signal at a radio circuitry of an at least partially implantable stimulation device, the power signal generated by a midfield powering device, and, using a therapy delivery circuitry that is coupled to the radio circuitry and to multiple electrodes of the stimulation device, providing the wide area stimulation therapy signal to a patient using at least a portion of the wirelessly received power signal. The implantable stimulation device may include at least two first electrodes including at least one anode and at least one cathode on, or at least partially in, a distal portion of the stimulation device and at least one second electrode on, or at least partially in, a proximal portion of the stimulation device. In such an embodiment, providing the far field stimulation therapy signal may comprise switching, using the therapy delivery circuitry, one of the first electrodes off such that a far field electric field is generated between at least one of the first electrodes and the at least one second electrode. The method may further include switching on, using the therapy delivery circuitry, the first electrode that was switched off and switching off the at least one second electrode, and providing a localized stimulation therapy to the patient using at least a portion of the wirelessly received power, the localized stimulation therapy being generated between at least two of the first electrodes.

In some embodiments, the step of wirelessly receiving a power signal at a radio circuitry of an at least partially implantable stimulation device comprises generating an electrical current at a conductive wire in the stimulation device in response to the power signal being incident on the wire. In such embodiments, at least one of the first electrodes and the at least one second electrode may be electrically connected to the therapy delivery circuitry through the conductive wire. In some embodiments, the method comprises switching on, using the therapy delivery circuitry, the first electrode that was switched off, providing a localized stimulation therapy to the patient using at least a portion of the wirelessly received power, the localized stimulation therapy being generated between at least two of the first electrodes, and providing, simultaneously with the localized stimulation therapy, a wide area stimulation therapy. The method advantageously provides both localized and wide area stimulation therapy.

In accordance with several embodiments, a system comprises or consists essentially of a midfield powering device and an at least partially implantable, biocompatible stimulation device wirelessly coupled to the midfield powering device. In some embodiments, the stimulation device comprises a circuitry housing including therapy generation circuitry, a distal portion including a plurality of first electrodes electrically coupled to the therapy generation circuitry, and a proximal portion opposite the distal portion, the proximal portion including at least one second electrode electrically coupled to the therapy generation circuitry. In one embodiment, a distance between a most proximal of the first electrodes of the distal portion and a most distal of the at least one second electrode of the proximal portion is greater than one and a half centimeters (e.g., between 1.5 cm and 3 cm, between 2 cm and 4 cm, between 1.5 cm and 2 cm, between 2 cm and 2.5 cm, overlapping ranges thereof, or any value within the recited ranges). In one embodiment, a distance between directly adjacent electrodes of the first electrodes is less than ten millimeters (e.g., between eight and ten millimeters, between six and ten millimeters, between six and eight millimeters, between five and nine millimeters, between five and seven millimeters, between four and eight millimeters, between two and six millimeters, between one and five millimeters, overlapping ranges thereof, or any value within the recited ranges). The circuitry housing may be situated between the first electrodes and the at least one second electrode.

In some embodiments, the therapy generation circuitry comprises a plurality of switches, each of the plurality of switches electrically connected to one of (1) an electrode of the plurality of first electrodes and (2) an electrode of the at least one second electrode. The therapy generation circuitry may be configured to close all switches such that all electrodes are electrically active and the stimulation device provides a wide area stimulation therapy simultaneously with a localized stimulation therapy.

In accordance with several embodiments, a system comprises or a midfield powering device and two implantable stimulation devices wirelessly coupled to the midfield powering device. For example, a first and second stimulation device each comprise or consist essentially of an antenna housing including an antenna situated therein to receive electric signals from the midfield powering device, a circuitry housing including therapy generation circuitry, and a plurality of electrodes electrically coupled to the therapy generation circuitry. The first and second stimulation devices may be arranged and configured to produce a wide area stimulation therapy between at least one electrode of the electrodes of the first stimulation device and at least one electrode of the electrodes of the second stimulation device. In some implementations, a distance between directly adjacent electrodes of the electrodes is less than ten millimeters (e.g., between eight and ten millimeters, between six and ten millimeters, between six and eight millimeters, between five and nine millimeters, between five and seven millimeters, between four and eight millimeters, between two and six millimeters, between one and five millimeters, overlapping ranges thereof, or any value within the recited ranges). A conductive wire may be electrically connected between an electrode of the electrodes of the first stimulation device and an electrode of the electrodes of the second stimulation device. In some embodiments, respective electrodes of the first stimulation device are configured as an anode and a cathode and respective electrodes of the second stimulation device are configured as a cathode and an anode and the therapy generation circuitry provides a localized stimulation therapy simultaneously with the wide area stimulation therapy. The electrodes in each of the stimulation devices may include a first electrode in a proximal portion of the stimulation device and a second electrode in a distal portion of the stimulation device, the proximal portion opposite the distal portion. The circuitry housing and the antenna housing may be situated between the first and second electrode or the circuitry housing and the antenna housing may be situated in a proximal portion of the stimulation device and the first and second electrode may be situated in an opposite distal portion of the stimulation device.

In accordance with several embodiments, a system comprises a biocompatible implant device. The implant device comprises or consists essentially of a rigid body having opposing surfaces that include a width that is smaller than a length, a plurality of electrodes coupled to the body and located at a periphery of the implant device, and a circuitry housing coupled to the body. The circuitry housing includes therapy delivery circuitry that is electrically coupled to the plurality of electrodes and configured to wirelessly receive electrical energy and use at least a portion of the received electrical energy to deliver an electrostimulation therapy to a subject body via one or more of the plurality of electrodes. In some embodiments, the two opposing surfaces of the rigid body of the implant device are substantially planar and substantially elliptical in shape. The circuitry housing may be situated at least partially between two focal points of a surface of the opposing surfaces. In some embodiments, the circuitry housing comprises one of a helix-shaped antenna and a patch antenna therein.

In some embodiments, the plurality of electrodes comprises at least four electrodes substantially evenly distributed about the periphery of the implant device. In some embodiments, a top surface of the rigid body is elliptically-shaped with a major axis and a minor axis, and two of the at least four electrodes are situated on respective intersections of the major axis and the peripheral edge of the body, and two of the at least four electrodes are situated on respective intersections of the minor axis and the peripheral edge of the body.

In some embodiments, a first portion of the rigid body includes a male or female connection feature (e.g., a screw hole, a receptacle, a fastener or other interface member). An implant structure may be attached to the first portion of the rigid body and the male or female connection feature or member may be located in the implant structure. In one embodiment, the implant structure comprises two bars generally parallel to the major axis of the body and coupled to and extending away from the body, and one bar connected between the two bars, the one bar being generally parallel to the minor axis of the body. The male or female connection feature or member (e.g., screw hole or other interface member) may be in the one bar generally parallel to the minor axis of the body. In some embodiments, a suture is connected to the first portion of the body. The system may further comprise a powering device (e.g., midfield powering device) configured to provide electrical energy to the implant device.

In accordance with several embodiments, a device comprises or consists essentially of a substrate, a first circuitry layer on a first surface of the substrate, a second circuitry layer in the substrate, a planar electromagnetic transmission element on a second surface of the substrate opposite the first surface of the substrate, and a Faraday cage cover over the first circuitry layer. The second circuitry layer may comprise a ground plane, which may be patterned to include slots for excitation of the transmission element. In some embodiments, the Faraday cage is patterned such that a footprint of the Faraday cage does not overlap with the slots. The device may include vias electrically connecting the Faraday cage cover to the second circuitry layer. The vias may be situated at or near edges of the slots in the second circuitry layer and/or at or near edges of the Faraday cage.

In some embodiments, a thermally conductive material is positioned or located between components of the first circuitry layer and the Faraday cage to conductively transfer heat from the components (e.g., discrete high-power electronic components) to the Faraday cage. In some embodiments, the first circuitry layer comprises control hardware including a power amplifier. One or more of the vias may be configured to transfer electromagnetic energy from the control hardware in the Faraday cage to the planar electromagnetic transmission element external to the Faraday cage.

In accordance with several embodiments, a system for manipulating an evanescent field at or near an external tissue surface to transmit power and/or data wirelessly to multiple target devices implanted in the tissue is provided. The system comprises or consists essentially of an RF signal generator system configured to provide multiple different sets of RF signals, each set comprising two or more separate signals, and a midfield transmitter including multiple excitation ports. The midfield transmitter is coupled to the RF signal generator system and configured to transmit the multiple different sets of RF signals at respective different times via the excitation ports, which are configured to receive respective ones of the separate signals from each set of RF signals. Each of the transmitted sets of RF signals includes a non-negligible magnetic field (H-field) component that is substantially parallel to the external tissue surface, and each set of transmitted RF signals is selected to differently manipulate an evanescent field at or near the tissue surface to transmit a power or data signal to respective different target devices implanted in the tissue.

In some embodiments, the system further comprises or consists essentially of first and second implantable devices, each of the first and second devices including respective receiver circuitry configured to receive at least one of the multiple different sets of RF signals transmitted by the midfield transmitter. The RF signal generator system may be configured to provide, for each set of RF signals, two or more separate signals having different signal characteristics, wherein each of the transmitted sets of RF signals differently manipulates the evanescent field at the tissue surface to direct the power or data signal to a selected one of the first and second implantable devices. In some embodiments, the midfield transmitter is configured to transmit a first one of the sets of RF signals to the first implantable device for a first duration and the midfield transmitter is configured to transmit a second one of the sets of RF signals to the second implantable device for a subsequent second duration.

In some embodiments, the first implantable device is configured to provide an electrostimulation therapy in response to receiving the first one of the sets of RF signals and over a therapy duration that is less than or equal to the first duration. In other embodiments, the first implantable device is configured to provide an electrostimulation therapy over a duration that is less than or equal to a sum of the first and second durations. The first implantable device may comprise therapy energy storage circuitry, and may be configured to provide an electrostimulation therapy, using energy from the therapy energy storage circuitry, over a duration that exceeds the first duration.

In some embodiments, the system further comprises a feedback control circuitry configured to update a transmission power of at least one of the sets of RF signals from the midfield transmitter based on information about a power signal received from the midfield transmitter at one or more of the first and second implantable devices. The system may also comprise a backscatter sensor configured to monitor a backscatter signal in response to transmission of sets of RF signals from the midfield transmitter and the feedback control circuitry may be configured to use information about the backscatter signal to identify a portion of a power signal received at the first and/or second implantable device. In some embodiments, the system comprises a surface electromyography (EMG) sensor configured to monitor muscle activity at or near the tissue surface and the feedback control circuitry is configured to use information about the muscle activity to update the transmission power of at least one of the sets of RF signals from the midfield transmitter.

In some embodiments, the first implantable device is configured to receive a portion of a first one of the RF signals at a first time when the first one of the RF signals has a first signal characteristic and the second implantable device is configured to receive a portion of a second one of the RF signals at a second time when the second one of the RF signals has a different second signal characteristic. In some embodiments, one of the sets of RF signals is configured to manipulate the evanescent field at or near the tissue surface to transmit the power or data signal simultaneously to both of the first and second implantable devices.

At least one of the first and second implantable devices may comprise therapy delivery circuitry (e.g., circuitry adapted to provide neural stimulation therapy) coupled to the receiver circuitry. The therapy delivery circuitry may be configured to provide an electrostimulation signal to the tissue (e.g., neural tissue) using a received portion of at least one of the sets of RF signals transmitted by the midfield transmitter. In some embodiments, at least one of the first and second implantable devices includes sensor circuitry coupled to the receiver circuitry. The sensor circuitry may be configured to sense a physiologic parameter and may be powered at least in part by a received portion of at least one of the sets of RF signals transmitted by the midfield transmitter. The sensor circuitry can determine an electrode impedance of one or more electrodes of the implantable device. The implantable device, in one or more embodiments can change a stimulation parameter (e.g., frequency, power, burst frequency, duty cycle, phase, among others), such as by using control circuitry, in response to data received from a sensor. The sensor can be on or communicatively coupled to the implantable device, such as to be internal or external to the body.

In some embodiments, the RF signal generator is configured to generate a first set of RF signals that includes first and second signals that are phase-shifted relative to each other and the RF signal generator is configured to generate a second set of RF signals that includes third and fourth signals that are differently phase-shifted relative to each other, wherein the evanescent field is differently manipulated in response to the midfield transmitter transmitting the first and second sets of RF signals to direct transmission of respective wireless power or data signals of the first and second sets of RF signals to respective ones of the first and second implantable devices. In some embodiments, the RF signal generator is configured to generate a first set of RF signals that includes first and second signals that have different first and second signal amplitude characteristics and the RF signal generator is configured to generate a second set of RF signals that includes third and fourth signals that have different amplitude characteristics than the first and second signals, wherein the evanescent field is differently manipulated in response to the midfield transmitter transmitting the first and second sets of RF signals to direct transmission of respective wireless power or data signals of the first and second sets of RF signals to respective ones of the first and second implantable devices. The midfield transmitter may be configured to provide the multiple different sets of RF signals using duty cycled pulses, with each pulse provided at a saturation power of an amplifier circuitry of the midfield transmitter.

In accordance with several embodiments, a transmitter (e.g., midfield transmitter) for manipulating an evanescent field at or near an external tissue surface to transmit power and/or data wirelessly to multiple target devices implanted in the tissue comprises an RF signal generator configured to provide an RF signal to first and second excitation channels. The transmitter further comprises a phase shifter included in the first excitation channel, with the phase shifter being configured to receive the RF signal from the RF signal generator and, in response, to provide a phase-shifted first signal for a first duration and a phase-shifted second signal for a subsequent second duration. The transmitter may further comprise first and second excitation ports coupled to the RF generator and the phase shifter, respectively. The excitation ports are configured to concurrently transmit, for the first duration, a reference RF signal from the first or second excitation channel and the phase-shifted first signal to direct a wireless power signal to a first device implanted at a first tissue location and the excitation ports are configured to concurrently transmit, for the subsequent second duration, the reference RF signal from the first or second excitation channel and the phase-shifted second signal to direct a wireless power signal to a second device implanted at a second tissue location.

In accordance with several embodiments, a method for manipulating an evanescent field at or near an external tissue surface to transmit power and/or data wirelessly to multiple target devices implanted in the tissue comprises generating multiple different sets of RF signals, each set comprising two or more separate signals having different signal characteristics. The method further comprises transmitting, for a first duration and from a midfield transmitter via multiple excitation ports, a first one of the multiple different sets of RF signals to manipulate the evanescent field at or near the external tissue surface and to thereby direct power to a first implantable device implanted within tissue. The method also comprises transmitting, for a subsequent second duration and from the midfield transmitter via the same or different multiple excitation ports, a second one of the multiple different sets of RF signals to manipulate the evanescent field at or near the external tissue surface and to thereby direct power to a second implantable device implanted within tissue. The method may also comprise receiving, at the midfield transmitter, an indication of a power transfer efficiency from the midfield transmitter to the first and/or second implantable device. The transmitting steps comprise providing a non-negligible magnetic field (H-field) signal component that is substantially parallel to the external tissue surface.

In some embodiments, the step of receiving the indication of the power transfer efficiency includes receiving a data signal at the midfield transmitter from the first and/or second implantable device. In some embodiments, the step of receiving the indication of the power transfer efficiency includes receiving a backscatter signal at the midfield transmitter in response to the transmitting the first or the second set of RF signals.

The method may further comprise, based on the indication of the power transfer efficiency, changing a signal characteristic of one or more of the separate signals corresponding to the first set of RF signals to provide an updated set of RF signals and then transmitting the updated set of RF signals to the first or second implantable device. The method may comprise providing a delay between transmitting the first and second sets of RF signals. The step of transmitting the first set of RF signals may comprise providing a first pulse at a saturation power of the midfield transmitter and the step of transmitting the second set of RF signals may comprise providing a second pulse at the saturation power of the midfield transmitter.

In some embodiments, the method comprises receiving, at the first implantable device, at least a portion of the first set of RF signals transmitted by the midfield transmitter, and, in response, delivering a neural electrostimulation therapy to the tissue either concurrently with the receiving of the first set of RF signals or asynchronously with the receiving of the first set of RF signals.

In accordance with several embodiments, a system for manipulating an evanescent field at or near an external tissue surface to direct transmission of wireless power and/or data signals within the tissue is provided. The system comprises first and second target devices implanted in the tissue. The target devices may comprise a neural stimulation therapy device and/or a diagnostic (e.g., sensor) device configured to receive power and/or data wirelessly. The system further comprises a remote RF field generator configured to generate and transmit a first field and a midfield coupler including multiple sub-wavelength structures and at least one tunable device configured to adjust a RF signal transmission characteristic of the midfield coupler. The midfield coupler is configured to be positioned at or near the external tissue surface so as to receive a portion of the first field from the remote RF field generator and, in response, to modulate the received portion of the first field to control an evanescent field at the tissue surface and thereby direct wireless power and/or data signals from the midfield coupler to the first and second target devices in a time-multiplexed manner. The midfield coupler is configured to use respective different parameters of the at least one tunable device to communicate the power and/or data signals to the first and second target devices implanted in the tissue. In one embodiment, the midfield coupler is configured to perform a "greedy" parameter search algorithm to identify a preferred parameter value for the tunable device to use to communicate the power and/or data signals to the first and/or second target devices.

In some embodiments, the at least one tunable device comprises a capacitor coupled to one or more of the sub-wavelength structures and includes an adjustable capacitance. The midfield coupler may be configured to use respective first and different second capacitance values of the capacitor to communicate the signals to the first and second target devices. In some embodiments, the at least one tunable device comprises an inductor coupled to one or more of the sub-wavelength structures and includes an adjustable inductance. The midfield coupler may be configured to use respective first and different second inductance values of the inductor to communicate the signals to the first and second target devices. In some embodiments, the at least one tunable device comprises a resistor coupled to one or more of the sub-wavelength structures and includes an adjustable resistance. The midfield coupler may be configured to use respective first and different second resistance values of the resistor to communicate the signals to the first and second target devices.

The at least one tunable device may comprise an adjustable phase shifter coupled to one or more of the sub-wavelength structures and configured to provide respective first and different second phase delays to communicate the signals to the first and second target devices. The midfield coupler may be configured to perform a "greedy" phase search algorithm to identify a preferred phase delay to use to communicate the power and/or data signals to the first and/or second target devices.

In some embodiments, the system comprises memory (e.g., a non-volatile storage device or other memory circuitry) configured to store parameter information for the at least one tunable device, the stored parameter information including known-good parameter information corresponding to a previous successful power and/or data exchange with one or both of the first and second target devices. At startup, the midfield coupler may be configured to use a stored parameter value for the at least one tunable device to communicate the power and/or data signals to the first target device and the midfield coupler may be configured to iteratively update the stored parameter value to identify a preferred parameter value to use to further communicate the power and/or data signals.

In some embodiments, the system comprises sensor circuitry configured to receive a backscatter signal in response to the midfield coupler communicating the power and/or data signals to the first and second target devices. The midfield coupler may be configured to use information about the backscatter signal to update or adjust a parameter of the at least one tunable device. In some embodiments, the system comprises one or more sensors (e.g., an EMG sensor and/or accelerometer) configured to sense a tissue response to the signals communicated by the midfield coupler at or near the external tissue surface. The midfield coupler may be configured to use information about the sensed tissue response to update or adjust a parameter of the at least one tunable device.

The system may comprise a second midfield coupler configured to communicate other power and/or data signals to the same first and second target devices. In one embodiment, the two midfield couplers are communicatively coupled and are configured to concurrently provide power signals to the first target device. In one embodiment, the two midfield couplers are communicatively coupled and are configured to concurrently provide different respective power and/or data signals to the first and second target devices.

In accordance with several embodiments, an apparatus for receiving, processing, and transmitting an RF field (the transmitted RF field including a non-negligible H-field component that is substantially parallel to the body tissue surface) externally to body tissue to control an evanescent field at the body tissue surface and thereby direct wireless power and/or data signals to target devices implanted within the tissue in a time-multiplexed manner is provided. The apparatus comprises or consists essentially of multiple sub-wavelength structures configured to receive and transmit RF signals and a tunable device configured to adjust an RF signal transmitted by the sub-wavelength structures by changing an electrical characteristic of at least one of the sub-wavelength structures, wherein different parameter values of the at least one tunable device configure the apparatus to communicate the power and/or data signals to respective different target devices implanted in the tissue.

In accordance with several embodiments, a method for manipulating an evanescent field at or near an external tissue surface to transmit power and/or data wirelessly to multiple target devices implanted in the tissue comprises receiving RF energy from a first remote RF field source using multiple sub-wavelength structures of a midfield coupler. The method further comprises modulating the received RF energy using the midfield coupler to provide a first output signal, the modulating including using a first value of a first tunable device coupled to the sub-wavelength structures. The method also comprises transmitting the first output signal to a first target device implanted in a first tissue location and modulating the received RF energy using the midfield coupler to provide a subsequent second output signal, the modulating including using a second value of the first tunable device. The method further comprises transmitting the second output signal to a second target device implanted in a different second tissue location.

In some embodiments, the method comprises receiving, at the first target device, at least a portion of the transmitted first output signal and, in response, providing a neural electrostimulation therapy at the first tissue location using a portion of the received signal. The method may also comprise performing a "greedy" parameter value search algorithm to identify a preferred value for the first tunable device to use to communicate power and/or data from the midfield coupler to one or both of the first and second target devices.

In some embodiments, using the first value of the first tunable device comprises using a first inductance, capacitance, and/or resistance value for the midfield coupler to communicate with the first target device and using the second value of the first tunable device comprises using a different second inductance, capacitance, and/or resistance value for the midfield coupler to communicate with the second target device. In some embodiments, using the first value of the first tunable device includes using a first phase shift value for the midfield coupler to communicate with the first target device and using the second value of the first tunable device comprises using a different second phase shift value for the midfield coupler to communicate with the second target device. In some embodiments, using the first value of the first tunable device comprises using a first amplitude value for the midfield coupler to communicate with the first target device and using the second value of the first tunable device comprises using a different second amplitude value for the midfield coupler to communicate with the second target device.

In accordance with several embodiments, a system for covering a wearable external device to be worn by a user comprises one of a pocket and a sleeve comprising one or more top layers of fabric and one or more bottom layers of fabric. The bottom layers of fabric are closer to a body of the user than the top layers of fabric when the pocket or sleeve is worn. The bottom layers comprise a first layer of fabric that is a soft, compliant material and a second layer of fabric that is one of a heat insulating material and/or a water resistant material. The second layer of fabric is located further from the body of the user when the pocket or sleeve is worn. The top layer of fabric comprises a third layer of fabric that comprises a heat conducting material. The system comprises an external stimulator device (e.g., any of the external devices or midfield couplers described herein) located in the pocket or sleeve between the top and bottom layers of fabric. The external stimulator device is adapted to provide electromagnetic energy to an implanted medical device.

The top layers of fabric may include a fourth layer of fabric further from the body of the user than the third layer of fabric when the pocket or sleeve is worn, the fourth layer comprising an elastic band. The elastic band may include a plurality of holes in at least a portion of the band. In some embodiments, the holes are advantageously taller than they are wide. However, the holes may have substantially the same height and width in other embodiments or the holes may be wider than they are tall.

In some embodiments, the system comprises an article of clothing that includes the pocket or sleeve, wherein the pocket or sleeve is situated at a location on the article of clothing such that it is above or near a target tissue location (e.g., an S3 foramen) of the body. The external stimulator device may comprise location circuitry configured to communicate with an implanted device and provide an indication of whether the device is properly located near the implanted device.

In some embodiments, the external stimulator device comprises a first attachment mechanism and the pocket or sleeve comprises a corresponding second attachment mechanism. The attachment mechanisms may be located such that when the attachment mechanisms are mated the external stimulator device is properly located relative (e.g., proximate or near) the implanted device.

In some embodiments, the external stimulator device comprises a top cover and bottom cover both including a thermoplastic material, the top cover being further away from the body of the user when the device is worn. The external stimulator device (e.g., the midfield coupler of the external stimulator device) may be situated between the top cover and the bottom cover. In some embodiments, the top cover includes fins configured to radiate heat towards the third layer of fabric. In some embodiments, one or more of the top cover and the bottom cover includes one or more air vents (e.g., one, two, three, four, or more than four) configured to transport air towards the top cover. In some embodiments, the top and bottom covers each include two or four air vents.

Circuitry may be situated between the top and bottom covers. The circuitry may be adapted to generate an audible or tactile output, indication or alert (e.g., to vibrate or make a sound) in response to determining the location of the external stimulator device is not situated sufficiently near the implanted device. The circuitry may be configured to determine that the location of the external stimulator device is not sufficiently situated near the implanted device by determining that a received signal strength of a signal from the implanted device is below a threshold value. In some embodiments, the circuitry is configured to generate a different audible or tactile output (e.g., provide a different vibration or make a different sound) in response to determining the position of the external device is proper.

In some embodiments, one or more of the top and bottom covers include a plurality of recesses to hold air therein. The top and bottom cover may include a footprint that is rectangular with rounded corners, with all edges of the top and bottom covers being rounded. In one embodiment, the edges of the bottom cover are rounded to include a smaller radius of curvature than the edges of the top cover.

In accordance with several embodiments, an external stimulator device (e.g., any of the external devices or midfield couplers described herein) comprises or consists essentially of a top cover, a bottom cover mechanically coupled to the top cover, location circuitry situated between the top and bottom covers to communicate with an implanted device and provide an indication of whether the device is properly located near an implanted device, and a midfield coupler situated between the top and bottom covers, the midfield coupler adapted to provide electromagnetic energy to the implanted device. The top cover may include fins configured to radiate heat away from the external stimulator device. One or both of the top cover and the bottom cover may include one or more (e.g., one, two, three, four, or more than four) air vents configured to transport air towards the top cover.

In accordance with several embodiments, a method for wirelessly communicating data from an implantable device to an external source device is provided. The method comprises transmitting, from an external source device, a midfield signal using a first antenna comprising at least first and second excitation ports, receiving the midfield signal using a second antenna coupled to an implantable device, and modulating a signal path between the second antenna and a load circuitry of the implantable device, according to a communication control signal, to thereby generate and transmit a backscatter signal using the second antenna. The backscatter signal includes information about the implantable device. The method further comprises receiving the backscatter signal using the first excitation port of the first antenna of the external source device and generating, using the external source device, a predicted self-interference signal based on the midfield signal. The method also may comprise extracting, using the external source device, the information about the implantable device from the received backscatter signal using the predicted self-interference signal.

In some embodiments, generating the predicted self-interference signal comprises using information about a frequency-dependent signal leakage between the first and second excitation ports and information about a magnitude of an excitation signal driving the second excitation port. The method may comprise combining the predicted self-interference signal, a real (e.g., actual) self-interference signal received from the first excitation port of the first antenna, and the received backscatter signal, using the external source device, to provide a time-varying information signal and a DC signal component. Extracting the information about the implantable device may comprise extracting the information about the implantable device from the information signal.

In some embodiments, generating the predicted self-interference signal based on the midfield signal includes generating a signal that is 180 degrees offset from the actual self-interference signal received from the first excitation port of the first antenna. The method may include measuring a magnitude of the DC signal component and, when the magnitude exceeds a specified threshold magnitude, adjusting the predicted self-interference signal. Adjusting the predicted self-interference signal may comprise adjusting an amplitude or phase characteristic of the predicted self-interference signal. The method may also comprise adjusting a magnitude or phase of the predicted self-interference signal based on a magnitude of the DC signal component.

In some embodiments, the backscatter signal includes information about a characteristic of the implantable device itself or information about a therapy provided, or to be provided, by the implantable device. In some embodiments, the backscatter signal includes information about a physiologic characteristic sensed or measured by the implantable device.

The method may further comprise providing an RF carrier signal using the external source device, and generating the midfield signal using at least one phase-shifted version of the RF carrier signal to excite one of the first and second excitation ports. In some embodiments, the step of generating the predicted self-interference signal based on the midfield signal comprises using a differently phase-shifted version of the RF carrier signal. The step of extracting the information about the implantable device from the received backscatter signal using the predicted self-interference signal may comprise summing the predicted self-interference signal with the received backscatter signal and with an actual (e.g., real) self-interference signal received from the first excitation port of the first antenna. The midfield signal may comprise a power signal, a data signal, or a power signal with data encoded in the power signal.

In accordance with several embodiments, a wireless communication system using a backscatter signal to communicate information from an implantable device to an external midfield source device comprises an external midfield source device configured to provide a midfield signal by concurrently exciting multiple ports of a unitary RF antenna using respective multiple excitation signals, wherein at least one of the ports is configured to receive a first backscatter signal. The system further comprises a first implantable device configured to receive the midfield signal from the external midfield source device and to provide the first backscatter signal based on the received midfield signal. The external midfield source may be configured to encode instructions in the midfield signal, for use by the first implantable device, to introduce a specified phase perturbation in the first backscatter signal.

In some embodiments, the first implantable device comprises modulator circuitry coupled to an antenna. The modulator circuitry may be configured to provide the specified phase perturbation in the first backscatter signal by modulating a tuning characteristic of the antenna in the first implantable device. Modulating the tuning characteristic of the antenna in the first implantable device may involve using amplitude shift key (ASK) modulation.

The external midfield source device may comprise control circuitry that is configured to update the specified phase perturbation based on a quality characteristic of the first backscatter signal when it is received from the first implantable device. The system may further comprise a second implantable device configured to receive the midfield signal from the external midfield source device and to provide a second backscatter signal, wherein the external midfield source device is configured to encode first and second instructions in the midfield signal, for use by the first and second implantable devices, respectively, to introduce different specified phase perturbations in the first and second backscatter signals.

In some embodiments, the system further comprises processor circuitry configured to generate a correction signal, based on an expected self-interference between the multiple ports of the unitary RF antenna, and the external midfield source device is configured to extract information from the first backscatter signal about the first implantable device using the correction signal. The processor circuitry may be a component of the external midfield source device.

In some embodiments, the external midfield source device comprises an RF source signal generator configured to provide an RF carrier signal to (1) a first signal processor circuitry configured to provide respective RF drive signals, based on the RF carrier signal, to the multiple ports of the unitary RF antenna, and to (2) a second signal processor circuitry configured to provide a self-interference cancellation signal, based on the RF carrier signal, wherein the external midfield source device is configured to apply the self-interference cancellation signal to the first backscatter signal to extract information about the first implantable device that is encoded in the first backscatter signal.

In accordance with several embodiments, a method for extracting information from a backscatter signal received using a first one of multiple RF ports comprising portions of a unitary antenna in a midfield transceiver device is provided. The method comprises generating a self-interference mitigation signal based on a priori information about signal leakage characteristics between the multiple RF ports of the midfield transceiver device, receiving, using the first one of the multiple RF ports, the backscatter signal from an implantable device in response to a midfield power and/or data signal, the backscatter signal including an information signal encoded in the backscatter signal by the implantable device, and extracting the information signal from the backscatter signal using the self-interference mitigation signal.

In some embodiments, generating the self-interference mitigation signal is based on calculated or measured information about a signal leakage between respective pairs of the multiple RF ports of the midfield transceiver device. The method may further comprise providing the power and/or data signal from the midfield transceiver device, using the multiple RF ports, to the implantable device, wherein the power and/or data signal is based on an RF carrier signal, and wherein the generating the self-interference mitigation signal comprises providing an amplitude-modulated and/or phase-modulated version of the RF carrier signal. The method may further comprise determining a quality characteristic of the extracted information signal from the backscatter signal and, based on the quality characteristic, selectively updating the self-interference mitigation signal to enhance the quality.

In accordance with several embodiments, a method for wirelessly communicating information from an implantable device to an external midfield transceiver comprises modulating a wirelessly-received midfield signal at the implantable device to thereby transmit a backscatter signal that is encoded, according to the modulation, with implantable device information, receiving the backscatter signal at the external midfield transceiver, and decoding the backscatter signal using a self-interference mitigation signal that is based on measured or predicted interference characteristics associated with multiple, concurrently-excited ports of a unitary RF antenna of the external midfield transceiver. In some embodiments, the implantable device information includes one or more of information about a therapy provided by the implantable device, information about a therapy to be provided by the implantable device, information about a power conversion efficiency for the implantable device, or information about an electrode impedance characteristic of an electrode coupled to the implantable device. Modulating the wirelessly-received midfield signal may be performed according to a modulation scheme dictated by the external midfield transceiver.

In accordance with several embodiments, a method of providing a neural stimulation therapy comprises wirelessly receiving a power signal at or using receiver circuitry in an implantable neural stimulation device. The power signal is generated and transmitted by a midfield coupler device and includes a non-negligible magnetic field (H-field) component that is substantially parallel to a surface of the midfield coupler device. The method further comprises, using a therapy delivery circuitry that is coupled to the receiver circuitry and to multiple electrodes that are configured to deliver electrostimulation signals to one or more neural targets, providing a neural stimulation therapy using a portion of the wirelessly received power signal, including sequentially providing stimulation signals to respective different electrostimulation vectors, the vectors corresponding to different combinations of the multiple electrodes, with a non-stimulation interval provided between each stimulation signal provided to a different vector. In some embodiments, providing the neural stimulation therapy comprises providing the neural stimulation therapy multiple times with the same non-stimulation interval provided between each therapy.

In some embodiments, the method comprises generating and transmitting the power signal (which may be a microwave signal) using the midfield coupler device, including focusing the power signal to a location within body tissue that is within a wavelength, as measured in air, of the power signal. The step of wirelessly receiving the power signal may involve using an E-field or magnetic-field (e.g., H-field) based antenna coupled to the implantable neural stimulation device.

In some embodiments, sequentially providing the stimulation signals comprises providing at least first and second neural stimulation signals at or near the same neural target using respective different electrostimulation vectors, wherein one of the first and second neural stimulation signals is less optimal than the other one of the first and second neural stimulation signals for eliciting a patient response to the therapy. Providing the at least first and second neural stimulation signals may comprise providing signals having substantially the same pulse width, amplitude, or frequency characteristic. In some embodiments, providing the at least first and second neural stimulation signals comprises providing signals having different pulse width, amplitude, or frequency characteristics.

In some embodiments, sequentially providing the stimulation signals comprises providing at least four discrete neural stimulation signals to a neural target using respective different electrostimulation vectors, wherein at least one of the discrete neural stimulation signals is more optimal than the others for eliciting a patient response to the therapy. Providing the at least four discrete neural stimulation signals may comprise providing signals having substantially the same pulse width, amplitude, or frequency characteristic or providing signals having at least two different pulse width, amplitude, or frequency characteristics.

The method may further comprise identifying, using processor circuitry that is communicatively coupled to the implantable neural stimulation device, multiple available neural stimulation vectors corresponding to the multiple electrodes that are configured to deliver the neural stimulation therapy, and selecting, using the same or different processor circuitry, at least two of the identified neural stimulation vectors for use by the therapy delivery circuitry to deliver the neural stimulation therapy to the one or more neural targets. The selecting step may comprise selecting first and second neural stimulation vectors, wherein one of the selected vectors is previously-known to be more effective than the other in eliciting a patient response to the therapy. In some embodiments, the selecting step is performed without a priori knowledge of an effectiveness of one or more of the selected vectors for eliciting a patient response to the therapy. In some embodiments, the selecting step comprises selecting a first vector that includes a first electrode as an anode and includes multiple commonly-coupled other electrodes as a cathode, and selecting a second vector that includes a second electrode as an anode and includes the first electrode commonly-coupled with at least one other electrode as a cathode.

The selecting step may comprise selecting at least three different neural stimulation vectors for use by the therapy delivery circuitry to deliver the neural stimulation therapy, wherein the providing the neural stimulation therapy includes providing respective stimulation signals to each of the at least three selected vectors, in turn, with the non-stimulation interval provided between each stimulation signal, and wherein an order in which the respective stimulation signals are provided is randomly selected. In some embodiments, sequentially providing stimulation signals to the respective different electrostimulation vectors with a non-stimulation interval between each stimulation signal comprises providing a first stimulation signal, comprising a portion of the neural stimulation therapy, using a first one of the electrostimulation vectors, following the first stimulation signal, inhibiting delivery of a neural stimulation therapy from all of the electrostimulation vectors for the non-stimulation interval, and following the non-stimulation interval, providing a subsequent second stimulation signal, comprising a portion of the neural stimulation therapy, using a different second one of the electrostimulation vectors.

In some embodiments, providing the neural stimulation therapy to a patient is repeated multiple times with the same or different non-stimulation interval between each neural stimulation therapy signal provided. In some embodiments, providing the neural stimulation therapy to the patient is repeated multiple times, each time using a different order in which the neural stimulation therapy signal is provided to the different electrostimulation vectors.

In some embodiments, the step of wirelessly receiving the power signal comprises receiving portions of the same or different power signal at two different implantable neural stimulation devices, with each device including two or more electrodes configured to deliver a neural stimulation signal, and wherein using the therapy delivery circuitry includes using two different therapy delivery circuitry to provide portions of the neural stimulation therapy, with each therapy delivery circuitry being associated with a different one of the implantable neural stimulation devices.

In some embodiments, sequentially providing the stimulation signals with a non-stimulation interval provided between each stimulation signal comprises inhibiting a stimulation signal from being delivered by the implantable neural stimulation device for the non-stimulation interval. In one embodiment, the interval is at least about 50 milliseconds (e.g., at least 40 milliseconds, at least 50 milliseconds, at least 60 milliseconds, at least 70 milliseconds, at least 80 milliseconds, at least 90 milliseconds, at least 100 milliseconds, between 50 and 100 milliseconds, between 80 and 120 milliseconds, between 100 and 150 milliseconds, overlapping ranges thereof, or any value within the recited ranges). Other smaller or larger intervals may also be used.

In accordance with several embodiments, an implantable therapy delivery device (e.g., adapted to provide neural electrostimulation) comprises or consists essentially of receiver circuitry including an electric-field or magnetic-field based antenna configured to receive a wireless microwave power signal from a midfield transmitter circuitry when the receiver circuitry is implanted within tissue and therapy delivery circuitry coupled to the receiver circuitry, the therapy delivery circuitry configured to provide a series of electrostimulation signals using a portion of the received wireless microwave power signal from the midfield transmitter circuitry. The therapy delivery circuitry comprises an output stage configured to provide the sequential series of electrostimulation signals to respective different electrostimulation vectors corresponding to different pairs of electrodes that are implanted in the tissue.

The implantable therapy delivery device can further include at least three electrodes (e.g., three electrodes, four electrodes, five electrodes, six electrodes, seven electrodes, eight electrodes, or more than eight electrodes) configured to be implanted in the tissue at or near a neural stimulation target. The at least three electrodes may be axially arranged along an implantable lead. In some embodiments, the therapy delivery circuitry is configured to randomly select an order for providing the series of electrostimulation signals using different pairs or groupings of the at least three electrodes.

The therapy delivery circuitry may be configured to repeatedly provide the series of electrostimulation signals for a specified number of iterations or for a specified duration. In some embodiments, the output stage comprises a first output configured to provide a first signal in the series of electrostimulation signals to a first pair or group of electrodes corresponding to a first electrostimulation vector and a second output configured to provide a subsequent second signal in the series of electrostimulation signals to a different second pair or group of electrodes corresponding to a different second electrostimulation vector, with at least one electrode being common to the first and second pairs or groups of electrodes.

In some embodiments, the therapy circuitry output stage is configured to inhibit delivery of electrostimulation signals from the first and second outputs for a delay interval between the first and subsequent second signals. The first output may be configured to provide the first signal having a first amplitude, pulse width, or frequency characteristic and the second output may be configured to provide the second signal having the same first amplitude, pulse width, or frequency characteristic. In some embodiments, the first output is configured to provide the first signal having a first amplitude, pulse width, or frequency characteristic and the second output is configured to provide the second signal having a different second amplitude, pulse width, or frequency characteristic.

In some embodiments, the therapy circuitry output stage is configured to provide the sequential series of electrostimulation signals to the respective different electrostimulation vectors including at least one vector that is suboptimal for eliciting a patient response. In some embodiments, the output stage is configured to provide the sequential series of electrostimulation signals to the respective different electrostimulation vectors, selected from among a set of available electrostimulation vectors, wherein one of the selected vectors is more optimal than at least one other selected vector for eliciting a patient response.

The implantable neural stimulation device may also comprise memory (e.g., nonvolatile memory or memory circuitry) coupled to the receiver circuitry. The memory is configured to store instructions received from the midfield transmitter circuitry about which of multiple available electrostimulation vectors to use to provide the sequential series of electrostimulation signals.

In accordance with several embodiments, a system comprises or consists essentially of a midfield transmitter configured to transmit wireless signals at a first frequency and an at least partially implantable biocompatible device including receiver circuitry including an antenna that receives the wireless signals from the midfield transmitter and a therapy delivery circuitry coupled to the receiver circuitry, the therapy delivery circuitry configured to provide a therapy signal comprising a series of at least two electrostimulation pulses provided using respective vectors corresponding to different combinations of the at least three electrodes, with a specified delay interval between each pulse, wherein the series of pulses is repeated at least twice. The wireless signals include a non-negligible magnetic field (H-field) component that is substantially parallel to a surface of the midfield transmitter. The midfield transmitter is adapted to focus the wireless signals to a location within tissue that is within about one wavelength, as measured in air, of the wireless signals.

In accordance with several embodiments, a method of providing a neural electrostimulation therapy comprises providing a neural electrostimulation therapy to a neural target using a first pair of electrodes implanted in patient tissue. The method comprises providing a first electrostimulation signal at a first frequency, and providing, substantially concurrently with the first electrostimulation signal and using a second pair of electrodes implanted in the patient tissue, a second electrostimulation signal at a different second frequency that is less than the first frequency. An amplitude characteristic of the first electrostimulation signal may be modulated by a phase characteristic of the second electrostimulation signal, or vice-versa.

In some embodiments, modulating (e.g., amplifying) the amplitude characteristic of the first electrostimulation signal is performed by using a specified phase characteristic of the second electrostimulation signal. The method may further comprise wirelessly receiving a power signal at or using receiver circuitry in an implantable neural electrostimulation device. The power signal may be a power signal generated and transmitted by a midfield coupler device that includes a non-negligible magnetic field (H-field) component that is substantially parallel to a surface of the midfield coupler device. In some embodiments, the implantable neural stimulation device comprises the first and second pairs of electrodes and the first and second electrostimulation signals comprise portions of the received power signal. The method may further comprise generating the power signal using a signal generator circuitry in the midfield coupler device and transmitting the power signal from the midfield coupler device using an electromagnetic structure that is configured to generate an evanescent field outside of body tissue. Transmitting the power signal may comprise focusing the power signal to a location within body tissue that is within a wavelength, as measured in air, of the power signal. The power signal may be a microwave signal.

In some embodiments, the method comprises selecting, for therapy delivery, and using processor circuitry in an implantable neural electrostimulation device or in a midfield power transmitter device or midfield coupler device, at least two neural electrostimulation vectors for providing the neural electrostimulation therapy. The selected electrostimulation vectors correspond respectively to the first and second pairs of electrodes and the first and second pairs of electrodes may be coupled to the implantable neural electrostimulation device.

In some embodiments, providing the first electrostimulation signal comprises providing a signal having a lesser peak amplitude characteristic than a peak amplitude characteristic of the second electrostimulation signal. In some embodiments, providing the first electrostimulation signal is performed using first and second electrodes that are axially spaced along a lead portion of an implantable neural electrostimulation device and providing the second electrostimulation signal is performed using third and fourth electrodes that are axially spaced along the lead portion and axially spaced from the first and second electrodes along the lead portion.

While continuously providing the first electrostimulation signal at the first frequency, the second electrostimulation signal may be inhibited after a first duration and, substantially concurrently with the first electrostimulation signal, a third electrostimulation signal at a third frequency may be provided. In one embodiment, the amplitude characteristic of the first electrostimulation signal is differently modulated by the respective phase characteristics of the first and second electrostimulation signals. Providing the third electrostimulation signal may be performed using a different third pair of electrodes implanted in the patient tissue or using the second pair of electrodes implanted in the patient tissue.

In some embodiments, providing the first electrostimulation signal using the first pair of electrodes is performed using electrodes disposed on a first implantable lead and providing the second electrostimulation signal using the second pair of electrodes comprises using electrodes disposed on a different second implantable lead.

The method may further comprise sensing an intrinsic neural signal using a sensor disposed at or near a second neural target and using processor circuitry to determine a frequency or phase characteristic of the sensed intrinsic neural signal. The method may also comprise selecting one of the first and second frequencies based on the determined frequency or phase characteristic of the sensed intrinsic neural signal using the processor circuitry.

In some embodiments, the method comprises periodically inhibiting the providing the second electrostimulation signal while continuously providing the first electrostimulation signal. In some embodiments, the first frequency of the first electrostimulation signal is about 120 Hz and the second frequency of the second electrostimulation signal is about 20 Hz. The first frequency may be between 100 Hz and 500 Hz (e.g., between 100 Hz and 150 Hz, between 110 and 140 Hz, between, 120 Hz and 160 Hz, between 200 Hz and 400 Hz, between 300 Hz and 500 Hz, overlapping ranges thereof, or any value within the recited ranges) and the second frequency may be between 1 Hz and 80 Hz (e.g., between 1 Hz and 10 Hz, between 5 Hz and 30 Hz, between 10 Hz and 30 Hz, between 15 Hz and 50 Hz, between 20 Hz and 60 Hz, between 30 Hz and 80 Hz, between 30 Hz and 60 Hz, overlapping ranges thereof, or any value within the recited ranges).

In some embodiments, the method comprises identifying a neural pathology in a patient based on a sensed physiological signal from the patient, and in response, selecting amplitude characteristics for the first and second electrostimulation signals to overdrive the sensed physiological signal from the patient. The method may comprise timing the providing of the first or second electrostimulation signals to coincide with an intrinsic neural pulse event in a patient body to augment, improve or enhance one or more characteristics of the intrinsic neural pulse event.

In accordance with several embodiments, a system comprises a midfield transmitter configured to transmit wireless signals at a first frequency and an at least partially implantable biocompatible device including receiver circuitry including an antenna that receives the wireless signals from the midfield transmitter and therapy delivery circuitry, coupled to the receiver circuitry. The wireless signals may include a non-negligible H-field component and the midfield transmitter may be specifically adapted to focus the wireless signals to a location within tissue that is within about one wavelength, as measured in air, of the wireless signals. In some embodiments, the therapy delivery circuitry is configured to provide a phase-amplitude coupled therapy signal that includes a first signal component provided using a first neural electrostimulation vector and a second signal component provided using a different second neural electrostimulation vector, with the second signal component being provided substantially concurrently with the first signal component.

The biocompatible device may comprise at least four electrodes that are axially spaced apart along a lead portion of the biocompatible device, with two of the four electrodes being configured for use as the first neural electrostimulation vector and the other two of the four electrodes being configured for use as the second neural electrostimulation vector. Each of the at least four electrodes may be a ring electrode, or cylindrical electrode. Other shapes or configurations of electrodes may also be used.

In some embodiments, the therapy delivery circuitry comprises a first oscillator circuitry configured to provide the first signal component having a first frequency characteristic and a first amplitude characteristic and a second oscillator circuitry configured to provide the second signal component having a different second frequency characteristic and a different second amplitude characteristic. In one embodiment, the first frequency characteristic is greater than the second frequency characteristic and the second amplitude characteristic is greater than the first amplitude characteristic. In one embodiment, the second frequency characteristic is greater than the first frequency characteristic and the first amplitude characteristic is greater than the second amplitude characteristic. In some embodiments, the therapy delivery circuitry is configured to adjust an amplitude or frequency characteristic of at least one of the first and second signal components of the phase-amplitude coupled therapy signal to overcome a patient's neural pathophysiology or to otherwise improve neurologic function (e.g., to overcome symptoms, such as related to one or more of a body movement disorder, Parkinson's disease, dementia, Alzheimer's disease, Creutzfeldt-Jakob disease, Huntington's disease, depression, dystonia, or epilepsy, among others).

In accordance with several embodiments, systems and methods for embedding communication signals with electrostimulation therapy are provided. For example, a method for wirelessly communicating data between an external source device and an implantable device may comprise generating and transmitting a midfield power signal using an external source device and receiving the midfield power signal at an implantable device implanted below a tissue surface and providing a nearfield electrostimulation therapy using the implantable device and a portion of the received midfield power signal. The method may also comprise receiving, at the external source device, a farfield signal that corresponds to the nearfield electrostimulation therapy. In some embodiments, receiving the farfield signal is accomplished using electrodes coupled to the tissue surface and to the external source device. The method may further comprise using the external source device and, based on the received farfield signal, reporting information to a user and/or to a remote device about the nearfield electrostimulation therapy and/or reporting information to a user and/or to a remote device about the implantable device. The method may also comprise updating a characteristic of the midfield power signal and generating and transmitting an updated midfield power signal to the same or different implantable device.

In some embodiments, providing the nearfield electrostimulation therapy comprises providing multiple therapy pulses interleaved with one or more data communication intervals, with each data communication interval comprising multiple data signal pulses. In some embodiments, providing the nearfield electrostimulation therapy comprises providing the therapy pulses at a first frequency and providing, within each data communication interval, the data signal pulses at a higher second frequency. In some embodiments, providing the nearfield electrostimulation therapy comprises providing multiple therapy pulses, wherein at least one of the therapy pulses includes an amplitude-modulated portion, and wherein the amplitude-modulated portion encodes information about the nearfield electrostimulation therapy and/or about the implantable device.

The method may further comprise reporting information to a user and/or to a remote device about the nearfield electrostimulation therapy. This reporting step may comprise, for example, providing an audible, vibratory, or visual indication about whether the nearfield electrostimulation therapy was successfully provided by the implantable device. In some embodiments, the reporting step comprises providing information about a quantity or quality of the midfield power signal received by the implantable device.

The method may comprise updating a characteristic of the midfield power signal and generating and transmitting the updated midfield power signal, including adjusting an amplitude, phase, or frequency characteristic of the updated signal. In some embodiments, the method comprises using a pocket, sleeve, or article of clothing (such as described herein) that is configured to maintain electrodes of the external source device in electrical contact with the tissue surface.

In response to receiving the midfield power signal at the implantable device, the method may comprise generating the nearfield electrostimulation therapy using a generator circuitry in the implantable device. This generating step may comprise generating a signal pulse train having a pulse-width modulated or pulse-amplitude modulated portion that encodes information for the external source device about the therapy and/or about the implantable device itself.

In some embodiments, the method comprises measuring, using the implantable device, a characteristic of the midfield power signal received by the implantable device, encoding, using the implantable device, information about the measured characteristic in the nearfield electrostimulation therapy, decoding, using the external source device, the information about the measured characteristic in the nearfield electrostimulation therapy, and reporting information to a user and/or to a remote device about the implantable device, including the information about the measured characteristic of the midfield power signal received by the implantable device. In some embodiments, generating and transmitting the midfield power signal using the external source device comprises encoding specified information about a pulse pattern, frequency, range of frequencies, signal burst, amplitude, pulse width, or waveform morphology for the implantable device to use to provide the nearfield electrostimulation therapy.

The step of receiving the farfield signal that corresponds to the nearfield electrostimulation therapy may comprise determining whether the received signal corresponds to the specified information about the pulse pattern, frequency, range of frequencies, signal burst, amplitude, pulse width, or waveform morphology. In some embodiments, providing the nearfield electrostimulation therapy using the implantable device comprises providing a pulse-based therapy wherein a pulse pattern of the pulse-based therapy encodes the information about the nearfield electrostimulation, or the information about the implantable device. Providing the pulse-based therapy with the encoded information may comprise introducing a phase offset in the pulse pattern corresponding to the encoded information.

In accordance with several embodiments, an implantable neural stimulation therapy delivery device comprises or consists essentially of receiver circuitry including an electric field or magnetic field based antenna configured to receive a midfield power signal from an external source device when the receiver circuitry is implanted within tissue and therapy delivery circuitry, coupled to the receiver circuitry, that is configured to provide signal pulses to electrostimulation electrodes using a portion of the received midfield power signal from the external source device. The signal pulses may advantageously comprise electrostimulation therapy pulses and data pulses.

In some embodiments, the therapy delivery circuitry is configured to interleave a discrete series of data pulses between successive therapy pulses. The discrete series of data pulses may encode information about the implantable device itself or about a therapy provided by the implantable device. In some embodiments, the therapy delivery circuitry is configured to embed multiple data pulses in a therapy pulse. In some embodiments, the therapy delivery circuitry is configured to amplitude-modulate or pulse width-modulate a portion of the therapy pulse according to the multiple data pulses.

The therapy delivery circuitry may be configured to provide the data pulses during a blanking period between successive therapy pulses. In some embodiments, the therapy delivery circuitry is configured to provide the data pulses at a frequency that is at least twice the frequency of the therapy pulses. The therapy delivery circuitry may be configured to encode information about a status of the implantable device and/or about a therapy provided by the implantable device in the data pulses.

The implantable neural stimulation therapy delivery device may further comprise power detector circuitry configured to measure an amount of power received via the midfield power signal. In some embodiments, the therapy delivery circuitry is configured to encode information about the measured amount of power in the data pulses.

The data pulses may comprise pulses having less than about a 2-volt peak amplitude and/or having a frequency of about 100 kHz or more. In some embodiments, the therapy pulses comprise pulses having a pulse frequency that is about an order of magnitude less than a pulse frequency of the data pulses.

In accordance with several embodiments, an external transmitter/receiver (transceiver) device comprises a midfield transmitter including multiple subwavelength structures configured to concurrently transmit respective multiple RF signals to a target device implanted in tissue, an electrode pair configured to be disposed at an external surface of the tissue, the electrode pair configured to receive an electrical signal via the tissue, the electrical signal corresponding to an electrostimulation therapy delivered to the tissue by the target device, and a demodulator circuitry coupled to the electrode pair and configured to demodulate a portion of the received electrical signal to recover a data signal originated by the target device. In some embodiments, the external transceiver device comprises demodulator circuitry configured to discriminate data pulses from therapy pulses in the electrical signal. The demodulator circuitry may be configured to identify a modulated portion of a therapy pulse in the electrical signal and to demodulate the identified portion to recover the data signal. In some embodiments, the external transceiver device comprises user feedback circuitry, the user feedback circuitry including an audible, vibratory, or visual alert that can be provided to a user based on the recovered data signal.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 11A illustrates, by way of example, a perspective view diagram of a proximal portion of an embodiment of an implantable device.

FIG. 11B illustrates, by way of example, a perspective view diagram of a proximal portion of another embodiment of an implantable device.

FIG. 11C illustrates, by way of example, a perspective view diagram of a proximal portion of yet another embodiment of an implantable device.

FIG. 12A illustrates, by way of example, a perspective view diagram of an embodiment of an implantable device with an external housing invisible to show the internal circuitry of the implantable device.

FIG. 12B illustrates, by way of example, an exploded view diagram of a portion of the implantable device in the dashed box labelled "12B" in FIG. 12A.

FIG. 13A illustrates, by way of example, a perspective view diagram of an embodiment of a proximal portion of an implantable device and attachable tines.

FIG. 13B illustrates, by way of example, a perspective view diagram of an embodiment of the proximal portion of the implantable device and attachable tines.

FIG. 13C illustrates, by way of example, a perspective view diagram of an embodiment of the implantable device with attached tines.

FIG. 14A illustrates, by way of example, a perspective view diagram of an embodiment of a system for attaching tines to an implantable device.

FIG. 14B illustrates, by way of example, a perspective view diagram of an embodiment of the system of FIG. 14A with the tines being pushed closer to the implantable device.

FIG. 14C illustrates, by way of example, a perspective view diagram of an embodiment of the system of FIG. 14B with the tines attached to the implantable device.

FIG. 18 illustrates, by way of example, a perspective view diagram of an embodiment of a suture and tine deployment mechanism attached to a proximal portion of an implantable device.

FIG. 19 illustrates, by way of example, a perspective view diagram of an embodiment of the suture and tine deployment mechanism of FIG. 18 with radiopaque markers on the tine deployment mechanism.

FIG. 20 illustrates, by way of example, a perspective view diagram of an embodiment of a suture attached to a proximal portion of an implantable device.

FIG. 25A illustrates, by way of example, a perspective view diagram of an embodiment of a stylet in a conduit of the implantable device.

FIG. 25B illustrates, by way of example, a perspective view diagram of another embodiment of a stylet in a conduit of the implantable device.

FIG. 29 illustrates, by way of example, a perspective view diagram of an embodiment of a catheter and dilator for creating a path for or to an implantable device within a body.

FIG. 30 illustrates, by way of example, a perspective view diagram of an embodiment of another system for situating a pushrod and sheath within a body.

FIG. 31A illustrates, by way of example, a perspective view diagram of an embodiment of a pushrod and a suture attached to a proximal end of the implant.

FIG. 31B illustrates, by way of example, a perspective view diagram of an embodiment of the pushrod over the suture and attached to an attachment structure on the proximal end of the implantable device and the catheter.

FIG. 31C illustrates, by way of example, a perspective view diagram of an embodiment of the implantable device within the catheter.

FIG. 31D illustrates, by way of example, a perspective view diagram of an embodiment of the implantable device partially out of the catheter.

FIG. 32A illustrates, by way of example, a perspective view diagram of an embodiment of a system that includes the system of FIG. 31A positioned at a target anatomy (e.g., an S3 foramen in this example).

FIG. 32B illustrates, by way of example, a perspective view diagram of an embodiment of a system that includes the system of FIG. 32A positioned at a target anatomy with the catheter and the pushrod removed.

FIG. 32C illustrates, by way of example, an exploded view diagram of an embodiment of a proximal portion of the dashed box labelled "32C" in FIG. 32B.

FIG. 33A illustrates, by way of example, a perspective view diagram of an embodiment of an implantable device extraction system.

FIG. 33B illustrates, by way of example, an exploded view diagram of an embodiment of interlaced sutures to assist in implantable device extraction.

FIG. 33C illustrates, by way of example, an exploded view diagram of an embodiment of the system of FIG. 33B with a needle situated over the interlaced sutures.

FIG. 36 illustrates, by way of example, a perspective view diagram of an embodiment of an implantable device.

FIG. 37 illustrates, by way of example, a perspective view diagram of another embodiment of an implantable device.

FIGS. 41A and 41B illustrate, by way of example, a diagram of an embodiment of a technique for assembling an implantable stimulation device.

FIG. 44 illustrates, by way of example, a perspective view diagram of an embodiment of the device of FIG. 43 from the perspective of the arrow labelled "44" in FIG. 43.

FIG. 45 illustrates, by way of example, a perspective view diagram of an embodiment of an implant/explant system.

FIG. 46 illustrates, by way of example, a perspective view diagram of an embodiment of an implant/explant system.

FIG. 54 illustrates, by way of example, a perspective view diagram of an embodiment of an implantable stimulation device.

FIG. 55A illustrates, by way of example, a cross-section diagram of an embodiment of the implantable stimulation device of FIG. 54 in the direction of the arrows labelled "55A/55B".

FIG. 55B illustrates, by way of example, another cross-section diagram of an embodiment of the implantable stimulation device of FIG. 54 in the direction of the arrows labelled "55A/55B".

FIG. 57 illustrates, by way of example, a perspective view diagram of an embodiment of another implantable stimulation device.

FIG. 58A illustrates, by way of example, a perspective view diagram of an embodiment of a plurality of stimulation devices of FIG. 57 implanted in a body with an external midfield powering device external to the body.

FIG. 59 illustrates, by way of example, a perspective view diagram of an embodiment of another implantable stimulation device.

FIG. 60 illustrates, by way of example, a perspective view diagram of an embodiment of a plurality of stimulation devices of FIG. 59 implanted in a body with an external midfield powering device external to the body.

FIG. 61 illustrates, by way of example, a logical circuitry diagram of an embodiment of a plurality of stimulation devices of FIG. 59 within range of respective electric fields generated therebetween.

FIG. 83 illustrates, by way of example, a perspective view diagram of an embodiment of the external device situated in a sleeve that includes the top and bottom layers and an attachment mechanism on a top layer of the sleeve.

FIG. 84A illustrates, by way of example, a perspective view diagram of an embodiment of the external device situated in a sleeve that includes a cushion material on a bottom layer of the sleeve.

FIG. 84B illustrates, by way of example, a perspective view diagram of an embodiment of the external device situated in a sleeve that includes a cushion material on the external device and in the sleeve.

FIG. 85 illustrates, by way of example, a perspective view diagram of an embodiment of the external device situated in a sleeve that is situated between layers of clothing or in a pocket of the clothing.

FIG. 86 illustrates, by way of example, a perspective view diagram of an embodiment of an undergarment that includes a fastening mechanism that allows a user to open a bottom portion of the undergarment while wearing the undergarment.

FIG. 87 illustrates, by way of example, a perspective view diagram of an embodiment of the external device in a closed position.

FIG. 88 illustrates, by way of example, a perspective view diagram of an embodiment of the external device in an open position so as to show internal circuitry, a top cover, and a bottom cover.

FIG. 89 illustrates, by way of example, a perspective view diagram of an embodiment of the external device in a closed position.

FIG. 90 illustrates, by way of example, a perspective view diagram of an embodiment of the external device in an open position so as to show internal circuitry, a top cover, and a bottom cover.

FIG. 91 illustrates, by way of example, a perspective view diagram of an embodiment of a cover (e.g., a top or bottom cover) of the external device that include two air vents.

FIG. 92 illustrates, by way of example, a perspective view diagram of an embodiment of a cover (e.g., a top or bottom cover) of the external device that include four air vents.

FIG. 93 illustrates, by way of example, a perspective view diagram of an embodiment of a cover (e.g., a top or bottom cover) of the external device that includes fins for heat conduction.

Figure 94:
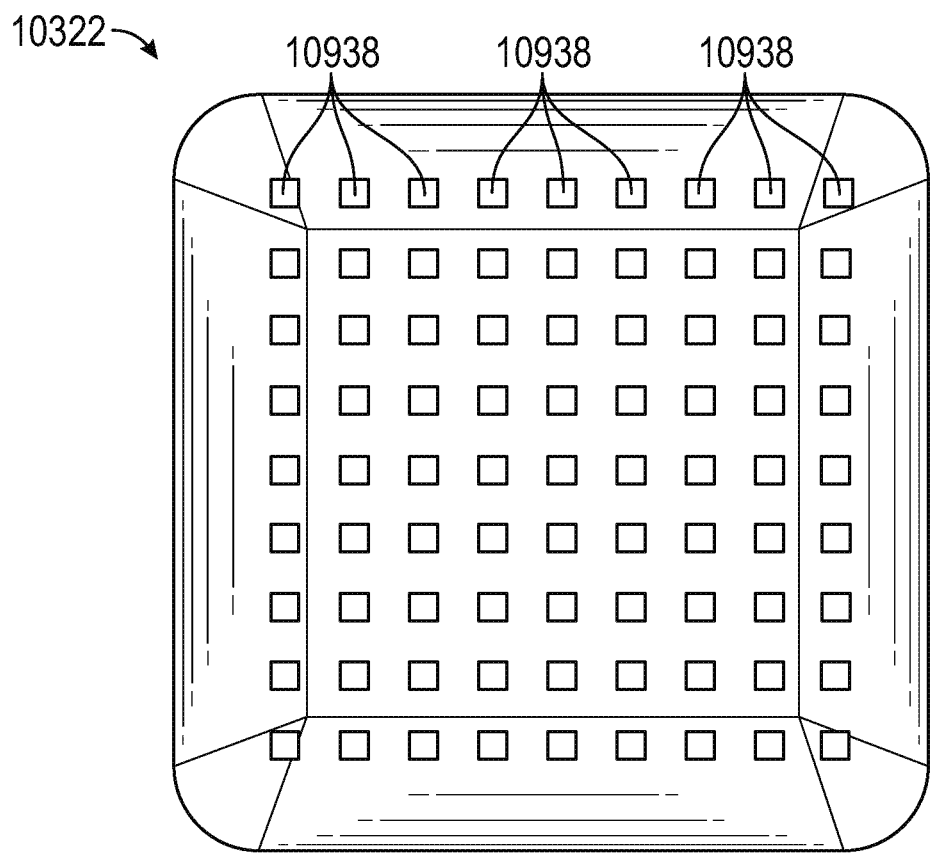

FIG. 94 illustrates, by way of example, another perspective view diagram of an embodiment of a cover (e.g., a top or bottom cover) of the external device that includes fins for heat conduction.

FIG. 95 illustrates, by way of example, a perspective view diagram of another embodiment of the external device in an open position so as to show internal circuitry, a top cover, and a bottom cover.

FIG. 96 illustrates, by way of example, a perspective view diagram of another embodiment of the external device in an open position so as to show internal circuitry, a top cover, and a bottom cover.

FIG. 97 illustrates, by way of example, a perspective view diagram of an embodiment of the external device in a closed position with a fastening mechanism attached to a cover of the external device.

FIG. 98 illustrates, by way of example, a block diagram of an embodiment of a system for communicating with an implanted device.

FIG. 99 illustrates, by way of example, a block diagram of an embodiment of another system for communicating with an implanted device.

FIG. 100 illustrates, by way of example, a block diagram of an embodiment of another system for communicating with an implanted device.

Figure 101A:
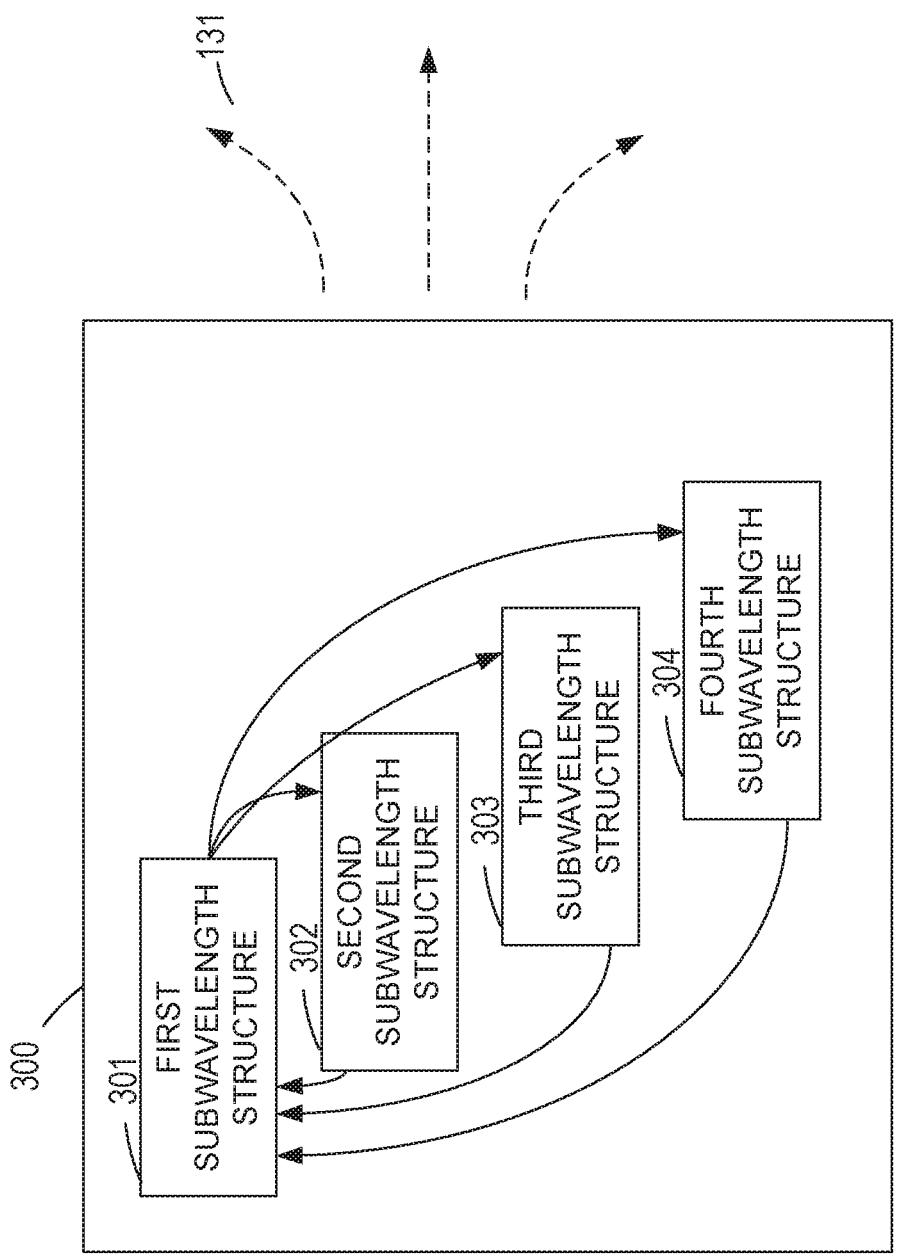

FIG. 101A illustrates, by way of example, a diagram of embodiments of various cross-structure leakage paths of a midfield antenna.

Figure 101B:
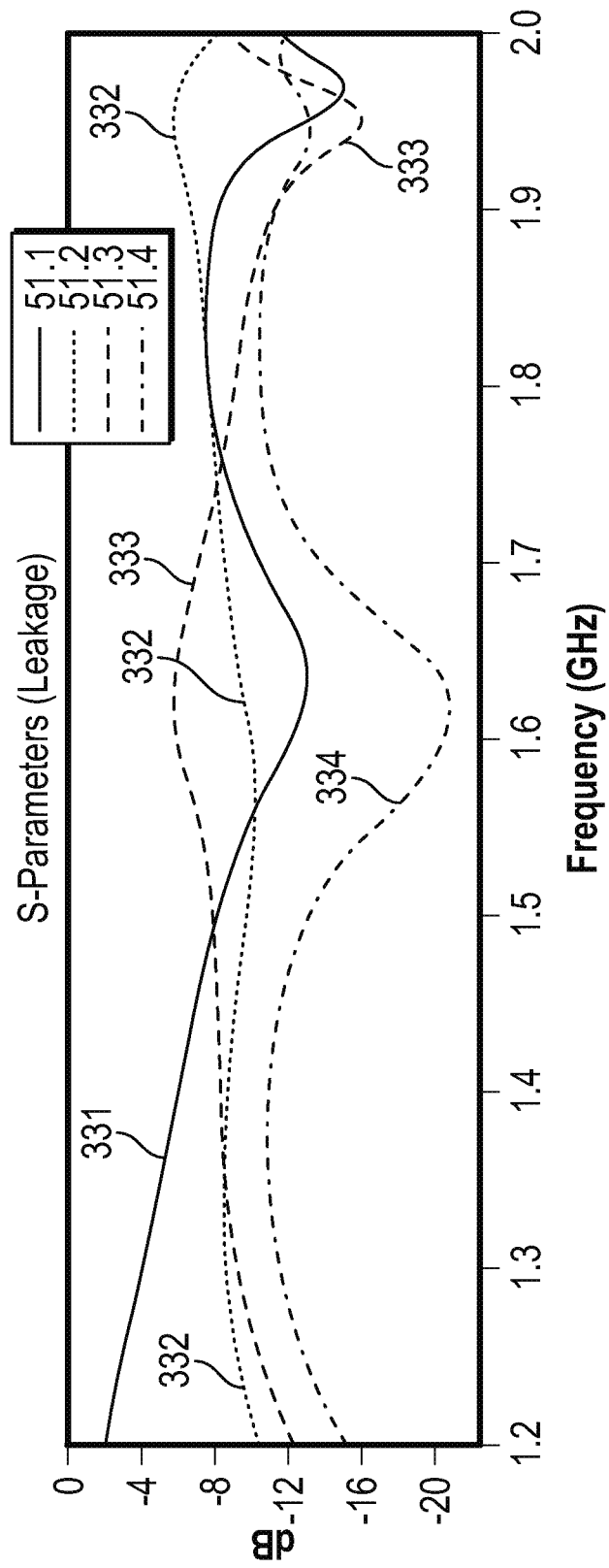

FIG. 101B illustrates, by way of example, a chart that shows embodiments of frequency-dependent leakage paths between various subwavelength structures in an antenna.

Figure 102:
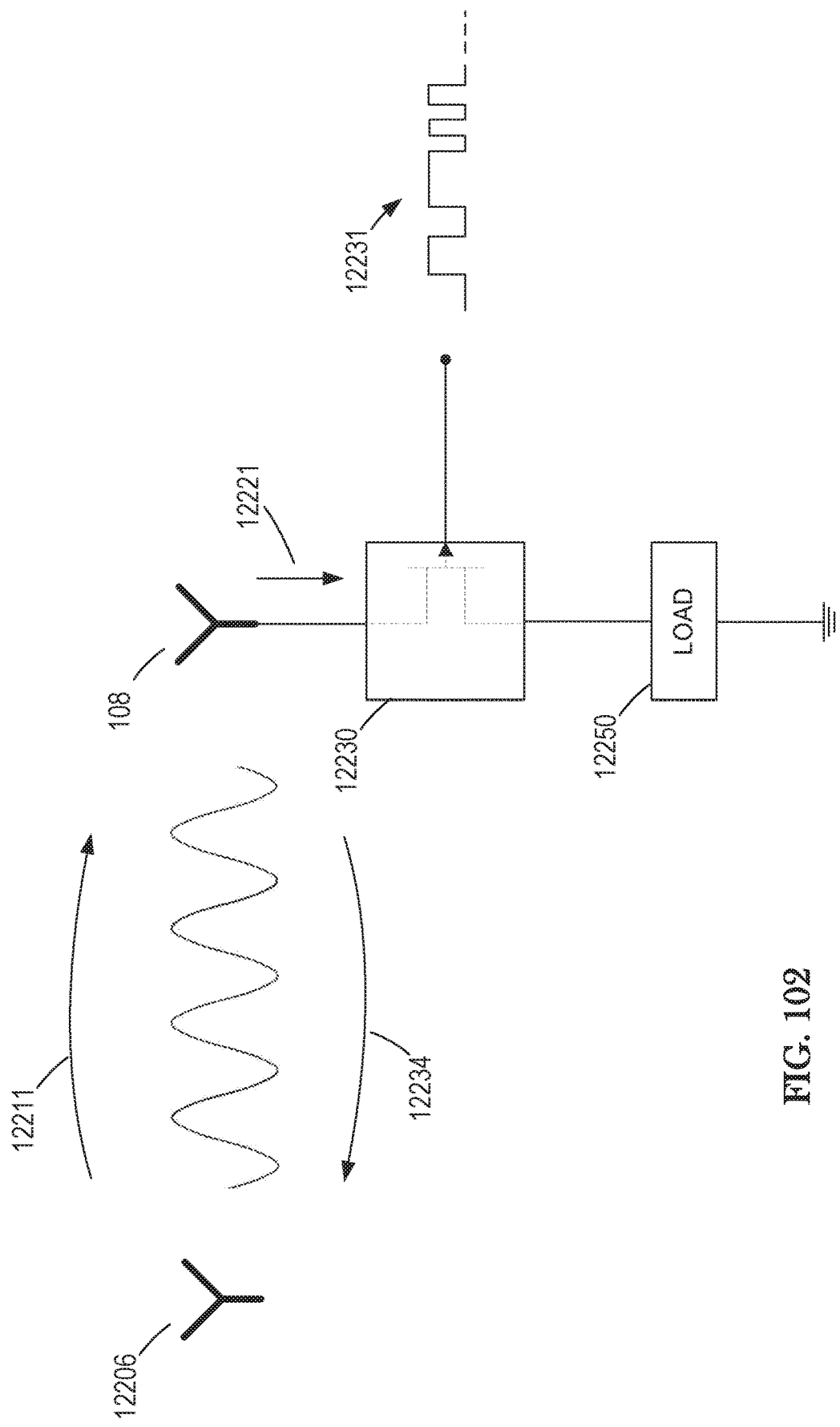

FIG. 102 illustrates, by way of example, a schematic of an embodiment of a backscatter communication system.

Figure 103:
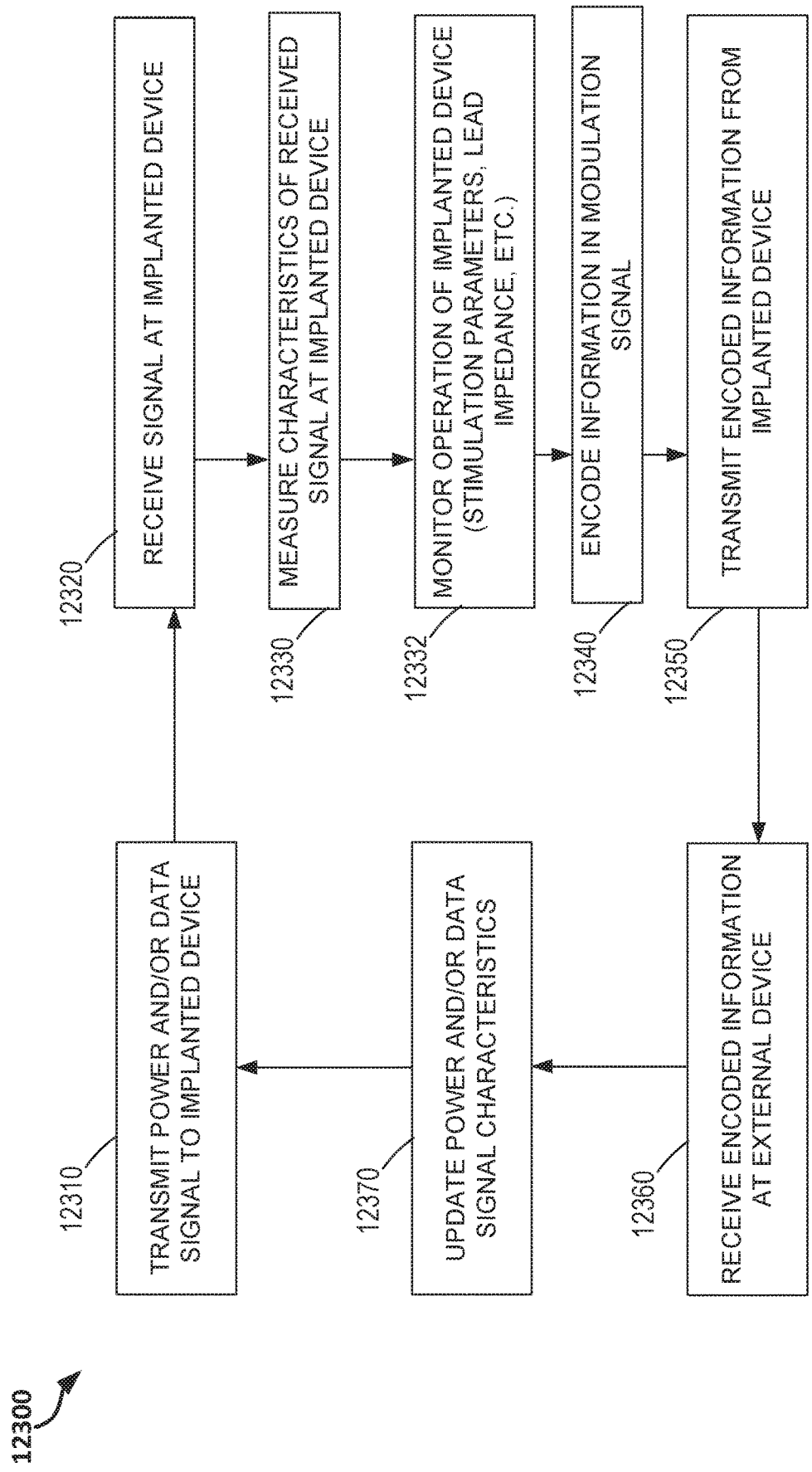

FIG. 103 illustrates, by way of example, a diagram of an embodiment of a method that includes updating a broadcast signal based on information about an implanted device.

Figure 104:
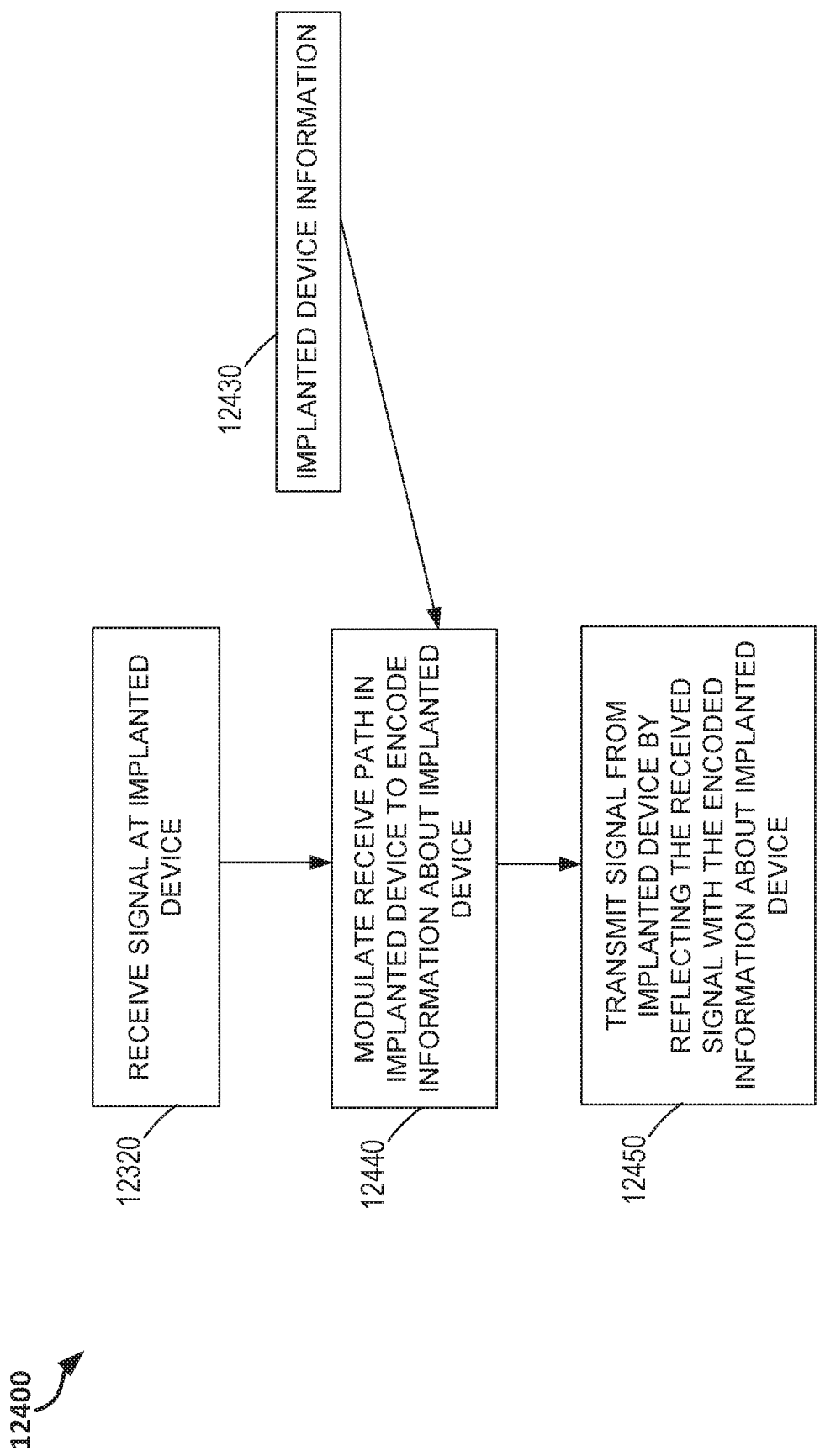

FIG. 104 illustrates, by way of example, a diagram of an embodiment of a method that includes modulating an antenna signal receive path for a wireless signal.

Figure 105:
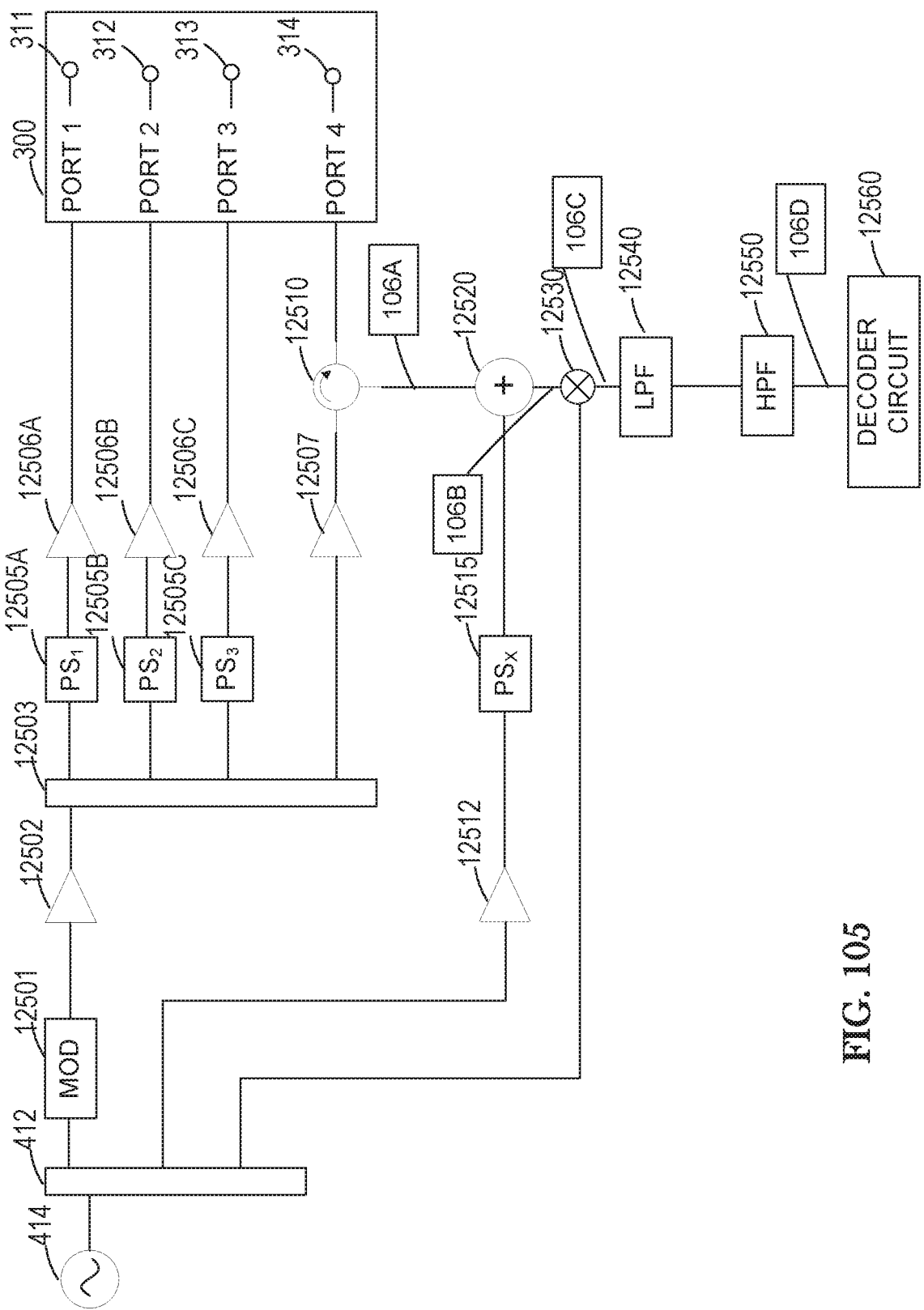

FIG. 105 illustrates, by way of example, a schematic diagram of an embodiment of a system configured to excite a midfield antenna and receive a backscatter signal.

FIGS. 106A-106D illustrate, by way of example, a diagram of an embodiment of signal frequencies corresponding to different portions of the system of FIG. 105.

Figure 107:
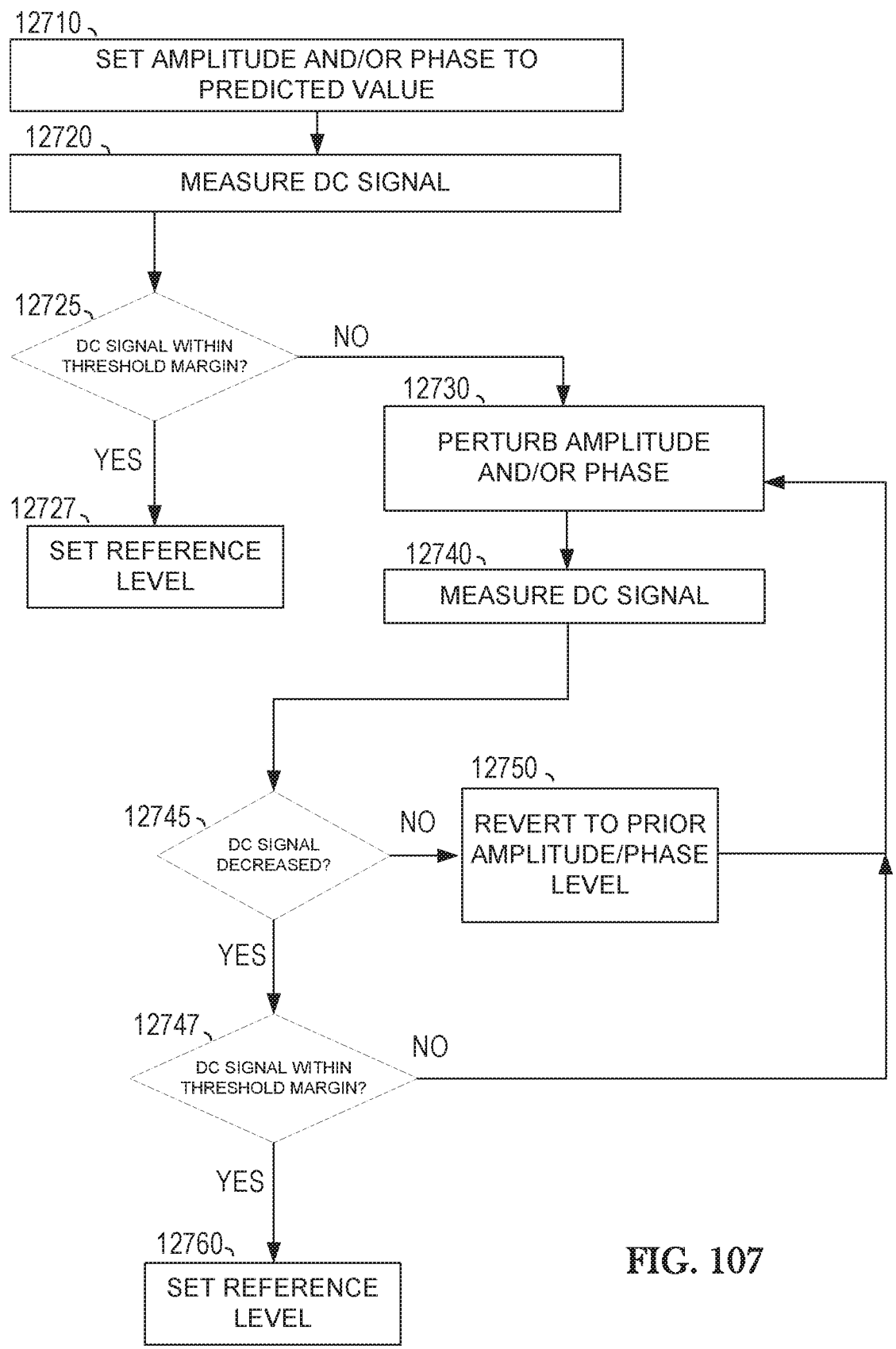

FIG. 107 illustrates, by way of example, a diagram of an embodiment of a method that includes adjusting an amplitude and/or phase characteristic of a cancellation signal.

Figure 108:
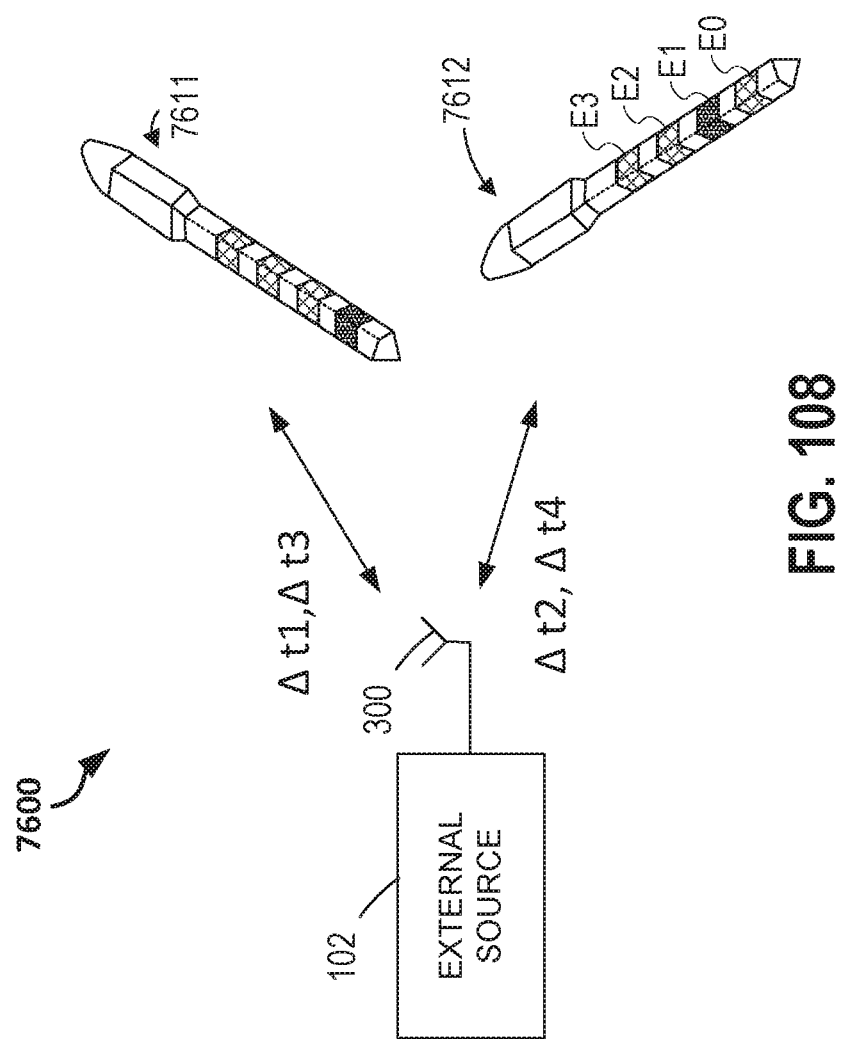

FIG. 108 illustrates, by way of example, a diagram of an embodiment of a system for selectively providing power and/or data communication to multiple target devices.

Figure 109:
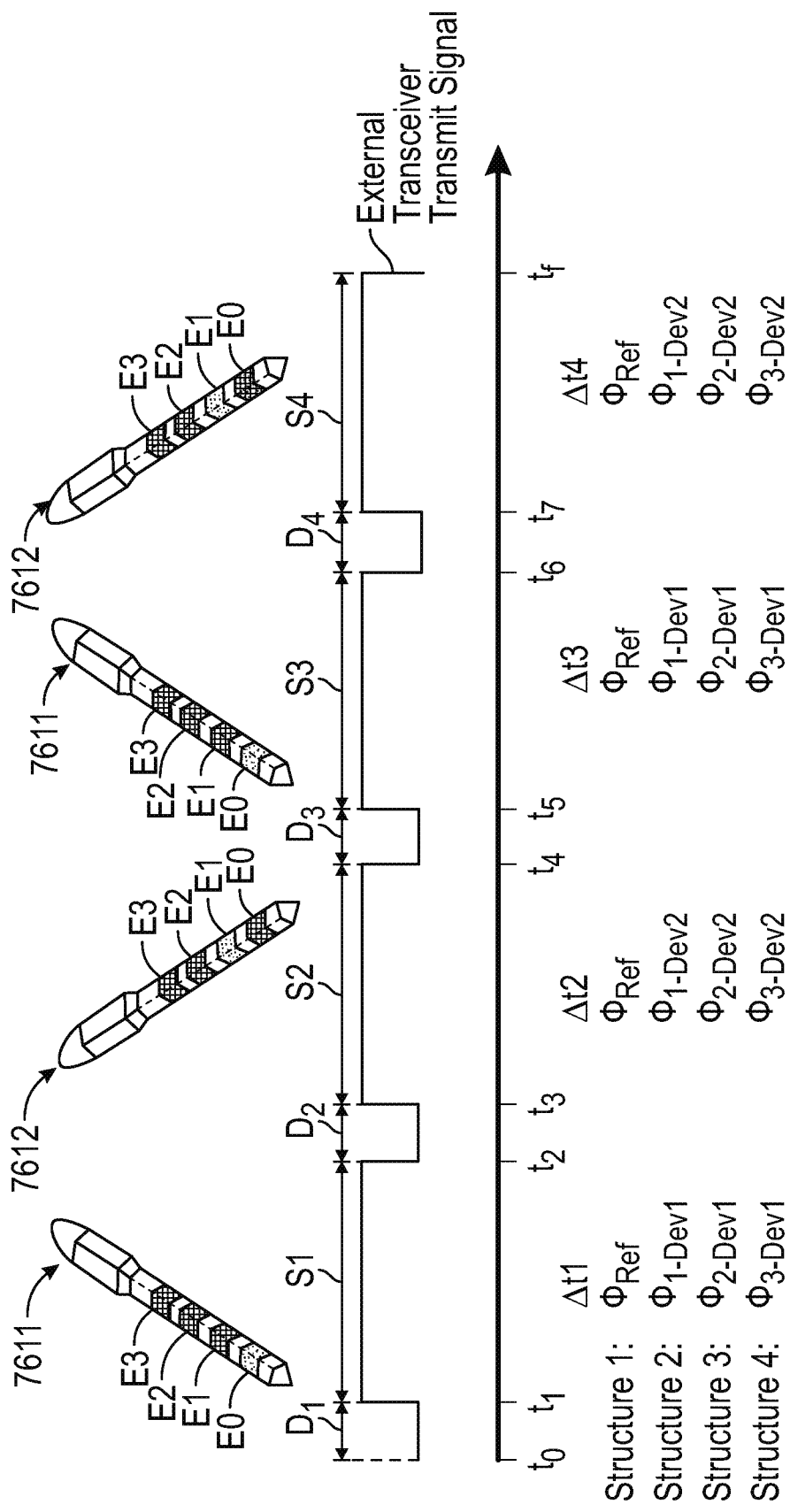

FIG. 109 illustrates, by way of example, a diagram of an embodiment of a method that includes using different signal characteristics to communicate power and/or data signals to different target devices at different times.

Figure 110:
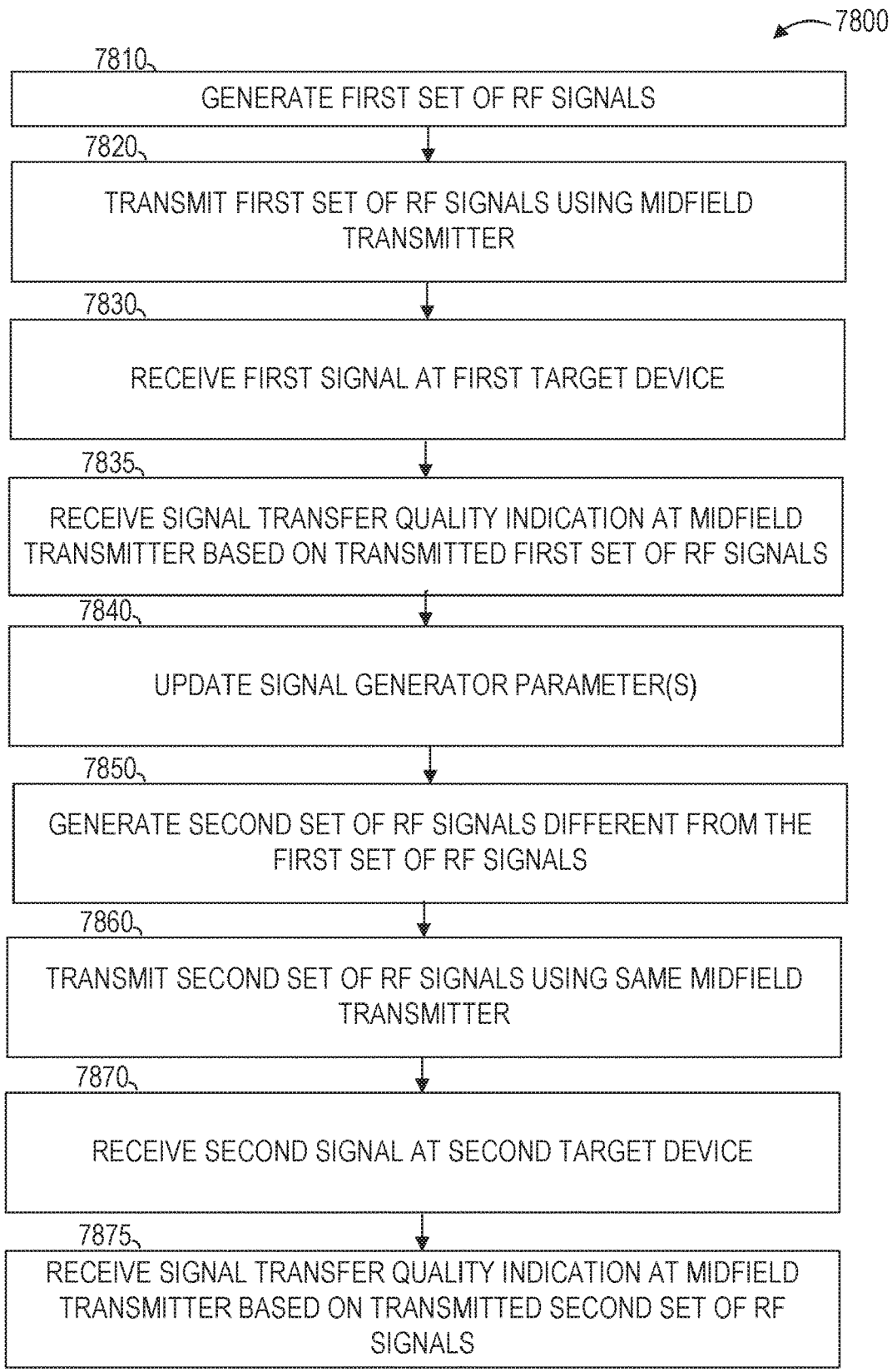

FIG. 110 illustrates, by way of example, a diagram of an embodiment of a method that includes receiving power transfer efficiency information from multiple target devices.

Figure 111:
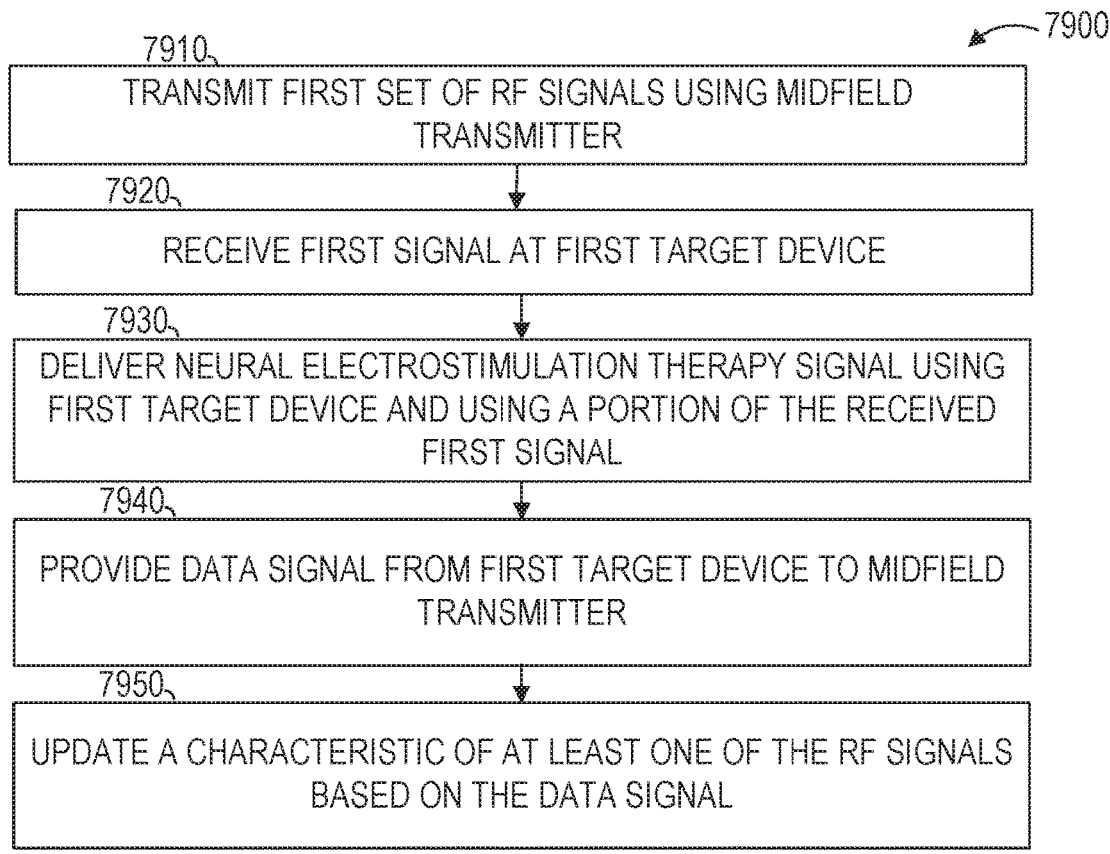

FIG. 111 illustrates, by way of example, a diagram of an embodiment of a method that includes updating a characteristic of at least one signal in a set of RF signals based on a data signal received from a target device.

Figure 112:
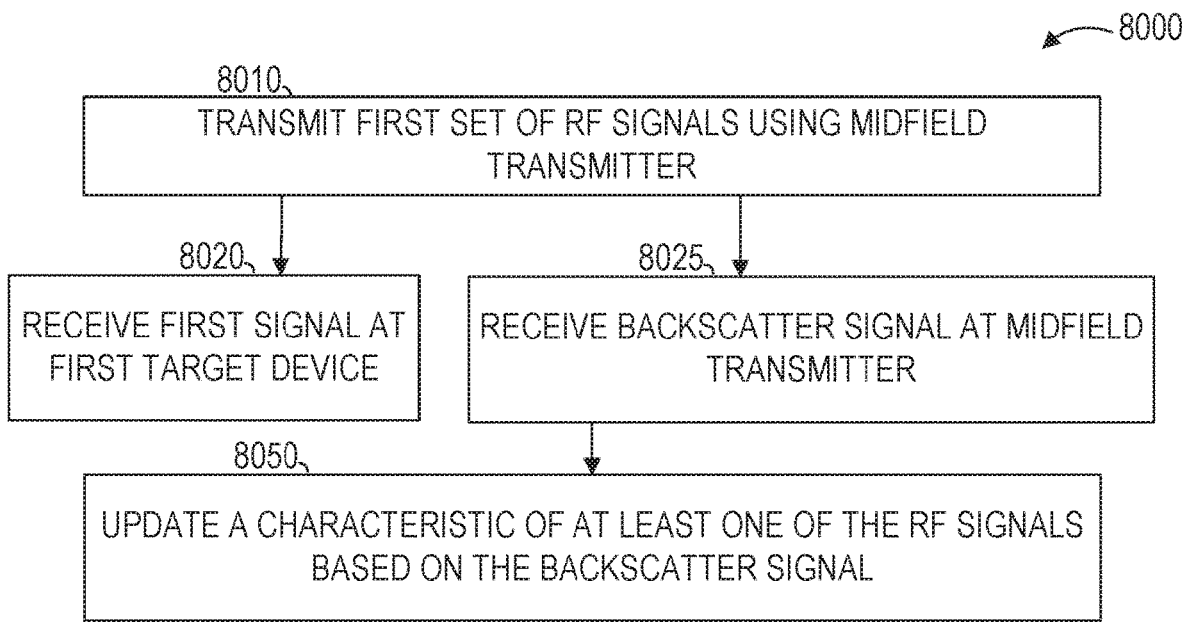

FIG. 112 illustrates, by way of example, a diagram of an embodiment of a method that includes updating a characteristic of at least one signal in a set of RF signals based on a backscatter signal.

Figure 113:
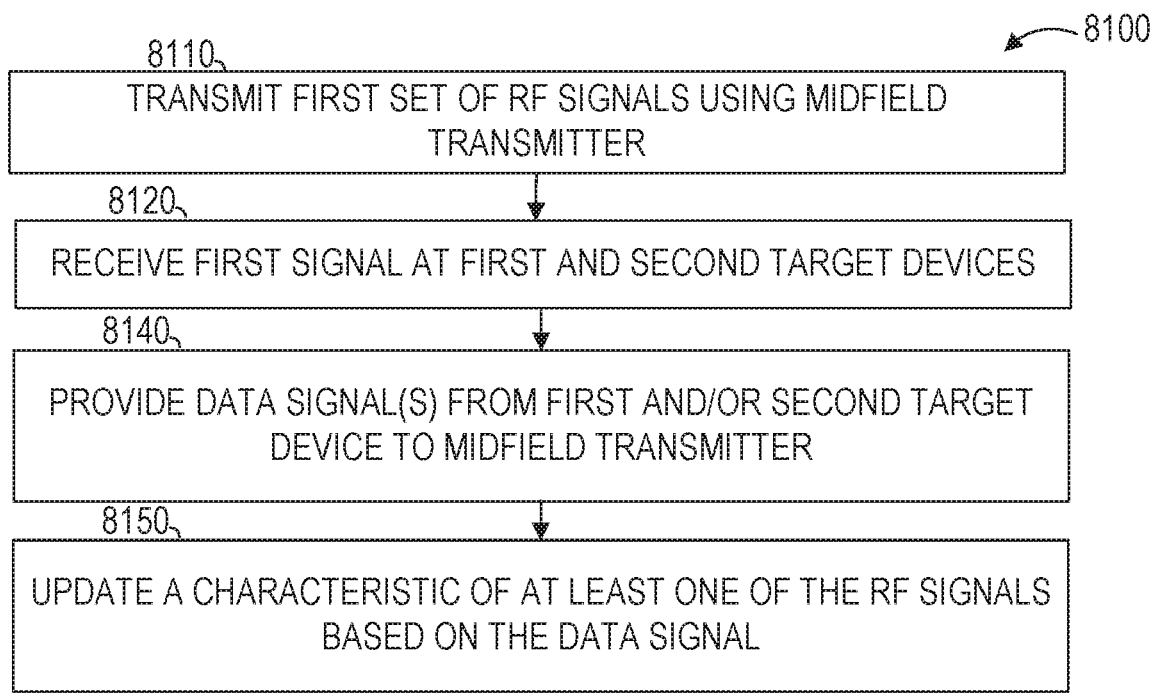

FIG. 113 illustrates, by way of example, a diagram of an embodiment of a method that includes updating a characteristic of at least one signal in a set of RF signals based on a data signal received from a target device.

Figure 114:
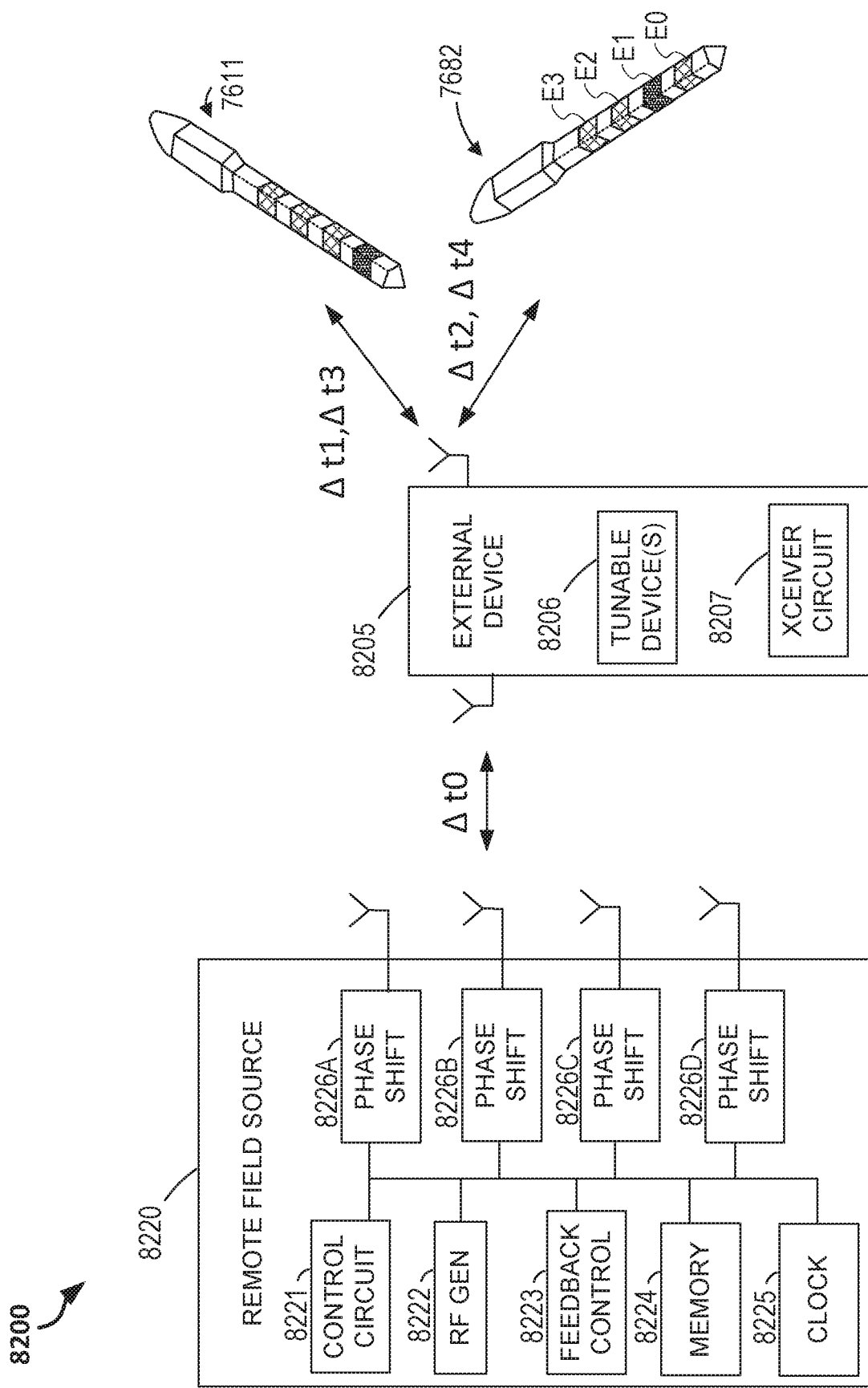

FIG. 114 illustrates, by way of example, a diagram of an embodiment of a system for selectively providing power and/or data to multiple target devices using a remote RF source and a midfield coupler.

Figure 115:
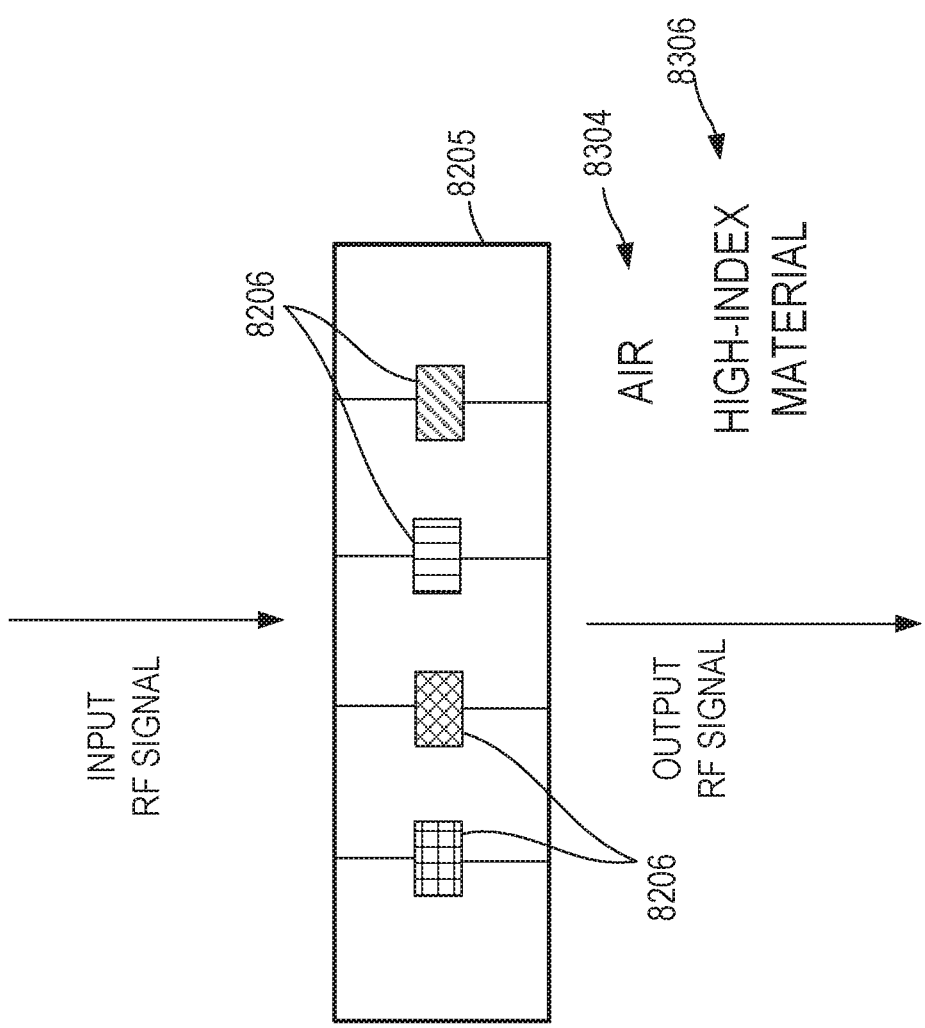

FIG. 115 illustrates, by way of example, a diagram of an embodiment of a midfield coupler with multiple tunable devices.

Figure 116:
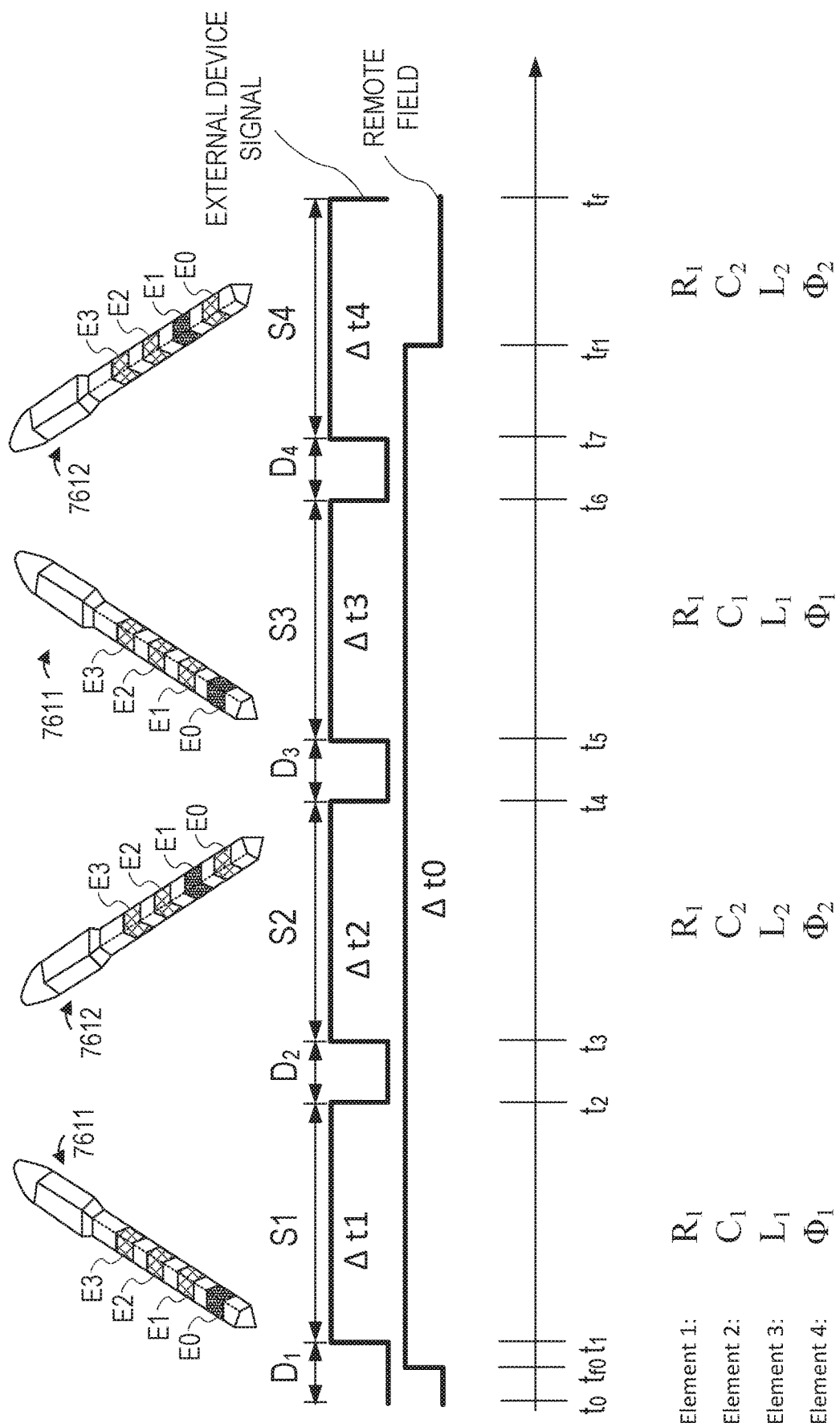

FIG. 116 illustrates, by way of example, a diagram of an embodiment of a method that includes using different signal characteristics to communicate power and/or data signals to different target devices at different times.

Figure 117:
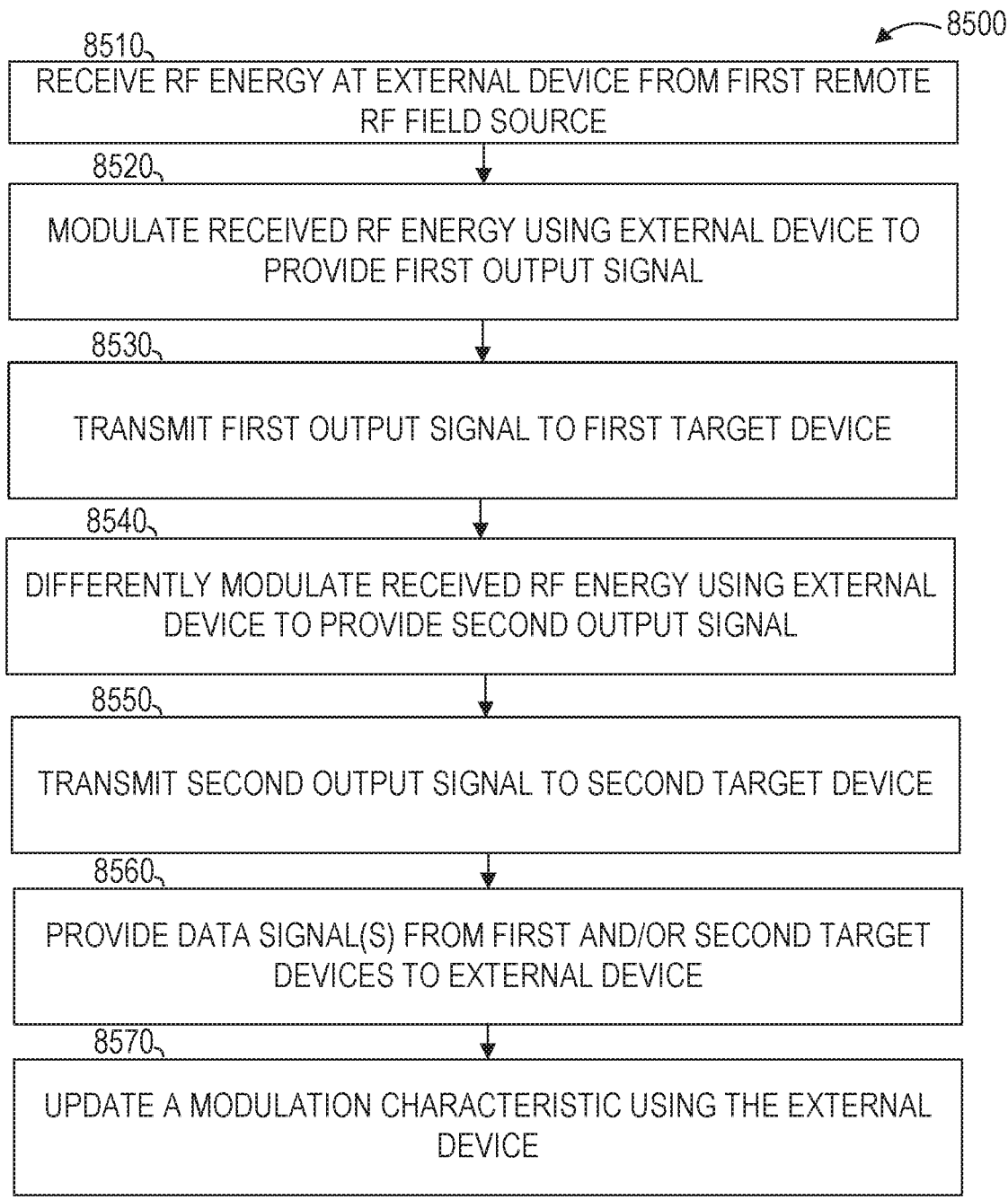

FIG. 117 illustrates, by way of example, a diagram of an embodiment of a method that includes updating a modulation characteristic using an external device.

Figure 118:
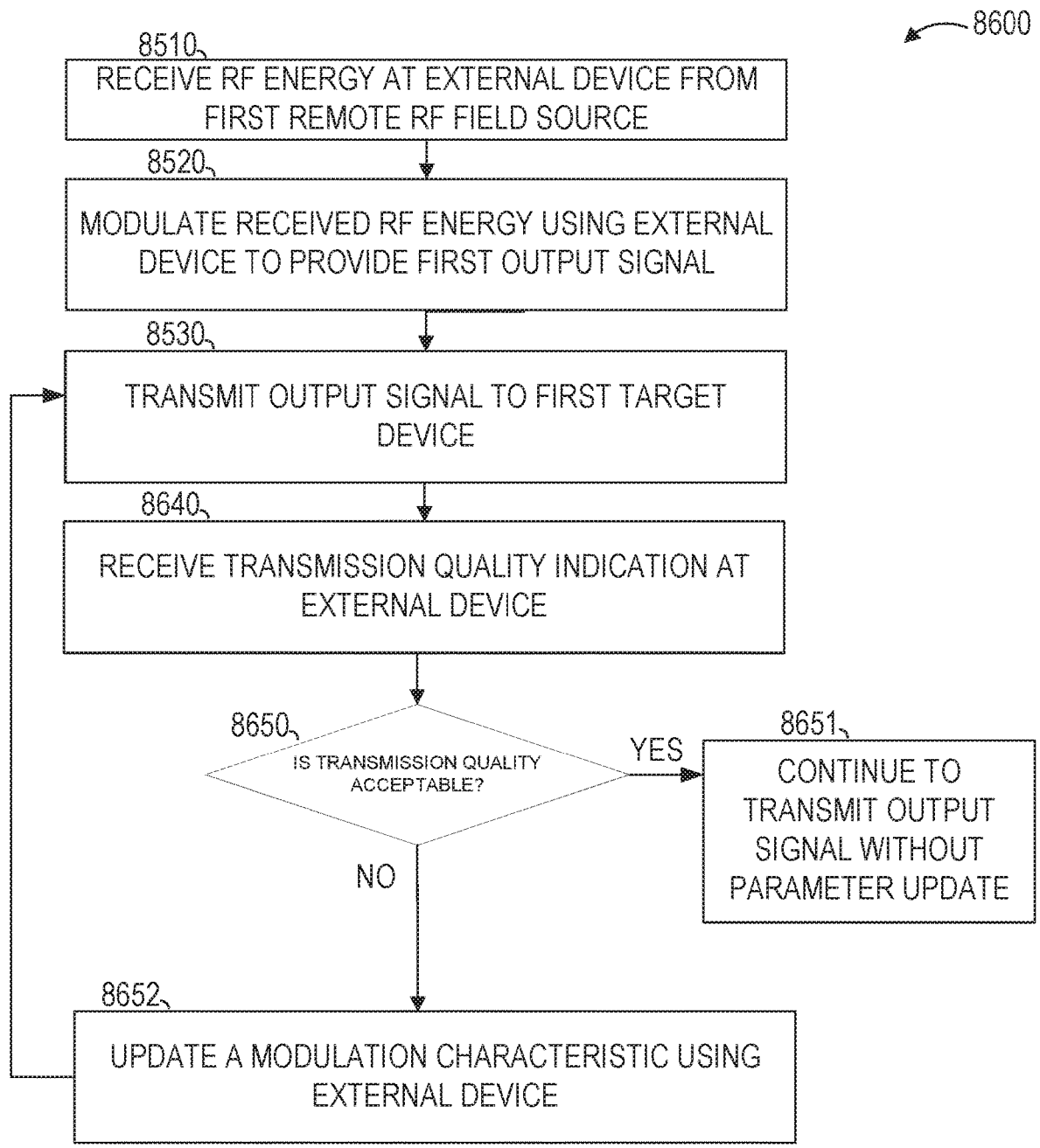

FIG. 118 illustrates, by way of example, a diagram of an embodiment of a method that includes conditionally updating a modulation characteristic using an external device.

Figure 119:
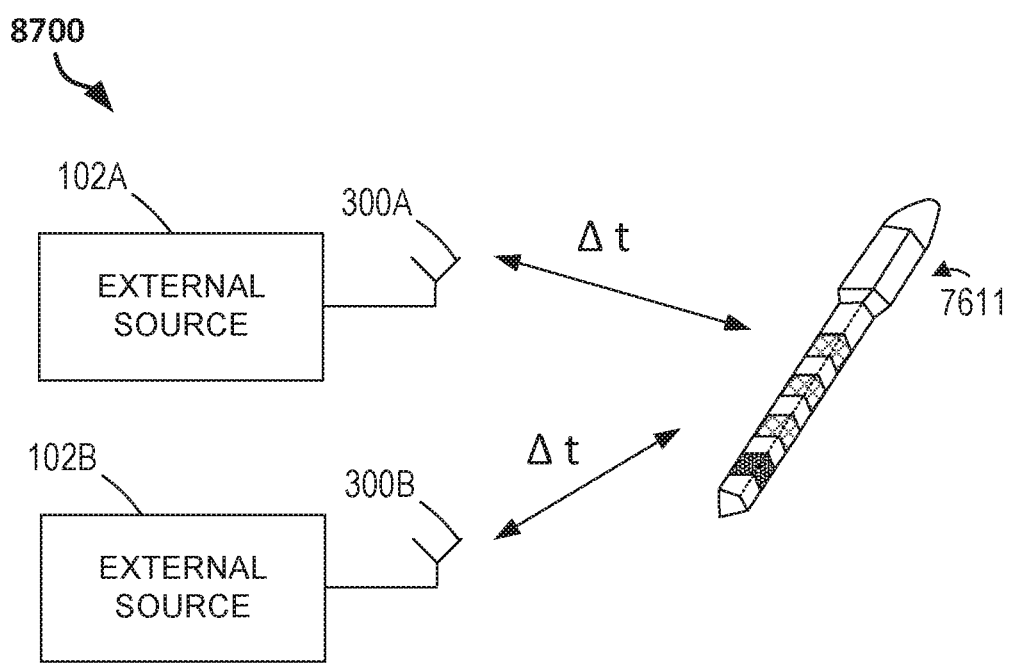

FIG. 119 illustrates, by way of example, a diagram of an embodiment of a system that includes multiple external midfield transceivers.

Figure 120:
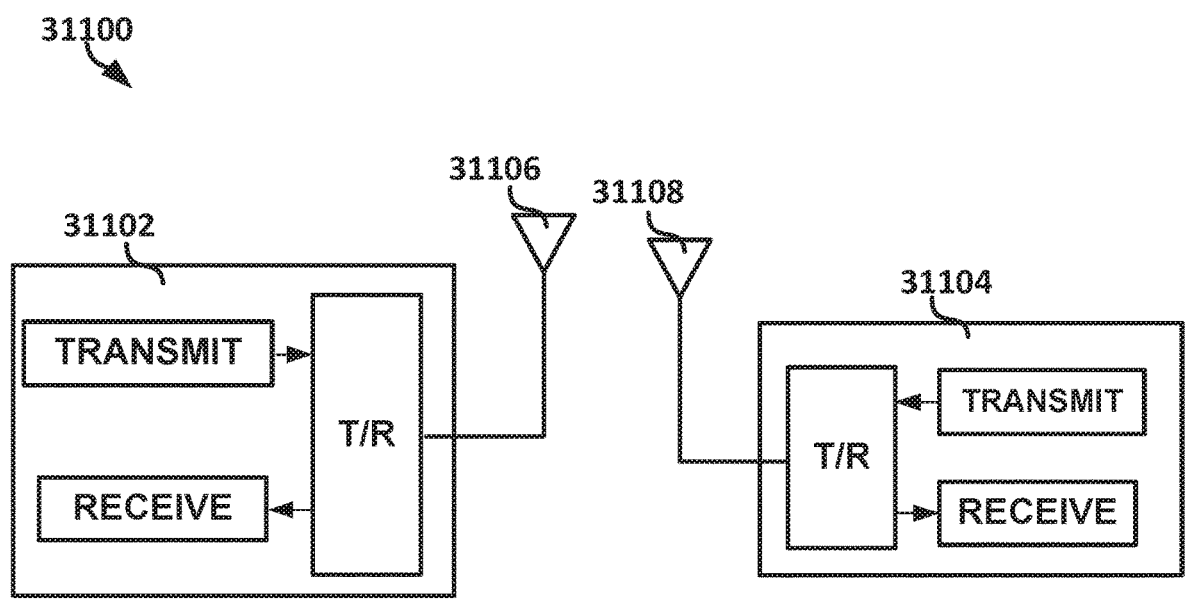

FIG. 120 illustrates, by way of example, a diagram of an embodiment of a communication system.

Figure 121:
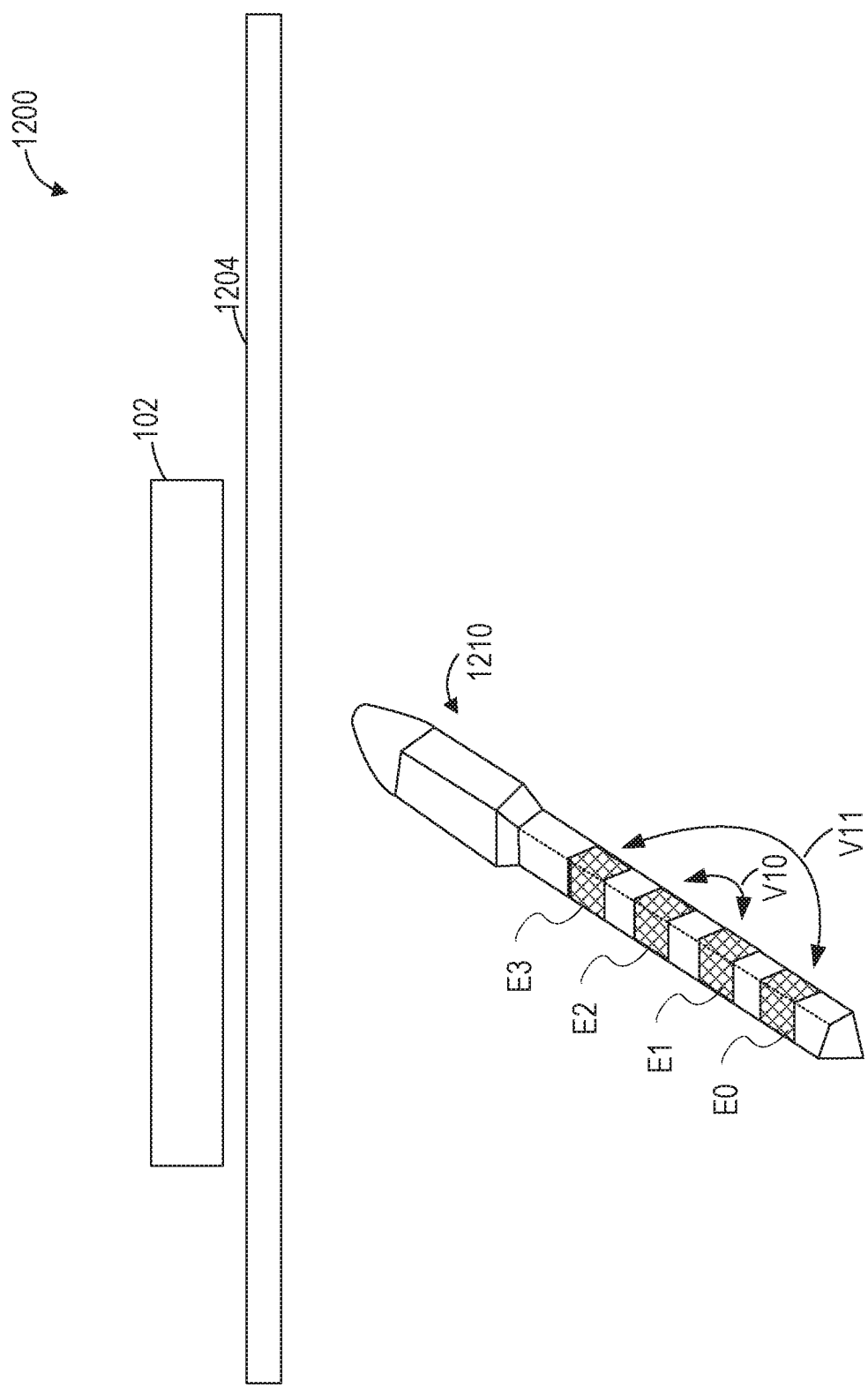

FIG. 121 illustrates, by way of examples, a diagram of an embodiment of a receiver device implanted in tissue.

Figure 122:
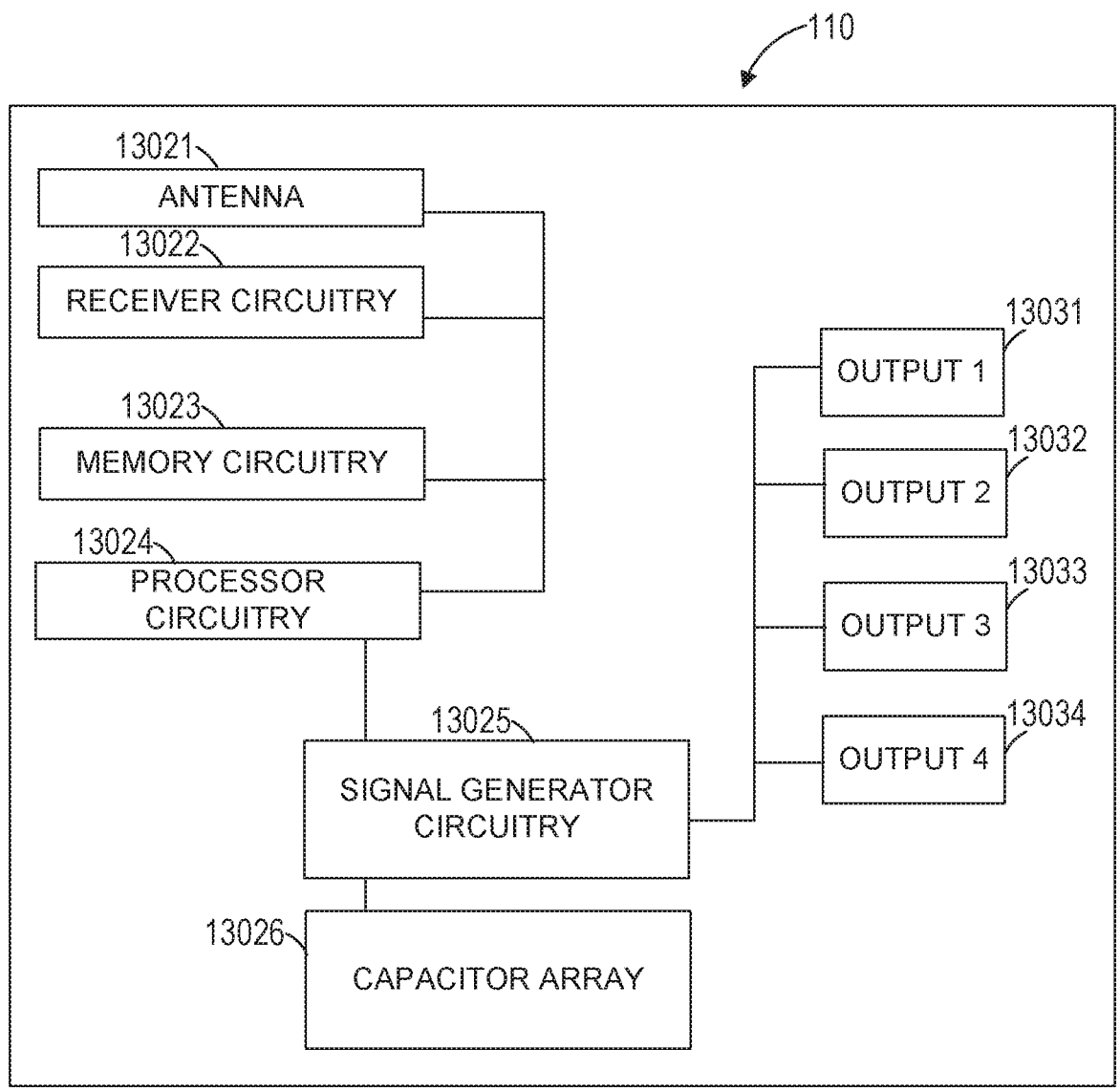

FIG. 122 illustrates, by way of example, a diagram of an embodiment of a multi-polar therapy delivery device.

FIG. 123 illustrates, by way of example, a diagram of an embodiment of available electrostimulation vectors in a four-pole electrostimulation system.

Figure 124A:
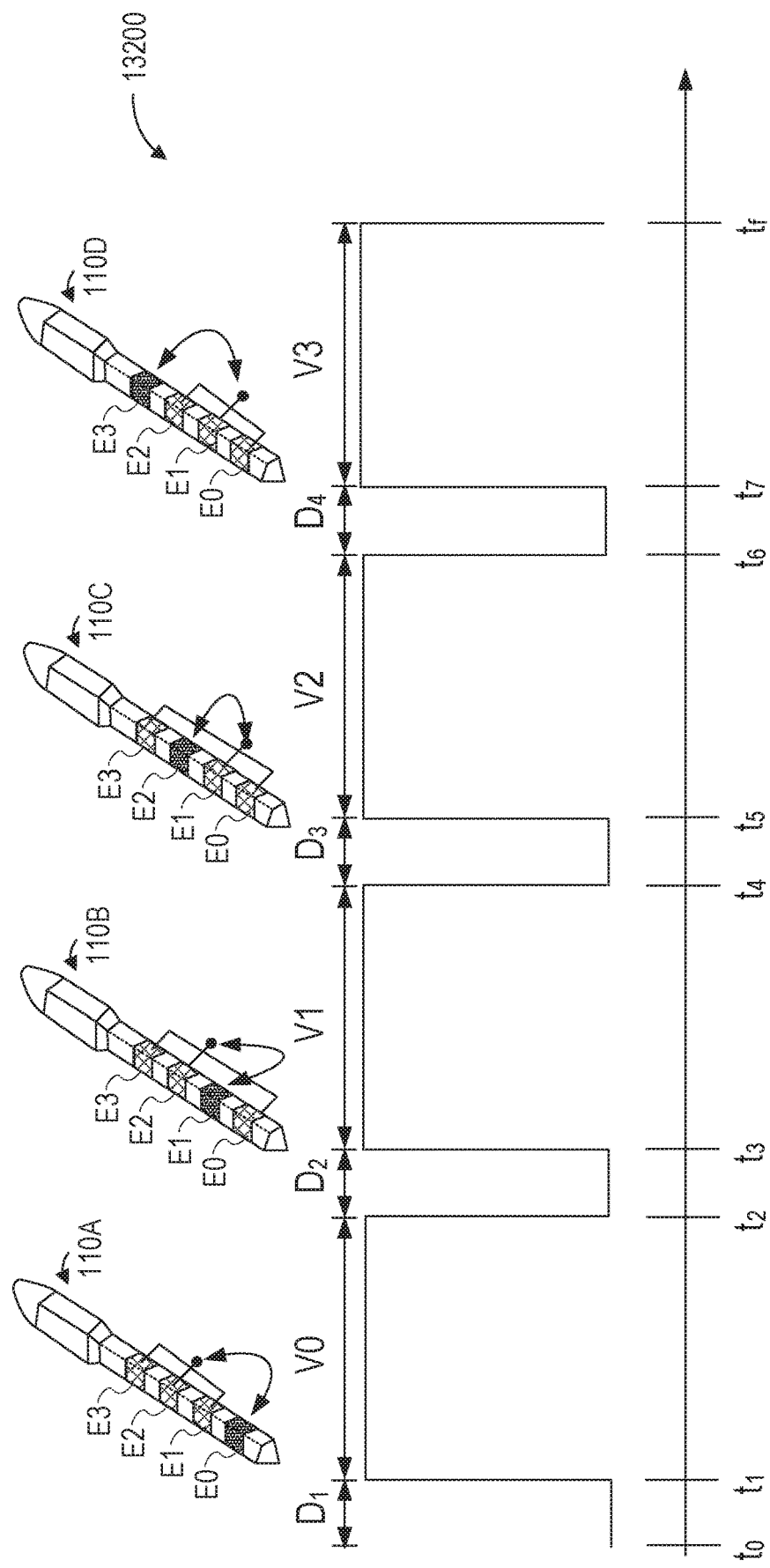

FIG. 124A illustrates, by way of example, a diagram of an embodiment of a neural stimulation therapy delivery sequence.

Figure 124B:
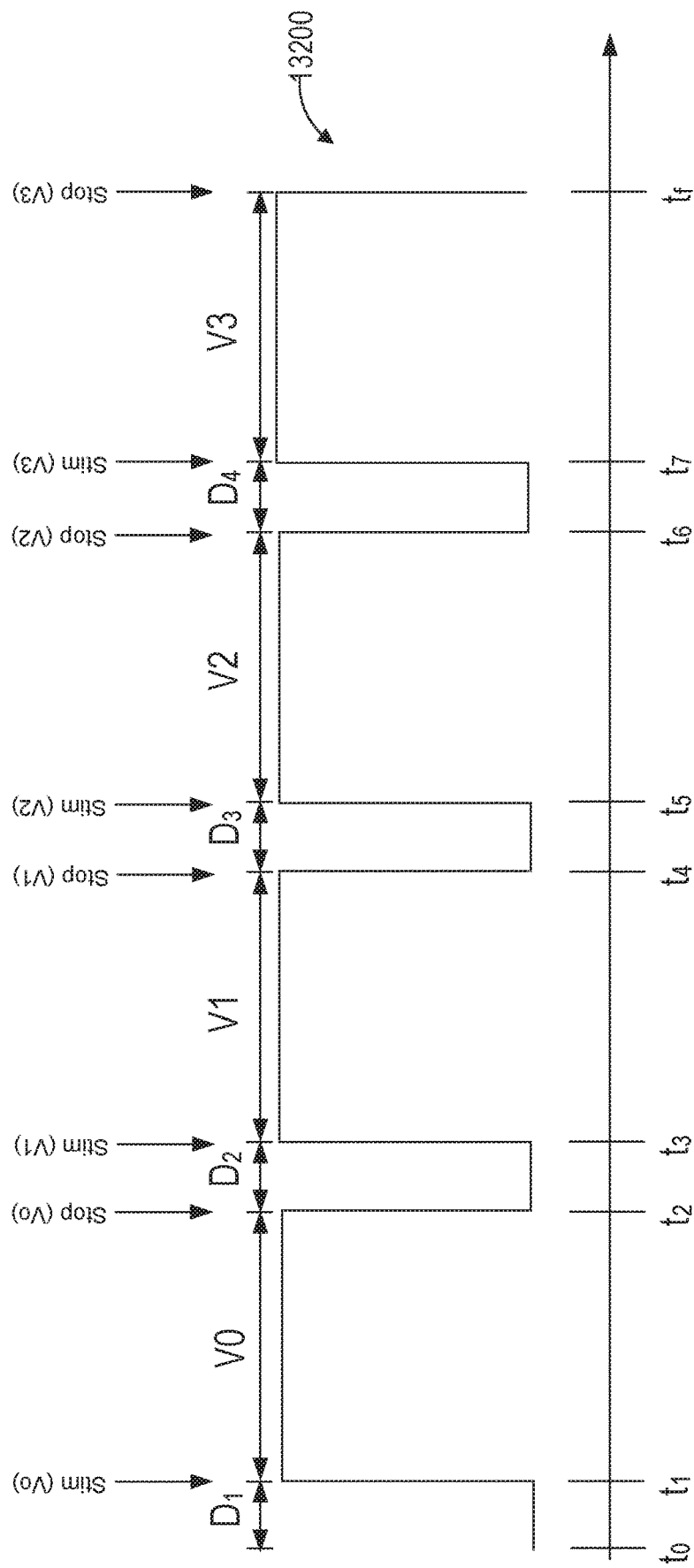

FIG. 124B illustrates, by way of example, a diagram of an embodiment of receiving therapy delivery instructions at a stimulation device.

Figure 125:
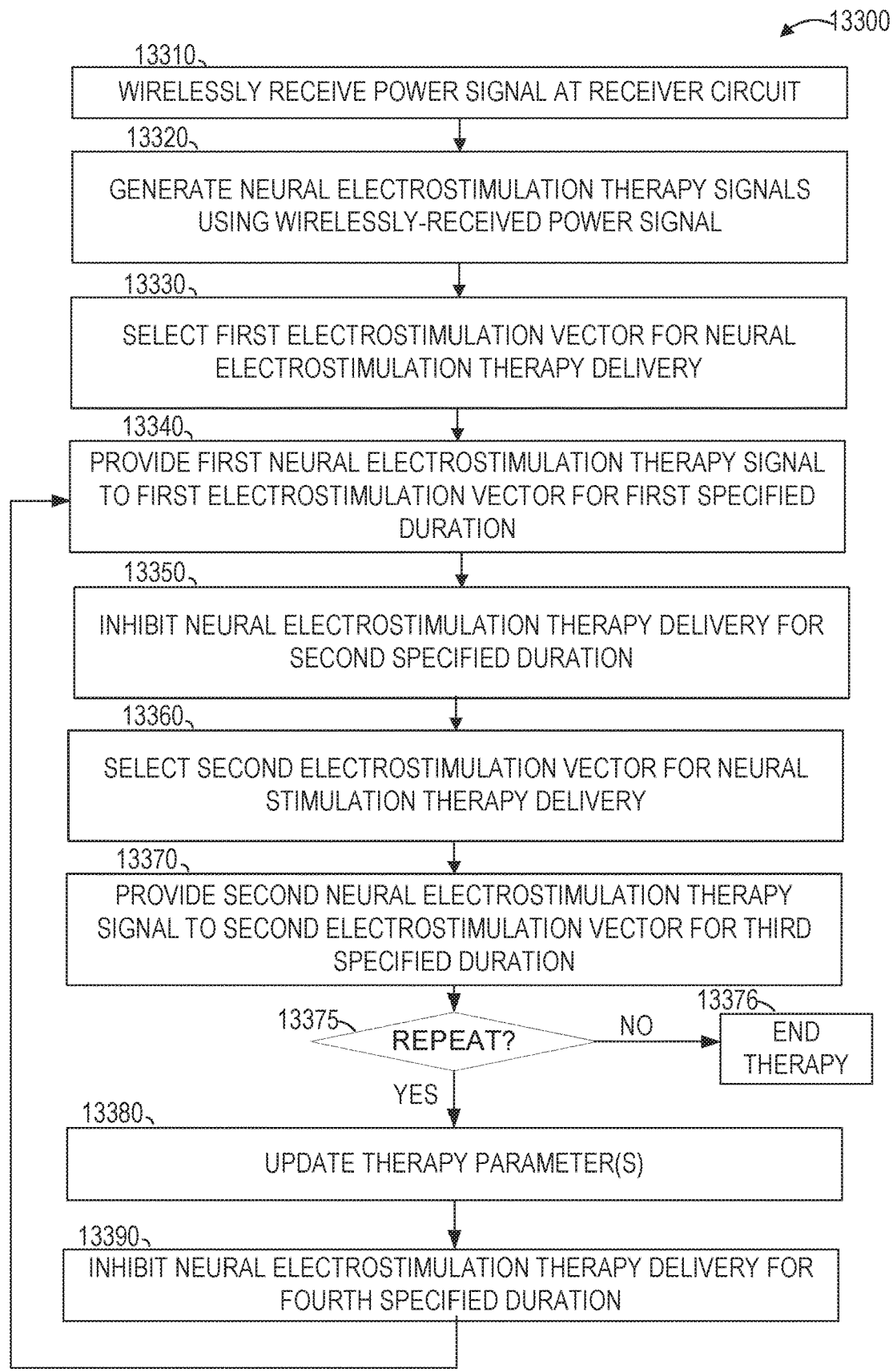

FIG. 125 illustrates, by way of example, a diagram of an embodiment of a method that includes providing a neural stimulation therapy.

Figure 126:
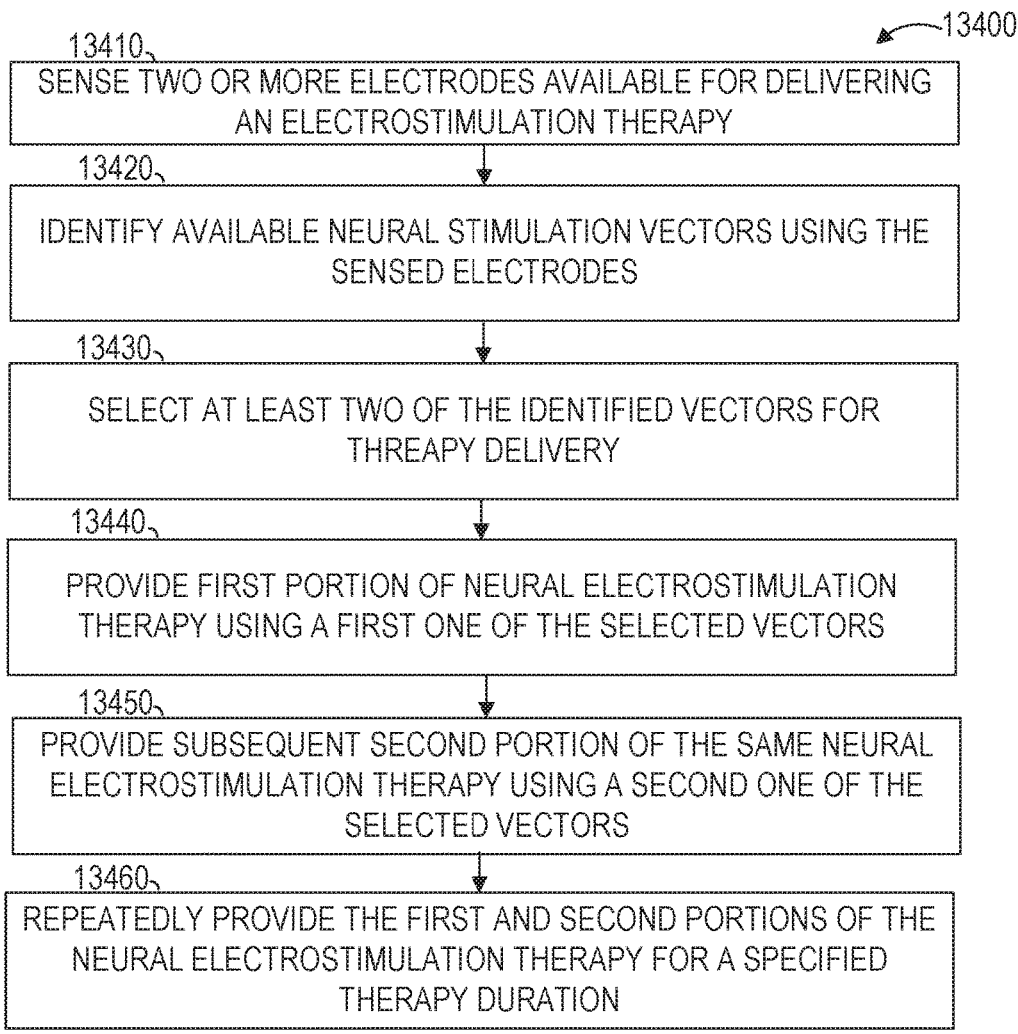

FIG. 126 illustrates, by way of example, a diagram of an embodiment of a method that includes identifying or selecting electrostimulation vectors for use in providing a neural stimulation therapy.

Figure 127:
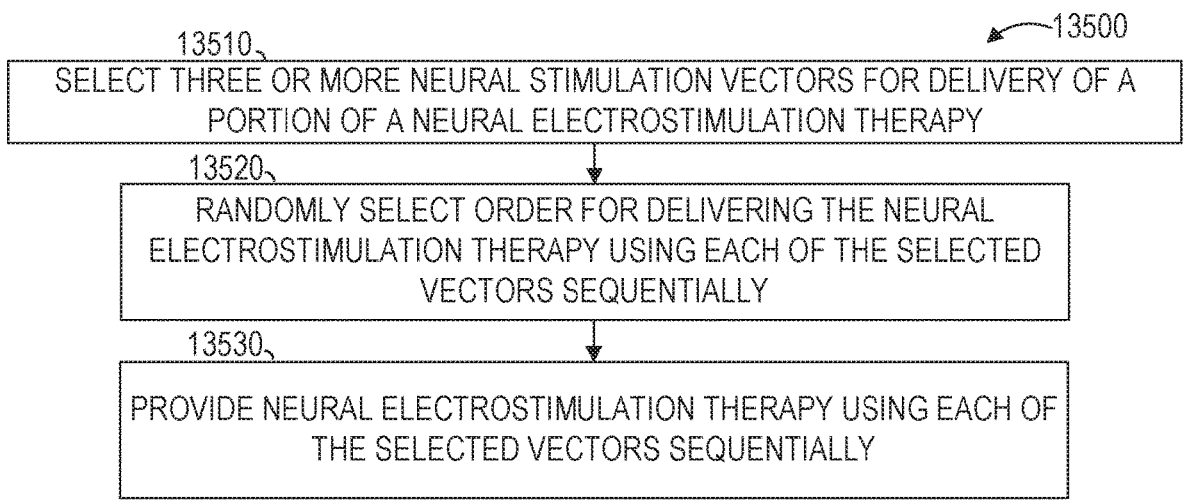

FIG. 127 illustrates, by way of example, a diagram of an embodiment of a method that includes randomly selecting an order for delivering a neural stimulation therapy via multiple vectors.

Figure 128:
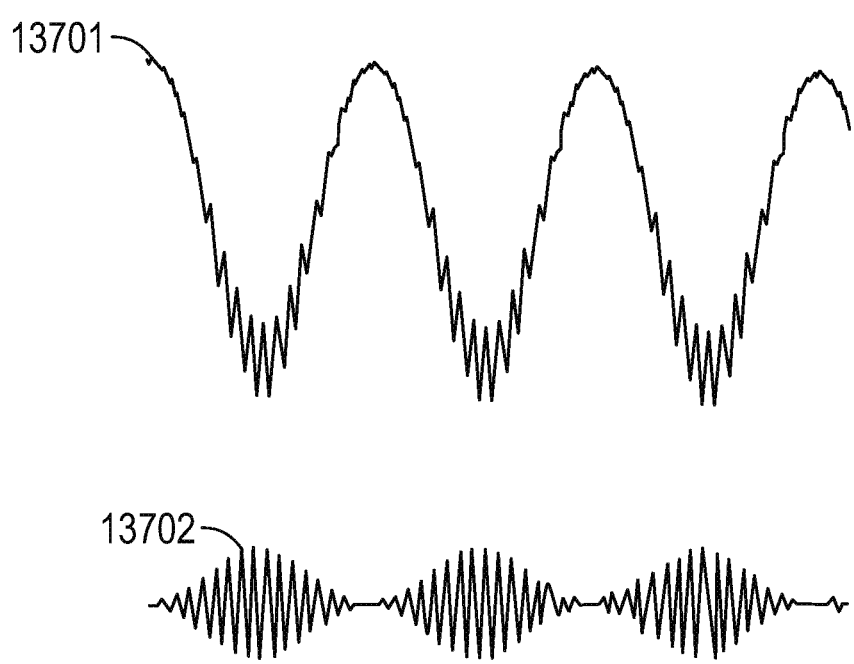

FIG. 128 illustrates, by way of example, a diagram of an embodiment of phase-amplitude coupled signals.

Figure 129:
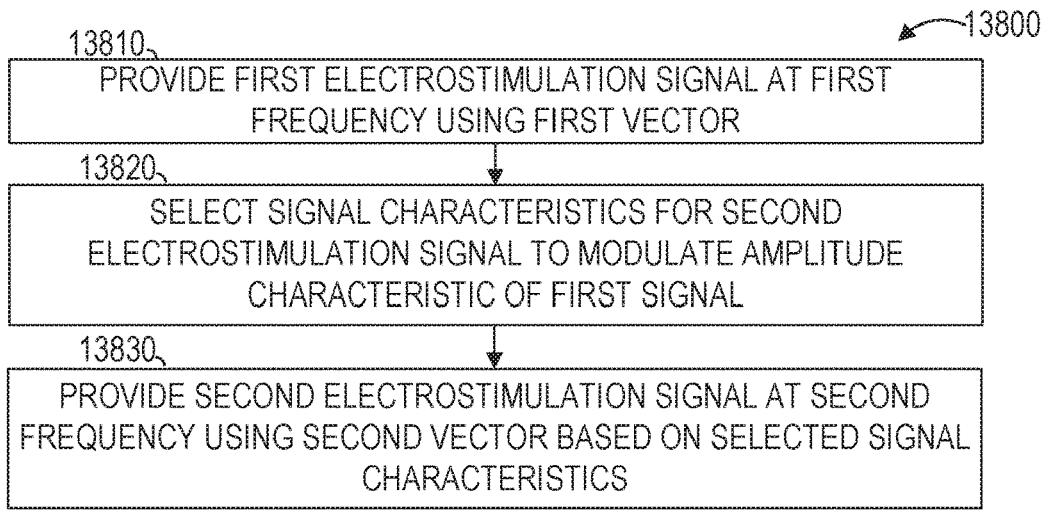

FIG. 129 illustrates, by way of example, a diagram of an embodiment of a method for concurrently providing a neural electrostimulation therapy.

Figure 130:
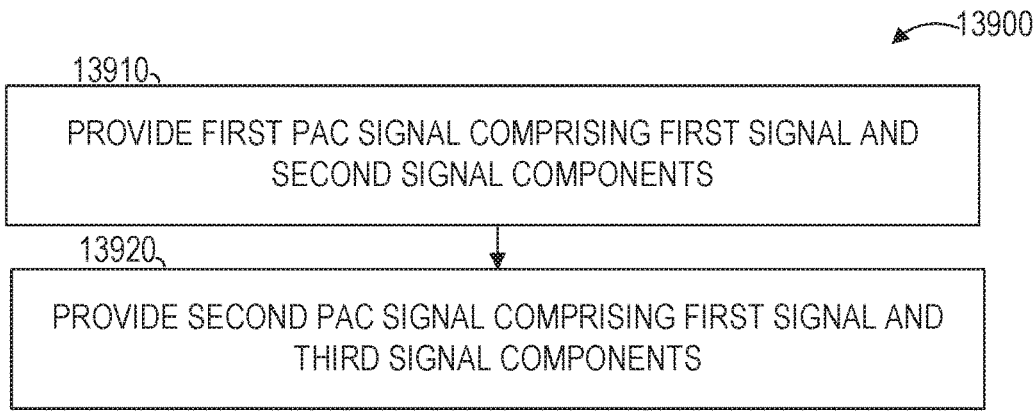

FIG. 130 illustrates, by way of example, a diagram of an embodiment of a method that includes providing multiple phase-amplitude coupled therapy signals.

Figure 131:
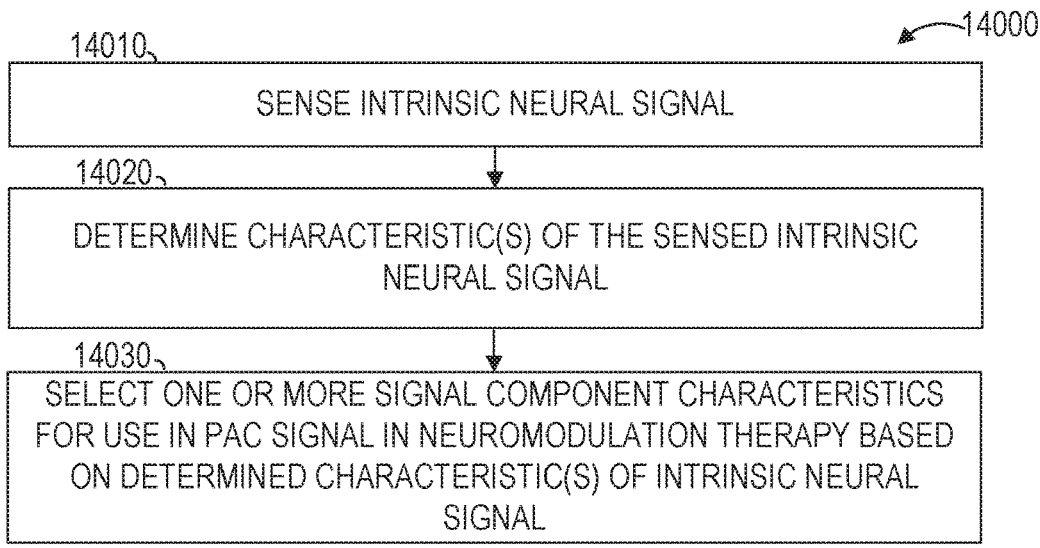

FIG. 131 illustrates, by way of example, a diagram of an embodiment of a method that includes selecting one or more signal component characteristics for use in a PAC signal.

Figure 132:
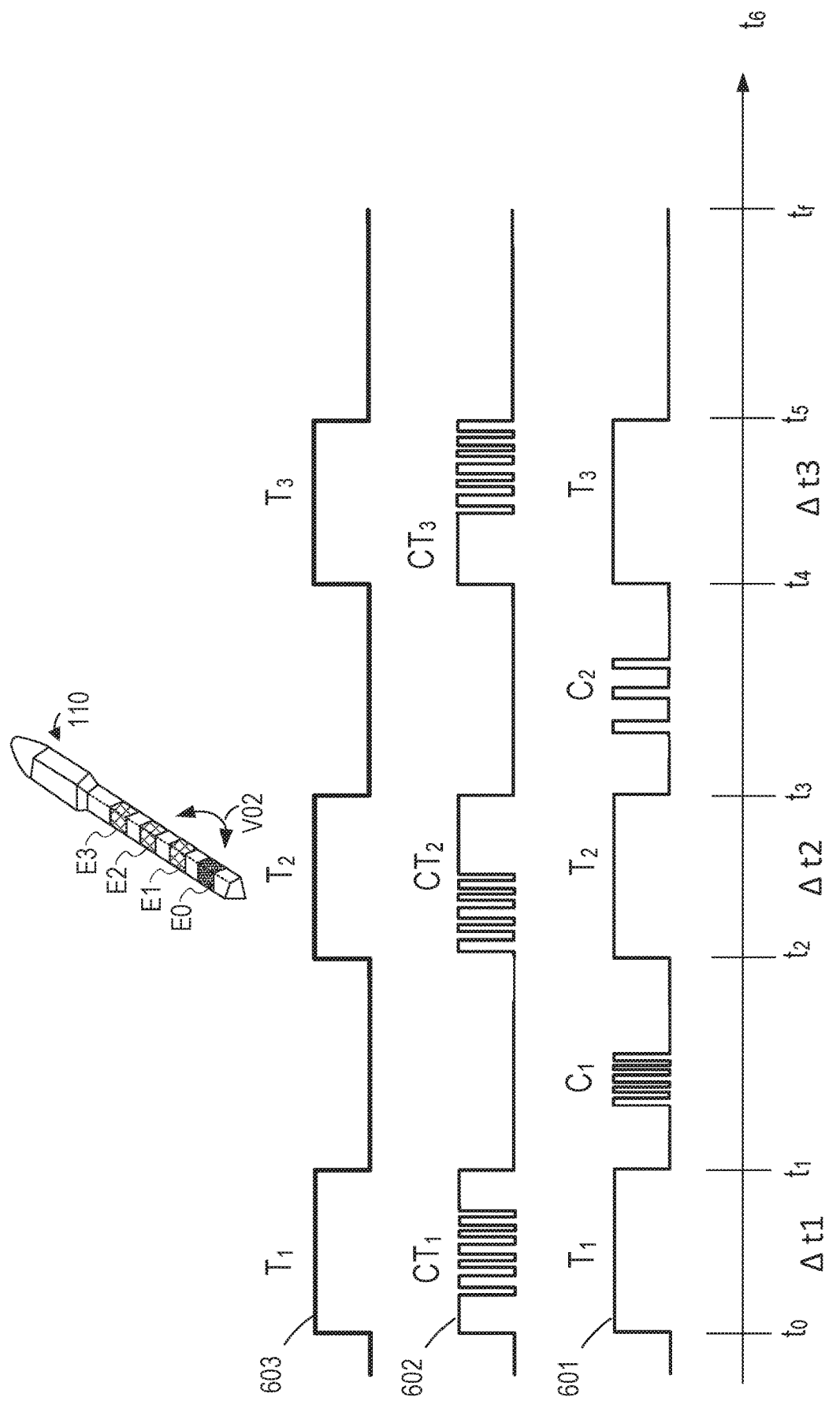

FIG. 132 illustrates, by way of example, a diagram of an embodiment of therapy signals with data signal components.

Figure 133:
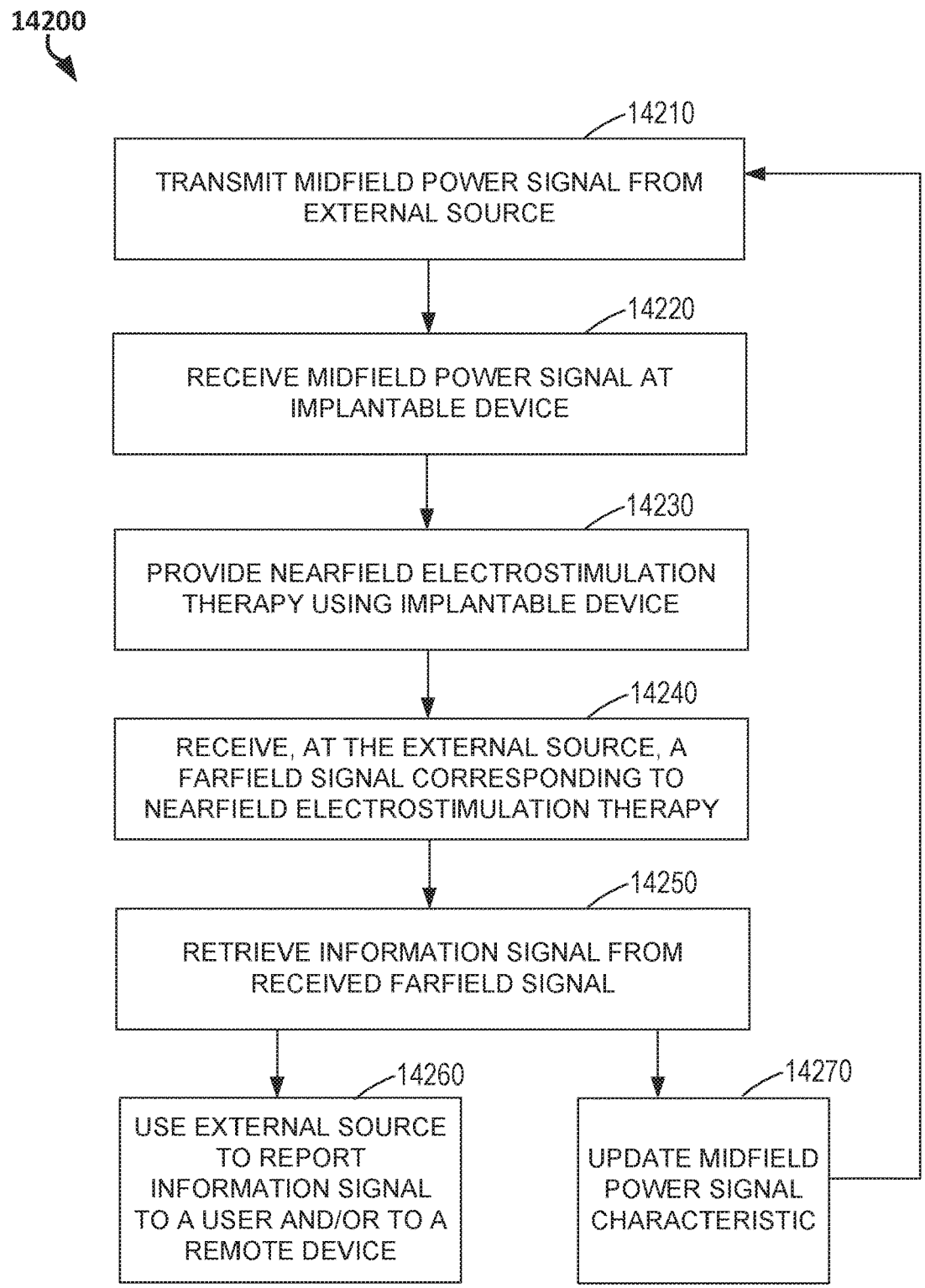

FIG. 133 illustrates, by way of example, a diagram of an embodiment of a method that includes retrieving an information signal from a farfield signal.

Figure 134:
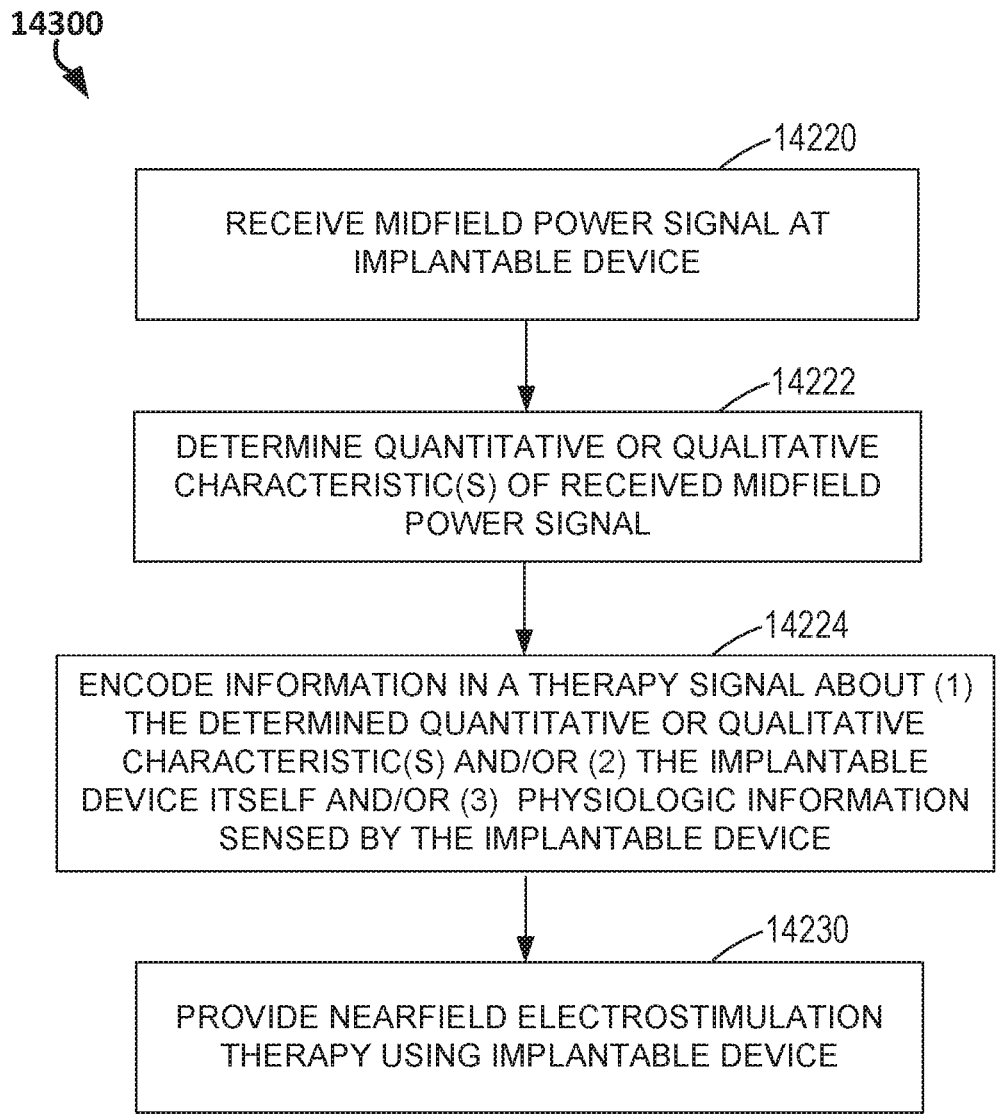

FIG. 134 illustrates, by way of example, a diagram of an embodiment of a method that includes encoding information in a therapy signal.

Figure 135:
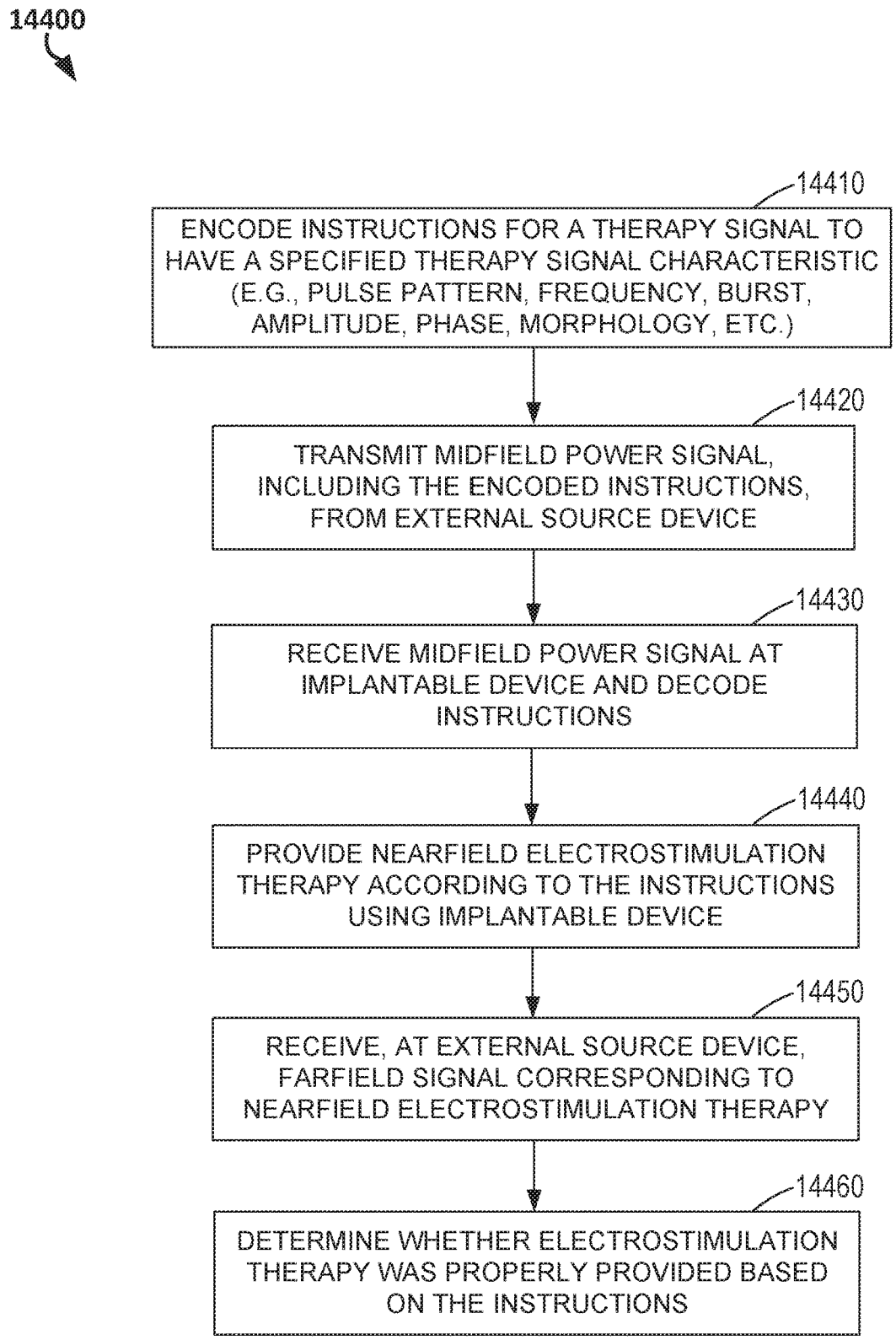

FIG. 135 illustrates, by way of example, a diagram of an embodiment of a method that includes determining whether a therapy was properly provided.

Figure 136:
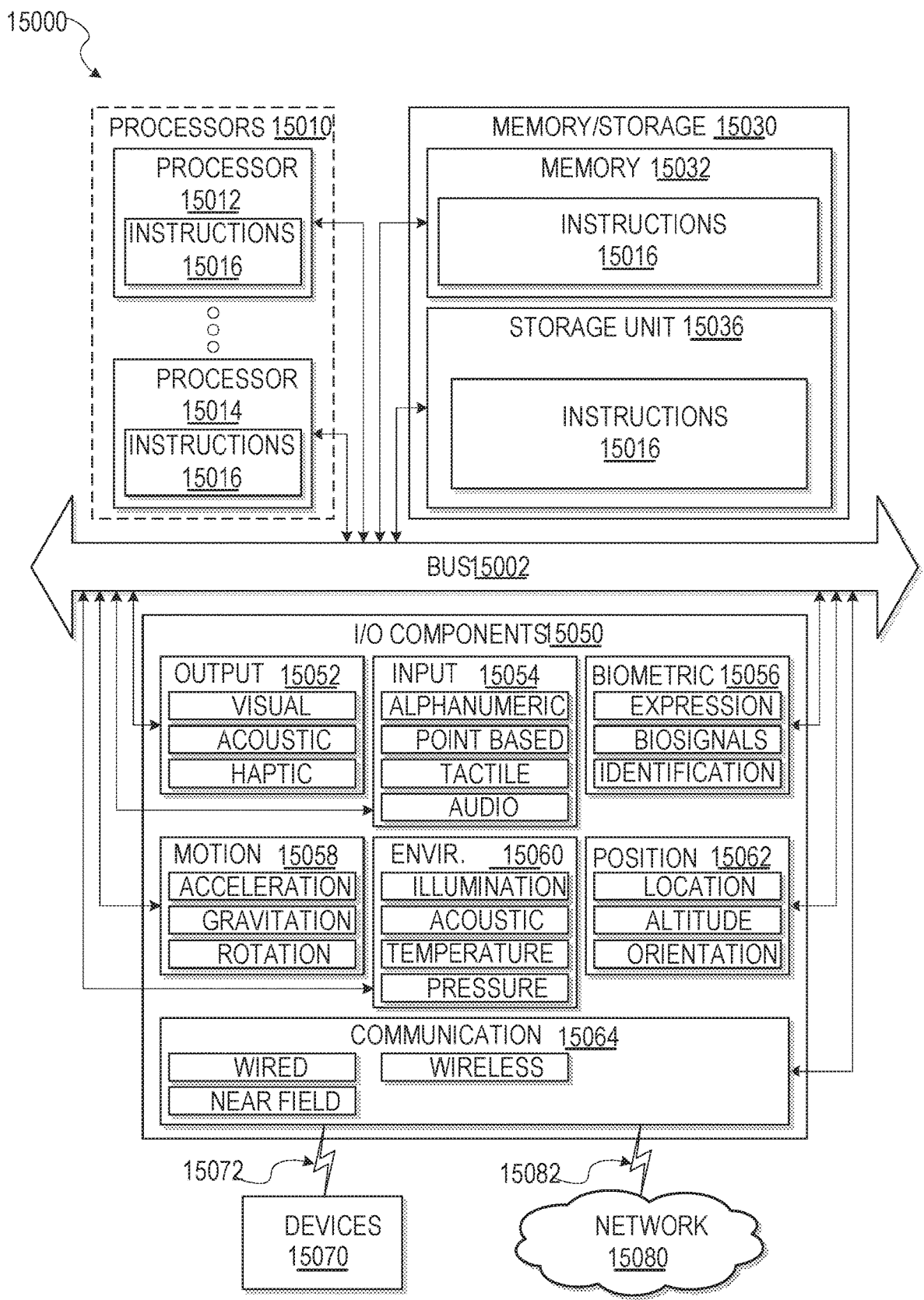

FIG. 136 illustrates, by way of example, a system with which one or more methods discussed herein can be performed.

DESCRIPTION OF EMBODIMENTS

Midfield powering technology can provide power to a deeply implanted electrostimulation device from an external power source located on or near a tissue surface, such as at an external surface of a user's skin. The user can be a clinical patient or other user. The midfield powering technology can have one or more advantages over implantable pulse generators. For example, a pulse generator can have one or more relatively large, implanted batteries and/or one or more lead systems. Midfield devices, in contrast, can include relatively small battery cells that can be configured to receive and store relatively small amounts of power. A midfield device can include one or more electrodes integrated in a unitary implantable package. Thus, in some examples, a midfield-powered device can provide a simpler implant procedure over other conventional devices, which can lead to a lower cost and a lower risk of infection or other implant complications. One or more of the advantages can be from an amount of power transferred to the implanted device. The ability to focus the energy from the midfield device can allow for an increase in the amount of power transferred to the implanted device.

An advantage of using midfield powering technology can include a main battery or power source being provided externally to the patient, and thus low power consumption and high efficiency circuitry requirements of conventional battery-powered implantable devices can be relaxed. Another advantage of using midfield powering technology can include an implanted device that can be physically smaller than a battery-powered device. Midfield powering technology can thus help enable better patient tolerance and comfort along with potentially lower costs to manufacture and/or to implant in patient tissue.

There is a current unmet need that includes communicating power and/or data using midfield transmitters and receivers, such as to communicate power and/or data from an external midfield coupler or source device to one or more implanted neural stimulation devices and/or one or more implanted sensor devices. The unmet need can further include communicating data from the one or more implanted neural stimulation devices and implanted sensor devices to the external midfield coupler or source device.

In one or more embodiments, multiple devices can be implanted in patient tissue and can be configured to deliver a therapy and/or sense physiologic information about a patient and/or about the therapy. The multiple implanted devices can be configured to communicate with one or more external devices. In one or more embodiments, the one or more external devices are configured to provide power and/or data signals to the multiple implanted devices, such as concurrently or in a time-multiplexed (e.g., "round-robin") fashion. The provided power and/or data signals can be steered or directed by an external device to transfer the signals to an implant efficiently. Although the present disclosure may refer to a power signal or data signal specifically, such references are to be generally understood as optionally including one or both of power and data signals.

Several embodiments described herein can be advantageous because they include one, several, or all of the following benefits: (i) a system configured to (a) communicate power and/or data signals from a midfield coupler device to an implantable device via midfield radiofrequency (RF) signals, (b) generate and provide a therapy signal via one or more electrodes coupled to the implantable device, the therapy signal including an information component, and producing a signal incident to providing the therapy signal, (c) receive a signal, based on the therapy signal, using electrodes coupled to the midfield coupler device, and (d) at the midfield coupler device or another device, decode and react to the information component from the received signal; (ii) a dynamically configurable, active midfield transceiver that is configured to provide RF signals to modulate an evanescent field at a tissue surface and thereby generate a propagating field within tissue, such as to transmit power and/or data signals to an implanted target device; (iii) an implantable device including an antenna configured to receive a midfield power signal from the midfield transceiver and including a therapy delivery circuitry configured to provide signal pulses to electrostimulation electrodes using a portion of the received midfield power signal, wherein the signal pulses include therapy pulses and data pulses, and the data pulses can be interleaved with or embedded in the therapy pulses; (iv) an implantable device configured to encode information, in a therapy signal, about the device itself, such as including information about the device's operating status, or about a previously-provided, concurrent, or planned future therapy provided by the device; (v) a midfield transceiver including electrodes that are configured to sense electrical signals at a tissue surface; and/or (vi) adjustable wireless signal sources and receivers that are configured together to enable a communication loop or feedback loop.

In one or more embodiments, one or more of these benefits and others can be realized using a system for manipulating an evanescent field at or near an external tissue surface to transmit power and/or data wirelessly to one or more target devices implanted in the tissue. In one or more embodiments, one or more of these benefits can be realized using a device or devices implanted in a body or capable of being implanted in a body and as described herein. In one or more embodiments, one or more of these benefits can be realized using a midfield powering and/or communication device (e.g., a transmitter device and/or a receiver device or a transceiver device).

A system can include a signal generator system adapted to provide multiple different sets of signals (e.g., RF signals). Each set can include two or more separate signals in some embodiments. The system can also include a midfield transmitter including multiple excitation ports, the midfield transmitter coupled to the RF signal generator system, and the midfield transmitter being adapted to transmit the multiple different sets of RF signals at respective different times via the excitation ports. The excitation ports can be adapted to receive respective ones of the separate signals from each set of RF signals. Each of the transmitted sets of RF signals can include a non-negligible magnetic field (H-field) component that is substantially parallel to the external tissue surface. In one or more embodiments, each set of transmitted RF signals is adapted or selected to differently manipulate an evanescent field at or near the tissue surface to transmit a power and/or data signal to one or more target devices implanted in the tissue via a midfield signal instead of via inductive near-field coupling or radiative far-field transmission.

In one or more embodiments, one or more of the above-mentioned benefits, among others, can be realized, at least in part, using an implantable therapy delivery device (e.g., that is adapted to provide neural stimulation) that includes receiver circuitry including an antenna (e.g., an electric-field or magnetic field based antenna) configured to receive a midfield power signal from an external source device, such as when the receiver circuitry is implanted within tissue. The implantable therapy delivery device can include therapy delivery circuitry. The therapy delivery circuitry can be coupled to the receiver circuitry. The therapy delivery circuitry can be configured to provide signal pulses to one or more energy delivery members (e.g., electrostimulation electrodes), which may be integrally coupled to a body of the therapy delivery device or positioned separately from (e.g., not located on) the body of the therapy delivery device), such as by using a portion of the received midfield power signal from the external source device (e.g., sometimes referred to herein as an external device, an external source, an external midfield device, a midfield transmitter device, a midfield coupler, a midfield powering device, a powering device, or the like, depending on the configuration and/or usage context of the device). The signal pulses can include one or more electrostimulation therapy pulses and/or data pulses. In one or more embodiments, one or more of the above-mentioned benefits, among others, can be realized, at least in part, using an external transmitter and/or receiver (e.g., transceiver) device that includes an electrode pair configured to be disposed at an external tissue surface, and the electrode pair is configured to receive an electrical signal via the tissue. The electrical signal can correspond to an electrostimulation therapy delivered to the tissue by the therapy delivery device. A demodulator circuitry can be coupled to the electrode pair and can be configured to demodulate a portion of the received electrical signal, such as to recover a data signal originated by the therapy delivery device.

In one or more embodiments that include using a midfield wireless coupler, tissue can act as a dielectric to tunnel energy. Coherent interference of propagating modes can confine a field at a focal plane to less than a corresponding vacuum wavelength, for example, with a spot size subject to a diffraction limit in a high-index material. In one or more embodiments, a receiver (e.g., implanted in tissue) positioned at such a high energy density region, can be one or more orders of magnitude smaller than a conventional near-field implantable receiver, or can be implanted more deeply in tissue (e.g., greater than 1 cm in depth). In one or more embodiments, a transmitter source described herein can be configured to provide electromagnetic energy to various target locations, including for example to one or more deeply implanted devices. In an example, the energy can be provided to a location with greater than about a few millimeters of positioning accuracy. That is, a transmitted power or energy signal can be directed or focused to a target location that is within about one wavelength of the signal in tissue. Such energy focusing is substantially more accurate than the focusing available via traditional inductive means and is sufficient to provide adequate power to a receiver on a millimeter scale. In other wireless powering approaches using near-field coupling (inductive coupling and its resonant enhanced derivatives), evanescent components outside tissue (e.g., near the source) remain evanescent inside tissue, which does not allow for effective depth penetration. Unlike near-field coupling, energy from a midfield source is primarily carried in propagating modes and, as a result, an energy transport depth is limited by environmental losses rather than by intrinsic decay of the near-field. Energy transfer implemented with these characteristics can be at least two to three orders of magnitude more efficient than near-field systems.

One or more of the systems, apparatuses, and methods discussed herein can be used to help treat fecal or urinary incontinence (e.g., overactive bladder), such as by stimulating the tibial nerve or any branch of the tibial nerve, such as but not limited to the posterior tibial nerve, one or more nerves or nerve branches originating from the sacral plexus, including but not limited to S1-S4, the tibial nerve, and/or the pudendal nerve. Urinary incontinence may be treated by stimulating one or more of muscles of the pelvic floor, nerves innervating the muscles of the pelvic floor, internal urethral sphincter, external urethral sphincter, and the pudendal nerve or branches of the pudendal nerve.

One or more of the systems, apparatuses, and methods discussed herein can be used to help treat sleep apnea and/or snoring by stimulating one or more of a nerve or nerve branches of the hypoglossal nerve, the base of the tongue (muscle), phrenic nerve(s), intercostal nerve(s), accessory nerve(s), and cervical nerves C3-C6. Treating sleep apnea and/or snoring can include providing energy to an implant to sense a decrease, impairment, or cessation of breathing (such as by measuring oxygen saturation).

One or more of the systems, apparatuses, and methods discussed herein can be used to help treat vaginal dryness, such as by stimulating one or more of Bartholin gland(s), Skene's gland(s), and inner wall of vagina. One or more of the systems, apparatuses, and methods discussed herein can be used to help treat migraines or other headaches, such as by stimulating one or more of the occipital nerve, supraorbital nerve, C2 cervical nerve, or branches thereof, and the frontal nerve, or branches thereof. One or more of the systems, apparatuses, and methods discussed herein can be used to help treat post-traumatic stress disorder, hot flashes, and/or complex regional pain syndrome such as by stimulating one or more of the stellate ganglion and the C4-C7 of the sympathetic chain.

One or more of the systems, apparatuses, and methods discussed herein can be used to help treat neuralgia (e.g., trigeminal neuralgia), such as by stimulating one or more of the sphenopalatine ganglion nerve block, the trigeminal nerve, or branches of the trigeminal nerve. One or more of the systems, apparatuses, and methods discussed herein can be used to help treat dry mouth (e.g., caused by side effects from medications, chemotherapy or radiation therapy cancer treatments, Sjogren's disease, or by other cause of dry mouth), such as by stimulating one or more of Parotid glands, submandibular glands, sublingual glands, submucosa of the oral mucosa in the oral cavity within the tissue of the buccal, labial, and/or lingual mucosa, the soft palate, the lateral parts of the hard palate, and/or the floor of the mouth and/or between muscle fibers of the tongue, Von Ebner glands, glossopharyngeal nerve (CN IX), including branches of CN IX, including otic ganglion, a facial nerve (CN VII), including branches of CN VII, such as the submandibular ganglion, and branches of T1-T3, such as the superior cervical ganglion.

One or more of the systems, apparatuses, and methods discussed herein can be used to help treat a transected nerve, such as by sensing electrical output from the proximal portion of a transected nerve and delivering electrical input into the distal portion of a transected nerve, and/or sensing electrical output from the distal portion of a transected nerve and delivering electrical input into the proximal portion of a transected nerve. One or more of the systems, apparatuses, and methods discussed herein can be used to help treat cerebral palsy, such as by stimulating one or more muscles or one or more nerves innervation one or more muscles affected in a patient with cerebral palsy. One or more of the systems, apparatuses, and methods discussed herein can be used to help treat erectile dysfunction, such as by stimulating one or more of pelvic splanchnic nerves (S2-S4) or any branches thereof, the pudendal nerve, cavernous nerve(s), and inferior hypogastric plexus.

One or more of the systems, apparatuses, and methods discussed herein can be used to help treat menstrual pain, such as by stimulating one or more of the uterus and the vagina. One or more of the systems, apparatuses, and methods discussed herein can be used as an intrauterine device, such as by sensing one or more PH and blood flow or delivering current or drugs to aid in contraception, fertility, bleeding, or pain. One or more of the systems, apparatuses, and methods discussed herein can be used to incite human arousal, such as by stimulating female genitalia, including external and internal, including clitoris or other sensory active parts of the female, or by stimulating male genitalia.

One or more of the systems, apparatuses, and methods discussed herein can be used to help treat hypertension, such as by stimulating one or more of a carotid sinus, left or right cervical vagus nerve, or a branch of the vagus nerve. One or more of the systems, apparatuses, and methods discussed herein can be used to help treat paroxysmal supraventricular tachycardia, such as by stimulating one or more of trigeminal nerve or branches thereof, anterior ethmoidal nerve, and the vagus nerve. One or more of the systems, apparatuses, and methods discussed herein can be used to help treat vocal cord dysfunction, such as by sensing the activity of a vocal cord and the opposite vocal cord or just stimulating one or more of the vocal cords by stimulating nerves innervating the vocal cord, the left and/or Right recurrent laryngeal nerve, and the vagus nerve.

One or more of the systems, apparatuses, and methods discussed herein can be used to help repair tissue, such as by stimulating tissue to do one or more of enhancing microcirculation and protein synthesis to heal wounds and restoring integrity of connective and/or dermal tissues. One or more of the systems, apparatuses, and methods discussed herein can be used to help asthma or chronic obstructive pulmonary disease, such as by one or more of stimulating the vagus nerve or a branch thereof, blocking the release of norepinephrine and/or acetylcholine and/or interfering with receptors for norepinephrine and/or acetylcholine.

One or more of the systems, apparatuses, and methods discussed herein can be used to help treat cancer, such as by stimulating, to modulate one or more nerves near or in a tumor, such as to decrease the sympathetic innervation, such as epinephrine/NE release, and/or parasympathetic innervation, such as Ach. One or more of the systems, apparatuses, and methods discussed herein can be used to help treat diabetes, such as by powering a sensor inside the human body that detects parameters of diabetes, such as a glucose level or ketone level and using such sensor data to adjust delivery of exogenous insulin from an insulin pump. One or more of the systems, apparatuses, and methods discussed herein can be used to help treat diabetes, such as by powering a sensor inside the human body that detects parameters of diabetes, such as a glucose level or ketone level, and using a midfield coupler to stimulate the release of insulin from islet beta cells.

One or more of the systems, apparatuses, and methods discussed herein can be used to help treat neurological conditions, disorders or diseases (such as Parkinson's disease (e.g., by stimulating an internus or nucleus of the brain), Alzheimer's disease, Huntington's disease, dementia, Creutzfeldt-Jakob disease, epilepsy (e.g., by stimulating a left cervical vagus nerve or a trigeminal nerve), post-traumatic stress disorder (PTSD) (e.g., by stimulating a left cervical vagus nerve), or essential tremor, such as by stimulating a thalamus), neuralgia, depression, dystonia (e.g., by stimulating an internus or nucleus of the brain), phantom limb (e.g., by stimulating an amputated nerve, such an ending of an amputated nerve), dry eyes (e.g., by stimulating a lacrimal gland), arrhythmia (e.g., by stimulating the heart), a gastrointestinal disorder, such as obesity, gastroesophageal reflux, and/or gastroparesis, such as by stimulating a C1-C2 occipital nerve or deep brain stimulation (DBS) of the hypothalamus, an esophagus, a muscle near sphincter leading to the stomach, and/or a lower stomach, and/or stroke (e.g., by subdural stimulation of a motor cortex). Using one or more embodiments discussed herein, stimulation can be provided continuously, on demand (e.g., as demanded by a physician, patient, or other user), or periodically.

In providing the stimulation, an implantable device can be situated up to five centimeters or more below the surface of the skin. A midfield powering device is capable of delivering power to those depths in tissue. In one or more embodiments, an implantable device can be situated between about 2 centimeters and 4 centimeters, about 3 centimeters, between about 1 centimeter and five centimeters, less than 1 centimeter, about two centimeters, or other distance below the surface of the skin. The depth of implantation can depend on the use of the implanted device. For example, to treat depression, hypertension, epilepsy, and/or PTSD the implantable device can situated between about 2 centimeters and about four centimeters below the surface of the skin. In another example, to treat sleep apnea, arrhythmia (e.g., bradycardia), obesity, gastroesophageal reflux, and/or gastroparesis the implantable device can be situated at greater than about 3 centimeters below the surface of the skin. In yet another example, to treat Parkinson's, essential tremors, and/or dystonia the implantable device can be situated between about 1 centimeter and about 5 centimeters below the surface of the skin. Yet other examples include situating the implantable device between about 1 centimeter and about 2 centimeters below the surface of the skin, such as to treat fibromyalgia, stroke, and/or migraine, at about 2 centimeters to treat asthma, and at about one centimeter or less to treat dry eyes.

Although many embodiments included herein describe devices or methods for providing stimulation (e.g., electrostimulation), the embodiments may be adapted to provide other forms of modulation (e.g., denervation) in addition to or instead of stimulation. In addition, although many embodiments included herein refer to the use of electrodes to deliver therapy, other energy delivery members (e.g., ultrasound transducers or other ultrasound energy delivery members) or other therapeutic members or substances (e.g., fluid delivery devices or members to deliver chemicals, drugs, cryogenic fluid, hot fluid or steam, or other fluids) may be used or delivered in other embodiments.

Figure 1:
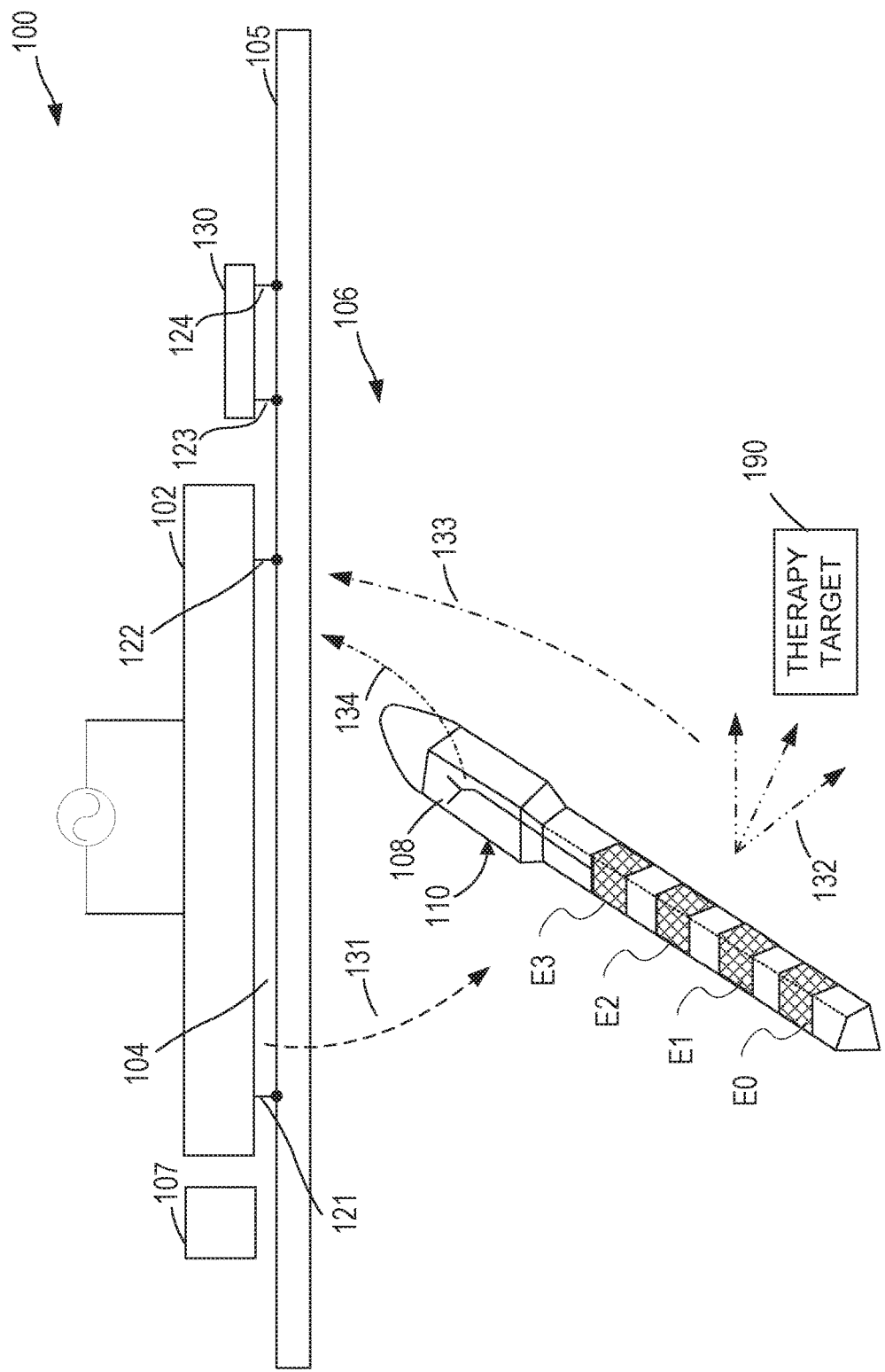
FIG. 1 illustrates, by way of example, a schematic of an embodiment of a system using wireless communication paths.

FIG. 1 illustrates, by way of example, a schematic of an embodiment of a system 100 using wireless communication paths. The system 100 includes an example of an external source 102, such as a midfield transmitter source, sometimes referred to as a midfield coupler, located at or above an interface 105 between air 104 and a higher-index material 106, such as body tissue. The external source 102 can produce a source current (e.g., an in-plane source current). The source current (e.g., in-plane source current) can generate an electric field and a magnetic field. The magnetic field can include a non-negligible component that is parallel to the surface of the source 102 and/or to a surface of the higher-index material 106 (e.g., a surface of the higher-index material 106 that faces the external source 102). In accordance with several embodiments, the external source 102 may comprise structural features and functions described in connection with the midfield couplers and external sources included in WIPO Publication No. WO/2015/179225 published on Nov. 26, 2015 and titled "MIDFIELD COUPLER", which is incorporated herein by reference in its entirety.

The external source 102 can include at least a pair of outwardly facing electrodes 121 and 122. The electrodes 121 and 122 can be configured to contact a tissue surface, for example, at the interface 105. In one or more embodiments, the external source 102 is configured for use with a sleeve, pocket, or other garment or accessory that maintains the external source 102 adjacent to the higher-index material 106 (see, e.g., the subsection herein titled "DISCREET EXTERNAL DEVICE COUPLING TO IMPLANTED DEVICE", for example), and that optionally maintains the electrodes 121 and 122 in physical contact with a tissue surface. In one or more embodiments, the sleeve, pocket, or other garment or accessory can include or use a conductive fiber or fabric, and the electrodes 121 and 122 can be in physical contact with the tissue surface via the conductive fiber or fabric. Sleeves, pockets, or other garments or accessories suitable for use with the external source 102 are described in further detail, for example, in at least the subsection herein titled "DISCREET EXTERNAL DEVICE COUPLING TO IMPLANTED DEVICE."

In one or more embodiments, more than two outwardly facing electrodes can be used and processor circuitry on-board or auxiliary to the source 102 can be configured to select an optimal pair or group of electrodes to use to sense farfield signal information (e.g., signal information corresponding to a delivered therapy signal or to a nearfield signal). In such embodiments, the electrodes can operate as antennas. In one or more embodiments, the source 102 includes three outwardly facing electrodes arranged as a triangle, or four outwardly facing electrodes arranged as a rectangle, and any two or more of the electrodes can be selected for sensing and/or can be electrically grouped or coupled together for sensing or diagnostics. In one or more embodiments, the processor circuitry can be configured to test multiple different electrode combination selections to identify an optimal configuration for sensing a farfield signal (an example of the processor circuitry is presented in FIG. 2A, among others).

FIG. 1 illustrates an embodiment of an implantable device 110, such as can include a multi-polar therapy delivery device configured to be implanted in the higher-index material 106. In one or more embodiments, the implantable device 110 includes all or a portion of the circuitry 500 from FIG. 5, discussed in further detail below. In one or more embodiments, the implantable device 110 is implanted in tissue below the tissue-air interface 105. In FIG. 1, the implantable device 110 includes an elongate body and multiple electrodes E0, E1, E2, and E3 that are axially spaced apart along a portion of the elongate body. The implantable device 110 includes receiver and/or transmitter circuitry (not shown in FIG. 1, see e.g., FIGS. 2A, 2B, and 4, among others) that can enable communication between the implantable device 110 and the external source 102.

The various electrodes E0-E3 can be configured to deliver electrostimulation therapy to patient tissue, such as at or near a neural or muscle target. In one or more embodiments, at least one electrode can be selected for use as an anode and at least one other electrode can be selected for use as a cathode to define an electrostimulation vector. In one or more embodiments, electrode E1 is selected for use as an anode and electrode E2 is selected for use as a cathode. Together, the E1-E2 combination defines an electrostimulation vector V12. Various vectors can be configured independently to provide a neural electrostimulation therapy to the same or different tissue target, such as concurrently or at different times.

In one or more embodiments, the source 102 includes an antenna (see, e.g., FIG. 3) and the implantable device 110 includes an antenna 108 (e.g., and electric field-based or magnetic field-based antenna). The antennas can be configured (e.g., in length, width, shape, material, etc.) to transmit and receive signals at substantially the same frequency. The implantable device 110 can be configured to transmit power and/or data signals through the antenna 108 to the external source 102 and can receive power and/or data signals transmitted by the external source 102. The external source 102 and implantable device 110 can be used for transmission and/or reception of RF signals. A transmit/receive (T/R) switch can be used to switch each RF port of the external source 102 from a transmit (transmit data or power) mode to a receive (receive data) mode. A T/R switch can similarly be used to switch the implantable device 110 between transmit and receive modes. See FIG. 4, among others, for examples of T/R switches.

Figure 3:
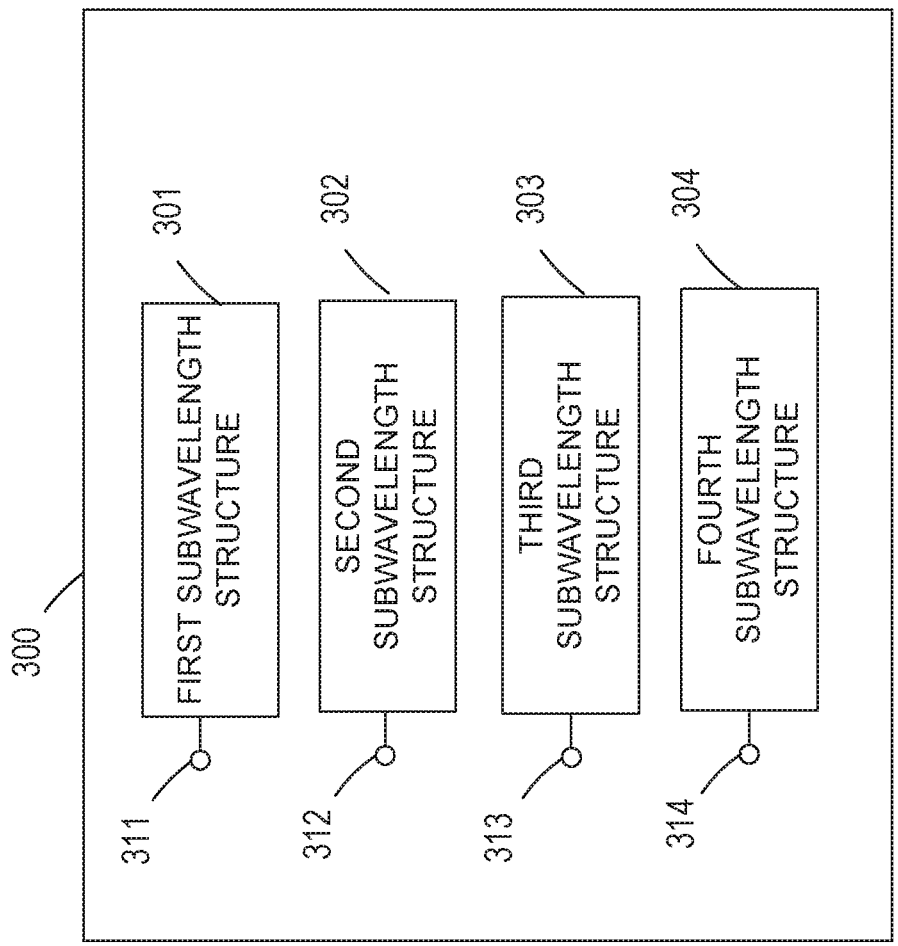
FIG. 3 illustrates, by way of example, a schematic view of an embodiment of a midfield antenna with multiple subwavelength structures.
Figure 4:
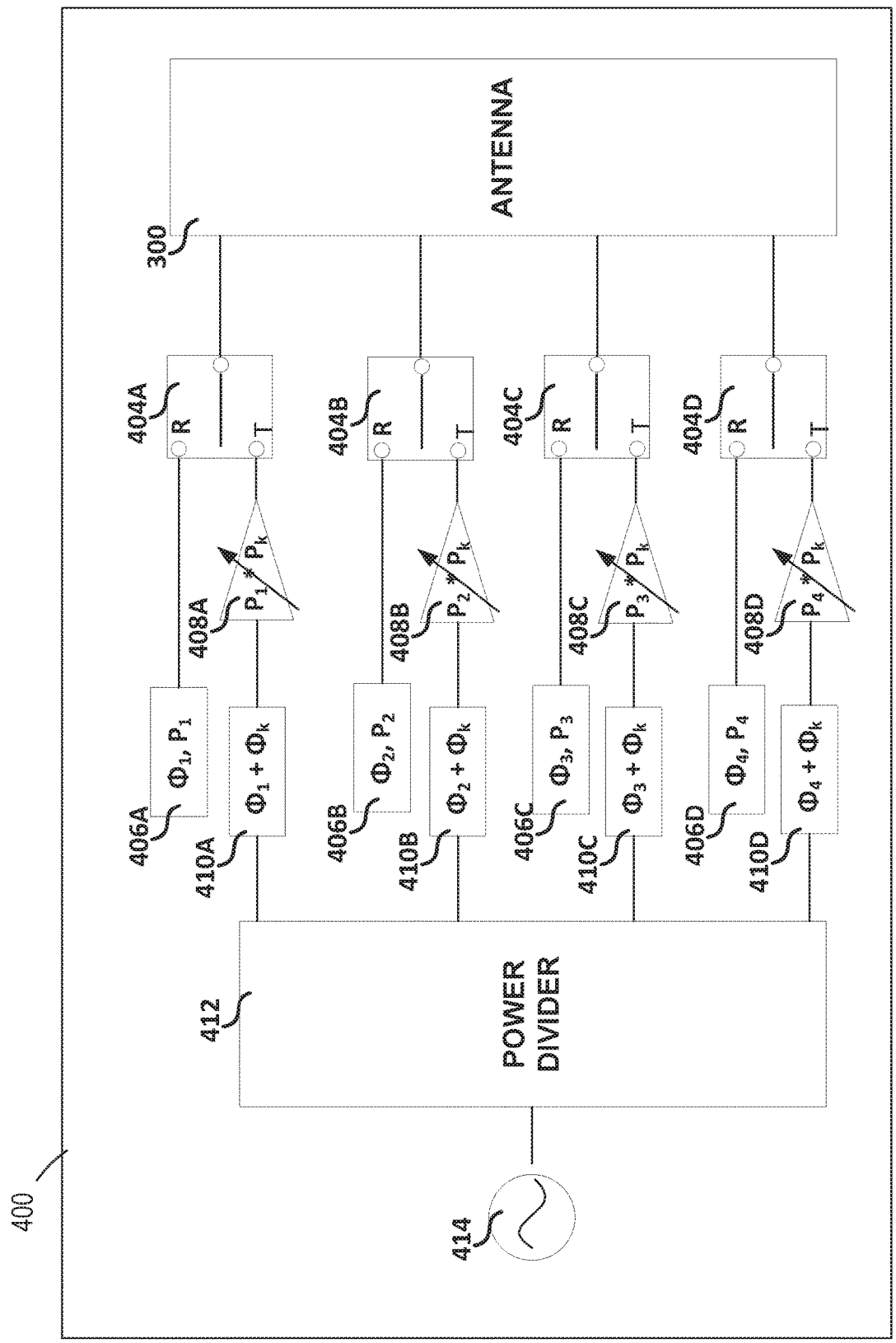
FIG. 4 illustrates, by way of example, a diagram of an embodiment of a phase-matching and/or amplitude-matching network for a midfield source device.

In one or more embodiments, a receive terminal on the external source 102 can be connected to one or more components that detect a phase and/or amplitude of a received signal from the implantable device 110. The phase and amplitude information can be used to program a phase of the transmit signal, such as to be substantially the same relative phase as a signal received from the implantable device 110. To help achieve this, the external source 102 can include or use a phase-matching and/or amplitude-matching network, such as shown in the embodiment of FIG. 4. The phase-matching and/or amplitude matching network can be configured for use with a midfield antenna that includes multiple ports, such as shown in the embodiment of FIG. 3.

Referring again to FIG. 1, in one or more embodiments, the implantable device 110 can be configured to receive a midfield signal 131 from the external source 102. The midfield signal 131 can include power and/or data signal components. In some embodiments, a power signal component can include one or more data components embedded therein. In one or more embodiments, the midfield signal 131 includes configuration data for use by the implantable device 110. The configuration data can define, among other things, therapy signal parameters, such as a therapy signal frequency, pulse width, amplitude, or other signal waveform parameters. In one or more embodiments, the implantable device 110 can be configured to deliver an electrostimulation therapy to a therapy target 190, such as can include a neural target (e.g., a nerve), a muscle target, or other tissue target. An electrostimulation therapy delivered to the therapy target 190 can be provided using a portion of a power signal received from the external source 102. Examples of the therapy target 190 can include nerve tissue or neural targets, for example including nerve tissue or neural targets at or near cervical, thoracic, lumbar, or sacral regions of the spine, brain tissue, muscle tissue, abnormal tissue (e.g., tumor or cancerous tissue), targets corresponding to sympathetic or parasympathetic nerve systems, targets at or near peripheral nerve bundles or fibers, at or near other targets selected to treat incontinence, urinary urge, overactive bladder, fecal incontinence, constipation, pain, neuralgia, pelvic pain, movement disorders or other diseases or disorders, deep brain stimulation (DBS) therapy targets or any other condition, disease or disorder (such as those other conditions, diseases, or disorders identified herein).

Delivering the electrostimulation therapy can include using a portion of a power signal received via the midfield signal 131, and providing a current signal to an electrode or an electrode pair (e.g., two or more of E0-E3), coupled to the implantable device 110, to stimulate the therapy target 190. As a result of the current signal provided to the electrode(s), a nearfield signal 132 can be generated. An electric potential difference resulting from the nearfield signal 132 can be detected remotely from the therapy delivery location. Various factors can influence where and whether the potential difference can be detected, including, among other things, characteristics of the therapy signal, a type or arrangement of the therapy delivery electrodes, and characteristics of any surrounding biologic tissue. Such a remotely detected electric potential difference can be considered a farfield signal 133. The farfield signal 133 can represent an attenuated portion of the nearfield signal 132. That is, the nearfield signal 132 and the farfield signal 133 can originate from the same signal or field, such as with the nearfield signal 132 considered to be associated with a region at or near the implantable device 110 and the therapy target 190, and with the farfield signal 133 considered to be associated with other regions more distal from the implantable device 110 and the therapy target 190. In one or more embodiments, information about the implantable device 110, or about a previously-provided or future planned therapy provided by the implantable device 110, can be encoded in a therapy signal and detected and decoded by the external source 102 by way of the farfield signal 133.

In one or more embodiments, the device 110 can be configured to provide a series of electrostimulation pulses to a tissue target (e.g., neural target). For example, the device 110 can provide multiple electrostimulation pulses separated in time, such as using the same or different electrostimulation vectors, to provide a therapy. In one or more embodiments, a therapy comprising multiple signals can be provided to multiple different vectors in parallel, or can be provided in sequence such as to provide a series or sequence of electrostimulation pulses to the same neural target. Thus, even if one vector is more optimal than the others for eliciting a patient response, the therapy as a whole can be more effective than stimulating only the known-optimal vector because (1) the target may experience a rest period during periods of non-stimulation, and/or (2) stimulating the areas nearby and/or adjacent to the optimal target can elicit some patient benefit.

The system 100 can include a sensor 107 at or near the interface 105 between air 104 and the higher-index material 106. The sensor 107 can include, among other things, one or more electrodes, an optical sensor, an accelerometer, a temperature sensor, a force sensor, a pressure sensor, or a surface electromyography (EMG) device. The sensor 107 may comprise multiple sensors (e.g., two, three, four or more than four sensors). Depending on the type of sensor(s) used, the sensor 107 can be configured to monitor electrical, muscle, or other activity near the device 110 and/or near the source 102. For example, the sensor 107 can be configured to monitor muscle activity at a tissue surface. If muscle activity greater than a specified threshold activity level is detected, then a power level of the source 102 and/or of the device 110 can be adjusted. In one or more embodiments, the sensor 107 can be coupled to or integrated with the source 102, and in other examples, the sensor 107 can be separate from, and in data communication with (e.g., using a wired or wireless electrical coupling or connection), the source 102 and/or the device 110.

The system 100 can include a farfield sensor device 130 that can be separate from, or communicatively coupled with, one or more of the source 102 and the sensor 107. The farfield sensor device 130 can include two or more electrodes and can be configured to sense a farfield signal, such as the farfield signal 133 corresponding to a therapy delivered by the device 110. The farfield sensor device 130 can include at least one pair of outwardly facing electrodes 123 and 124 configured to contact a tissue surface, for example, at the interface 105. In one or more embodiments, three or more electrodes can be used, and processor circuitry on-board or auxiliary to the farfield sensor device 130 can select various combinations of two or more of the electrodes for use in sensing the farfield signal 133. In one or more embodiments, the farfield sensor device 130 can be configured for use with a sleeve, pocket, or other garment or accessory that maintains the farfield sensor device 130 adjacent to the higher-index material 106, and that optionally maintains the electrodes 123 and 124 in physical contact with a tissue surface. In one or more embodiments, the sleeve, pocket, or other garment or accessory can include or use a conductive fiber or fabric, and the electrodes 123 and 124 can be in physical contact with the tissue surface via the conductive fiber or fabric. Sleeves, pockets, or other garments or accessories suitable for use with the farfield sensor device 130 are described in the subsection herein titled "DISCREET EXTERNAL DEVICE COUPLING TO IMPLANTED DEVICE." An example of at least a portion of a farfield sensor device 130 is further described herein in connection with FIG. 2B.

In one or more embodiments, the external source 102 provides a midfield signal 131 including power and/or data signals to the implantable device 110. The midfield signal 131 includes a signal (e.g., an RF signal) having various or adjustable amplitude, frequency, phase, and/or other signal characteristics. The implantable device 110 can include an antenna, such as described below, that can receive the midfield signal 131 and, based on characteristics of receiver circuitry in the implantable device 110, can modulate the received signal at the antenna to thereby generate a backscatter signal. In one or more embodiments, the implantable device 110 can encode information in the backscatter signal 112, such as information about a characteristic of the implantable device 110 itself, about a received portion of the midfield signal 131, about a therapy provided by the implantable device 110, and/or other information. The backscatter signal 112 can be received by an antenna at the external source 102 and/or the farfield sensor device 130, or can be received by another device. In one or more embodiments, a biological signal can be sensed by a sensor of the implantable device 110, such as a glucose sensor, an electropotential (e.g., an electromyography sensor, electrocardiograph (ECG) sensor, resistance, or other electrical sensor), a light sensor, a temperature, a pressure sensor, an oxygen sensor, a motion sensor, or the like. A signal representative of the detected biological signal can be modulated onto the backscatter 112. Other sensors are discussed elsewhere herein, such as with regard to FIG. 136, among others. In such embodiments, the sensor 107 can include a corresponding monitor device, such as a glucose, temperature, ECG, EMG, oxygen, or other monitor, such as to receive, demodulate, interpret, and/or store data modulated onto the backscatter signal.

In one or more embodiments, the external source 102 and/or the implantable device 110 can include an optical transceiver configured to facilitate communication between the external source 102 and the implantable device 110. The external source 102 can include a light source, such as a photo laser diode or LED, or can include a photo detector, or can include both of a light source and a photo detector. The implantable device 110 can include a light source, such as a photo laser diode or LED, or can include a photo detector, or can include both of a light source and a photo detector. In an embodiment, the external source 102 and/or implantable device 110 can include a window, such as made of quartz, glass, or other translucent material, adjacent to its light source or photo detector.

In an embodiment, optical communications can be separate from or supplemental to an electromagnetic coupling between the external source 102 and the implantable device 110. Optical communication can be provided using light pulses modulated according to various protocols, such as using pulse position modulation (PPM). In an embodiment, a light source and/or photo detector on-board the implantable device 110 can be powered by a power signal received at least in part via midfield coupling with the external source 102.

In an embodiment, a light source at the external source 102 can send a communication signal through skin, into subcutaneous tissue, and through an optical window (e.g., quartz window) in the implantable device 110. The communication signal can be received at a photo detector on-board the implantable device 110. Various measurement information, therapy information, or other information from or about the implantable device can be encoded and transmitted from the implantable device 110 using a light source provided at the implantable device 110. The light signal emitted from the implantable device 110 can travel through the same optical window, subcutaneous tissue, and skin tissue, and can be received at photo detector on-board the external source 102. In an example, the light sources and/or photo detectors can be configured to emit and/or receive, respectively, electromagnetic waves in the visible or infrared ranges, such as in a range of about 670-910 nm wavelength (e.g., 670 nm-800 nm, 700 nm-760 nm, 670 nm-870 nm, 740 nm-850 nm, 800 nm-910 nm, overlapping ranges thereof, or any value within the recited ranges).

Figure 2A:
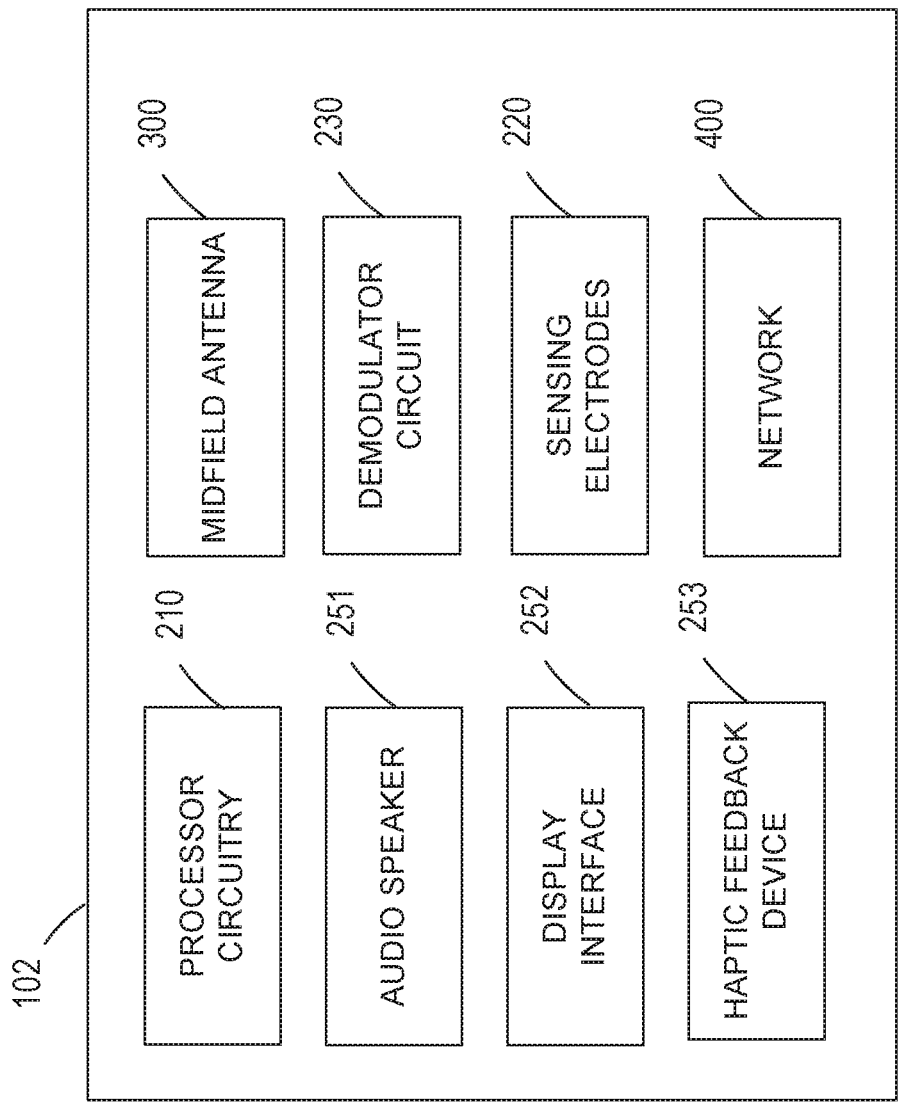
FIG. 2A illustrates, by way of example, a block diagram of an embodiment of a midfield source device.

FIG. 2A illustrates, by way of example, a block diagram of and embodiment of a midfield source device, such as the external source 102. The external source 102 can include various components, circuitry, or functional elements that are in data communication with one another. In the example of FIG. 2A, the external source 102 includes components, such as processor circuitry 210, one or more sensing electrodes 220 (e.g., including the electrodes 121 and 122), a demodulator circuitry 230, a phase-matching or amplitude-matching network 400, a midfield antenna 300, and/or one or more feedback devices, such as can include or use an audio speaker 251, a display interface 252, and/or a haptic feedback device 253. The midfield antenna 300 is further described below in the embodiment of FIG. 3, and the network 400 is further described below in the embodiment of FIG. 4. The processor circuitry 210 can be configured to coordinate the various functions and activities of the components, circuitry, and/or functional elements of the external source 102.

The midfield antenna 300 can be configured to provide a midfield excitation signal, such as can include RF signals having a non-negligible H-field component that is substantially parallel to an external tissue surface. In one or more embodiments, the RF signals can be adapted or selected to manipulate an evanescent field at or near a tissue surface, such as to transmit a power and/or data signal to respective different target devices (e.g., the implantable device 110) implanted in tissue. The midfield antenna 300 can be further configured to receive backscatter or other wireless signal information that can be demodulated by the demodulator circuitry 230. The demodulated signals can be interpreted by the processor circuitry 210. The midfield antenna 300 can include a dipole antenna, a loop antenna, a coil antenna, a slot or strip antenna, or other antenna. The antenna 300 can be shaped and sized to receive signals in a range of between about 400 MHz and about 4 GHz (e.g., between 400 MHz and 1 GHz, between 400 MHz and 3 GHz, between 500 MHz and 2 GHz, between 1 GHz and 3 GHz, between 500 MHz and 1.5 GHz, between 1 GHz and 2 GHz, between 2 GHz and 3 GHz, overlapping ranges thereof, or any value within the recited ranges). For embodiments incorporating a dipole antenna, the midfield antenna 300 may comprise a straight dipole with two substantially straight conductors, a folded dipole, a short dipole, a cage dipole, a bow-tie dipole or batwing dipole.

The demodulator circuitry 230 can be coupled to the sensing electrodes 220. In one or more embodiments, the sensing electrodes 220 can be configured to receive the farfield signal 133, such as based on a therapy provided by the implantable device 110, such as can be delivered to the therapy target 190. The therapy can include an embedded or intermittent data signal component that can be extracted from the farfield signal 133 by the demodulator circuitry 230. For example, the data signal component can include an amplitude-modulated or phase-modulated signal component that can be discerned from background noise or other signals and processed by the demodulator circuitry 230 to yield an information signal that can be interpreted by the processor circuitry 210. Based on the content of the information signal, the processor circuitry 210 can instruct one of the feedback devices to alert a patient, caregiver, or other system or individual. For example, in response to the information signal indicating successful delivery of a specified therapy, the processor circuitry 210 can instruct the audio speaker 251 to provide audible feedback to a patient, can instruct the display interface 252 to provide visual or graphical information to a patient, and/or can instruct the haptic feedback device 253 to provide a haptic stimulus to a patient. In one or more embodiments, the haptic feedback device 253 includes a transducer configured to vibrate or to provide another mechanical signal.

Figure 2B:
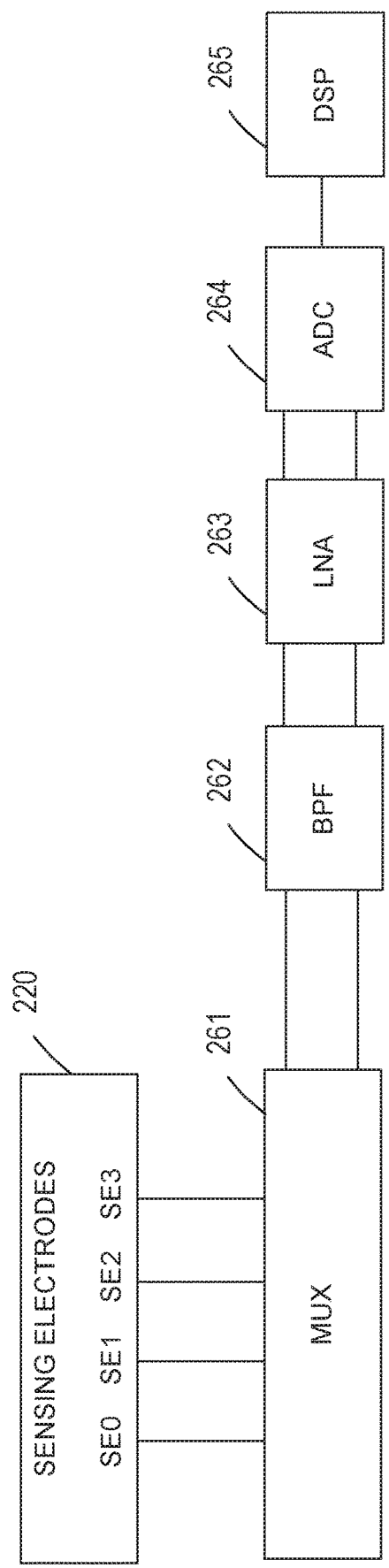
FIG. 2B illustrates, by way of example, a block diagram of an embodiment of a portion of a system configured to receive a signal.

FIG. 2B illustrates generally a block diagram of a portion of a system configured to receive a farfield signal. The system can include the sensing electrodes 220, such as can include the electrodes 121 and 122 of the source 102, or the electrodes 123 and 124 of the farfield sensor device 130. In the example of FIG. 2B, there are at least four sensing electrodes represented collectively as the sensing electrodes 220, and individually as SE0, SE1, SE2, and SE3; however, other numbers of sensing electrodes 220 may also be used. The sensing electrodes can be communicatively coupled to a multiplexer circuitry 261. The multiplexer circuitry 261 can select pairs of the electrodes, or electrode groups, for use in sensing farfield signal information. In one or more embodiments, the multiplexer circuitry 261 selects an electrode pair or grouping based on a detected highest signal to noise ratio of a received signal, or based on another relative indicator of signal quality, such as amplitude, frequency content, and/or other signal characteristic.

Sensed electrical signals from the multiplexer circuitry 261 can undergo various processing to extract information from the signals. For example, analog signals from the multiplexer circuitry 261 can be filtered by a band pass filter 262. The band pass filter 262 can be centered on a known or expected modulation frequency of a sensed signal of interest. A band pass filtered signal can then be amplified by a low-noise amplifier 263. The amplified signal can be converted to a digital signal by an analog-to-digital converter circuitry (ADC) 264. The digital signal can be further processed by various digital signal processors 265, as further described herein, such as to retrieve or extract an information signal communicated by the implantable device 110.

FIG. 3 illustrates, by way of example, a schematic view of an embodiment of a midfield antenna 300 with multiple subwavelength structures 301, 302, 303, and 304. The midfield antenna 300 can include a midfield plate structure with a planar surface. The one or more subwavelength structures 301-304 can be formed in the plate structure. In the example of FIG. 3, the antenna 300 includes a first subwavelength structure 301, a second subwavelength structure 302, a third subwavelength structure 303, and a fourth subwavelength structure 304. Fewer or additional subwavelength structures can be used. The subwavelength structures can be excited individually or selectively by one or more RF ports (e.g., first through fourth RF ports 311, 312, 313, and 314) respectively coupled thereto. A "subwavelength structure" can include a hardware structure with dimensions defined relative to a wavelength of a field that is rendered and/or received by the external source 102. For example, for a given $\lambda_0$ corresponding to a signal wavelength in air, a source structure that includes one or more dimensions less than $\lambda_0$ can be considered to be a subwavelength structure. Various designs or configurations of subwavelength structures can be used. Some examples of a subwavelength structure can include a slot in a planar structure, or a strip or patch of a conductive sheet of substantially planar material. Examples of subwavelength structures are provided in at least the subsection herein titled "COMPACT INTEGRATION OF ELECTRONIC CONTROL HARDWARE WITH ELECTROMAGNETIC TRANSMITTING ELEMENT."

FIG. 4 illustrates generally the phase-matching or amplitude-matching network 400. In an embodiment, the network 400 can include the antenna 300, and the antenna 300 can be electrically coupled to a plurality of switches 404A, 404B, 404C, and 404D, for example, via the first through fourth RF ports 311, 312, 313, and 314 illustrated in FIG. 3. The switches 404A-D are each electrically coupled to a respective phase and/or amplitude detector 406A, 406B, 406C, and 406D, and a respective variable gain amplifier 408A, 408B, 408C, and 408D. Each amplifier 408A-D is electrically coupled to a respective phase shifter 410A, 410B, 410C, and 410D, and each phase shifter 410A-D is electrically coupled to a common power divider 412 that receives an RF input signal 414 to be transmitted using the external source 102.

In one or more embodiments, the switches 404A-D can be configured to select either a receive line ("R") or a transmit line ("T"). A number of switches 404A-D of the network 400 can be equal to a number of ports of the midfield source 402. In the example of the network 400, the midfield source 402 includes four ports (e.g., corresponding to the four subwavelength structures in the antenna 300 of the example of FIG. 3), however any number of ports (and switches), such as one, two, three, four, five, six, seven, eight or more, can be used.

The phase and/or amplitude detectors 406A-D are configured to detect a phase ($\Phi 1$, $\Phi 2$, $\Phi 3$, $\Phi 4$) and/or power (P1, P2, P3, P4) of a signal received at each respective port of the midfield source 402. In one or more embodiments, the phase and/or amplitude detectors 406A-D can be implemented in one or more modules (hardware modules that can include electric or electronic components arranged to perform an operation, such as determining a phase or amplitude of a signal), such as including a phase detector module and/or an amplitude detector module. The detectors 406A-D can include analog and/or digital components arranged to produce one or more signals representative of a phase and/or amplitude of a signal received at the external source 102.

The amplifiers 408A-D can receive respective inputs from the phase shifters 410A-D (e.g., Pk phase shifted by $\Phi k$, $\Phi 1+\Phi k$, $\Phi 2+\Phi k$, $\Phi 3+\Phi k$, or $\Phi 4+\Phi k$). The output of the amplifier, O, is generally the output of the power divider, M when the RF signal 414 has an amplitude of 4*M (in the embodiment of FIG. 4), multiplied by the gain of the amplifier Pi*Pk. Pk can be set dynamically as the values for P1, P2, P3, and/or P4 change. $\Phi k$ can be a constant. In one or more embodiments, the phase shifters 410A-D can dynamically or responsively configure the relative phases of the ports based on phase information received from the detectors 406A-D.

In one or more embodiments, a transmit power requirement from the midfield source 402 is Ptt. The RF signal provided to the power divider 412 has a power of 4*M. The output of the amplifier 408A is about M*P1*Pk. Thus, the power transmitted from the midfield coupler is M*(P1*Pk+ P2*Pk+P3*Pk+P4*Pk)=Ptt. Solving for Pk yields Pk=Ptt/ (M*(P1+P2+P3+P4)).

The amplitude of a signal at each RF port can be transmitted with the same relative (scaled) amplitude as the signal received at the respective port of the midfield coupler coupled thereto. The gain of the amplifiers 408A-D can be further refined to account for any losses between the transmission and reception of the signal from the midfield coupler. Consider a reception efficiency of $\eta$=Pir/Ptt, where Pir is the power received at the implanted receiver. An efficiency (e.g., a maximum efficiency), given a specified phase and amplitude tuning, can be estimated from an amplitude received at the external midfield source from the implantable source. This estimation can be given as $\eta \approx$(P1+ P2+P3+P4)/Pit, where Pit is an original power of a signal from the implanted source. Information about a magnitude of the power transmitted from the implantable device 110 can be communicated as a data signal to the external source 102. In one or more embodiments, an amplitude of a signal received at an amplifier 408A-D can be scaled according to the determined efficiency, such as to ensure that the implantable device receives power to perform one or more programmed operation(s). Given the estimated link efficiency, q, and an implant power (e.g., amplitude) requirement of Pir', Pk can be scaled as Pk=Pir'/[$\eta$(P1+P2+P3+P4)], such as to help ensure that the implant receives adequate power to perform the programmed functions.

Control signals for the phase shifters 410A-D and the amplifiers 408A-D, such as the phase input and gain input, respectively, can be provided by processing circuitry that is not shown in FIG. 4. The circuitry is omitted to not overly complicate or obscure the view provided in FIG. 4. The same or different processing circuitry can be used to update a status of one or more of the switches 404A-D between receive and transmit configurations. See the processor circuitry 210 of FIG. 2A and its associated description for an example of processing circuitry.

Figure 5:
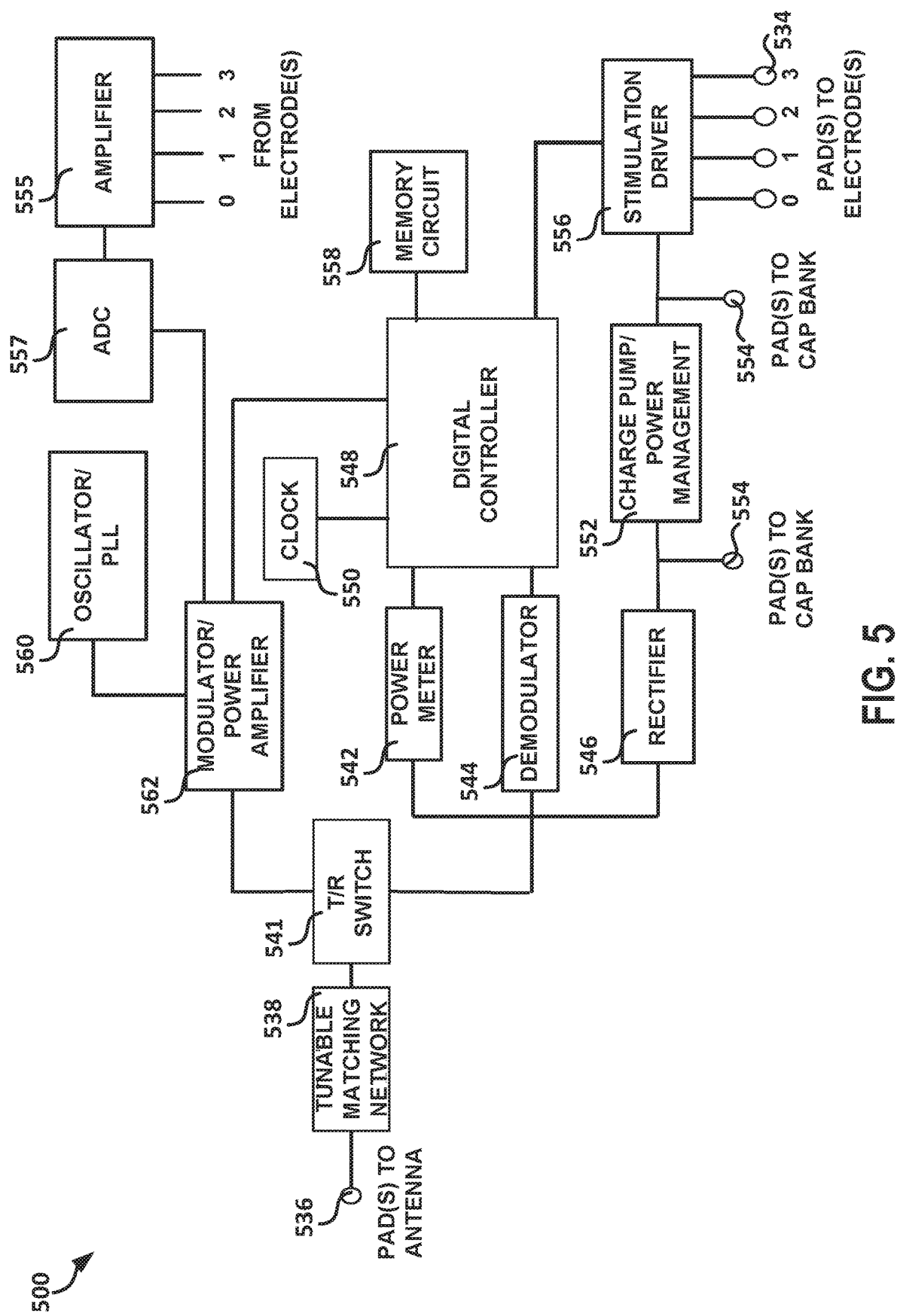
FIG. 5 illustrates, by way of example, a diagram of an embodiment of circuitry of an implantable device.

FIG. 5 illustrates, by way of example, a diagram of an embodiment of circuitry 500 of the implantable device 110, or target device. The circuitry 500 includes one or more pad(s) 536, such as can be electrically connected to the antenna 108. The circuitry 500 can include a tunable matching network 538 to set an impedance of the antenna 108 based on an input impedance of the circuitry 500. The impedance of the antenna 108 can change, for example, due to environmental changes. The tunable matching network 538 can adjust the input impedance of the circuitry 500 based on the varying impedance of the antenna 108. In one or more embodiments, the impedance of the tunable matching network 538 can be matched to the impedance of the antenna 108. In one or more embodiments, the impedance of the tunable matching network 538 can be set to cause a portion of a signal incident on the antenna 108 reflect back from the antenna 108, thus creating a backscatter signal.

A transmit-receive (T/R) switch 541 can be used to switch the circuitry 500 from a receive mode (e.g., in which power and/or data signals can be received) to a transmit mode (e.g., in which signals can be transmitted to another device, implanted or external). An active transmitter can operate at an Industrial, Scientific, and Medical (ISM) band of 2.45 GHZ or 915 MHz, or the 402 MHz Medical Implant Communication Service (MICS) band for transferring data from the implant. Alternatively, data can be transmitted using a Surface Acoustic Wave (SAW) device that backscatters incident radio frequency (RF) energy to the external device. See at least the subsection herein titled "SURFACE ACOUSTIC WAVE BASED COMMUNICATION DEVICE" for further discussion on a SAW based backscatter approach.

The circuitry 500 can include a power meter 542 for detecting an amount of received power at the implanted device. A signal that indicates power from the power meter 542 can be used by a digital controller 548 to determine whether received power is adequate (e.g., above a specified threshold) for the circuitry to perform some specified function. A relative value of a signal produced by the power meter 542 can be used to indicate to a user or machine whether an external device (e.g., the source 102) used to power the circuitry 500 is in a suitable location for transferring power and/or data to the target device.

In one or more embodiments, the circuitry 500 can include a demodulator 544 for demodulating received data signals. Demodulation can include extracting an original information-bearing signal from a modulated carrier signal. In one or more embodiments, the circuitry 500 can include a rectifier 546 for rectifying a received AC power signal.

Circuitry (e.g., state logic, Boolean logic, or the like) can be integrated into the digital controller 548. The digital controller 548 can be configured to control various functions of the receiver device, such as based on the input(s) from one or more of the power meter 542, demodulator 544, and/or the clock 550. In one or more embodiments, the digital controller 548 can control which electrode(s) (e.g., E0-E3) are configured as a current sink (anode) and which electrode(s) are configured as a current source (cathode). In one or more embodiments, the digital controller 548 can control a magnitude of a stimulation pulse produced through the electrode(s).

A charge pump 552 can be used to increase the rectified voltage to a higher voltage level, such as can be suitable for stimulation of the nervous system. The charge pump 552 can use one or more discrete components to store charge for increasing the rectified voltage. In one or more embodiments, the discrete components include one or more capacitors, such as can be coupled to pad(s) 554. In one or more embodiments, these capacitors can be used for charge balancing during stimulation, such as to help avoid tissue damage.

A stimulation driver circuitry 556 can provide programmable stimulation through various outputs 534, such as to an electrode array. The stimulation driver circuitry 556 can include an impedance measurement circuitry, such as can be used to test for correct positioning of the electrode(s) of the array. The stimulation driver circuitry 556 can be programmed by the digital controller to make an electrode a current source, a current sink, or a shorted signal path. The stimulation driver circuitry 556 can be a voltage or a current driver. The stimulation driver circuitry 556 can include or use a therapy delivery circuitry that is configured to provide electrostimulation signal pulses to one or more electrodes, such as using at least a portion of a received midfield power signal from the external source 102. In one or more embodiments, the stimulation driver circuitry 556 can provide pulses at frequencies up to about 100 kHz. Pulses at frequencies around 100 kHz can be useful for nerve blocking.

The circuitry 500 can further include a memory circuitry 558, such as can include a non-volatile memory circuitry. The memory circuitry 558 can include storage of a device identification, neural recordings, and/or programming parameters, among other implant related data.

The circuitry 500 can include an amplifier 555 and analog digital converter (ADC) 557 to receive signals from the electrode(s). The electrode(s) can sense electricity from nerve signals within the body. The nerve signals can be amplified by the amplifier 555. These amplified signals can be converted to digital signals by the ADC 557. These digital signals can be communicated to an external device. The amplifier 555, in one or more embodiments, can be a trans-impedance amplifier.

The digital controller 548 can provide data to a modulator/power amplifier 562. The modulator/power amplifier 562 modulates the data onto a carrier wave. The power amplifier 562 increases the magnitude of the modulated waveform to be transmitted.

The modulator/power amplifier 562 can be driven by an oscillator/phase locked loop (PLL) 560. The PLL disciplines the oscillator so that it remains more precise. The oscillator can optionally use a different clock from the clock 550. The oscillator can be configured to generate an RF signal used to transmit data to an external device. A typical frequency range for the oscillator is about 10 kHz to about 2600 MHz (e.g., from 10 kHz to 1000 MHz, from 500 kHz to 1500 kHz, from 10 kHz to 100 kHz, from 50 kHz to 200 kHz, from 100 kHz to 500 kHz, from 100 kHz to 1000 kHz, from 500 kHz to 2 MHz, from 1 MHz to 2 MHz, from 1 MHz to 10 MHz, from 100 MHz to 1000 MHz, from 500 MHz to 2500 MHz, overlapping ranges thereof, or any value within the recited ranges). Other frequencies can be used, such as can be dependent on the application. The clock 550 is used for timing of the digital controller 548. A typical frequency of the clock 550 is between about one kilohertz and about one megahertz (e.g., between 1 kHz and 100 kHz, between 10 kHz and 150 kHz, between 100 kHz and 500 kHz, between 400 kHz and 800 kHz, between 500 kHz and 1 MHz, between 750 kHz and 1 MHz, overlapping ranges thereof, or any value within the recited ranges). Other frequencies can be used depending on the application. A faster clock generally uses more power than a slower clock.

A return path for a signal sensed from a nerve is optional. Such a path can include the amplifier 555, the ADC 557, the oscillator/PLL 560, and the modulator/power amplifier 562. Each of these items and connections thereto can optionally be removed.

In one or more embodiments, the digital controller 548, the amplifier 555, and/or the stimulation driver circuitry 556, among other components of the circuitry 500, can comprise portions of a state machine device. The state machine device can be configured to wirelessly receive power and data signals via the pad(s) 536 and, in response, release or provide an electrostimulation signal via one or more of the outputs 534. In one or more embodiments, such a state machine device needs not retain information about available electrostimulation settings or vectors, and instead the state machine device can carry out or provide electrostimulation events after, and/or in response to, receipt of instructions from the source 102.

For example, the state machine device can be configured to receive an instruction to deliver a neural electrostimulation therapy signal, such as at a specified time or having some specified signal characteristic (e.g., amplitude, duration, etc.), and the state machine device can respond by initiating or delivering the therapy signal at the specified time and/or with the specified signal characteristic(s). At a subsequent time, the device can receive a subsequent instruction to terminate the therapy, to change a signal characteristic, or to perform some other task. Thus the device can optionally be configured to be substantially passive, or can be configured to be responsive to received instructions (e.g., contemporaneously received instructions).

I. Implantable Device Configurations

Section headings herein, like the one above ("IMPLANTABLE DEVICE CONFIGURATIONS"), are provided to guide a reader generally to material corresponding to the topic indicated by the heading. However, discussions under a particular heading are not to be construed as applying only to configurations of a single type; instead, the various features discussed in the various sections or subsections herein can be combined in various ways and permutations. For example, some discussion of features and benefits of external devices may be found in the text and corresponding figures under the present section heading "IMPLANTABLE DEVICE CONFIGURATIONS".

A. Implantable Stimulation Devices and Steering and Affixing Mechanisms Therefore This section describes embodiments and/or features of therapy devices, guiding mechanisms for situating an implantable device (e.g., the therapy device) within tissue, and/or affixing mechanisms for helping ensure the implantable device does not appreciably move when situated within the tissue. One or more embodiments regard therapy devices for treatment of incontinence (e.g., urinary incontinence, fecal incontinence), overactive bladder, pain or other conditions or symptoms, such as those described elsewhere herein.

An advantage of an implantable device discussed in this section (and others) can include one or more of: (i) a configurable implantable device that can be altered in shape and/or electrode configuration to help target a site for electrostimulation within a body; (ii) an implantable device that can be implanted and then affixed at a target location (such as an S3 foramen); (iii) an implantable device with improved signal reception efficiency (e.g., using (1) a dielectric material surrounding an antenna, the dielectric material including a dielectric constant that is between a dielectric constant of human tissue and that of air, or (2) multiple antennas in the implantable device, such as to include a primary antenna inductively coupled to a secondary antenna), (iv) a thinner, discreet implantable device that can be implanted in areas of thinner tissue, such as between skin and bone; (v) an implantable device that can provide an electrostimulation pattern that an elongated tubular implantable device is not able to provide (due to the location of the electrodes and shape of the implantable device; and (vi) a network of implantable devices that can provide a local or wide area stimulation individually or in combination, among others.

In accordance with several embodiments, a system includes an implantable device comprising an elongated member having a distal portion and a proximal portion. The device includes a plurality of electrodes, a circuitry housing, circuitry within the circuitry housing adapted to provide electrical energy to the plurality of electrodes, an antenna housing, and an antenna (e.g., a helical antenna) in the antenna housing. The plurality of electrodes is situated or located along the distal portion of the elongated member. The circuitry housing is attached to the proximal portion of the elongated member. The circuitry is hermetically sealed or encased within the circuitry housing. The antenna housing is attached to the circuitry housing at a proximal end of the circuitry housing opposite to an end of the circuitry housing attached to the elongated member.

The system may optionally comprise an external midfield power source adapted to provide a power or electrical signal or energy to the implantable device. The implantable device may be adapted to communicate information (e.g., data signals) to an antenna of the external source via the antenna. One, more than one or all of the electrodes may optionally be located at a proximal portion or central portion of the elongated member instead of the distal portion. The circuitry housing may optionally be attached to a distal portion or central portion of the elongated member. The antenna housing may not be attached to the circuitry housing or may not be attached to the proximal end of the circuitry housing. The antenna housing may optionally include a dielectric material with a dielectric constant between that of human tissue and air, such as a ceramic material. The ceramic material may optionally cover the antenna. The elongated member may optionally be flexible and/or cylindrical. The electrodes may optionally be cylindrically-shaped and positioned around a circumference of the elongated member.

The elongated member may optionally include a channel extending through the elongated member from a proximal end of the member to the distal portion of the elongated member and a memory metal wire situated in the channel, the memory metal wire pre-shaped in an orientation to provide curvature to the elongated member. The memory metal may optionally be shaped to conform to a shape of an S3 foramen and generally match a curve of a sacral nerve. The antenna may be a primary antenna and the device may further include a secondary antenna in a housing attached to the antenna housing, the secondary antenna shaped and positioned to provide a near field coupling with the primary antenna. The device may optionally include one or more sutures attached at one or more of: (1) a proximal portion of the antenna housing; (2) a proximal portion of the circuitry housing; and (3) an attachment structure attached to a proximal end of the antenna housing. The antenna may optionally be coupled to a conductive loop of the circuitry situated in a proximal portion of the circuitry housing. There may be a ceramic material between the antenna and the conductive loop.

Figure 6:
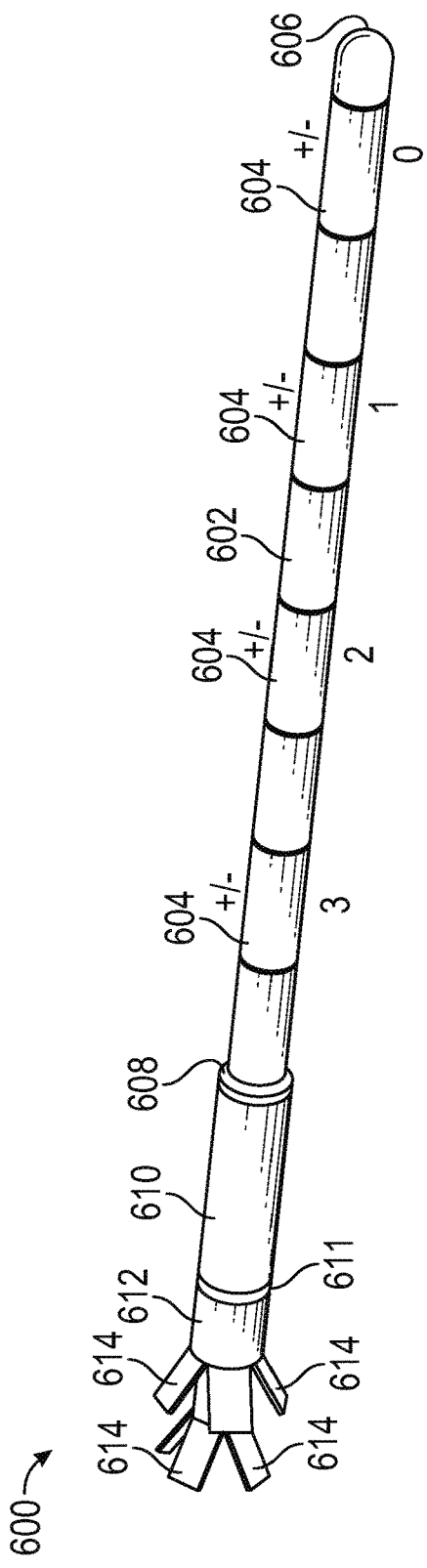
FIG. 6 illustrates, by way of example, a perspective view diagram of an embodiment of an implantable device.

FIG. 6 illustrates, by way of example, a perspective view diagram of an embodiment of an implantable device 600. The implantable device 110 can include one or more features of the implantable devices discussed in this section. The implantable device 600, as illustrated, includes an elongated, distal body portion 602. The body portion 602 includes a plurality of electrodes 604 embedded at least partially therein and/or affixed thereto. The body portion 602 includes a distal end 606 and a proximal end 608. The proximal end 608 is affixed to a circuitry housing 610. The circuitry housing 610 is affixed to an antenna housing 612. The antenna housing 612, as illustrated, includes a plurality of tines 614 affixed thereto.

The body portion 602, electrodes 604, circuitry housing 610, and antenna housing 612 are illustrated as being generally cylindrical. The implantable device 600 is configured to be powered wirelessly (e.g., through electromagnetic waves incident on the implantable device 600 and external to the body in which the implantable device 600 is implanted). The implantable device 600 is configured to provide stimulation (e.g., neurostimulation, muscle stimulation, other electrostimulation) or other forms of modulation (e.g., denervation) to a therapy site within a patient (e.g., a human or other animal patient). The implantable device 600 can be situated within a patient using a catheter (discussed with regard to FIGS. 26A-35B, and elsewhere herein).

The body portion 602 can include a flexible material. In one or more embodiments, the flexible material can include polyurethane, silicone, epoxy and/or any other flexible material. In one or more embodiments, the body portion 602 can include a shape memory polymer. The flexible material can provide the ability to shape the body portion 602, such as while the body portion 602 is internal to the patient.

The electrodes 604 illustrated include an electrode array of four stimulation electrodes 604 along the body portion 602. The electrodes 604, in one or more embodiments, include platinum, iridium, stainless steel, titanium, titanium nitride, or other conductive material. In one or more embodiments, the electrodes include a platinum and iridium alloy, such as a combination that is 90% platinum and 10% iridium. Other combinations are possible (e.g., 85% platinum and 15% iridium, 95% platinum and 5% iridium, 80% platinum and 20% iridium). In one or more embodiments, the electrodes can include a coating, such as with a material that can improve electrical performance in a specified medium, such as a body. In one or more embodiments, the electrodes 604 are electrically separated from one another, such as by one or more electrical switches. In one or more embodiments, the electrodes 604 are about one to ten millimeters (e.g., one to three, two to five, two to eight, three to six, four to nine, five to seven, six to ten, two to four, overlapping ranges thereof, or any value within the recited ranges, such as three millimeters) in width (along the elongated dimension of the body portion 602). In one or more embodiments, the electrodes 604 are separated by about one to ten millimeters (e.g., one to three, two to five, two to eight, three to six, four to nine, five to seven, six to ten, two to four, overlapping ranges thereof, or any value within the recited ranges, such as three mm). In one or more embodiments, the diameter of the electrodes is about one to five millimeters (e.g., one to two, one to three, two to four, three to five, overlapping ranges thereof, or any value within the recited ranges, such as 1.1 mm. 1.2 mm, 1.3 mm, 1.4 mm, 1.5 mm, 1.6 mm, 1.7 mm, 1.8 mm, 1.9 mm, 2.0 mm). The electrodes 604 are, respectively, electrically connected to circuitry 716 (see FIG. 7) and hermetically enclosed in the circuitry housing 610.

The circuitry housing 610 can provide a hermetic enclosure for the circuitry 716. The circuitry housing 610 can include titanium (e.g., commercially pure, 6Al/4V or another alloy), platinum, stainless steel, or a ceramic material (such as zirconia or alumina, for example), or other hermetic, biocompatible material. The circuitry housing 610 provides an airtight space for the circuitry 716. If a metallic material is used for the circuitry housing 610, the circuitry housing 610 can be used as part of the electrode array, such as can effectively increase the number of selectable electrodes 604 for stimulation or other modulation.

An antenna housing 612 can be located at a proximal end 611 of the circuitry housing 610. An antenna 718 (see FIGS. 12A-12C, for example) within the antenna housing 612 can be used for powering and communication to and/or from the implantable device 600, such as from a device external to the patient or subject.

Rather than being hermetic, the circuitry housing 610 can be backfilled to prevent ingress of moisture therein. The backfill material can include a non-conductive, waterproof material, such as an epoxy, parylene, Tecothane® material, a copy thereof, or another material.

In one or more embodiments, tines 614 can be attached at a proximal portion of the antenna housing 612 (see FIGS. 14A, 14B, 14C, 15A, 15B, 15C, 16A, and 16B, among others, for a view of a proximal portion of the antenna housing 612). The tines 614 can provide the ability to affix (e.g., attach or couple) the implantable device 600 at a specific location within the patient. The tines 614 can be configured to affix the implantable device 600 to a specific anatomical structure. The tines 614 can be made of a polymer or other flexible or semi-flexible material, such as can include silicone, polyurethane, epoxy, or like materials. The tines 614 can flare away from a central axis of the antenna housing 612 such that a distal portion of a given tine 614 is closer to the central axis than a more proximal portion of the given tine 614, such as is shown in FIG. 6, among other FIGS.

Figure 7:
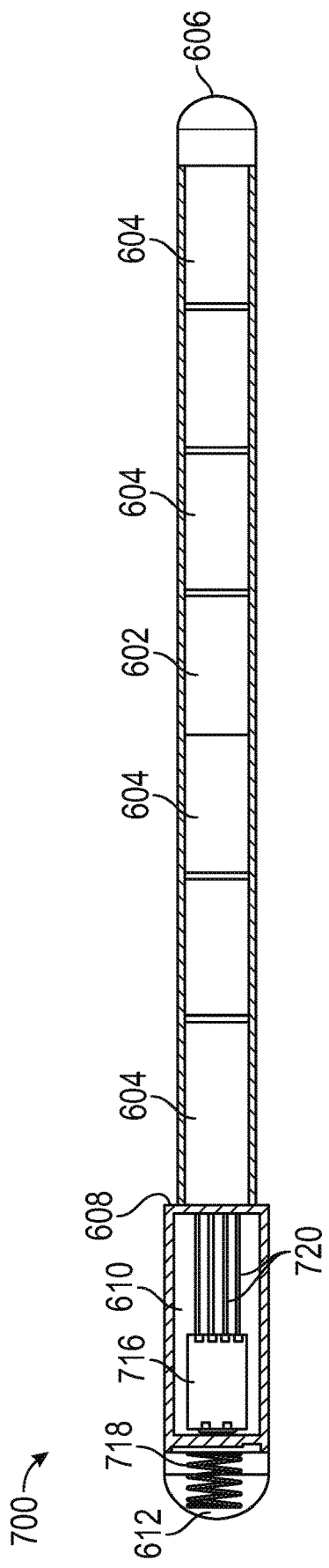
FIG. 7 illustrates, by way of example, a perspective view diagram of another embodiment of an implantable device that shows internal circuitry and an antenna internal to the device.

FIG. 7 illustrates, by way of example, a perspective view diagram of another embodiment of an implantable device 700 that shows internal circuitry 716 and an antenna 718. The circuitry housing 610 and the antenna housing 612 are shown as transparent so as to not obscure the view of the items internal thereto.

The circuitry 716 is configured to provide a programmable control for each electrode 604 in the electrode array. Any of the electrodes along the array can be programmed, using or based on signals from the source 102 received at the circuitry 716, as a current source or sink. Each of the electrodes 604 can be independently addressed for current or voltage amplitude in generally the same manner. For example, to reach further into the patient, the electrode labelled "0" can be programmed as a current source. Any one or more of the other electrodes, in this example, can be programmed as a current sink.

The circuitry 716 is shown housed within the circuitry housing 610. The circuitry 716 is electrically connected to the electrode array, such as at the distal portion of the circuitry housing 610 by respective electrical connections 720. The circuitry 716 is electrically coupled to the antenna 718, such as through an inductive coupling or a wired connection. The antenna 718 and/or electrodes 604 can be encapsulated in a non-hermetic material and connected to the circuitry 716, such as by using one or more feedthrough connections, such as discussed with regard to FIGS. 8A and 8B.

Figure 8A:
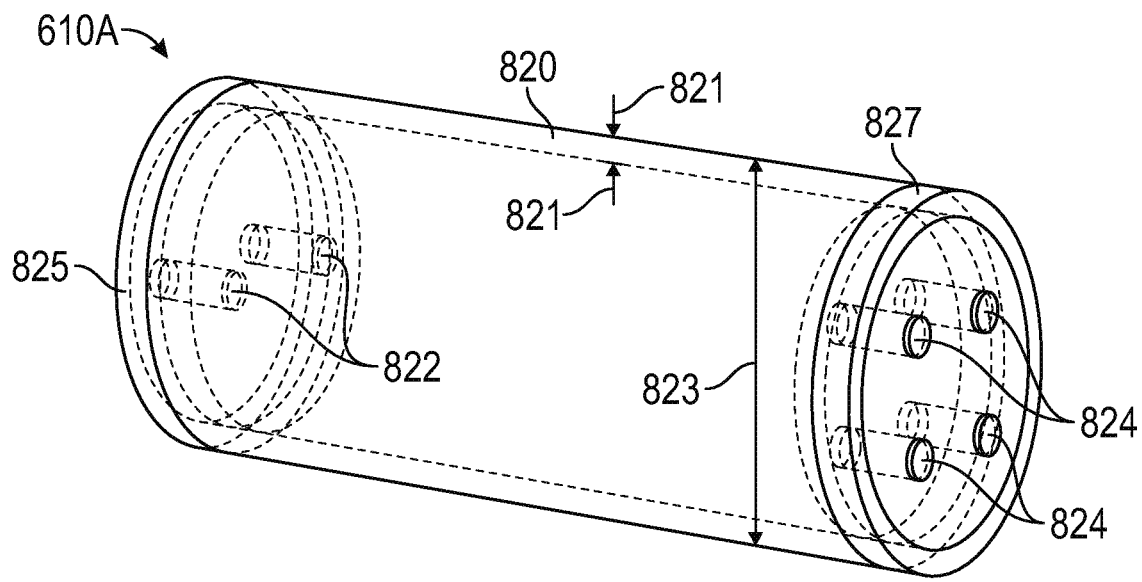
FIG. 8A illustrates, by way of example, a perspective view diagram of an embodiment of circuitry housing.

FIG. 8A illustrates, by way of example, a perspective view diagram of an embodiment of a circuitry housing 610A. The circuitry housing 610A as illustrated includes a wall 820 (e.g., a casing), proximal feedthroughs 822, and distal feedthroughs 824. In an embodiment, a wall thickness 821 can be between about 25 micrometers and about 400 micrometers (e.g., less than 400 micrometers, less than 350 micrometers, less than 300 micrometers, less than 250 micrometers, less than 200 micrometers, less than 150 micrometers, less than 130 micrometers, less than 125 micrometers, less than 120 micrometers, less than 115 micrometers, less than 110 micrometers, less than 100 micrometers, less than 50 micrometers, between 25 micrometers and 100 micrometers, between 40 micrometers and 60 micrometers, between 50 micrometers and 100 micrometers, between 100 micrometers and 200 micrometers, between 150 micrometers and 400 micrometers, between 200 micrometers and 350 micrometers, overlapping ranges thereof, or any value within the recited ranges, such as 50 micrometers), and can depend on the material(s) used to create the circuitry housing 610A. In an embodiment, an outer diameter 823 of the circuitry housing 610A can be about 1 mm to 3 mm (e.g., 1 mm to 2 mm, 1.5 mm to 2.5 mm, 1.50 mm to 1.75 mm, 2 mm to 3 mm, overlapping ranges thereof, or any value within the recited ranges, such as 1.66 mm, 1.70 mm, 1.60 mm, 1.55 mm, 1.72 mm). The circuitry housing 610A can be created using a machining process or can be drawn, cast, molded, or otherwise provided. The circuitry housing 610A can be made of a metal, metal alloy, ceramic, or similar material, such as can include a combination of platinum and iridium. The circuitry housing 610A can include a dielectric film, such as polyimide, lining an inner surface thereof, such as to provide more electrical insulation for circuitry housed within the circuitry housing 610A.

The proximal feedthroughs 822 and the distal feedthroughs 824 provide a space through which a wire (a conductive wire or non-conductive wire) can be passed from inside the circuitry housing 610A to outside the circuitry housing 610A. The feedthroughs 822 pass through a proximal portion 825 of the circuitry housing 610A, such as to provide a wire to an antenna 718 in the antenna housing 612 or other proximal destination, such as external to the patient's body. The feedthroughs 824 pass through a distal portion 827 of the circuitry housing 610A, such as to provide a wire to a respective electrode 604 or a distal portion of the body portion 602, such as the distal end 606.

FIG. 8A illustrates the circuitry housing 610A as including a bipolar proximal feedthrough 822 (e.g., two feedthroughs through the proximal portion 825) and a quadripolar distal feedthrough 824 (e.g., four feedthroughs through the distal portion 827). The circuitry housing 610A can be used in embodiments that include a wired connection between the antenna 718 and the circuitry 716.

Figure 8B:
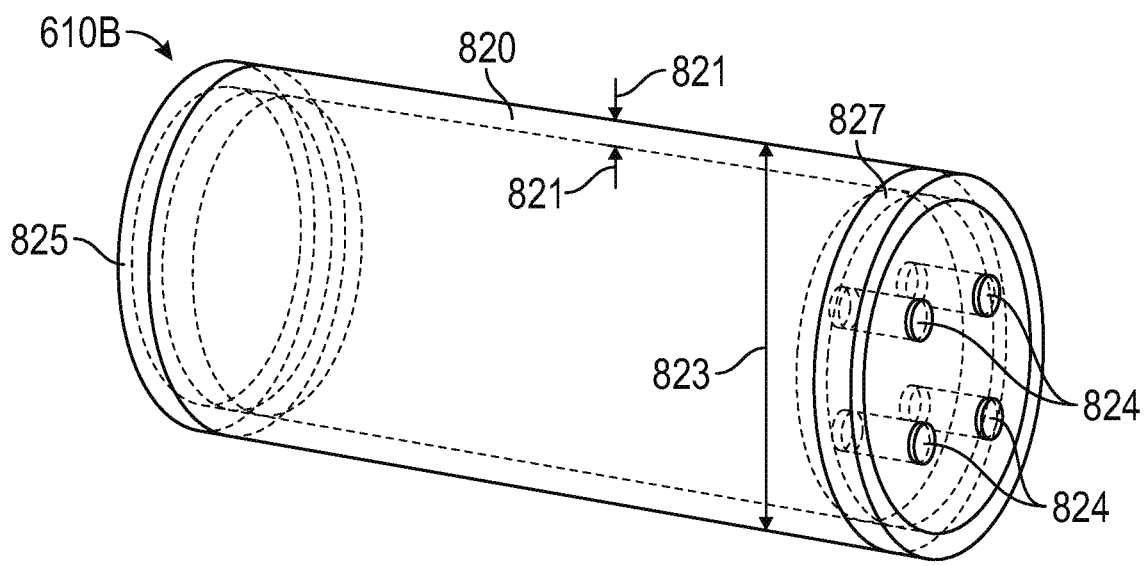
FIG. 8B illustrates, by way of example, a perspective view diagram of another embodiment of the circuitry housing.

FIG. 8B illustrates, by way of example, a perspective view diagram of another embodiment of a circuitry housing 610B. The circuitry housing 610B includes distal feedthroughs 824 and no proximal feedthroughs 822. Note that while the number of distal feedthroughs 824 is illustrated as four, the number of distal feedthroughs 824 can be any number two or greater in various embodiments. The number of distal feedthroughs 824 and proximal feedthroughs 822 can be limited by the outer diameter 823 of the circuitry housing 610B and a diameter of the feedthroughs 824/822.

The circuitry housing 610B can be used in an embodiment in which there is an inductive (e.g., near field) coupling between the circuitry 716 and the antenna 718. The feedthroughs 824 can be used for electrical connections to the electrodes 604, or a mechanical connection to a distal portion of the body portion 602, such as the distal end 606.

Figure 9:
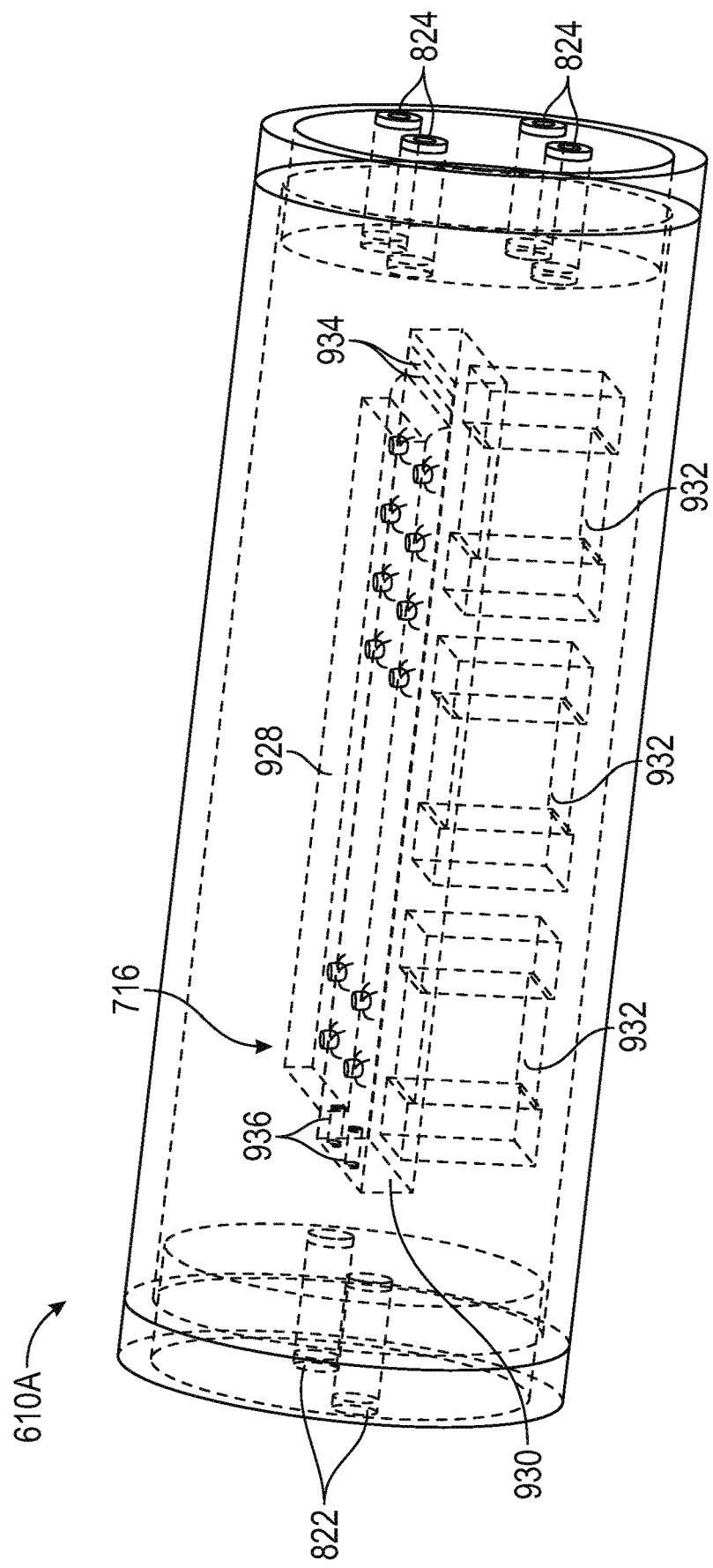
FIG. 9 illustrates, by way of example, a perspective view diagram of an embodiment of the circuitry housing that shows the circuitry internal to the circuitry housing of FIG. 8A.

FIG. 9 illustrates, by way of example, a perspective view diagram of the embodiment of the circuitry housing 610A that shows the circuitry 716 internal thereto. The circuitry 716, as illustrated, includes an Application Specific Integrated Circuitry (ASIC) 928, a board 930, and discrete components (e.g., one or more inductors, capacitors, resistors, diodes, transistors, switches, oscillators, or the like). The ASIC 928 can be designed as a System-on-Chip (SoC) package. In one or more embodiments, the substrate for the SoC can be thinned to 625 micrometers or less (e.g., between about 50 micrometers and 250 micrometers, about 100 micrometers, between about 75 micrometers and about 125 micrometers, between about 100 micrometers and 300 micrometers, between about 50 micrometers and 625 micrometers, or other thickness within a range provided). The ASIC 928 can be attached to the board 930 (e.g., a printed circuit board (PCB)), such as by using a flip-chip attachment. The material for the board 930 can be a glass-reinforced epoxy laminate comprising a composite material composed of woven fiberglass cloth with an epoxy resin binder that is flame resistant (e.g., FR4 material), aluminum nitride, polyimide, or the like. The thickness of the board 930 can be less than 125 microns (e.g., between 50 and 100 microns, greater than 75 and less than 125 microns, greater than 100 and less than 125 microns, between 75 and 100 microns, between 100 and 120 microns, overlapping ranges thereof, or any value within the recited ranges), in one or more embodiments. The discrete components 932 can be surface mount or other components.

Pads 934 can be used for electrical connections to wires that are fed through the feedthroughs 824. Pads 936 can be used for electrical connections to wires that are fed through the feedthroughs 822. The connections to the pads 934/936 can include wire bonds, magnet wire, extension of the feedthrough wires, flat ribbon wires, and/or soldered connections to a flexible board substrate, among others.

FIG. 5 illustrates, by way of example, a diagram of an embodiment of circuitry 500 that can be housed by the circuitry housing 610, such as can include the ASIC 928, the board 930, or other components of FIG. 9. The ASIC 928 can be an SoC integrating functions for wireless RF power harvesting, RF communications, digital control, and therapy delivery. The ASIC 928 can be manufactured using (complementary metal-oxide semiconductor) CMOS technology, such as can use a 0.18 micron or other process.

Figure 10:
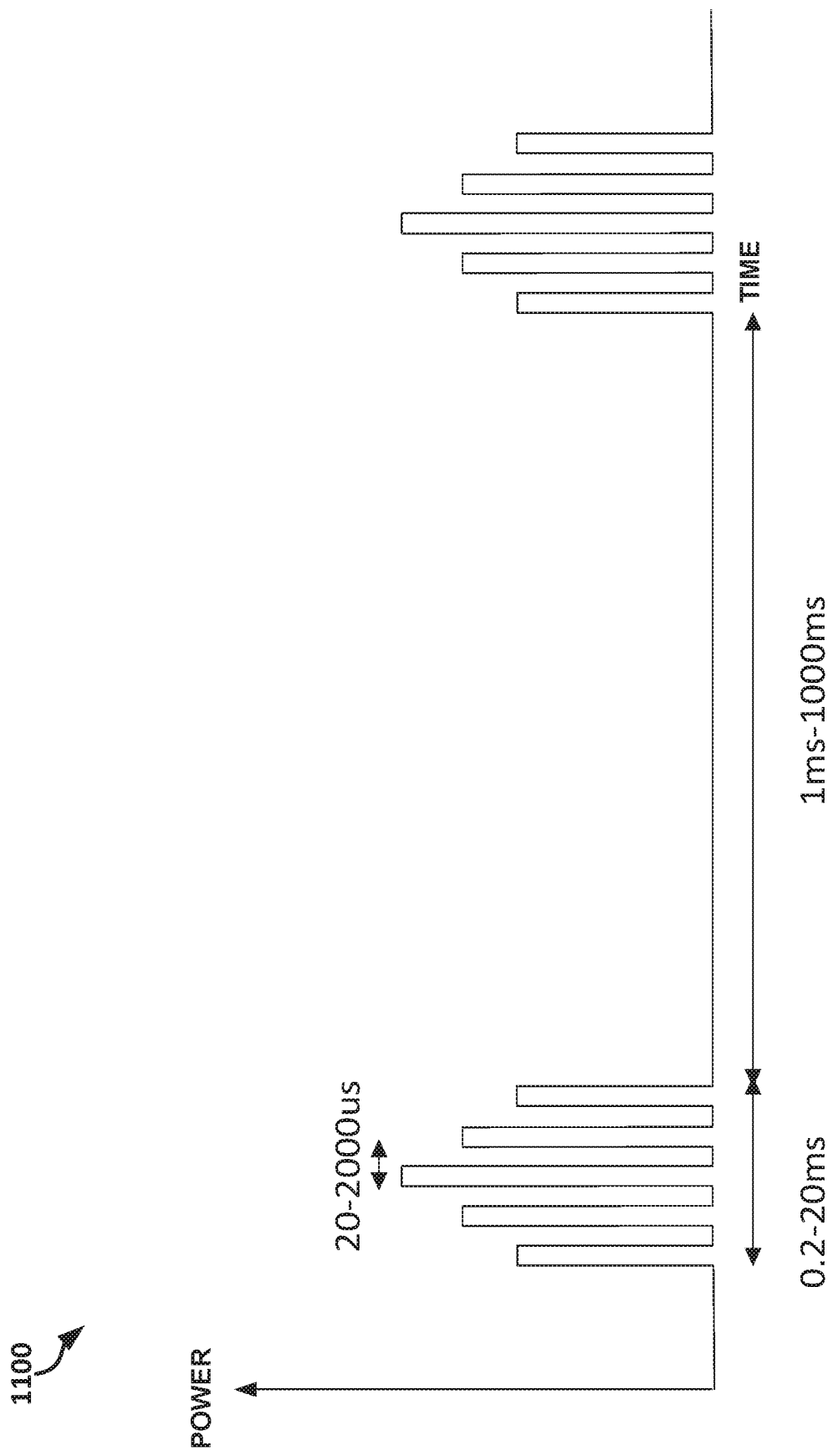
FIG. 10 illustrates, by way of example, a signal power vs time graph for a stimulation pulse from an implantable device.

FIG. 10 illustrates, by way of example, a graph showing an example 1100 of signal power vs. time for a stimulation pulse from the implantable device 600, such as created by the circuitry 1000, such as can include one or more of the components of the circuitry 716. The stimulation waveform can be controlled using stimulation driver circuitry 556. The stimulation can be wirelessly programmed from an external powering unit for varying amplitudes (e.g., 0-10V in voltage controlled case or 0-10 mA in current controlled case) in discrete levels. Control of stimulation waveforms can include the use of a digital to analog converter (DAC) of the stimulation driver circuitry 556.

The stimulation can be digitally programmed for varying pulse frequencies (e.g., between about 0.1 Hz to 100,000 Hz, between 1 Hz and 1 kHz, between 0.1 Hz and 100 Hz, between 100 Hz and 1 kHz, between 500 Hz and 2 kHz, between 1 Hz and 10 kHz, between 5 kHz and 15 kHz, between 10 kHz and 20 kHz, between 1 kHz and 10 kHz, between 1 kHz and 15 kHz, between 50 kHz and 100 kHz, overlapping ranges thereof, or any value within the recited ranges) and pulse widths (e.g., between about 10-1000 microseconds, between 10 and 500 microseconds, between 10 and 100 microseconds, between 50 and 200 microseconds, between 100 and 500 microseconds, between 250 and 750 microseconds, between 400 and 1000 microseconds, between 500 and 1000 microseconds, between 750 and 1000 microseconds, between 400 and 800 microseconds, overlapping ranges thereof, or any value within the recited ranges). The stimulation can be monophasic or biphasic. Monophasic means the stimulation current flows in only one direction. A biphasic signal flows in both directions (e.g., positive and negative pulses, such as can be provided in a non-overlapping, partially-overlapping, or substantially concurrent manner). In an embodiment, a biphasic signal can be "charge balanced" such that there is effectively zero net charge movement (i.e., an amount of signal that is positive is about the same as an amount of signal is negative). The stimulation shape can be generally rectangular, exponential, or other shape. The stimulation waveform can be programmed to emit a burst of pulses (e.g., between 1 and 1000 pulses, between 1 and 100 pulses, between 50 and 200 pulses, between 10 and 500 pulses, between 100 and 400 pulses, between 250 and 750 pulses, between 500 and 1000 pulses, between 300 and 800 pulses, between 750 and 1000 pulses, overlapping ranges thereof, or any value within the recited ranges). A burst of pulses can be followed by a period without pulses, another series of pulses, and so on, such as shown in FIG. 10. In some embodiments, the period of time between pulses ranges between 1 ms and 1000 ms (e.g., between 1 ms and 100 ms, between 10 ms and 150 ms, between 50 ms and 500 ms, between 100 ms and 800 ms, between 150 ms and 450 ms, between 200 ms and 600 ms, between 250 ms and 1000 ms, between 400 ms and 800 ms, between 500 ms and 1000 ms, between 750 ms and 1000 ms, overlapping ranges thereof or any value within the recited ranges). Of course, values outside of these ranges could also be used. In some embodiments, each burst of pulses may have a duration between 0.1 ms and 100 ms (e.g., between 0.1 ms and 1 ms, between 0.2 and 20 ms, between 0.1 ms and 10 ms, between 1 ms and 10 ms, between 5 ms and 50 ms, between 10 ms and 100 ms, between 10 ms and 50 ms, between 20 ms and 80 ms, between 30 ms and 60 ms, between 60 ms and 100 ms, overlapping ranges thereof, or any value within the recited ranges. Of course, values outside of these ranges could also be used. In some embodiments, each pulse has a duration of between 20 microseconds and 2000 microseconds (e.g., between 20 microseconds and 50 microseconds, between 20 microseconds and 200 microseconds, between 50 microseconds and 500 microseconds, between 100 microseconds and 1000 microseconds, between 500 microseconds and 2000 microseconds, between 1000 microseconds and 2000 microseconds, between 100 microseconds and 500 microseconds, overlapping ranges thereof, or any value within the recited ranges). Of course, values outside of these ranges could also be used. The stimulation driver circuitry 556 can be programmed to ramp a stimulation pulse upwards (e.g., pulses with increasing amplitude), such as in response to activation to a programmed amplitude. Upon deactivation of stimulation, the stimulation driver circuitry 556 amplitude can be programmed to ramp the stimulation pulse downwards (e.g., using pulses with decreasing amplitude) to zero. The stimulation pulses can be synchronized in time with various parameters, such as with features of various stimulation waveforms from other wireless implants at other anatomical locations.

The stimulation driver circuitry 556 can be programmed to ramp a stimulation pulse upwards (e.g., pulses with increasing amplitude), such as in response to activation to a programmed amplitude. Upon deactivation of stimulation, the stimulation driver circuitry 556 amplitude can be programmed to ramp the stimulation pulse downwards (e.g., using pulses with decreasing amplitude) to zero. The stimulation pulses can be synchronized in time with various parameters, such as with features of various stimulation waveforms from other wireless implants at other anatomical locations.

FIG. 11A illustrates, by way of example, a perspective view diagram of a proximal portion of an embodiment of an implantable device 1200A. The device 1200A can be powered through signals received at an antenna 718A housed in the antenna housing 612. The antenna housing 612 can be in a proximal portion of the device 1200A. The antenna 718A can be connected to the circuitry 716 through one or more of the feedthroughs 822. In one or more embodiments, the antenna 718A can be a dielectric rod antenna, helically shaped, a coil, or other shape. The device 1200A includes the circuitry housing 610A. In one or more embodiments, the antenna 718A can be an asymmetric dipole antenna, such as with the circuitry housing 610A serving as part of the dipole. In one or more embodiments, the antenna can be a dielectric rod antenna.

FIG. 11B illustrates, by way of example, a perspective view diagram of a proximal portion of another embodiment of an implantable device 1200B. The device 1200B is similar to the device 1200A with the device 1200B including a helically-shaped antenna 718B and the circuitry housing 610B. A normal vector of the antenna 718B can be generally parallel to a magnetic field induced by the antenna 718B. The antenna 718B can include a helical traveling wave antenna with its normal vector generally parallel with a pointing vector of an incident wave. The antenna can also be an asymmetric dipole antenna with the hermetic package serving as part of the dipole. As previously discussed, the antenna can be a dielectric rod antenna.

In one or more embodiments, the antenna housing 612 can be gold brazed to the circuitry housing 610A-B. In one or more embodiments, the antenna housing 612 can include an epoxy, tecothane, or other RF transparent and protective material. The antenna 718B can be coupled in the near field to the circuitry housing 610B, such as to help increase the amount of electromagnetic energy captured by antenna 718C.

In one or more embodiments, the antenna housing 612 can include a ceramic material, such as zirconia or alumina. Because the dielectric constant of zirconia is closer to that of muscle, embodiments including zirconia or other ceramic materials can help stabilize the impedance of the antenna 718 and decrease the change in impedance when the antenna 718 is surrounded by different tissue types. The power transfer efficiency, while the antenna 718 is surrounded by a lower permittivity tissue, is increased when using a ceramic housing. In this case, the antenna 718 can be composed as a single ceramic structure with the feedthrough.

Rather than using a feedthrough to connect the antenna 718, the power can be transferred from an antenna outside the circuitry housing 610 to a structure (e.g., another antenna) within the circuitry housing 610. The energy transfer can occur or be effected inductively through a ceramic cap 1264. The ceramic cap 1264 can be used to seal one end of the circuitry housing 610B. In one or more embodiments, a loop or helix structure can be encapsulated in the antenna housing 612 outside the circuitry housing 610B. Electromagnetic energy from outside the body is transferred to the antenna 718B, which in turn transfers the energy to the antenna 718C within the circuitry housing 610B. In effect, the antenna 718B acts as a relay to the antenna 718C within the circuitry housing 610B. The antenna 718C within the package can be connected to the circuitry 716 (e.g., through the pad 936).

FIG. 11C illustrates, by way of example, a perspective view diagram of a proximal portion of yet another embodiment of an implantable device 1200C. An alternative antenna structure includes the use of multiple antennas that are not physically connected with a conductor. For example, a loop 718E can serve as a primary antenna. The loop 718E can be connected (through the feedthrough 832) to the circuitry 716. One or more surrounding loops 718D can capture energy and transfer it to the primary antenna (the loop 718E) through near field coupling. In contrast to a single, larger loop with the same additive cross-sectional area as multiple, smaller loops, each of the smaller loops can be operated below their self-resonant frequency while within tissue.

FIG. 12A illustrates, by way of example, a perspective view diagram of an embodiment of an implantable device 1300A with an external housing invisible to show the internal circuitry of the implantable device. FIG. 12B illustrates, by way of example, an exploded view diagram of a portion of the implantable device 1300A in the dashed box labelled "12B" in FIG. 12A. In one or more embodiments, an antenna 718F can be placed within a circuitry housing 610C. In such embodiments, the material of the circuitry housing 610C is made of an RF transparent material such as zirconia, alumina, or glass, or other ceramic material, rather than a metal. The antenna 718F can be a helical antenna that is wrapped around the circuitry 716. Such a configuration can provide a more compact package as compared to other embodiments.

In the embodiment shown in FIGS. 12A and 12B, quadripolar feedthroughs are situated in both sides of the circuitry housing 610C. Such a configuration can help allow for an increased number of electrodes (8 in this case but other numbers of electrodes (e.g., 1, 2, 3, 4, 5, 6, 7, 9, 10, 11, 12, more than 12), as compared to other embodiments previously discussed.

FIG. 13A illustrates, by way of example, a perspective view diagram of an embodiment of a proximal portion of an implantable device and attachable tine system 1400A. FIG. 13B illustrates, by way of example, a perspective view diagram of an embodiment of the proximal portion of the implantable device and attachable tine system 1400B of FIG. 13A. FIG. 13C illustrates, by way of example, a perspective view diagram of an embodiment of an implantable device 1400C with tines attached thereto. The tines 614 can be used for fixation of the implantable device, such as by grappling tissue. A growth of a fibrous tissue aid can provide additional long term fixation, such as to help prevent migration of the implant. However, in some cases, fixation with tines 614 is not useful, such as for a temporary implant that is used for a trialing period. The trialing period can be to determine if a patient has a proper therapeutic response. In one or more embodiments, the tines 614 cannot be affixed to the implant during the trialing period, such as to allow the device to be more easily removed from the patient. After a trial period is complete that shows a proper therapeutic response to the therapy, the tines 614 can be added to the device, such as shown in FIGS. 13A-13C.

The system 1400A-B can include an attachment structure 1468 affixed to or integrally formed with the antenna housing 612. The attachment structure 1468 can be situated at a proximal end of the antenna housing 612. The tines 614 can be a part of a structure that includes a cap 1470 that fits over the attachment structure 1468 and/or the antenna housing 612. The cap 1470 can fit over the structure 1468 and the tine structure can be slid onto the implantable device, such as is shown in FIGS. 13B and 13C.

A non-circular structure 1466 at a proximal end of the tine structure can help lock the tines 614 into place on the implantable device. The structure 1468 allows for tines to be attached to the implantable device, such as while the device is placed at the target anatomy. The mating of the structure 1468 and the cap 1470 can help make it more difficult for the tines 614 to rotate (e.g., about a longitudinal axis of the implantable device 600). This limited motion advantageously helps keeps the tines 614 in place, in accordance with several embodiments.

FIG. 14A illustrates, by way of example, a perspective view diagram of an embodiment of a system 1500A for attaching tines 614 to an implantable device. FIG. 14B illustrates, by way of example, a perspective view diagram of the system of FIG. 14A with the tines 614 being pushed closer to the circuitry housing 610. FIG. 14C illustrates, by way of example, a perspective view diagram of the system of FIG. 14B with the tines 614 attached to the circuitry housing 610.

The tines 614 can be guided to a proximal portion of the implantable device 600, such as by using a suture 1476 that extends at least to a surface of the anatomical structure (e.g., such as can extend external to the patient's body). The cap 1470 can have an opening therethrough that allows the tines 614 to fit around the suture 1476. Using a hollow pushrod 1472 that has the suture 1476 therethrough, the tines 614 can be pushed into place through tissue and attached to the implant, such as shown in FIGS. 14A-14C. The suture 1476 can be held taut. The tines 614 and pushrod 1472 can be inserted while the suture 1476 is held taut. The suture 1476 provides a guide to the implantable device 600 while also providing a tension against which the tines 614 can be attached.

Figure 15A:
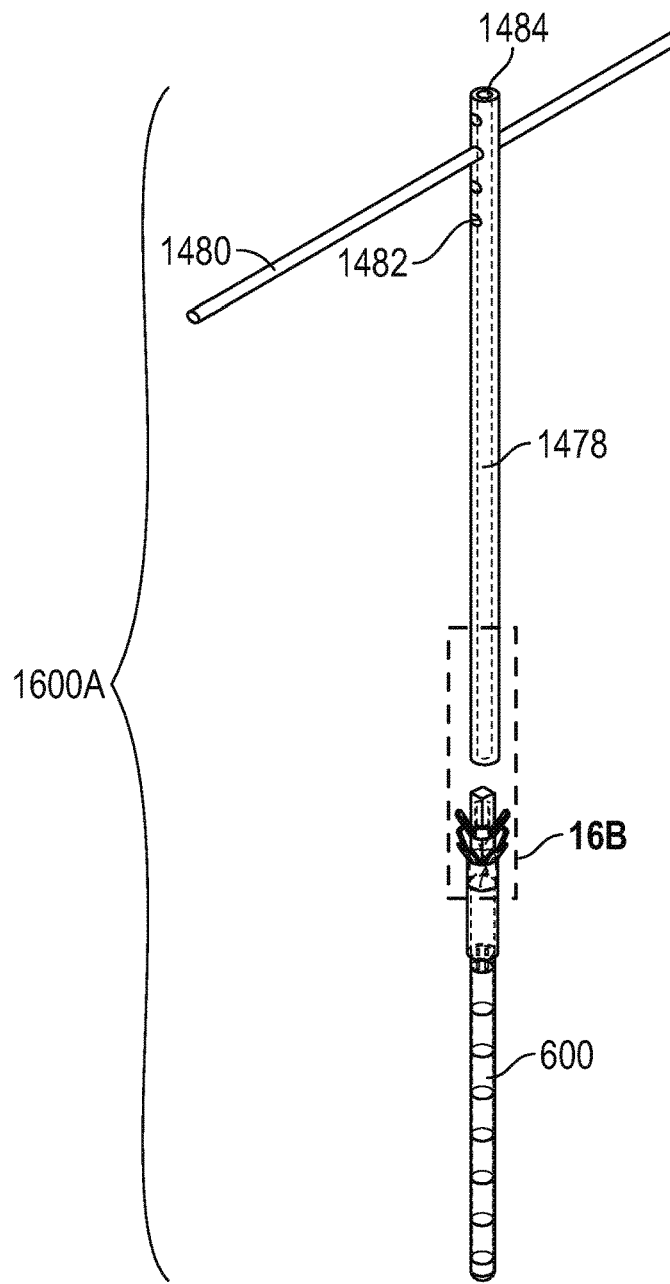
FIG. 15A illustrates, by way of example, a perspective view diagram of an embodiment of a system for securing tines to an implantable device.
Figure 15B:
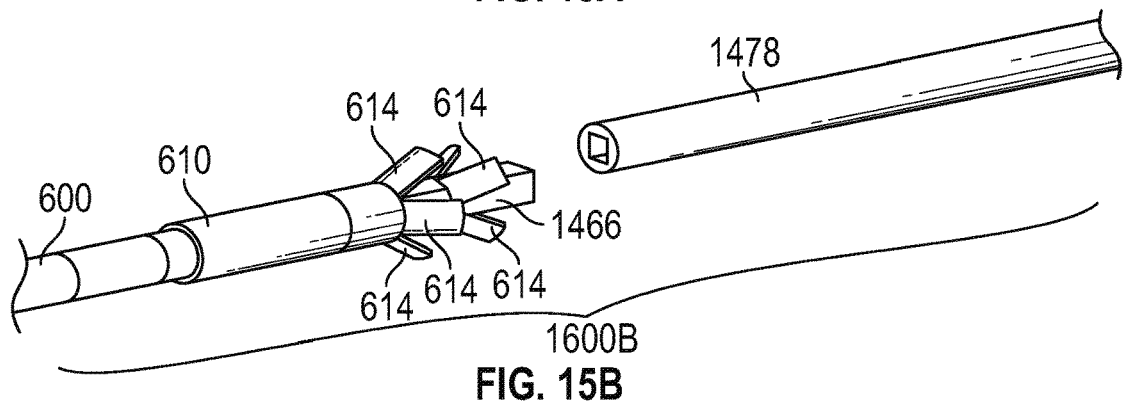
FIG. 15B illustrates, by way of example, an exploded view diagram of an embodiment of a system for securing tines to an implantable device as depicted in the dashed box labelled "15B" in FIG. 15A.

FIG. 15A illustrates, by way of example, a perspective view diagram of an embodiment of a system 1600B for securing tines 614 to an implantable device. FIG. 15B illustrates, by way of example, an exploded view diagram of an embodiment of the area corresponding to the dashed box labelled "15B" in FIG. 15A. The attachment structure 1466 can include a non-circular, symmetric shape (a cube or hexagon, or other polygon) or non-symmetric shape. The attachment structure 1466 can be molded at the proximal end of the implantable device 600. A pushrod 1478 (such as can include a mating socket device) can be used to turn the structure that includes the tines 614. Turning the pushrod 1478 while attached to the structure 1466 can lock the tines 614 into place, such as to help ensure that the implantable device 600 does not move after implantation. The pushrod 1478 can include a hole 1484 therethrough. A suture 1476 (e.g., a suture attached to the implanted device) can be threaded through the hole 1484 to guide the pushrod 1478 to the attachment structure 1466. Such embodiments can help control the depth, angle, rotation, and/or curvature direction of the electrode array of the implant during placement.

Figure 15C:
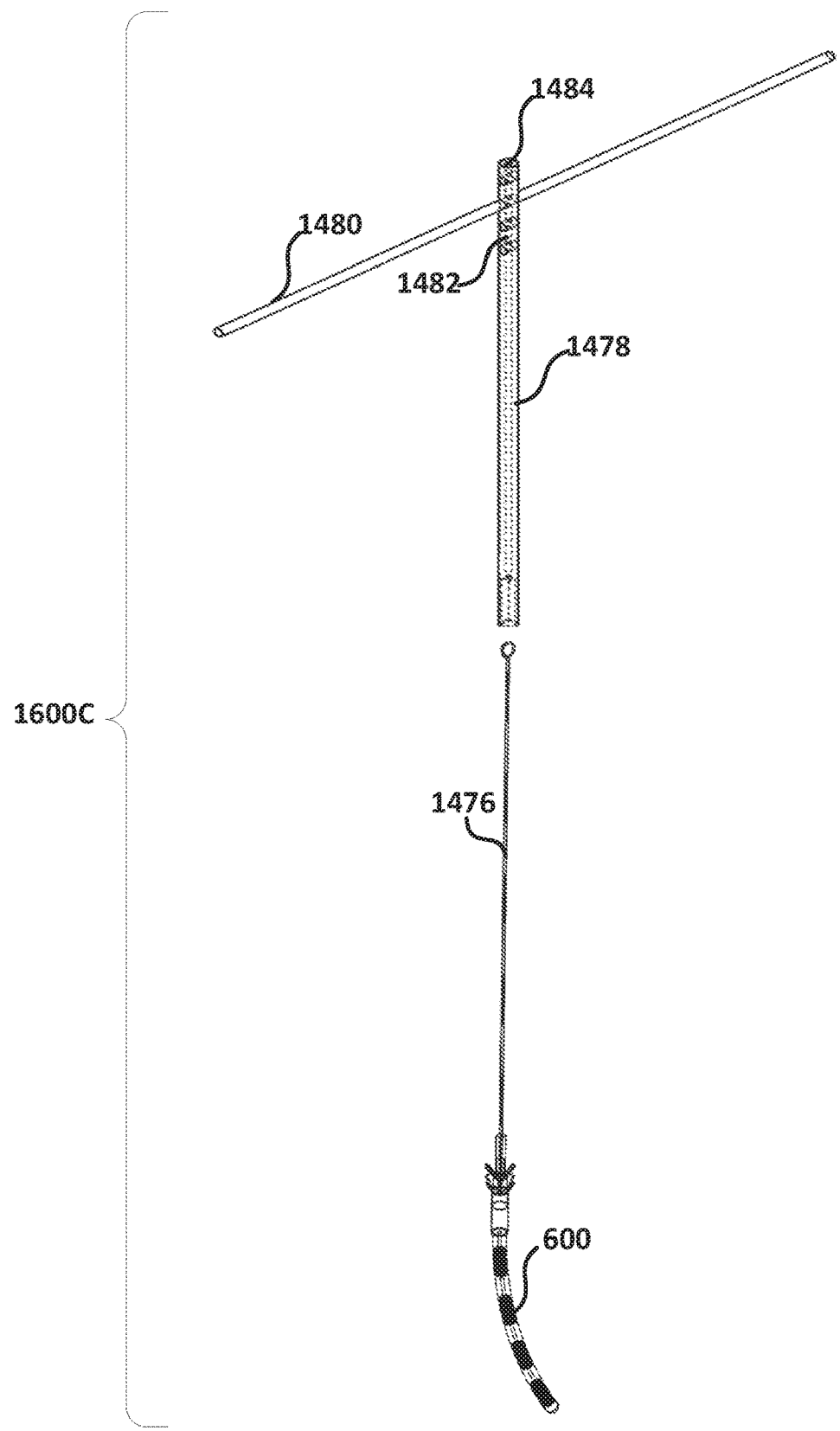
FIG. 15C illustrates, by way of example, a perspective view diagram of an embodiment of a system for steering an implantable device.

FIG. 15C illustrates, by way of example, a perspective view diagram of an embodiment of a system 1600C for steering an implantable device 600. The implantable device 600 includes the suture 1476 attached thereto. The suture 1476 can be threaded through the hole 1484. The suture 1476 can guide the pushrod 1478 to the implantable device 600, such as to situate a polygon attachment mechanism on an end of the push rod with the attachment structure 1466.

Figure 15D:
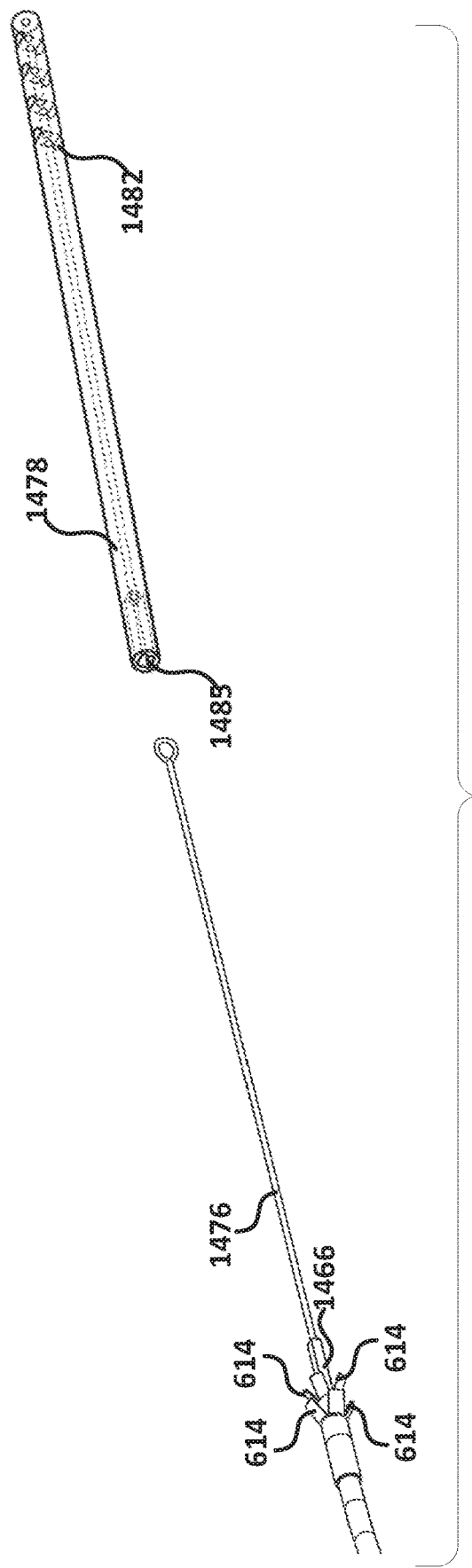
FIG. 15D illustrates, by way of example, an exploded view diagram of an embodiment of a portion of the system which is a portion of the system of FIG. 15C.
Figure 15E:
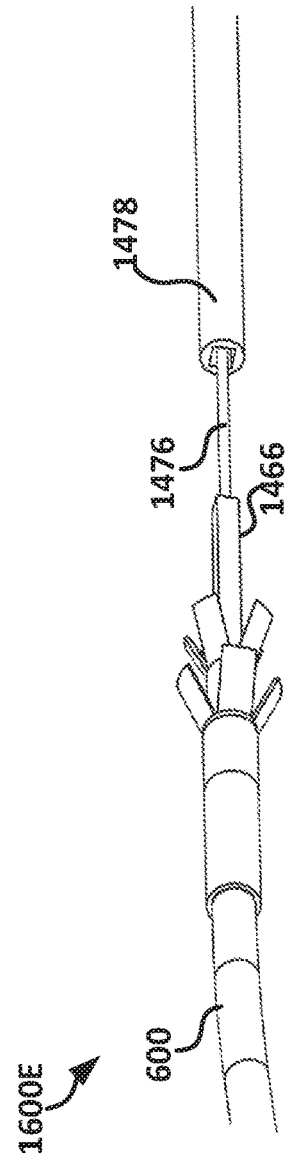
FIG. 15E illustrates, by way of example, an exploded view diagram of an embodiment of a system that includes the pushrod over the suture.

FIG. 15D illustrates, by way of example, an exploded view diagram of an embodiment of a portion of the system 1600D which is a portion of the system 1600C. An attachment structure 1485 is configured to mate with the attachment structure 1466. FIG. 15E illustrates, by way of example, an exploded view diagram of a system 1600E that includes the pushrod 1478 over the suture 1476.

The pushrod 1478 can provide an ability to steer the implant (e.g., the implantable device 600) by applying a moment in the desired direction. For example, this allows personnel to pull the implant away from the body (e.g., out of a catheter or patient) out of a catheter if the implant or the catheter are not in the correct location. When the implant is in the correct position, a mechanism can be used to release the implant, such as can include a button coupled to a bearing that, when pressed, releases the bearing and allows the pushrod 1478 to be released from the implant, such as is similar to a socket driver. In one or more embodiments, the pushrod 1478 can be used as a microwave waveguide to transmit energy to the implant, such as can be used to test the positioning of the implant by activating it.

The implantable device can be situated in a catheter. The pushrod 1478 can be attached to the attachment structure 1466. This pushrod 1478 can include bore holes 1482 that extend laterally through a distal portion thereof. The pushrod 1478 can then be pressed into the catheter (into the patient's body) and when the implantable device has been driven to a desired depth, an insertion handle 1480 can be placed through a laterally extending bore hole 1482 and the pushrod 1478 can be rotated to point the implantable device in the desired direction.

Figure 15F:
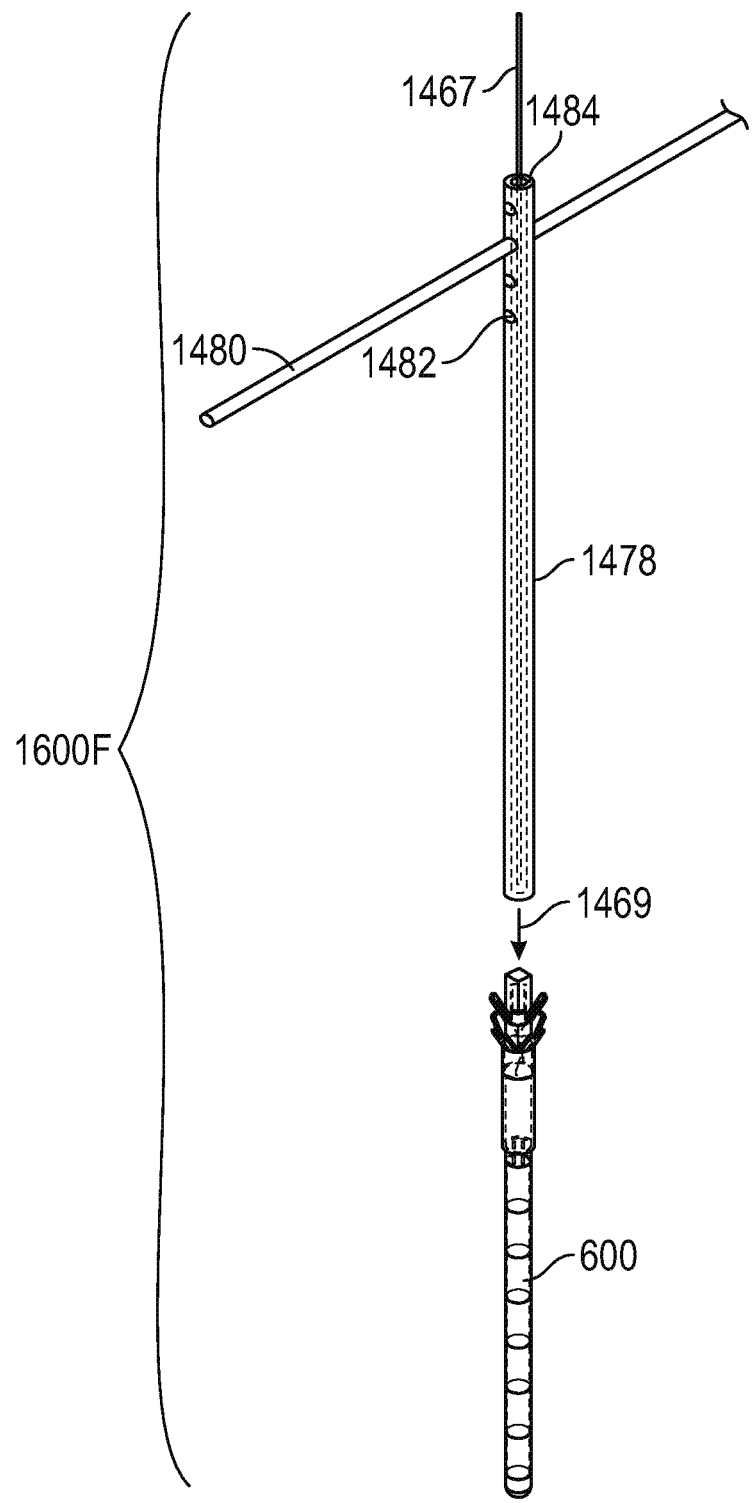
FIG. 15F illustrates, by way of example, a perspective view diagram of a system for detaching the push rod from the implantable device.

FIG. 15F illustrates, by way of example, a perspective view diagram of an embodiment of a system 1600F for detaching the pushrod 1478 from the implantable device 600. A second pushrod 1467 can be inserted into the hole 1484 (e.g., alongside the suture 1476). The second pushrod 1467 can contact the implantable device 600, such as at the attachment structure 1466. In one or more embodiments, the second pushrod 1467 can be held in place while the first pushrod 1478 is retracted to separate the pushrod 1478 from the implantable device 600. In one or more embodiments, the second pushrod 1467 can be made of a metal, such as a memory metal material (e.g., nitinol) or other metal or metal alloy.

Figure 16B:
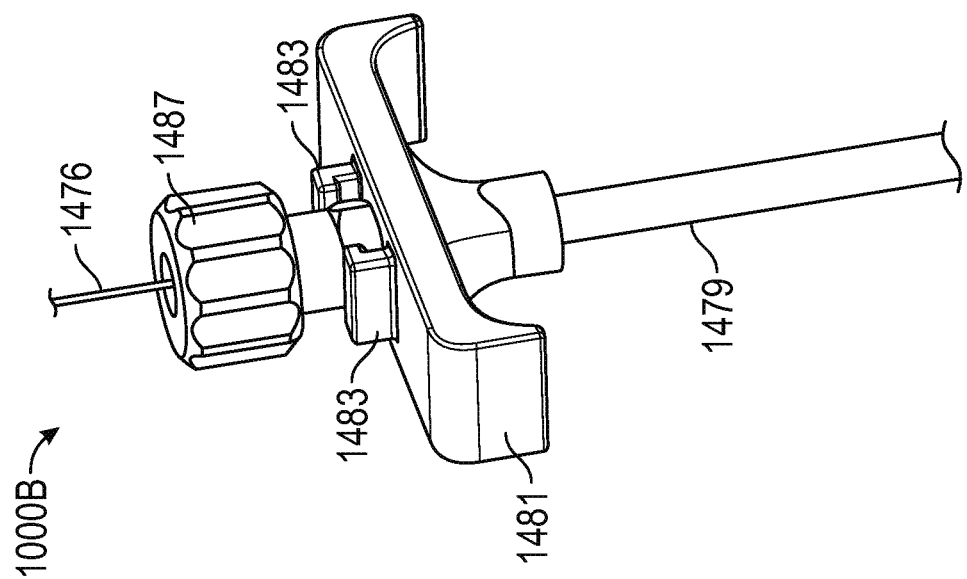
FIG. 16B illustrates, by way of example, a perspective view diagram of an embodiment of the suture securing system of FIG. 16A with the suture secured to a pushrod.
Figure 16A:
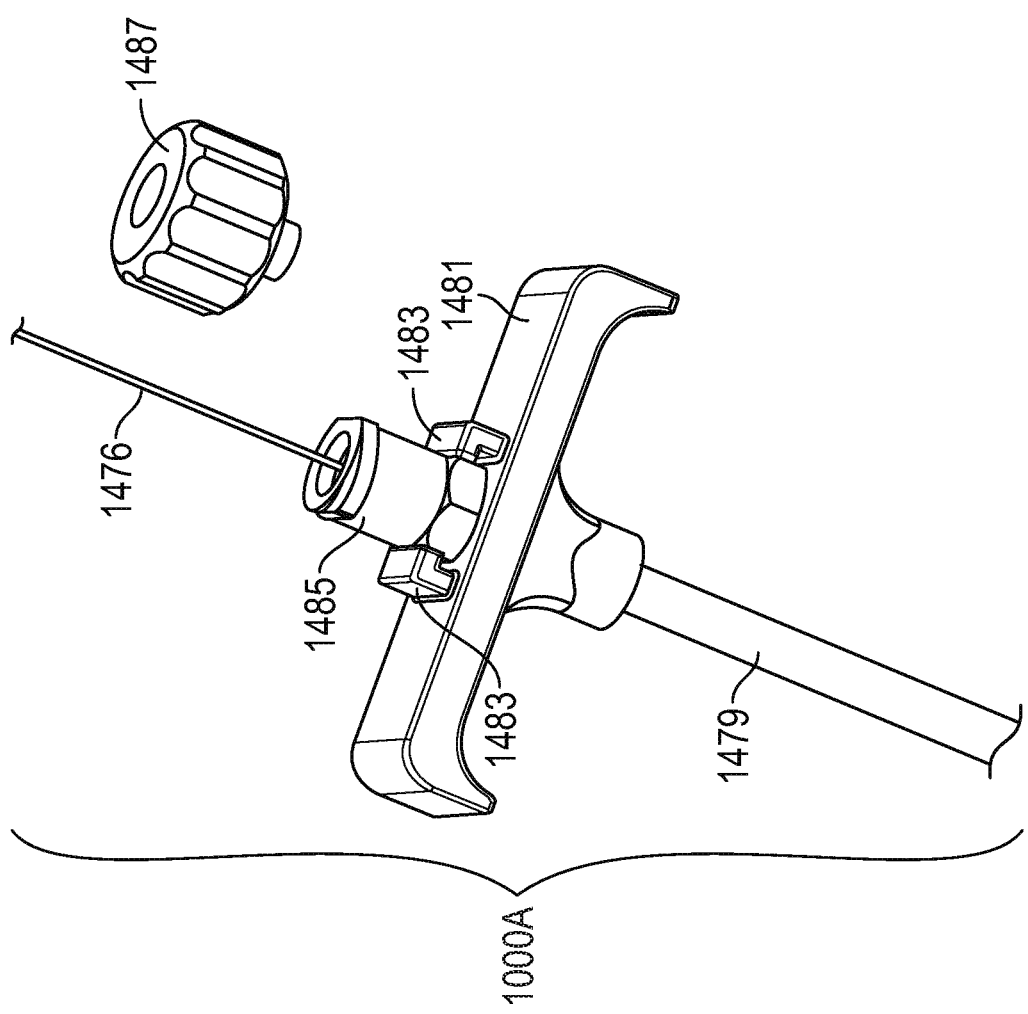
FIG. 16A illustrates, by way of example, a perspective view diagram of an embodiment of a suture securing system.

FIG. 16A illustrates, by way of example, a diagram of an embodiment of a suture securing system 1000A. The system 1000A as illustrated includes a pushrod that includes a hollow rod portion 1479, a handle 1481, detents 1483, and a female mating structure 1485, a male mating structure 1487, and a suture 1476. The pushrod can be used as described with regard to the pushrod 1478. The male mating structure 1487 can be a male luer cap, in one or more embodiments. The female mating structure 1485 can include a female luer thread, in one or more embodiments. As the structure 1487 is coupled with the structure 1485 (e.g., screwed onto the structure 1485) a tapered opening 1493 of the structure 1487 puts pressure on a mating tapered structure 1495, such as to squeeze the tapered structure 1495 and put mechanical pressure on the suture, thus mechanically securing the suture 1476 to the pushrod, such as to secure the pushrod at a specific location.

FIG. 16B illustrates, by way of example, a diagram of an embodiment of a system 1000B that includes the male mating structure 1487 attached to the female mating structure 1485 (most of the female mating structure 1485 is occluded in FIG. 16B). The suture 1476 is secured to the pushrod in FIG. 16B.

Figure 17A:
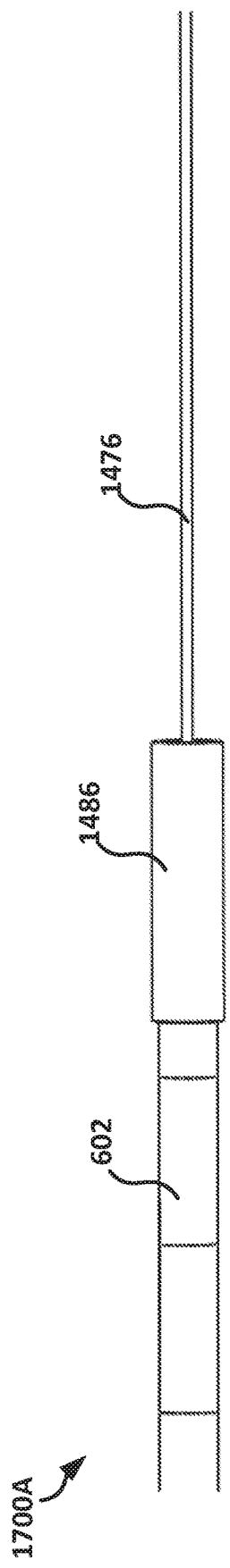
FIGS. 17A, 17B, and 17C illustrate, by way of example, perspective view diagrams of an embodiment of a system for deploying tines of an implantable device.
Figure 17B:
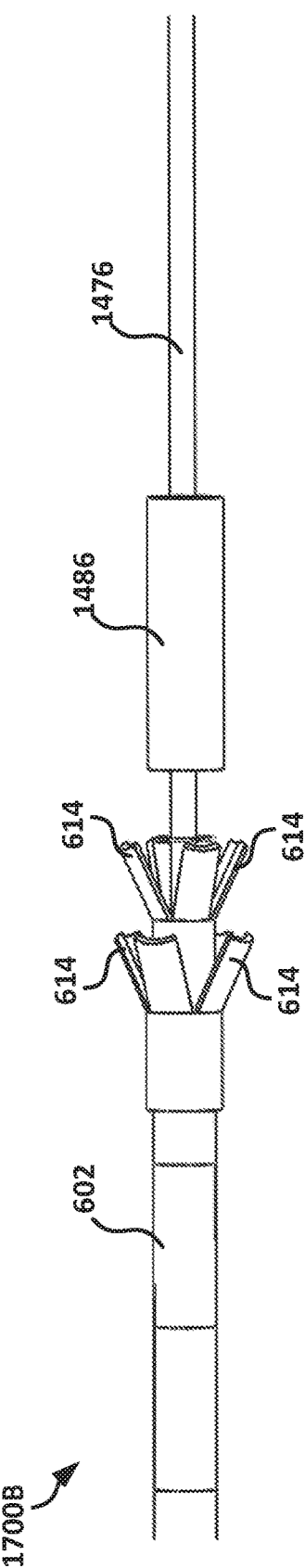
Figure 17C:
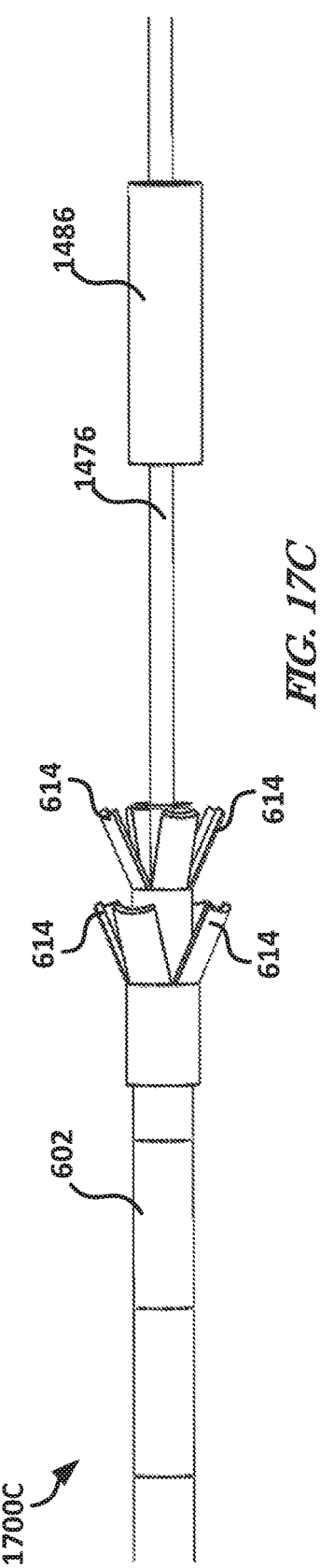

FIGS. 17A, 17B, and 17C illustrate, by way of example, perspective view diagrams of an embodiment of a system 1700A, 1700B, and 1700C for deploying tines 614 of an implantable device. During a trialing period, a cap 1486 can surround the tines 614 to keep them in an un-deployed position. The cap 1486 can include an RF transparent material, such as to help prevent interference with powering of the implant or other signals to an antenna of the implantable device. The cap 1486 can be connected to a suture 1476, such as to allow for easy deployment of the tines 614 by pulling on the suture 1476. The cap 1486 can be retrieved through the tissue, such as by using the suture 1476 as a guide. Alternatively, the cap 1486 can be composed of a bio-absorbable material such that the cap 1486 can be left in the body and will degrade overtime and eventually expose the tines 614.

FIG. 18 illustrates, by way of example, a perspective view diagram of an embodiment of a tine deployment system 1800 attached to a proximal portion of an implantable device. The implantable device can be connected to multiple sutures 1488 and 1490. One suture 1490 can be used to extract the implantable device, and one suture 1488 can be used to deploy the tines 614. The sutures 1488 and 1490 can be concentric or side by side. In one or more embodiments, only one suture 1488 or 1490 is used. An embodiment can include only the suture 1488 if it is known that a patient will not need device removal. An embodiment can include only the suture 1490 if the tines do not need to be deployed or are already deployed. The suture 1490 can be pulled to remove the implantable device 600 from the body.

FIG. 19 illustrates, by way of example, a perspective view diagram of an embodiment of the suture and tine deployment system 1800 of FIG. 18 with radiopaque markers 1492 on the suture 1488. The suture 1488 can also include radio-opaque markers 1492. This allows for the suture 1488 to be visible under fluoroscopy so that the suture 1488 can be located below the skin surface after implantation. A tool can be used to hook onto the subcutaneous suture 1488, such as can be accomplished with imaging guidance. In case that the suture 1488 has broken, the radio-opaque marker 1492 can help aid a physician in guiding an extraction tool to grasp the proximal end of the implant and/or indicate to the physician a location of the broken suture and that the suture 1488 is broken.

FIG. 20 illustrates, by way of example, a perspective view diagram of an embodiment of a system 2000 including a suture attached to a proximal portion of an implantable device. The suture 1490 can be attached to the implant at one or more positions, such as can include a proximal end of the implantable device 600, the circuitry housing 610, the antenna housing 612, or another location of the implantable device 600. Multiple connection points can help strengthen the connection. Multiple connection points can help aid in steering a proximal portion of the implant during extraction.

Figure 21:
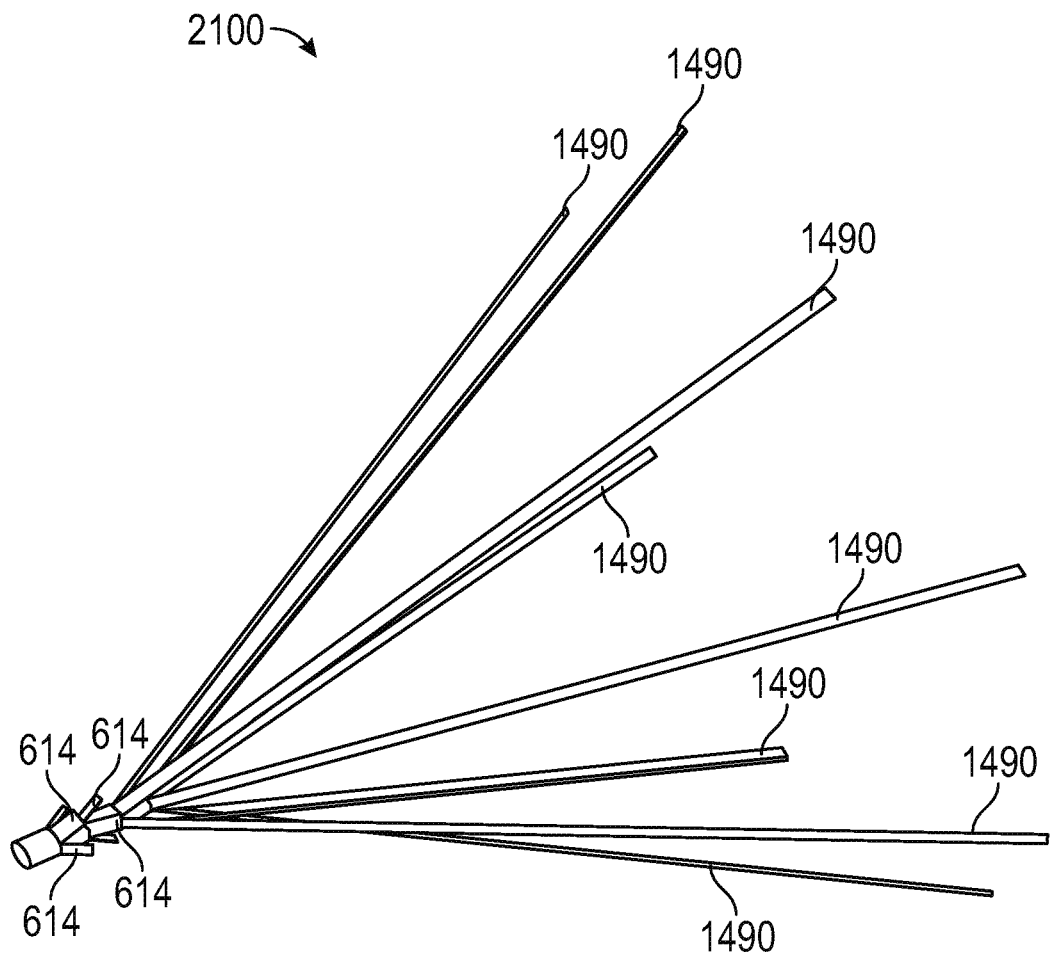
FIG. 21 illustrates, by way of example, a perspective view diagram of an embodiment of a plurality of sutures attached to a proximal portion of an implantable device.

FIG. 21 illustrates, by way of example, a perspective view diagram of an embodiment of a plurality of sutures 1490 attached to a proximal portion of an implantable device. Multiple sutures 1490 can be attached, such as around the circumference of the proximal end of the implantable device. Such multiple sutures can be used to help steer the implantable device during extraction.

Figures 22A, 22B, 22C, 22D:
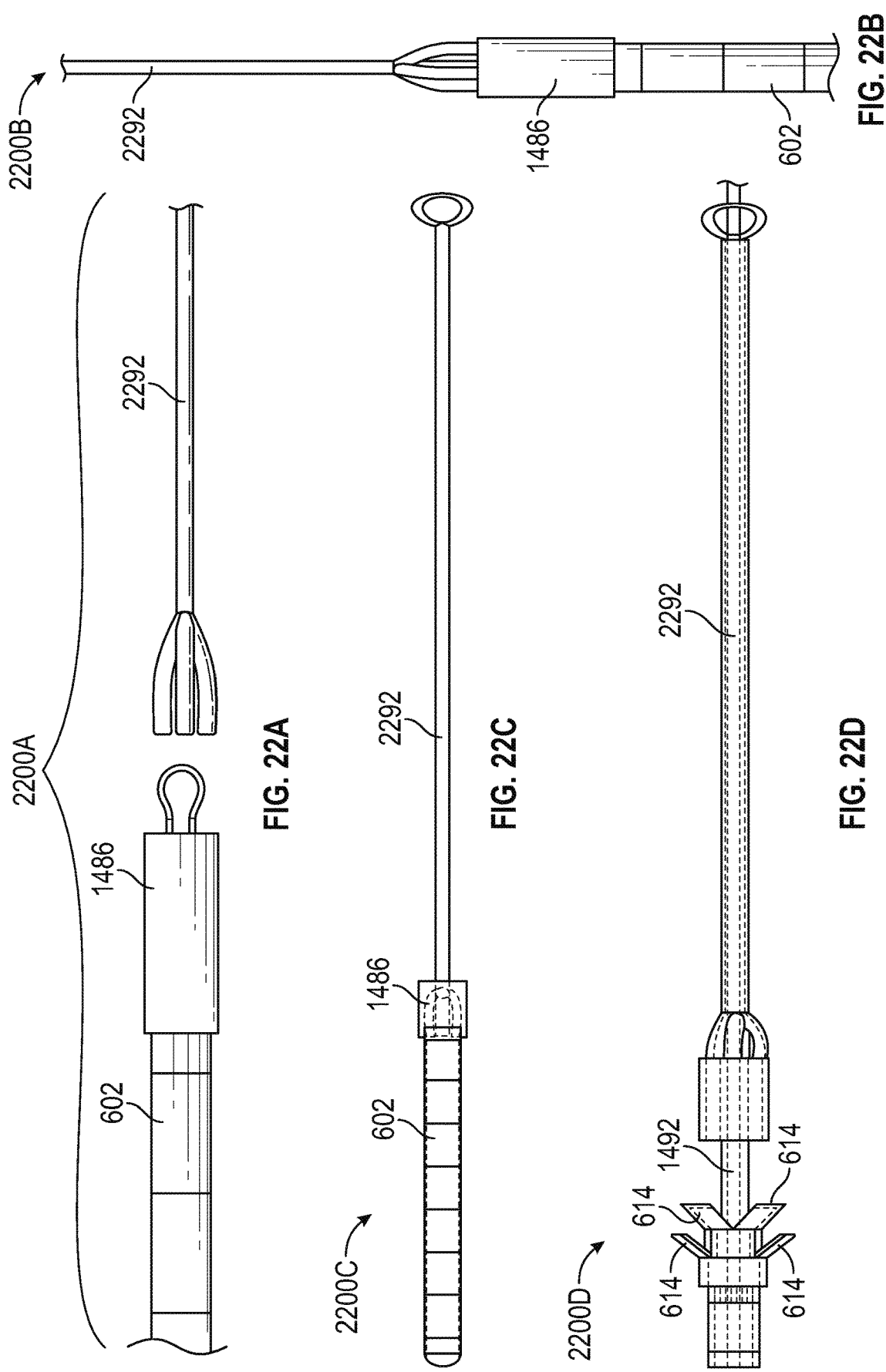
FIG. 22A illustrates, by way of example, a perspective view diagram of an embodiment of a suture and a proximal portion of an implantable device.
FIG. 22B illustrates, by way of example, a perspective view diagram of an embodiment of the suture attached to the implantable device of FIG. 22A.
FIG. 22C illustrates, by way of example, a perspective view diagram of an embodiment of a suture and a proximal portion of an implantable device in which the suture is attached to a circuitry housing.
FIG. 22D illustrates, by way of example, a perspective view diagram of an embodiment of a suture and tine deployment mechanism with the tines deployed.

FIG. 22A illustrates, by way of example, a perspective view diagram of an embodiment of a system 2200A including a suture 2292 and a proximal portion of an implantable device. FIG. 22B illustrates, by way of example, a perspective view diagram of an embodiment of the suture 2292 attached to the implantable device of FIG. 22A. FIG. 22C illustrates, by way of example, a perspective view diagram of an embodiment of a system 2200C including the suture 2292 and a proximal portion of an implantable device in which the suture is attached to the implantable device. FIG. 22D illustrates, by way of example, a perspective view diagram of an embodiment of the suture 2292 and tine deployment mechanism with the tines 614 deployed. The suture 2292 can be attached to the implantable device at multiple positions such as for strengthening the connection and to aid in steering the proximal end of the implantable device during extraction. For extraction, the suture 2292 can be connected, such as at or near the skin surface, to a rod which can be drawn through a distal end of a dilator. By pulling on the rod while pushing the dilator, a channel can be created to the implantable device. This channel can be used for extraction of the implantable device.

Figure 23C:
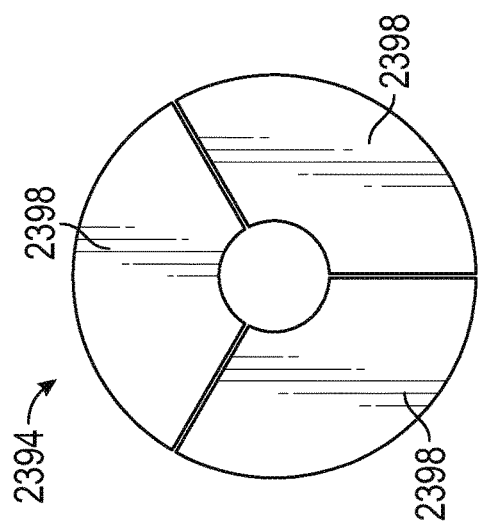
FIG. 23C illustrates, by way of example, a perspective view diagram of an embodiment of the grasping mechanism in a closed position.
Figure 23B:
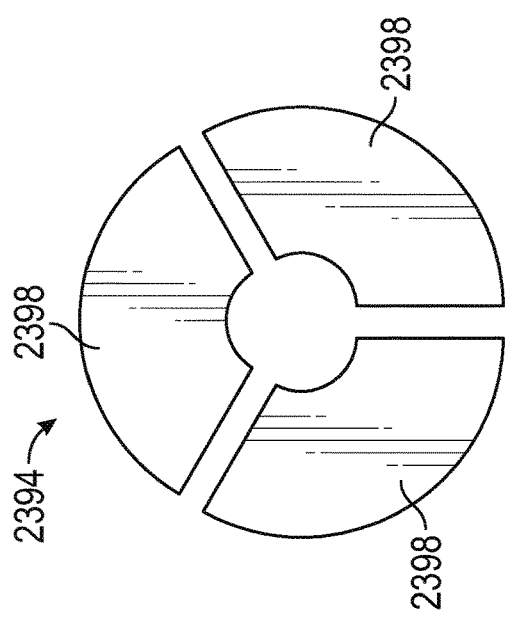
FIG. 23B illustrates, by way of example, a perspective view diagram of an embodiment of the grasping mechanism in an open position.
Figure 23A:
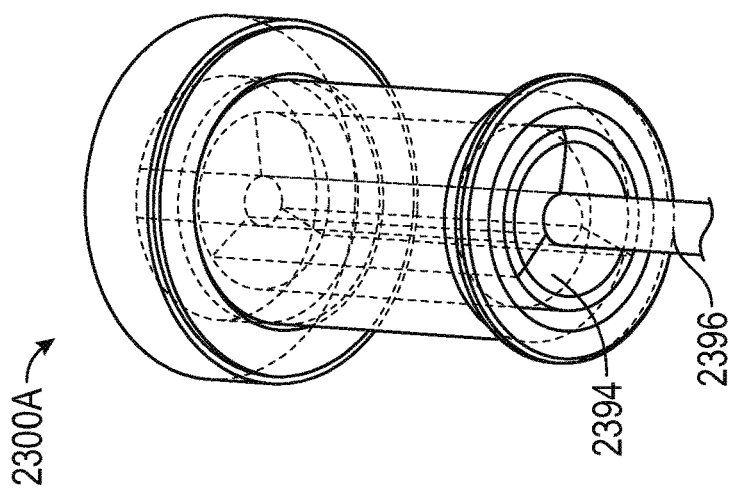
FIG. 23A illustrates, by way of example, a perspective view diagram of an embodiment of a suture attached to a grasping mechanism.

FIG. 23A illustrates, by way of example, a perspective view diagram of an embodiment of a system 2300A including a rod 2396 attached to a grasping mechanism. FIG. 23B illustrates, by way of example, a perspective view diagram of an embodiment of the grasping mechanism 2394 in an open position. FIG. 23C illustrates, by way of example, a perspective view diagram of an embodiment of the grasping mechanism 2394 in a closed position.

If the proximal end of the suture 1488 is subcutaneous, a grasping mechanism 2394 can be used to grab onto the proximal end of the suture 1488, effectively extending the suture 1488 to be transcutaneous. This extension can then be fed through a dilator, such as to position the dilator relative to the implantable device. In cases where pulling a suture is inadequate to remove the implantable device, or in a chronic implantation cases in which the suture may no longer be viable, a mechanical instrument can be used for retrieval of the implantable device. A mechanical rod 2396 shaped grasping instrument (see FIG. 23A) can be inserted within a catheter. At the distal tip of an instrument, a grasping mechanism 2394 can extend from the rod 2396 and clamp the proximal end of the implantable device or the suture 1488. The grasping mechanism 2394 can be spring loaded, such as with high leverage, to provide adequate friction between claws 2398 of the grasping mechanism 2394 and the implantable device or suture, such that the physician can apply sufficient pull force to remove the implantable device. Alternatively, the grasping mechanism 2394 can include a ratchet based retention mechanism, such as can be similar to that of a mechanical pencil.

Figure 24A:
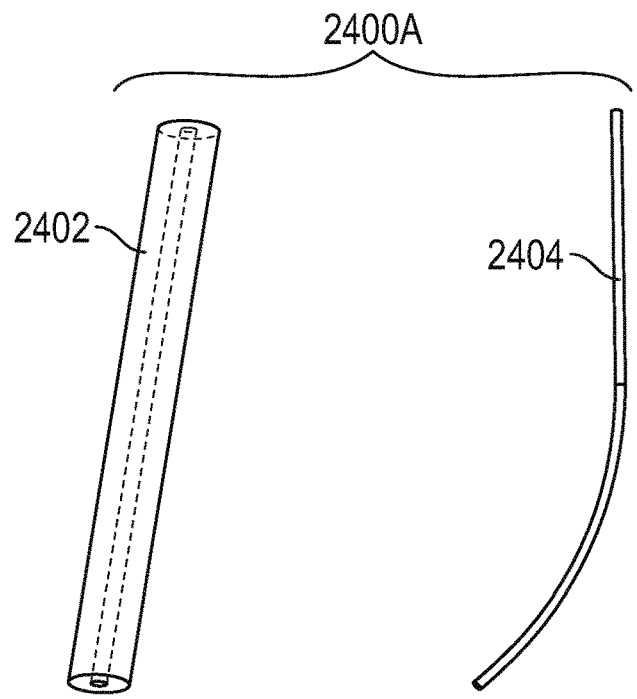
FIG. 24A illustrates, by way of example, a perspective view diagram of an embodiment of an implantable device and a memory metal.
Figure 24B:
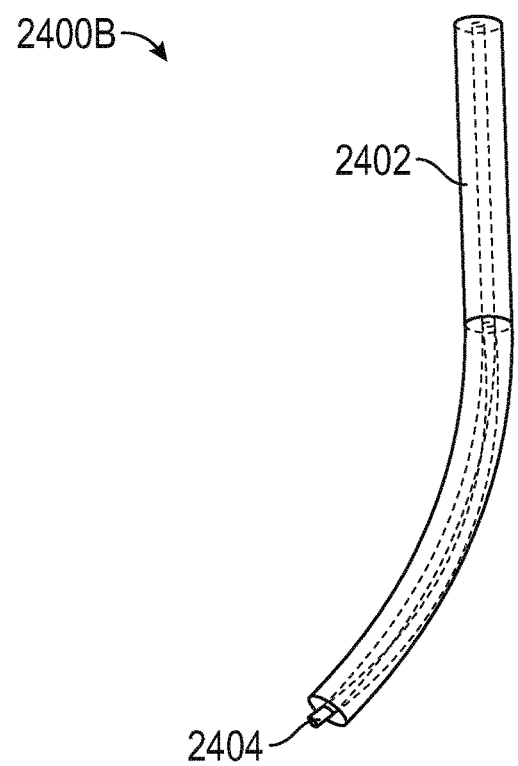
FIG. 24B illustrates, by way of example, a perspective view diagram of an embodiment of the memory metal in a conduit of the implantable device.

FIG. 24A illustrates, by way of example, a perspective view diagram of an embodiment of a shaping system 2400A for shaping an implantable device 2402. FIG. 24B illustrates, by way of example, a perspective view diagram of an embodiment of a system 2400B that includes the system 2400A in operation. Consider the implantable device 600. The electrodes 604 can be curved relative to one another to extend along a target nerve or other anatomical structure. In one or more embodiments, this curving of the implantable device 600 can be done using a curved stylet that is tunneled through a lead in a body of the implantable device 600. The curved stylet can allow the physician to orient the tip of the electrode array to the correct location and/or orientation.

For a wireless, leadless implantable device 2402, an alternate technique is shown here. A preformed, curved memory wire 2404 (e.g., nitinol or other memory metal) can be integrated into the implantable device 2402, such as is shown in FIG. 24B. The curvature of the wire 2404 can be predetermined to be ideal for a specific anatomical target. Although the implantable device 2402 is curved, it can be easily straightened to fit through a straight catheter for implantation. As the implantable device exits the catheter or other delivery device at the target anatomical site, the natural bias of the implantable device 2402, as provided by the memory wire 2404, causes the implantable device to curve. A pushrod (e.g., the pushrod 1478) that is temporarily connected to the implantable device can help allow a physician to guide the implantable device 2402 to the correct location with the correct curvature orientation. In one or more embodiments, a bend or curvature in an implantable device can be created by molding (e.g., reflowing) the implantable device to a specific shape.

FIG. 25A illustrates, by way of example, a perspective view diagram of an embodiment of a stylet 2506 in an internal conduit of the implantable device, or implant 2500A. Rather than using memory wire 2404 within a channel inside the implantable device to provide a suitable bend for the target anatomy, such as is discussed with regard to FIGS. 24A-24B, a stylet 2506 can be inserted into a continuous channel that travels through the implantable device to the distal end 606. Alternatively, the stylet 2506 can be curved around the circuitry housing 610, such as shown in FIG. 25B or a channel can be included in the implantable device 600 which allows the stylet 2506 to curve around the circuitry 716 in the circuitry housing 610. Alternatively, the hermetic package can include a channel such that the stylet 2506 is able to pass through a channel that passes through or around the circuitry 716. The physician can then control the electrode array in a manner similar to a lead-type electrode array. The stylet 2506 can be situated in a proper location using a pushrod and catheter or by situating the stylet 2506 in the implantable device prior to implantation. Rather than using the memory wire 2404, the implantable device 600 can be shaped by molding (e.g., reflowing) the implantable device 600, such as by using a mold.

Figure 26A:
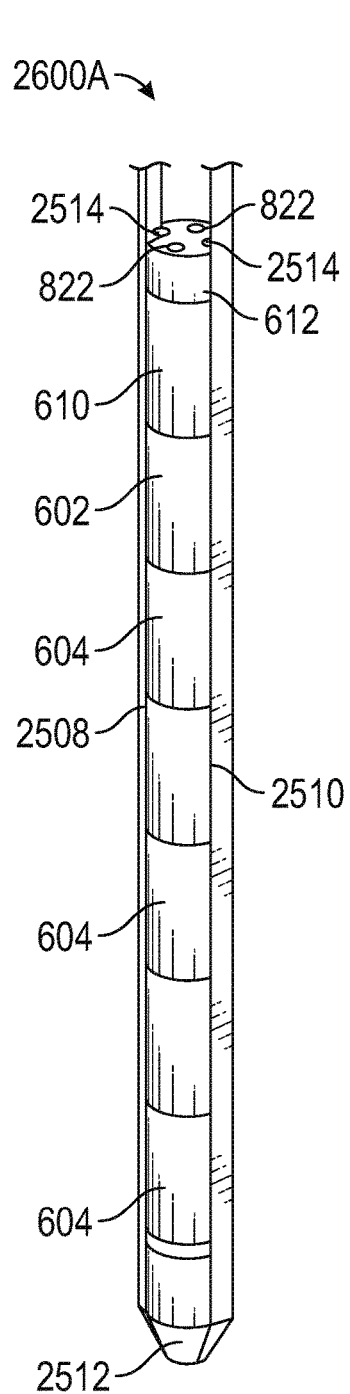
FIG. 26A illustrates, by way of example, a perspective view diagram of an embodiment of a system for guiding the implantable device.
Figure 26B:
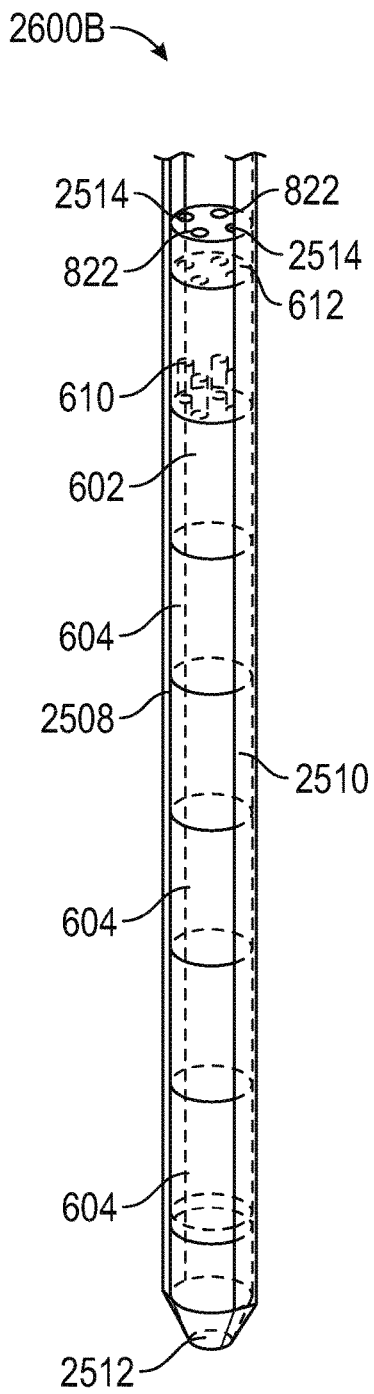
FIG. 26B illustrates, by way of example, a perspective view diagram of an embodiment of FIG. 26A with some portions removed to show the stylet within the implantable device.
Figure 26C:
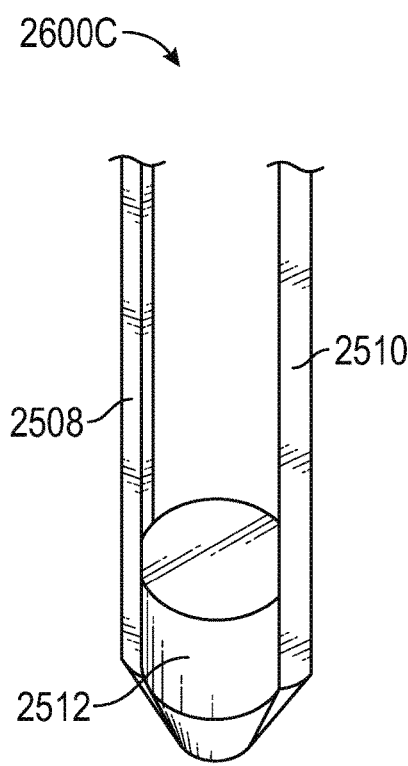
FIG. 26C illustrates, by way of example, an exploded view diagram of an embodiment of a steering mechanism of the system of FIGS. 26A and 26B.

FIG. 26A illustrates, by way of example, a perspective view diagram of an embodiment of a system 2600A for guiding an implantable device. FIG. 26B illustrates, by way of example, a perspective view diagram of an embodiment of a system 2600B that includes the system 2600A of FIG. 26A with some portions transparent to show a stylet within the implantable device. FIG. 26C illustrates, by way of example, an exploded view diagram of an embodiment of a steering mechanism 2600C of the system of FIGS. 26A and 26B. FIG. 26A illustrates a steerable electrode 604 on a wireless implantable device that includes two stylets 2508 and 2510 on opposing sides of the electrodes 604. The stylets 2508 and 2510 can be, at least partially, inserted into respective channels 2514. The channels 2514 can either partially or fully enclose the stylets 2510 and 2508 therein, such as to at least partially enclose the stylets 2510 and 2508 within the structure of the electrodes 604. The channel 2514 can extend to about the tip of the implantable device (the distal end 606). Applying force on one of the stylets 2508 and 2510 and less force on the other stylet 2508 and 2510 steers the distal end 606 of the implantable device. For example, applying force on the left stylet 2508 in the direction of the distal end causes the electrode array tip to bend to the right due to the increased length of the stylet 2508 in the associated channel 2514.

The stylets 2508 and 2510 can be temporarily attached to distal tip 2512. By applying enough force to the stylet 2508/2510, the stylet 2508/2510 can be removed from the temporary attachment and removed from the body. In another case, the steering mechanism 2600C can be used as a test electrode or an array of test electrodes. If the electrode array is left in the patient, then trimmers could be used to cut a length of the dual stylets that do not touch the electrodes 604. In one or more embodiments, the steering mechanism 2600C can be made of biodegradable material, such that the patient's body decomposes the steering mechanism while the steering mechanism 2600C is in the patient. In one or more embodiments, the electrode 604 and the dual stylets 2508 and 2510 are inserted into the patient through a catheter. The catheter in this case can be made of two concentric materials. An inner concentric material can be twisted or maneuvered in such a way to cut the extensions of the dual stylets without the need of inserting another tool.

Figure 27B:
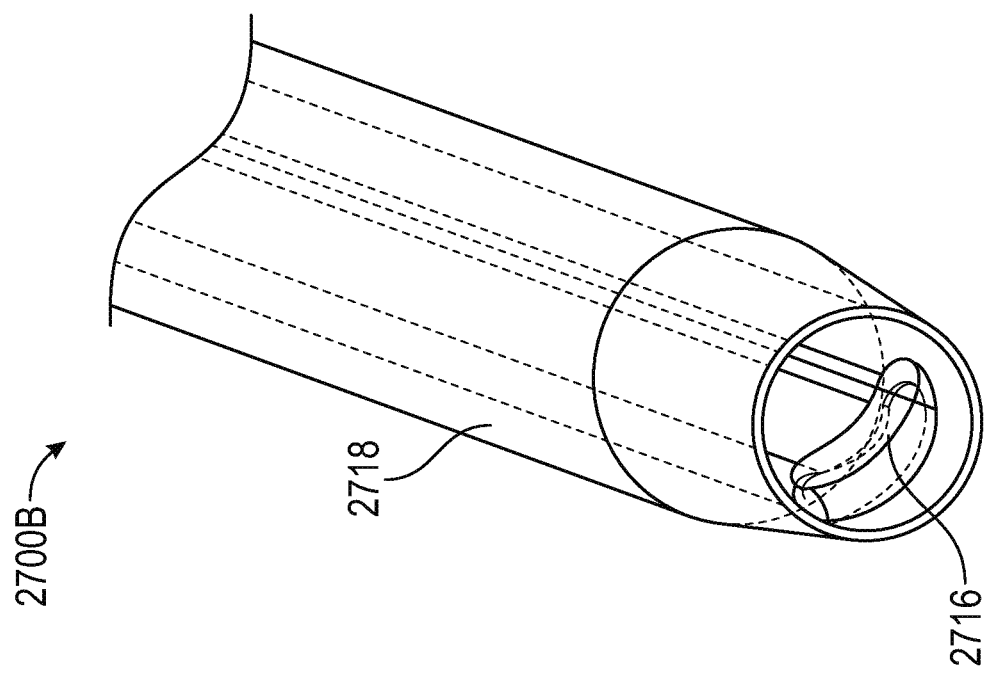
FIG. 27B illustrates, by way of example, an exploded view diagram of an embodiment of a distal portion of a catheter with the guiding mechanism of FIG. 27A situated within the catheter.
Figure 27A:
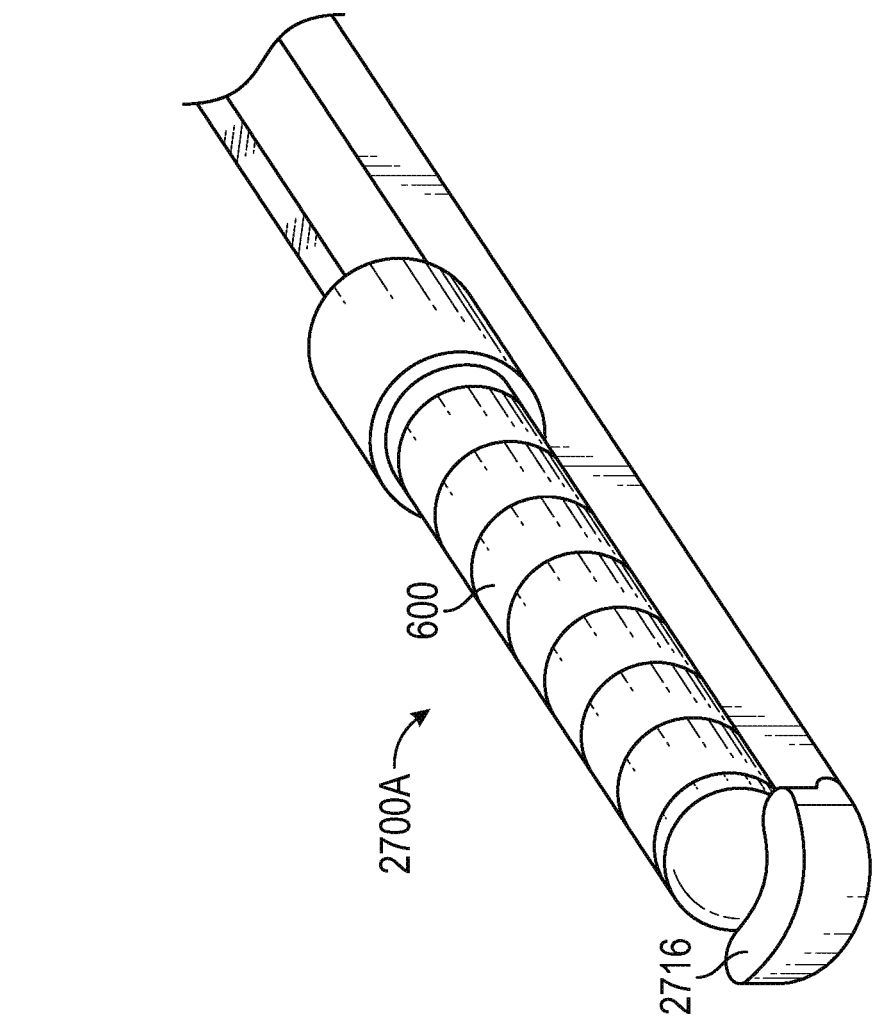
FIG. 27A illustrates, by way of example, an exploded view diagram of an embodiment of a distal portion of an implantable device and a guiding mechanism to provide curvature to the implantable device.

FIG. 27A illustrates, by way of example, an exploded view diagram of an embodiment of a distal portion of a system 2700A including an implantable device 600 and a guiding mechanism 2716 to provide curvature to the implantable device 600. FIG. 27B illustrates, by way of example, an exploded view diagram of an embodiment of a distal portion of a system 2700B including a catheter 2718 with the guiding mechanism 2716 of FIG. 27A situated within the catheter 2718. A guiding mechanism 2716 that includes a redirecting wedge can be used to guide the direction of the implantable device 600. The guiding mechanism 2716 can include a curvature that matches a contour of the implantable device 600. A pushrod can be used to advance the implantable device along the guiding mechanism 2716. When the implantable device 600 is pushed to the end of the guiding mechanism, the curve (e.g., wedge) of the guiding mechanism 2716 redirects the implantable device 600 to a curved orientation. The curve of the guiding mechanism 2716 can be configured such that when the implantable device 600 is pushed across the curve, the resulting curve of the implantable device matches a curve of target anatomy.

The curve at the tip of the guiding mechanism 2716 forces the implantable device 600 to bend at the same curvature as that of the guiding mechanism 2716 as the implantable device 600 is advanced along the curved tip. The guiding mechanism 2716 can be positioned using a catheter 2718 near a target anatomy which can benefit from a curvature in providing better stimulation to a target anatomy or improved electrode impedance, for example. The guiding mechanism 2716 can be configured to fit within the catheter 2718 along with the implantable device 600. The guiding mechanism 2716 can include a marking (e.g., a radiopaque marking or other marking) to indicate a location of the curved tip of the guiding mechanism 2716. The marking can be used to determine if the curved tip is deployed beyond the tip of the catheter 2718 and/or whether the guiding mechanism 2716 is properly located within the catheter 2718 or the target anatomy.

Figure 28:
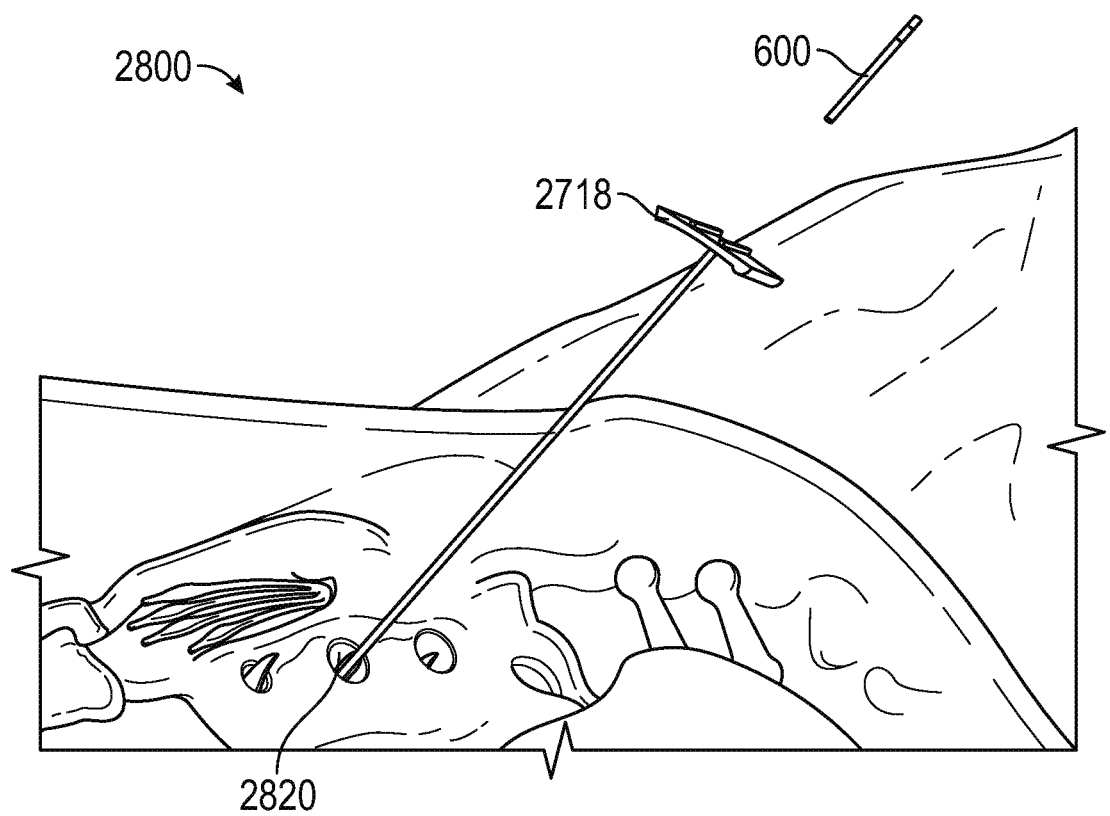
FIG. 28 illustrates, by way of example, a perspective view diagram of an embodiment of a system for situating an implantable device within a body.

FIG. 28 illustrates, by way of example, a perspective view diagram of an embodiment of a system 2800 for situating the implantable device 110 within a target anatomy. The target anatomy illustrated in FIG. 28 is an S3 foramen 2820. The implantable device 600 can be injected to the target anatomy 2820 using the catheter 2718. The implantable device 600 can be sized to be delivered through the catheter 2718. The catheter 2718, in one or more embodiments, can range in size from 4F to 10F (e.g., from 4F to 7F, from 5F to 9F, from 6F to 10F, from 4F to 6F, from 8F to 10F, overlapping ranges thereof, or any value within the recited ranges). In the example of FIG. 28, the implantable device 600 can be injected through the third sacral foramen (i.e. the S3 foramen) to a location near the sacral nerve, such as to help treat incontinence, urinary urge, fecal incontinence, constipation, and/or pelvic pain. Alternatively, the implantable device 600 can be injected through soft tissue surrounding the spinal cord to the dorsal root ganglion or to peripheral nerves to treat pain or can be injected through a bore in the skull for deep brain stimulation, for example.

FIG. 29 illustrates, by way of example, a perspective view diagram of an embodiment of a system 2900 including a catheter 2718 and dilator 2922 for situating the implantable device 600 within a body. In one or more embodiments, access to the target nerve can be initially performed using a hollow needle (not shown in the FIGS.), such as under imaging guidance (e.g., fluoroscopy, ultrasound, or the like). The needle can include radio-opaque markers thereon to aid in positioning. The physician my send electrical current through the needle to test for a proper physiologic response and help ensure that the needle is in a proper location. After sufficient placement of the needle is established, a guidewire can be inserted through the needle to a distal tip of the needle. The needle can then be retracted while the guidewire is held in place. Next, the hollow dilator 2922 is placed inside of a catheter 2718. The catheter 2718 and dilator 2922 combination can then be placed over the guidewire and used to create a dilated channel to the target anatomy. The dilator 2922 and guidewire can then be removed. The remaining catheter 2718 creates a tunnel to access the target anatomy through which the implantable device 600 can be situated, oriented, or other placed at the proper location.

FIG. 30 illustrates, by way of example, a perspective view diagram of an embodiment of another system 3000 for situating an implantable device 600 within a body. A pushrod 3024 can be used to push the implantable device 600 through the catheter 2718 to the target anatomy. The pushrod 3024 can be hollow, such as to allow a suture connected to the implantable device to pass through the pushrod 3024. The proximal end of the suture can remain above the skin surface of the patient. The implantable device 600 is placed into the catheter 2718 and can have its proximal end connected to the pushrod 3024. The pushrod 3024, in one or more embodiments, includes a socket driving mechanism as previously discussed. Force is applied to the proximal end of the pushrod 3024 to guide the implantable device 600 to an anatomical location. The pushrod 3024 can then be used to hold the implantable device 600 at a set location while the physician pulls on the catheter 2718 to remove it. This action, in one or more embodiments, deploys the tines 614 which expand when exposed. The pushrod 3024 can be removed, leaving the implantable device 600 in place. The resistance to movement provided by the tines 614 can be adequate to separate the implantable device from the pushrod, or a release mechanism, such as a button and bearing or a button and connector device, can be used to release the pushrod 3024 from the implantable device 600. In some embodiments, a second pushrod can be inserted into the pushrod 3024, such as to separate the implantable device 600 from the pushrod 3024 (see FIG. 15F, for example).

Portions of this process are illustrated in FIGS. 31A, 31B, 31C, and 31D. The system 3100A of FIG. 31A illustrates a pushrod 1478 and a suture 1488 attached to a proximal end of the implantable device 600. The system 3100B of FIG. 31B illustrates the pushrod 1478 over the suture 1488 and attached to an attachment structure 1466 on the proximal end of the implantable device 600 and the catheter 2718. The system 3100C of FIG. 31C illustrates the implantable device within the catheter 2718. The system 3100D of FIG. 31D illustrates the implantable device 600 exiting a distal end of the catheter 2718. The distal end of the catheter 2718 can press the tines towards a center of the implantable device 600 and can be released to a full extending position after exiting the catheter 2718. The suture 1488 can include radiopaque markers 1492 thereon. The implantable device 600 is illustrated as being in a pre-curved position, such as can include using a memory wire.

FIG. 32A illustrates, by way of example, a perspective view diagram of an embodiment of a system 3200A that includes the system 3100A positioned at a target anatomy (e.g., an S3 foramen 2820 in this example). The system 3200A includes the implantable device 600 partially external to the catheter 2718 and partially through the S3 foramen 2820. The pushrod 1478 is at least partially within the catheter 2718 and the suture 1488 extends out of the patient's body. The system 3200A includes the implantable device 600 partially external to the catheter 2718 and partially through the S3 foramen 2820. The pushrod 1478 is at least partially within the catheter 2718 and the suture 1488 extends out of the patient's body. FIG. 32B illustrates, by way of example, a perspective view diagram of an embodiment of a system 3200B that includes the system 3200A positioned at a target anatomy with the catheter 2718 and the pushrod 1478 removed. The suture 1488 is illustrated as extending beyond a surface of the patient's skin 3226.

FIG. 32C illustrates, by way of example, an exploded view diagram of a proximal portion of items in the dashed box labelled "32C" in FIG. 32B. The proximal portion 3200C includes a retaining device 3228 through a loop on the suture 1488. The retaining device 3228 can help ensure that the suture 1488 remains at least partially external to the patient's body. Such a configuration helps ensure easy access to the suture 1488 in case the implantable device 600 is to be removed from the patient.

Implantable devices discussed herein can be powered using mid-field power technology such as discussed with respect to the source 102 and elsewhere herein. Mid-field powering technology discussed herein can provide for efficient power transfer to an implantable device, such as can be at a visceral depth. The mid-field powering technology can provide an ability to steer, or focus, a power signal.

FIG. 33A illustrates, by way of example, a perspective view diagram of an embodiment of an implantable device extraction system 3300A. The system 3300A as illustrated includes a needle 3332 with an extension suture 3330 running there through. At the distal end of the needle 3332, the extension suture 3330 can be sticking out, and can be connected to the suture 1488 attached to the implantable device 600.

The extension suture 3330 can be tied or otherwise connected to the suture 1488 that is attached to the implantable device 600. Such a system can help in extracting the implantable device 600 from a patient's body if the retaining device 3228 is missing, or the suture 1488 is otherwise fully internal to the patient's body. FIG. 33B illustrates, by way of example, an exploded view diagram of an embodiment of interlaced sutures to assist in implantable device extraction. This figure illustrates the sutures 3330 and 1488 interlaced or otherwise connected. FIG. 33C illustrates, by way of example, an exploded view diagram of an embodiment of the system of FIG. 33B with the needle 3332 situated over the interlaced sutures. The needle 3332 can be guided by the suture 1488 to the implantable device 600.

FIGS. 34A, 34B, 34C, and 34D illustrate, by way of example, perspective view diagrams of an embodiment of an implantable device extraction system 3400A, 3400B, 3400C, and 3400D, respectively. The system 3400A is similar to the system 3300C with the needle 3332 inserted through the skin to the implantable device 600. The proximal end the suture 1488 is attached to the extension suture 3330. In the embodiments of FIGS. 33A-33C, the extension suture 3330 is pre-tunneled through needle 3332. However, the needle 3332 can be extended over the extension suture 3330 after the extension suture 3330 is coupled to the suture 1488.

Figure 34A:
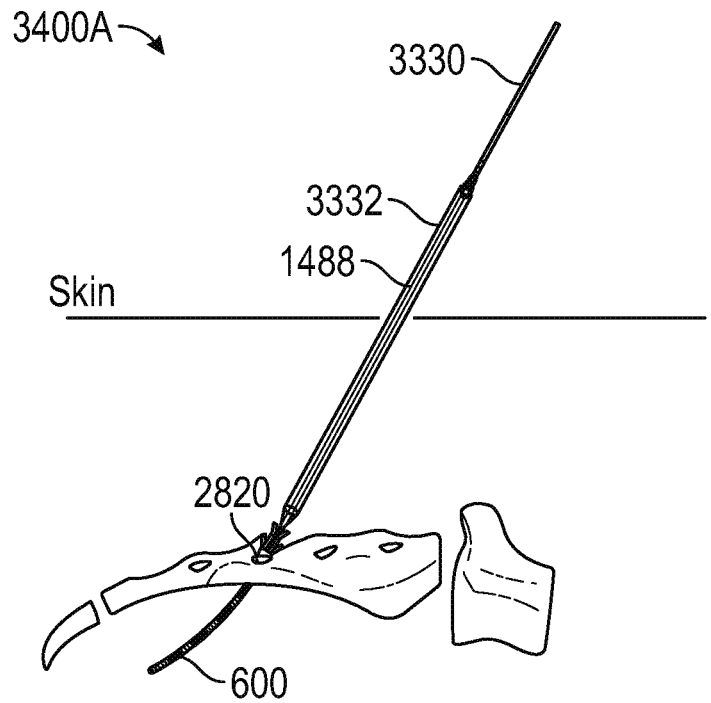
FIGS. 34A, 34B, 34C, and 34D illustrate, by way of example, perspective view diagrams of an embodiment of an implantable device extraction system.

After the sutures 3330 and 1488 are securely connected, the physician (or other operating personnel) can pull the connected sutures until they are taut. The needle 3332 can then be inserted while maintaining the suture 1488 taut. The suture 1488 is used as a guide to the implantable device 600. FIG. 34A illustrates an embodiment after this procedure has been accomplished.

Figure 34B:
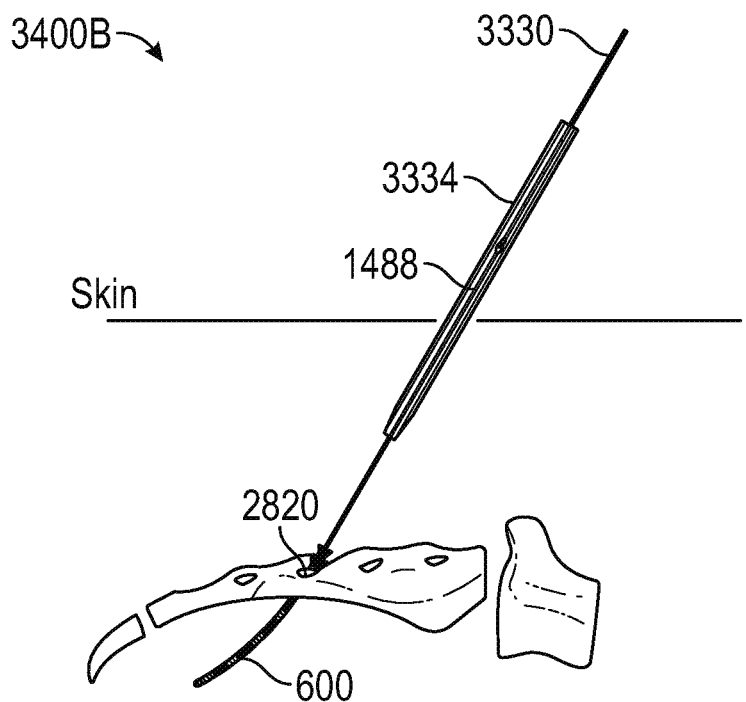

The needle 3332 can be removed and replaced with a dilator 3334, such as is shown in FIG. 34B. The dilator 3334 can be placed over the needle 3332 and then the needle 3332 can be removed and the dilator 3334 placed through skin, such as while keeping the suture 1488 taut (e.g., using one or more structures discussed with regard to FIGS. 16A-16B, manual pressure, or the like). The needle 3332 includes an outer diameter that is less than an inner diameter of the dilator 3334.

Figure 34C:
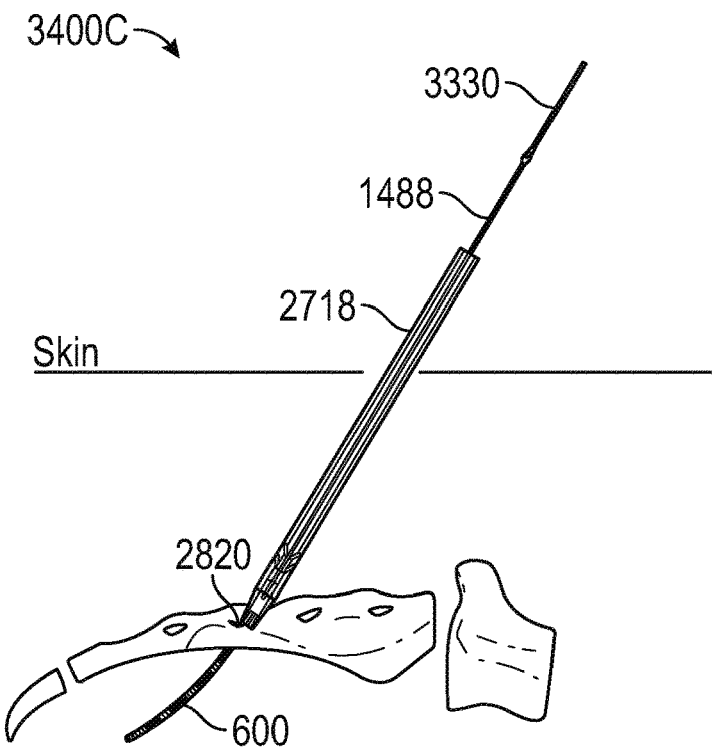

Tissue can be dilated using larger dilators until a catheter 2718 with an inner diameter larger than a largest diameter of the implantable device 600 can be inserted into the patient. In some embodiments that include the tines 614, the tines 614 are the portion of the implantable device 600 with the largest diameter. In such embodiments, the inner diameter of the catheter 2718 and/or dilator 3334 should be larger than the effective diameter of the tines 614. FIG. 34C illustrates the catheter 2718 and/or dilator 3334 over a portion of the implantable device 600 and the suture 1488.

Figure 34D:
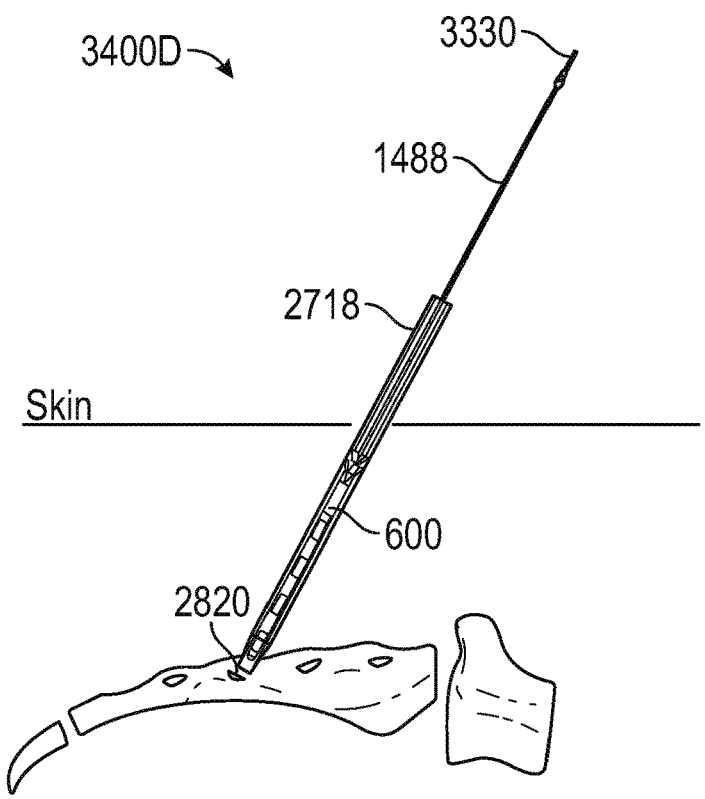

The catheter 2718 can be held in place, such as to help make sure the catheter 2718 does not retract. Pulling force can be applied to the suture 3330 and/or 1488 in order to allow the implantable device 600 to be extracted from the body through the catheter 2718. FIG. 34D illustrates the implantable device 600 within the catheter 2718 as it is being extracted from the body. The catheter 2718 can then be removed from the body.

Figure 35A:
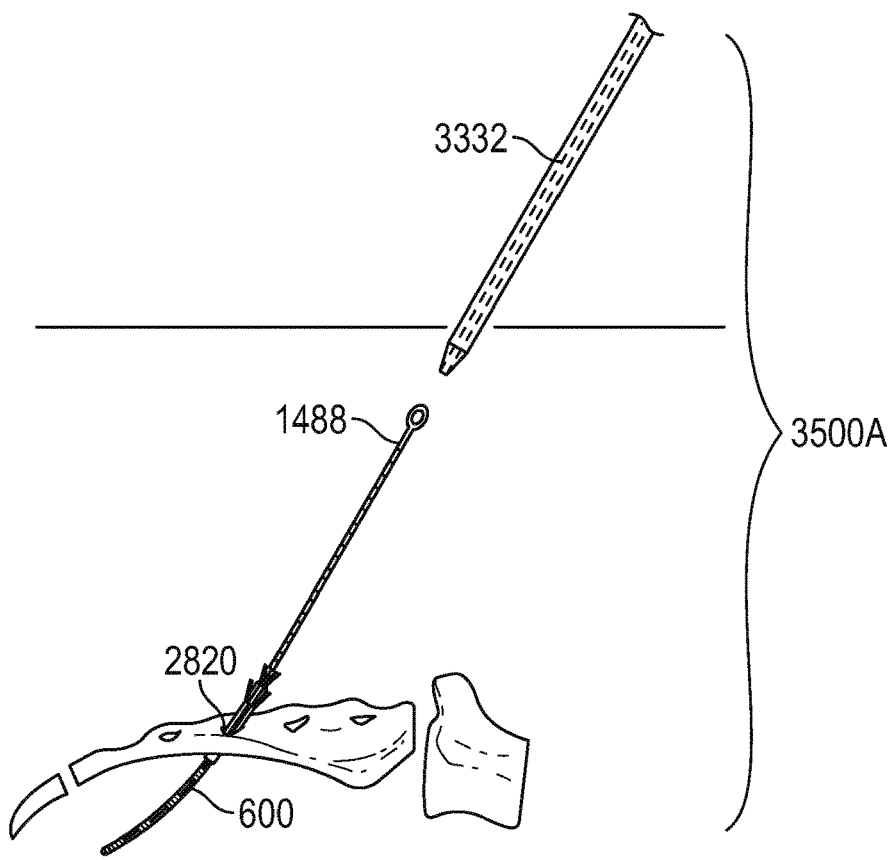
FIGS. 35A and 35B illustrate, by way of example, exploded view diagrams of an embodiment of another implantable device extraction system.
Figure 35B:
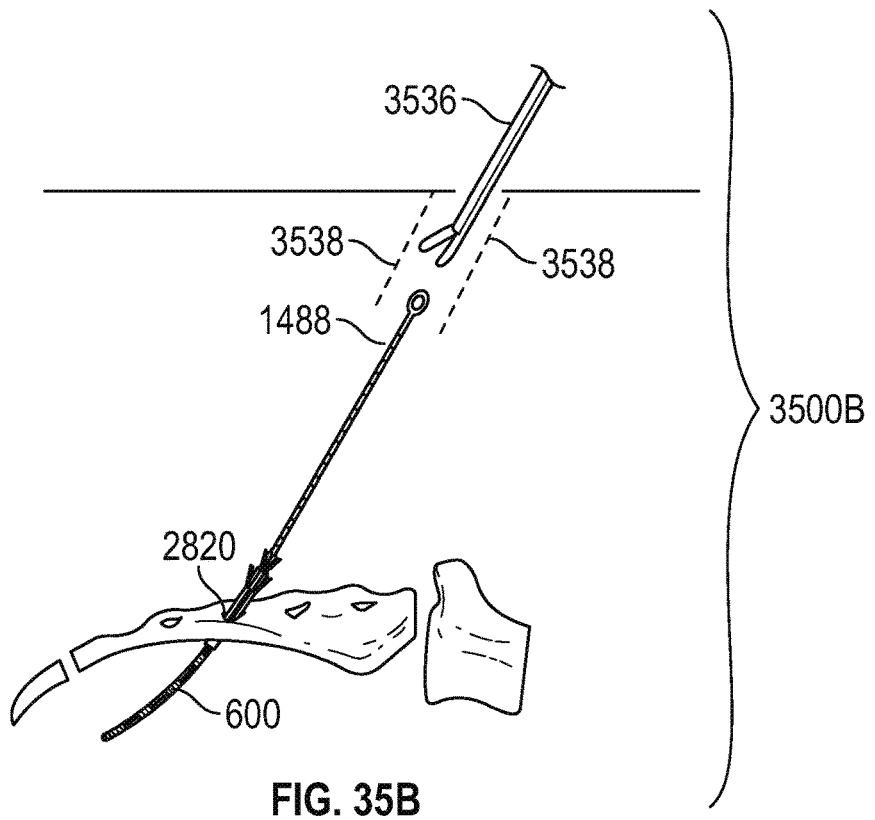

FIGS. 35A and 35B illustrate, by way of example, exploded view diagrams of an embodiment of another implantable device extraction system 3500A and 3500B, respectively. Again, if the retaining device 3228 has been removed and/or string has been retracted into body, fluoroscopic guidance (using radiopaque markers on the suture 1488) can be used to find the suture 1488. These radiopaque markings can help allow personnel to locate the suture 1488 within the body. As shown in FIG. 35A, the needle 3332 can be used (e.g., under fluoroscopic guidance) to burrow an opening to the suture 1488. The opening is indicated by dashed lines 3538 in FIG. 35B. A mechanical grasper 3536 can be deployed into the hole created by the needle 3332. The grasper 3536 can mechanically grab the suture 1488 and be used to pull the suture 1488 out of the body. A process, such as one similar to that discussed with regard to FIGS. 33A-33C and 34A-34D, can be used to extract the implantable device 600 (with or without the extension suture 3330).

B. Implantable Stimulation Devices Including Hollow Lumen

In accordance with several embodiments, an implantable stimulation device includes a lumen (e.g., a tubular element that is hollow, such as to include a channel therethrough) in which a stylet or other guiding device can be inserted. In one or more embodiments, the lumen can be used to help situate the device at a specified or desired location and/or can aid in assembling a portion of the device.

One or more embodiments can include a hollow lumen that traverses substantially an entire length of the implantable device, such as to extend from a proximal end of the device to at or near a distal end of the device. The hollow lumen can aid in manufacturing the implantable device. Additionally, or alternatively, the hollow lumen can help in positioning the implantable device into a particular location near tissue or otherwise internal to a patient. The hollow lumen can include an opening therein that is sufficiently large to allow a stylet to be situated therein.

Implantable devices can be difficult to properly place. It can be difficult to steer the implantable device to a desired location within a body.

An addition of a central lumen that goes nearly all or all of the way through the device, such as to an internal surface of an outer casing at the distal end thereof can help alleviate concerns with pushing a device into place and can also provide placement of devices that do not include any leads. Such an implantable device configuration can allow for the insertion of a stylet into the device to the distal tip and allows for a non-lead implantable device to be accurately placed. Using such a hollow lumen, a sheath that is used to help guide the device and/or a pushrod can be unnecessary.

Also, the hollow lumen can help provide an aid in manufacturing the device. With a hollow lumen, a distal feedthrough conductor can be attached to the circuitry assembly with the hollow lumen already brazed into place. With a hollow lumen, a circuitry housing and/or antenna housing can be placed into position over a distal feedthrough flange and/or a proximal flange of the hollow lumen. A proximal feedthrough conductor can be attached to circuitry of the device with excess conductor length. The excess conductor length can serve as a service loop in device assembly. The hollow lumen can serve as a fixture that can help position the circuitry housing and/or the antenna housing into a final position for brazing and/or welding.

FIG. 36 illustrates, by way of example, an embodiment of an at least partially implantable, biocompatible device 3600. The device 3600 as illustrated includes an outer casing 3602, electrodes 3604A, 3604B, 3604C, and 3604D, a hollow lumen comprising lumen portions 3606A and 3606B (and lumen hole 3832A in some embodiments (see FIG. 38)), circuitry 3608, a circuitry housing 3616, distal feedthroughs 3612A and 3612B, proximal feedthroughs 3614A and 3614B, an antenna housing 3618, an antenna 3610, feedthrough plates 3620 and 3624, and an end plate 3622.

The distal feedthroughs 3612A-B can be similar to the feedthroughs 824. The proximal feedthroughs 3614A-B can be similar to the feedthroughs 822. The circuitry 3608 can include components, such as one or more of those illustrated in FIG. 5. The circuitry 3608 can be similar to components in the circuitry housing 610A, such as shown in FIG. 9. The antenna 3610 can be similar to the antenna 718A-E or other antenna discussed with regard to the implantable device 110, such as the antenna 108. The outer casing 3602 can be similar to the body portion 602. The electrodes 3604A-D can be similar to the electrodes E0-E3. The circuitry housing 3616 can be similar to the circuitry housing 610A-B. The antenna housing 3630 can be similar to the antenna housing 612.

The plurality of electrodes 3604A, 3604B, 3604C, and 3604D (e.g., ring electrodes) are exposed on the outer casing 3602. Conductors connecting the electrodes 3604A-D to the circuitry 3608 and some distal feedthroughs are not shown in FIG. 36 so as to help in not obscuring the view. The outer casing 3602 can include a dielectric material, such as can include a silicone or thermoplastic elastomer.

The hollow lumen portion 3606B extends from a proximal end 3626 of the device 3600 to a proximal side of the feedthrough plate 3624. The hollow lumen portion 3606A extends from a distal side of the feedthrough plate 3624 to a distal end 3628 of the device 3600. In one or more embodiments, the hollow lumen portions 3606A-B combine to form a hollow lumen that extends from the proximal end of the device 3600 to the distal end 3628 of the device 3600.

In one or more embodiments, the hollow lumen portion 3606A can be affixed to an electrode assembly of the device (e.g., the outer casing 3602, the electrodes 3604A-D thereon, and the conductors attached to the electrodes). In one or more other embodiments, the hollow lumen portion 3606A can be situated in and not affixed to the outer casing 3602. In such embodiments, the hollow lumen portion 3606A can be affixed to the feedthrough plate 3624. In one or more embodiments, the hollow lumen portion 3606A can be made of a flexible material, such as a memory metal, such as MP35N, nitinol, or other memory metal. In one or more other embodiments, the hollow lumen portion 3606A can be made of a thermoplastic, such as Tecothane® material. Using a flexible material for the hollow lumen portion 3606A allows the outer casing 3602 to remain flexible in embodiments in which the outer casing 3602 is made of a flexible material. Such flexibility can help provide mobility in positioning and shaping of the implantable device 3600.

The hollow lumen portion 3606B can be affixed to one or more of the feedthrough plates 3620 and/or 3624 and/or the end plate 3622. In one or more embodiments, the hollow lumen portion 3606B can be made of a hermetic material, such as a metallized ceramic, glass, quartz, sapphire, platinum, platinum-iridium, a memory metal, a combination thereof or the like. In one or more embodiments, the hollow lumen portion 3606B is made of a rigid (non-flexible) material.

The circuitry 3608 as illustrated includes a flex circuitry, however the circuitry 3608 can include a rigid circuitry, such as can be similar to that shown in FIG. 9. The circuitry 3608 provides energy harvesting, power management, and/or stimulation signal capabilities, such as to provide stimulation to tissue through the electrodes 3604A-D. The circuitry 3608 is electrically connected to the antenna 3610, such as through conductors in the proximal feedthroughs 3614A-B. The antenna 3610 can include a dipole antenna, a loop antenna, a coil antenna, a slot or strip antenna, or other antenna. The antenna 3610 can be shaped and sized to receive signals in a range of between about 400 MHz and about 3 GHz (e.g., between 400 MHz and 1 GHz, between 500 MHz and 2 GHz, between 1 GHz and 3 GHz, between 500 MHz and 1.5 GHz, between 1 GHz and 2 GHz, between 2 GHz and 3 GHz, overlapping ranges thereof, or any value within the recited ranges).

The circuitry 3608 is electrically connected to the electrodes 3604A-D through conductors in the distal feedthroughs 3612A-B. The circuitry 3608 is encased in a circuitry housing 3616. The circuitry housing 3616, in one or more embodiments, is separate from the outer casing 3602. In such embodiments, the circuitry housing 3616 and the outer casing 3602 can each be affixed to the feedthrough plate 3624. In one or more embodiments, the circuitry housing 3616 can be affixed directly to the outer casing 3602, such as without the feedthrough plate 3624. In such embodiments, the distal feedthroughs 3612A-B can be part of the outer casing 3602 and/or the circuitry housing 3616, such as in embodiments in which the outer casing 3602 or the circuitry housing 3616 include the feedthrough plate 3624 as an integral part thereof. The circuitry housing 3616 can be made of titanium, ceramic, or other biocompatible and/or hermetic material.

The antenna 3610 is encased in the antenna housing 3618. The antenna housing 3618, in one or more embodiments, is separate from the circuitry housing 3616 and the outer casing 3602. In such embodiments, the antenna housing 3618 can be affixed to the circuitry housing 3616 by affixing the antenna housing 3618 and the circuitry housing 3616 to the feedthrough plate 3620, such as by welding and/or brazing the antenna housing 3618 and/or the circuitry housing 3616 to the feedthrough plate 3620. The antenna housing 3618 as illustrated is located more proximal than the circuitry housing 3616, such as to situate the antenna 3610 more proximal than the circuitry 3608. The plate 3622 can hermetically seal the antenna housing 3618 from the external environment.

FIG. 37 illustrates, by way of example, a perspective view diagram of another embodiment of an implantable device 3700. The implantable device 3700 is similar to the device 3600 with the device 3700 including an encapsulant 3730 encapsulating the antenna 3610 and not including the antenna housing 3618 and also not including the plate 3622. The hollow lumen portion 3606B as illustrated in FIG. 37 extends beyond the proximal end 3626 of the device 3700. As illustrated in FIG. 36 the hollow lumen portion 3606B extends to the proximal end 3626 of the device 3600. In one or more other embodiments, the hollow lumen portion 3606B can extend from at or near the distal end 3628 (internal to the outer casing 3602) to near, but not to, the proximal end 3626. In such embodiments, the end plate 3622 or the encapsulant 3730 can include an opening therein that provides access to the hollow lumen.

Figure 38:
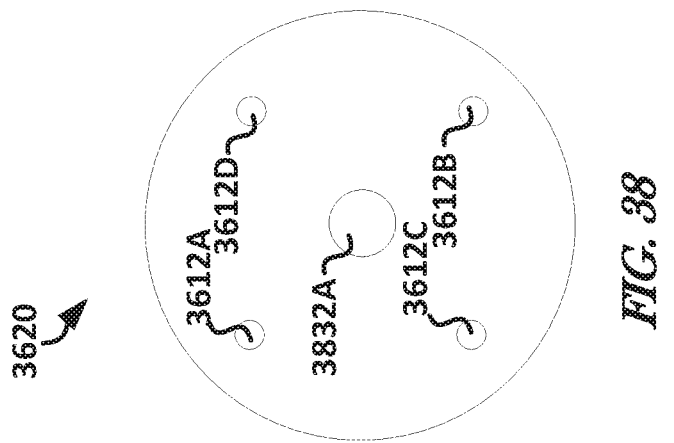
FIG. 38 illustrates, by way of example, a perspective view diagram of an embodiment of a distal feedthrough plate.

FIG. 38 illustrates, by way of example, a perspective view diagram of an embodiment of the feedthrough plate 3620. The feedthrough plate 3620 as illustrated includes a plurality of distal feedthroughs 3612A-D. The feedthroughs 3612A-D provide a path for a conductor to travel through the feedthrough plate 3620, such as while providing a hermetic seal or otherwise protecting the conductors therein. The conductors in the distal feedthroughs 3612A-D are each respectively coupled to an electrode 3604A-D and to the circuitry 3608, such as to a pad of the pads 934. While there are four distal feedthroughs 3612A-D illustrated in the feedthrough plate 3620, there can be any number of distal feedthroughs, such as can include a single distal feedthrough for each of the electrodes on the implantable device. The feedthrough plate 3620 as illustrated includes a lumen hole 3832A on/to which the hollow lumen portion 3606A can be situated or affixed. A periphery of the lumen hole 3832A is thus about the same as a periphery of the hollow lumen portion 3606A. In one or more embodiments, the hollow lumen portion 3606A can be welded or brazed to the feedthrough plate 3620. The reverse side (e.g., proximal side) of the feedthrough plate 3620 can look the same as the side depicted (e.g., the distal side). The hollow lumen portion 3606B can be connected to the lumen hole 3832A on the reverse side of the feedthrough plate 3620.

Figure 39:
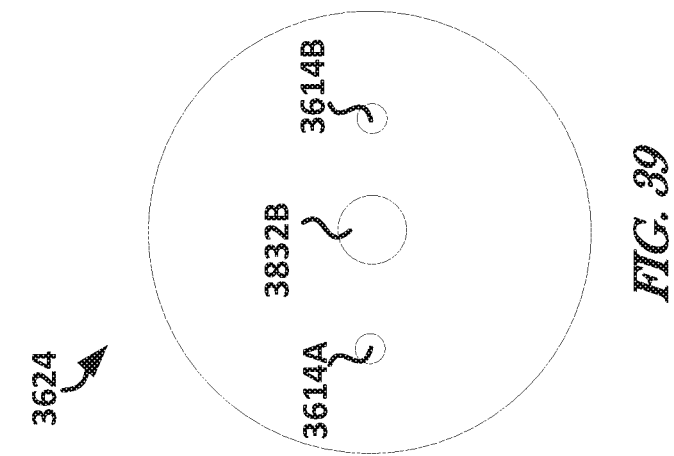
FIG. 39 illustrates, by way of example, a perspective view diagram of an embodiment of a proximal feedthrough plate.

FIG. 39 illustrates, by way of example, a perspective view diagram of an embodiment of the feedthrough plate 3624. The feedthrough plate 3624 as illustrated includes a plurality of proximal feedthroughs 3614A-B. The feedthroughs 3614A-B provide a path for a conductor to travel through the feedthrough plate 3624 while providing a hermetic seal. The conductors in the proximal feedthroughs 3614A-B are each respectively coupled to the antenna 3610 and to the circuitry 3608, such as a pad of the pads 936. The feedthrough plate 3624 as illustrated includes a lumen hole 3832B in which the hollow lumen portion 3606B can be situated. An outer perimeter of the lumen hole 3832B is thus larger than an outer perimeter of the hollow lumen portion 3606B. In one or more embodiments, the hollow lumen portion 3606B can be welded or brazed to the feedthrough plate 3624 around the lumen hole 3832A, such as to affix the feedthrough plate 3624 to the hollow lumen portion 3606B.

Figure 40:
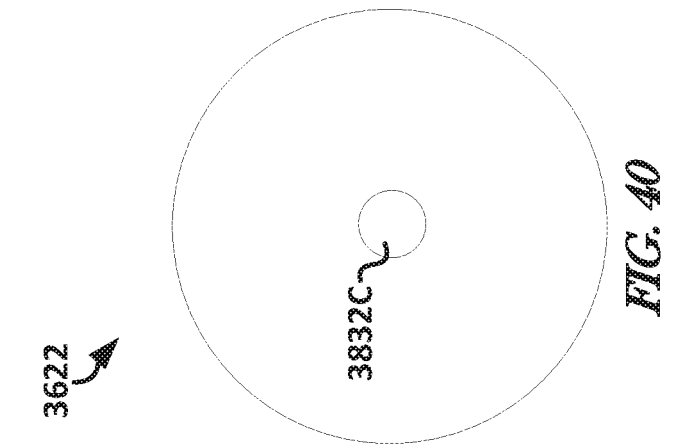
FIG. 40 illustrates, by way of example, a perspective view diagram of an embodiment of an end plate.

FIG. 40 illustrates, by way of example, a perspective view diagram of an embodiment of the end plate 3622. The end plate 3622 as illustrated includes a lumen hole 3832C in which the hollow lumen 3606 can be situated. An outer perimeter of the lumen hole 3832C can thus be larger than an outer perimeter of the hollow lumen portion 3606B. In one or more embodiments, the hollow lumen portion 3606B can be welded or brazed to the feedthrough plate 3624 around the lumen hole 3832A, such as to affix the feedthrough plate 3624 to the hollow lumen 3606.

Figure 41B:
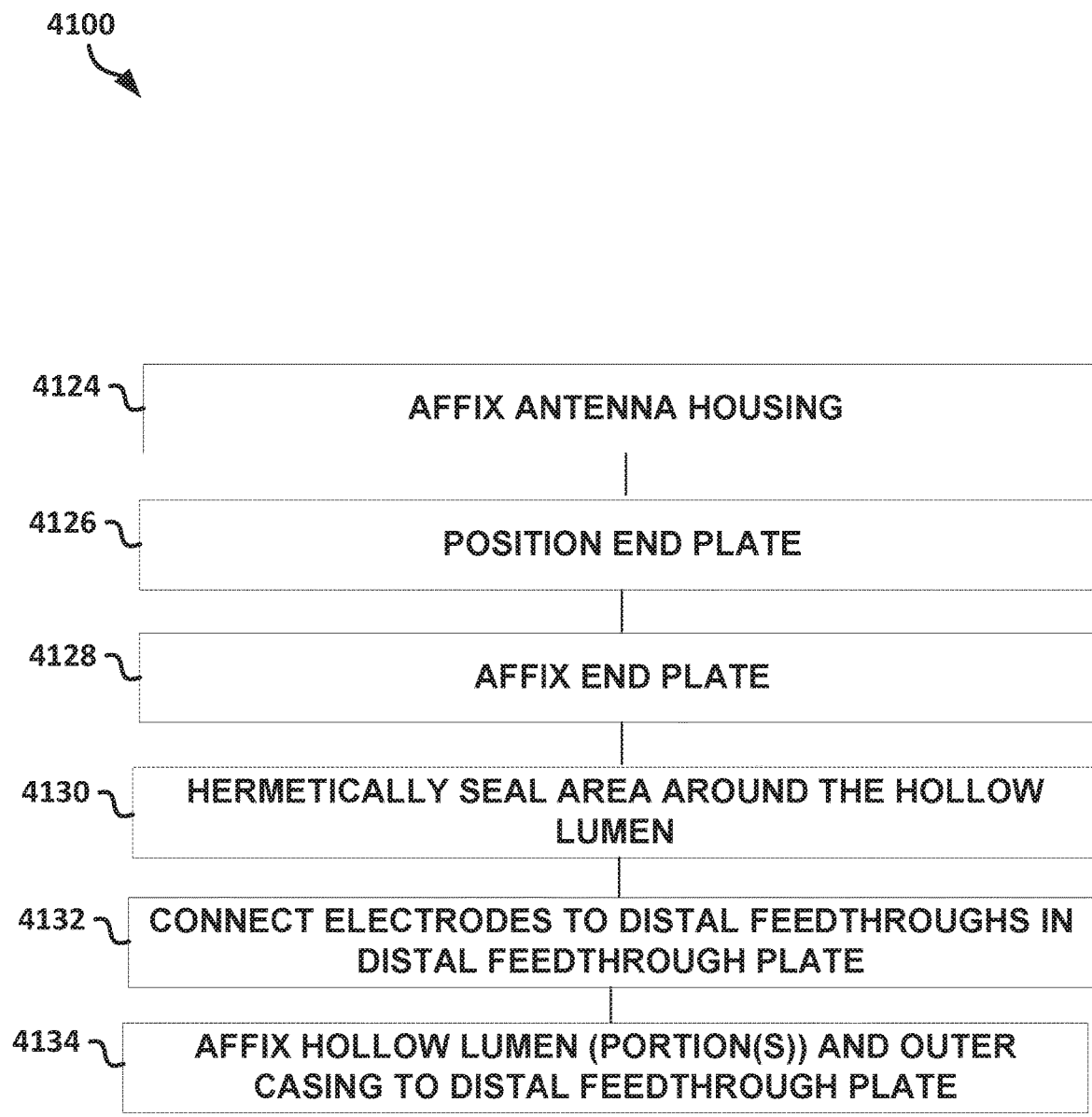

FIGS. 41A and 41B illustrate, by way of example, a diagram of a technique 4100 (e.g., a method) for assembling an implantable device that includes a hollow lumen, such as the device 3600 or 3700. The technique 4100, as illustrated, includes situating the feedthrough plate 3620 over the hollow lumen portion 3606A (and, in one or more embodiments, on a proximal end of the outer casing 3602), at operation 4102; electrically connecting conductors (at a proximal side of the feedthrough plate 3620) to the circuitry 3608, at operation 4108; positioning circuitry 3608 within the circuitry housing 3616, at operation 4110; positioning circuitry housing 3616 (on the outer casing 3602 or feedthrough plate 3620), at operation 4112; affixing distal side of circuitry housing 3616 to feedthrough plate 3620 or outer casing 3602, at operation 4114; electrically connecting conductors from the proximal feedthrough 3614A-B to the circuitry 3608, at operation 4116; positioning feedthrough plate 3624 (on the circuitry housing 3616 and/or over the hollow lumen portion 3606B), at operation 4118; affixing the feedthrough plate 3624 to the circuitry housing 3616, at operation 4120; positioning the antenna housing 3618 (over the hollow lumen portion 3606B and/or on the feedthrough plate 3624), at operation 4122; affixing the antenna housing 3618 to the feedthrough plate 3624 and/or the circuitry housing 3616, at operation 4124; positioning end plate 3622 (over the hollow lumen portion 3606A and/or on the antenna housing 3618), at operation 4126; affixing the end plate 3622 to the antenna housing 3618, at operation 4128; hermetically sealing area around the hollow lumen portion 3606B (e.g., an area between the lumen hole 3832C), such as by welding (in the case of a metal), brazing (in the case of a ceramic) or melting glass (in the case of glass), at operation 4130; connecting electrodes (through a conductor) to respective distal feedthroughs 3612A-D in the feedthrough plate 3620, at operation 4132; and affixing the hollow lumen portion(s) 3606A-B and/or the outer casing 3602 to the feedthrough plate 3620, at operation 4134.

The operations 4122, 4124, 4126, and 4128 are optional, as the antenna housing 3618 and the end plate 3622 are not used in some embodiments. In such embodiments, the technique 4100 can alternatively include encapsulating the antenna 3610 in an encapsulant 3730 (e.g., a dielectric material), such as by situating the encapsulant (and curing the encapsulant in some embodiments). The encapsulant 3730 can be situated on the feedthrough plate 3620, such as to cover the feedthroughs 3614A-B on the proximal side of the feedthrough plate 3620. The encapsulant 3730 can be situated around the hollow lumen portion 3606B and the antenna 3610, such as to fully encapsulate the antenna 3610. As operation 4118 is performed, the conductors on the distal side of the feedthrough plate 3620 will generally form respective service loops.

C. Rigid Implantable Devices

Figure 42:
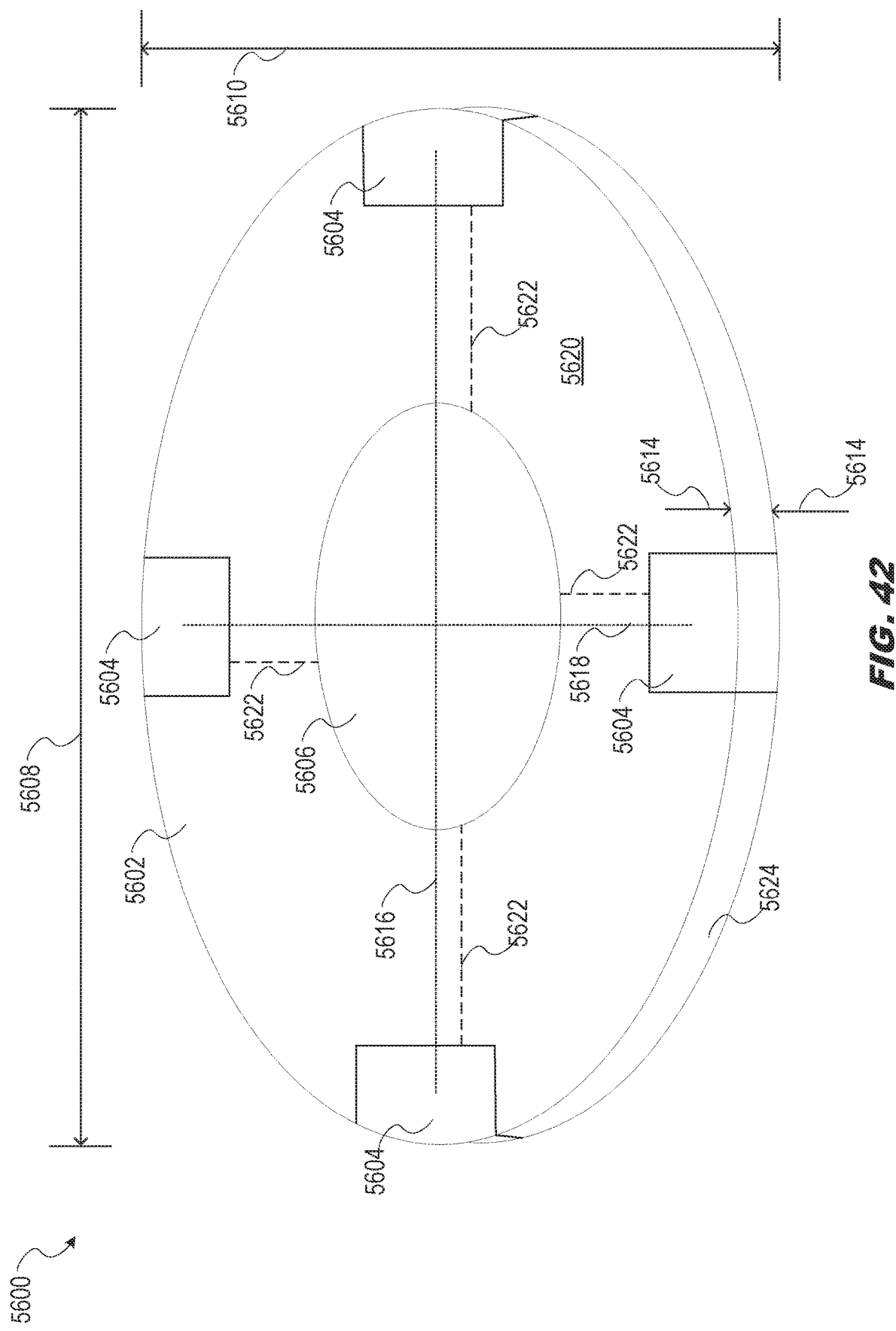
FIG. 42 illustrates, by way of example, a perspective view diagram of an embodiment of an implantable stimulation device.

FIG. 42 illustrates, by way of example, a perspective view diagram of an embodiment of an implantable device 5600, such as can be used for nerve stimulation. In several embodiments, an implantable device comprises a rigid configuration. Such implantable devices, in one or more embodiments, can include an oblong shape. The implantable device 5600 as illustrated includes a disc shaped body portion 5602, a plurality of electrodes 5604, and a circuitry housing 5606.

The body portion 5602 can be made of a rigid biocompatible material, such as can include platinum, iridium, titanium, ceramic, zirconia, alumina, glass, and/or a combination thereof among others. The body portion 5602 can be longer (length indicated by arrow 5608) than it is wide (width indicated by arrow 5610). A thickness (indicated by arrows 5614) can be less than the width. An example range of lengths of the body portion 5602 includes about six millimeters to about four centimeters (e.g., six millimeters to one centimeter, eight millimeters to two centimeters, one centimeter to four centimeters, two centimeters to four centimeters, once centimeter to three centimeters, overlapping ranges thereof, or any value within the recited ranges). An example range of widths of the body portion 5602 includes about six millimeters to about four centimeters (e.g., six millimeters to one centimeter, eight millimeters to two centimeters, one centimeter to four centimeters, two centimeters to four centimeters, once centimeter to three centimeters, overlapping ranges thereof, or any value within the recited ranges). An example range of thicknesses of the body portion 5602 includes about a half a millimeter to about five millimeters (e.g., half a millimeter to one millimeter, one millimeter to two millimeters, one millimeter to four millimeters, two millimeters to four millimeters, three millimeters to five millimeters, half a millimeter to 2.5 millimeters, once centimeter to three centimeters, overlapping ranges thereof, or any value within the recited ranges).

The body portion 5602 includes electrodes 5604 located along a periphery thereof. The electrodes 5604, as illustrated, are located on the periphery. The electrodes 5604 are illustrated as about evenly distributed on the periphery, such that a distance between directly adjacent electrodes (directly adjacent as the periphery is traversed clockwise or anti-clockwise) is generally uniform (e.g., within ten percent of being uniform). The electrodes 5604, as illustrated, are located at respective intersections of a bisector of the length or width and the periphery. A length bisector is indicated by dotted line 5618 and a width bisector is indicated by dotted line 5616. In an embodiment in which the body portion has an elliptical footprint, the length bisector (dotted line 5618) is the minor axis and the width bisector (dotted line 5616) is the major axis of the footprint. While the device 5600 is illustrated as including four electrodes 5604, the device 5600 can include one or more electrodes. For example, the device can include two, three, four, five, six, seven, eight or more electrodes located on the periphery of the device 5600.

The body portion 5602 includes a circuitry housing 5606 at least partially therein. In one or more embodiments, the circuitry housing 5606 can be flush with a surface 5620 of the body portion 5602. The circuitry housing 5606 can provide a hermetic seal for electric or electronic components and interconnects housed therein, or can otherwise provide protection for the circuitry housed therein, such as without being hermetic. The electric or electronic components can include one or more transistors, resistors, capacitors, inductors, diodes, central processing units (CPUs), field programmable gate arrays (FPGAs), Boolean logic gates, multiplexers, switches, regulators, amplifiers, power sources, charge pumps, oscillators, phase locked loops (PLLs), modulators, demodulators, radios (receive and/or transmit radios), buffers, circulators, amplifiers, and/or antennas (e.g., a helical shaped antenna or a patch antenna, among others), or the like, such as other circuitry of the implantable device discussed elsewhere herein. The components in the circuitry housing 5606 can be arranged to form stimulation therapy generation circuitry to provide stimulation therapy signals to the electrodes 5604, a receiver (to receive power and/or data signals from a midfield device), a transmitter (to provide data signals to the midfield device), and/or an electrode selection circuitry (to select which electrode(s) are anode(s) and which are cathode(s)). The electrodes 5604 can be respectively electrically connected to circuitry in the circuitry housing 5606, such as by using a unipolar feedthrough and an insulated conductor 5622.

In one or more embodiments, a side 5624 of the device 5600 can be flat, such as to form an edge. In one or more embodiments, the side 5624 can be rounded. The surface 5620 and an opposing surface (view of opposing surface occluded in FIG. 42) of the device 5600 can be substantially flat (e.g., have a flattening ratio of about 0.9 or greater) or can be rounded at least in a portion thereof. Each of the electrodes 5604 and the circuitry housing 5606 can be flush with the surface 5620 (and the same or different on the opposite surface, which can be generally the same as the view in FIG. 42).

Figure 43:
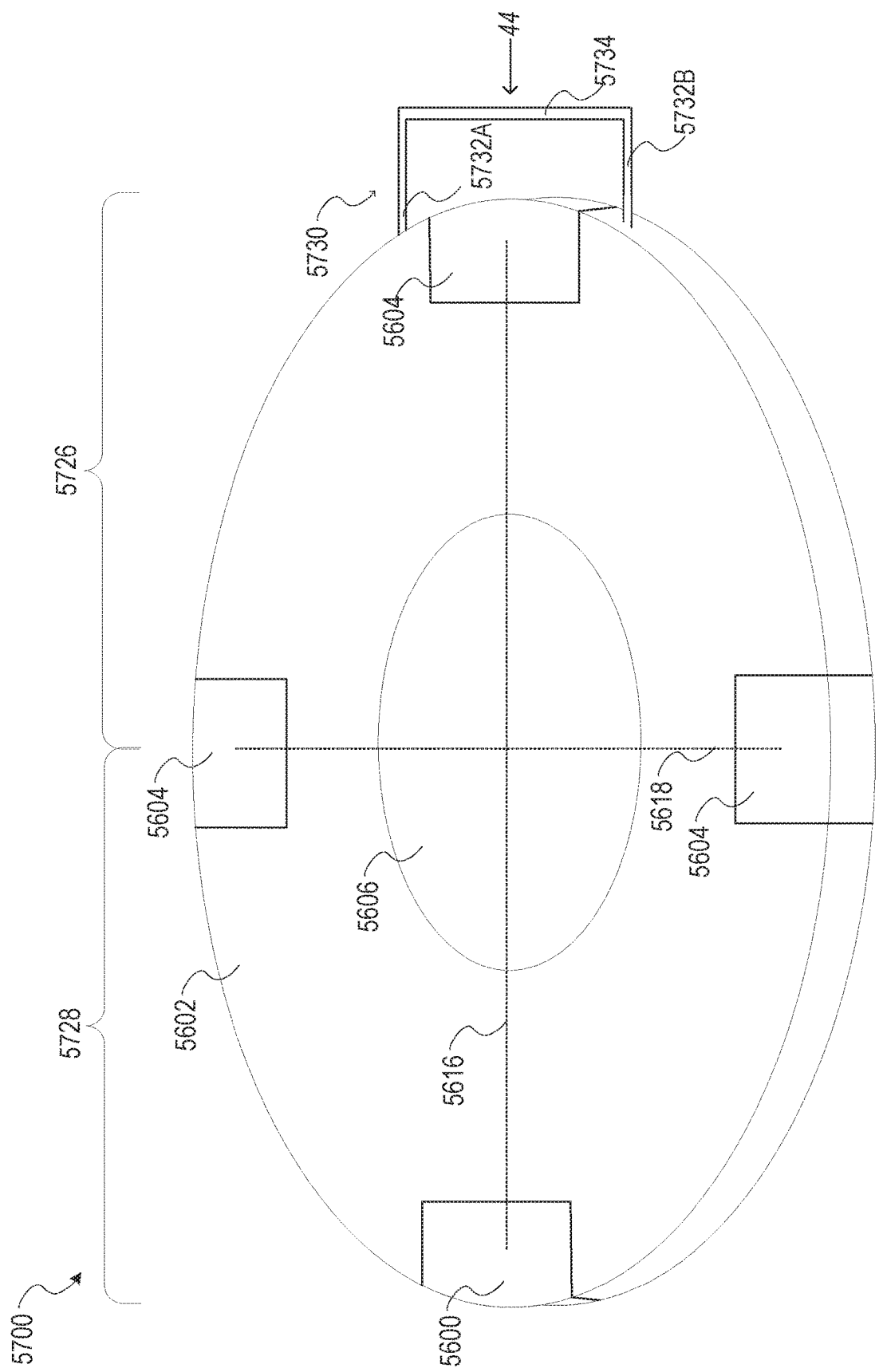
FIG. 43 illustrates, by way of example, a perspective view diagram of an embodiment of another implantable stimulation device.

FIG. 43 illustrates, by way of example, a perspective view diagram of an embodiment of another implantable stimulation device 5700. The implantable stimulation device 5700 is similar to the stimulation device 5600 with the device 5700 including an implant/explant structure 5730. The implant/explant structure 5730 is located on a proximal portion 5726 of the device 5700. The device 5700 includes a distal portion 5728 opposite the proximal portion 5726. The distal and proximal portions are defined relative to the direction the device 5700 will be implanted and do not necessarily connote orientation after implantation. The device 5700 is arranged to be implanted distal portion 5728 first and proximal portion 5726 thereafter, even though, after implantation, the distal portion 5728 may be closer to a surface of the skin than the proximal portion 5726.

The implant/explant structure 5730 as illustrated includes three bars 5732A, 5732B, and 5734. The bars 5732A-B as illustrated are generally parallel to the major axis (the dotted line 5616). The bar 5734 is generally perpendicular to the bars 5732A-B. A suture (not shown in FIG. 43) can be attached to the implant/explant structure 5730. The suture, in one or more embodiments can be attached to the bar 5734. The bar 5734 can include a male or female connector (e.g., a clip, screw hole, hole, or other connection or interface mechanism) to which a pushrod may be attached, such as for implantation of the device 5700. Note that, while the bars of the implant/explant structure 5730 are illustrated as being straight, they can be curved, or some other shape.

FIG. 44 illustrates, by way of example, a perspective view diagram of the device 5700 from the perspective of the arrow labelled "44" in FIG. 43. The device 5700 as illustrated includes a connector 5836 to which a push rod and/or a suture may be attached. The connector 5836 can be a screw hole, a hole, a clip, detent, or other male or female interface or coupling means for attaching the push rod and/or suture to the device 5700.

FIG. 45 illustrates, by way of example, a perspective view diagram of an embodiment of an implant/explant system 5900. The implant/explant system 5900, as illustrated, includes a suture 5938 and a pushrod 5940. The pushrod 5940 as illustrated includes screw threads 5942. The screw threads 5942 can be screwed into the connector 5836 in embodiments in which the connector includes a screw hole. The connector 5836 and the mating connector on the pushrod 5940 (e.g., the screw threads 5942 in the example of FIG. 45) can be attachable and detachable. Thus, the pushrod 5940 can be used to implant the device 5700 and the pushrod 5940 can be removed, leaving the device 5700 implanted.

FIG. 46 illustrates, by way of example, a perspective view diagram of an embodiment of an implant/explant system 6000. The system 6000 as illustrated includes the pushrod 5940 attached to the implant/explant structure 5730. The device 5700 is in a catheter 6046 that pierced skin 6044 of a user. The catheter 6046 can have angled sidewalls, such as to help guide the device 5700 into the proper orientation and/or to help the catheter pierce the skin 6044. The pushrod 5940 can be used to force the device 5700 under the skin 6044 and into a proper location in the body.

In one or more embodiments, the device 5600/5700 can be implanted into the body without using a catheter. In such embodiments, an incision can be made through the skin and tissue under the skin to create a tunnel to a desired location. The device 5600/5700 can then be inserted into the tissue through the tunnel, such as by using a pushrod or a flatter, more flexible obstacle stick or obturator (flatter and more flexible than the pushrod).

Figure 47:
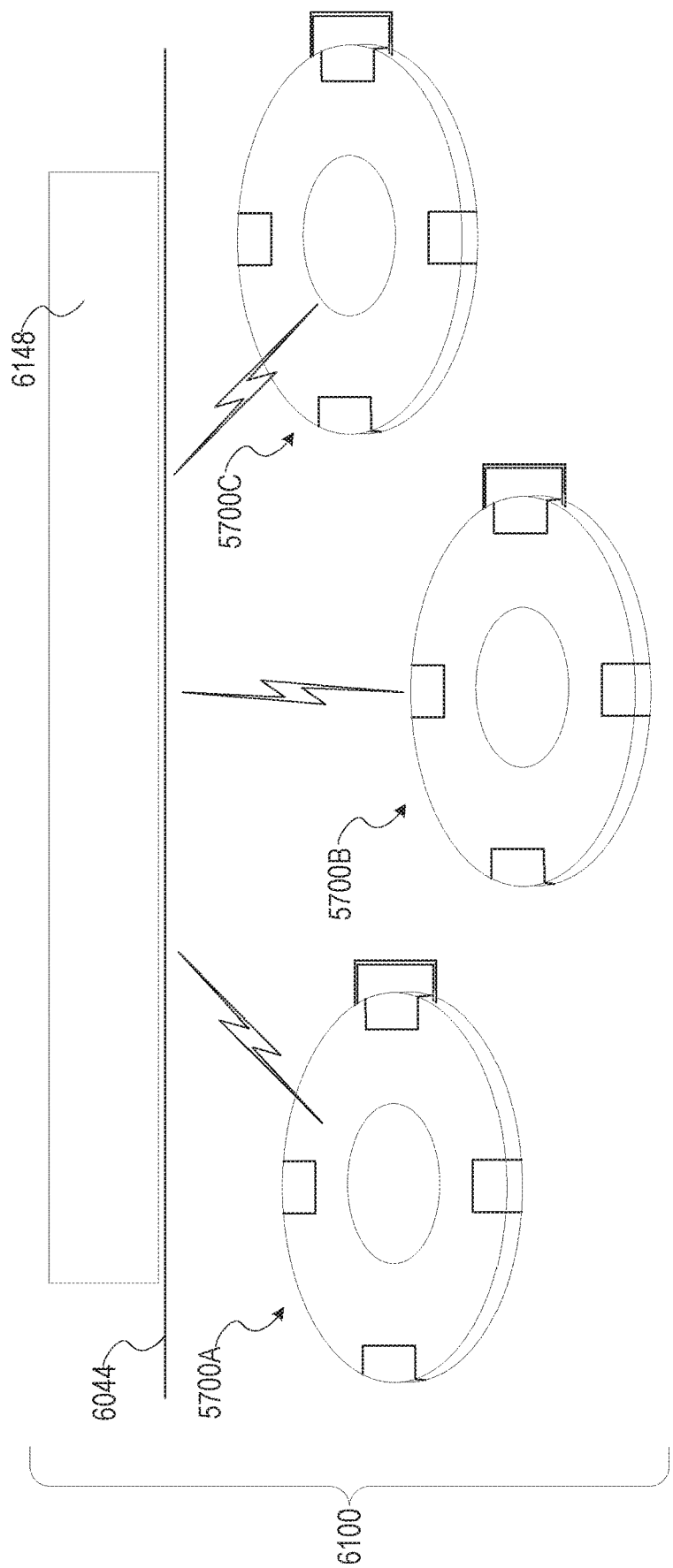
FIG. 47 illustrates, by way of example, a perspective view diagram of an embodiment of another implant/explant system.

FIG. 47 illustrates, by way of example, a perspective view diagram of an embodiment of an implant system 6100. The implant system 6100, as illustrated, includes a plurality of implantable devices 5700A, 5700B, and 5700C and a midfield powering device 6148. The stimulation devices 5700A-C are specific embodiments of the device 5700. The midfield device 6148 produces directed and focused electromagnetic fields. The midfield device 6148 can be similar to or the same as the midfield device 5028 or the source 102. The midfield powering device 6148 provides electromagnetic signals to each of the stimulation devices 5700A-C that can be used, by the circuitry in the circuitry housing 5606, such as to power the stimulation device 5700A-C and produce stimulation therapy.

The focus and direction of the electromagnetic field produced by the midfield powering device 6148 can be altered by adjusting a phase of a signal produced by one or more antennas of the midfield powering device 6148.

When using a time domain multiplexing communication system between an external transmitter and an implanted receiver, the phase and amplitude can be dynamically adjusted to help focus energy (e.g., more efficiently focus energy) at the implanted receiver, such as with using a power detector at the stimulation device for feedback. The midfield device 6148 can provide power and/or data signals to the implantable devices 5700A-C in a time domain multiplexed manner, such as to provide signals to one of the devices 5700A-C at one time and to another of the devices 5700A-C at another time.

One or more features of the implantable devices discussed herein can include: (1) a generally flattened (e.g., planar) and rigid (non-flexible and non-stretchable) body; (2) electrodes spaced radially (e.g., spaced apart with about 90 degrees between adjacent electrodes in the example of four electrodes), such as to enable spatial stimulation patterns; (3) the body can be shortened along one axis (width as discussed herein) to allow the stimulation device to pass through a smaller incision and dilated entry path than if both axes are the same length; (4) it can accommodate a screw type implant and explant tool, such as by using an implant/explant structure; (5) the stimulation devices do not require lead tunneling or a pocket for a self-contained implantable pulse generator, such as is required for many self-contained stimulation devices; and/or (6) the stimulation devices can be sized and implanted so as to be cosmetically unnoticeable without the presence of the external stimulator.

One or more embodiments of stimulation devices discussed herein include a generally flattened, rigid configuration. These devices can be used to stimulate one or more peripheral nerves, such as an occipital or super orbital nerve structure. Such implants can provide stimulation to the motor cortex. The devices discussed herein can be implanted into muscular tissue, such as to help affix the implant in location. Such an implant can help alleviate concerns associated with Twiddler's syndrome, for example.

The stimulation devices can be used to help alleviate symptoms related to migraines, other headaches, or fibromyalgia, such as by stimulating an occipital or trigeminal nerve. The stimulation devices can provide functionality of an occipital stimulator implant. Implanting multiple stimulation devices near the target nerve can allow for more or varied spatial stimulation patterns.

The stimulation devices can be used to provide epidural stimulation in the spine. The stimulation devices can be used to provide cortical stimulation, such as for a stroke patient, such as to help alleviate movement and/or other neurological disorders associated with the stroke.

D. Surface Acoustic Wave Based Communication Devices and Methods

In accordance with several embodiments, an implantable stimulation device comprises a surface acoustic wave (SAW) device, such as to provide one or more backscatter signals. In one or more embodiments, the SAW device provides a time delay (e.g., a buffer) for a portion of a signal to be transmitted back to a powering and/or communication device (e.g., any of the external devices or sources described herein, such as source 102).

Midfield powering technology can help enable the powering of a deeply implanted stimulation device from an external source located on or near the surface of a patient's skin. While power delivery is important to activate a device, two-way communication can help allow the outside world to know that the implant is in-fact powered and/or to provide feedback signals for manipulating fields (e.g., one or more evanescent fields), such as to better focus a power signal on the implanted device. Further, two-way communication can help allow for transmission of data from an implanted sensor integrated with (on or near) the implanted device.

Some communication schemes can have one or more disadvantages when used for communicating with an implanted device (e.g., a deeply implanted device), such as a device with strict power limitation in the microwatt range. Active transmission schemes integrating an on-chip oscillator in the implanted device have limited oscillator accuracy without an integrated phase lock loop, micro electro-mechanical system (MEMS), and/or crystal oscillator. Using a phase lock loop increases the start-up time and power consumption, sometimes beyond the power buffering capability of a small off-chip capacitor even when duty cycled. The limited oscillator accuracy can make detection of the signal difficult due to the increased noise bandwidth and center frequency tracking.

Passive communication schemes, such as load modulation, deal with a strong interferer, which is the powering signal (often times >50 dB greater in signal strength than the communication signal). Unlike in inductive coupling approaches of power transfer, with midfield powering, a signal is loaded more by the tissue itself than the receive antenna of the implanted device. In accord with some embodiments, using schemes such as backscatter can be difficult because of the limited time delay between the implanted device and external device.

Discussed in this subsection are implantable devices that can include a SAW device and systems and methods for using the same. Described is one or more communication schemes between an external device and an implantable device. The implantable device can include a SAW device as a time delay (e.g., signal buffer) element. The SAW device can be used to store (e.g., temporarily store) an electromagnetic wave as a propagating mechanical wave, such as in a piezoelectric substrate. An implantable device can temporarily store the wave energy in the SAW device. When the implantable device is in transmit mode, the time delayed radio frequency (RF) energy from the SAW device can be used (e.g., as a carrier wave or on its own) for data transmission back to the external device. During this time, the external device may refrain from transmitting an energizing signal, such as when the external device is in receive mode. In such embodiments, there may not be a strong interfering signal from the external device that can cause interference in a signal transmitted from the implantable device. Such embodiments can help provide communications from the implantable device to the external device using less power. Such embodiments can help provide communications to the external device that are more easily detected at the transmitter, at least because a portion of the signal from the implantable device to the external device may not include an interfering signal from the transmitter.

Direct Current (DC) energy can be stored on the implantable device so as to power the implantable device while it is transmitting (e.g., stimulation energy from the external device 4202 (e.g., the source 102) and/or a signal to the external device). This energy can be, at least partially, used to modulate the carrier signal transmitted from the implant. In one or more embodiments, the SAW device can be used simultaneously as a bandpass filter for the implant transmission downlink, such as to help reject out of band sources, such as for increased immunity to noise or other signal interference.

Figure 48:
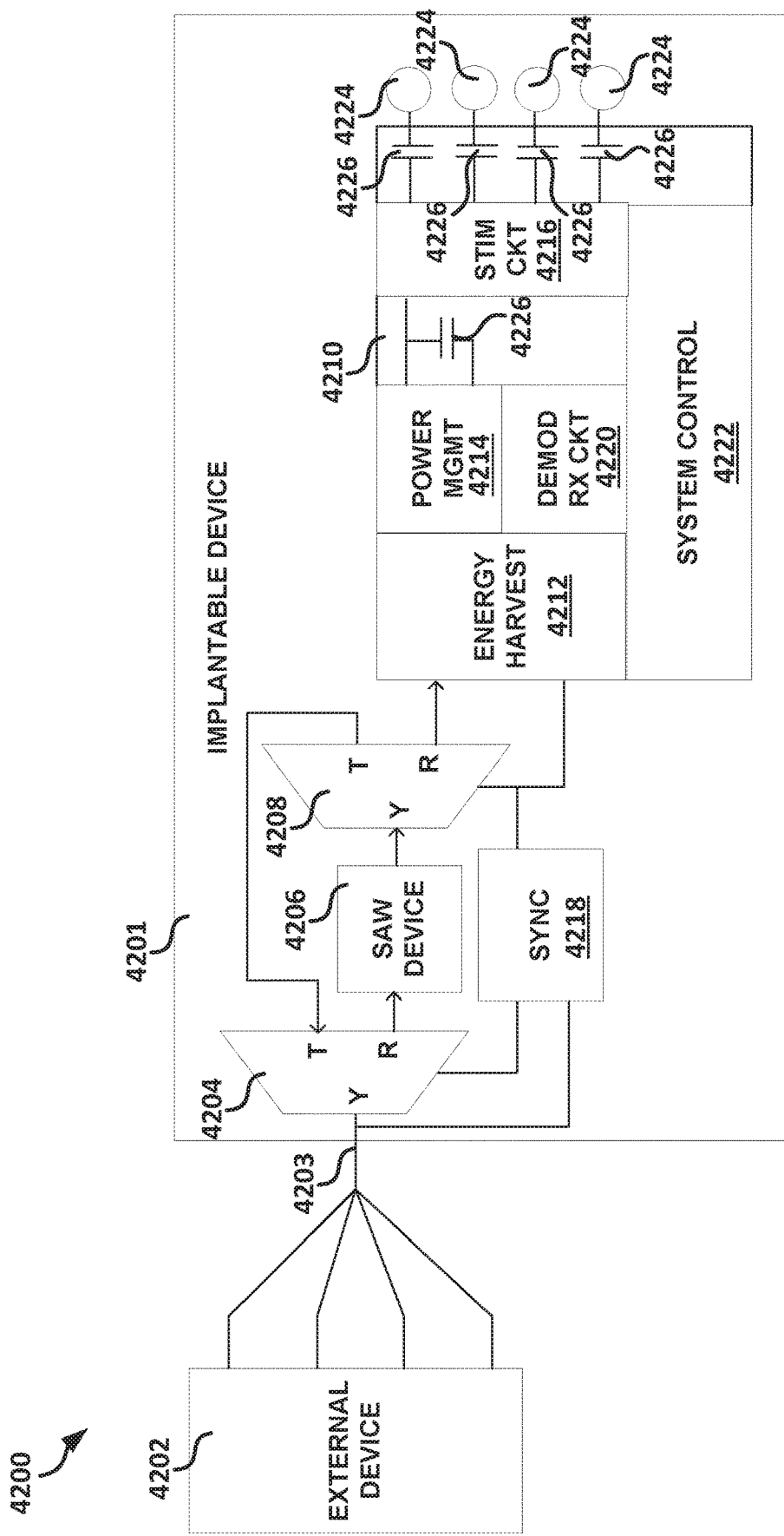
FIG. 48 illustrates, by way of example, a perspective view diagram of an embodiment of a communication and/or stimulation system.

FIG. 48 illustrates, by way of example, a logical block diagram of an embodiment of a system 4200. The system 4200 as illustrated includes an external device 4202 and an implantable device 4201. The external device 4202 can provide power and/or communication signals to the implantable device 4201. In one or more embodiments, the external device 4202 can include a midfield source that provides a midfield signal to the implantable device 4201. Midfield signals and sources are discussed elsewhere herein. The circuitry 500 can include one or more of the components of the implantable device 4201, the circuitry 4400 (see FIG. 50), the circuitry 4500 (see FIG. 51), the circuitry 4600 (see FIG. 52), and/or the circuitry 4700 (see FIG. 53).

The implantable device 4201 receives signals from the external device 4202 and provides signals to the external device 4202. These signals are represented by the line 4203. The implantable device 4201 can provide modulation (e.g., stimulation therapy, denervation, or other therapy to a location in a body, such as to modulate (e.g., stimulate) a nerve, muscle, or other tissue. The implantable device 4201 can provide data signals to the external device 4202.

The implantable device 4201 as illustrated includes a first switch 4204, a SAW device 4206, a second switch 4208, circuitry 4210, synchronization circuitry 4218, and electrodes 4224. The switches 4204 and/or 4208 can include one or more transistors or mechanical switches arranged to provide alternate electrical paths for electrical signals from the external device 4202 (a receive path) and to the external device 4202 (a transmit path). The transmit path includes the "T" of the respective switches 4204 and 4208 and the receive path includes the "R" of the respective switches 4204 and 4208.

The SAW device 4206 includes a material that has an elasticity that provides a medium to convert an electric signal incident thereon into a mechanical wave in the SAW device 4206. The SAW device 4206 then converts the mechanical wave back into an electric signal. Since the propagation of the mechanical wave occurs slower than the propagation of an electric signal in a normal conductor, the SAW device 4206 advantageously acts as a time delay element for the electric signal, in accordance with several embodiments. A piezoelectric material can be used as a transducer that converts between mechanical and electrical waves in SAW devices.

The circuitry 4210 as illustrated includes energy harvesting circuitry 4212, power management circuitry 4214, stimulation circuitry 4216, demodulator receive circuitry 4220, system control circuitry 4222, and capacitors 4226.

The energy harvesting circuitry 4212 can include a rectifier and one or more capacitors to help store a rectified signal. The energy harvesting circuitry 4212 can power the implantable device 4201, such as when a stimulation signal is being received from the external device 4202 and in some embodiments after a stimulation is received is received from the external device 4202.

The stimulation circuitry 4216 provides electrical signals to electrodes 4224. The stimulation circuitry 4216 can include one or more switches to choose which electrode(s) are anodes and which are cathodes.

The synchronization circuitry 4218 can include circuitry to determine when the implantable device 4201 is to be in a transmit mode and when the implantable device 4201 is to be in a receive mode. The synchronization circuitry 4218 can determine an amplitude of an envelope of a signal from the external device 4202. Based on the amplitude of the envelope, the synchronization circuitry 4218 can determine the proper mode. When the envelope is sufficiently large (e.g., above a threshold), the implantable device 4201 can be in or switched to receive mode and the external device 4202 can be in transmit mode. When the envelope is sufficiently small (e.g., below a second, sometimes different, threshold) the implantable device 4201 can be switched to or in transmit mode and the external device 4202 can be in or switched to receive mode. An amplitude of the envelope is a difference between consecutive maximum and minimum voltages of the signal.

Figure 49:
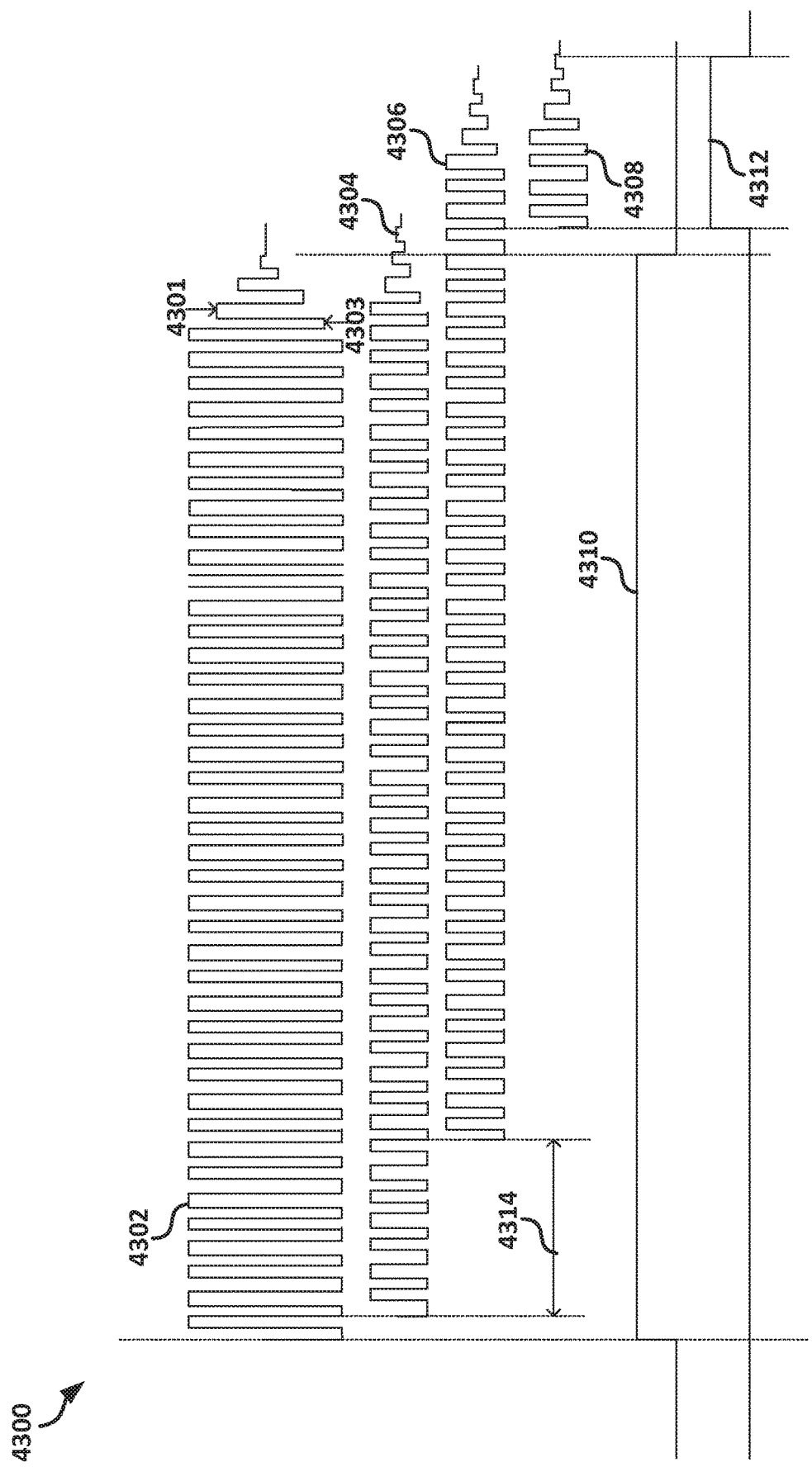
FIG. 49 illustrates, by way of example, a waveform diagram of an embodiment of signals in a communication and/or stimulation system.

FIG. 49 illustrates, by way of example, a wave diagram of an embodiment of electric signals 4300 in a system that includes a SAW device. The signals 4300 as illustrated include a signal 4302 from an external device, a signal 4304 representative of received power at the implantable device 4201, a signal 4306 as delayed by the SAW device 4206, a signal 4308 that is to be used as (1) a carrier wave in modulating a signal transmission to the external device 4202 or (2) as a signal to be transmitted back to the external device 4202 without modulation, an energizing cycle 4310, and a transmission cycle 4312.

The signal 4302 is from the external device 4202 and provides electric power and a base signal from which to provide data from the implantable device 4201 to the external device 4202. The signal 4304 represents the signal received at an antenna of the implantable device 4201. The delay between the start of the signal 4302 and the signal 4304 is a propagation delay from the signal 4302 travelling to an antenna of the implantable device 4201. The signal 4306 is at least a portion of the signal 4304 after being processed through the SAW device 4206. The SAW device 4206 provides a time delay 4314 to the propagation of the signal 4302 (e.g., the portion of the signal 4302 that is incident on the SAW device 4206).

The signal 4308 represents the signal that can be used to transmit data to the external device 4202. The signal 4308 is the signal that remains after an energizing cycle 4310 is complete and during a communication cycle 4312. The energizing cycle 4310 indicates a time frame during which the external device 4202 is transmitting. The energizing cycle 4310 indicates a general time frame in which the signal 4304 can be used for energy harvesting, such as by the harvesting circuitry 4212. While the energizing cycle 4310 is illustrated as ending at the time the signal 4302 is done being transmitted, the energizing cycle 4310 can last past the time the signal 4302 is done being transmitted.

While the external device 4202 is in transmit mode and the implantable device 4201 is in receive mode, the implantable device 4201 can operate to harvest power from the signal 4304 and/or decode data from the signal, such as is indicated by the energizing cycle 4310. After the power harvest period ends, the external device 4202 can be switched to receive mode and the implantable device 4201 can be switched to transmit mode. After the switching of the implantable device is complete, the remaining signal from the SAW device 4206 can be used (1) as a carrier wave that can be used to modulate one or more signals to be transmitted to the external device 4202 or (2) as a stimulating signal that is provided to the antenna to provide data to the external device 4202. In the first case, the external device 4202 can decode the data encoded on the carrier wave. In the second case, the external device 4202 can interpret a signal received as a binary "1" and no signal received as a binary "0" (or vice versa). The second case is simpler as far as circuitry on the implantable device 4201, but provides only a single bit every transmission, while the first case includes more circuitry on the implantable device (e.g., to modulate the signal) but can transmit more than one bit at a time.

FIG. 49 illustrates a minimum 4303 and a consecutive maximum 4301. The amplitude of the envelope at that point is the voltage difference between the maximum 4301 and the minimum 4303 (taking into consideration the signs of the respective voltages). The synchronization circuitry 4218 can compare a determined envelope amplitude to a specified threshold. If the envelope amplitude is below the specified threshold, the synchronization circuitry 4218 can provide a signal indicating that the implantable device 4201 is to switch to a transmit mode, such as to provide data to the external device 4202.

The demodulator receive circuitry 4220 can include a demodulator to separate information present on a modulated signal from a carrier wave. The system control circuitry 4222 can include a digital controller or processing circuitry, such as is discussed elsewhere herein. The capacitors 4226 can include one or more buffer and/or bypass capacitors.

In general, an external energizer (e.g., a powering and/or communication device that operates external to tissue in which an implantable device is situated and operates) can be used to focus energy to the implantable device 4201. With both switches 4204 and 4208 in receive mode, the signal from the external device 4202 can be used to power/communicate to/with the implantable device 4201. A downward edge of the powering signal envelope can be detected, such as by the synchronization circuitry 4218 to indicate when a power cycle is ended. In response to detecting or determining the power cycle has ended, the T/R switches 4204 and 4208 can be changed to transmit mode. In transmit mode, the implantable device 4201 can transmit the buffered RF signal. The amount of RF signal buffered in the SAW device 4206 can be between 20-500 nanoseconds (e.g., between 20 and 200 nanoseconds, between 50 and 250 nanoseconds, between 100 and 400 nanoseconds, between 200 and 500 nanoseconds, between 300 and 450 nanoseconds, between 200 and 400 nanoseconds, overlapping ranges thereof, or any value within the recited ranges), or approximately 100-300 nanoseconds (e.g., 100 to 200 nanoseconds, 150 to 250 nanoseconds, 200 to 300 nanoseconds, 150 to 300 nanoseconds, 100 to 250 nanoseconds, overlapping ranges thereof, or any value within the recited ranges) per millimeter of signal propagation length of the SAW device 4206 with a tradeoff being buffer time versus size of SAW device. The RF signal can be modulated with a load, either trying to match or matching the impedance to the transmit antenna or shorting to ground. In one or more embodiments, the presence or absence of an "echoed" RF signal determines bit "0" or "1". In such scheme, one or more bits can be transmitted every power cycle.

Figure 50:
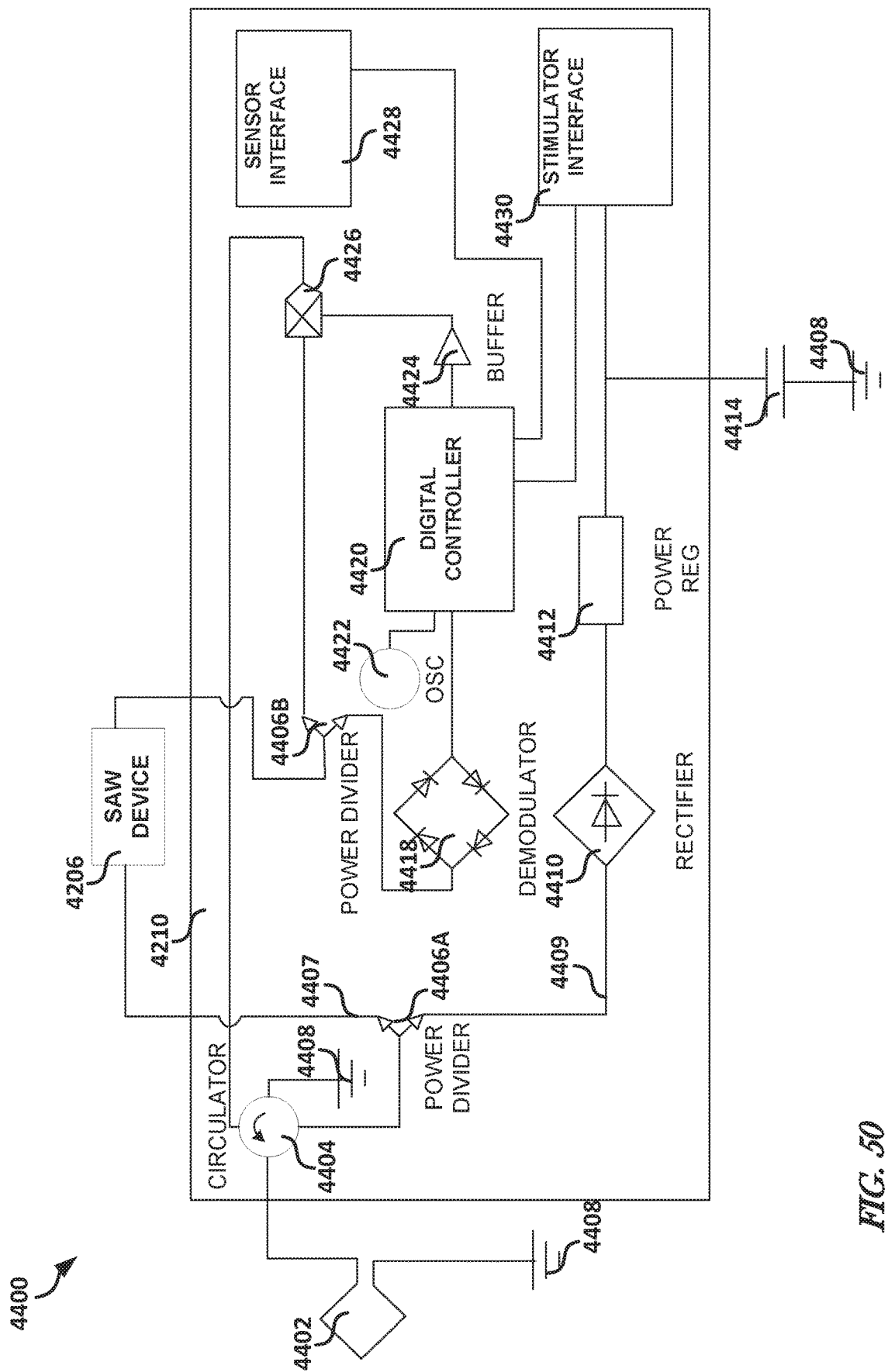
FIG. 50 illustrates, by way of example, a schematic diagram of an embodiment of circuitry of an implantable device.

FIG. 50 illustrates, by way of example, a wiring diagram of an embodiment of circuitry 4400 that can be included in the implantable device 4201. The circuitry 4400 as illustrated includes an antenna 4402, the SAW device 4206, the circuitry 4210, and a buffer capacitor 4414.

The antenna 4402 receives electromagnetic waves and converts the electromagnetic waves to electric signals. The antenna 4402 can include a dipole, coil, helix-shaped, patch, or other antenna. In one or more embodiments, the antenna 4402 can be sized and shaped to receive signals in a subset of frequencies between about 420 Megahertz and about 4 Gigahertz (e.g., between 400 MHz and 1 GHz, between 400 MHz and 3 GHz, between 500 MHz and 2 GHz, between 1 GHz and 3 GHz, between 500 MHz and 1.5 GHz, between 1 GHz and 2 GHz, between 2 GHz and 3 GHz, overlapping ranges thereof, or any value within the recited ranges). The antenna 4402 can be similar to other antennas discussed herein. The signal from the antenna 4402 can be provided to a circulator 4404.

A circulator is a passive component. The circulator 4404 is a multiple port device that transfers a signal entering any port to the next port in rotation (as indicated by the arrow on the circulator 4404). The circulator 4404 provides multiple paths for electrical signals incident thereon, depending on which port of the circulator 4404 the signals are incident. Signals from the antenna 4402 are provided to a power divider 4406A.

A power divider is a passive component. The power divider 4406A divides the signal incident thereon into two signals and provides them onto two respective signal paths (e.g., the path 4407 and the path 4409 in the example of the power divider 4406A). The power divider 4406A provides a portion of the signal received to a rectifier 4410 and another portion of the signal received to the SAW device 4206.

A rectifier converts an alternating current (AC) signal into a direct current (DC) signal by allowing a current to flow therethrough in only one direction. The rectifier 4410 converts the AC signal received from the power divider 4406A into a DC signal that is provided to a power regulator 4412.

A power regulator receives an electrical signal at a first power and produces a signal at a generally constant second power. The power regulator 4412 generally provides a ceiling to an amount of power provided at the output thereof. The power regulator 4412 provides regulated power to a stimulator interface 4430. A buffer capacitor 4414 can store energy for later usage. The stimulator interface 4430 can include the stimulation circuitry 4216, capacitors 4226, and/or the electrodes 4224.

The SAW device 4206 receives another portion of the signal from the power divider 4406A. The SAW device 4206 provides a time delay to a signal incident thereon. The signal from the SAW device 4206 is provided to another power divider 4406B. The power divider 4406B provides a portion of the signal from the SAW device 4206 to a modulator 4426 and another portion of the signal to a demodulator 4418.

A demodulator separates information modulated onto a carrier signal from the carrier signal itself. The demodulator 4418 is an analogue part to the modulator 4426. The output (e.g., information) from the demodulator 4418 is provided to the digital controller 4420.

The digital controller 4420 receives a signal from an oscillator 4422 and information from the demodulator 4418 and the sensor interface 4428. The digital controller 4420 can use the oscillator 4422 as a clock. The digital controller 4420 can alter operations of the implantable device based on the information from the demodulator 4418 and/or the sensor interface 4428. The operations can include which electrode(s) 4224 are operating as cathode(s) and/or anode(s), a duty cycle of a stimulation wave, an amplitude or frequency of the stimulation wave, or other operation of the sensor interface 4428 or stimulator interface 4430.

The digital controller 4420 can provide a data signal to a buffer 4424. A buffer electrically isolates an output from an input. The buffer 4424 generally allows an impedance of the output to be unaffected by the impedance of the input. The buffer 4424 provides information signals from the digital controller 4420 to the modulator 4426.

A modulator modulates information (in the form of electrical signals) onto a baseband signal. The modulator 4426 modulates information from the digital controller 4420 onto a baseband signal provided by the power divider 4406B. The modulated signal from the modulator 4426 is provided to the circulator 4404. The modulated signal from the circulator 4404 is provided to the antenna 4402. The antenna 4402 transmits the modulated signal to the external device 4202.

Figure 51:
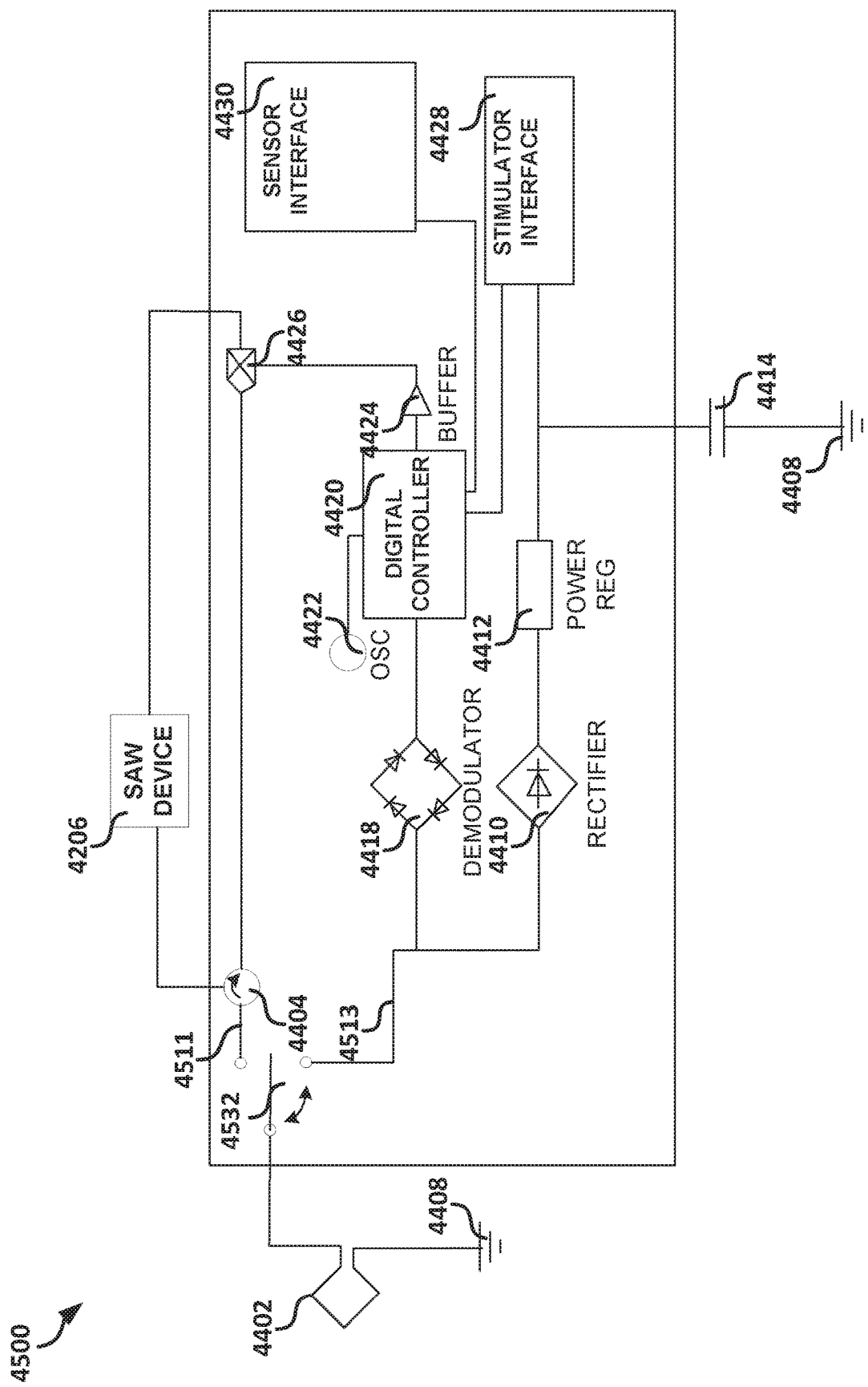
FIG. 51 illustrates, by way of example, a schematic diagram of another embodiment of circuitry of an implantable device.

FIG. 51 illustrates, by way of example, a wiring diagram of another embodiment of circuitry 4500 that can be included in the implantable device 4201. The circuitry 4500 can perform the same operations as the circuitry 4400, with the circuitry 4500 including only a single circulator 4404, no power dividers, and including a T/R switch 4532, such as is similar to the switches 4204 and 4208.

In the circuitry 4500, a signal is received at the antenna 4402. The signal from the antenna 4402 is provided to the switch 4532. In receive mode, the switch 4532 provides signals to the electrical path 4513 and in transmit mode, the switch 4532 receives signals along the electrical path 4511 and provides signals to the SAW device 4206. Along the receive path, the signal from the switch 4532 is provided to a demodulator 4418 and a rectifier 4410.

Signals from the rectifier 4410 are provided to the power regulator 4412. Signals from the power regulator 4412 are provided to the many components of the circuitry 4500 to receive power (e.g., the stimulator interface 4430, sensor interface 4428, digital controller 4420, or other components that require power to operate).

Signals from the demodulator 4418 are provided to the digital controller 4420. Signals from the digital controller 4420 are buffered by the buffer 4424 and provided as an input to the modulator 4426.

Signals incident on the circulator 4404 from the switch 4532 are provided to the SAW device 4206. The SAW device 4206 buffers the signal and provides the signal as an input to the modulator 4426. The modulator 4426 modulates the signal from the buffer 4424 onto the signal received from the SAW device 4206 (e.g., using the signal from the SAW device 4206 as a carrier wave). The modulated signal is provided to the circulator 4404 which provides the modulated signal to the switch 4532. The switch 4532 provides the modulated signal to the antenna 4402. The antenna 4402 transmits the modulated signal to the external device 4202.

Figure 52:
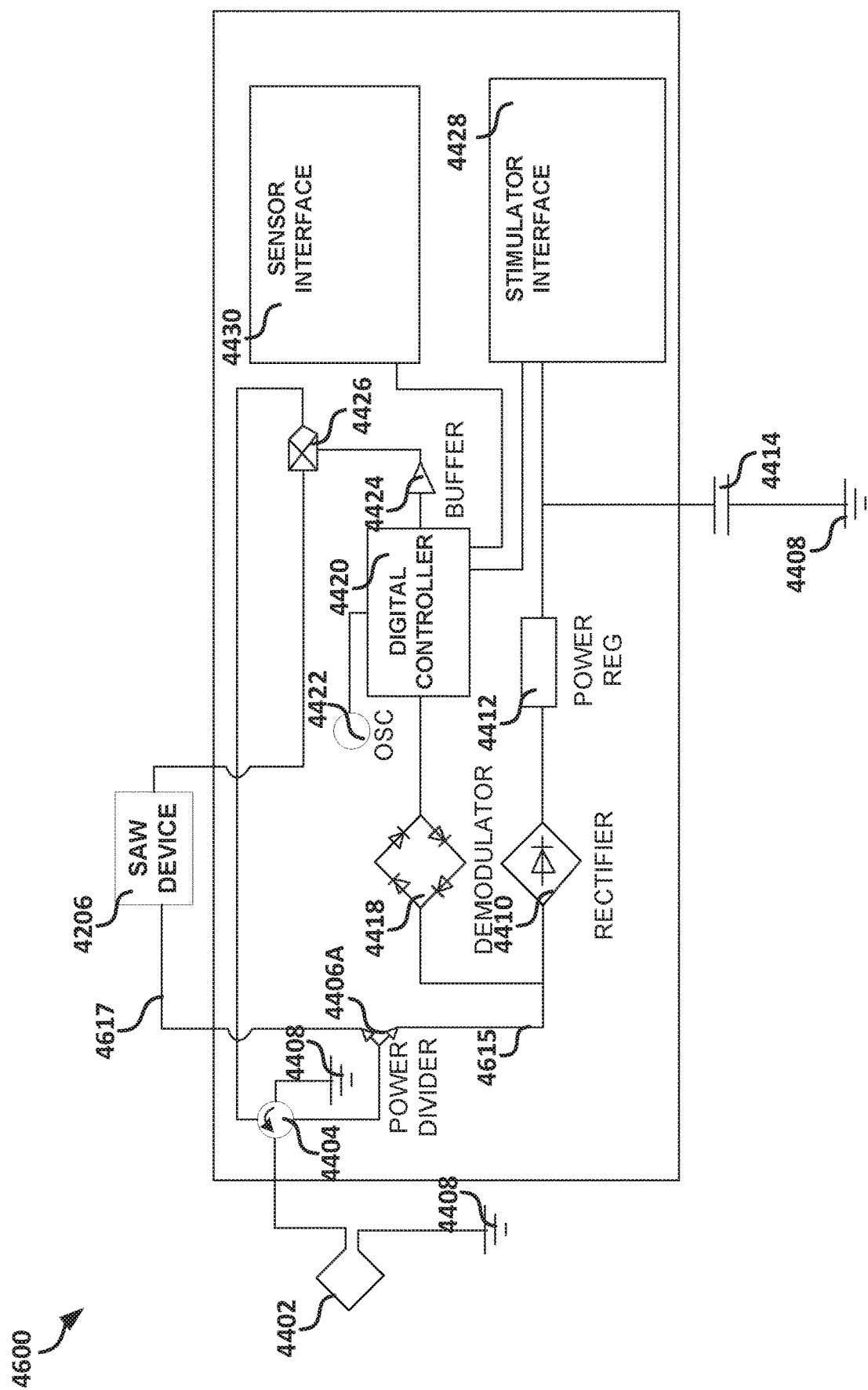
FIG. 52 illustrates, by way of example, a schematic diagram of yet another embodiment of circuitry of an implantable device.

FIG. 52 illustrates, by way of example, a wiring diagram of another embodiment of circuitry 4600 that can be included in the implantable device 4201. The circuitry 4600 can perform substantially the same operations as the circuitry 4400 and 4500, with the circuitry 4600 including only a single circulator 4404, single power divider 4406A, and no switches.

In the circuitry 4600, a signal is received at the antenna 4402. The signal from the antenna 4402 is provided to the circulator 4404. The circulator 4404 provides signals from the antenna 4402 to the power divider 4406A. The power divider 4406A divides the signals incident thereon into two signals, one signal for the electrical path 4615 and another signal for the electrical path 4617.

Signals from the rectifier 4410 are provided to the power regulator 4412. Signals from the power regulator 4412 are provided to components of the circuitry to receive power (e.g., the stimulator interface 4430, sensor interface 4428, digital controller 4420, or other components that require power to operate (e.g., active components)).

Signals from the demodulator 4418 are provided to the digital controller 4420. Signals from the digital controller 4420 are buffered by the buffer 4424 and provided as an input to the modulator 4426.

Signals from the power divider 4406A and on the electrical path 4617 are provided to the SAW device 4206. The SAW device 4206 buffers the signal and provides the signal as an input to the modulator 4426. The modulator 4426 modulates or adjusts the signal from the buffer 4424 onto the signal received from the SAW device 4206 (e.g., using the signal from the SAW device 4206 as a carrier wave). The modulated signal is provided to the circulator 4404. The circulator 4404 provides the signal from the modulator 4426 to the antenna 4402. The antenna 4402 transmits the modulated signal to the external device 4202.

Figure 53:
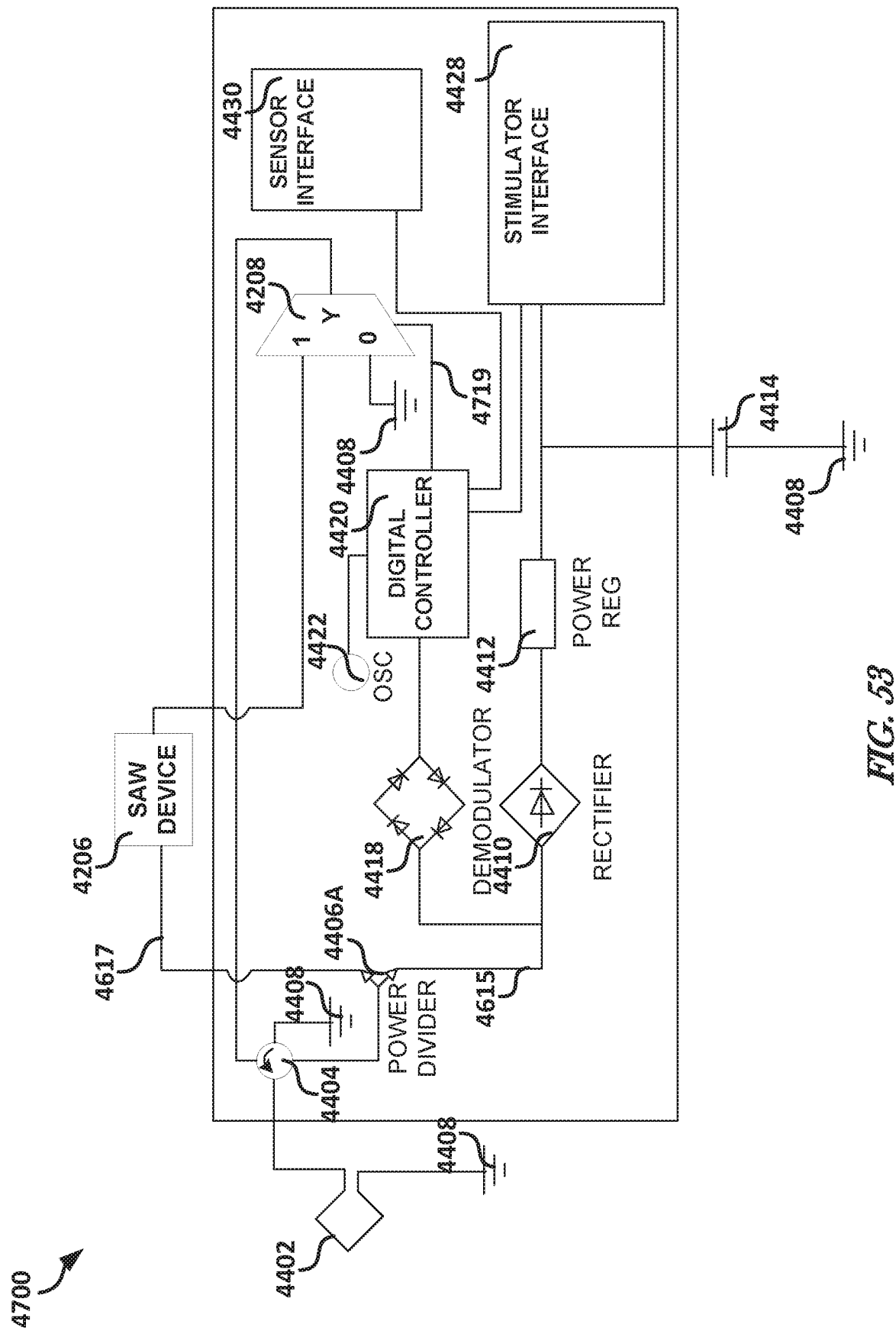
FIG. 53 illustrates, by way of example, a schematic diagram of yet another embodiment of circuitry of an implantable device.

Note that FIGS. 50, 51, and 52 each include a modulator 4426. The modulator 4426 is optional. In one or more embodiments, a signal from the SAW device 4206 can be provided to the antenna 4402 in cases where a first bit of binary information is to be provided to the external device 4202 and the signal from the SAW device 4206 can be grounded in cases where a second bit of binary information is to be provided to the external device 4202. FIG. 53 illustrates a wiring diagram of such circuitry.

FIG. 53 illustrates, by way of example, a wiring diagram of another embodiment of circuitry 4700 that can be included in the implantable device 4201. The circuitry 4700 is similar to the circuitry 4600, with the circuitry 4700 including a switch 4208 in place of the modulator 4426. A first input of the switch 4208 can be coupled to a reference voltage (e.g., ground), such as a DC reference voltage. A second input of the switch 4208 can be coupled to the output of the SAW device 4206. The digital controller 4420 provides a signal to the switch 4208 (on the connection 4719) that determines if the switch 4208 outputs the zero line or the one line.

Similar circuitries can be realized by replacing the modulator 4426 of the circuitry 4400 and 4500 with a switch 4208. Note that the buffer 4424 can be removed in such embodiments.

E. Combined Localized and Wide Area Therapy Stimulation

In accordance with several embodiments, therapy devices are adapted to provide one or more of a localized therapy stimulation and a wide area therapy stimulation. In one or more embodiments, both the localized therapy and the wide area stimulation can be provided simultaneously. In some embodiments, the localized therapy and the wide area stimulation is provided separately, or non-simultaneously.

An advantage of one or more embodiments discussed in this subsection can include one or more of: (i) increased area of stimulation, such as by producing an electric field between a proximal electrode and a distal electrode, that can reduce constraints on positioning of the implantable device, (ii) increased flexibility in type of stimulation provided, such as by allowing for a wide area stimulation (less intense stimulation over a wider area) and/or a local area stimulation (more intense stimulation over a smaller region), or both; (iii) increased flexibility in type of stimulation provided, such as by including two implantable devices that can provide therapy individually or therebetween (such as to provide a signal that originates at one implantable device and travels to another implantable device, stimulating tissue therebetween), among others.

FIG. 54 illustrates, by way of example, a perspective view diagram of an embodiment of an implantable stimulation device 4800. The stimulation device 4800 as illustrated includes a plurality of first electrodes 4802A and 4802B separated by a dielectric material 4804. The stimulation device 4800 as illustrated further includes a circuitry housing 4806. The circuitry housing 4806, first electrodes 4802A-B, and the dielectric material 4804 are illustrated as being in a distal portion 4812 of the stimulation device 4800. The stimulation device 4800 as illustrated further includes a second electrode 4802C and an attachment device 4808. The second electrode 4802C and the attachment device 4808 are illustrated as being in a proximal portion 4814 of the stimulation device 4800. The circuitry housing 4806 can be in the proximal portion 4814 of the stimulation device. In one or more embodiments, the number of first electrodes can be greater than two (e.g., three, four, five, six, seven, eight, or more). In one or more embodiments, the number of second electrodes can be greater than one (e.g., two, three, four, five, six, seven, eight, or more).

A distance (indicated by the arrow 4813) between a most proximal electrode of the first electrodes (electrode 4802B in the example of FIG. 54) and a most distal electrode of the at least one second electrode (electrode 4802C in the example of FIG. 48) can be greater than one and a half centimeters and less than ten centimeters. A distance (indicated by the arrow 4811) between two directly adjacent electrodes of the first electrodes (electrodes 4802A and 4802B in the example of FIG. 54) can be less than one and a half centimeters, in one or more embodiments. In one or more embodiments, the distance between two directly adjacent electrodes of the first electrodes can be less than ten millimeters.

The circuitry housing 4806 can be made of similar or same materials and/or configured similar to other circuitry housings discussed herein, such as the circuitry housing 610A-C, 3616, or other circuitry housing. The electrodes 4802A-C can be made of similar or same materials and/or configured similar to other electrodes discussed herein, such as the electrodes 604, E0-E4, or other electrodes.

FIG. 55A illustrates, by way of example, a cross-section diagram of the implantable stimulation device of FIG. 54 in the direction of the arrows labelled "55A/55B". The stimulation device 4900A as illustrated includes a casing 4916 around two insulated electrical conductors 4920 and 4922. The electrical conductor 4920 can act as an antenna and can be electrically coupled to circuitry in the circuitry housing 4806. The electrical conductor 4922 can electrically connect the electrode 4802C to the circuitry in the circuitry housing 4806. A dielectric material 4924 can surround the electrical conductors 4920 and 4922. The dielectric material 4924 can help reduce cross-talk between the conductors 4920 and 4922, such as to help electrically isolate signals on the conductors 4920 and 4922 from one another.

FIG. 55B illustrates, by way of example, another cross-section diagram of the implantable stimulation device of FIG. 54 in the direction of the arrows labelled "55A/55B". The implantable stimulation device 4900B is similar to the stimulation device 4900A, but only includes a single conductor 4926 instead of two conductors 4920 and 4922 (as in the device 4900A). The single conductor 4926 can electrically connect the electrode 4802C to the circuitry in the circuitry housing 4806, such as is similar to the electrical conductor 4922. In addition, the electrical conductor 4926 can act as an antenna for the stimulation device 4900B. The electrical conductor 4926 can provide electrical signals to the electrode 4802C at one time and relay electrical signals incident thereon to the circuitry in the circuitry housing at another time. The electrical conductor 4926 can be time domain multiplexed to act as an electrical wire and an antenna (at differing times). The circuitry in the circuitry housing 4806 can switch the function of the electrical conductor 4926 by activating and/or deactivating one or more switches in the electrical path of the electrical conductor 4926 (see circuitry discussed elsewhere herein, such as the circuitry 500, 4400, 4500, 4600, and 4700, for examples of switches and circuitry configurations).

Figure 56:
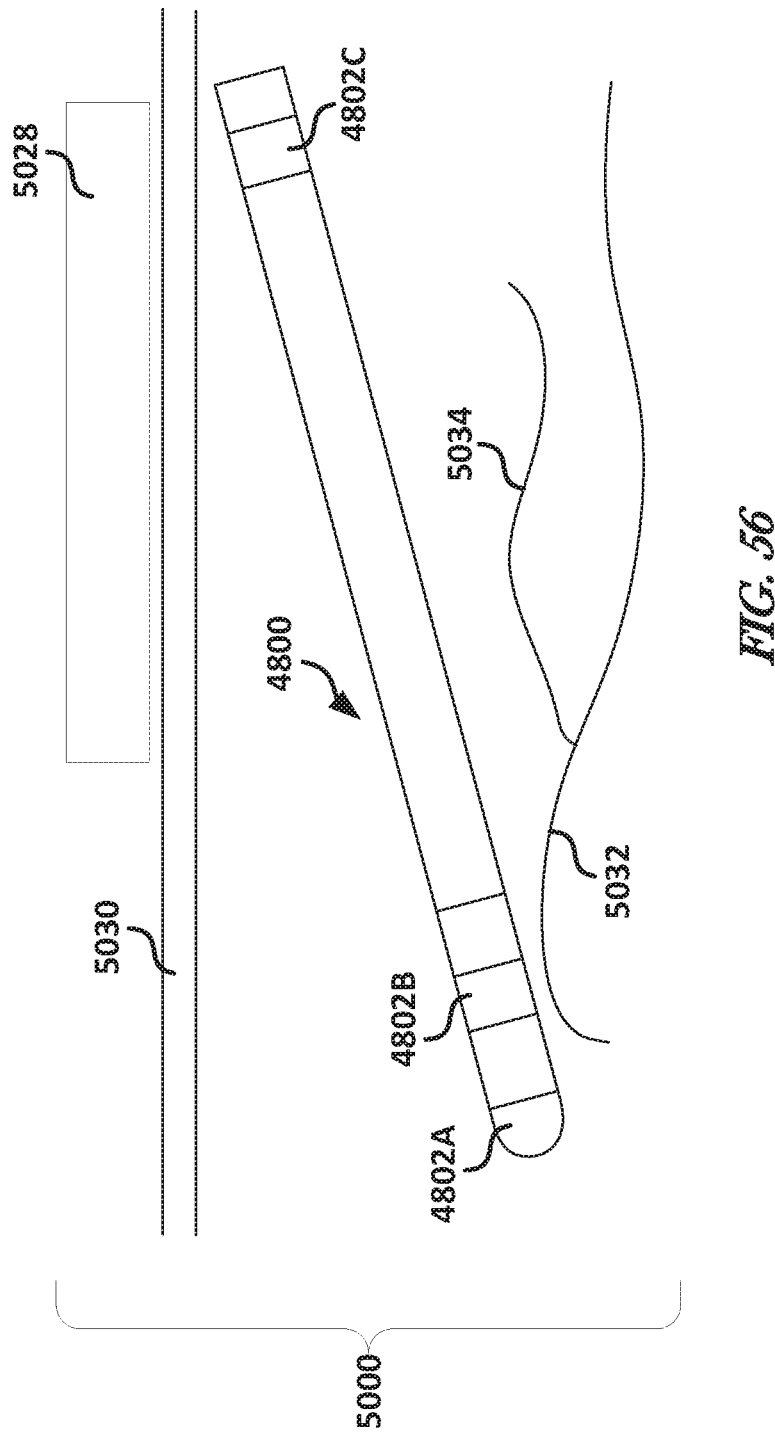
FIG. 56 illustrates, by way of example, a perspective view diagram of an embodiment of the stimulation device of FIG. 54 implanted in a body with an external midfield powering device external to the body.

FIG. 56 illustrates, by way of example, a perspective view diagram of an embodiment of the stimulation device of FIG. 54 implanted in a body with an external midfield device 5028 external to the body. The midfield device 5028 can communicate signals to the implantable stimulation device 4800 and/or receive signals from the implantable stimulation device 4800. The midfield device 5028 can be similar to the source 102 or other external transmitter devices, powering devices, or couplers discussed herein. The midfield device 5028 can be proximate a surface of skin 5030 of a user, such as directly on the skin or with some fabric, adhesive, dielectric material (e.g., silicone), among others between the skin 5030 and the midfield device 5028.

The midfield device 5028 provides electrical power to the stimulation device 4800 from outside the body. The power from the midfield device 5028 can at least partially be used by therapy generation circuitry in the circuitry housing 4806 to provide stimulation therapy to a nerve 5032 and/or 5034 of the body. Stimulation therapy can be provided to the nerve 5032 and 5034 at different times or simultaneously. For example, the electrodes 4802A and 4802B can be configured (by activating and/or deactivating switches of the circuitry in the circuitry housing) as anode and cathode (or vice versa), respectively, and the electrode 4802C can be open (part of an incomplete circuitry so as to be non-conductive). Such a configuration can provide a localized stimulation therapy, such as through an electric field that is produced between the two electrodes 4802A-B, such as to provide stimulation therapy to the nerve 5032. In another example, either one of the electrodes 4802A-B can be configured as an anode or cathode and the electrode 4802C can be configured as a corresponding cathode or anode. Such a configuration can provide a wide area stimulation therapy, such as through an electric field that is produced between the electrode 4802A or 4802B and the electrode 4802C. In this configuration, therapy may be delivered to the nerve 5034 and, in some cases, the nerve 5032. In yet another example, the electrodes 4802A and 4802B can be configured as anode and cathode (or vice versa), respectively, and the electrode 4802C can be configured as either an anode or a cathode. Such a configuration can provide both a wide area stimulation therapy and a localized stimulation therapy, simultaneously.

An advantage, from a clinical perspective, can include the wide area stimulation field allowing for less precise electrode position placement relative to the target nerve(s). From the clinician's perspective, this stimulation system allows room for electrode placement error. After implantation, the stimulation system can be reprogrammed rather than surgically revised as well.

FIG. 57 illustrates, by way of example, a perspective view diagram of an embodiment of another implantable stimulation device 5100. The stimulation device 5100 as illustrated includes only the two electrodes 4802A-B. The stimulation device 5100 as illustrated includes the dielectric material 4804 between the two electrodes 4802A-B. The stimulation device 5100 as illustrated further includes a circuitry housing 4806 and an antenna housing 5136. The antenna housing 5136 can be include the same or similar materials and/or be configured similar to or the same as other antenna housings discussed herein, such as the antenna housings 612, 3618, 3630, or other antenna housing discussed herein.

FIG. 58A illustrates, by way of example, a perspective view diagram of an embodiment of a system 5200A including a plurality of stimulation devices 5100A and 5100B (respective specific embodiments of the stimulation device 5100 of FIG. 57) implanted in a body with an external midfield device 5028 external to the body. The multiple implanted stimulation devices 5100 can provide localized stimulation therapy or simultaneously provide both localized stimulation therapy and wide area stimulation therapy. The localized stimulation therapy can be provided by configuring the electrode 4802A and 4802C both anodes or cathodes and the electrode 4802B and 4802D both cathodes or anodes. The wide area stimulation therapy and localized therapy can be provided by configuring the electrodes 4802A-B as anode and cathode (or vice versa), respectively, and configuring the electrodes 4802C-D as cathode and anode (or vice versa), respectively.

The midfield device 5028 can be configured to alter a direction of a signal provided therefrom, such as by adjusting a phase of a signal provided by one or more antennas (e.g., coupler elements, sometimes referred to as subwavelength structures) on the midfield device 5028. See FIGS. 5, 62, 63, and/or 105 for a discussion of a phase altering network configured to adjust the phase provided by one or more antennas). The direction of the signal can be configured such that an electromagnetic field from the midfield powering device 5028 is focused on the stimulation device 5100A at a first time, such as to provide electrical power to the stimulation device 5100A. The phase(s) of signal(s) provided by one or more of the antennas of the midfield device 5028 can then be altered such that an electric field from the midfield device 5028 is focused on the stimulation device 5100B, such as to provide electrical power to the stimulation device 5100B.

In one or more embodiments, the circuitry in the circuitry housing 4806 can include one or more capacitors that can be charged using the electric field from the midfield powering device 5028 (see, e.g., FIGS. 5 and 48, among others, for examples of a capacitor(s) that can be included in the circuitry in the circuitry housing 4806). A capacitor can be discharged to provide power to the stimulation device, such as at times when the midfield powering device 5028 is not providing power to the stimulation device 5100A-B or when the therapy generation circuitry is to provide therapy. Using the capacitor, both of the stimulation devices 5100A-B can provide therapy simultaneously, such as to provide a wide area stimulation therapy between electrodes of the two stimulation devices 5100A-B, such as to a nerve 5238. In one or more embodiments, one of the stimulation devices 5100A can be powered directly by the midfield powering device 5028 and the other of the stimulation devices 5100B can be powered by the capacitor (after charging using the electric field provided by the midfield powering device 5028).

In one or more embodiments, stimulation therapy from each device can be synchronized, such as to provide a wide area stimulation. The synchronization can be controlled by a communication signal from the midfield device or from synchronization circuitry (see FIG. 48) that synchronizes the timing of therapy production and/or therapy initialization.

Figure 58B:
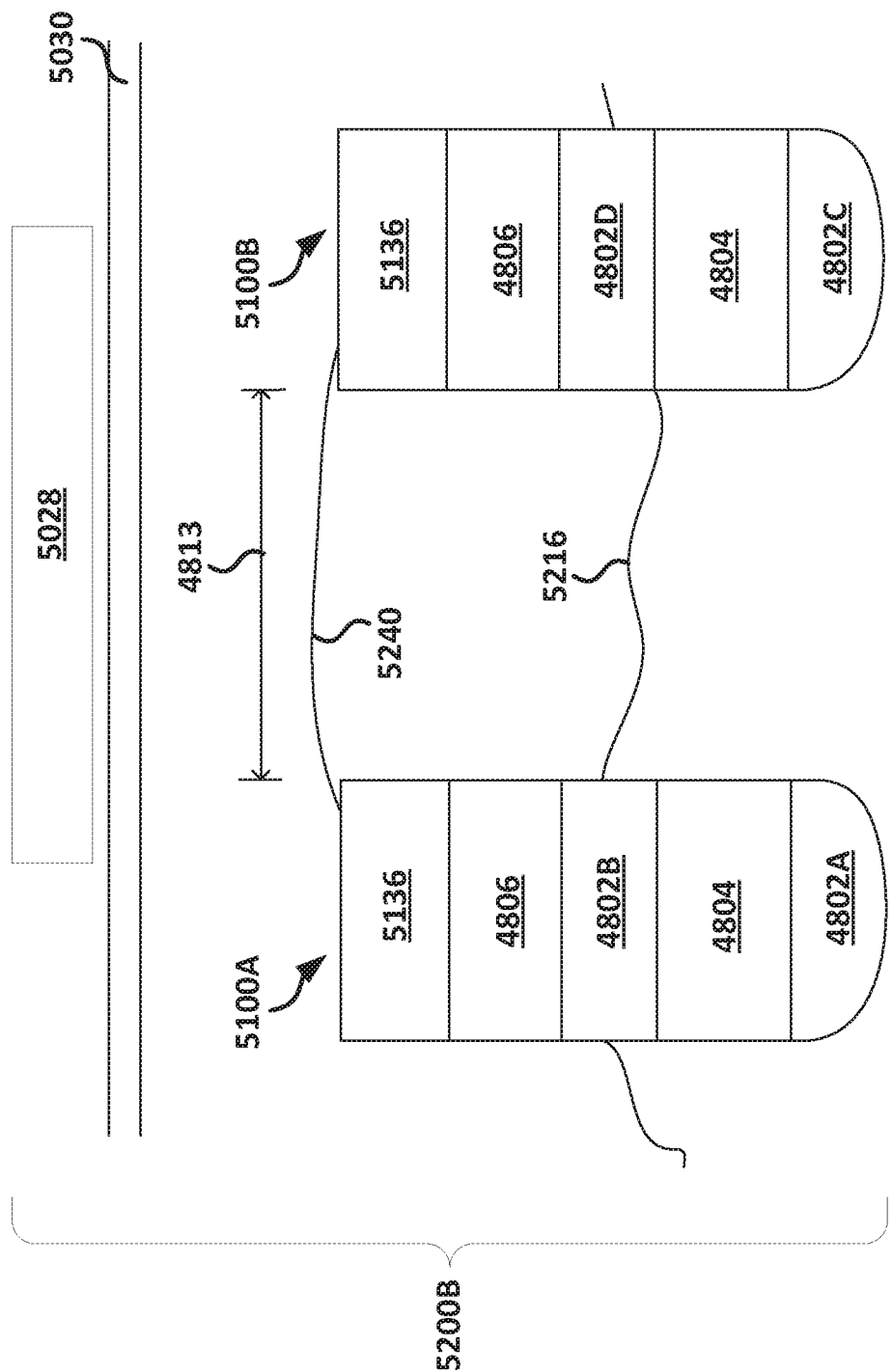
FIG. 58B illustrates, by way of example, a perspective view diagram of another embodiment of a plurality of stimulation devices of FIG. 57 implanted in a body with an external midfield powering device external to the body.

FIG. 58B illustrates, by way of example, a perspective view diagram of an embodiment of a system 5200B including the plurality of stimulation devices 5100A and 5100B implanted in a body with an external midfield powering device 5028 external to the body. The system 5200B is similar to the system 5200A, with the system 5200B including an insulated conductor 5240 electrically connected to both the stimulation devices 5100A-B. Such an insulated conductor 5240 helps the system 5200A to provide only a wide area stimulation therapy, only a localized stimulation therapy, or to provide both a localized and wide area stimulation therapy (simultaneously or non-simultaneously). The system 5200B can provide only a wide area stimulation therapy by configuring one or more of the electrodes 4802A and 4802B as an anode and configuring one or more of the electrodes 4802C and 4802D as a cathode (or vice versa). The system 5200B can provide only a localized stimulation therapy by configuring the electrodes 4802A and 4802C as anodes and the electrodes 4802B and 4802D as cathodes (or vice versa). The system 5200B can provide both localized and wide area stimulation therapy simultaneously by configuring the electrodes 4802A and 4802D as anodes and the electrodes 4802B and 4802C as cathodes (or vice versa). This is in contrast to the system 5200A, which can only provide either only localized stimulation therapy or simultaneously provide localized stimulation therapy and wide area stimulation therapy. The distance between the devices 5100A and 5100B can be the same as or similar to the distance indicated by the arrows 4813 as discussed elsewhere herein.

FIG. 59 illustrates, by way of example, a perspective view diagram of an embodiment of another implantable stimulation device 5300. The stimulation device 5300 is similar to the stimulation device 5100, with the stimulation device 5300 including the electrodes 4802A-B spaced further apart, such as to provide a wide area stimulation therapy therebetween. A distance between the electrodes 4802A-B (indicated by arrow 5342) can be increased (relative to that shown in FIG. 57) by situating the circuitry housing 4806 and the antenna housing 4808 between the electrodes 4802A-B (such as shown in FIG. 59) or lengthening the dielectric material 4804 (in the direction of the arrows). The distance between the electrodes 4802A-B can be greater than 1.5 cm (to provide a wide area stimulation therapy) or less than 1.5 cm (to provide a localized stimulation therapy). Other distances may also be used as desired and/or required to effect the different types of stimulation.

FIG. 60 illustrates, by way of example, a perspective view diagram of an embodiment of a system 5400 including a plurality of stimulation devices 5300A and 5300B (respective specific embodiments of the stimulation device 5300 of FIG. 59) implanted in a body with an external midfield device 5028 external to the body. The system 5400 is similar to the system 5200A, with the system 5400 configured to provide a wide area stimulation therapy using electrodes of the same stimulation device. A distance (indicated by arrow 5444) between the stimulation devices 5300A and 5300B can be greater than one and a half centimeters, such as to provide a wide area stimulation therapy between electrodes of the devices 5300A-B, or can be less than 1.5 cm, such as to provide a localized stimulation therapy between electrodes of the devices 5300A-B. The stimulation therapy provided by the devices 5300A-B can be incident on a nerve 5446 or a branch 5448 and/or 5450 of the nerve 5446.

FIG. 61 illustrates, by way of example, a logical circuitry diagram of an embodiment of a plurality of stimulation devices of FIG. 59 within range of respective electric fields generated therebetween. Resistors 5452A, 5452B, 5452C, 5452D, 5452E, and 5452F represent impedances between the electrodes on each end of the resistor 5452A-F. The resistor 5452A represents an impedance between the electrodes 4802A and 4802D. The resistor 5452B represent an impedance between the electrodes 4802B and 4802C. The resistor 5452C represents an impedance between the electrodes 4802B and 4802D. The resistor 5452D represent an impedance between the electrodes 4802A and 4802C. The resistor 5452E represents an impedance between the electrodes 4802A and 4802B. The resistor 5452F represent an impedance between the electrodes 4802D and 4802C. Generally speaking, the impedance of the resistors 5452E and 5452F is less than the impedance of the resistors 5452A and 5452B, which are less than the impedance of the resistors 5452C and 5452D. The strength of the electric field generated between two electrodes is generally inversely proportional to the value of the impedance of the resistor between the electrodes. The wide area stimulation therapy generally has a weaker electric field, but provides therapy to wider volume than the localized therapy stimulation.

II. External Device Configurations

A. Compact Integration of Electronic Control Hardware with Electromagnetic Transmitting Element This subsection is generally related to packaging of an electromagnetic transmission element (e.g., the source 102, midfield device 6148 or 5028, among other external transmission elements), with electronic control hardware. More specifically, one or more embodiments in this subsection regard devices, systems, and methods that include the electromagnetic transmission element mounted to the same board as the control hardware.

Control hardware can include electronics components (passive components (e.g., diodes, transistors, resistors, capacitors, inductors, or the like), discrete integrated circuits, logic components (e.g., logic gates, multiplexers, or the like), application specific integrated circuits (ASICs)) as well as metallic traces which connect signal and power pads for each of the components. During a design process, the coupling between the electronic control hardware and an electromagnetic transmission element (e.g., an antenna) is carefully managed, and almost inevitably results in a loss of efficiency for the electromagnetic transmission element and/ or a loss of signal integrity for the electronic components. This loss of efficiency and/or signal integrity becomes more impactful in packages with compact designs. Embodiments discussed in this subsection can help overcome the loss of efficiency in the transmission element and/or the loss of signal integrity in the electronic components.

Embodiments in this subsection include devices, systems, and methods for integrating control hardware into a planar electromagnetic transmission element in an electronic device package (e.g., on a printed circuitry board (PCB), a flexible substrate, or other medium on which an electronic device can reside).

There are many types of planar electromagnetic transmission elements including a microstrip or patch antenna, a slot antenna, or a combination thereof. These antennas can be made in a variety of shapes and sizes and configured to interact (efficiently) with a wide variety of electromagnetic signal frequencies. Another type of planar electromagnetic transmission element includes a mid-field antenna, such as a midfield antenna described in WIPO Publication No. WO/2015/179225 published on Nov. 26, 2015 and titled "MIDFIELD COUPLER", which is incorporated herein by reference in its entirety.

Decreasing a form factor of a package that includes such a planar electromagnetic transmission element is difficult due, at least in part, to efficiency and signal losses from electromagnetic radiation communicating between components near the electromagnetic transmission element. Thus, integrating control hardware into a planar antenna or electromagnetic element on a printed computer board (PCB) can cause undesirable losses in the signal integrity and performance of the electromagnetic control element. These effects can be even more of a concern when package size must be reduced and the electromagnetic transmission element covers a majority of a footprint of the package.

In the case of a mid-field powering coupler (electromagnetic transmission element), the planar metal pattern which provides efficient energy transfer to an implanted device (e.g., an implanted medical device) may be several centimeters in length in both dimensions (length and width). Control hardware (e.g., electronic hardware components) can be used to provide Radio Frequency (RF) power to ports of the mid-field coupler, modulate the RF signal for communication with the implanted device, receive communications from the implanted device, and/or provide a user interface for the patent/clinician to set one or more parameters of the circuitry or receive data from the implanted device. The control hardware can be designed on a separate PCB from the mid-field powering coupler, but at the cost of size (form factor).

For attaching the circuitry (the electromagnetic transmission device and the control hardware) to the body, it can be beneficial to have dimensions of the integrated device (electromagnetic transmission element and control hardware) be near the same size as the electromagnetic transmission element, which can be the largest part of the transmission element, so as to reduce the form factor of the integrated circuitry. To reduce the form factor further, the electronic components can be integrated on the same substrate as the mid-field powering coupler. For example, in a two board integrated circuitry where the RF signal is sourced from a board separate from the midfield coupler (e.g., the control hardware is on a board separate from the electromagnetic transmission element) the circuitry may have an overall thickness of 15 mm or more. In contrast, a single board solution (e.g., a device that includes the control hardware on the same board as the electromagnetic transmission element) can have an overall thickness of about 3 mm (e.g., 1 mm to 5 mm, 2 mm to 4 mm). The volume saved from the integration can be used for additional battery capacity or allowing the device to be housed in a thinner package that is less obtrusive or visible, such as when the device is worn.

However, due to the limited area of outer layers of a circuitry substrate (e.g., a PCB or flexible substrate), it can be difficult to integrate the components and traces with the electromagnetic transmission element. In one or more embodiments, the hardware control components can be placed on the same layers as the patterned electromagnetic transmission element and microstrip feed lines for excitation of the electromagnetic transmission element. The placement of these components and traces along these layers can cause undesired coupling that can cause communication between the control hardware and the electromagnetic transmission element, resulting is loss of signal integrity and/or power transfer efficiency.

An advantage of one or more embodiments discussed in this subsection can include one or more of: (i) circuitry operating with reduced noise from the environment; and (ii) a mid-field powering device with a reduced form factor, such as compared to one with control circuitry and a transmission element on separate boards; among others.

Figure 62:
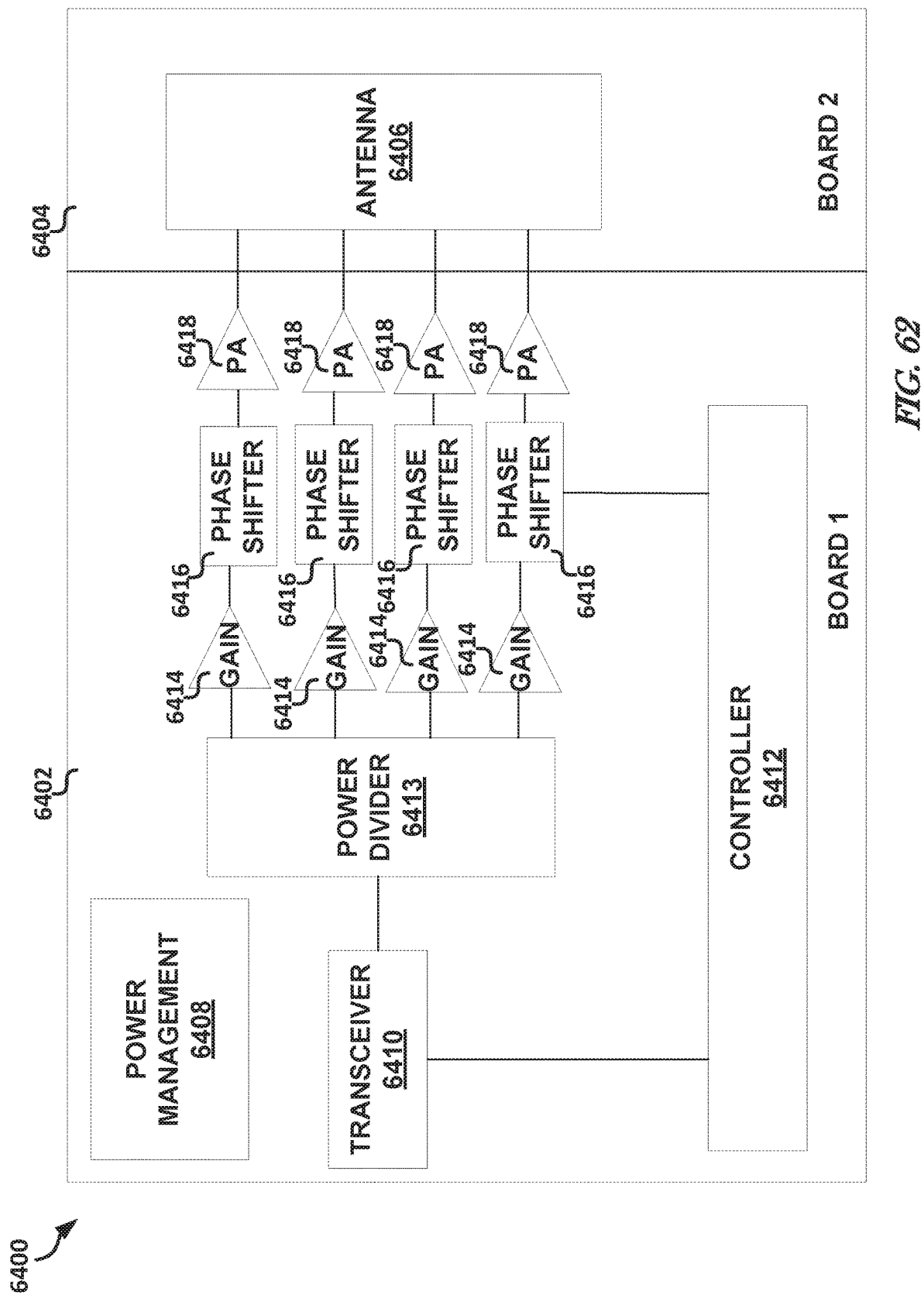
FIG. 62 illustrates, by way of example, a diagram of an embodiment of a system including control hardware and an electromagnetic transmission element (e.g., the antenna).
Figure 64:
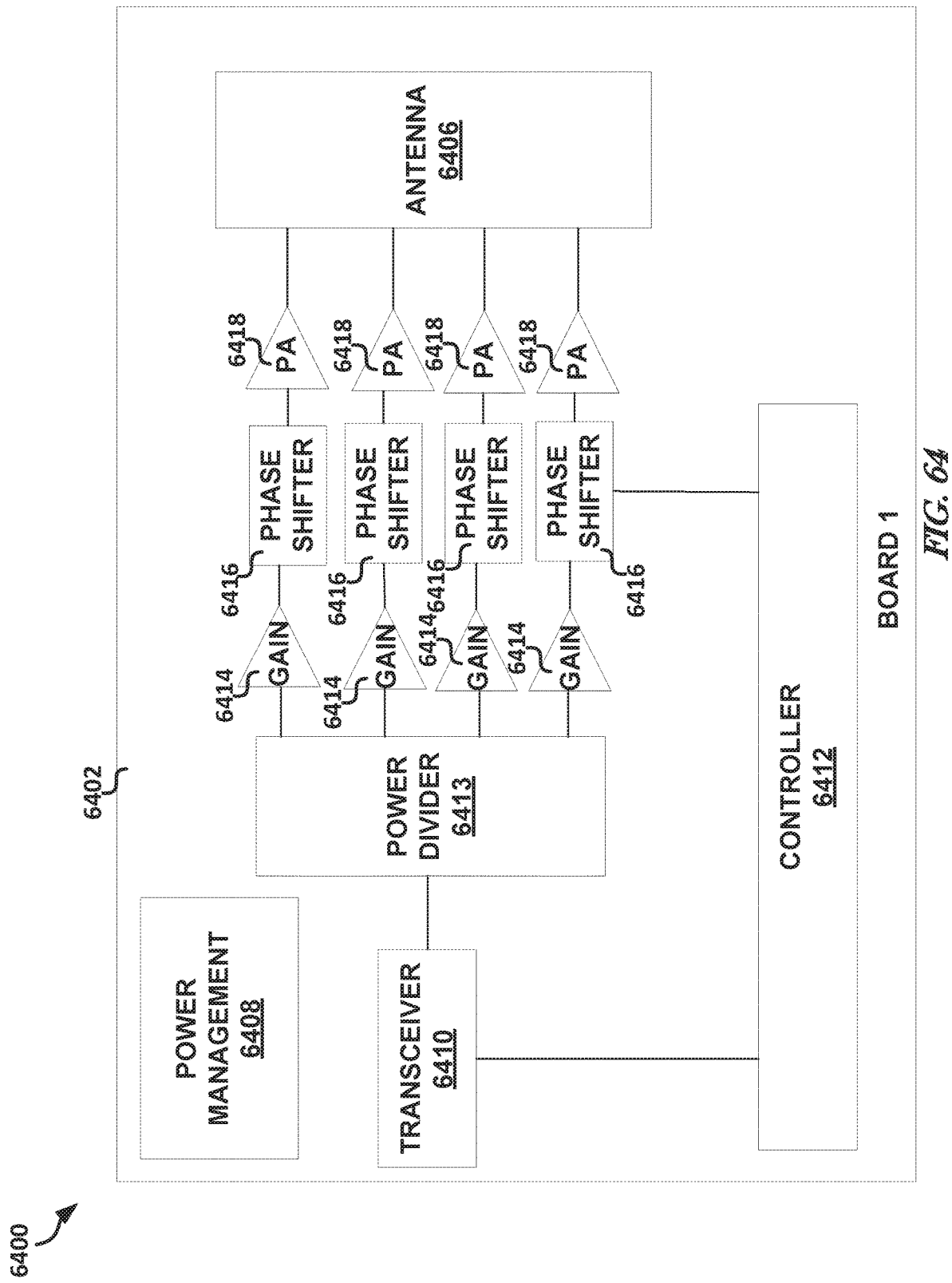
FIG. 64 illustrates, by way of example, a diagram of an embodiment of a system that includes the control hardware and the electromagnetic transmission element on a single board (e.g., substrate).
Figure 65:
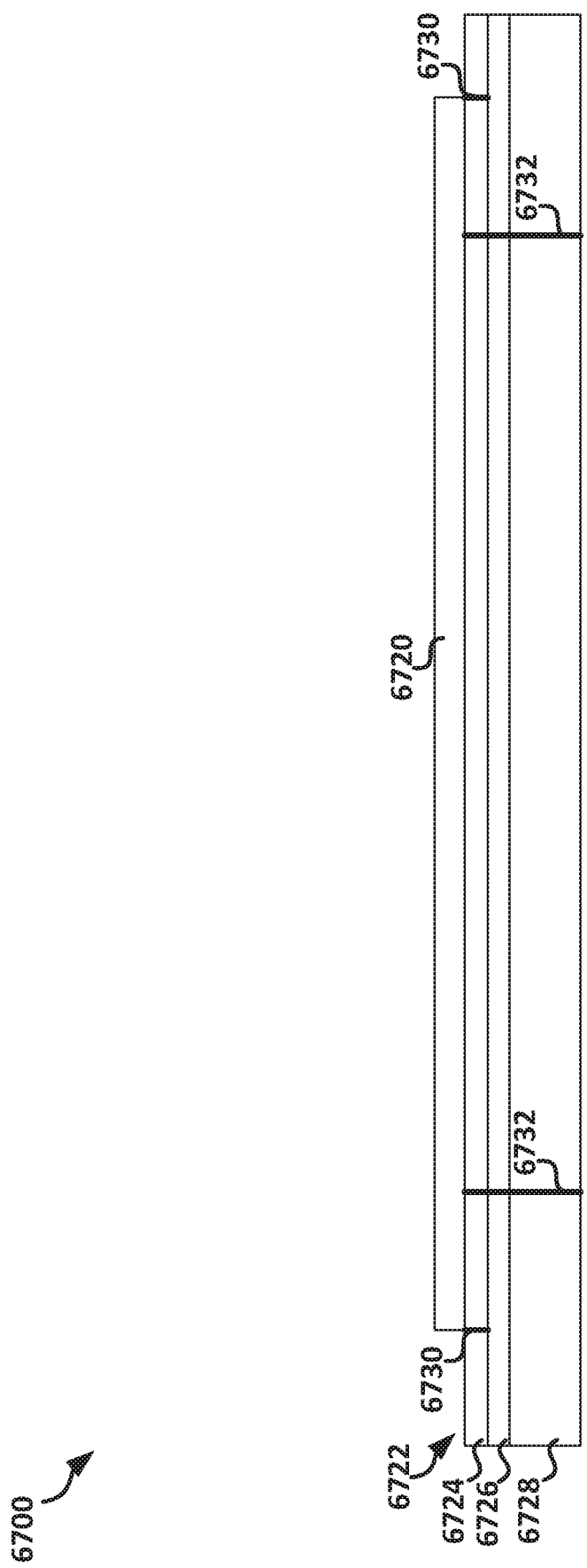
FIG. 65 illustrates, by way of example, a perspective view diagram of an embodiment of a system that includes the control hardware and the electromagnetic transmission element on a single board.

FIG. 62 illustrates, by way of example, a diagram of an embodiment of a system 6400 including control hardware and an electromagnetic transmission element (e.g., the antenna 6406). The system 6400 includes the control hardware on a first board 6402 and the antenna 6406 on a second board 6404. Such a system includes a form factor that is large compared to a system that includes the control hardware and the transmission element on a single board, such as shown in FIGS. 64 and 65, for example.

The control hardware, in the embodiment illustrated in FIG. 62, includes power management circuitry 6408, a transceiver 6410, a controller 6412, a power divider 6413, a plurality of gain amplifiers 6414, a plurality of phase shifters 6416, and a plurality of power amplifiers 6418. The power management circuitry 6408 can include one or more voltage regulators, current regulators, rectifiers, capacitors, or other power circuitry. The power management circuitry 6408 can provide power signals to other components of the control hardware, such as to power the control hardware.

The transceiver 6410 in one or more embodiments can be replaced with just a transmitter. The transceiver 6410 can provide RF signals to the power divider 6413, such as with or without data modulated onto the RF signals. The controller 6412 can provide functionality and/or include components similar to or the same as that of the processor circuitry 210, or other similar circuitry discussed herein. The power divider 6413 can provide functionality and/or include components similar to or the same as that of the power divider 412, or other power dividers discussed herein. The gain amplifiers 6414 increase an amplitude of a signal at an input port thereof. The phase shifters 6416 can provide functionality and/or include components similar to or same as that of the phase shifter 410, or other phase shifters discussed herein. The power amplifiers 6418 can provide functionality and/or include components similar to or same as that of the power amplifiers 408, or other power amplifiers discussed herein. The antenna 6406 can be a multi-port antenna with a plurality of subwavelength structures, such as is discussed with regard to the antenna of the source 102 and illustrated in FIG. 3, for example.

Figure 63:
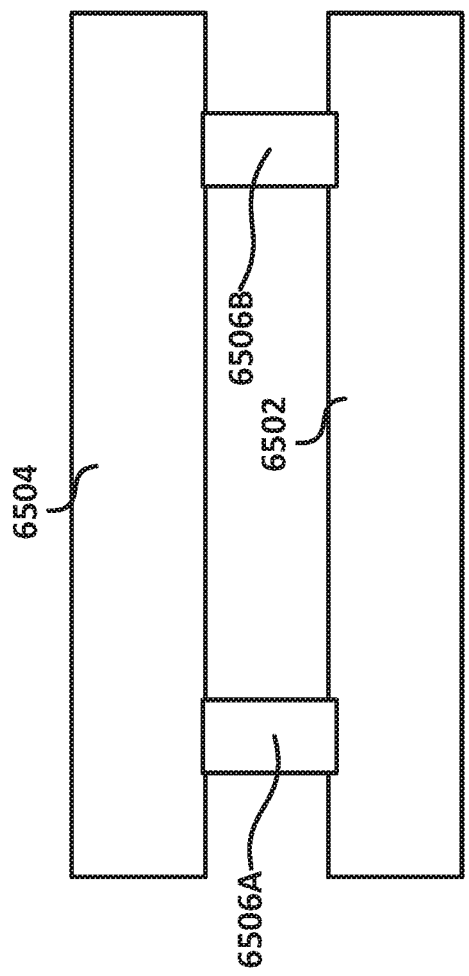
FIG. 63 illustrates, by way of example, a perspective view diagram of an embodiment of a system that includes the control hardware and the electromagnetic transmission element on separate boards.

FIG. 63 illustrates, by way of example, a perspective view diagram of an embodiment of a system 6500 that includes the control hardware and the electromagnetic transmission element on separate boards. The system as illustrated includes a midfield coupler on a first board 6502, control hardware on a second board 6504 and RF connectors 6506A and 6506B electrically and mechanically coupling the first and second boards. The system 6500 is an implementation of the system 6400.

FIG. 64 illustrates, by way of example, a diagram of an embodiment of a system 6600 that includes the control hardware and the electromagnetic transmission element on a single board (e.g., substrate). Such a system can include a form factor that is smaller as compared to the system 6400.

FIG. 65 illustrates, by way of example, a perspective view diagram of an embodiment of a system 6700 that includes the control hardware and the electromagnetic transmission element on a single board 6722. The system 6700 as illustrated includes the control hardware and the transmission element on a top layer of the substrate (not illustrated in the view provided by FIG. 65. See FIGS. 66-71 for views of the transmission element and/or control hardware). The transmission element is separated from the control hardware by a faraday cage 6720 or other element that excludes electrostatic or electromagnetic influences, such as to shield the control hardware from electromagnetic radiation of the transmission element and vice versa.

The faraday cage 6720 can be a part of the electromagnetic transmission element that radiates. The control components are fully integrated within a conductive surface of the transmission element using the faraday cage 6720. In such embodiments, the faraday cage 6720 is acting both as a shield (for the control components) and as a radiating element of the transmission element. Due to the skin depth of the material used for the faraday cage 6720, the electromagnetic currents at the outer surface of the faraday cage that induce radiation do not penetrate more than several microns at gigahertz frequencies. Thus, the internal components can advantageously be shielded from the electromagnetic fields induced by the faraday cage 6720 radiating as part of the transmission element, in accordance with one or more embodiments.

In one or more embodiments, the board 6722 can include multiple layers, such as a first layer 6724, a second layer 6726, and a third layer 6728. The third layer 6728 can be thicker than the first layer 6724 and the second layer 6726. In one or more embodiments, the board 6722 can be made of an FR4 substrate (e.g., a glass-reinforced epoxy laminate comprising a composite material composed of woven fiberglass cloth with an epoxy resin binder that is flame resistant), a silicon substrate, ajinomoto buildup film (ABF), a dielectric, or other material. The control hardware can be situated on a top surface of the first layer 6724 along with routing (e.g., traces) between components of the control hardware. The components of the control hardware (e.g., high power components) may have thermally conductive material applied to conduct heat to the faraday cage 6720.

A ground plane can be situated on the second layer 6726. The faraday cage 6720 can be shorted to the ground plane by one or more vias 6730. One or more vias 6732 can provide a signal to a port of a slot 6734 (e.g., a resonating element) on the third layer 6728. The signal to the port can be from one of the power amplifiers 6418. The faraday cage 6720 and the ground plane can be configured with corresponding slots (a slot pattern) that match the slots 6734 (see FIGS. 66-71 for a view of the matching slots).

The first layer 6724 and the second layer 6726 may have the same thickness or different thicknesses. The thickness of each of the first layer 6724 and the second layer 6726 may range from 1 mil to 20 mil (e.g., from 1 mil to 10 mil, from 2 mil to 8 mil, from 3 mil to 6 mil, from 5 mil to 15 mil, from 10 mil to 20 mil, overlapping ranges thereof, or any value within the recited ranges, such as 5 mil). The third layer 6728 may have a thickness in the range of 50 mil to 150 mil (e.g., 50 mil to 100 mil, 60 mil to 120 mil, 70 mil to 100 mil, 80 mil to 90 mil, 60 mil to 80 mil, 80 mil to 110 mil, 90 mil to 150 mil, 70 mil to 120 mil, 100 mil to 150 mil, overlapping ranges thereof, or any value within the recited ranges, such as eighty-five mil. The dimensions provided and the number of layers of the board described are merely non-limiting examples and many variations are possible.

In one or more embodiments, the control hardware components are placed on a surface layer of the board 6722 with a majority of the routing provided on the same surface layer. In the embodiment of FIG. 65, the control hardware and most of the routing are on a top surface of the first layer 6724 (e.g., the surface on which the faraday cage 6720 is mounted).

In one or more embodiments, the slot mid-field pattern (e.g., ground plane) can be printed on, or at least partially in, the second layer 6726 (e.g., the layer immediately below the first layer 6724). In one or more embodiments, the second layer 6726 can also serve as a ground plane. One or more vias 6730 can be included that connect the first layer 6724 with the second layer 6726, such as to short the faraday cage 6720 at the top layer to ground. In one or more embodiments, the vias 6730 can be at or near the edges of the mid-field pattern and/or the edges of the slots which form the midfield element. Layers between the ground plane and excitation ports along a bottom surface of the third layer 6728 may be used for limited traces. In some embodiments, microstrip excitation slots or feeds are positioned along or adjacent a bottom surface of the third layer 6728.

Figure 66:
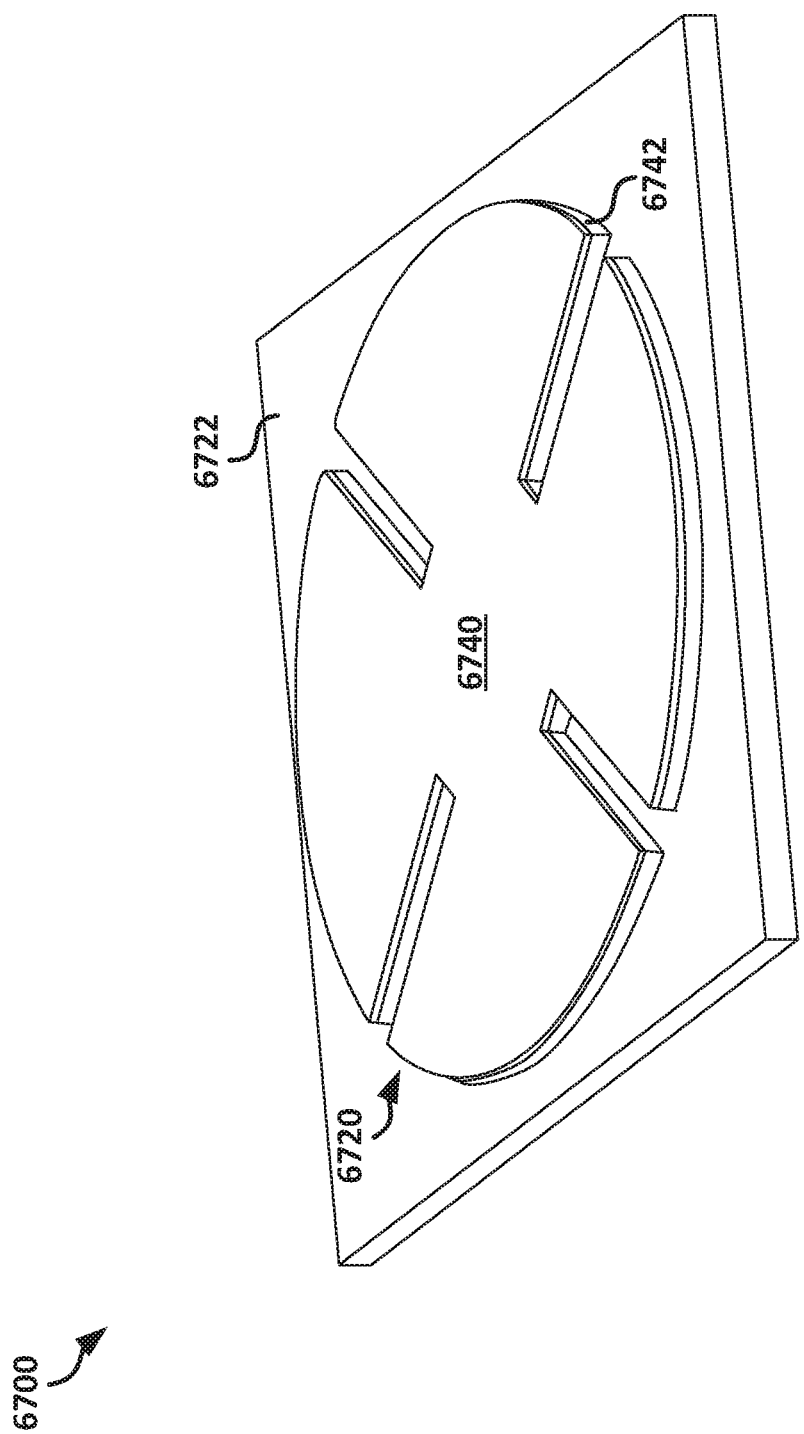
FIG. 66 illustrates, by way of example, a perspective view diagram of an embodiment of a system that includes a faraday cage cover over components of control circuitry.
Figure 67:
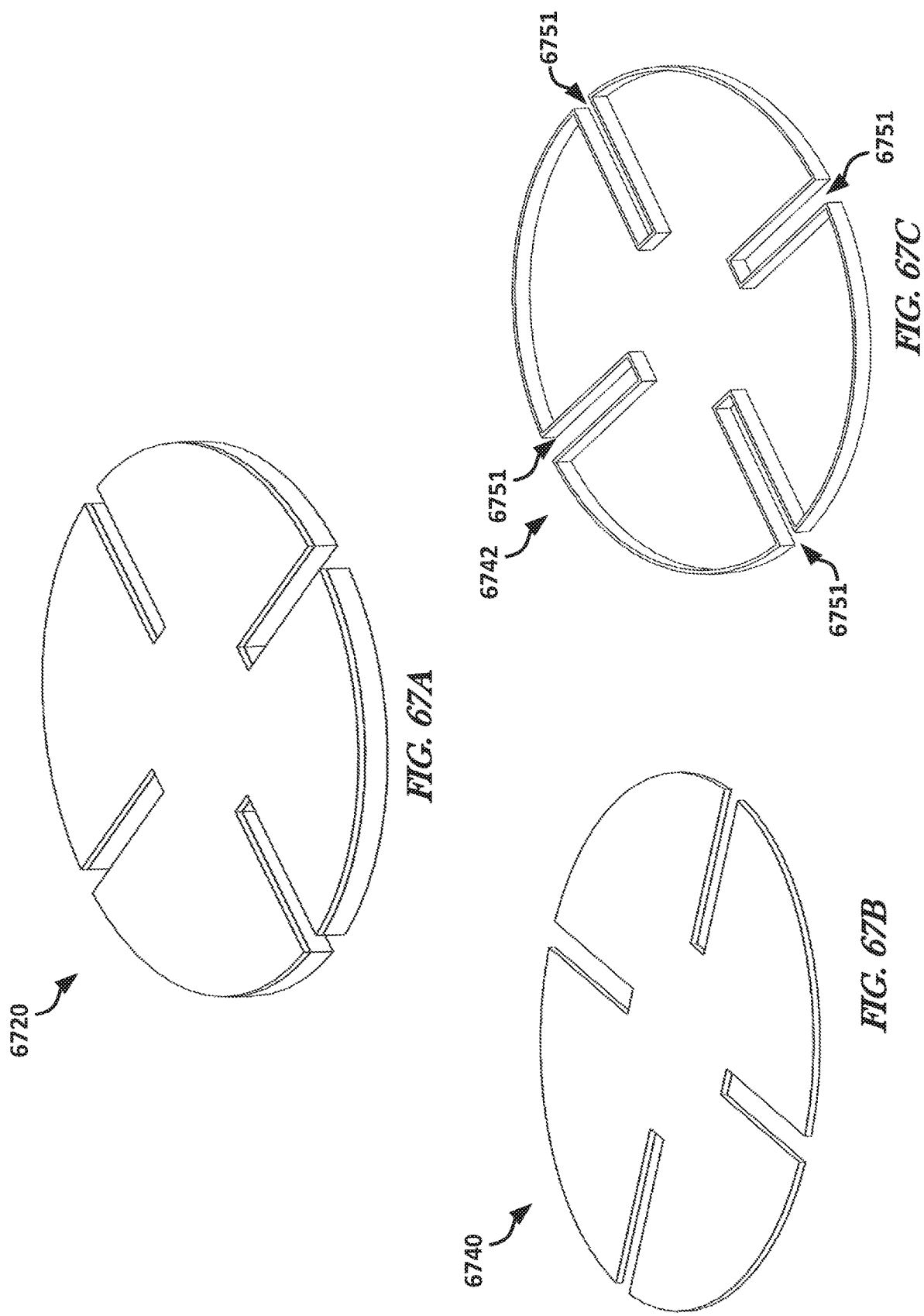
FIG. 67A illustrates, by way of example, a perspective view diagram of an embodiment a faraday cage.
FIG. 67B illustrates, by way of example, a perspective view diagram of an embodiment of a cover of the faraday cage of FIG. 67A.
FIG. 67C illustrates, by way of example, a perspective view diagram of an embodiment of a base of the faraday cage of FIG. 67A.

FIG. 66 illustrates, by way of example, a perspective view diagram of an embodiment of the system 6700 of FIG. 65. The perspective of FIG. 66 provides a view of a cover 6740 and a base 6742 of the faraday cage 6720. FIG. 67A illustrates, by way of example, a perspective view diagram of an embodiment of the faraday cage 6720. FIG. 67B illustrates, by way of example, a perspective view diagram of an embodiment of the faraday cage cover 6740. FIG. 67C illustrates, by way of example, a perspective view diagram of an embodiment of the faraday cage base 6742.

Figure 69:
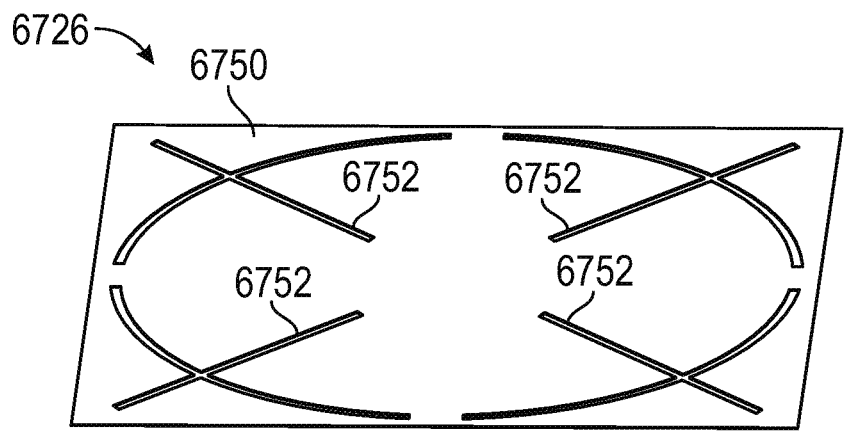
FIG. 69 illustrates, by way of example, a perspective view diagram of an embodiment of a top layer of the board of FIG. 66.
Figure 70:
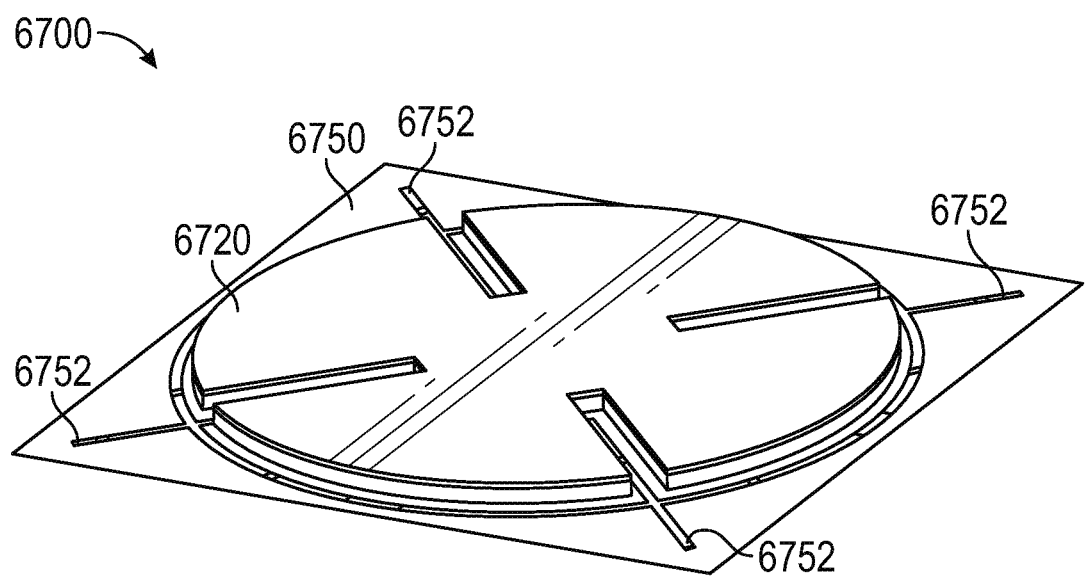
FIG. 70 illustrates, by way of example, a perspective view diagram of an embodiment of the top layer of the board with the faraday cage situated thereon.

The geometry of the faraday cage cover 6740, in one or more embodiments, can accommodate and not interfere with (e.g., can be complementary to, such as to be configured for) the slot pattern of the electromagnetic transmission element (see FIGS. 69 and 70). The faraday cage cover 6740 can be implemented with a stamped or machined metal plate. Possible materials include copper, steel, or aluminum. The faraday cage cover 6740 can be implemented with a solid material, a wire mesh, or a combination thereof.

The faraday cage 6720 can be formed by the faraday cage cover 6740 which forms a conductive shield above the components while a ground plane 6750 (see FIG. 69) forms the base of the faraday cage 6720, below the components. Vias 6730 at the edges of the slots in the faraday cage 6720 and on edges of the cage base 6742 can help form sides of the faraday cage 6720. A fully enclosed cage can effectively be formed between the cover above the components and the layer below the components, such as in the shape of the midfield transmitter pattern.

The faraday cage cover 6740 with the ground plane 6750 effectively serve as a thick patterned conductor, such as the faraday cage 6720 and the transmission element. As long as the metal sheets above and below the components/traces are greater than several skin-depths in thickness, then effectively from the perspective on the electromagnetic transmission element, the faraday cage with the ground plane is a metallic plate.

In the embodiments of FIGS. 65 and 66, the faraday cage 6720 is over components of control circuitry. In the embodiments shown, the faraday cage 6720 is attached to the board 6722 using a conductive adhesive, such as solder, conductive paste, electrically conductive tape, or other conductive adhesion mechanism. The board 6722 is illustrated as a four-layer board manufactured using a four-layer process, but other board designs can be used, such as can include fewer or more layers. The faraday cage cover 6740 is illustrated as being a solid material, but in other embodiments can be mesh or otherwise include one or more holes, perforations, slots or slits therethrough.

Figure 68:
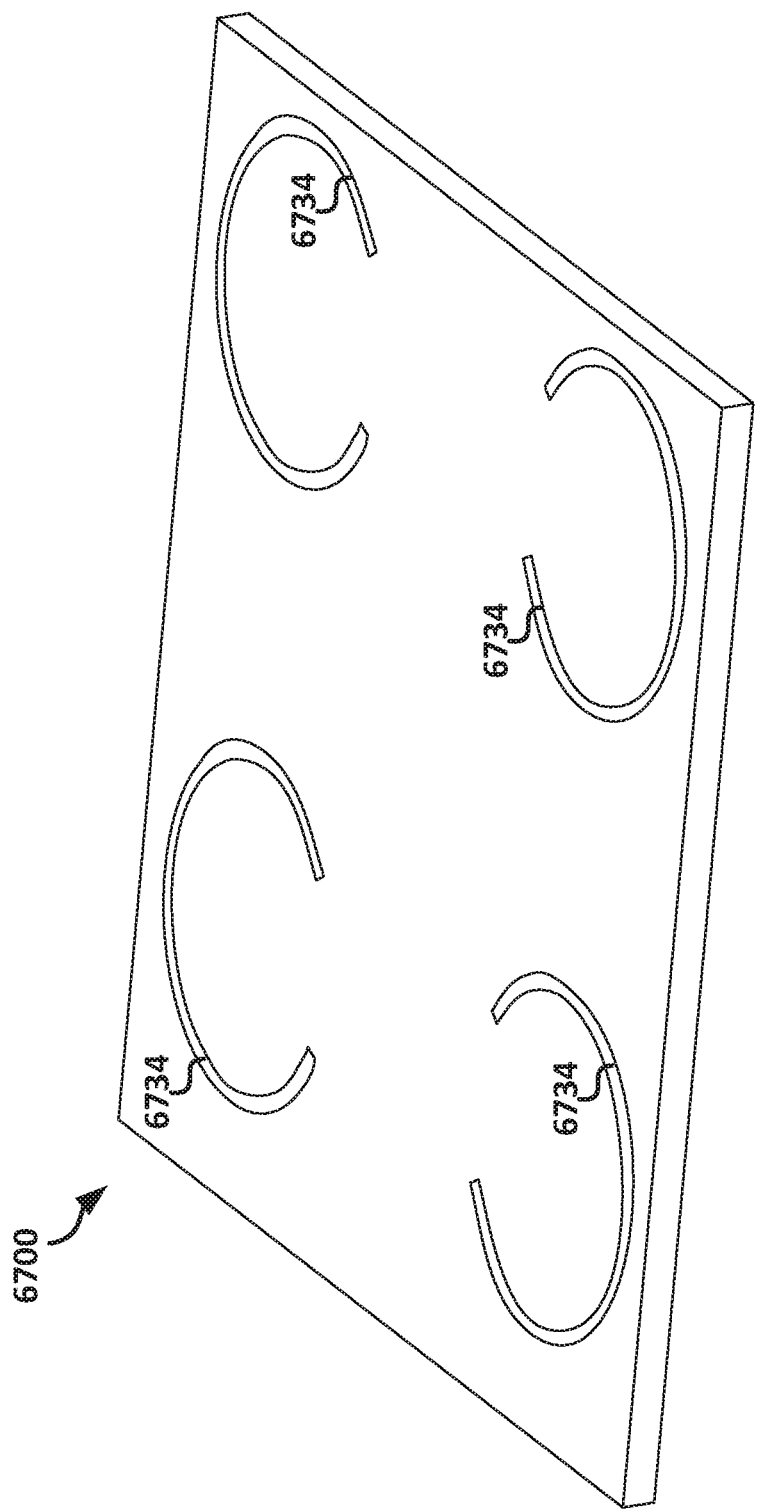
FIG. 68 illustrates, by way of example, a perspective view diagram of an embodiment of the system of FIG. 66 from a back side of the board.

FIG. 68 illustrates, by way of example, a perspective view diagram of the system 6700 from an opposite side as that shown in FIG. 66. One or more microstrip RF slots 6734 can excite the transmission element (e.g., the combination of the slots 6752 in the ground plane 6750 and the faraday cage 6720), such as can be used if the pattern were formed with a thicker metal layer. From the RF circuitry perspective, the effective thick slot element allows for wideband enhancement of the electromagnetic transmission element. Electromagnetic energy is transferred to the transmission element, which the faraday cage 6720 is a part of, from components (e.g., oscillator, power amplifier, phase compensation circuitry, and so forth) inside the faraday cage 6720. A via one or more vias 6732 connects the output of power amplifier from within the faraday cage 6720 to the slots 6734 of the electromagnetic element outside of the cage, thus transferring electromagnetic energy internal to the faraday cage 6720 to the external environment through a via 6732. The slots 6734 can be open circles or open ellipse shapes, such as shown in FIG. 68.

In addition, from the perspective of thermal management, the patterned metal plate (faraday cage cover, patterned ground plane, and/or vias) can be used for dissipation of heat. Thermally conductive material such as thermal grease, thermal tape, or thermal epoxy can be used as a thermal conductor between the components inside the faraday cage 6720 and the faraday cage base 6742 and/or the faraday cage cover 6740. The thermal conductor can help radiate heat away from the components inside the cage 6720 to the external environment.

FIG. 69 illustrates, by way of example, a perspective view diagram of an embodiment of the second layer 6726. The second layer 6726 as illustrated includes the ground plane 6750 and slots 6752 in the ground plane 6750. The faraday cage base 6742 can include slots 6751 therein so as to not interfere with the slots 6752. FIG. 70 illustrates, by way of example, a perspective view diagram of an embodiment of the system 6700 with the top layer 6724 of the board 6722 removed so as to show the alignment of the slots 6752 and the slots 6751. As can be seen, the slots 6751 in the faraday cage base 6742 correspond to locations where the slots 6752 are present in the second layer 6726 (e.g., slot pattern of the electromagnetic transmission element). Thus, the footprint of the faraday cage base 6742 does not overlap or is not coincident with any portion of the slots 6752 in the embodiments shown. The patterned midfield plate pattern is at the second layer 6726 (first internal layer) and is shorted to the faraday cage 6720 with one or more vias between the pattern of the electromagnetic transmission element (e.g., midfield coupler) and the faraday cage 6720.

Figure 71:
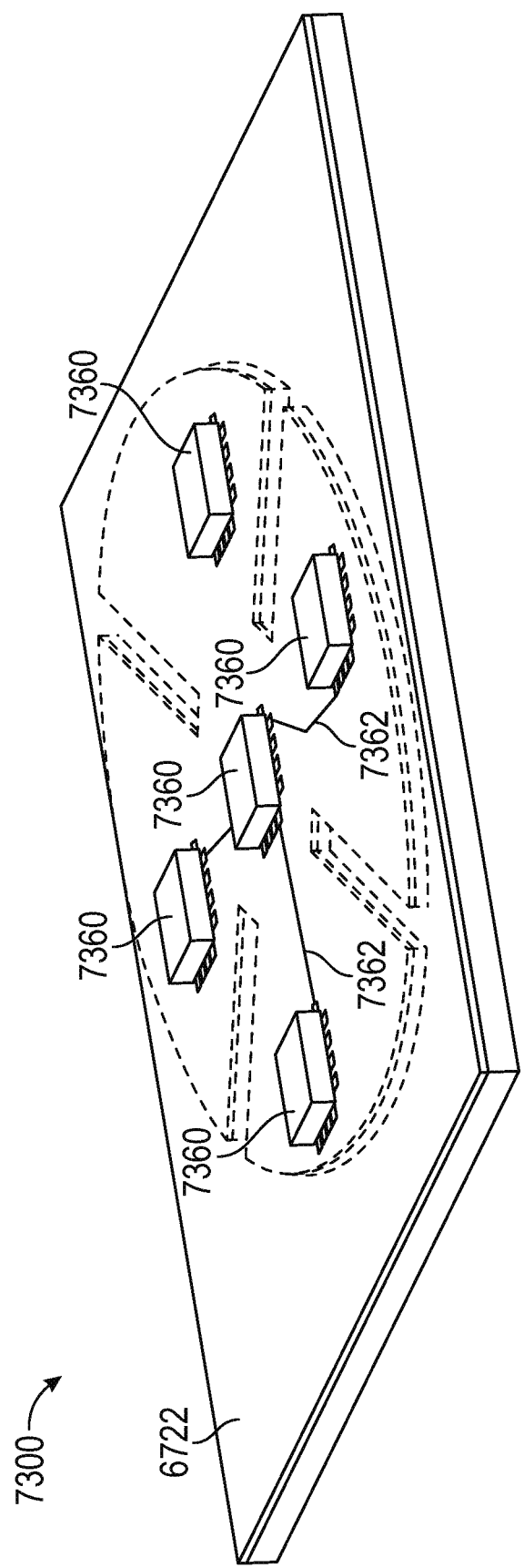
FIG. 71 illustrates, by way of example, a perspective view diagram of an embodiment of the system of FIG. 66 that includes the faraday cage cover removed so as to illustrate the discrete components under the faraday cage.

FIG. 71 illustrates, by way of example, a perspective view diagram of an embodiment of the system 6700 that includes the faraday cage 6720 removed so as to illustrate the discrete components 7360 under the faraday cage cover, in the faraday cage 6720, and on the first layer 6724. While the components are illustrated as chips, the components can include one or more resistors, capacitors, inductors, integrated circuits, transistors, logic gates, oscillators, state logic components, multiplexers, switches, connectors, or other electrical or electronic components, such as one or more of those in the circuitry of the external device (e.g., the circuitry of the system 6400, 400, or other external device circuitry discussed herein). The discrete components 7360 can be electrically connected by one or more traces 7362 on the first layer 6724. A thermal paste, grease, or other substance, material, or coating can be situated on and/or around one or more of the discrete components 7360 and/or between the discrete components 7360 and the faraday cage 6720, such as to conduct heat away from the components 7360 to the faraday cage cover 6740 or faraday cage base 6742. The thermal paste or grease can transfer heat from the electrical or electronic components and other elements in contact with or sufficiently near the thermal paste or grease to the faraday cage 6720 and subsequently the surrounding environment.

B. Discreet External Device Coupling to Implanted Device

This subsection generally relates to positioning and/or retention of an external device near a therapy site. More specifically, described in this subsection are devices, systems, and methods for discrete positioning and/or verification of the positioning of the external device external to the therapy site. This subsection relates to positioning and/or retention of an external device near a therapy site. More specifically, described in this section are devices, systems, and methods for discrete positioning and/or verification of the positioning of a device external to the therapy site.

Although considerable progress has been made in the realm of medical device therapy, there still exists a need for comfortable, wearable medical devices that interact with an implanted medical therapy device. The device should be comfortable and relatively unnoticeable to the eye for a better user experience. The current form factor for such devices is prohibitively large, such that an individual wearing such a therapy device is uncomfortable and/or embarrassed because the device is noticeable.

Discussed in this subsection are wearable elements which allow for a comfortable and/or efficient way of carrying an external device that can provide energy to an implanted therapy device. In one or more embodiments, a system includes an implantable sacral neuromodulation device, such as can be implanted in a patient, and can include an implantable communicating element configured to send and/or receive a wireless signal to/from an external device (a wearable device). The external device can include, for example, an antenna, battery, and/or electronics (e.g., control circuitry, such as circuitry of the source 102, antenna 300, or other external device discussed herein). The system can further include a wearable element (e.g., clothing, a band, or other wearable garb) configured to be worn by a user (e.g., a patient) and the external device coupled to or in the wearable element. The external device can be configured to send and/or receive a wireless signal to communicate with the implantable device. In one or more embodiments, the external device can be placed in multiple locations relative to the wearable element.

The external device can have a variety of configurations. In one or more embodiments, the external device can include an antenna (e.g., a power and/or data transmitter, such as a midfield transmitter) positioned above an S3 foramen and configured to power an implantable device (e.g., an implantable neurostimulator). In one or more embodiments, the implantable device can include an internal inductive coil and the external device can include an external inductive coil. The coils can be configured to resonate at substantially the same frequency, such as to maximize power coupling. The wearable element (e.g., the external device) can include a location mechanism configured to indicate proper alignment between the external device and the implantable device. The location mechanism may be included in the circuitry of the external device.

In one or more embodiments, the system can include a first external device and a second external device that are coupled to one another and are positionable above the S3 foramen. The second external device can be electrically coupled to the first external device. In one or more embodiments, the first external device can be configured to receive data from the implantable device and the second external device can be configured to provide power to the first external device.

The external device can have a variety of configurations. In one or more embodiments, the external device can include a flexible battery adapted to flex in response to motion of a user wearing the flexible battery. In one or more embodiments, the wearable element can be formed from a plurality of elastic straps. The wearable element can be adjustable to a variety of patient sizes and shapes. In still other embodiments, the wearable element can be a belt, pants, shorts, a vest, a sash, an undergarment, or an adhesive patch. In some embodiments, the wearable element can include at least one pocket formed therein. The pocket can be movable relative to the wearable element. In one or more embodiments, the pocket includes at least one battery disposed therein which is configured to provide power to the external device.

Methods are provided for communicating with and powering an implantable/implanted device. The external device can be activated to wirelessly transfer a signal through tissue to the implantable device. For example, the external device can deliver energy to the implantable device and/or receive data from the implantable device. The external device can include an external inductive coil or midfield device. The implantable device can include an internal inductive coil or other electromagnetic signal receiving element. One or more of these elements may be used to transfer a communication signal or to generate power at the implantable device.

Wireless communication can be used to position an external device on/in the wearable element worn by a patient at one of a plurality of locations, such as to align the external device with a communicating element on an implanted device. While the external device can be positioned at a variety of locations, in one or more embodiments the external device may be ideally positioned on or over a skin surface in proximity to the implanted device. The implanted device may send a wireless signal to the external device, such as can include signals indicating information regarding the amount of energy being transferred, acknowledgement of programming signals for the external device, and/or malfunction or error warnings. The external device can be configured to communicate to the patient through audio tones, visual displays, or vibration. This can be used to help guide the patient to place and/or secure the external device at a location that is sufficient or even ideal for wireless power transfer. The external device may communicate battery level of the external device in addition to other statuses to the user. This may help a patient understand when to change or charge a battery of the external device.

The external device can be positioned on/in the wearable element or at a distance apart from the wearable element. For example, the wearable element can include a plurality of flexible straps, and the external device can be removably mated to the flexible straps, such as in proximity to the implantable device. Additionally, or alternatively, the external device can be disposed within a pocket affixed to the wearable element. In one or more embodiments, the wearable element can be a flexible battery. The external device can be coupled to the flexible battery and can deliver energy to the implantable device, such as energy that originated at the flexible battery.

Figure 72:
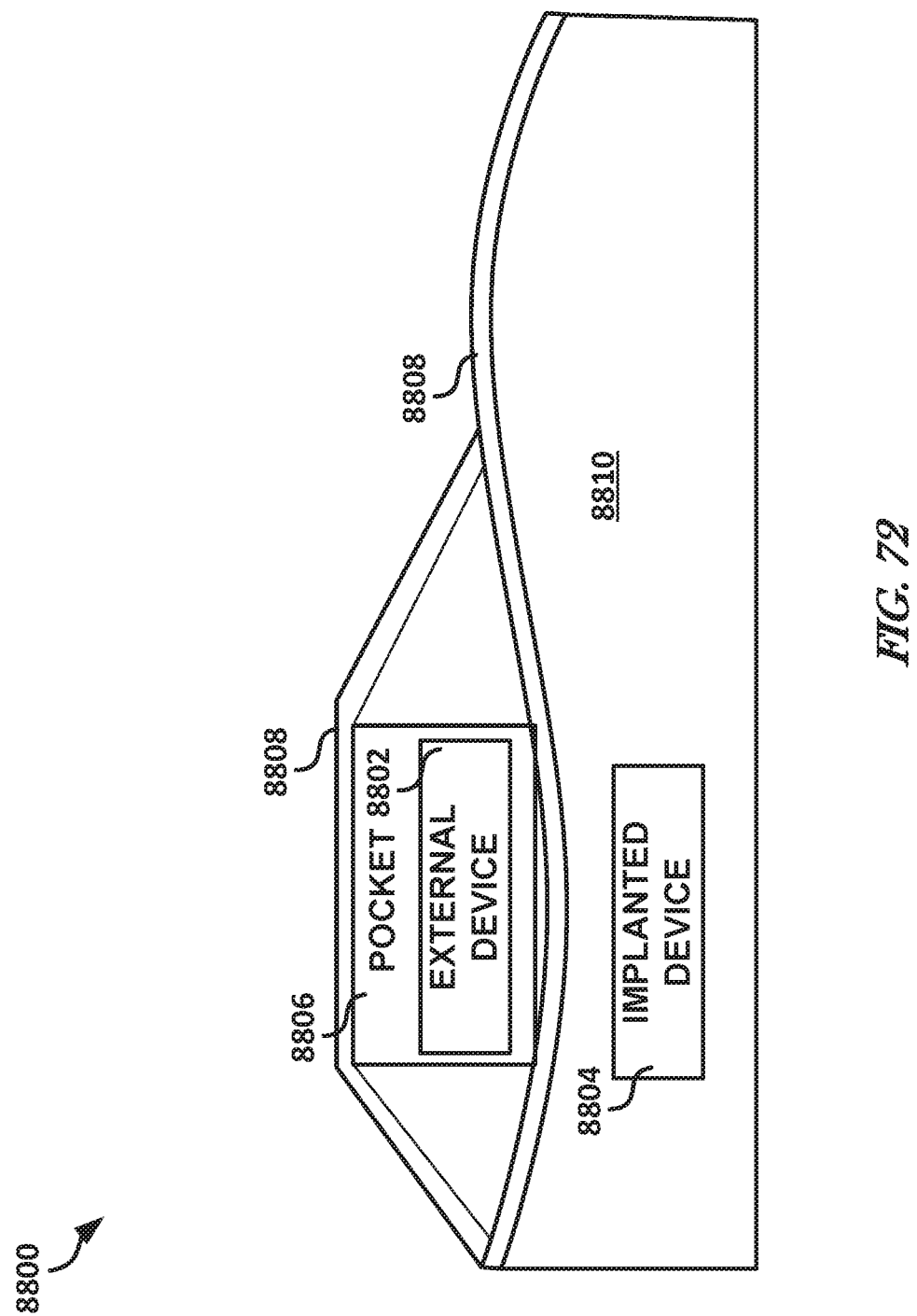
FIG. 72 illustrates, by way of example, a block diagram of an embodiment of a system for providing power to or stimulating an implanted device.

FIG. 72 illustrates, by way of example, an embodiment of a system 8800 for communication of one or more signals between an implanted device 8804 and an external device 8802. The implanted device 8804 can be similar to or the same as any of the implantable devices discussed herein, such as the implantable device 110, 600, 700, or other implantable device. The external device 8802 can be similar to or the same as any of the external devices discussed herein, such as the source 102, the antenna 300, or the like.

The external device 8802 can be situated in and/or affixed at a position within a pocket 8806. The pocket 8806 can be internal to a wearable element 8808, such as an undergarment, pants, shirt, panty hose, shorts, bodysuit, and so forth. The implanted device 8804 can be implanted under the surface a user's skin, such as to be internal to a user's body 8810. The external device 8802 can transfer power and/or data to the implanted device 8804. In one or more embodiments, the implanted device 8804 can be implanted deeper than 40 mm into the body 8810. In one or more embodiments, the external device 8802 is positioned in a sleeve (see FIGS. 83, 84A-84B, and 85). More details regarding each of the items depicted in FIG. 72 are provided with regard to the remaining FIGS. and other discussion herein.

Figure 73:
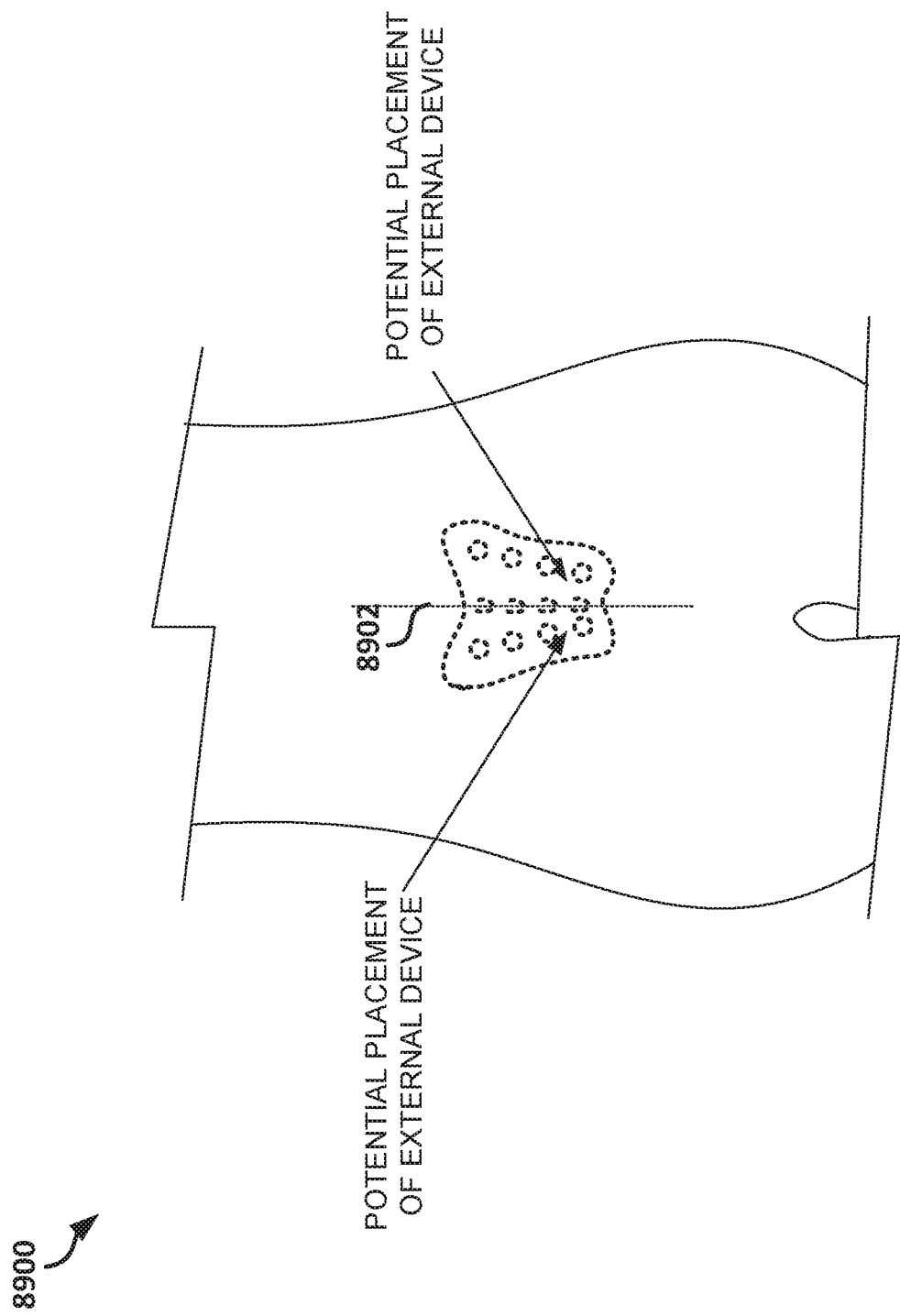
FIG. 73 illustrates, by way of example, a perspective view diagram of a portion of a human body with a view of a low back portion of the skeletal system.

FIG. 73 illustrates, by way of example, a back view diagram of a portion of a human body 8900 and potential placements locations for the external device 8802 and areas which the pocket 8806 can cover. As illustrated, the external device 8802 can be placed at or near a position of an S3 foramen, such as can be about 9-10 centimeter from the tip of the coccyx or sciatic notch and/or about two centimeters to the left or the right of a midline of the human body (indicated by a dashed line 8902).

Figure 74:
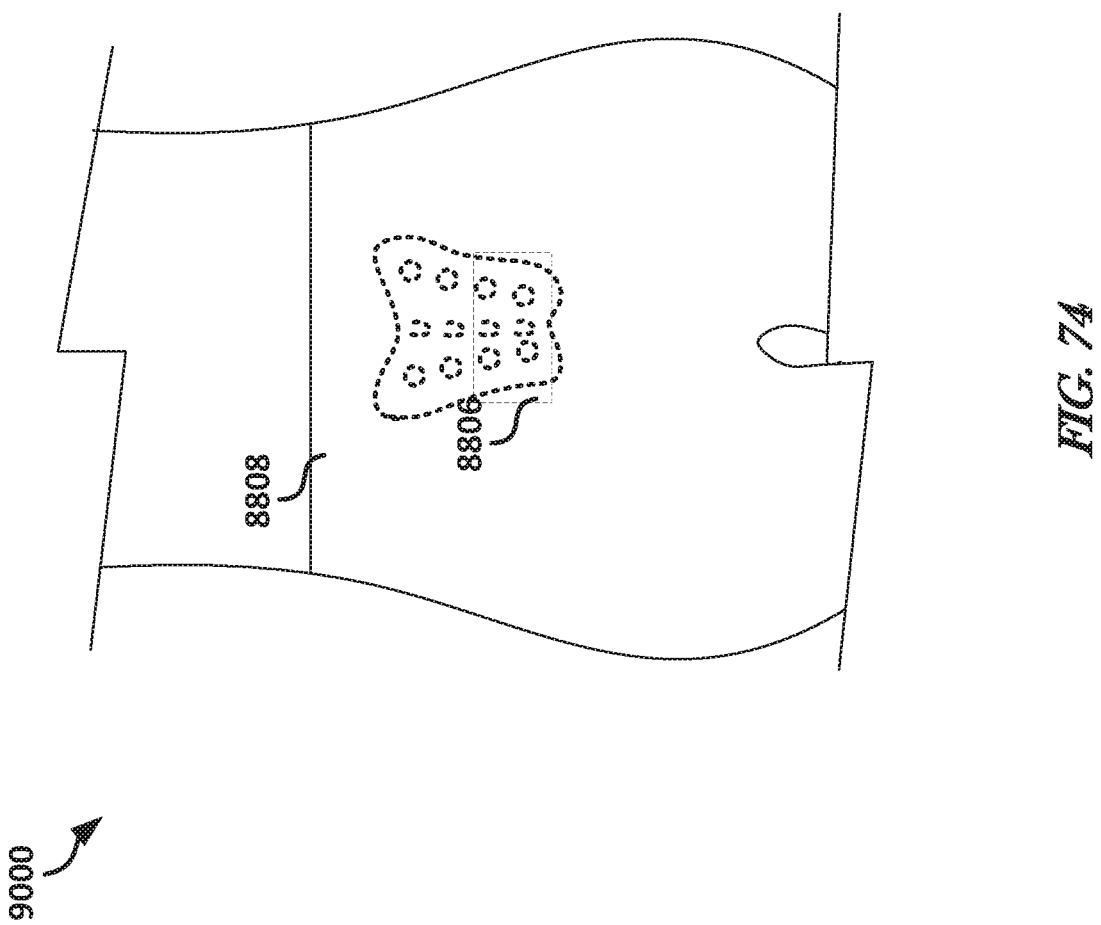
FIG. 74 illustrates, by way of example, a perspective view diagram similar to that of FIG. 73 with an embodiment of clothing including a pocket positioned over potential implant sites of a neurostimulator.

FIG. 74 illustrates, by way of example, a perspective view diagram of a human body 9000. The body 9000 as illustrated includes the wearable element 8808 with the pocket 8806 for housing the external device 8802. The pocket 8806 as illustrated spans at least two potential locations for placement of the eternal device 8802 as shown in FIG. 73. The pocket 8806, in one or more embodiments, may be narrower (in terms of its width relative to the width of the human body), such as to cover only a single potential location of the external device 8802. However, having the pocket 8806 span two or more potential locations allows for a single pocket to accommodate a wider variety of external device locations.

Figure 75:
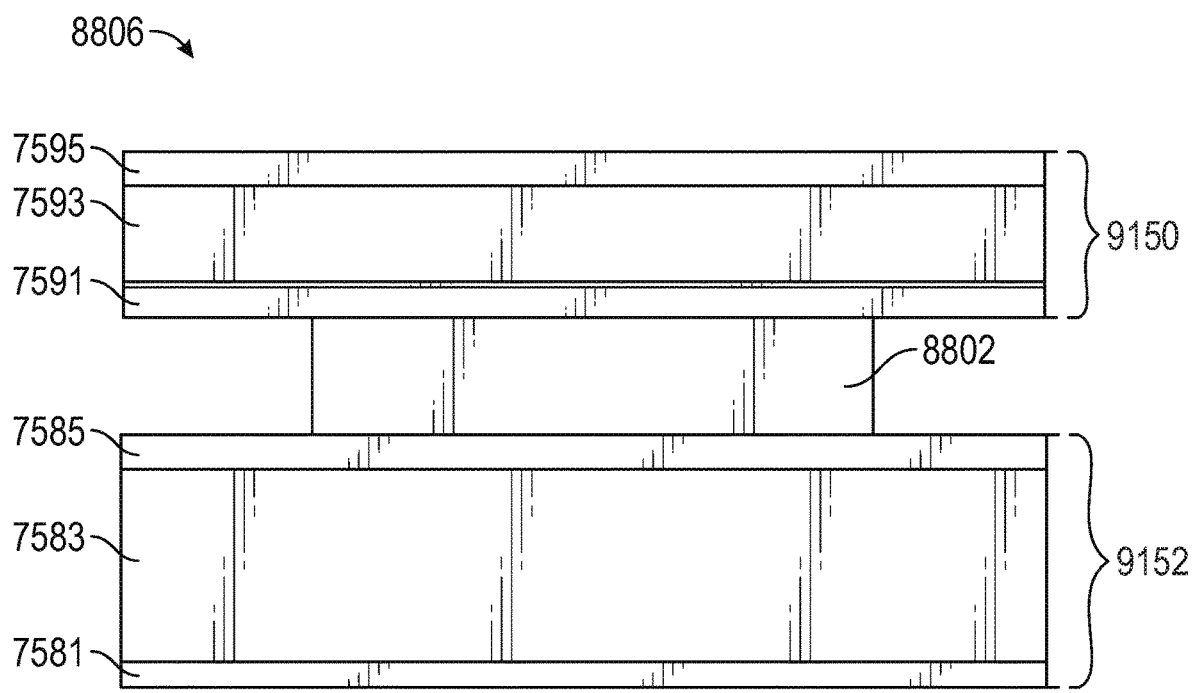
FIG. 75 illustrates, by way of example, a block diagram of an embodiment of layers of the pocket, such as the pocket shown in FIG. 74.

FIG. 75 illustrates, by way of example, an exploded view diagram of a portion of FIG. 72 that includes the pocket 8806 and the external device 8802. The pocket 8806 is illustrated as including a top pocket layer 9150 and a bottom pocket layer 9152. The top pocket layer 9150 is sometimes referred to as the "top layers". The bottom pocket layer 9152 is sometimes referred to as the "bottom layers". Note that the illustration of FIG. 75 can correspond to the layers of a sleeve as well. Each of the top and bottom pocket layers 9150 and 9152 are illustrated as including three fabric layers, however, each of the top and bottom pocket layers 9150 and 9152 may include fewer or more fabric layers. The pocket 8806 is illustrated as including six layers and the device 8802 is illustrated as being situated between layer 3 and layer 4 of the pocket. Note that the pocket 8806 may include fewer or more layers, depending on the application to be accommodated. As illustrated, the bottom pocket layer 9152 includes three layers, 7581 ("Layer 1"), 7583 ("Layer 2"), and 7585 ("Layer 3"). As illustrated the top pocket layer 9150 includes three layers, 7591 ("Layer 4"), 7593 ("Layer 5"), and 7595 ("Layer 6").

The Layer 1 of the pocket can include a soft, supple, and/or compliant material. This layer is closest to the user's skin and can provide comfort. The Layer 2 and/or Layer 3 can be insulating material(s) (e.g., materials that resist heat passing therethrough) and/or waterproof or water resistant, respectively. This heat insulating property of the material can help protect a user's skin from heat produced by the external device 8802 and deflect heat towards the top pocket layer 9150. The waterproof/water resistant property can help prevent moisture from travelling to the user's skin and help transport any such moisture towards the top layer(s). In one or more embodiments, one or more of the bottom pocket layer 9152 may be water wicking so as to transport water away from the user's skin towards the top layer(s).

One or more of the top layer(s) Layer 4, Layer 5, and/or Layer 6 may be a heat conductive material, such as to transport heat away from the user's body. One or more of the top layer(s) Layer 4, Layer 5, and/or Layer 6 may be compressive, such as to help ensure that the wearable element does not slip or otherwise move on the user's body and to help keep the external device positioned in a location at which it can communicate with the implantable/implanted device.

The wearable element can include a pocket or pockets in undergarments that can include one or more top and one or more bottom layers. As previously discussed Layer 1 can be a soft breathable material, such as polyester. This layer can be in direct contact with the skin. Layer 2 and/or Layer 3 can be made out of an insulating material. Layer 3 can be neoprene, Gore-Tex, Outlast, or other material that includes a low thermal conductivity, such as a material similar to neoprene. Layer 2 and/or 3 may completely prevent the penetration and/or absorption of liquid water (waterproof). Layers 2 and 3 can be the same material. Layer 2 and/or Layer 3, (the inside layer to the pocket, closest to the body) can include a one-way permeable material, such as GORE-TEX®, GORE WINDSTOPPER® membrane, polytetrafluoroethylene (ePTFE), hemp, sheep's wool, cotton, straw, aerogel, polyurethane, or the like.

The pocket can be ventilated to allow heat to dissipate, sometimes referred to as breathable. Layer 4 and/or layer 6 can include a breathable material that can allow the release of heat through the top (the side away from the human body). The top of the pocket can include a breathable material. The sides of the pocket can include a breathable and/or waterproof material.

Insulating materials can include, for example, one or more of: polyurethane foam, PYROGEL® XT, GORE-TEX®, GORE WINDSTOPPER® membrane, polytetrafluoroethylene (ePTFE), hemp, sheep's wool, cotton, straw, aerogel, polyurethane, a material with a high R-value, Outlast, or the like.

Figure 76:
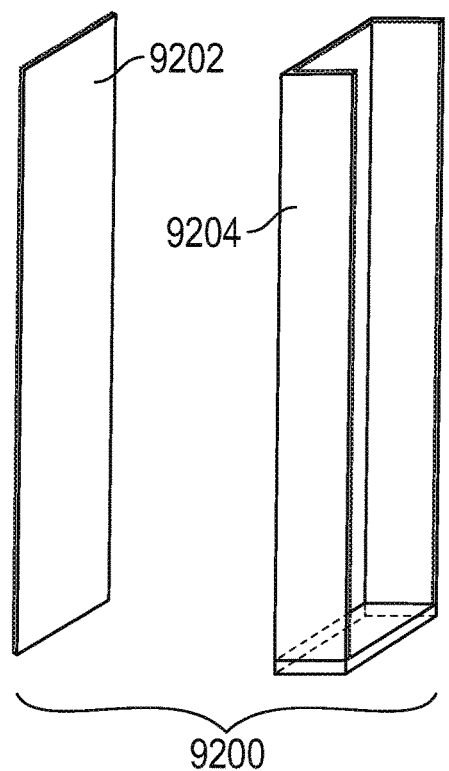
FIG. 76 illustrates, by way of example, a perspective view diagram of an embodiment of bottom layers of the pocket.
Figure 77:
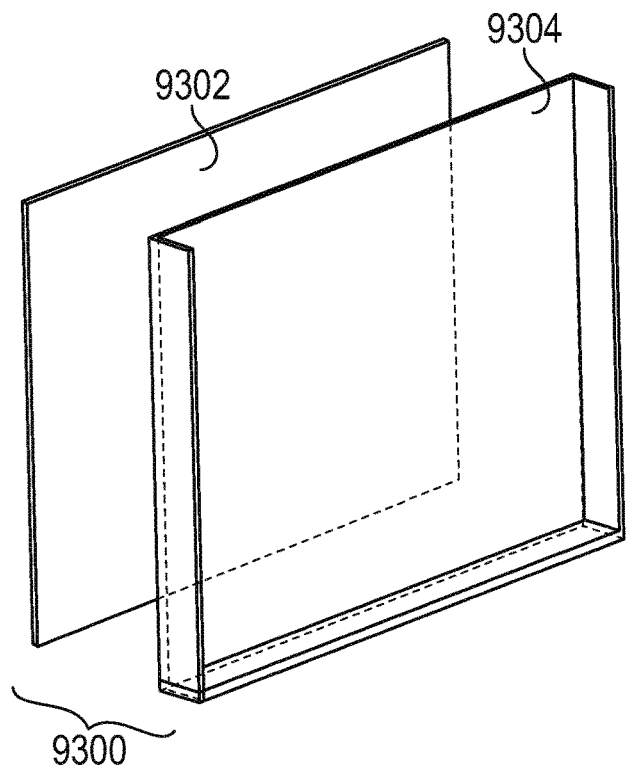
FIG. 77 illustrates, by way of example, a perspective view diagram of another embodiment of bottom layers of the pocket.

FIG. 76 illustrates, by way of example, a perspective view diagram of an embodiment of bottom layers 9200 of the pocket 8806. FIG. 77 illustrates, by way of example, a perspective view diagram of another embodiment of bottom layers 9300 of the pocket 8806. The bottom layers 9300 are similar to the bottom layers 9200 with the bottom layers 9300 covering multiple potential implant locations (one on each side of the spinus tubercles, for example) and the bottom layers 9200 only covering one such potential location. The bottom layers 9200 as illustrated include a first bottom layer 9202 and a second bottom layer 9204. The first bottom layer 9202 can be closer to the user's body than the second bottom layer 9204 when the layers 9200 are being worn. The layers 9202 and 9204 can be affixed to each other, such as by thread, adhesive, or other affixing means. The layers 9302 and 9304 are similar to the layers 9202 and 9204, respectively, with the layers 9302 and 9304 being wider than the layers 9202 and 9204 as previously discussed.

Figure 79:
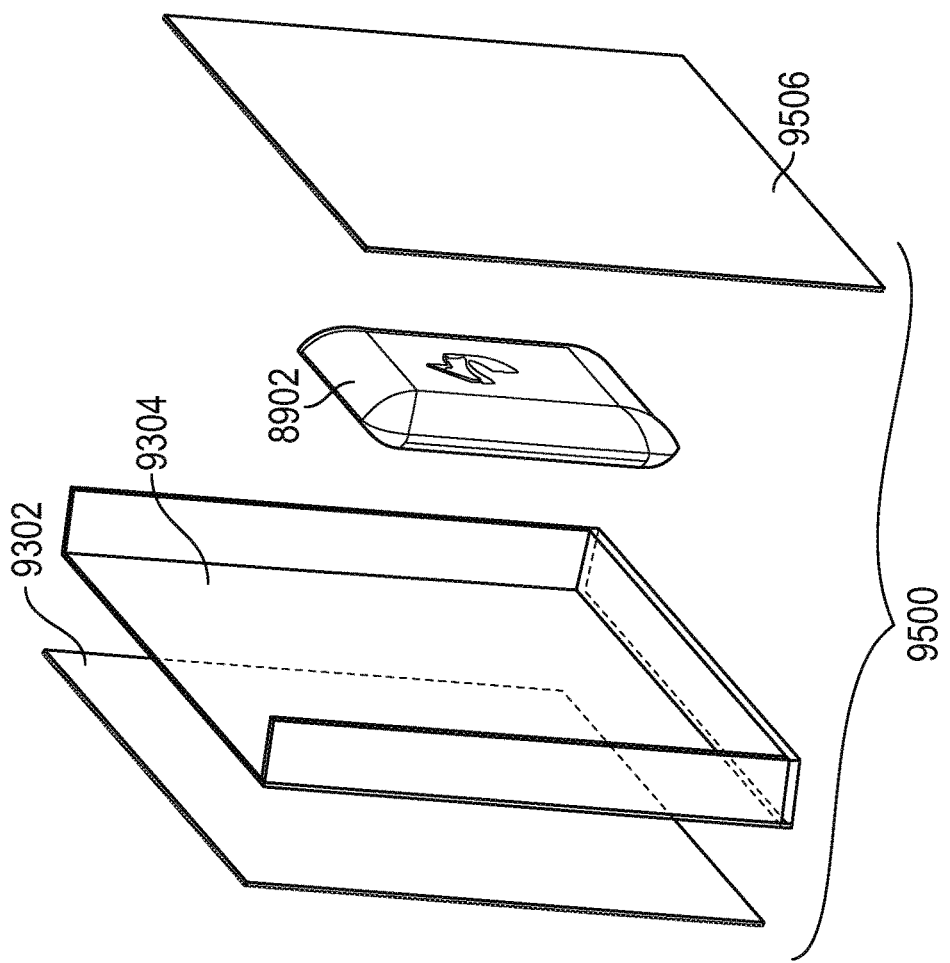
FIG. 79 illustrates, by way of example, a perspective view diagram of an embodiment of the bottom layers of FIG. 77 with an external device and a top layer.
Figure 78:
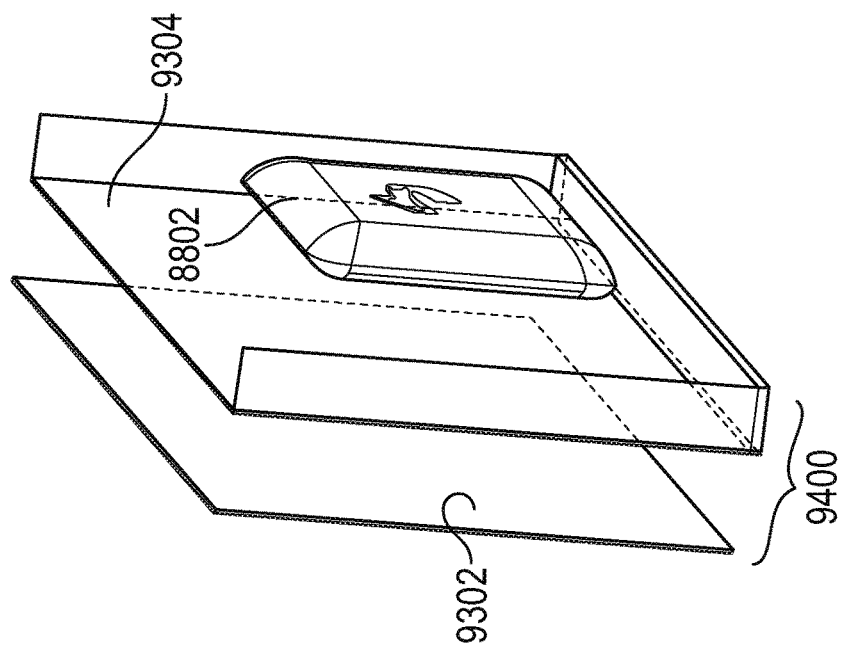
FIG. 78 illustrates, by way of example, a perspective view diagram of the embodiment of bottom layers of FIG. 77 with an external device situated by the layers.

FIG. 78 illustrates, by way of example, a perspective view diagram of the embodiment of bottom layers 9400, such as is similar to the layers 9300 of FIG. 77, with the external device 8802 attached to the inner most layer (layer 9304 of the bottom layers 9400 of FIG. 94). FIG. 79 illustrates, by way of example, a perspective view diagram of an embodiment of layers 9500 that include the bottom layers 9300 of FIG. 77 with an external device 8802 between the bottom layers and a top layer 9506. The top layer 9506 is the inner most top layer and can be in contact with the external device 8802. The layer 9506 and can be attached, such as by thread, adhesive, or other affixing means to any of the bottom layer(s), such as the layers 9302 and/or 9304.

Figure 80:
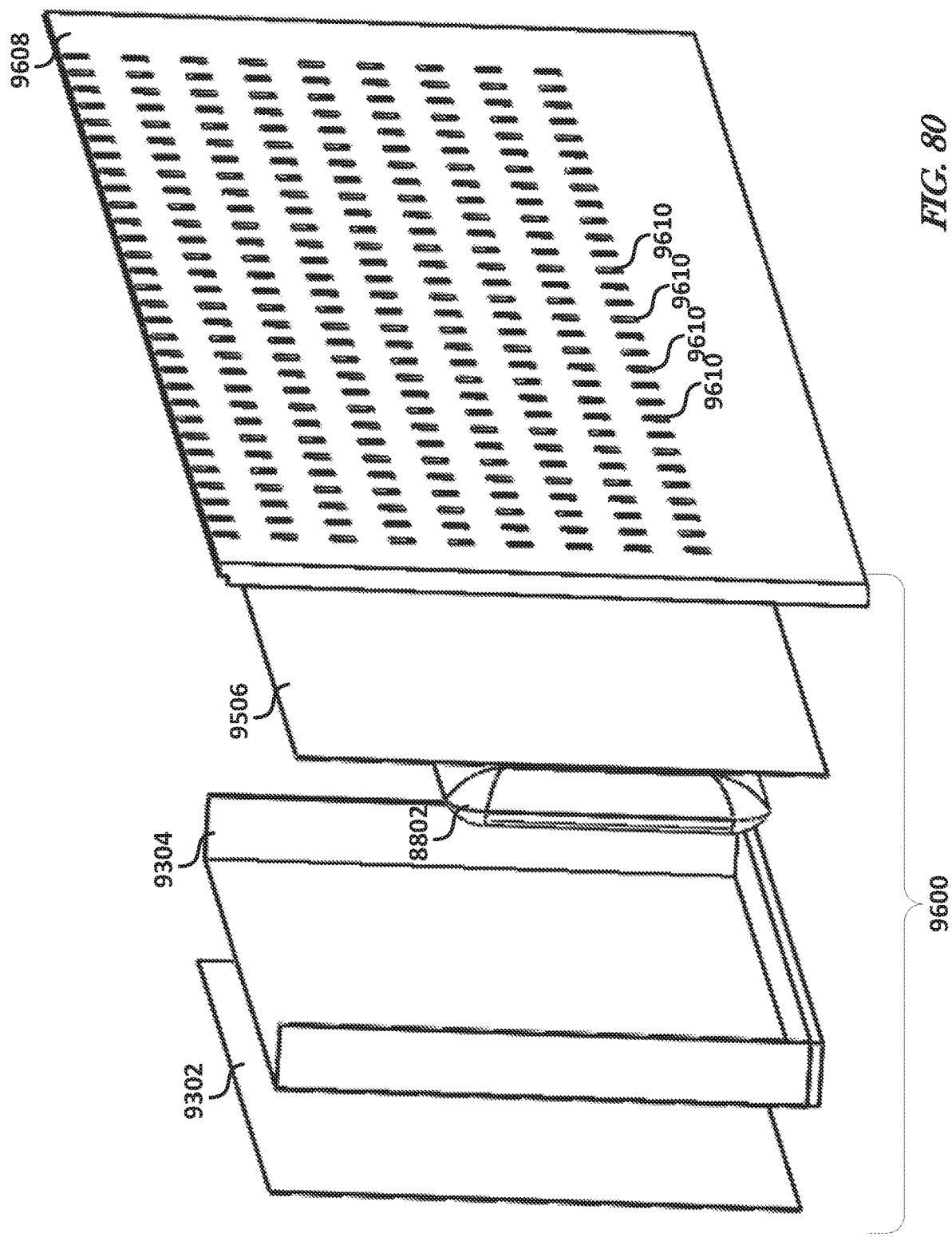
FIG. 80 illustrates, by way of example, a perspective view diagram of an embodiment of the bottom layers of FIG. 77 with an external device, a top layer, and an elastic band over the top layer.

FIG. 80 illustrates, by way of example, a perspective view diagram of an embodiment of layers 9600 similar to the layers 9500 with an elastic band 9608 over the top layer 9506. The elastic band 9608 as illustrated includes optional holes 9610 therethrough, such as to help provide a ventilation area through which heat can escape and/or air can be brought in, such as to keep the pocket 8806 breathable. The holes 9610 can each include a greater height dimension than width dimension, such as shown in FIG. 80. The height can be in generally the same direction as a height of the person wearing the wearable element. The width is generally perpendicular to the height. Such a configuration can allow the elastic band 9608 to stretch such as without compromising integrity or longevity of the band 9608. The holes 9610 can be positioned over just a portion of the band 9608, such as a portion over the layer 9506 or a portion thereof. The holes 9610 can alternatively be positioned over an entire width and height of the band 9608. The band 9608 illustrated is just a portion of the band so as to not obscure the view of the layers 9506, 9304, and 9302 and the external device 8802. The band 9608 will generally wrap completely around a human body so as to help apply a compressive force between the external device 8802 and the human body and help retain the external device in place.

Figure 82:
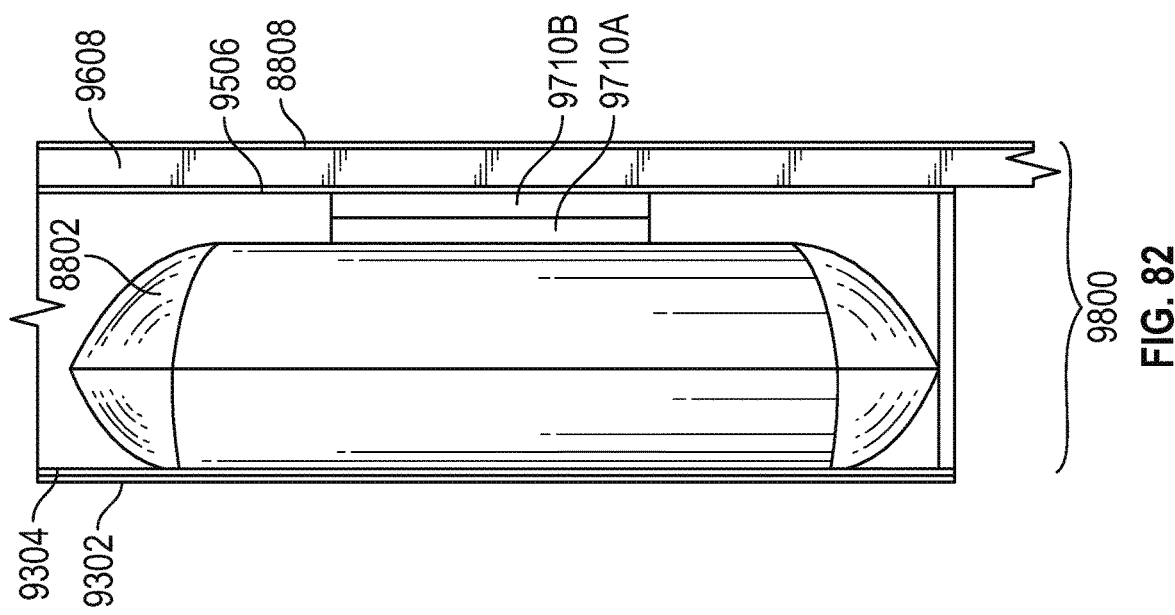
FIG. 82 illustrates, by way of example, a perspective view diagram of an embodiment of the system of FIG. 81 with the attachment mechanisms of the pocket and external device mated so as to secure the external device in the pocket.
Figure 81:
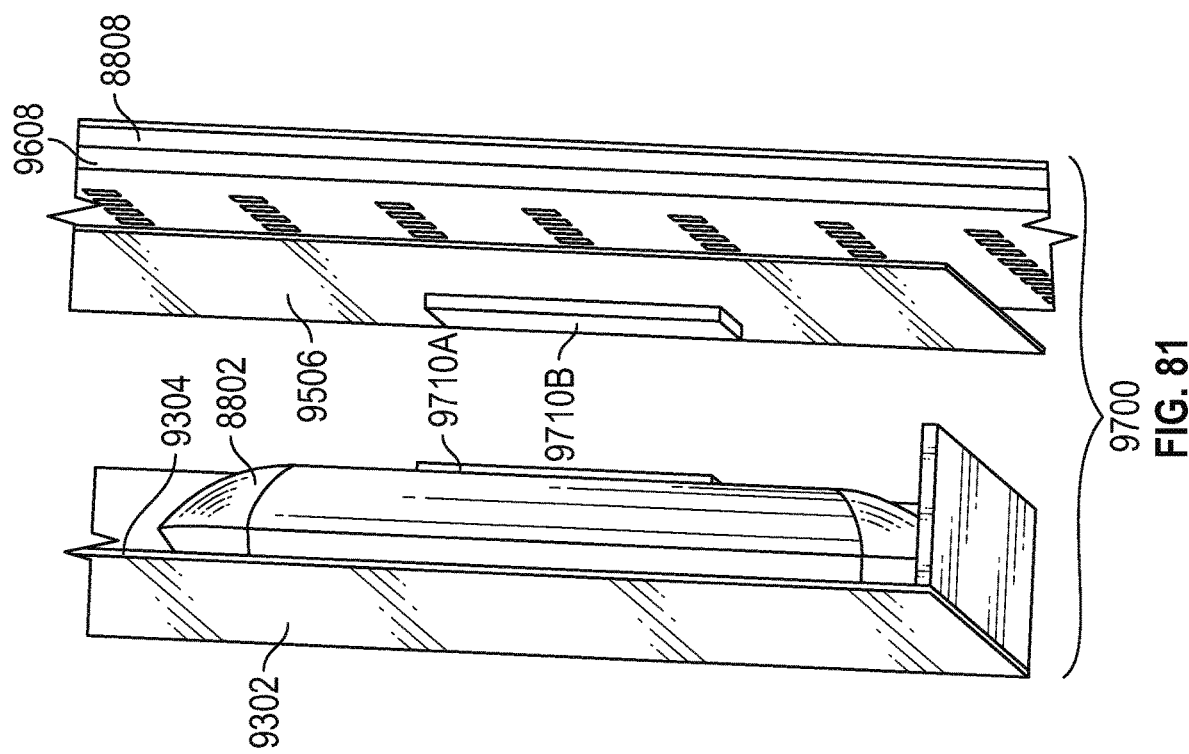
FIG. 81 illustrates, by way of example, a perspective view diagram of an embodiment of the layers of FIG. 80 with an external device, and including an attachment mechanism on both the external device and a top layer of the pocket.

FIG. 81 illustrates, by way of example, a perspective view diagram of an embodiment of a system 9700 including the layers 9600 with mating attachment mechanisms 9710A and 9710B on both the external device 8802 and the top layer 9506 of the pocket 8806. The layer 9506 includes the attachment mechanism 9710B on the innermost layer of the top layers. The attachment mechanism 9710B can be mated with the mating attachment mechanism 9710A on the external device 8802 (see also FIG. 97) or a mating attachment mechanism on a sleeve in which the external device 8802 may be situated (see. FIGS. 83, 84A, and 84B). Note that the attachment mechanisms 9710A-B are optional and the pocket 8806 can be sufficiently stretchable and include such dimensions so as to keep the device in the proper location without the need for such an attachment mechanism. The attachment mechanisms 9710A-B can include mechanical based fastening mechanisms, fabric hook and loop fasteners (e.g., VELCRO® fasteners), a magnet, a SCOTCH® fastener, or other attachment mechanism. The attachment mechanisms 9710A-B can be affixed to a layer or the external device 8802 using an adhesive. FIG. 82 illustrates, by way of example, a cross-section view diagram of an embodiment of a system 9800, similar to that of FIG. 81, with the attachment mechanisms 9710A-B of the pocket 8806 and external device 8802 mated so as to secure the external device 8802 in the pocket 8806.

FIG. 83 illustrates, by way of example, a cross-section view diagram of an embodiment of a system 9900 that includes the external device 8802 situated in a sleeve. The sleeve as illustrated includes the top layers 9506 and 9912, the bottom layers 9302 and 9304, and an attachment mechanism 9914 on the top layer 9912. The top layer 9912 can be similar to any of the top layers described with regard to FIG. 75. The attachment mechanism 9914 is similar to the attachment mechanisms 9710A-B.

FIG. 84A illustrates, by way of example, a perspective view diagram of an embodiment of a system 10000A similar to the system 9900, with the system 10000A including a cushion material 10016 on the bottom surface 9302. The cushion material 10016 helps provide support and protect the user from forces due to impact on the external device 8802. FIG. 84B illustrates, by way of example, a perspective view diagram of an embodiment of a system 10000B similar to the system 9900, with the system 10000B including the cushion material 10016 in the sleeve, such as on the bottom layer 9304 as opposed to on the bottom layer 9302.

FIG. 85 illustrates, by way of example, a cross-section view diagram of an embodiment of a system 10100 including a sleeve with the external device 8802 situated therein. The sleeve as illustrated is situated between layers of the wearable element 8808, such as in the pocket 8806. In the embodiment of FIG. 85, the sleeve is affixed to the wearable element 8808 through an attachment mechanism 9710A on the wearable element 8808 mated with a fastening mechanism 9710A on the top layer 9912. The attachment mechanisms 9710A-B as illustrated are within the wearable element 8808. Additionally, another pair of fastening mechanisms may help affix the sleeve to the external device 8802. One fastening mechanism can be situated on the top layer 9506 and the mating fastening mechanism can be situated on the external device 8802.

Figure 86:
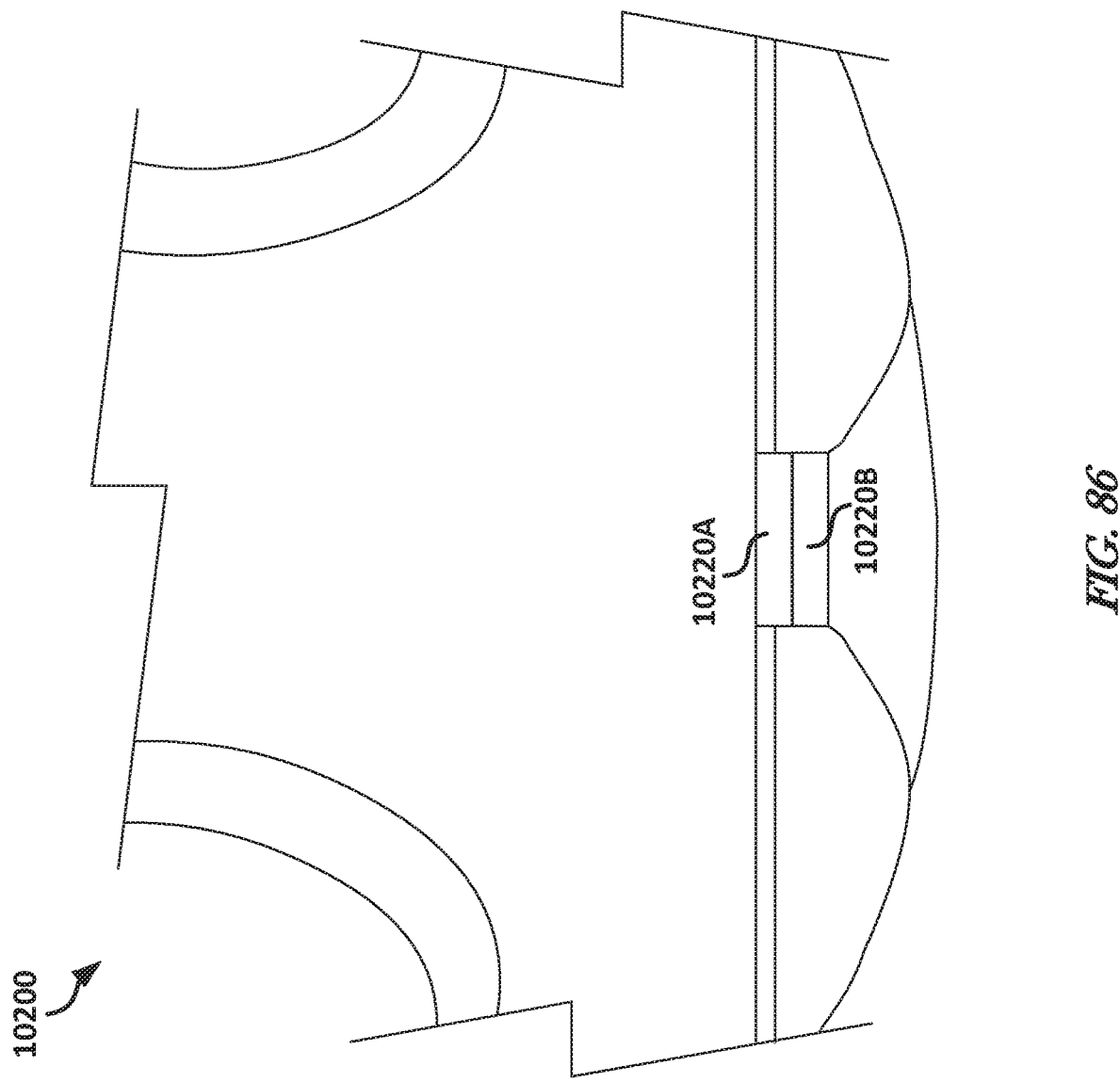

FIG. 86 illustrates, by way of example, a perspective view diagram of an embodiment of an undergarment 10200 that includes mating fastening mechanisms 10220A and 10220B. The fastening mechanisms 10220A-B allow a user to open a bottom portion of the undergarment 10200 while wearing the undergarment 10200. Such an undergarment 10200 can help provide a way for a user to go to the bathroom without moving the external device 8802 relative to the implanted device 8804. Consider that the undergarment 10200 can include the pocket 8806 or other location at which the external device 8802 can be affixed. Using such an undergarment, a user can uncouple the fastening mechanisms 10220A-B, do their business, recouple the fastening mechanisms 10220A-B, and all the while retain the position of the external device 8802 relative to the implanted device 8804. In other embodiments, a user may have to move the undergarment 10200, thus moving the device 8802 relative to the implanted device 8804. The user may then reposition the external device 8802 to a communicable position (a position at which the external device communicates reliably with the implanted device 8804), such as by performing the operations discussed with regard to the location circuitry (see FIGS. 98, 99, and 100).

FIG. 87 illustrates, by way of example, a perspective view diagram of an embodiment of the external device 8802 in a closed position. The external device 8802 as illustrated includes a top cover 10322 (the cover to contact or be more proximate with the top layer(s) of the pocket or sleeve) and a bottom cover 10324 (the cover to contact or be more proximate with the bottom layer(s)). Edges 10326A and 10326B of the top cover 10322 as illustrated include a greater radius of curvature than edges 10328A and 10328B of the bottom cover 10324. By including edges 10324A-B with a greater radius of curvature, the external device 8802 can remain more discreet when in use. The bulge created by the external device 8802 will be more discreet and less severe than with edges that include a smaller radius of curvature. The radius of curvature of the edges 10328A-B can be important for the comfort of the user. These edges, if too sharp, may cause discomfort for the user. Increasing the radius of curvature, however, can increase the overall footprint of the external device 8802.

Each of the top cover 10322 and the bottom cover 10324 may be formed of a thermoplastic, other material or layers of materials. A "thermoplastic" refers to a polymeric material that can be repeatedly (i.e.; more than once) softened by increases in temperature, and hardened by decreasing the temperature. The thermoplastic may be in the form of a solid or a foam. Thermoplastic polymeric foams may include, but are not limited to: expanded polystyrene, polyethylene, polypropylene, polyvinylchloride, and polycarbonate. Non-limiting examples of crosslinked thermoplastic foams include: polyethylene, polyethylene copolymers, and polyvinylchloride. Non-limiting examples of solid thermoplastic materials include: polycarbonates, poly(ethylene terephthalate), polyethylene (high density and low density), polyimide, polypropylene, and the like. One suitable thermoplastic material is a high density polyethylene.

The top cover 10322 of the external device 8802 faces away from the body. The top cover 10322 can include a high thermal conductivity, such as CoolPoly® Thermal Conductive plastic. The top cover 10322 can have a high specific heat, be a good heat sink, be "bump", and/or include fins 10938.

The bottom cover 10324 faces toward the skin when in proper use. The bottom cover 10324 is directly adjacent to the Layer 2 and/or Layer 3. The bottom cover 10324 can include an insulating material, such as PYROGEL® XT or OUTLAST® FR-LHS Thermoplastic Polyolefin Elastomers. The bottom cover 10324 can have a low thermal conductivity and/or a high specific heat.

FIG. 88 illustrates, by way of example, a perspective view diagram of an embodiment of the external device 8802 in an open position so as to show internal circuitry 10430 between the top cover 10322 and the bottom cover 10324. The circuitry 10430 can include control circuitry (e.g., components of the external device discussed elsewhere herein), an antenna (e.g., a midfield coupler), an inductive coil, a faraday cage, a speaker, a transmit and/or receive radio (see. FIGS. 98, 99, and 100), or the like. The control circuitry can provide power to the antenna that radiates electromagnetic energy. The electromagnetic energy can then be provided to the implanted device 8804 if the external device 8802 is properly situated related to the implanted device 8804.

FIG. 89 illustrates, by way of example, a perspective view diagram of an embodiment of the external device 8802 in a closed position. FIG. 90 illustrates, by way of example, a perspective view diagram of an embodiment of the external device 8802 in an open position so as to show internal circuitry 10530 between the top cover 10322 and the bottom cover 10324 and the inside of the bottom cover 10324. The inside of the bottom cover 10324 is illustrated as including a plurality of recesses 10632, such as to help insulate the bottom cover 10324 from heat.

Figure 92:
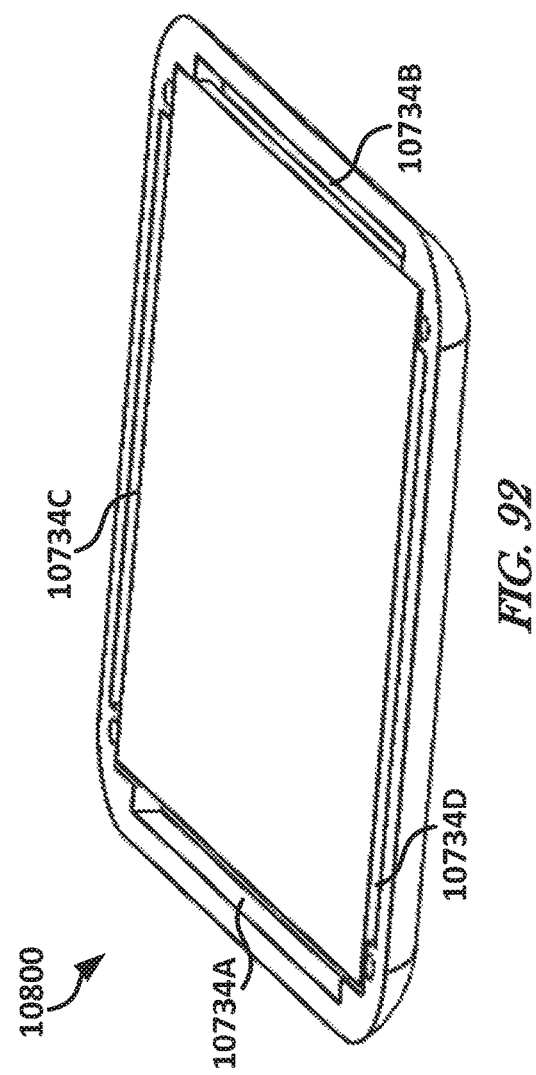
Figure 91:
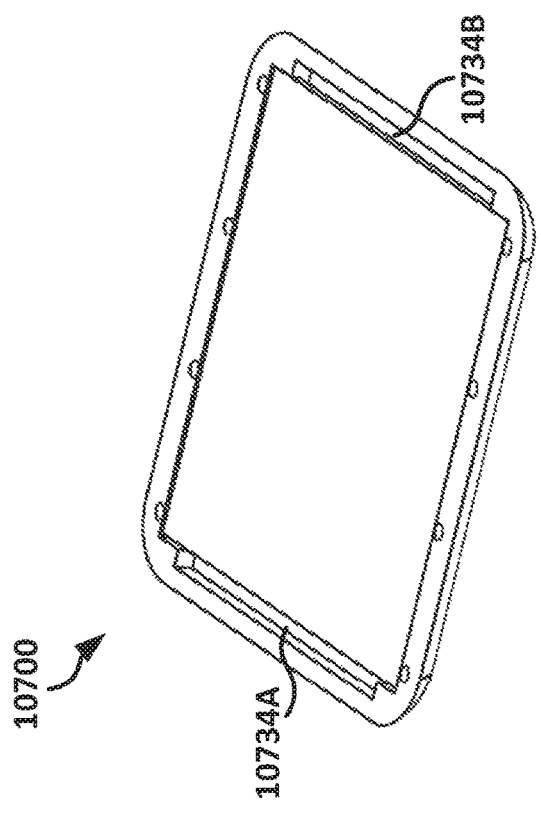

FIG. 91 illustrates, by way of example, a perspective view diagram of an embodiment of a cover 10700, such as can act as a top cover 10332 or bottom cover 10334 of the external device 8802. The cover 10700 as illustrated includes two air vents 10734A and 10734B. The two air vents 10734A-B can hold air to be dissipated away from the user's body. The two air vents 10734A-B as illustrated are on opposite sides of the cover 10700. FIG. 92 illustrates, by way of example, a perspective view diagram of an embodiment of a cover 10800, such as can act as the top cover 10332 or the bottom cover 10324 of the external device 8802. The cover 10800 as illustrated includes four air vents 10734A, 10734B, 10734C, and 10734D. One air vent 10734A-D is illustrated as running along each side of the cover 10800 and generally parallel to the corresponding side. Note that the embodiments discussed herein are not mutually exclusive and may be combined where possible. For example, a cover can include both the recesses 10632 and one or more air vents 10734A-D. Such an embodiment may help transport air from the recesses 10632 to the air vent(s) 9734A-D, such as to help dissipate heat away from the user's body. Note that the air vents are optional. In one or more embodiments, the recesses that help form the air vents are filled with a heat conductive or insulating material depending on if the vents are on the top cover or the bottom cover. In one or more embodiments, the air vents are not present.

Figure 93:
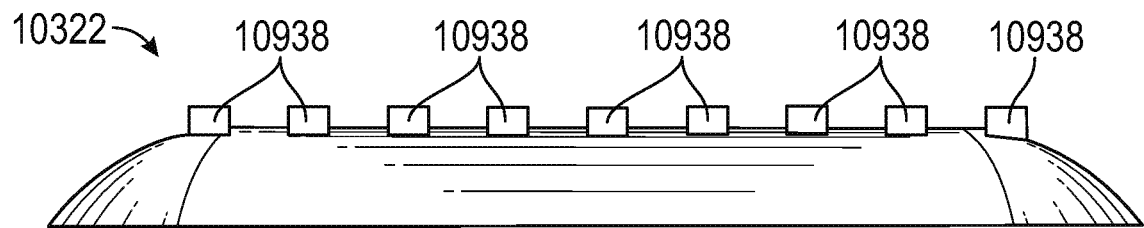

FIGS. 93 and 94 illustrate, by way of example, perspective view diagrams of an embodiment of the top cover 10322 of the external device 8802 that includes fins 10938. The fins 10938 can help conduct heat away from the user's body. The fins 10938 can be touching or near a heat conducting top layer (of the pocket 8806 or the sleeve). Note that the fins 10938 are optional. The fins 10938 can extend beyond an outer surface of the top cover 10322. One or more flat or planar heat sinks can additionally, or alternatively, be included, such as to dissipate heat.

FIG. 95 illustrates, by way of example, a perspective view diagram of another embodiment of the external device 8802 in an open position so as to show internal circuitry 10430, a top cover 10322, a bottom cover 10324, and connection elements 11138. In one or more embodiments, the connection elements 11138 can be magnetic and can mate with mating connection elements on the bottom cover 10324 (not shown in the perspective of FIG. 111). The connection elements 11138 as shown in FIG. 95 are situated along two, opposite sides of the external device 8802. In other embodiments, the connection elements 11138 can be situated along all sides of the external device 8802, can be situated just in the corners of the external device 8802 (as shown in FIG. 96), or other configuration. FIG. 96 illustrates, by way of example, a perspective view diagram of another embodiment of the external device 8802 in an open position so as to show the internal circuitry 10430, the top cover 10322, the bottom cover 10324, and connection elements 11138. The top cover 10322 can be reversibly secured to the bottom cover 10324 by including mating elements on each of the top cover 10322 and the bottom cover 10324, aligning the mating connection elements, and then making the connection elements contact each other.

FIG. 97 illustrates, by way of example, a perspective view diagram of an embodiment of the external device 8802 in a closed position with the attachment mechanism 9710A attached to a cover of the external device 8802. The attachment mechanism 9710A is discussed elsewhere herein.

FIG. 98 illustrates, by way of example, a block diagram of an embodiment of a system 11400 that includes multiple discrete external components (e.g., the external device 8802 and a battery 11442). The battery 11442 is external to the external device 8802 and situated near the external device 8802 in the pocket 8806 (or in the sleeve). In one or more embodiments, the battery 11442 may be situated outside the pocket 8806 or sleeve. In one or more embodiments, the battery 11442 includes one or more of a lithium polymer battery, a generally flat, flexible battery, a rechargeable battery (e.g., a wired battery charging capability or a wireless battery charging capability, such as through an inductive power link). The battery 11442 can provide electric power to the electric and electronic components (e.g., the internal circuitry 10430, such as can include a transceiver 11444 and other components, such as circuitry of the external device, the source 102, or the like).

The location circuitry 11446 includes electric or electronic components (e.g., resistors, transistors, inductors, capacitors, diodes, sensors, logic gates, oscillators, multiplexers, antennas, radios, ADCs, DACs, speakers, or the like) that aid the user in situating the external device 8802 in the proper location. The location circuitry 11446 can include components to determine a received signal strength (RSS) of a signal from the implanted device 8804. The RSS can be used to create a tone, such as through a speaker of the internal circuitry 10430 or the location circuitry 11446. The tone created can be modulated based on the value of the RSS so as to indicate to a user the relative value of the RSS. The user can then situate the external device 8802 at a location corresponding to a relatively high RSS (a tone that indicates a relatively high RSS). In one or more embodiments, the location circuitry 11446 includes a button that a user can press to initiate a placement operation and detection process. The location circuitry 11446 can provide the user with an indication (e.g., a tone or mechanical feedback, such as a vibration or pulse). The location circuitry 11446 can beep in response to the RSS dropping below a threshold value, such as to indicate to the user that the external device is not properly located. The location circuitry 11446 can refrain from beeping in response to determining the RSS is greater than (or equal to) a threshold value.

FIG. 99 illustrates, by way of example, a block diagram of an embodiment of a system 11500 that includes a single external device (the device 8802) in the pocket 8806. As is illustrated in FIG. 99, the battery 11442 can be included internal to the external device 8802, such as to be located between the top cover 10322 and the bottom cover 10324.

FIG. 100 illustrates, by way of example, a block diagram of an embodiment of a system 11600 that includes multiple discrete external devices (the device 8802 and other circuitry 11650) in the pocket 8806. The system 11600 is similar to the system 11400, with the system 11600 including only an antenna 11654 in the external device 8802, with all the remaining circuitry external to the external device 8802. The antenna 11654 is a component of the transceiver 11444 along with other circuitry. The control circuitry 11652 provides signals to the transceiver or antenna to cause the antenna to radiate electromagnetic energy, such as to the implanted device 8804. In one or more embodiments, the battery 11442 and/or the circuitry 11650 can be housed between a top cover and a bottom cover similar to the top cover 10322 and/or the bottom cover 10324, such as to help radiate heat away from the body.

The antenna 11654 and/or the circuitry 11650 can provide an indication of the location of the external device 8802 relative to the implanted device 8804. The circuitry 11650 can include a motor that can cause a vibration to modulate as the external device 8802 gets closer to/farther from the implanted device 8804. The circuitry 11650 can provide an alert to the patient if the implanted device 8804 inside the patient shifts relative to the external device 8802, such as can be detected by monitoring the RSS. The frequency at which the antenna 11654 radiates electromagnetic energy can be programmable. The circuitry 11650 can monitor an amount of energy available from the battery 11442 and provide a low battery warning (e.g., a sound or vibration) if the amount of energy available from the battery 11442 drops below a specified threshold. The circuitry 11650 can provide an indication to turn on an implanted device 8804 for treatment. The circuitry 11650 can be connected to a network, such as to provide alerts from a mobile phone or by email.

Devices that include a power transmitter, such as the external device 8802, can "overheat" and burn human skin unless they are carefully designed, especially when the device needs to be near the human body to operate properly. Data from at least one study indicates a "safe" heat absorption level of approximately 40 mW/cm$^2$. Near the overheating point, skin temperature increases approximately 0.80° C. for each additional 10 mW/cm$^2$ of absorbed power. During normal operation, the external device 8802 heats as a side effect of performing its intended function. Touching a heated device to human skin initiates a thermal transient transfer followed by a steady state. Using a pocket or sleeve around a device, or a device including an external housing, as discussed herein, such as can be used along with a device configured to transfer heat away from the body, can avoid pain and/or skin burns.

Considering steady-state and to verify thermal safety, a designer can place a finished device in ambient air, heat the device to steady state, measure a device's surface temperature, and compares the surface temperature to a "known-safe" temperature, such as 41° C. If the measured temperature is less than the "known-safe" or threshold temperature, the designer can conclude that the device will not cause pain or burning of the skin. Although checking the thermal safety of a device by comparing the surface temperature to the "known safe" temperature may be convenient, the following factors may limit its applicability: 1) when compared to human skin, the ambient air presumably provides a higher thermal resistance to heat moving from the tested device; And 2) the higher thermal resistance forces the device to reach a higher temperature than it reaches when in direct contact to a material or skin. Using ambient air, the thermal load likely produces conservative test results. However, device performance generally improves with increasing power dissipation, so the test may be unjustifiably conservative. Knowing skin-temperature response and the heat output per area of the external device 8802, the resulting skin temperature can be calculated without calculating or measuring an actual device temperature.

A problem solved by one or more embodiments discussed in this subsection can include an external device with a form factor that will conveniently and discreetly situate an external power transmitter over a desired anatomy (at a desired location). Another problem solved by one or more embodiments discussed in this subsection can include an external housing for the power transmitter (e.g., the power transmitter can be part of the circuitry 10430) that will not burn, heat, and/or generally be felt by the patient.

The form factor can include an undergarment with a pocket or other mechanism in which the device can be situated near the desired anatomy (e.g., the implanted device) and an external power transmitter device and/or pocket/sleeve can dissipate the heat produced by the power transmitter away from the body. The external form factor can include the wearable element, a battery to power the external device 8802, an antenna that is part of the internal circuitry 10430, electronics that are part of the internal circuitry 10430, the housing of the circuitry (the top cover 10322, the bottom cover 10324, and the connection elements 11138 and 11140), and/or a sleeve or pocket in which to situate the housing.

As previously discussed, human skin can be sensitive to the heat dissipated through a surface of the device. Accordingly, the skin or surface temperature of the external device or other components near the human body can be an important constraint. Temperatures at one or more surfaces of the external devices may become too hot to touch, thus leading to uncomfortable user experience. For example, a high temperature at any one of a housing surface or back cover surface, may cause a user to stop using the device altogether. Further, high temperature surfaces can become a safety hazard due to local skin burning. Thus, reducing a maximum temperature of the external devices can be an important consideration. In doing so, however, the internal temperature of handheld devices may need to be kept at temperature levels that do not have a detrimental effect on the operation and longevity of internal components.

An advantage of one or more embodiments can include an increased comfort, when wearing, of the external device for the patient. The systems discussed herein can be actively ventilated with heat and moisture regulation, such as can include air and water vapor permeability, rapid moisture absorption and conveyance capacity, absence of dampness, rapid drying, and/or low water absorption of the layer of clothing positioned to the skin. The systems discussed herein can have dimensional stability even when wet, durability, ease of cleaning and care, lightweight, and/or soft and pleasant to the touch. The systems can include a high heat transfer characteristic away from the human body, breathability, lightweight, and durability.

In accordance with several embodiments, the external device 8802 can be positioned above the left or right S3 foramen. The S3 foramina are usually located about 11 cm from the anal verge or 9 cm cephalad to the tip of the coccyx. The S3 foramina are usually located 1.5-2 cm lateral to the midline at the level of the sacral notches or about 9 cm above the coccygeal drop-off. The external device 8802 can include the location circuitry 11446 that will help the patient determine when the external device 8802 is placed over a proper location. The S3 foramina are located generally one finger breadth above and below the S4 and S2 foramina, respectively.

The external device 8802, such as can include the battery 11442 and/or other circuitry 11650, can be placed in the pocket or in a sleeve that includes layers similar to those discussed with regard to the pocket. A polymer coating can be used to line the inside of the sleeve or the pocket, such as to make it waterproof. In one or more embodiments, Layer 5 can include a type of compression/elastic band in order to compress the external device 8802 to the desired location. The compression band can be integrated into the wearable element. The compression band can include conduits (holes) large enough to allow for heat dissipation. The compression band can have multiple channels or channels of different sizes. The compression band can have a variety of elasticity properties. The compression band can be about 0.5 mm-2 mm thick (e.g., 0.5-1 mm, 1 mm-1.5 mm, 1.5 mm-2 mm, 1 mm-2 mm, 0.5 mm-1.5 mm, overlapping ranges thereof, or any value within the recited ranges). The compression band can include conduits (e.g., holes) that are larger in the y direction (parallel to the height of the user) compared to the x-direction (perpendicular to the height of the user). Such a configuration can help conserve the elasticity of the band, while still allowing for ventilation in the band. In one or more embodiments, a lower portion of the band may be void of conduits (as shown in FIG. 80), such as to help allow heat from the device to rise.

In one or more embodiments there may be more than one pocket 8806, such as to provide a means to place an external device, such as for multiple different implanted device locations in one garment. In one or more embodiments, there is a single pocket for the device 8802. The pocket can be configured to be positioned above the sciatic notch. The pocket can span a width starting from about 30 mm lateral from the center of the left S3 foramen to about 30 mm right from the center of S3 foramen. In one or more embodiments, the pocket can be a total of 140 mm (about 70 mm to the right of the midline, and about 70 mm to the left of the midline). Other dimensions may be used as desired and/or required (e.g., length of between 60 mm and 200 mm, between 60 mm and 100 mm, between 70 mm and 150 mm, between 90 mm and 180 mm, between 100 mm and 160 mm, between 120 mm and 180 mm, between 130 mm and 150 mm, between 140 mm and 200 mm, overlapping ranges thereof, or any value within the recited ranges). In one or more embodiments, there can be a left pocket and a right pocket, each above and on opposite sides of the sciatic notch, such as can include a back pocket on the back left side above the left S3 foramen and another back pocket that sits directly above the S3 foramen. Each pocket can be about 60 mm in width by 60 mm in height. Other dimensions or shapes may be used as desired and/or required (e.g., 50 mm×50 mm, 70 mm×70 mm, 60 mm×50 mm, 50 mm×60 mm).

As previously discussed, mechanisms can be used to keep the external device 8802 at a proper location within the pocket 8806. Such mechanisms can help intermittent users remove the external device 8802 and replace the external device 8802, such as without compromising the functionality of the external device 8802 or the implantable device 8804. The attachment mechanisms 9710A-B can include a mechanical based fastener such as a fabric hook and loop fastener (e.g., a VELCRO® fastener), a SCOTCH® fastener, or magnets on the unit to secure to a corresponding fastener (e.g., another VELCRO® fastener in the pocket. The VELCRO® or other fastener can allow the unit to be secured to the location. A zipper, gussets, bellows, layers with off-set slits, or extra material that folds over the pocket 8806 can be used to close off the pocket 8806 from the external environment. A bottom layer of the pocket or sleeve can be covered with a sticky material, such as to help hold the device in place. The Layer 2 and/or Layer 3 can be at least partially covered in a rubber/silicone/sticky type gel or similar to help hold the external device 8802 in place. The wearable element can be placed over the external device 8802 with rubber/gel lining the whole pocket to hold the external device 8802 in place.

The sleeve for the external device 8802 can include spandex or some type of SPANX® material that can cover the external device 8802. The sleeve for the external device 8802 can include a flap, such as to help encapsulate the external device 8802.

In one or more embodiments, a system can include a wearable element configured to be worn by a patient, and having an external device coupled thereto and configured to send and/or receive a wireless signal to communicate with an implanted device. The wearable element can include an attachment mechanism to situate the external device near (e.g., directly above, below, or to the side of) the S3 foramen so the external device will be in proximity to the implantable element. The external device 8802 can be placed at multiple locations on the wearable element. The external device 8802 can include an antenna positionable in proximity to the implanted device and configured to receive data from the implanted device or send power to the implanted device 8804. The external device 8802 can include location circuitry that provides an audible or tactile indication of the proper location of the external device 8802 on the wearable element. The external device 8802 can be a first external device and the system can include a second external device, wherein the first and second external devices are coupled to one another and positionable at multiple locations on the wearable element at a distance apart from one another. The second external device can be configured to provide power to the first external device. The second external device can include a flexible battery adapted to flex in response to motion of a user wearing the flexible battery. The wearable element can include one or more elastic straps. The wearable element can accommodate a variety of patient sizes and shapes. The wearable element can include one or more of an under garment, a pouch, a belt, and an adhesive patch. The wearable element can include at least one pocket formed therein. In one or more embodiments, the at least one pocket can be movable relative to the wearable element. The external device 8802 can include a top cover 10322 and a bottom cover 10324 as described herein.

A method for communicating with an implanted neurostimulator device, can include positioning an external device on or at least partially in a wearable element worn by a patient at one of a plurality of locations, such as to align the external device with the implanted neurostimulator device and activating the external device to transfer a wireless signal through tissue to the implanted neurostimulator device. The external device can be positioned on a skin surface positioned proximate the implanted neurostimulator device and surrounded by the wearable element. The wearable element can include a plurality of flexible straps, and the external device can be removably mated to the wearable element and positioned near (e.g., proximate to) the implanted neurostimulator device. The external device can be disposed within a pocket in the wearable element.

In one or more embodiments, the wearable element can include a form factor reducing garment, such as a SPANX® garment, spandex, yoga clothing, or the like. The external device 8802 can be worn on the wearable element. The wearable element's elasticity can be low enough to compress the external device to the desired location, while elastic enough for patient comfort. The wearable element can include a pocket for the external device. The pocket 8806 can include a one-way permeable material, such as GORE-TEX® material. The pocket can be one larger pocket with attaching mechanisms for variability in placement. The pocket can include a pocket within a pocket, so the patient can offset the external device in the x-y plane in order to make the wearable element universal for either the left or right sacral region. The wearable element can come in a variety of forms to match the patient's style. The styles can include shorts, briefs, hipsters, thongs, bodysuit, pantyhose, tights, or any type of clothes that would be considered an under garment. A sub-category of the styles can include the waist band height and the amount of leg and buttock coverage.

The elasticity and material of the wearable element can allow for different slimming levels. To smooth out curves, the wearable element material can be thinner. For shaping the body, the elasticity level can be decreased and/or the material thickness can be increased, or any combination of the two. For even more compression and sculpting, the material can be thicker and/or less elastic, or different combinations of the two to provide various levels of comfort. These combinations of material elasticity and thickness can allow the patient to choose from a variety of comfort levels and be an aesthetically pleasing solution, such as "Tummy-Taming", "Muffin Top-Reducing", or "Waist-Whittling".

The fabric may convey water vapor from body perspiration out through the material (be one-way permeable) while the pocket for the external device can remain impervious to external liquids. The wearable element may be actively ventilated, may provide heat and moisture regulation, and/or provide good air and water vapor permeability. The material can be machine washable and may not retain odors, in one or more embodiments.

An external layer of the pocket that can help keep the external device in the desired position may be dimensionally stable even when wet. The wearable element may be used as sleep wear or active wear. For sleepwear, the pants or shorts could be loose, such as with only the circumferential material that goes around the waist above the desired location made of the spandex material. The circumferential elastic part (e.g., the band 9608) of any of the active wear or sleep wear can be of uniform or non-uniform height around the waist.

Examples of different shapes, sizes, and styles of wearable elements include tight or non-tight shorts, such as mid-thigh shorts, high-thigh shorts, high-waist shorts, and/or mid-thigh shorts, briefs, such as high-waist briefs and/or retro briefs, hipsters, such as hi-hipster panty, panty boy shorts, and/or girl shorts, thongs, such as high-waisted thong, a bodysuit, such as an open bust bodysuit, a closed bust bodysuit, and/or a mid-thigh bodysuit suit, and pantyhose, such as a high waist and/or a no-show panty hose.

Some patients may not need or use constant stimulation from an implanted device, but can use stimulation intermittently from the external device 8802 to the implanted device 8804. This can be due, at least in part, to carryover effects of the electrostimulation. For example, a patient may only need stimulation one hour every 24 hours for continued efficacy of the therapy. What follows is some aspects surrounding an external device with design features specific to intermittent stimulation.

Sleepwear can include a pocket as discussed herein, such as for intermittent or constant treatment. The control circuitry 11652 can include a timer. The control circuitry 11652 can provide an indication to the user (noise, vibration, pulse, or other indication) in response to the timer beginning or expiring, such that the user can know how long to wear the external device 8802. The control circuitry 11652 can track the amount of dosage the patient has received. The control circuitry 11652 can calculate the decay of the dosage to inform the patient when a next stimulation dose is to be administered.

The external device 8802 can inform the user how long the device has been stimulating or has been turned on, such as through the control circuitry 11652. The control circuitry 11652 can automatically stop providing electrical power to the antenna in response to determining an appropriate stimulation "dosage" has been achieved.

The sleeve can have the fasteners for attachment, and for intermittent uses, the user can buy the fasteners off the shelf and stick it on to their clothing themselves, such as in embodiments in which the external device 8802 includes the location circuitry 11446. The control circuitry 11652 can use the timer to help ensure that electrostimulation is not provided to the implantable device 8804 for a specific amount of time.

The control circuitry 11652 can let the user know when the stimulation will begin and end, such as through noises and/or vibrations. The control circuitry 11652 can alert the user to indicate when the user is to remove the external device 8802 and/or when the user is to place the external device 8802 near the implanted device 8804. The control circuitry 11652 can annoy or keep alarming the user to put the external device 8802 near the implanted device 8804, such as in response to determining the external device 8802 is not sufficiently close to the implanted device 8804. In one or more embodiments, the control circuitry 11652 may constantly remind the user until the external device 8802 is correctly placed for stimulation. The reminder can have a "snooze" feature such as to remind the user after a specific amount of time has elapsed. The control circuitry 11652 can include a BlueTooth®, Wi-Fi®, Zigbee®, or other short range connection circuitry that can interface with a phone, through which a user can program the control circuitry 11652, such as to customize the alarm settings.

There can be a specific setting for the intermittent user that wears the device all day regardless of whether the stimulation is on or off. The external device 8802, such as through the control circuitry 11652, can let the patient know when the stimulation begins, ends, and/or the duration of stimulation. The external device 8802 can send an alert (e.g., an email, text, or other audible, visual or textual reminder) that a user can access via a mobile device (e.g., smartphone, tablet, computer via a software application program or a web browser). The alert may be sent by sending data over a wireless network. There can be a setting to insert the reminder on the user's calendar, such as through the control circuitry 11652.

The external device 8802 can have various sounds to indicate different alarms. These alarms can be programmed through a software application (app) on a mobile device (e.g., smartphone or computing device). The external device can be allowed to store a certain amount of data in its memory before it would have to be connected to the mobile device (e.g., phone), software application on the mobile device, or network, such as to upload the data before it is overwritten. The user can track how long, for how many days, hours, etc. the user has stimulated the implanted device, such as by using the software application. The external source 102 can be pre-programmed with a selection of therapy regimes, such that the user can select using the software application. The user defined regimes may also be customized by the user, such as to allow the user to define their own timing settings, reminders, sounds, vibrations, power on, power off, settings, stimulation schedule, etc. The software application can provide the user with the ability to find the device (in case the user has misplaced the external device 8802), such as where the external source 102, such as through the control circuitry 11652 can ping when a feature is selected on the software application or a command is otherwise provided to the software application.

The control circuitry 11652 can include a safety feature which prevents overheating of the external device 8802, such as can include monitoring of a temperature sensor reading and cutting power to the external device 8802 if a threshold temperature is met or exceeded.

A password or other security mechanism can be required by the control circuitry 11652 or the app in order to adjust stimulation settings, such as power of stimulation, duration, etc. of the stimulation. The control circuitry 11652 can include device can include a Light Emitting Diode (LED) or other light that can be red or green, or whichever color to indicate the device is on, off, or searching for the implanted device, for example.

III. Therapy and/or Data Signal Configurations

A. Backscatter Communication Techniques

FIG. 101A illustrates, by way of example, embodiments of various cross-structure leakage paths of a midfield antenna 300. In the embodiment of FIG. 101A, any one or more of the first, second, third, and fourth subwavelength structures 301-304 can be excited (e.g., using separate or discrete signals via respective RF ports) and the midfield signal 131 can be transmitted from the antenna 300. As a result of the first subwavelength structure 301 being excited, one or more leakage signals are received at the other structures, for example, because the various subwavelength structures of the antenna 300 can share a common substrate or can be otherwise electrically coupled. For example, leakage signals from the first subwavelength structure 301 can be transmitted from the first subwavelength structure 301 to the second subwavelength structure 302, transmitted to the third subwavelength structure 303, and transmitted to the fourth subwavelength structure 304. Similarly, leakage signals from the second subwavelength structure 302 can be transmitted from the second subwavelength structure 302 to the first subwavelength structure 301, transmitted to the third subwavelength structure 303, and so on.

In the embodiment of FIG. 101, leakage signals from the first subwavelength structure 301 are shown being transmitted to the second, third, and fourth subwavelength structures 302-304, and leakage signals from each of the second, third, and fourth subwavelength structures 302-304 are shown being transmitted to the first subwavelength structure 301. For clarity of the illustration, only several of the many possible leakage or interference signal paths are illustrated in FIG. 101A. For example, the only leakage signal that is illustrated as originating from the second subwavelength structure 302 is the leakage signal that is transmitted from the second subwavelength structure 302 to the first subwavelength structure 301, however, other leakage signals originating from the second subwavelength structure 302 are transmitted to the other structures as well.

The cross-structure leakage can be used constructively or intentionally in some cases to influence the midfield signal 131 generated and transmitted by the antenna 300. In other examples, the cross-structure leakage can be undesirable or can lead to complications in transmitting or receiving RF signals from the antenna 300. Various factors can contribute to the relative strength or influence of one or more leakage signals on other subwavelength structures or on the midfield signal 131 transmitted from the antenna 300. For example, a physical layout or geometry of the subwavelength structures can influence a magnitude or frequency characteristic that can be emphasized or deemphasized in leakage among the structures. In an example, an antenna with subwavelength structures arranged asymmetrically will exhibit different cross-structure leakage effects than an antenna with the subwavelength structures arranged symmetrically.

FIG. 101B illustrates, by way of example, a chart that shows embodiments of frequency-dependent leakage paths between various subwavelength structures in an antenna. The x-axis shows an excitation frequency and the y-axis shows a relative signal response amplitude in decibels (dB). In FIG. 101B, a first trace 331 corresponds to a response of the first subwavelength structure 301 to a test stimulus, for example, when no test stimulus is applied to other subwavelength structures of the antenna 300. The first trace 331 represents how much power is reflected from the first subwavelength structure 301. At 0 dB, all of the excitation power is reflected from the first subwavelength structure 301 and no signal is radiated from the antenna 300. At approximately 1.62 GHz, the first trace 311 is about −13 dB, which implies that if 3 dBm of power or test stimulus is delivered to the first subwavelength structure 301, then −10 dBm is reflected. The remainder of the power is "accepted" by or delivered to the antenna, and is radiated or absorbed as a signal loss by the antenna 300.

A second trace 332 corresponds to a leakage path between the first and second subwavelength structures 301 and 302.

That is, the second trace 332 indicates a power level of a signal received at the second subwavelength structure 302 relative to a power level of a signal input to the first subwavelength structure 301. For example, when the second trace 332 is at 0 dB, all of the power of a test stimulus that is delivered to the first subwavelength structure 301 is present at the second subwavelength structure 302. When the second trace 332 at −10 dB (e.g., around 1.55 GHz), then a 1 watt (30 dBm) stimulus applied to the first subwavelength structure 301 corresponds to 20 dBm (or 0.1 watts) of power received at the second subwavelength structure 302. Similarly, a third trace 333 corresponds to a leakage path between the first and third subwavelength structures 301 and 303, and a fourth trace 334 corresponds to a leakage path between the first and fourth subwavelength structures 301 and 304.

In an example, the backscatter signal 134 from the implantable device 110 can be received using one of the first, second, third, or fourth subwavelength structures 301-304, as further described below. Information about one or more of the different leakage paths between and among the subwavelength structures can be considered when receiving and processing the backscatter signal 134.

FIG. 102 illustrates, by way of example, a diagram of an embodiment of a system that illustrates how the antenna 108 of the implantable device 110 can be used to receive, modulate, and transmit a signal. Generally, current flowing on a transmitting antenna 12206 (e.g., corresponding to the antenna 300) leads to a first transmitted signal 12211 and a voltage induced on a receiving antenna, such as on the antenna 108. If the antenna 108 is connected to a load 12250, then a current 12221 can be induced at the antenna 108, on a signal path between the antenna 108 and the load 12250, in response to the first transmitted signal 12211 arriving at the antenna 108. The induced current 12221 at the antenna 108 leads to radiation or signal transmission from the receiving antenna 108. The radiation, or backscatter signal 12234, from the antenna 108 can be transmitted back to the original transmitting antenna 12206 and can induce a voltage on the transmitting antenna 12206. The induced voltage on the transmitting antenna 12206 can thus provide a signal that can be detected by circuitry or a load coupled to the transmitting antenna 12206.

The induced current 12221 can be based on the load 12250 that is coupled to the antenna 108. Changes in the load 12250 can influence characteristics of the induced current 12221, which in turn can influence characteristics of the backscatter signal 12234. In FIG. 102, a modulation device 12230 is coupled to the antenna 108, and the modulation device 12230 can be configured to modulate the induced current 12221. In one or more embodiments, the modulation device 12230 includes a switch or transistor configured to act as a portion of a load for the antenna 108. When the transistor's gate receives a specified threshold signal, a signal sufficient to turn the transistor on, a current signal can readily travel through the modulation device 12230. When the transistor's gate is off, then no current signal travels through the modulation device 12230. Since the induced current 12221, and thus the backscatter signal 12234, depend on a load presented to the antenna, the embodiment of FIG. 102 can provide a modulated backscatter signal 12234 according to a modulation signal 12231 provided to the modulation device 12230. In one or more embodiments, the modulation signal 12231 is a PWM signal. In one or more embodiments, the backscatter signal 12234 can be provided as a relatively short burst of (dedicated) high frequency pulses that occur at separate times, or the backscatter signal 12234 can be provided as a pulse position modulated or pulse width modulated signal. Other data or signal modulation schemes can similarly be used.

In one or more embodiments, the modulation signal 12231 can be a relatively low frequency signal relative to the first transmitted signal 12211. Thus, modulation switching control circuitry, such as in the implantable device, can operate at various data communication frequencies that can be less than an RF carrier frequency of the first transmitted signal 12211. The modulation switching control circuitry can operate at relatively low frequencies, corresponding to a power savings for the implantable device relative to other devices that use an RF generator circuitry.

FIG. 103 illustrates, by way of example, a diagram of a method 12300 that includes updating a broadcast signal based on information about an implanted device. At operation 12310, the method 12300 includes transmitting a power and/or data signal to an implanted device. For example, operation 12310 can include transmitting the midfield signal 131 from the antenna 300 of the external source 102. At operation 12320, the signal transmitted by the external source 102 can be received by the implantable device 110. At operation 12330, one or more characteristics of the received signal can be measured using the implantable device 110. For example, a magnitude of a power signal received, or an efficiency of a power transfer, can be measured or calculated, such as using processor circuitry (e.g., digital controller of FIG. 5) on board the implantable device 110.

At operation 12332, information about one or more of an operating characteristic of the implantable device 110, a therapy provided by the implantable device 110, or a physiologic parameter sensed by the implantable device 110, can be monitored by the implantable device 110. For example, information about an electrostimulation parameter, an electrode impedance characteristic, or other information can be monitored. At operation 12340, the information measured at operation 12330 and/or the information monitored at operation 12332 can be encoded into a data signal and used to generate the modulation signal 12231.

At operation 12350, the encoded information can be transmitted from the implanted device 110, for example, via the backscatter signal 12234. At operation 12360, the encoded information can be received at the external source 102. The processor circuitry 210 of the external source 102 can be used to decode the received signal, such as to extract the measured or monitored information from the implantable device 110. In one or more embodiments, at operation 12310, the method 12300 can include using the decoded information to update a power and/or data signal transmission characteristic. The method 12300 can return to operation 12310 to transmit a subsequent power and/or data signal, such as using the updated transmission characteristic.

FIG. 104 illustrates, by way of example, a diagram of an embodiment of a method 12400 that includes modulating an antenna signal receive path for a wireless signal. The method 12400 can begin with operation 12320, including receiving the signal transmitted by the external source 102 using the implantable device 110. At operation 12440, the method 12400 includes modulating a receive path in the implanted device to encode implanted device information 12430 in a communication signal. Modulating the receive path can be performed according to the example of FIG. 102, for example, using the modulation device 12230 to modulate a signal path between the antenna 108 and a load 12250. At operation 12450, the method 12400 can include transmitting a signal from the implantable device 110 by reflecting a portion of the received signal (e.g., the first transmitted signal 12211 from the antenna 300 of the external source 102) according to the modulation.

FIG. 105 illustrates, by way of example, a schematic diagram of an embodiment of a system configured to excite a midfield antenna and receive a backscatter signal. The example of FIG. 105 includes a source configured to provide the RF input signal 414, and the power divider 412, or splitter, configured to provide multiple instances or portions of an RF drive signal, such as to the antenna 300. The example includes modulation circuitry 12501 for modulating the RF drive signal, and a first preamplifier 12502. The example includes a signal splitter 12503 that divides the RF drive signal into multiple different RF signals, such as to provide multiple signals for respective different ones of the RF ports on the antenna 300.

Multiple signal channels can extend from the signal splitter 12503 to the antenna 300. A first signal channel can include first phase shifter circuitry 12505A and first amplifier circuitry 12506A, a second signal channel can include a different second phase shifter circuitry 12505B and different second amplifier circuitry 12506B, and so on. Each of the signal channels extending from the signal splitter 12503 can thus be separately adjusted or tuned to have different phase and/or amplitude characteristics for differently exciting the antenna 300 via respective RF ports.

In one or more embodiments, a fourth channel extends from the signal splitter 12503 to the antenna 300 and includes fourth amplifier circuitry 12507 and a circulator 12510. The circulator 12510 can be configured to enable use of a corresponding RF port, such as the fourth RF port 314, for both excitation via the RF input signal 414 and reception of the backscatter signal 12234. A signal received from the antenna 300, after processing by the circulator 12510, is illustrated in the example of FIG. 106A.

The example of FIG. 105 further includes a cancellation signal path from the power divider 412 to summing circuitry 12520. The cancellation signal path includes adjustable amplifier circuitry 12512 and adjustable phase shift circuitry 12515. Using the summing circuitry 12520, signals from the cancellation signal path can be summed with the backscatter signal 134 received via the antenna 300 (e.g., via an electrical signal received from the fourth RF port 314) to provide a summed signal (see FIG. 106B). In an example, the cancellation signal path provides, at the summing circuitry 12520, a signal having substantially equal amplitude and opposite phase to an expected interference signal portion received via the fourth RF port 314.

In one or more embodiments, a cancellation signal provided (e.g., after the phase shift circuitry 12515) can be defined at least in part as $-(Lc*[S_{41}P_1+S_{42}P_2+S_{43}P_3])$, where Lc is a leakage from the circulator, and Px corresponds to a transmit power for a designated port. Thus, in one or more embodiments, an appropriate cancellation signal can be determined based on prior knowledge of the behavior or self-interference of the various ports of the antenna 300. FIG. 107 illustrates an embodiment of selecting or determining an appropriate canceling signal.

The example of FIG. 105 further includes an auxiliary signal path configured to carry an auxiliary signal from the power divider 412 to mixer circuitry 12530. At the mixer circuitry 12530, the summed signal from the summing circuitry 12520 can be mixed with the auxiliary signal to provide a data signal (see FIG. 106C).

The example of FIG. 105 further includes a low-pass filter 12540, a high-pass filter 12550, and a decoder circuitry 12560. The decoder circuitry 12560 can be used to extract encoded information from the data signal after the data signal is processed by the filters 12540 and 12550. The filters 12540 and 12550 help to "clean up" the data signal to facilitate data extraction by removing noise (see FIG. 106D). For example, the filters can be used to filter out and substantially remove various harmonics generated as a result of mixing the received signal with the RF carrier.

FIGS. 106A-106D illustrate, by way of example, signal diagrams of embodiments corresponding to different portions of the system of FIG. 105. For example, the signal diagram illustrated in FIG. 106A corresponds to the portion of FIG. 105 labeled "106A", the signal diagram illustrated in FIG. 126B corresponds to the portion of FIG. 105 labeled "106B", and so on. In FIGS. 106A-106D, $f_0$ corresponds to a center frequency of a self-interference or leakage signal, such as due to cross-coupling and leakage effects of the antenna 300, described above. Sidebands of the leakage signal include components of the backscatter signal 12234. These sidebands are generally centered around $f_0-f_{BS}$ and $f_0+f_{BS}$. In one or more embodiments, $f_0$ is around 915 MHz, however, other center frequencies can be used (e.g., at or around the range of 860-960 MHz, at or around 2.45 GHz, or at or around 402 MHz to about 405 MHz, or at other frequencies). The backscatter signal 12234 can be modulated according to, for example, 40-320 kHz, however other modulation frequencies can be used (e.g., between 40 and 100 kHz, between 60 and 200 kHz, between 100 and 300 kHz, between 150 and 250 kHz, between 200 and 300 kHz, between 150 and 320 kHz, overlapping ranges thereof, or any value within the recited ranges). In one or more embodiments, the backscatter signal at $f_{BS}$ can be about 80-100 dB below the self-interference signal at $f_0$. Thus, a problem to be solved includes suppressing the self-interference signal and extracting data from the backscatter signal. A solution includes using the circuitry of FIG. 105 to introduce the cancellation signal and auxiliary signal to cancel a portion of the backscatter signal related to the self-interference of the antenna 300 itself. That is, self-interference due to coupling between ports of the antenna 300 can be significant, and the self-interference can be predicted and canceled using an opposing signal from the RF source (e.g., 180 degrees out of phase with the self-interference signal).

In an embodiment, FIG. 106A represents a communication signal modulated according to a specified modulation scheme (e.g., to encode information) that includes sidebands and a carrier frequency. FIG. 106B can represent a combination of the modulated communication signal with a cancellation signal that is 180 degrees out of phase with the communication signal. The cancellation signal can be selected or tuned based on characteristics of the adjustable amplifier circuitry 12512 and the adjustable phase shift circuitry 12515 in the cancellation signal path. Thus, the leakage signal at $f_0$ can be reduced to a DC signal with sidebands that can be extracted with a high-pass filter. In one or more embodiments, the combination of the modulated communication signal with the cancellation signal can improve a signal-to-noise ratio of the backscatter signal by about 30 dB or more (e.g., 20 to 40 dB, 25 to 35 dB, 30 to 40 dB, 20 to 30 dB, overlapping ranges thereof, or any value within the recited ranges).

Figure 106C:
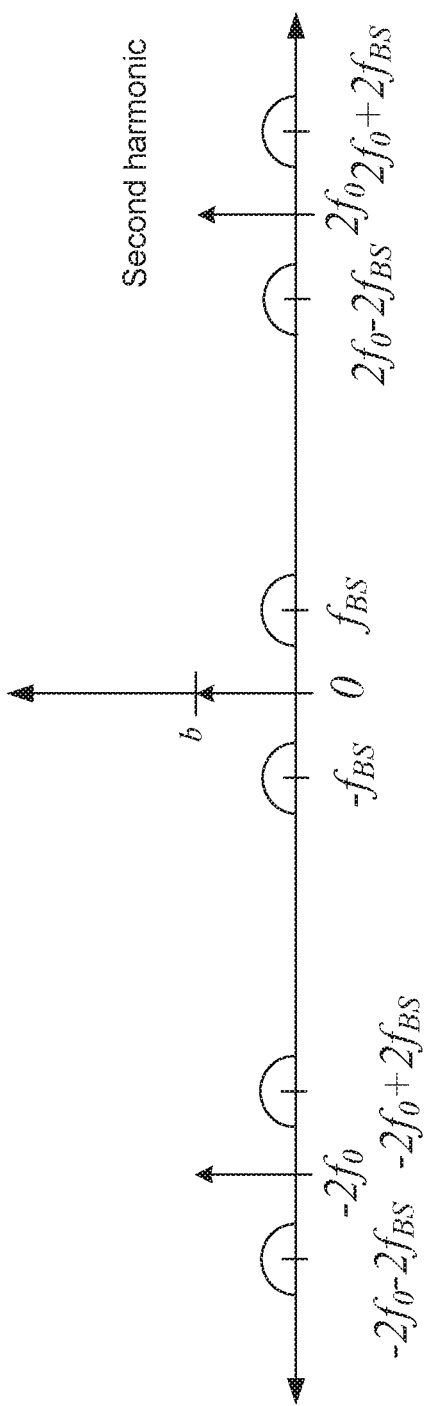
Figure 106D:
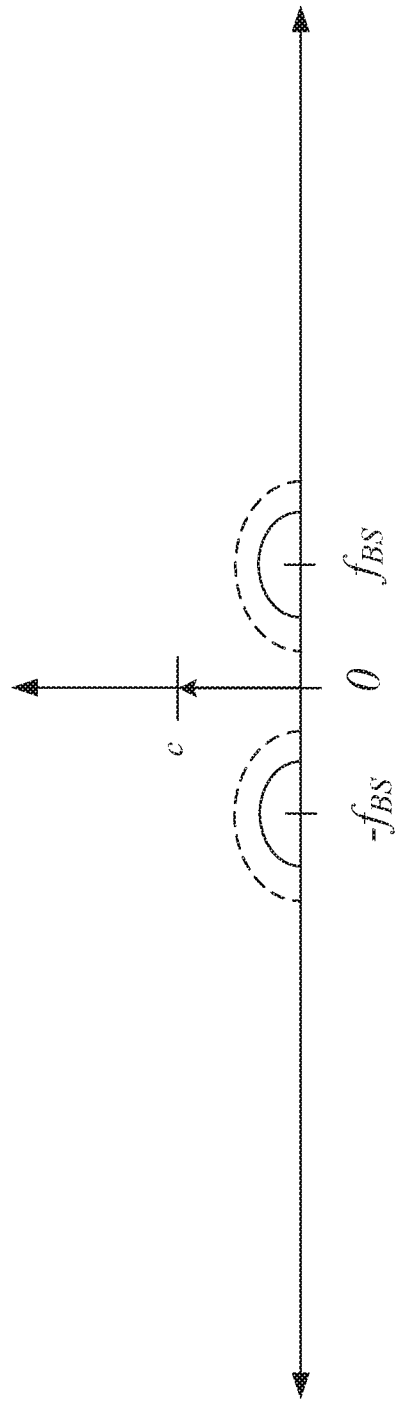

In one or more embodiments, FIG. 106C represents the communication signal after it is mixed with the auxiliary signal (e.g., a carrier signal) from the auxiliary signal path. The mixed signal includes various harmonic signal components that can be filtered out. FIG. 106D can represent the filtered backscatter signals that can be further analyzed or processed, such as using the processor circuitry 210, to retrieve information encoded by the implantable device 110. Further analog and/or digital filtering can be performed to recover data signal components.

In one or more embodiments, an initial model can be generated to describe the coupling characteristics, or self-interference, of the antenna 300. From that initial model, slight perturbations in the phase can be injected in the signal to create layers of cancellation in an algorithm. FIG. 107, for example, illustrates, by way of example, a diagram of an embodiment of a method 12700 that includes adjusting an amplitude and/or phase characteristic of a cancellation signal.

At 12710, the method of FIG. 107 includes setting a gain characteristic of the adjustable amplifier circuitry 12512 to an initial gain level, and/or setting a phase shift characteristic of the adjustable phase shift circuitry 12515 to an initial phase shift level, to provide a cancellation signal. At operation 12720, a DC component of the received signal can be measured when the external source 102 receives the backscatter signal 12234, such as to determine an effectiveness of the cancellation signal. At operation 12725, an amplitude characteristic of the measured DC signal can be compared with a threshold. If the DC signal is within a threshold margin, then the initial gain level and/or the initial phase shift level can be set as a reference and used for further signal processing. If the DC signal is outside of the threshold margin, then, at operation 12730, the initial gain level and/or the initial phase shift level can be changed or perturbed, such as at the same time or in turn.

After the gain and/or phase shift characteristics are perturbed, the method can continue at operation 12740 by measuring the DC component again. At operation 12745, if the DC signal level is not decreased, then at operation 12750 the method can revert to a prior gain and/or phase shift level, and then return to operation 12730 for further adjusting the gain and/or phase shift. If, at operation 12745, the DC signal level decreased, then the method continues at operation 12747 to check whether the DC signal level is within the specified threshold margin. If the signal is not within the specific margin, then the method returns to operation 12730 for further adjusting the gain and/or phase shift. If the signal is within the specified margin at operation 12747, then the method continues to operation 12760. At operation 12760, the adjusted gain and/or phase shift level(s) can be set as a reference for use in recovering data from the backscatter signal 12234.

In one or more embodiments, a self-jamming cancellation algorithm based on coupling or self-leakage characteristics of the antenna 300 includes (1) assuming an initial coupling or leakage characteristic between different ports of the antenna 300 (see, e.g., the example of FIG. 3), (2) determining an n-order polynomial equation to fit or model the leakage characteristic, (3) using the external source 102, sending a command to the implantable device 110 to introduce an expected phase perturbation into a backscatter signal to be received by the external source 102 (such a low-level phase modulation, also known as phase jitter modulation, can be in the form of a regular pattern or a pseudo-random pattern, or the backscatter circuitry can use OOK modulation of the backscatter signal (e.g., with full modulation depth) by modulating the backscatter signal with a switch to detune a receive antenna, such as including modulating in the 0-1 MHz range), (4) subtracting the phase jitter from the received backscatter signal at the external source 102 to obtain a signal of interest (e.g., in the OOK method, the received signal can be mixed with the transmitter carrier RF signal and filtered to extract the modulated signal), and (5) updating the external source 102, e.g. to adapt to a degraded received signal, by instructing the external source to send a different phase jitter instruction to the implantable device 110. In one or more embodiments that includes multiple implantable devices powered by a single external source 102, each implantable device 110 can have a unique identification code and the external source 102 can transmit a unique phase jitter command to each implantable device 110.

B. Active Power Management Techniques for Wireless Implantable Devices

Generally discussed in this subsection are systems, devices, and methods for providing or delivering a therapy using an implantable device. In one or more embodiments, the therapy includes an electrostimulation therapy provided to one or more neural targets in a body. In one or more embodiments, the electrostimulation therapy is provided using an implant device that wirelessly receives power and data signals from a midfield transmitter (e.g., an external source, such as the source 102).

There is a current unmet need that includes communicating power and/or data using midfield transmitters and receivers, such as to communicate power and/or data from an external midfield coupler to one or more implanted neural stimulation devices and/or one or more implanted sensor devices.

In one or more embodiments, multiple devices can be implanted in patient tissue and can be configured to deliver a therapy and/or sense physiologic information about a patient. The multiple implanted devices can be configured to communicate with one or more external devices. In one or more embodiments, the one or more external devices are configured to provide power and/or data signals to the multiple implanted devices, such as concurrently or in a time-multiplexed (e.g., "round-robin") fashion. The provided power and/or data signals can be steered or directed by an external device to efficiently transfer the signals to an implantable device. Although the present disclosure may refer to a power signal or data signal specifically, such references are to be generally understood as optionally including one or both of power and data signals.

Several embodiments described herein are particularly advantageous because they include one, several, or all of the following benefits: (i) a dynamically configurable, active midfield transceiver that is configured to provide RF signals to modulate an evanescent field at a tissue surface and thereby generate a propagating field within tissue, such as to transmit power and/or a data signal to an implanted target device, (ii) a dynamically configurable, substantially passive midfield transceiver or lens that is configured to receive remote RF signals and in response provide RF signals to modulate an evanescent field at a tissue surface and thereby generate a propagating field within tissue, such as to transmit power and/or a data signal to an implanted target device; (iii) a tunable device for changing one or more RF signal receipt or transmission characteristics; (iv) feedback circuitry for updating or adjusting one or more signal receipt or transmission characteristics based on previous or current signal transmission activity; (v) adjustable midfield and far-field RF signal sources that can change a power transmit level based on information from one or more other midfield devices or implanted devices; (vi) providing power and/or data signals to multiple target devices using a common source device, such as concurrently or at different time intervals; (vii) sensing backscatter signal information to determine a quality of a signal transmission to a target device implanted in tissue; and/or (viii) providing power and/or data signals to one target device using multiple different source devices.

In one or more embodiments, the digital controller 548, the amplifier 555, and/or the stimulation driver circuitry 556, among other components of the circuitry 500, can comprise portions of a state machine device. See FIG. 5 for the digital controller 548, amplifier 555, and/or the stimulation driver circuitry 556. The state machine device can be configured to wirelessly receive power and data signals via the pad(s) 536 and, in response, release or provide an electrostimulation signal via one or more of the outputs 534. In one or more embodiments, such a state machine device needs not retain information about available electrostimulation settings or vectors, and instead the state machine device carries out or provides electrostimulation events substantially immediately after, and in response to, receipt of instructions from the wireless transmitter.

For example, the state machine device can be configured to receive an instruction to deliver a neural electrostimulation therapy signal, such as at a specified time or having some specified signal characteristic (e.g., amplitude, duration, etc.), and the state machine device can respond by initiating or delivering the therapy signal. At a subsequent time, the device can receive a subsequent instruction to terminate the therapy, to change a signal characteristic, or to perform some other task. Thus, the device can optionally be configured to be substantially passive, or responsive to contemporaneously-received instructions.

In some embodiments of the midfield source devices described herein, a target or focal region can be adjusted, such as without mechanical reconfiguration of the source, using degrees of freedom provided by the amplitudes and phases of the input port signals. Such field directing or focusing can be useful in applications in which a source may be used to power implantable devices configured to interact with organs in rhythmic motion (e.g., due to breathing or heartbeat), to power one or more implantable devices, or to power an implantable device that is movable inside the body.

To shift a focal region, excitation signal characteristics for different subwavelength structures (e.g., subwavelength structures that are part of the same or different source device) can be configured and reconfigured, such as in real-time, such as to enable various field patterns to be provided.

FIG. 108 illustrates, by way of example, a diagram of an embodiment of a system 7600 for selectively providing power and/or a data communication signals to (respective) multiple target devices. The system 7600 includes the antenna 300 (see FIG. 3), such as can be included or used in the source 102 (see FIG. 1). The antenna 300 can be configured to communicate power and/or data signals to one or both of a first target device 7611 and a second target device 7612. That is, the external midfield device (e.g., the antenna 300 or circuitry that can be electrically coupled thereto, such as illustrated in FIG. 4 among other FIGS.) can be configured to manipulate an evanescent field at or near an external tissue surface to direct transmission of wireless power and/or data signals within the tissue, such as to the first and/or second target device 7611 and 7612. In FIG. 108, the first and second target devices 7611 and 7612 are therapy delivery or sensor devices, and each includes multiple electrodes E0, E1, E2, and E3. Other target devices can similarly be used and may have different numbers and/or configurations of electrodes. The first target device 7611 and the second target device 7612 can be similar to or the same as the implantable device 110, 600, 700, or other implantable device discussed herein.

In one or more embodiments, the external midfield device communicates signals to the first and second target devices 7611 and 7612 at different, non-overlapping time intervals. For example, the external midfield device can send signals to and/or receive signals from the first target device 7611 during a first interval $\Delta t1$ and a third interval $\Delta t3$, and the external midfield device can send signals to and/or receive signals from the second target device 7612 during a second interval $\Delta t2$ and a fourth interval $\Delta t4$. The external midfield device can communicate power and/or data in a round-robin manner, with the antenna 300 providing different signals to different targets at different times. Optionally, the external midfield device provides a blanking period or delay between the different communication intervals. An example illustrating communication intervals is presented graphically in FIG. 109.

FIG. 109 illustrates, by way of example, a diagram of an embodiment of a method that includes using different signal characteristics to communicate power and/or data signals to different target devices at different times. In the method of FIG. 109, the external midfield device corresponds to the source 102 of FIG. 1. That is, the external midfield device includes four subwavelength structures that can be separately excited by respective RF drive signals. In one or more embodiments, the amplifiers 408A-D and/or the phase shifters 410A-D from the example of FIG. 4 can be respectively coupled to the subwavelength structures of the external midfield device, such as to provide separate RF drive signals to each of the subwavelength structures. The subwavelength structures of the external midfield device can be concurrently excited to transmit a set of RF signals that together can influence evanescent and propagating waves, such as to direct power and/or data communication signals to various targets within tissue.

FIG. 109 illustrates a series of signals, including first, second, third, and fourth signals S1, S2, S3, and S4, respectively, that are sequentially transmitted from the external midfield device to one or the other of the first and second target devices 7611 and 7612. Each of the signals S1-S4 can be transmitted by the external midfield device when the transceiver is configured in a specified manner to influence evanescent fields at the tissue surface and, as a result, generate a propagating signal directed or focused toward a specified target. For example, during a first transmission interval $\Delta t1$ and during a third transmission interval $\Delta t3$, the external midfield device is configured to transmit the first and third signals S1 and S3, respectively, to the first target device 7611.

In FIG. 109, the external device transmit signal illustrates generally that an RF signal, or a set of RF signals, is transmitted over a specified interval. Although the external device transmit signal is illustrated as a square wave, it can represent other, time-varying or static signals transmitted during the various specified intervals. For example, the first signal S1 can correspond to a first PWM signal having a first duty cycle that is provided during the first transmission interval $\Delta t1$, and the second signal S2 can correspond to a different PWM signal having a second duty cycle that is provided during the second transmission interval $\Delta t2$. Other signal types can similarly be used.

During the first transmission interval $\Delta t1$ and the third transmission interval $\Delta t3$, the external midfield device is configured to excite a first one of its subwavelength structures ("Structure 1") using a reference RF drive signal, such as can have a reference phase angle $\Phi_{Ref}$ and can be provided at an amplifier power saturation level Psat, to transmit the first signal S1 or the third signal S3 to the first target device 7611. During the first transmission interval Δt1 and the third transmission interval Δt3, the external midfield device is configured to excite second, third, and fourth subwavelength structures ("Structure 2", "Structure 3", "Structure 4") using phase-shifted versions of the reference RF drive signal. For example, the second subwavelength structure can receive an excitation signal that is phase-shifted from the reference by $\Phi_{1-Dev1}$, the third subwavelength structure can receive an excitation signal that is phase-shifted from the reference by $\Phi_{2-Dev1}$, and the fourth subwavelength structure can receive an excitation signal that is phase-shifted from the reference by $\Phi_{3-Dev1}$. In one or more embodiments, any two or more of $\Phi_{1-Dev1}$, $\Phi_{2-Dev1}$, and $\Phi_{3-Dev1}$ can refer to the same or different phase-shift magnitude.

In one or more embodiments, each of the subwavelength structures can receive an RF drive signal having a different power characteristic. Any one or more of the signals provided to the first through fourth subwavelength structures can be provided at its respective amplifier power saturation level, or at some other power level. In one or more embodiments, each amplifier that is coupled to a subwavelength structure can have a current supply that is tuned to change the amplifier's saturation power. As a result, one or more of the structures can be driven by different power levels, yet each drive signal can be provided under saturation conditions.

In one or more embodiments, the first signal S1 transmitted during the first transmission interval Δt1 is the same power and/or data signal that is transmitted as the third signal S3 during the third transmission interval Δt3. In one or more embodiments, the first signal S1 is different than the third signal S3. That is, the first signal S1 and the third signal S3 can include different levels of power and/or can include different data or information transmitted from the external midfield device to the first target device 7611.

During the second transmission interval Δt2 and the fourth transmission interval Δt4, the external midfield device is configured to excite a first one of its subwavelength structures using a reference RF drive signal, such as can be provided at an amplifier saturation level Psat, to transmit the second signal S2 and the fourth signal S4 to the second target device 7612. The second target device 7612 can be in a location other than the location of the first target device 7611. During the second transmission interval Δt2 and the fourth transmission interval Δt4, the external midfield device is configured to excite second, third, and fourth subwavelength structures using phase-shifted versions of the reference RF drive signal. For example, the second subwavelength structure can receive an excitation signal that is phase-shifted from the reference by $\Phi_{1-Dev2}$, the third subwavelength structure can receive an excitation signal that is phase-shifted from the reference by $\Phi_{2-Dev2}$, and the fourth subwavelength structure can receive an excitation signal that is phase-shifted from the reference by $\Phi_{3-Dev2}$. In one or more embodiments, any two or more of $\Phi_{1-Dev2}$, $\Phi_{2-Dev2}$, and $\Phi_{3-Dev2}$ can refer to the same or different phase-shift magnitude. In one or more embodiments, at least one of $\Phi_{1-Dev2}$, $\Phi_{2-Dev2}$, or $\Phi_{3-Dev2}$ is different than its corresponding $\Phi_{1-Dev1}$, $\Phi_{2-Dev1}$, and $\Phi_{3-Dev1}$, such that the field transmitted from the external midfield device differently influences an evanescent field during transmission of the first and second signals S1 and S2 to differently direct propagating waves toward the first and second target devices 7611 and 7612, respectively.

FIG. 110 illustrates, by way of example, a diagram of an embodiment of a method 7800 that includes receiving power transfer efficiency information from multiple target devices. At operation 7810, the method can include generating a first set of RF signals. In one or more embodiments, and with reference to FIG. 4, generating a first set of RF signals can include dividing the RF input signal 414 and providing multiple separate signals, such as including phase-modulated and/or amplitude-modulated versions of a reference signal, to one or more output ports or subwavelength structures in a transmitter or transceiver, such as the external midfield device. At operation 7820, the method can include transmitting the first set of RF signals by exciting multiple different subwavelength structures in the external midfield device using respective separate RF signals.

At operation 7830, and in response to the transmitting the first set of RF signals at operation 7820, the method 7800 can include receiving a first signal at a target device, such as at the first target device 7611. The received first signal can include at least a portion of the transmitted set of RF signals from the external midfield device. That is, the set of RF signals transmitted by the external midfield device can create a propagating wave signal, and at least a portion of that propagating wave signal can be received by receiver circuitry (e.g., comprising a portion of the demodulator 544 or the rectifier 546 of the example of FIG. 5) at the target device (e.g., an implantable device).

At operation 7835, the method can include receiving a signal transfer quality indication at the external midfield device, such as based on the first signal received at the first target device 7611. In one or more embodiments, the signal transfer quality indication includes a data signal transmitted from the first target device 7611 to the external midfield device (e.g., transmitted using RF, near-field, optical, or other communication channel). The data signal can include information about a quantity of power received and/or information about a quality or coherence of data received at operation 7830.

In one or more embodiments, the signal transfer quality indication includes receiving a backscatter signal at the external midfield device, such as substantially concurrently with the transmitting the first set of RF signals at operation 7820. At operation 7835, the received backscatter signal can include information about a portion of the transmitted first set of RF signals that is received by the first target device 7611. That is, based on characteristics of the received backscatter signal, the external midfield device can be configured to determine how much of a power signal transmitted was received at the first target device 7611. In one or more embodiments, an amplitude of a backscatter signal can be proportional to an amount of power received at a target device. In one or more embodiments, a power transfer efficiency characteristic can be determined based on the amplitude of the backscatter signal, or based on a received signal transfer quality indication.

At operation 7840, one or more parameters of the external midfield device can be updated or adjusted, such as to reconfigure the external midfield device for power and/or data communication with the second target device 7612. For example, updating the signal generator parameters at operation 7840 can include updating a phase-modulation or amplitude-modulation characteristic associated with one or more of the RF signal channels coupled to subwavelength structures of the external midfield device. At operation 7850, the method 7800 includes generating a second set of RF signals using the updated signal generator parameters. In FIG. 110, the second set of RF signals generated at operation 7850 is different than the first set of RF signals generated at operation 7810. That is, at least one of the signals in the first set of RF signals includes a characteristic (e.g., amplitude, frequency, phase, morphology, etc.) that is different than at least one of the signals in the second set of RF signals. At operation 7860, the method 7800 includes transmitting the second set of RF signals, such as using the same external midfield device. In one or more embodiments, the same transceiver is used but different excitation ports and/or subwavelength structures are used to transmit the first and second sets of RF signals at operations 7810 and 7860.

At operation 7870, and in response to the transmitting the second set of RF signals at operation 7860, the method 7800 can include receiving a second signal at a target device, such as at the second target device 7612. The received second signal can include at least a portion of the transmitted second set of RF signals from the external midfield device. That is, the second set of RF signals transmitted by the external midfield device can create a propagating wave signal, and at least a portion of that propagating wave signal can be received by receiver circuitry (e.g., comprising a portion of the demodulator 544 or the rectifier 546 of the example of FIG. 5) at the second target device 7612.

At operation 7875, the method 7800 can include receiving a signal transfer quality indication at the external midfield device, such as based on the second signal received at the second target device 7612. In one or more embodiments, the signal transfer quality indication includes a data signal transmitted from the second target device 7612 to the external midfield device (e.g., transmitted using RF, near-field, optical, or other communication channel). The data signal can include information about a quantity of power received and/or information about a quality or coherence of data received at operation 7870.

FIG. 111 illustrates, by way of example, a diagram of an embodiment of a method 7900 that includes updating a characteristic of at least one signal in a set of RF signals based on a data signal received from a target device. At operation 7910, the method 7900 includes transmitting a first set of RF signals using a midfield transmitter. For example, the transmitting can include exciting multiple different subwavelength structures in the external midfield device using respective separate RF signals.

At operation 7920, such as in response to the transmitting the first set of RF signals at operation 7910, the method 7900 can include receiving a first signal at a target device, such as at the first target device 7611. The received first signal can include at least a portion of the transmitted set of RF signals from the external midfield device. That is, the set of RF signals transmitted by the external midfield device at operation 7910 can create a propagating wave signal, and at least a portion of that propagating wave signal can be received by receiver circuitry (e.g., comprising a portion of the demodulator 544 or the rectifier 546 of the example of FIG. 5) at the first target device 7611.

At operation 7930, the method 7900 can include delivering a neural electrostimulation therapy signal using the first target device 7611, and using at least a portion of the first signal received at operation 7920. For example, the first signal received at operation 7920 can include a power signal that can be stored, at least temporarily, by the first target device 7611, such as by using one or more capacitors. The power signal can be provided to the stimulation driver circuitry 556, for example, which can be coupled to one or more electrodes (e.g., E0-E3) of the first target device 7611. The stimulation driver circuitry 556 can use the power signal to provide an electrostimulation signal to provide a therapy.

At operation 7940, the method 7900 can include providing a data signal from the first target device 7611 to the external midfield device. The data signal can include information about the therapy signal delivered at operation 7930, or the data signal can include information about a status of the first target device 7611, among other things. For example, the data signal can include information about a remaining or available power, such as can be used by the first target device 7611 and/or the external midfield device to determine whether or when to request or provide an additional power signal transfer from the external midfield device to the first target device 7611. In one or more embodiments, the data signal includes information about a quality of the first signal received at operation 7920. Based on the quality information, the external midfield device can update or adjust a device parameter to enhance the quality of subsequent transmissions.

For example, at operation 7950, the external midfield device can update a characteristic of at least one of the RF signals, in the first set of RF signals, based on the data signal provided by the first target device 7611 at operation 7940. Updating a characteristic can include changing one or more of a signal amplitude, frequency, phase, morphology, or other characteristic of at least one of the signals in the first set of RF signals. When at least one of the signals in the set of RF signals is changed, then the evanescent field at the tissue surface can be differently manipulated, such as to differently direct a propagating wave within tissue.

FIG. 112 illustrates, by way of example, a diagram of an embodiment of a method 8000 that can include updating a characteristic of at least one signal in a set of RF signals based on a backscatter signal. At operation 8010, the method 8000 includes transmitting a first set of RF signals using a midfield transmitter. For example, the transmitting can include exciting multiple different subwavelength structures in the external midfield device using respective separate RF signals to generate a propagating field in tissue.

At operation 8020, the method 8000 can include receiving a first signal at the first target device 7611, such as described above at operation 7920. Substantially concurrently with operation 8020, and at operation 8025, the external midfield device can receive a backscatter signal, such as in response to the transmitted first set of RF signals at operation 8010. The backscatter signal can include a diffused portion of the transmitted first set of RF signals. Based on the status of the first target device 7611 (e.g., the first target device 7611 being in a transmit mode or a receive mode), the first target device 7611 can influence or modulate the portion of the first set of RF signals that is reflected or backscattered toward the transmitter or external midfield device. In one or more embodiments, the backscatter signal is proportional to the received power at the first target device 7611.

At operation 8050, based on the received backscatter signal at operation 8025, the method 8000 can include updating a characteristic of at least one of the RF signals in the transmitted first set of RF signals. For example, if the backscatter signal has an amplitude other than an expected amplitude, then the external midfield transceiver can change one or more characteristics of the RF signals in the first set of RF signals, such as to redirect a propagating wave toward the first target device 7611.

FIG. 113 illustrates, by way of example, a diagram of an embodiment of a method 8100 that includes updating a characteristic of at least one signal in a set of RF signals based on a data signal received from a target device. At operation 8110, the method 8100 includes transmitting a first set of RF signals using a midfield transmitter (e.g., the antenna 300, the source 102, or other midfield device discussed herein). For example, the transmitting can include exciting multiple different subwavelength structures in the external midfield device using respective separate RF signals to generate a propagating field in tissue.

At operation 8120, and in response to the transmitting the first set of RF signals at operation 8110, the method 8100 can include receiving a first signal at first and second target devices, such as at the first target device 7611 and at the second target device 7612. The first signal can be received substantially concurrently by the first and second target devices 7611 and 7612. The received first signal can include at least a portion of the transmitted set of RF signals from the external midfield device. That is, the set of RF signals transmitted by the external midfield device can create a propagating wave signal, and at least a portion of that propagating wave signal can be received by respective receiver circuitry (e.g., comprising a portion of the demodulator 544 or the rectifier 546 of the circuitry of FIG. 5) at the target devices.

At operation 8140, the method 8100 includes providing a data signal from one or both of the first target device 7611 and the second target device 7612 to the external midfield device. In one or more embodiments, the data signals include information about a status of the target devices, or a therapy delivered from one or both of the target devices, among other things. For example, the data signal can include information about a remaining or available power, such as can be used by the first target device 7611 and/or the external midfield device to determine whether or when to request or provide an additional power signal from the external midfield device to the first target device 7611. In one or more embodiments, the data signal includes information about a quality of the first signal received by one or both of the target devices at operation 8120. Based on the quality information, the external midfield device can update or adjust a device parameter to enhance the quality of subsequent transmissions, such as by directing or steering a subsequent propagating wave signal toward one or the other of the first and second target devices 7611 and 7612.

In one or more embodiments, at operation 8150, the external midfield device can update a characteristic of at least one of the RF signals, in the first set of RF signals, such as based on one or both of the data signals provided by the first or second target devices 7611 and 7612 at operation 8140. Updating a characteristic can include changing one or more of a signal amplitude, frequency, phase, morphology, or other characteristic of at least one of the signals in the first set of RF signals. When at least one of the signals in the set of RF signals is changed, then the evanescent field at the tissue surface can be differently manipulated, such as to differently direct a propagating wave within tissue. For example, as a result of updating a signal characteristic at operation 8150, a different second set of RF signals can be provided by the external midfield device, such as to direct transmission of a power or data signal to only one of the first and second target devices 7611 and 7612, or to another device.

FIG. 114 illustrates, by way of example, a diagram of an embodiment of a system 8200 for selectively providing power and/or data communication to multiple target devices using a remote RF source and a midfield device. The system 8200 includes a remote field source 8220, an external device 8205, and multiple target devices. The external device 8205 can be configured to receive a field or an electromagnetic, remote signal from the remote field source 8220, modulate the received signal, and in response communicate power and/or data signals to one or both of the first target device 7611 and the second target device 7612. That is, the external device 8205 can be configured to manipulate an evanescent field at or near an external tissue surface to direct transmission of wireless power and/or data signals within the tissue, such as to the first and/or second target device 7611 and 7612. The external device 8205 can be configured to communicate the power and/or data signals to a target device concurrently or asynchronously with receiving the remote signal from the remote field source 8220.

The remote field source 8220 can be configured to provide an electromagnetic field or remote RF signal (herein, "remote signal") that can be received and/or modulated by the external device 8205. The remote field source 8220 can include an RF generator circuitry 8222 that is configured to generate one or more RF signals based on instructions from a control circuitry 8221. The control circuitry 8221 can provide signal parameter information to the RF generator circuitry 8222, such as can include amplitude, frequency, phase, waveform morphology, or other signal parameter information. The remote field source 8220 can further include a memory circuitry 8224 or clock circuitry 8225 in data communication with one or more of the control circuitry 8221 and RF generator circuitry 8222, such as to store the signal parameter information and/or to trigger signal generation. In one or more embodiments, the remote field source 8220 includes a feedback control circuitry 8223 that can use the control circuitry 8221 to change one or more signal parameters and thereby change a characteristic of the remote signal that is provided. In one or more embodiments, the remote field source 8220 includes multiple RF outputs, and the multiple outputs can be excited independently. The multiple outputs can be excited concurrently or at separate times. In one or more embodiments, each output is coupled to a different phase shifter 8226A-8226D that can be used to change a characteristic of the outputted remote signal. Other signal-modifying elements can be included at or before the outputs, such as amplifier or attenuator circuitry.

The external device 8205 can include various hardware structures that are configured to receive a portion of the remote signal from the remote field source 8220 and, in response, transmit one or more different signals to the target devices. The external device 8205 can receive far field energy, such as from the remote field source 8220, and can use at least a portion of the received energy to manipulate an evanescent field and direct a power and/or data signal to a target device. In one or more embodiments, the external device 8205 includes a control circuitry that harvests at least a portion of the energy received from the remote field source 8220 and controls one or more tunable devices 8206. The tunable devices 8206 can be used to change a characteristic of an input or receiver circuitry, such as to facilitate reception of the remote signal from the remote field source 8220. The tunable devices 8206 can be used to change a characteristic of an output or transmitter circuitry, such as to change a characteristic of a power and/or data signal transmitted from the external device 8205 to one of the first and second target devices 7611 and 7612. In one or more embodiments, the external device 8205 includes a transceiver circuitry 8207 configured to relay data communications between the remote field source 8220 and one or more target devices.

The remote field source 8220 can provide or broadcast the remote signal over a field interval $\Delta t0$. In response, the external device 8205 can communicate power and/or data to the first and/or second target devices 7611 and 7612 over the first through fourth intervals $\Delta t1$-$\Delta t4$. The field interval $\Delta t0$ can optionally at least partially overlap in time with one or more of the first through fourth intervals Δt1-Δt4. Other transmission interval schemes can similarly be used. The discussion of FIG. 84 includes an example of using the remote field source 8220 and the external device 8205 to communicate multiple signals to different target devices.

In one or more embodiments, the external device 8205 and/or the remote field source 8220 can include or use a sensor, such as the sensor 107 in the example of FIG. 1. Information from the sensor can be used by the external device 8205 and/or by the remote field source 8220 to update a signal characteristic or therapy parameter.

FIG. 115 illustrates, by way of example, a schematic of an embodiment of the external device 8205 (sometimes referred to as a midfield coupler, external source, or external device) with multiple tunable devices 8206. The external device 8205 is provided above an interface between air 8304 and a higher-index material 8306, such as body tissue. In one or more embodiments, the external device 8205 can be conceptualized as a lens that receives an electromagnetic signal and focuses or directs the received signal in a specified and controlled manner.

The external device 8205 can include one or more subwavelength structures configured to receive an input RF signal (e.g., a far-field RF signal), and can include the same or other subwavelength structures configured to transmit one or more output RF signals to influence an evanescent wave at a tissue surface and thereby communicate power and/or data to one or more target devices.

The tunable devices 8206 can include various passive or active devices that can be used to change an electrical signal characteristic. Some examples of a tunable element include a capacitor, resistor, inductor, amplifier circuitry, phase modulation circuitry, or other element, device, or circuitry that can be configured to receive an electrical signal and, in response, provide a different or updated electrical signal.

In one or more embodiments, the external device 8205 includes control circuitry that controls parameters of the tunable devices 8206. For example, the control circuitry can be configured to change a capacitance of a capacitor element in the external device 8205 to change an RF output signal characteristic. In one or more embodiments, the control circuitry is powered using a portion of an RF signal received at the external device 8205 from the remote field source 8220. The control circuitry can include components similar to, or the same as the processor circuitry 210, digital controller 548, or other control circuitry discussed herein.

In one or more embodiments, the external device 8205 includes memory circuitry (not shown in FIG. 114, see FIG. 136 for one or more embodiments of memory circuitry) that can be used to store parameter information for the tunable devices 8206. In one or more embodiments, the memory circuitry (e.g., nonvolatile, read-only, and/or flash memory) stores configuration information for the external device 8205, and the configuration information can include reference parameter information for the tunable devices 8206, historical parameter value information for the tunable devices 8206, or other information regarding a configuration or operating status of the external device 8205, the remote field source 8220, or one or more remote target devices.

FIG. 116 illustrates, by way of example, a diagram of an embodiment of a method that includes using different signal characteristics to communicate power and/or data signals to different target devices at different times. The external device 8205 can receive a remote field signal over the field interval Δt0. The remote field signal can include power and/or data for use by the external device 8205 to facilitate communication from the external device 8205 to the first and second target devices 7611 and 7612.

In one or more embodiments, the external device 8205 includes the same or similar features to those described above for the source 102 of FIG. 1. That is, the external device 8205 can include multiple (e.g., four) subwavelength structures that can be separately excited by respective RF drive signals. The subwavelength structures of the external device 8205 can be separately or concurrently excited to transmit a set of RF signals that together can influence evanescent and propagating waves, such as to direct power and/or data communication signals to various targets within tissue.

FIG. 116 illustrates a series of signals, including first, second, third, and fourth signals S1, S2, S3, and S4, respectively, that are sequentially transmitted from the external device 8205 to one or the other of the first and second target devices 7611 and 7612. Each of the signals S1-S4 is transmitted by the external device 8205 when it is configured in a specified manner to influence evanescent fields at the tissue surface and, as a result, generate a propagating signal directed or focused toward a specified target. For example, during a first transmission interval Δt1 and during a third transmission interval Δt3, the external device 8205 is configured to transmit the first and third signals S1 and S3, respectively, to the first target device 7611.

In FIG. 116, the external device signal illustrates generally that an RF signal, or a set of RF signals, is transmitted over specified intervals. Although the external device signal is illustrated as a square wave, it can represent other, time-varying or static signals transmitted during the various specified intervals. For example, the first signal S1 can correspond to a first PWM signal having a first duty cycle that is provided during the first transmission interval Δt1, and the second signal S2 can correspond to a different PWM signal having a second duty cycle that is provided during the second transmission interval Δt2. Other signal types can similarly be used.

As shown in FIG. 116, the remote field signal is transmitted, such as from the remote field source 8220 to the external device 8205, over the field interval Δt0 that begins at time to and ends at time $t_{f1}$. In response to receipt of the remote field signal at the external device 8205, the external device 8205 can modulate the received signal, and/or generate a new signal, to provide the first signal S1 to the first target device 7611. As shown in FIG. 116, the first signal S1 is transmitted beginning at time $t_1$ following time $t_{f0}$. The duration between $t_1$ and $t_{f0}$ can represent a power-up or charging time for the external device 8205, or the external device 8205 can be instructed to inhibit transmission of the first signal S1 until the specified time $t_1$. The remote field can be provided substantially continuously over at least the first, second, and third signals S1, S2, and S3. Other transmission configurations can similarly be used, for example, the remote field can be intermittently provided or received at the external device 8205, and the external device can include one or more signal storage circuitry that can be used to store power signals that can be later used to transmit power and/or data to a target device. For example, the remote field can terminate at a time $t_{f1}$, such as before transmission of the fourth signal S4 is completed. That is, at least a portion of the fourth signal S4 can be transmitted from the external device 8205 when the remote field is absent, for example by configuring the external device 8205 to use a power signal stored at the external device 8205.

FIG. 116 illustrates how various ones of the tunable devices 8206 can be configured during different signal transmission intervals. For example, Element 1, such as a resistor, can be configured to influence a remote field reception characteristic at the external device 8205. At least during the field interval Δt0, Element 1 can be configured to have a parameter value R1, such as can be selected to optimize receipt of the remote field signal at the external device 8205. If a characteristic of the remote field changes, then Element 1 can also change to enhance or maintain a signal reception quality.

Elements 2, 3, and 4 can correspond to signal transmission characteristics from the external device 8205. That is, by tuning or changing the values of Elements 2, 3, or 4, different signals can be transmitted or modulated by the external device 8205. During the first transmission interval Δt1 and the third transmission interval Δt3, the external device 8205 can be configured such that Element 2 (e.g., a capacitor) has a parameter value C1, Element 3 (e.g., an inductor) has a parameter value L1, and Element 4 (e.g., a phase shifter) has a parameter value $\Phi_1$. Under this configuration, the external device 8205 can be configured to transmit the first signal S1 or the third signal S3, such as in response to receiving the remote field signal, to the first target device 7611.

At time t3, one or more of the values of Elements 2, 3, and 4 can be changed such that the external device 8205 can be configured to transmit the different second signal S2 or fourth signal S4. For example, during the second transmission interval Δt2 and the fourth transmission interval Δt4, the external device 8205 can be configured such that Element 2 has a parameter value C2, Element 3 has a parameter value L2, and Element 4 has a parameter value $\Phi_2$. Under this configuration, the external device 8205 can be configured to transmit the second signal S2 or the fourth signal S4, such as in response to receiving the remote field signal, to the second target device 7612.

By selecting different parameter values for the Elements 1-4, the external device 8205 can thus be configured to receive different remote field signals and/or to transmit different signals to one or more target devices by differently modulating an evanescent field. For example, during transmission of the first and second signals S1 and S2, an evanescent field at a tissue surface can be differently modulated and thereby differently direct propagating waves toward the first and second target devices 7611 and 7612, respectively.

FIG. 117 illustrates, by way of example, a diagram of an embodiment of a method 8500 that includes updating a modulation characteristic using the external device 8205. At operation 8510, the method 8500 can include receiving RF energy at the external device 1205, such as from the remote field source 8220. Receiving the RF energy can include receiving the remote field from the example of FIG. 116, such as during a field interval Δt0. In one or more embodiments, the external device 8205 is configured by one or more of the tunable devices 8206 to receive the RF energy from a specified source.

At operation 8520, the method 8500 includes modulating the RF energy, received at operation 8510, using the external device 8205. In response to modulating the RF energy using the external device 8205 and one or more of the tunable devices 8206, the method 8500 can include providing a first output signal. The first output signal can be selected to modulate an evanescent field in a specified manner to transmit a propagating wave to a target device. For example, at operation 8530, the external device 8205 can be configured to transmit the first output signal to the first target device 7611. In one or more embodiments, operation 8530 can correspond to using the external device 8205 to transmit the first signal S1, from the example of FIG. 116, to the first target device 7611.

At operation 8540, the method 8500 can include differently modulating the RF energy, received at operation 8510, using the external device 8205. Differently modulating the RF energy can include configuring one or more of the tunable devices 8206 of the external device 8205 to be differently valued than during the operation 8520. Based on the differently configured tunable devices 8206, the external device 8205 can provide a second output signal. At operation 8550, the external device 8205 can be configured to transmit the second output signal to the second target device 7612. In one or more embodiments, operation 8550 can correspond to using the external device 8205 to transmit the second signal S2, from the example of FIG. 116, to the second target device 7612.

At operation 8560, one or more data signals can be provided from the first and/or second target devices 7611 and 7612 to the external device 8205. The one or more data signals can include, among other things, information for use by a control circuitry in the external device 8205 to determine whether or when to update or adjust one or more of the tunable devices 8206. For example, the one or more data signals can include information about a quality of a power signal received at the first target device 7611 from the external device 8205. If the information indicates a poor quality of the power signal received, then at operation 8570 the external device 8205 can select one or more new or different parameter values for one or more of the tunable devices 8206, such as to update an evanescent field modulation characteristic, and thereby differently direct a subsequent power signal to the first target device 7611 or to another specified location or device.

In one or more embodiments, one or more data signals can be provided from the first and/or second target devices 7611 and 7612 to the remote field source 8220. The data signals can be provided directly to the remote field source 8220 or can be transmitted to the remote field source 8220 using an intermediate device such as the transceiver circuitry 8207 of the external device 8205. In response to the data signals, the remote field source 8220 can update a field characteristic of the remote field, for example, to increase a transmission power or to change a frequency of the remote field. For example, if insufficient power is received at the first target device 7611 to carry out a therapy event, then the external device 8205 and/or the remote field source 8220 can change one or more parameters to attempt to increase a magnitude of power that is available to the first target device 7611.

FIG. 118 illustrates, by way of example, a diagram of an embodiment of a method 8600 that includes conditionally updating a modulation characteristic using an external device. The method 8600 can include operations 8510, 8520, and 8530 from the method 8500 of FIG. 117. At operation 8640, the method 8600 includes receiving a transmission quality indication at the external device 8205. Receiving the transmission quality indication can include receiving a data signal from the first target device 7611, the data signal including information about a quality of a previous or current signal transmission from the external device 8205 to the first target device 7611. In one or more embodiments, receiving the transmission quality indication at the external device 8205 includes receiving a backscatter signal in response to the transmitting the output signal at operation 8530. In one or more embodiments, receiving the transmission quality indication at the external device 8205 includes receiving information about whether or how a task was performed by the first target device 7611, and then inferring a transmission quality between the external device 8205 and the first target device 7611 based on the task information.

At operation 8650, the method 8600 can include determining whether the received transmission quality indication is acceptable, that is, whether it meets or exceeds a specified threshold quality level. The threshold quality level can be programmed into the external device 8205, or can be dynamically set or adjusted by the external device 8205 based on various factors. For example, the threshold quality level can be set differently depending on a criticality of the information in the output signal transmitted at 8530.

If the transmission quality level is determined, at operation 8650, to be acceptable, then the method can continue at operation 8651 with continuing to transmit an output signal from the external device 8205 without performing a parameter update. If the transmission quality level is not determined to be acceptable, then the method 8600 can continue at operation 8652 by updating a modulation characteristic using the external device 8205. Updating the modulation characteristic at operation 8652 can include changing a parameter of one or more of the tunable devices 8206 and thus configure the external device 8205 to provide or transmit a different or updated output signal. For example, after updating the modulation characteristic at operation 8652, the method can continue by returning to operation 8530 to transmit the output signal to the first device 7611.

In one or more embodiments, the feedback loop can include a "greedy" search algorithm that looks for improvements in the received transmission quality indication at operations 8640 and 8650. If an incremental improvement in transmission quality is observed for a given set of signal transmission parameter values at the external device 8205, then the update at operation 8652 can include subsequent updates of parameters that are similarly valued to those parameters under which the incremental improvement was observed.

In one or more embodiments, the feedback loop that includes operations 8530, 8640, 8650, and 8652 can continue for a specified number of iterations or until an acceptable transmission quality level is achieved. For example, at startup of the external device 8205 and/or of a target device, the system can perform the operations of FIG. 118 to iteratively identify an optimal configuration for sending or receiving power and/or data signals. In one or more embodiments, operation 8652 includes retrieving previous, known-good parameter values for one or more of the tunable devices 8206, such as from a memory circuitry on board the external device.

The various examples of FIGS. 117 and 118 are described with respect to the external device 8205. One of more of the procedures described in these examples can be similarly performed by the external midfield device to receive signal transmission quality information and, in response, update a characteristic of the external midfield device to enhance or adjust a quality of subsequent signal transmissions from the external midfield device to a target device.

FIG. 119 illustrates, by way of example, a diagram of an embodiment of a system 8700 that includes multiple external midfield transceivers. The system 8700 includes a first antenna 300A and a second antenna 300B. The first and second antennas 300A and 300B can the same or similar features as the external midfield device described above in connection with FIG. 108.

Both of the first and second external midfield antennas 300A and 300B can be configured to transmit power and/or data signals to the first target device 7611. In one or more embodiments, both of the first and second antennas 300A and 300B are configured to transmit a separate power signal to the first target device 7611 concurrently, that is, during a common interval Δt. In one or more embodiments, the transmitted power signals from the first and second antennas 300A and 300B are selected to interfere constructively and a resulting or combined field is received by the first target device 7611. In one or more embodiments, the first and second antennas 300A and 300B comprise two of multiple external transceivers arranged as a mesh network, wherein each of the multiple external transceivers is configured to exchange data to help coordinate power transfers or data transfers to the first target device 7611 or to other devices.

C. Wireless Neural Therapy Delivery Systems and Methods Using a Series of Electrostimulation Signals Systems, methods and devices described herein advantageously facilitate placement and programming of implantable therapy delivery devices (e.g., neural stimulation devices) by providing for rapid selection of electrode pairs, or vectors, so that several available anode/cathode stimulation combinations are energized for a short duration of time through a period of a rotation sequence. A total period to complete a rotation sequence could be as short as 1 second or less. Off times, such as when an anode/cathode combination is being switched, can be very short.

Such an electrode or vector selection procedure can have several desirable consequences. For example, a clinician can locate an electrode array in an approximate location near a neural target. The clinician need not perform intraoperative test stimulations to ensure that an optimal configuration is programmed. Instead, an optimal configuration will be used for at least a portion of a therapy event. As a result, less time is consumed at implant and programming costs can be minimized.

In an example, a clinician can program a large number of different electrode combinations or vectors for use (see, e.g., FIG. 131, below) and the clinician can be less concerned that some of the programmed vectors will result in suboptimal stimulation at a targeted nerve structure. At least because the implantable devices discussed herein can wirelessly receive power signals via a midfield coupling, a clinician is not constrained by the implanted device's electrode switching times, its discharge circuit that delivers stimulation to the electrodes, or larger power consumption rates from a battery that would result in premature depletion in conventional battery-laden implanted devices. One or more of the vectors can be configured, such that when selected and power is provided to the electrodes of the vector, a stimulation signal is steered to a target. Different vectors can steer the stimulation to different locations. A phase and/or amplitude shifting network, similar to that described with regard to the external device, can be implemented in the implantable device 110 to help steer the stimulation.

When using a time domain multiplexing communication system between an external transmitter and an implanted receiver, the phase and amplitude can be dynamically adjusted to help focus energy (e.g., more efficiently focus energy) at an implanted receiver device, such as with or without using a power detector. One or more of a power detector and a phase detector can be used at the implantable device or at the stimulation device, such as to provide feedback regarding the operation and/or location of the implantable device.

FIG. 120 illustrates, by way of examples, a diagram of an embodiment of a communication system 31100, such as can be time-domain multiplexed. The system 31100 can include an external midfield transceiver 31102, such as can be similar to or the same as the source 102, and an implantable transceiver 31104, such as can be similar to or the same as the implantable device 110. The transceiver 31102 includes a communicatively coupled midfield antenna 31106 and the transceiver 31104 includes a communicatively coupled electric field or magnetic field based antenna 31108. The antennas 31106 and 31108 can be configured (e.g., in length, width, shape, material, etc.) to transmit and receive signals at substantially the same frequency. The transceiver 31104 can transmit data signals through the antenna 31108 to the transceiver 31102 and can receive power and data signals transmitted by the transceiver 31102 through the antenna 31106.

The external midfield coupler (external transmitter) and implantable device transceiver (that includes the implantable device antenna) can be used for both transmission and reception of RF signals. T/R switches can be used to switch each RF port of the external transmitter from transmit (transmit data or power) mode to receive (receive data) mode. A T/R switch can be used to switch the implantable device between transmit (data transmission mode) and receive (power or data receive) modes.

An output of the receive terminal (on the external transmitter) of the T/R switch can be connected to one or more components that detect the phase and/or amplitude of the received signal from the implantable device. This phase and amplitude information can be used to program the phase of the transmit signal to be substantially the same relative phase as the received signal. To help achieve this, the transceiver 31102 can include a phase-matching or amplitude-matching network. The network can be used with a midfield coupler that includes multiple ports, such as the antenna 300.

FIG. 121 illustrates, by way of example, an embodiment of a system including a multi-polar therapy delivery device 110 implanted in tissue. In an example, the device 110 is implanted in tissue below a tissue-air interface 1204. In the example of FIG. 121, the device 110 includes an elongate body and multiple electrodes E0, E1, E2, E3, and E4 that are axially spaced apart along a portion of the elongate body. The device 110 includes receiver and/or transmitter circuits that enable communication between the device 110 and a source 102. In an example, the source 102 is a midfield source, such as the source 102 discussed above in the embodiments of FIG. 1 and FIG. 2, respectively.

The various electrodes E0-E3 can be configured to deliver a neural electrostimulation therapy to patient tissue, such as at or near a neural target. In an example, at least one electrode can be selected for use as an anode and at least one other electrode can be selected for use as a cathode to define an electrostimulation vector. In the example of FIG. 1, electrode E1 is selected for use as an anode and electrode E2 is selected for use as a cathode. Together, the E1-E2 combination defines an electrostimulation vector "V10". Similarly, electrode E0 is selected for use as an anode and electrode E3 is selected for use as a cathode to define another electrostimulation vector "V11". The vectors can be configured independently to provide a neural electrostimulation therapy to the same or different neural target, such as concurrently or at different times.

In one or more embodiments, the device 110 can be configured to provide a series of electrostimulation pulses to a neural target. For example, the device 110 can provide multiple electrostimulation pulses separated in time, such as using the same or different electrostimulation vectors, to provide a therapy. That is, a single therapy event can include multiple different electrostimulation signal components, such as provided using different portions of the same device 110.

In one or more embodiments, the single therapy event includes at least two electrostimulation signals or pulses provided, in turn, to the same or different neural target, using different electrostimulation vectors, and optionally using different electrostimulation signal characteristics. In one or more embodiments, a delay or non-stimulation interval can be provided between each electrostimulation signal. The delay can be due in part to a switching time in the device 110 to switch an output circuit between the at least first and second vectors used for the therapy event. The delay can be fixed or adjustable, and can optionally be different between each signal component that comprises a portion of a therapy event.

In one or more embodiments, at least one electrostimulation signal provided to a particular vector, of multiple signals provided to multiple respective vectors and comprising a portion of a therapy event, can be more optimal than others for treating a patient. However, repeatedly stimulating the same neural target via the same electrostimulation vector can have undesired consequences. For example, a therapeutic benefit of the stimulation can wane over time as a target learns or adapts to the stimulation. To address this problem, the present inventors have recognized that it can be desirable to give an optimal vector or target a "rest", that is, to provide a period of non-stimulation.

In one or more embodiments, a therapy comprising multiple signals can be provided to multiple different vectors in turn, such as to provide a series or sequence of electrostimulation pulses to the same neural target. In this example, even if one vector is more optimal than the others for eliciting a patient response, then the therapy as a whole can be more effective than stimulating only the known-optimal vector because (1) the target will receive a rest during periods of non-stimulation, and (2) stimulating the areas nearby or adjacent to the optimal target can elicit some patient benefit.

In one or more embodiments, a system configured to deliver a series of electrostimulation pulses using multiple different vectors in a sequence can be easier to program than a device that may require manual evaluation and selection of electrostimulation vectors from among multiple available vectors. For example, if a system is configured to provide a therapy by cycling through all available electrostimulation electrode combinations and vectors, then at least one of the vectors is likely to be more optimal or more beneficial to the patient than the others, and that at least one of the vectors will provide an electrostimulation signal for at least a portion of a therapy event. Excess or less optimal therapies or signals can be nonetheless delivered to other locations, or using non-optimal vectors, for example with less concern about power consumption because the device 110 receives its electrostimulation power wirelessly from an external source.

FIG. 122 illustrates, by way of example, a diagram of an embodiment of a multi-polar therapy delivery device, such as the device 110 of FIG. 1. In one or more embodiments, the device 110 includes an antenna 13021, such as a dipole, helically-shaped, coil, or other antenna, such as can be configured to receive power or data communication signals from the source 13002. The device 110 can include receiver circuitry 13022, such as coupled to the antenna 13021. The receiver circuitry 13022 can receive or interpret one or more signals received via the antenna 13021. In one or more embodiments, the device 110 includes processor circuitry 13024 and memory circuitry 13023 (e.g., volatile, nonvolatile, random access, read only, or the other data storage device). The processor circuitry 13024 can be configured to act in coordination with the receiver circuitry 13022 to receive power or data signals from the source 13002 and direct the signals to one or more of the memory circuitry 13023, a signal generator circuitry 13025, or a capacitor array 13026. In one or more embodiments, the processor circuitry 13024 can perform operations of the digital controller 548. The items of the device 110 can be used with one or more items of the circuitry 500.

In one or more embodiments, the signal generator circuitry 13025 is configured to use power signals received via the antenna 13021 to generate a therapy signal, such as a neural electrostimulation or modulation signal. The therapy signal can include an AC signal having one or more adjustable characteristics. The one or more adjustable characteristics can include a waveform morphology shape, amplitude, phase, frequency, pulse width, timing, or other characteristic. In one or more embodiments, the signal generator circuitry 13025 is coupled to the capacitor array 13026. The capacitor array 13026 stores electrostimulation energy from the signal generator circuitry 13025. One or more of the signal generator circuitry 13025 and the processor circuitry 13024 can selectively discharge stored electrostimulation energy, for example, to provide a therapy via one or more outputs of the device 110.

The device 110 includes multiple possible outputs, and each output can include output circuitry or other hardware configured to provide an electrostimulation signal to a target. In one or more embodiments, the device 110 includes a first output 13031 that includes, among other things, an output stage of a therapy signal amplifier or a hardware coupler for coupling the first output 13031 to a therapy delivery electrode (e.g., one or more of the electrodes E0-E3 or other electrode(s) of the implantable device discussed herein). The device 110 in the embodiment of FIG. 122 includes second, third, and fourth outputs 13032, 13033, and 13034, such as can each be similarly configured to the first output 13031.

In one or more embodiments, the signal generator circuitry 13025 can time delivery of electrostimulation signals via one or more of the first, second, third, and fourth outputs 13031-13034. For example, the signal generator circuitry 13025 can provide different electrostimulation signals to one or more of the outputs 13031-13034 in a serial or parallel manner. That is, in one or more embodiments, the signal generator circuitry 13025 can be configured to provide different, discrete electrostimulation signals from each of at least two of the first through fourth outputs 13031-13034 in turn, such as one following another in time. In one or more embodiments, the signal generator circuitry 13025 can be configured to provide different, discrete electrostimulation signals from each of at least two of the first through fourth outputs 13031-13034 concurrently, such as at least partially overlapping in time.

In one or more embodiments, processor circuitry 13024 and/or signal generator circuitry 13025 comprise portions of a state machine device (e.g., similar to other state machine devices discussed herein). The state machine device can be configured to wirelessly receive power and data signals via the antenna 13021 and, in response, release or provide an electrostimulation signal via one or more of the first-fourth outputs 13031-13034. In one or more embodiments, such a state machine device needs not retain information about available electrostimulation settings or vectors, and instead the state machine device carries out or provides electrostimulation events substantially immediately after, and in response to, receipt of instructions from the wireless transmitter.

For example, the state machine device can be configured to receive an instruction to deliver a neural electrostimulation therapy signal, such as at a specified time or having some specified signal characteristic (e.g., amplitude, duration, frequency, specified number of pulses, etc.), and the state machine device can respond by initiating or delivering the therapy signal. At a subsequent time, the device can receive a subsequent instruction to terminate the therapy, to change a signal characteristic, or to perform some other task. Thus the device 110 can optionally be configured to be substantially passive, or responsive to contemporaneously-received instructions.

FIG. 123 illustrates, by way of example, of a table 13100 showing an embodiment of available electrostimulation vectors in a four-pole electrostimulation system. The table 13100 is a partial list of potential combinations of four discrete electrodes. In the embodiment shown, table 13100 includes a first column labeled "Vector" that provides a name or designation for a given combination of electrodes. The table 13100 includes second, third, fourth, and fifth columns, labeled E0, E1, E2, and E3, respectively, such as corresponding to the electrodes of the device 110 in the example of FIG. 1. Entries in the table 13100 include "A" to indicate that a cell corresponds to an anode of a vector, and "C" to indicate that a cell corresponds to a cathode of a vector. The table 13100 merely illustrates examples, and more examples are possible, some of which can be realized by simply switching "C" with "A" and "A" with "C" in the table 13100.

Two or more of the available electrodes can be electrically coupled to form an anode or cathode. For example, in the table 13100, a first vector V0 includes E0 as an anode and includes E1, E2, and E3 commonly coupled as a cathode. A second vector V1 includes E1 as an anode and includes E0, E2, and E3 commonly coupled as a cathode. In one or more embodiments, any two or more of the available electrodes can be coupled to form an anode or cathode. In one or more embodiments, or any one or more of the electrodes can be unused, such as can be designed in the table 13100 by shaded cells.

FIG. 124A illustrates, by way of example, a diagram of an embodiment of a first neural electrostimulation therapy event 13200. In the example of FIG. 124A, the first therapy event 13200 includes four discrete electrostimulation signals, each of which is provided via a different electrostimulation vector and, optionally, using different signal characteristics. For example, the electrostimulation signals can be provided via different electrostimulation vectors that are available to the device 110 of FIG. 1.

In the embodiment of FIG. 124A, the device 110 is illustrated having four different configurations. In a first configuration 110A, the device 110 is configured to use electrode E0 as an anode and to use electrodes E1, E2, and E3 commonly coupled as a cathode (e.g., corresponding to a first vector V0 in the table 13100). In a second configuration 110B, the device 110 is configured to use electrode E1 as an anode and to use electrodes E0, E2, and E3 commonly coupled as a cathode (e.g., corresponding to a second vector V1 in the table 13100). In a third configuration 110C, the device 110 is configured to use electrode E2 as an anode and to use electrodes E0, E1, and E3 commonly coupled as a cathode (e.g., corresponding to a third vector V2 in the table 13100). In a fourth configuration 110D, the device 110 is configured to use electrode E3 as an anode and to use electrodes E0, E1, and E2 commonly coupled as a cathode (e.g., corresponding to a fourth vector V3 in the table 13100).

In the embodiment of FIG. 124A, the first therapy event 13200 extends from an initial time t0 to a final time tf. A first delay interval, D1, starts at time t0 and ends at time t1. During D1, the device 110 can undergo a configuration routine, such as to place the device 110 in the first configuration 110A with the electrode E0 as an anode and the other electrodes commonly coupled as a cathode. At time t1, a first one of the discrete electrostimulation signals can be provided via the first vector V0. The first one of the discrete electrostimulation signals can have first signal characteristics, include a first waveform morphology shape, amplitude, phase, frequency, pulse width, timing, or other characteristic. Generally, a frequency characteristic is selected such that at least one full signal cycle can be delivered, such as between times t1 and t2. In one or more embodiments, a frequency characteristic is selected such that multiple signal cycles are delivered, such as between times t1 and t2. The first one of the signals can terminate at time t2, at which time a second delay interval D2 can begin. The second delay interval D2 can be the same or different than the first delay interval, e.g., in terms of duration or activity. In one or more embodiments, during the second delay interval D2, therapy delivery from the device 110 is inhibited as the device 110 changes from the first configuration 110A to the second configuration 110B.

At time t3, a second one of the discrete electrostimulation signals can be provided via the second vector V1. The second one of the discrete electrostimulation signals can have second signal characteristics, include a second waveform morphology shape, amplitude, phase, frequency, pulse width, timing, or other characteristic. In one or more embodiments, at least one or more of the second signal characteristics are the same as the first signal characteristics, or at least one or more of the second signal characteristics are different than the first signal characteristics. For example, the first one of the discrete electrostimulation signals can have a first amplitude characteristic and a first frequency characteristic, and the second one of the discrete electrostimulation signals can have the same first amplitude characteristic and same first frequency characteristic. In an alternative example, the first one of the discrete electrostimulation signals can have a first amplitude characteristic and a first frequency characteristic, and the second one of the discrete electrostimulation signals can have a different second amplitude characteristic and a different second frequency characteristic.

The second one of the discrete electrostimulation signals can terminate at time t3, at which time a third delay interval D3 can begin, and so on. Any one or more of the electrostimulation signal characteristics can be the same or different for the various signals delivered using the device configurations 110A, 110B, 110C, or 110D.

In one or more embodiments, the delay characteristics D1, D2, D3, and D4 can have the same duration or can be different. Similarly, the durations corresponding to each of the discrete electrostimulation signals (e.g., provided via vectors V0, V1, V2, and V3, in the example of FIG. 124A) can be the same or different.

In one or more embodiments, a therapy event can include multiple iterations of the first neural electrostimulation therapy event 13200. For example, at time tf, a therapy can return to time t0 and repeat the sequence of discrete electrostimulation signals provided using the multiple vectors as shown. In one or more embodiments, one or more signal characteristics, vectors, or other system attributes can be the same or different for each repeated sequence of signals.

In the embodiment of FIG. 124A, each of the discrete electrostimulation signals can be provided for substantially the same duration, and each of the delay intervals can have substantially the same duration. For example, each electrostimulation signal can be provided for about 200 ms, and each delay interval can be about 50 ms, such that the therapy comprising the four discrete components illustrated in FIG. 124A is about 1 second in duration. Other intervals and durations may be used as desired and/or required. The therapy can be repeated for a specified duration or for a specified number of iterations.

FIG. 124B illustrates, by way of example, a diagram of an embodiment of the first neural electrostimulation therapy event 13200 that includes receiving therapy delivery instructions at a stimulation device. In one or more embodiments, the stimulation device includes the device 110 configured at least in part as a state machine. The state machine can be configured to respond to received power signals and/or instructions by initiating or inhibiting therapy signal delivery, such as substantially contemporaneously with receipt of the instructions. In one or more embodiments, an instruction can include information about, among other things, a vector to use, a therapy duration, or a signal characteristic, such as an amplitude, waveform morphology, frequency, or other characteristic.

In the example of FIG. 124B, a first instruction, Stim(V0), can be received at time t1. In response, the device 110 can be configured to provide a first electrostimulation signal, such as using the first vector V0. In one or more embodiments, the first instruction further includes information about one or more signal characteristics for the first electrostimulation signal, such as a first amplitude characteristic and a first frequency characteristic.

The device 110 can provide the first electrostimulation signal substantially continuously, such as until a subsequent instruction is received from a transmitter device. For example, the device 110 can provide the first electrostimulation signal using vector V0 until the device 110 receives a second instruction, Stop(V0), such as at time t2. The Stop(V0) instruction can be interpreted by the device 110 as an indication that the first electrostimulation signal should be terminated or inhibited from being delivered.

At time t3, a third instruction, Stim(V1), can be received. In response, the device 110 can be configured to provide a second electrostimulation signal, such as using the second vector V1. In one or more embodiments, the second instruction further includes information about one or more signal characteristics for the second electrostimulation signal, such as a second amplitude characteristic and a second frequency characteristic. The second amplitude characteristic and/or the second frequency characteristic can be the same or different than the first amplitude and frequency characteristics used in response to the Stim(V0) instruction.

In one or more embodiments, the device 110 can provide the second electrostimulation signal substantially continuously, such as until a subsequent instruction is received from the transmitter device. For example, the device 110 can provide the second electrostimulation signal using vector V1 until the device 110 receives a fourth instruction, Stop(V1), such as at time t4. The embodiment of FIG. 124B can continue with additional instructions Stim(V2) and Stim(V3) to provide respective electrostimulation signals at subsequent times t5 and t7, respectively, and instructions Stop(V2) and Stop(V3) to inhibit therapy delivery at times t6 and tf.

FIG. 125 illustrates, by way of example, an embodiment of a method 13300 that includes providing a neural stimulation therapy. At operation 13310, the method can include receiving a power signal at or using receiver circuitry. For example, at 13310, the method 13300 can include wirelessly receiving a power signal at the receiver circuitry 13022 of the device 110, such as from a midfield transmitter. At operation 13320, the method 13300 can include generating one or more neural stimulation therapy signals, such as using the signal generator circuitry 13025. In one or more embodiments, the operation 13320 includes using a portion of the power signal received at 13310 to generate all or a portion of the therapy signals.

At operation 13330, the method 13300 can include selecting a first electrostimulation vector for neural electrostimulation therapy delivery. For example, selecting a first electrostimulation vector can include selecting a vector from among multiple available vectors, such as corresponding to entries in the table 13100 in the embodiment of FIG. 123. Selecting the first electrostimulation vector at operation 13330 can include selecting one or more electrostimulation signal characteristics for use with the first electrostimulation vector. For example, one or more of a signal waveform morphology shape, amplitude, phase, frequency, pulse width, timing, or other characteristic can be selected.

At operation 13340, the method 13300 can include providing a first neural electrostimulation therapy signal to a first electrostimulation vector (e.g., corresponding to the duration between t1 and t2 in the embodiment of FIG. 124A). In one or more embodiments, providing the first neural electrostimulation therapy signal at operation 13340 includes providing an electrostimulation therapy for a specified first duration using the vector that was selected at operation 13330. At operation 13350, the method 13300 can include inhibiting subsequent delivery of a neural electrostimulation therapy, such as for a specified second duration (e.g., corresponding to D1 in the example of FIG. 124A). One or more additional neural electrostimulation therapy signals can be provided following the second duration.

At operation 13360, the method 13300 can include selecting a second electrostimulation vector for neural electrostimulation therapy delivery. For example, selecting a second electrostimulation vector can include selecting a vector from among multiple available vectors, such as corresponding to entries in the table 13100 in the embodiment of FIG. 123, including a vector other than the first vector selected at operation 13330. Selecting the second electrostimulation vector at operation 13360 can include selecting one or more electrostimulation signal characteristics for use with the second electrostimulation vector. For example, one or more of a signal waveform morphology shape, amplitude, phase, frequency, pulse width, timing, or other characteristic can be selected.

At operation 13370, the method 13300 can include providing a second neural electrostimulation therapy signal to a second electrostimulation vector (e.g., corresponding to the duration between t3 and t4 in the embodiment of FIG. 124A). In one or more embodiments, providing the second neural electrostimulation therapy signal at operation 13370 includes providing an electrostimulation therapy for a specified third duration using the vector that was selected at operation 13360. The third duration can be the same as or different than the first or second durations.

At operation 13375, the method 13300 can include a decision whether or not to repeat the electrostimulation therapy that includes at least the first and second signals. If the therapy is not to be repeated, then the therapy can end at operation 13376. If the therapy is to be repeated, then the therapy can continue at operation 13380 with optionally updating a therapy characteristic. For example, one or more of a signal waveform morphology shape, amplitude, phase, frequency, pulse width, timing, or other characteristic of a therapy signal can be updated or changed at operation 13380.

At operation 13390, the method 13300 can include inhibiting subsequent delivery of a neural electrostimulation therapy, such as for a specified fourth duration. One or more additional neural electrostimulation therapy signals can be provided following the fourth duration. For example, following the fourth duration, the method 13300 can return to operation 13340 to provide the first neural electrostimulation therapy signal using the first electrostimulation vector, such as using the same or different therapy signal characteristics.

FIG. 126 illustrates, by way of example, a diagram of a method 13400 that includes identifying or selecting electrostimulation vectors for use in providing a neural stimulation therapy. At operation 13410, the method 13400 can include sensing two or more electrodes that are available for delivering an electrostimulation therapy. For example, referring to the device 110 of FIG. 122, the processor circuitry 13024 can be configured to identify or sense two or more electrodes that are coupled to the signal generator circuitry 13025, such as via one or more output circuitry, and are available for use to provide an electrostimulation therapy.

At operation 13420, the method 13400 can include identifying available neural stimulation vectors using the electrodes sensed at operation 13410. In one or more embodiments, the operation 13410 can include sensing the four electrodes E0, E1, E2, and E3 in the implantable/implanted device (e.g., the device 110 or other implantable or implanted device discussed herein). At operation 13420, identifying the available vectors can include populating the table 13100 of available vectors using different combinations of the four electrodes. In one or more embodiments, identifying available neural stimulation vectors at operation 13420 includes identifying or defining vectors that include two or more electrodes that are electrically coupled.

At operation 13430, the method 13400 can include selecting at least two of the vectors identified at operation 13420 for therapy delivery. For example, the processor circuitry 13024 can be configured to select from the table 13100 two or more vectors. In one or more embodiments, the processor circuitry 13024 selects the two or more vectors based on prior learned or programmed information about the available vectors. For example, the processor circuitry 13024 can select one or more vectors using information about a measured or assumed efficacy of a therapy delivered using a particular vector.

At operation 13440, the method 13400 can include providing a first portion of a neural electrostimulation therapy using a first one of the vectors selected at operation 13430. Providing the first portion of the therapy can include providing a first electrostimulation signal having a first waveform morphology shape, amplitude, phase, frequency, pulse width, timing, or other signal characteristic. In the embodiment of FIG. 124A, providing the first portion of the neural electrostimulation therapy at operation 13440 can correspond to providing an electrostimulation signal via vector V0, such as by using the device 110. At operation 13450, the method 13400 can include providing a second portion of a neural electrostimulation therapy using a second one of the vectors selected at operation 13430. Providing the second portion of the therapy can include providing a second electrostimulation signal having a second waveform morphology shape, amplitude, phase, frequency, pulse width, timing, or other signal characteristic, such as can be the same or different than a corresponding characteristic of the first electrostimulation signal provided at operation 13440.

At operation 13460, the method 13400 can include repeatedly providing the first and second portions of the neural electrostimulation therapy. That is, at operation 13460, the method 13400 can include providing the first portion of the therapy followed by the second portion of the therapy, then followed by the first portion of the therapy, and so on, such as for a specified number of iterations or for a specified therapy duration.

In one or more embodiments, electrostimulation vectors selected for use can be associated with two or more different implantable devices, wherein each device includes two or more electrodes configured to provide a neural electrostimulation therapy. A source, such as the source 102 in the example of FIG. 1, can be configured to steer power and/or data to the multiple different implantable devices, and one or more processor circuits (e.g., the processor circuitry 210 in a first device, and a separate processor circuitry in a second device) can be configured to coordinate therapy delivery among the different implantable devices. For example, the source 1202 can be configured to wirelessly provide an electrostimulation power signal to a first implantable device configured to provide a first therapy at a first time, and another source (e.g., antenna 300A-300B) can be configured to wirelessly provide a subsequent electrostimulation power signal to a different second implantable device configured to provide a different second therapy at a subsequent second time.

FIG. 127 illustrates, by way of example, a diagram of an embodiment of a method 13500 that includes randomly selecting an order for delivering a neural stimulation therapy via multiple vectors. At operation 13510, the method 13500 can include selecting three or more different neural stimulation vectors for delivery of different portions of a neural electrostimulation therapy. Selecting the vectors can include, among other things, selecting from a table of available vectors, such as using the table 13130 in the embodiment of FIG. 123. In one or more embodiments, selecting the three or more neural stimulation vectors at operation 13510 includes using a programmer or user interface to present information about one or more available vectors to a user, and then receiving, from a user, an indication of one or more vectors to use for therapy delivery.

At operation 13520, the method 13500 can include randomly selecting an order for delivering a neural electrostimulation therapy using each of the selected vectors sequentially. For example, the processor circuitry 1222 can be configured to receive information about the selected three or more vectors and then select an order, at random, for providing different portions of an electrostimulation therapy to the selected three or more vectors. At operation 13530, the method 13500 can include providing the neural electrostimulation therapy using each of the selected vectors sequentially, such as according to the order selected at operation 13520.

In one or more embodiments, the operation 13510 can include using the processor circuitry 210 to select at least vectors V0, V1, and V2 for delivering respective portions of a neural electrostimulation therapy. In this example, at operation 13520, the processor circuitry 210 can select an order for delivering the respective portions of the therapy. The order can include, for example, a vector sequence of V0-V1-V2, or V1-V0-V2, or V2-V0-V1, and so on, as selected at random using the processor circuitry 210. The signal generator circuitry 13025 can then coordinate therapy delivery using the randomly selected vector sequence.

In one or more embodiments, other benefits of the systems and methods discussed herein can include simplifying programming of implanted, multipolar electrostimulation devices, such as by ensuring that at least one vector more optimal than others for therapy delivery can be selected for use. In addition, an automatically-generated programming algorithm can be used, such as with optimal and/or suboptimal stimulation sequences, which may be equivalent or superior in efficacy to using only known-optimal configurations. In an example, an optimal sequence can be one that elicits a physiologic or therapeutic response. Further, programming settings (e.g., stimulation signal amplitudes, waveforms, pulse durations, etc.) that may not be feasible in conventional implantable devices can be implemented, such as because various power or battery consumption characteristics of such conventional devices can be disregarded when an external power device is used to power an implantable device via a midfield coupling.

D. Dual-Frequency Electrostimulation for Neural Therapy

FIG. 128 illustrates, by way of example, of an embodiment of phase-amplitude coupled signals. In one or more embodiments, electrode pairs or vectors are selected or programmed by a clinician using a remote programmer or remote control. The clinician can specify various signal characteristics to be used when providing electrostimulation signals via the selected vectors. Such signal characteristics can include, but are not limited to, frequency or phase angle characteristics. In one or more embodiments, a dual-frequency stimulation configuration can be selectively enabled or disabled, that is, switched "on" and "off", according to instructions from a programmer.

Various patient behaviors can modulate or influence phase-amplitude coupling in intrinsic neural signals. Phase-amplitude coupling can also be involved in sensory integration, memory process, and attentional selection. Such coupling can be observed in several brain regions including in the hippocampus, basal ganglia, and neocortex.

In the embodiment of FIG. 128, a first phase-amplitude coupled signal 13701 includes a combination of high and low frequency signals, wherein a power or amplitude of the high frequency signal's envelope changes with a phase of the low frequency signal's oscillation period. A second signal 13702 includes the higher frequency signal component from the first phase-amplitude coupled signal 13701.

In one or more embodiments, cross-frequency or phase-amplitude coupling can be quantified or measured, for example, by identifying a relationship between an activity that modulates low frequency oscillations (e.g., a sensory or motor input), and local cortical activity (e.g., local computations), such as can be correlated to an amplitude of higher frequency oscillation.

In one or more embodiments, a therapeutic phase-amplitude coupled neural electrostimulation signal (PAC signal) can be provided using multiple, concurrently delivered signal components. In one or more embodiments, a patient's symptoms, such as related to one or more of a body movement disorder, Parkinson's disease, Alzheimer's disease, Huntington's disease, depression, neuralgia, dystonia, epilepsy, migraines or headaches, or any other condition, disease or disorder described herein, among others, can be alleviated or reduced using a PAC signal-based neuromodulation therapy. Some patient disorders or physiologies can be associated with an intrinsic phase-amplitude coupled neural signal. A therapeutic PAC signal can be provided to cancel, mitigate, normalize, overcome, or otherwise influence an intrinsic phase-amplitude coupled neural signal, such as can be associated with an abnormal or diseased patient state.

In one or more embodiments, a physiological effect of a PAC signal-based neuromodulation therapy does not wane over time, or remains effective for a longer duration than a traditional non-PAC signal-based therapy. Repeatedly stimulating the same neural target via the same electrostimulation vector can have undesired consequences. For example, a therapeutic benefit of the stimulation can wane over time as a target nerve area learns or adapts to the stimulation. Stimulating a vector or target with a PAC signal can help at least partially overcome one or more of the problems discussed.

FIG. 129 illustrates, by way of example, a diagram of an embodiment of a method 13800 of concurrently providing a neural electrostimulation therapy. At operation 13810, the method 13800 includes providing a first electrostimulation signal at a first frequency using a first vector. For example, operation 13810 can include providing a first electrostimulation signal, such as having first amplitude, phase, and frequency characteristics, using the first vector V10 of the device 110 in the embodiment of FIG. 1.

At operation 13820, one or more signal characteristics can be selected for a second electrostimulation signal. The characteristics can be selected to modulate an amplitude characteristic of the first signal provided at operation 13810. For example, a phase or frequency characteristic can be selected for the second signal to be different than a phase or frequency characteristic of the first signal such that, when the signals are concurrently delivered to a similar target neural area, a combination of the first and second signals is a phase-amplitude coupled signal. At operation 13830, the method 13800 can include providing the second electrostimulation signal at a second frequency using a second vector. For example, operation 13830 can include providing a second electrostimulation signal, such as having second amplitude, phase, and frequency characteristics, using the second vector V11 of the device 110 in the example of FIG. 1.

FIG. 130 illustrates, by way of example, a method 13900 that includes providing multiple phase-amplitude coupled therapy signals. At operation 13910, the method 13900 can include providing a first PAC signal comprising first and different second signal components. In one or more embodiments, the first signal component can have an amplitude characteristic that is modulated by a phase characteristic of the second signal component when the first and second signal components are provided substantially concurrently to a similar target.

At operation 13920, the method 13900 can include providing a second PAC signal comprising the first signal component in combination with a different third signal component. That is, at operation 13920, the first signal component can have an amplitude characteristic that is modulated by a phase characteristic of the third signal component when the first and third signal components are provided substantially concurrently to a similar target. Alternatively, at operation 13920, the third signal component can have an amplitude characteristic that is modulated by a phase characteristic of the first signal component when the first and third signal components are provided substantially concurrently to a similar target.

FIG. 131 illustrates, by way of example, a diagram of an embodiment of a method 14000 that includes selecting one or more signal component characteristics for use in a PAC signal. At operation 14010, the method 14000 can include sensing an intrinsic neural signal from a subject. One or more sensors disposed on, in, or near a patient body can be configured to receive the intrinsic neural signal. At operation 14020, one or more characteristics of the intrinsic neural signal can be determined. For example, at operation 14020, an amplitude or timing characteristic of the sensed intrinsic neural signal can be determined. In one or more embodiments, a patient pathology can be identified based on one or more characteristics of the sensed intrinsic signal.

At operation 14030, one or more signal component characteristics can be selected for use in a neural electrostimulation therapy. The neural electrostimulation therapy can include a PAC signal that includes at least two different electrostimulation signals delivered via different electrodes corresponding to different electrostimulation vectors. Based on the determined characteristics of the intrinsic neural signal at operation 14020, characteristics of the at least two different electrostimulation signals in the PAC signal can be selected. For example, the intrinsic neural signal may be weak or may have an undesirable waveform morphology. In response, the processor circuitry 13024 of the device 110 can be configured to select a high amplitude first signal and a lower amplitude second signal, such as having different frequency characteristics. When the selected signals are concurrently delivered via spatially overlapping electrostimulation vectors, the undesirable waveform morphology of the intrinsic signal can be masked or overcome by the combination of the higher amplitude, phase-amplitude modulated, delivered signals.

E. Systems and Methods for Embedding Communication Signals with Electrostimulation Therapy Generally discussed in this subsection are systems, devices, and methods for providing or delivering a patient therapy using an implantable device. In one or more embodiments, the patient therapy includes a modulation (e.g., an electrostimulation) therapy provided to one or more neural targets in a patient body. In one or more embodiments, the modulation (e.g., electrostimulation) therapy is provided using an implant device that wirelessly receives power and data signals from a midfield transmitter. Systems, devices, and methods discussed herein can be used to communicate data between internal and external devices. In one or more embodiments, a therapy provided by an implanted or internal device includes an information signal that can be received and interpreted by an external device.

FIG. 132 illustrates, by way of example, a diagram of embodiments of various therapy signals with data signal components. A first electrostimulation therapy signal 14101 (e.g., a nearfield signal) includes multiple therapy signal pulses interleaved with, or spaced apart in time from, one or more data signal pulses. A second electrostimulation therapy signal 14102 includes therapy signal pulses with embedded data signal pulses. The data signal pulses are provided at a sufficiently high frequency, or over a sufficiently brief duration, such that substantially no physiologic response is elicited in response to the data signal pulses being provided at or near the therapy target 190.

In one or more embodiments, a maximum data signal frequency can be limited by an absolute refractory period of a target tissue, such as a neuron or neural tissue. An absolute refractory period includes a time during which a subsequent stimulus delivered to a previously-excited neural target will not lead to a subsequent action potential, no matter how strong a subsequent stimulus is. The absolute refractory period, in one or more embodiments, can be about 1 to 2 milliseconds. In one or more embodiments, the first and second therapy signals 14101 and 14102 include data signal pulses provided at a sufficiently high frequency and/or sufficiently low amplitude and/or at a specified timing interval such that a neurological response to the pulse signal is avoided.

In one or more embodiments, the implantable device 110 provides the first signal 14101, such as using an electrode vector comprising electrodes E0 and E2. The first signal 14101 begins at time to and terminates later at time $t_f$. At $t_0$, the first signal 14101 includes a first therapy pulse $T_1$ having a first pulse duration, $\Delta t_1$. The first signal 14101 includes a subsequent second therapy pulse $T_2$, beginning at time $t_2$, and having a second pulse duration $\Delta t_2$. In one or more embodiments, the first and second pulse durations $\Delta t_1$ and $\Delta t_2$ are substantially the same, however, other durations can similarly be used.

Amplitude and frequency characteristics of the therapy pulses can be selected to elicit a therapeutic or other physiologic response. For example, the therapy pulses can have a peak amplitude of about 5 volts or less (in one or more embodiment about 1, 2, 3, 4, or 5 volts peak amplitude can be used) and can have a pulse frequency of 10 kHz or less (e.g., 4 kHz to 10 kHz, 6 kHz to 10 kHz, 8 kHz to 10 kHz, 2 kHz to 6 kHz, 500 Hz to 2 kHz, 200 Hz to 1 kHz, 10 Hz to 100 Hz, overlapping ranges thereof, 2 kHz or less, or any value within the recited ranges). In one or more embodiments, the pulse frequency can be on the order of tens of cycles per second. In one or more embodiments, the pulse frequency can be about 50 Hz and the first signal 14101 is configured to provide a spinal electrostimulation therapy. In one or more embodiments, the pulse frequency can be about 120 Hz and the first signal 14101 is configured to provide deep brain stimulation therapy. In one or more embodiments, the pulse frequency can be 500 Hz to 2000 Hz and is configured to provide a burst signal-based therapy. Generally, a therapy pulse frequency of the first signal 14101 is sufficiently low and a therapy pulse amplitude of the first signal 14101 is sufficiently high to elicit a therapeutic effect.

In addition to the therapy pulses $T_1$, $T_2$, and $T_3$, the first signal 14101 further includes data communication intervals that include data signal pulses. The communication intervals can be interleaved with the therapy pulses. That is, the communication intervals occur during blanking intervals or periods between therapy pulses when no therapy pulses or therapy-related signal components are provided by the implantable device 110. In one or more embodiments, the first signal 14101 includes a first communication interval $C_1$ between the first and second therapy pulses $T_1$ and $T_2$, and a second communication interval $C_2$ between the second and third therapy pulses $T_2$ and $T_3$.

During the communication intervals, the same or different electrodes of the implantable device 110, such as used to provide the first and second therapy pulses $T_1$ and $T_2$, can be excited to produce the data signal pulses. The data signal pulses can include pulse-width modulated pulses, frequency modulated pulses, or amplitude modulated pulses that encode information into a signal that can be delivered by the implantable device 110. A farfield signal generated as a result of the delivered modulated pulse signal can be received and decoded by the external source 102 or by another receiver device. For example, the first communication interval $C_1$ can include a first pulse-width modulated (PWM) data signal. The first PWM data signal can be provided at a frequency that is sufficiently high, and/or at a signal amplitude that is sufficiently low, such that a physiologic response to the signal can be avoided. In one or more embodiments, the first PWM data signal is provided at a frequency that is at least one and preferably two or three orders of magnitude higher than a frequency of the therapy pulse components of the first signal 14101. In one or more embodiments, the first PWM data signal is provided at an amplitude that is less than a specified threshold amplitude that corresponds to a known physiologic capture or response-provoking amplitude threshold. The second communication interval $C_2$ can include a second PWM signal. The second PWM signal can optionally have different characteristics than the first PWM signal, such as to encode different information than is encoded in the first PWM signal. In one or more embodiments, therapy pulses and data signals can be provided by the implantable device 110 using the same or different electrodes.

In one or more embodiments, the implantable device 110 provides the second signal 14102, such as using an electrode vector comprising electrodes E0 and E2. The second signal 14102 begins at time to and terminates later at time $t_f$. At $t_0$, the second signal 14102 includes a first composite therapy pulse $CT_1$ having a first pulse duration, $\Delta t_1$. The second signal 14102 includes a subsequent second composite therapy pulse $CT_2$, beginning at time $t_2$, and having a second pulse duration $\Delta t_2$. In one or more embodiments, the first and second pulse durations $\Delta t_1$ and $\Delta t_2$ are substantially the same, however, other durations can similarly be used. Amplitude and frequency characteristics of the first and second composite therapy pulses $CT_1$ and $CT_2$ are selected to elicit a therapeutic response.

Each of the first and second composite therapy pulses $CT_1$ and $CT_2$ includes data signal components. That is, each composite therapy pulse includes a pulse signal portion that includes an embedded data signal. The embedded data signal components can include pulse-width modulated pulses, frequency modulated pulses, or amplitude modulated pulses that encode information into a signal that can be received and decoded by the external source 102 or by another receiver device, such as the farfield sensor device 130. For example, the first composite therapy pulse $CT_1$ can include a first pulse-width modulated (PWM) pulse portion. The first PWM pulse portion can be provided at a frequency that is sufficiently high, and/or at a signal amplitude that is sufficiently high, such that a therapeutic response is elicited or provoked. That is, the first PWM pulse portion can be sufficiently high frequency such that the frequency of the signal exceeds a refractory period of a neural target and therefore an effect of the first PWM pulse portion is essentially the same as a constant electrostimulation signal or pulse provided over the same duration.

As shown in the embodiment of FIG. 132, the composite therapy pulses $CT_1$, $CT_2$, and $CT_3$, can include data signal components that are embedded with therapy pulses at different time intervals or locations with respect to an overall pulse duration. For example, the first composite therapy pulse $CT_1$ includes a data signal component that begins a short duration after time $t_0$, and the data signal component terminates a short duration before $t_1$. In one or more embodiments, the data signal component of $CT_1$ and other composite therapy pulses can begin a specified or fixed duration after a rising edge of a pulse. The second composite therapy pulse $CT_2$ includes a data signal component that coincides with the onset of the second composite therapy pulse $CT_2$ at $t_2$, and the third composite therapy pulse $CT_3$ includes a data signal component that begins after $t_4$ and coincides with a terminal portion of the third composite therapy pulse $CT_3$ at $t_5$. Thus a data signal component can be embedded with essentially any portion of a pulse that includes other pulse portion(s) that are configured to elicit a physiologic response. In one or more embodiments, a data signal component can be embedded at specified intervals, randomly, or substantially continuously with a therapy signal.

FIG. 132 includes a third electrostimulation therapy signal 14103 that represents an effect of either one of the first and second therapy signals 14101 and 14102. For example, since the embedded data signal components in the second therapy signal 14102 are provided at a sufficiently high frequency and/or amplitude, a physiologic effect of the second therapy signal 14102 is essentially or effectively the same as a physiologic effect of the third therapy signal 14103. Similarly, since the interleaved data signals in the first therapy signal 14101 are provided at a sufficiently high frequency and/or low amplitude (e.g., sub-capture threshold), a physiologic effect of the first therapy signal 14101 is essentially or effectively the same as a physiologic effect of the third therapy signal 14103.

FIG. 133 illustrates, by way of example, a diagram of an embodiment of a method 14200 that includes retrieving an information signal from a therapy-based signal. The method 14200 includes using a closed-loop system comprising the external source 102 and the implantable device 110. The implantable device 110 is configured to measure or sense information about one or more of power levels converted from the external source 102, actual therapy or electrostimulation parameters used by the implantable device 110, lead or electrode impedance characteristics of the implantable device 110, or other information. The measured or sensed information is encoded into a therapy signal at the implantable device 110 and then the therapy signal is provided by the implantable device 110 and sensed by the external source 102. Thus, a feedback or communication loop can be established between the external source 102 and the implantable device 110.

At operation 14210, the method 14200 includes transmitting a midfield power signal from the external source 102. Transmitting the midfield power signal can include in response to exciting one or more subwavelength structures on the antenna 300 to cause the antenna 300 to emit an RF signal having a non-negligible H-field component. At operation 14220, the method 14200 includes receiving the midfield power signal at the implantable device 110.

At operation 14230, the method 14200 includes providing a nearfield electrostimulation therapy using the implantable device 110. Operation 14230 can include providing the first or second therapy signals 14101 or 14102 from the embodiment of FIG. 132, or providing other signals, such as can include a data signal component. The data signal component can include encoded information about the implantable device 110, or about a therapy provided or to-be provided by the implantable device 110. Providing the nearfield electrostimulation therapy at operation 14230 can include providing a farfield signal that can be detected remotely from the implantable device 110. In one or more embodiments, providing the nearfield electrostimulation therapy includes providing therapy and data signal pulses from the same electrodes of the implantable device 110.

At operation 14240, the method 14200 includes receiving, at the external source 102, the farfield signal corresponding to the nearfield electrostimulation therapy. Receiving the farfield signal can include using the electrodes 121 and 122 that are coupled to the external source 102. The electrodes 121 and 122 can be coupled to a tissue surface near the implantable device 110, and can sense electrical activity resulting from the nearfield electrostimulation therapy provided at operation 14230.

At operation 14250, the method 14200 includes retrieving an information signal from the received farfield signal, such as using the external source 102. In one or more embodiments, retrieving the information signal includes using the processor circuitry 210 and/or the demodulator circuitry 230, from the embodiment of FIG. 2A, to receive an electrical signal from the electrodes 121 and 122 and process the electrical signal to extract information or data components from the electrical signal.

At operation 14260, the method 14200 includes using the external source 102 to report the information signal to a user and/or to a remote device. The information signal can be reported in various ways including audibly (e.g., using the audio speaker 251), visually or graphically (e.g., using the display interface 252), or using a vibratory or other mechanical signal (e.g., using the haptic feedback device 253). In one or more embodiments, the reporting at operation 14260 can indicate, among other things, that the implantable device 110 is working properly or improperly, that the implantable device 110 received the midfield power signal at operation 14220 at an acceptable or unacceptable efficiency level, that an adjustment is required to a positioning of the external source 102 and/or of the implantable device 110, or an error condition at one or more of the external source 102 and the implantable device 110.

At operation 14270, the method 14200 includes updating a midfield power signal characteristic, such as based on the retrieved information from operation 14250. For example, if the information signal indicates that an insufficient or unexpected amount of power was received at the implantable device 110 at operation 14220, then one or more midfield transmission signal characteristics can be updated or adjusted to attempt to improve the efficiency or efficacy of any subsequent transmissions.

FIG. 134 illustrates, by way of example, a diagram of an embodiment of a method 14300 that includes encoding information in a therapy signal. The method 14300 includes operations 14220 and 14230 from the method 14200 of FIG. 133, as described above. After operation 14220 and before operation 14230, the method 14300 includes at least one of operations 14222 and 14224.

At operation 14222, the method 14300 includes determining one or more quantitative or qualitative characteristics of a signal received by the implantable device 110 from the external source 102. In one or more embodiments, operation 14222 includes determining a quantity of power received or determining an efficiency of conversion from a received power signal to a power signal that is usable or consumable by the implantable device 110, such as to power the implantable device 110 itself or to provide energy for an electrostimulation therapy delivered by the implantable device 110. In one or more embodiments, operation 14222 includes analyzing the received signal to determine whether the signal includes data or instructions for use by the implantable device 110.

At operation 14224, the method 14300 includes encoding information in a therapy signal about the quantitative or qualitative characteristics determined at operation 14222, about the implantable device 110 itself, or about physiologic information sensed by the implantable device 110. For example, the information about the implantable device 110 itself can include information about a power or battery status, a therapy schedule, an implant date, a therapy history such as including information about which of multiple electrodes was used to provide a therapy, device diagnostics, device status, or device operation information, or device configuration information, such as including information about available electrodes, available electrostimulation vectors, or sensors that are integrated with or communicatively coupled to the implantable device 110. In one or more embodiments, the implantable device 110 is configured to sense physiologic information using its electrodes or other sensors (e.g., a part of the sensor interface 4428), and operation 14224 includes encoding such physiologic information for transmission in a therapy signal.

At operation 14230, the method 14300 includes providing the nearfield electrostimulation therapy, such as including providing the encoded information, using the implantable device 110. In one or more embodiments, operation 14230 includes providing a therapy signal with interleaved data signals (see, e.g., the first therapy signal 14101 comprising therapy pulses $T_1$, $T_2$, and $T_3$, and interleaved data signals at communication intervals $C_1$ and $C_2$). The interleaved data signals can be provided at a sufficiently high frequency, a sufficiently low amplitude, and/or for a sufficiently brief duration such that a physiologic response from tissue near the implantable device 110 is not provoked. In one or more embodiments, operation 14230 includes providing a therapy signal with data signals embedded with therapy pulses (see, e.g., the second therapy signal 14102 comprising composite therapy pulses $CT_1$, $CT_2$, and $CT_3$). The embedded data signals can be provided at a sufficient amplitude and frequency such that the physiologic effect of the signals is about the same as amplitude or frequency characteristics of a conventional therapy pulse provided for the same overall duration.

FIG. 135 illustrates, by way of example, a diagram of an embodiment of a method 14400 that includes determining whether a therapy was properly provided. At operation 14410, the method 14400 includes using an external source 102 to encode instructions into a power signal to be communicated from the external source 102 to the implantable device 110. The encoded instructions are for use by an implantable device 110 to generate and provide a therapy signal having one or more therapy signal characteristics specified by the instructions. A therapy signal characteristic can include, among other things, a specified pulse pattern, frequency, burst characteristic, amplitude, phase, waveform morphology, or other characteristic. At operation 14420, the method 14400 includes using the external source 102 to transmit a midfield power signal that includes the instructions encoded at operation 14410. Transmitting the midfield power signal can include in response to exciting one or more subwavelength structures on the antenna 300 to cause the antenna 300 to emit an RF signal having a non-negligible H-field component.

At operation 14430, the method 14400 can include receiving the midfield power signal at the implantable device 110, and using the implantable device 110 to decode the instructions. In one or more embodiments, the antenna 108 of the implantable device 110 receives the midfield power signal and provides a corresponding electrical signal to one or more of the demodulator 544, the digital controller 548, or another processor circuitry for decoding and processing. For example, the instructions including one or more specified therapy signal characteristics can be decoded from the electrical signal.

At operation 14440, the method 14400 includes providing a nearfield electrostimulation therapy according to the instructions decoded at operation 14430. For example, the stimulation driver circuitry 556 can be configured to implement the instructions, including the one or more specified therapy signal characteristics, to provide an electrostimulation signal to one or more of the outputs 534 to the electrode array of the implantable device 110. When the nearfield electrostimulation therapy is provided at operation 14440, a corresponding potential difference (e.g., as a result of an electric dipole moment) can be remotely detected, such as using the external source 102 or the farfield sensor device 130. The external source 102 and/or the farfield sensor device 130 can be electrically coupled to a skin surface near the implantable device 110 to receive the potential difference information resulting from the delivered therapy signal. In a tissue or other space distal from the electrostimulation electrodes and optionally distal from the therapy target 190, the electric field can be considered a farfield signal corresponding to the nearfield signal that results from the electrostimulation therapy. The nearfield electrostimulation therapy provided at operation 14440 can optionally include data signal components (see, e.g., the first and second therapy signals 14101 and 14102 in the embodiment of FIG. 132).

At operation 14450, the method 14400 includes receiving, via the sensing electrodes 220 of the external source 102, the farfield signal corresponding to the nearfield electrostimulation therapy provided at operation 14440. Receiving the farfield signal can include using the electrodes 121 and 122 that are coupled to the external source 102. The electrodes 121 and 122 can be coupled to a tissue surface near the implantable device 110, and can sense electrical activity resulting from the nearfield electrostimulation therapy provided at operation 14440. In one or more embodiments, the external source 102 can provide a second electrical signal corresponding to the farfield signal, such as using the processor circuitry 210.

At operation 14460, the method 14400 includes determining, based on the received farfield signal, whether the electrostimulation therapy was properly provided at operation 14440. The determining at operation 14460 can be performed using the external source 102, or using an external device in data communication with the external source 102. The determining at operation 14460 includes analyzing the second electrical signal corresponding to the farfield signal to determine whether characteristics of the nearfield and/or farfield signals correspond or conform to the one or more therapy signal characteristics specified at operation 14410. That is, the second electrical signal, which is derived from the farfield electrical signal, can be used to determine whether the nearfield electrostimulation therapy was properly provided at operation 14440 according to the instructions issued by the external source 102 at operation 14410. The external source 102 or the implantable device 110 can take remedial actions if it is determined that the therapy was improperly provided. For example, the external source 102 can transmit new or additional instructions to the implantable device 110, such as to update or modify one or more of the therapy signal characteristics, or the implantable device 110 can select or use a different electrostimulation vector to provide the therapy.

IV. Embodiments of Computer Hardware and/or Architecture

FIG. 136 illustrates, by way of example, a block diagram of an embodiment of a machine 15000 upon which one or more methods discussed herein can be performed or in conjunction with one or more systems or devices described herein may be used. FIG. 150 includes reference to structural components that are discussed and described in connection with several of the embodiments and figures above. In one or more embodiments, the implantable device 110, the source 102, the sensor 107, the processor circuitry 210, the digital controller 548, circuitry in the circuitry housing 610, 4806, 5606, and/or 3616, system control circuitry 4222, power management circuitry 4214 and/or 6408, the controller 6412, stimulation circuitry 4216, energy harvest circuitry 4212, synchronization circuitry 4218, the external device 4202, 5028, AND/OR 8802, control circuitry 8221, feedback control circuitry 8223, the implanted device 8804, location circuitry 11446, control circuitry 11652, other circuitry of the implantable device, and/or circuitry that is a part of or connected to the external source, such as the circuitry 10430, can include one or more of the items of the machine 15000. The machine 15000, according to some example embodiments, is able to read instructions from a machine-readable medium (e.g., a machine-readable storage medium) and to perform any one or more of the methodologies, one or more operations of the methodologies, or one or more circuitry functions discussed herein, such as the methods described with regard to FIGS. 41A-41B, 103, 104, 107, 110, 111, 112, 113, 117, 118, 125, 126, 127, 129-131, 133, 134, and/or 135. For example, FIG. 136 shows a diagrammatic representation of the machine 15000 in the example form of a computer system, within which instructions 15016 (e.g., software, a program, an application, an applet, an app, or other executable code) for causing the machine 15000 to perform any one or more of the methodologies discussed herein can be executed. The instructions transform the general, non-programmed machine into a particular machine programmed to carry out the described and illustrated functions in the manner described. In alternative embodiments, the machine 15000 operates as a standalone device or can be coupled (e.g., networked) to other machines. In a networked deployment, the machine 15000 can operate in the capacity of a server machine or a client machine in a server-client network environment, or as a peer machine in a peer-to-peer (or distributed) network environment. Various portions of the machine 15000 can be included in, or used with, one or more of the external source 102 and the implantable device 110. In one or more embodiments, different instantiations or different physical hardware portions of the machine 15000 are separately implanted at the external source 102 and the implantable device 110.

In one or more embodiments, the machine 15000 can comprise, but is not limited to, a server computer, a client computer, a personal computer (PC), a tablet computer, a laptop computer, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 15016, sequentially or otherwise, that specify actions to be taken by machine 15000. Further, while only a single machine 15000 is illustrated, the term "machine" shall also be taken to include a collection of machines 15000 that individually or jointly execute the instructions 15016 to perform any one or more of the methodologies discussed herein.

The machine 15000 can include processors 15010, memory 15030, or I/O components 15050, which can be configured to communicate with each other such as via a bus 15002. In one or more embodiments embodiment, the processors 15010 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuitry (ASIC), a Radio-Frequency Integrated Circuitry (RFIC), another processor, or any suitable combination thereof) can include, for example, processor 15012 and processor 15014 that can execute instructions 15016. The term "processor" is intended to include multi-core processors that can include two or more independent processors (sometimes referred to as "cores") that can execute instructions contemporaneously. Although FIG. 136 shows multiple processors, the machine 15000 can include a single processor with a single core, a single processor with multiple cores (e.g., a multi-core process), multiple processors with a single core, multiple processors with multiples cores, or any combination thereof.

The memory/storage 15030 can include a memory 15032, such as a main memory, or other memory storage, and a storage unit 15036, both accessible to the processors 15010 such as via the bus 15002. The storage unit 15036 and memory 15032 store the instructions 15016 embodying any one or more of the methodologies or functions described herein. The instructions 15016 can also reside, completely or partially, within the memory 15032, within the storage unit 15036, within at least one of the processors 15010 (e.g., within the processor's cache memory), or any suitable combination thereof, during execution thereof by the machine 15000. Accordingly, the memory 15032, the storage unit 15036, and the memory of processors 15010 are examples of machine-readable media.

As used herein, "machine-readable medium" means a device able to store instructions and data temporarily or permanently and can include, but is not be limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions 15016. The term "machine-readable medium" shall also be taken to include any medium, or combination of multiple media, that is capable of storing instructions (e.g., instructions 15016) for execution by a machine (e.g., machine 15000), such that the instructions, when executed by one or more processors of the machine 15000 (e.g., processors 15010), cause the machine 15000 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 15050 can include a wide variety of components to receive input, provide output, produce output, transmit information, exchange information, capture measurements, and so on. The specific I/O components 15050 that are included in a particular machine will depend on the type of machine. For example, portable machines such as mobile phones will likely include a touch input device or other such input mechanisms, while a headless server machine will likely not include such a touch input device. It will be appreciated that the I/O components 15050 can include many other components that are not shown in FIG. 150. The I/O components 15050 are grouped according to functionality merely for simplifying the following discussion and the grouping is in no way limiting. In various example embodiments, the I/O components 15050 can include output components 15052 and input components 15054. The output components 15052 can include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 15054 can include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 15050 can include biometric components 15056, motion components 15058, environmental components 15060, or position components 15062 among a wide array of other components. For example, the biometric components 15056 can include components to detect expressions (e.g., hand expressions, facial expressions, vocal expressions, body gestures, or eye tracking), measure physiologic signals (e.g., blood pressure, heart rate, body temperature, perspiration, or brain waves, neural activity, or muscle activity), identify a person (e.g., voice identification, retinal identification, facial identification, fingerprint identification, or electroencephalogram based identification), and the like.

The motion components 15058 can include acceleration sensor components (e.g., accelerometer), gravitation sensor components, rotation sensor components (e.g., gyroscope), and so forth. In one or more embodiments, one or more of the motion components 15058 can be incorporated with the external source 102 or the implantable device 110, and can be configured to detect motion or a physical activity level of a patient. Information about the patient's motion can be used in various ways, for example, to adjust a signal transmission characteristic (e.g., amplitude, frequency, etc.) when a physical relationship between the external source 102 and the implantable device 110 changes or shifts.

The environmental components 15060 can include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that can provide indications, measurements, or signals corresponding to a surrounding physical environment. The position components 15062 can include location sensor components (e.g., a Global Position System (GPS) receiver component), altitude sensor components (e.g., altimeters or barometers that detect air pressure from which altitude can be derived), orientation sensor components (e.g., magnetometers), and the like. In one or more embodiments, the I/O component(s) 15050 can be a part of the implantable device 110 and/or the external source 102.

Communication can be implemented using a wide variety of technologies. The I/O components 15050 can include communication components 15064 operable to couple the machine 15000 to a network 15080 or devices 15070 via coupling 15082 and coupling 15072 respectively. For example, the communication components 15064 can include a network interface component or other suitable device to interface with the network 15080. In further examples, communication components 15064 can include wired communication components, wireless communication components, cellular communication components, Near Field (nearfield) Communication (NFC) components, midfield communication components, farfield communication components, and other communication components to provide communication via other modalities. The devices 15070 can be another machine or any of a wide variety of peripheral devices.

Moreover, the communication components 15064 can detect identifiers or include components operable to detect identifiers. For example, the communication components 15064 can include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code. UCC RSS-2D bar code, and other optical codes), or acoustic detection components (e.g., microphones to identify tagged audio signals). In addition, a variety of information can be derived via the communication components 15064, such as, location via Internet Protocol (IP) geo-location, location via Wi-Fi® signal triangulation, location via detecting a NFC beacon signal that can indicate a particular location, and so forth.

In some embodiments, the systems comprise various features that are present as single features (as opposed to multiple features). For example, in one embodiment, the system includes a single external source and a single implantable device or stimulation device with a single antenna. Multiple features or components are provided in alternate embodiments.

In some embodiments, the system comprises one or more of the following: means for tissue stimulation (e.g., an implantable stimulation device), means for powering (e.g., a midfield powering device or midfield coupler), means for receiving (e.g., a receiver), means for transmitting (e.g., a transmitter), means for controlling (e.g., a processor or control unit), etc.

Although various general and specific embodiments are described herein, it will be evident that various modifications and changes can be made to these embodiments without departing from the broader spirit and scope of the present disclosure. Accordingly, the specification and drawings are to be regarded in an illustrative rather than a restrictive sense. The accompanying drawings that form a part of this application show, by way of illustration, and not of limitation, specific embodiments in which the subject matter can be practiced. The embodiments illustrated are described in sufficient detail to enable those skilled in the art to practice the teachings disclosed herein. Other embodiments can be used or derived therefrom, such that structural and logical substitutions and changes can be made without departing from the scope of this disclosure. This Detailed Description, therefore, is not to be taken in a limiting sense, and the scope of various embodiments is defined only by the appended claims, along with the full range of equivalents to which such claims are entitled. Specific embodiments or examples are illustrated and described herein, however, it should be appreciated that any arrangement calculated to achieve the same purpose can be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Each of these non-limiting examples or embodiments can stand on its own, or can be combined in various permutations or combinations with one or more of the other examples or embodiments.

The above detailed description includes references to the accompanying drawings, which form a part of the detailed description. The drawings show, by way of illustration, specific embodiments in which methods, apparatuses, and systems discussed herein can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 kHz" includes "10 kHz." Terms or phrases preceded by a term such as "substantially" or "generally" include the recited term or phrase. For example, "substantially parallel" includes "parallel" and "generally cylindrical" includes cylindrical.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention(s) and embodiments should be determined with reference to the appended claims, along with the full scope of equivalents to which such claims are entitled.

What is claimed is:

1. A system comprising:
    an external power source including first circuitry configured to provide radio frequency (RF) signals to a location in tissue; and
    an implantable device configured to receive the RF signals from the external power source, the implantable device including a distal portion and a proximal portion, wherein the implantable device includes second circuitry in a first housing, an antenna in a separate second housing in the proximal portion, and a first electrode on, or at least partially in, the distal portion, and wherein the antenna is electrically coupled to the second circuitry in the first housing and the first housing is situated between the second housing and the first electrode;
    wherein the external power source and the implantable device are configured to communicate at least in part using a backscatter signal, and wherein at least one sub-wavelength structure of the external power source is configured to receive the backscatter signal from the implantable device.

2. The system of claim 1, wherein the implantable device comprises a flexible, biocompatible, elongated member including the distal portion and the proximal portion; and
    a plurality of electrodes situated along the distal portion of the elongated member, wherein the plurality of electrodes includes the first electrode;
    wherein the second circuitry is hermetically sealed within the first housing and is configured to receive electrical energy from the external power source and to provide electrical energy to the plurality of electrodes.

3. The system of claim 1, wherein the second housing is attached to the first housing at a proximal end of the first housing that is opposite a distal end of the first housing.

4. The system of claim 1, wherein the antenna is a primary antenna and the system further comprises a secondary antenna in the second housing, the secondary antenna shaped and positioned to provide a near field coupling with the primary antenna.

5. The system of claim 1, wherein the implantable device further comprises:
    a feedthrough plate between and connected to the first and separate second housings; and
    an electrical conductor in a feedthrough of the feedthrough plate, the conductor electrically connected to the second circuitry and the antenna.

6. The system of claim 5, wherein the external power source further comprises:
    a top cover including a thermally conductive material; and
    a bottom cover including a thermally insulative material;
    wherein the top cover and bottom cover combine to enclose the first circuitry.

7. The system of claim 6, further comprising:
    thermally conductive fins coupled to the top cover;
    recesses in a surface of the bottom cover; and
    air vents in the surface of the bottom cover, the air vents thermally coupled to the recesses to dissipate heat towards the top cover.

8. The system of claim 1, wherein the implantable device comprises at least three electrodes, including the first electrode, configured to deliver a therapy to the tissue, and wherein the second circuitry includes a therapy delivery circuit configured to provide a therapy signal via one or more of the at least three electrodes, the therapy signal comprising a series of at least two electrostimulation pulses provided using respective vectors corresponding to different combinations of the at least three electrodes.

9. The system of claim 8, wherein the therapy delivery circuit is configured to provide the therapy signal with a specified delay interval between each pulse, and wherein the series of pulses is repeated at least twice.

10. The system of claim 1, wherein the external power source further comprises:
an RF signal generator system configured to provide multiple different sets of RF signals to two or more sub-wavelength structures of the external power source, each set comprising two or more separate signals; and
a transmitter circuit including excitation ports coupled to respective ones of the two or more sub-wavelength structures, the transmitter circuit coupled to the RF signal generator system, and the transmitter circuit configured to transmit the multiple different sets of RF signals at respective different times to the excitation ports, wherein the excitation ports receive respective ones of the separate signals from each set of RF signals, and wherein each of the transmitted sets of RF signals includes a non-negligible magnetic-field component that is substantially parallel to an external surface of the tissue; and
wherein each set of transmitted RF signals is selected to differently manipulate an evanescent field at or near the tissue surface to transmit a power or data signal to respective different target devices implanted in the tissue.

11. The system of claim 1, further comprising one or more sutures connected to the implantable device at one or more of: (1) a proximal portion of the second housing; (2) a proximal portion of the first housing; and (3) an attachment structure attached to a proximal end of the second housing.

12. The system of claim 1, further comprising tines extending outward from a longitudinal axis of the implantable device attached to the proximal portion.

13. The system of claim 1, wherein the second circuitry in the implantable device is configured to provide the backscatter signal using RF signals received from the external power source.

14. The system of claim 1, wherein the RF signals provided by the external power source comprise a midfield signal.

15. The system of claim 1, wherein the external power source is configured to use information from the backscatter signal to identify a portion of a power signal received by the implantable device.

16. The system of claim 1, wherein the backscatter signal comprises information about one or more of a therapy provided by the implantable device and a physiologic characteristic sensed or measured by the implantable device.

17. An implantable device comprising:
a biocompatible, elongated member including a distal portion and a proximal portion;
a plurality of cylindrical electrodes situated along the distal portion of the elongated member;
a cylindrical, hermetic circuitry housing attached to the proximal portion of the elongated member;
therapy signal circuitry hermetically sealed within the circuitry housing, wherein the therapy signal circuitry is configured to provide electrical energy to the plurality of electrodes;
an antenna housing attached to the circuitry housing at a proximal end of the circuitry housing opposite to an end of the circuitry housing attached to the elongated member;
an antenna in the antenna housing; and
backscatter communication circuitry hermetically sealed within the circuitry housing, wherein the backscatter communication circuitry is configured to use a first signal received via the antenna to provide a backscatter signal to a body-external source device, and wherein the body-external source device comprises a sub-wavelength structure configured to receive the backscatter signal.

18. The device of claim 17, wherein the antenna is a primary antenna and wherein the device further comprises:
a secondary antenna in a housing attached to the antenna housing, the secondary antenna shaped and positioned to provide a near field coupling with the primary antenna.

19. The device of claim 17, wherein the antenna is a helical antenna.

20. The device of claim 17, wherein the backscatter communication circuitry is configured to receive the first signal from the body-external source device.

21. The device of claim 20, wherein the first signal comprises a midfield signal.

22. The device of claim 17, wherein the backscatter signal comprises information about one or more of a therapy provided by the implantable device and a physiologic characteristic sensed or measured by the implantable device.

23. A system comprising:
an external power source comprising:
transmitter circuitry configured to provide wireless signals to a location in body tissue; and
receiver circuitry and at least one sub-wavelength structure configured to receive a backscatter signal; and
an implantable device comprising:
an antenna at a proximal portion of the implantable device, the antenna configured to receive the wireless signals from the external power source;
backscatter communication circuitry configured to use the wireless signals to provide the backscatter signal to the external power source; and
therapy signal circuitry configured to use the wireless signals to generate or adjust a therapy provided to the body tissue using one or more electrodes, wherein the one or more electrodes are coupled at a distal portion of the implantable device.

* * * * *